(12) United States Patent
Liu et al.

(10) Patent No.: US 10,682,410 B2
(45) Date of Patent: *Jun. 16, 2020

(54) DELIVERY SYSTEM FOR FUNCTIONAL NUCLEASES

(71) Applicant: President and Fellows of Harvard College, Cambridge, MA (US)

(72) Inventors: David R. Liu, Lexington, MA (US); John Anthony Zuris, Cambridge, MA (US); David B. Thompson, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/916,679

(22) PCT Filed: Sep. 5, 2014

(86) PCT No.: PCT/US2014/054247
§ 371 (c)(1),
(2) Date: Mar. 4, 2016

(87) PCT Pub. No.: WO2015/035136
PCT Pub. Date: Mar. 12, 2015

(65) Prior Publication Data
US 2016/0200779 A1 Jul. 14, 2016

Related U.S. Application Data

(63) Continuation of application No. 14/462,163, filed on Aug. 18, 2014, and a continuation of application No. 14/462,189, filed on Aug. 18, 2014.

(Continued)

(51) Int. Cl.
*A61K 47/12* (2006.01)
*A61K 9/127* (2006.01)
*A61K 38/45* (2006.01)
*C12N 9/96* (2006.01)
*C12N 9/12* (2006.01)
*C07K 14/00* (2006.01)
*A61K 38/46* (2006.01)
*C07K 14/435* (2006.01)
*C12N 9/22* (2006.01)
*C07K 14/195* (2006.01)
*A61K 38/17* (2006.01)
(Continued)

(52) U.S. Cl.
CPC ............ *A61K 47/12* (2013.01); *A61K 9/127* (2013.01); *A61K 38/1767* (2013.01); *A61K 38/45* (2013.01); *A61K 38/465* (2013.01); *C07K 14/00* (2013.01); *C07K 14/195* (2013.01); *C07K 14/43595* (2013.01); *C07K 14/463* (2013.01); *C07K 14/4702* (2013.01); *C12N 9/1241* (2013.01); *C12N 9/14* (2013.01); *C12N 9/22* (2013.01); *C12N 9/96* (2013.01); *C07K 2319/60* (2013.01); *C07K 2319/80* (2013.01); *C07K 2319/85* (2013.01); *C12Y 207/07* (2013.01); *C12Y 301/00* (2013.01)

(58) Field of Classification Search
CPC ... C12N 15/63; C12N 2310/20; C12N 15/113
See application file for complete search history.

(56) References Cited

U.S. PATENT DOCUMENTS 4,182,449 A 1/1980 Kozlow
4,235,871 A 11/1980 Papahadjopoulos et al.
(Continued)

FOREIGN PATENT DOCUMENTS

AU 2012244264 A1 11/2012
AU 2015252023 A1 11/2015
(Continued)

OTHER PUBLICATIONS

John A. Zuris Efficient Delivery of Genome-Editing Proteins In Vitro and In Vivo. Nat Biotechnol. Jan. 2015; 33(1): 73-80 (Year: 2015).*
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Barnes et al., Repair and genetic consequences of endogenous DNA base damage in mammalian cells. Annu Rev Genet. 2004;38:445-76.
Birling et al., Site-specific recombinases for manipulation of the mouse genome. Methods Mol Biol. 2009;561:245-63. doi: 10.1007/978-1-60327-019-9_16.
(Continued)

Primary Examiner — Kagnew H Gebreyesus
(74) Attorney, Agent, or Firm — Wolf, Greenfield & Sacks, P.C.

(57) ABSTRACT

Compositions, methods, strategies, kits, and systems for the supercharged protein-mediated delivery of functional effector proteins into cells in vivo, ex vivo, or in vitro are provided. Compositions, methods, strategies, kits, and systems for delivery of functional effector proteins using cationic lipids and cationic polymers are also provided. Functional effector proteins include, without limitation, transcriptional modulators (e.g., repressors or activators), recombinases, nucleases (e.g., RNA-programmable nucleases, such as Cas9 proteins; TALE nuclease, and zinc finger nucleases), deaminases, and other gene modifying/editing enzymes. Functional effector proteins include TALE effector proteins, e.g., TALE transcriptional activators and repressors, as well as TALE nucleases. Compositions, methods, strategies, and systems for the delivery of functional effector proteins into cells is useful for therapeutic and research purposes, including, but not limited to, the targeted manipulation of a gene associated with disease, the modulation of the expression level of a gene associated with disease, and the programming of cell fate.

30 Claims, 31 Drawing Sheets
Specification includes a Sequence Listing.

Related U.S. Application Data

(60) Provisional application No. 61/874,746, filed on Sep. 6, 2013.

(51) Int. Cl.
*C07K 14/46* (2006.01)
*C07K 14/47* (2006.01)
*C12N 9/14* (2006.01)

(56) References Cited

U.S. PATENT DOCUMENTS

| | | |
|---|---|---|
| 4,501,728 A | 2/1985 | Geho et al. |
| 4,737,323 A | 4/1988 | Martin et al. |
| 4,837,028 A | 6/1989 | Allen |
| 4,880,635 A | 11/1989 | Janoff et al. |
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 5,139,941 A | 8/1992 | Muzyczka et al. |
| 5,449,639 A | 9/1995 | Wei et al. |
| 5,767,099 A | 6/1998 | Harris et al. |
| 5,780,053 A | 7/1998 | Ashley et al. |
| 5,830,430 A | 11/1998 | Unger et al. |
| 5,835,699 A | 11/1998 | Kimura |
| 5,851,548 A | 12/1998 | Dattagupta et al. |
| 5,855,910 A | 1/1999 | Ashley et al. |
| 5,962,313 A | 10/1999 | Podsakoff et al. |
| 6,057,153 A | 5/2000 | Shaji et al. |
| 6,453,242 B1 | 9/2002 | Eisenberg et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,163,824 B2 | 1/2007 | Cox, III et al. |
| 7,479,573 B2 | 1/2009 | Chu et al. |
| 7,794,931 B2 | 9/2010 | Breaker et al. |
| 7,919,277 B2 | 4/2011 | Russell et al. |
| 7,993,672 B2 | 8/2011 | Huang et al. |
| 8,361,725 B2 | 1/2013 | Russell et al. |
| 8,394,604 B2 | 3/2013 | Liu et al. |
| 8,546,553 B2 | 10/2013 | Terns et al. |
| 8,569,256 B2 | 10/2013 | Heyes et al. |
| 8,680,069 B2 | 3/2014 | de Fougerolles et al. |
| 8,691,750 B2 | 4/2014 | Constien et al. |
| 8,697,359 B1 | 4/2014 | Zhang |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,795,965 B2 | 8/2014 | Zhang |
| 8,846,578 B2 | 9/2014 | McCray et al. |
| 8,993,233 B2 | 3/2015 | Zhang et al. |
| 8,999,641 B2 | 4/2015 | Zhang et al. |
| 9,068,179 B1 | 6/2015 | Liu et al. |
| 9,163,284 B2 | 10/2015 | Liu et al. |
| 9,228,207 B2 | 1/2016 | Liu et al. |
| 9,234,213 B2 | 1/2016 | Wu |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,388,430 B2 | 7/2016 | Liu et al. |
| 9,512,446 B1 | 12/2016 | Joung et al. |
| 9,526,724 B2 | 12/2016 | Oshlack et al. |
| 9,526,784 B2 | 12/2016 | Liu et al. |
| 9,737,604 B2 | 8/2017 | Liu et al. |
| 9,816,093 B1 | 11/2017 | Donohoue et al. |
| 9,840,690 B2 | 12/2017 | Karli et al. |
| 9,840,699 B2 | 12/2017 | Liu et al. |
| 9,873,907 B2 | 1/2018 | Zeiner et al. |
| 9,879,270 B2 | 1/2018 | Hittinger et al. |
| 9,938,288 B1 | 4/2018 | Kishi et al. |
| 9,944,933 B2 | 4/2018 | Storici et al. |
| 9,982,279 B1 | 5/2018 | Gill et al. |
| 9,999,671 B2 | 6/2018 | Liu et al. |
| 10,059,940 B2 | 8/2018 | Zhong |
| 10,077,453 B2 | 9/2018 | Liu et al. |
| 10,113,163 B2 | 10/2018 | Liu et al. |
| 10,167,457 B2 | 1/2019 | Liu et al. |
| 10,227,581 B2 | 3/2019 | Liu et al. |
| 10,323,236 B2 | 6/2019 | Liu et al. |
| 10,465,176 B2 | 11/2019 | Liu et al. |
| 2003/0082575 A1 | 5/2003 | Schultz et al. |
| 2003/0108885 A1 | 6/2003 | Schultz et al. |
| 2004/0003420 A1 | 1/2004 | Kuhn et al. |
| 2004/0115184 A1 | 6/2004 | Smith et al. |
| 2005/0222030 A1 | 10/2005 | Allison et al. |
| 2006/0088864 A1 | 4/2006 | Smolke et al. |
| 2006/0104984 A1 | 5/2006 | Littlefield et al. |
| 2006/0246568 A1 | 11/2006 | Honjo et al. |
| 2007/0264692 A1 | 11/2007 | Liu et al. |
| 2008/0124725 A1 | 5/2008 | Barrangou et al. |
| 2008/0182254 A1 | 7/2008 | Hall et al. |
| 2009/0130718 A1 | 5/2009 | Short |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0316643 A1 | 12/2010 | Eckert et al. |
| 2011/0059160 A1 | 3/2011 | Essner et al. |
| 2011/0104787 A1 | 5/2011 | Church et al. |
| 2011/0189776 A1 | 8/2011 | Terns et al. |
| 2011/0217739 A1 | 9/2011 | Terns et al. |
| 2012/0129759 A1 | 5/2012 | Liu et al. |
| 2012/0141523 A1 | 6/2012 | Castado et al. |
| 2012/0244601 A1 | 9/2012 | Bertozzi et al. |
| 2012/0270273 A1 | 10/2012 | Zhang et al. |
| 2013/0117869 A1 | 5/2013 | Duchateau et al. |
| 2013/0130248 A1 | 5/2013 | Haurwitz et al. |
| 2013/0158245 A1 | 6/2013 | Russell et al. |
| 2013/0165389 A1 | 6/2013 | Schellenberger et al. |
| 2013/0309720 A1 | 11/2013 | Schultz et al. |
| 2013/0344117 A1 | 12/2013 | Mirosevich et al. |
| 2014/0004280 A1 | 1/2014 | Loomis |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0186843 A1 | 7/2014 | Zhang et al. |
| 2014/0186958 A1 | 7/2014 | Zhang et al. |
| 2014/0234289 A1 | 8/2014 | Liu et al. |
| 2014/0248702 A1 | 9/2014 | Cong |
| 2014/0273037 A1 | 9/2014 | Wu |
| 2014/0273226 A1 | 9/2014 | Wu |
| 2014/0273230 A1 | 9/2014 | Chen et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |

(56) References Cited

U.S. PATENT DOCUMENTS

| | | |
|---|---|---|
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens et al. |
| 2015/0218573 A1 | 8/2015 | Loque et al. |
| 2015/0225773 A1 | 8/2015 | Farmer et al. |
| 2015/0252358 A1 | 9/2015 | Maeder et al. |
| 2015/0307889 A1 | 10/2015 | Petolino et al. |
| 2015/0315252 A1 | 11/2015 | Haugwitz et al. |
| 2016/0015682 A2 | 1/2016 | Cawthorne et al. |
| 2016/0017393 A1 | 1/2016 | Jacobson et al. |
| 2016/0017396 A1 | 1/2016 | Cann et al. |
| 2016/0032292 A1 | 2/2016 | Storici et al. |
| 2016/0032353 A1 | 2/2016 | Braman et al. |
| 2016/0046952 A1 | 2/2016 | Hittinger et al. |
| 2016/0046961 A1 | 2/2016 | Jinek et al. |
| 2016/0046962 A1 | 2/2016 | May et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0090622 A1 | 3/2016 | Liu et al. |
| 2016/0115488 A1 | 4/2016 | Zhang et al. |
| 2016/0138046 A1 | 5/2016 | Wu et al. |
| 2016/0186214 A1 | 6/2016 | Brouns et al. |
| 2016/0201040 A1 | 7/2016 | Liu et al. |
| 2016/0201089 A1 | 7/2016 | Gersbach et al. |
| 2016/0206566 A1 | 7/2016 | Lu et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0244784 A1 | 8/2016 | Jacobson et al. |
| 2016/0244829 A1 | 8/2016 | Bang et al. |
| 2016/0272965 A1 | 9/2016 | Zhang et al. |
| 2016/0281072 A1 | 9/2016 | Zhang |
| 2016/0304846 A1 | 10/2016 | Liu et al. |
| 2016/0304855 A1 | 10/2016 | Stark et al. |
| 2016/0312304 A1 | 10/2016 | Sorrentino et al. |
| 2016/0333389 A1 | 11/2016 | Liu et al. |
| 2016/0340662 A1 | 11/2016 | Zhang et al. |
| 2016/0345578 A1 | 12/2016 | Barrangou et al. |
| 2016/0346360 A1 | 12/2016 | Quake et al. |
| 2016/0346361 A1 | 12/2016 | Quake et al. |
| 2016/0346362 A1 | 12/2016 | Quake et al. |
| 2016/0348074 A1 | 12/2016 | Quake et al. |
| 2016/0350476 A1 | 12/2016 | Quake et al. |
| 2016/0369262 A1 | 12/2016 | Reik et al. |
| 2017/0009242 A1 | 1/2017 | McKinley et al. |
| 2017/0014449 A1 | 1/2017 | Bangera et al. |
| 2017/0020922 A1 | 1/2017 | Wagner et al. |
| 2017/0037432 A1 | 2/2017 | Donohoue et al. |
| 2017/0044520 A1 | 2/2017 | Liu et al. |
| 2017/0044592 A1 | 2/2017 | Peter et al. |
| 2017/0053729 A1 | 2/2017 | Kotani et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0073663 A1 | 3/2017 | Wang et al. |
| 2017/0073670 A1 | 3/2017 | Nishida et al. |
| 2017/0087224 A1 | 3/2017 | Quake |
| 2017/0087225 A1 | 3/2017 | Quake |
| 2017/0088587 A1 | 3/2017 | Quake |
| 2017/0088828 A1 | 3/2017 | Quake |
| 2017/0107536 A1 | 4/2017 | Zhang et al. |
| 2017/0107560 A1 | 4/2017 | Peter et al. |
| 2017/0114367 A1 | 4/2017 | Hu et al. |
| 2017/0121693 A1 | 5/2017 | Liu et al. |
| 2017/0145394 A1 | 5/2017 | Yeo et al. |
| 2017/0145405 A1 | 5/2017 | Tang et al. |
| 2017/0145438 A1 | 5/2017 | Kantor |
| 2017/0152528 A1 | 6/2017 | Zhang |
| 2017/0152787 A1 | 6/2017 | Kubo et al. |
| 2017/0159033 A1 | 6/2017 | Kamtekar et al. |
| 2017/0166928 A1 | 6/2017 | Vyas et al. |
| 2017/0175104 A1 | 6/2017 | Doudna et al. |
| 2017/0175142 A1 | 6/2017 | Zhang et al. |
| 2017/0191047 A1 | 7/2017 | Terns et al. |
| 2017/0191078 A1 | 7/2017 | Zhang et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0226522 A1 | 8/2017 | Hu et al. |
| 2017/0233703 A1 | 8/2017 | Xie et al. |
| 2017/0233756 A1 | 8/2017 | Begemann et al. |
| 2017/0247671 A1 | 8/2017 | Yung et al. |
| 2017/0247703 A1 | 8/2017 | Sloan et al. |
| 2017/0268022 A1 | 9/2017 | Liu et al. |
| 2017/0283797 A1 | 10/2017 | Robb et al. |
| 2017/0314016 A1 | 11/2017 | Kim et al. |
| 2017/0362635 A1 | 12/2017 | Chamberlain et al. |
| 2018/0064077 A1 | 3/2018 | Dunham et al. |
| 2018/0066258 A1 | 3/2018 | Powell |
| 2018/0068062 A1 | 3/2018 | Zhang et al. |
| 2018/0073012 A1 | 3/2018 | Liu et al. |
| 2018/0100147 A1 | 4/2018 | Yates et al. |
| 2018/0105867 A1 | 4/2018 | Xiao et al. |
| 2018/0119118 A1 | 5/2018 | Lu et al. |
| 2018/0127780 A1 | 5/2018 | Liu et al. |
| 2018/0155708 A1 | 6/2018 | Church et al. |
| 2018/0155720 A1 | 6/2018 | Donohoue et al. |
| 2018/0163213 A1 | 6/2018 | Aneja et al. |
| 2018/0170984 A1 | 6/2018 | Harris et al. |
| 2018/0179503 A1 | 6/2018 | Maianti et al. |
| 2018/0179547 A1 | 6/2018 | Zhang et al. |
| 2018/0201921 A1 | 7/2018 | Malcolm |
| 2018/0230464 A1 | 8/2018 | Zhong |
| 2018/0230471 A1 | 8/2018 | Storici et al. |
| 2018/0236081 A1 | 8/2018 | Liu et al. |
| 2018/0237787 A1 | 8/2018 | Maianti et al. |
| 2018/0245066 A1 | 8/2018 | Yao et al. |
| 2018/0265864 A1 | 9/2018 | Li et al. |
| 2018/0273939 A1 | 9/2018 | Yu et al. |
| 2018/0282722 A1 | 10/2018 | Jakimo et al. |
| 2018/0305688 A1 | 10/2018 | Zhong |
| 2018/0305704 A1 | 10/2018 | Zhang |
| 2018/0312825 A1 | 11/2018 | Liu et al. |
| 2018/0312828 A1 | 11/2018 | Liu et al. |
| 2018/0312835 A1 | 11/2018 | Yao et al. |
| 2018/0327756 A1 | 11/2018 | Zhang et al. |
| 2019/0093099 A1 | 3/2019 | Liu et al. |

(56) References Cited

U.S. PATENT DOCUMENTS

2019/0185883 A1 6/2019 Liu et al.
2019/0225955 A1 7/2019 Liu et al.
2019/0322992 A1 10/2019 Liu et al.

FOREIGN PATENT DOCUMENTS

| | | |
|---|---|---|
| AU | 2015101792 | 1/2016 |
| BR | 112015013786 A2 | 7/2017 |
| CA | 2894668 A1 | 6/2014 |
| CA | 2894681 A1 | 6/2014 |
| CA | 2894684 A1 | 6/2014 |
| CA | 2 852 593 A1 | 11/2015 |
| CN | 1069962 A | 3/1993 |
| CN | 103224947 A | 7/2013 |
| CN | 103233028 A | 8/2013 |
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 103981211 A | 8/2014 |
| CN | 103981212 A | 8/2014 |
| CN | 103981212 A | 8/2014 |
| CN | 104004778 A | 8/2014 |
| CN | 104004782 A | 8/2014 |
| CN | 104004782 A | 8/2014 |
| CN | 104017821 A | 9/2014 |
| CN | 104109687 A | 10/2014 |
| CN | 104178461 A | 12/2014 |
| CN | 104342457 | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104561095 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 A | 6/2015 |
| CN | 104725626 A | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| CN | 105039339 A | 11/2015 |
| CN | 105039399 A | 11/2015 |
| CN | 105063061 A | 11/2015 |
| CN | 105087620 A | 11/2015 |
| CN | 105112422 A | 12/2015 |
| CN | 105112445 A | 12/2015 |
| CN | 105112519 A | 12/2015 |
| CN | 105121648 A | 12/2015 |
| CN | 105132427 A | 12/2015 |
| CN | 105132451 A | 12/2015 |
| CN | 105177038 A | 12/2015 |
| CN | 105177126 A | 12/2015 |
| CN | 105210981 A | 1/2016 |
| CN | 105219799 A | 1/2016 |
| CN | 105238806 A | 1/2016 |
| CN | 105255937 A | 1/2016 |
| CN | 105274144 A | 1/2016 |
| CN | 105296518 A | 2/2016 |
| CN | 105296537 A | 2/2016 |
| CN | 105316324 A | 2/2016 |
| CN | 105316327 A | 2/2016 |
| CN | 105316337 A | 2/2016 |
| CN | 105331607 A | 2/2016 |
| CN | 105331608 A | 2/2016 |
| CN | 105331609 A | 2/2016 |
| CN | 105331627 A | 2/2016 |
| CN | 105400773 A | 3/2016 |
| CN | 105400779 A | 3/2016 |
| CN | 105400810 A | 3/2016 |
| CN | 105441451 A | 3/2016 |
| CN | 105462968 A | 4/2016 |
| CN | 105463003 A | 4/2016 |
| CN | 105463027 A | 4/2016 |
| CN | 105492608 A | 4/2016 |
| CN | 105492609 A | 4/2016 |
| CN | 105505976 A | 4/2016 |
| CN | 105505979 A | 4/2016 |
| CN | 105518134 A | 4/2016 |
| CN | 105518135 A | 4/2016 |
| CN | 105518137 A | 4/2016 |
| CN | 105518138 A | 4/2016 |
| CN | 105518139 A | 4/2016 |
| CN | 105518140 A | 4/2016 |
| CN | 105543228 A | 5/2016 |
| CN | 105543266 A | 5/2016 |
| CN | 105543270 A | 5/2016 |
| CN | 105567688 A | 5/2016 |
| CN | 105567689 | 5/2016 |
| CN | 105567734 A | 5/2016 |
| CN | 105567735 A | 5/2016 |
| CN | 105567738 A | 5/2016 |
| CN | 105593367 A | 5/2016 |
| CN | 105594664 A | 5/2016 |
| CN | 105602987 A | 5/2016 |
| CN | 105624146 A | 6/2016 |
| CN | 105624146 A | 6/2016 |
| CN | 105624187 A | 6/2016 |
| CN | 105624187 A | 6/2016 |
| CN | 105646719 A | 6/2016 |
| CN | 105646719 A | 6/2016 |
| CN | 105647922 A | 6/2016 |
| CN | 105647922 A | 6/2016 |
| CN | 105647962 A | 6/2016 |
| CN | 105647962 A | 6/2016 |
| CN | 105647968 A | 6/2016 |
| CN | 105647968 A | 6/2016 |
| CN | 105647969 A | 6/2016 |
| CN | 105647969 A | 6/2016 |
| CN | 105671070 A | 6/2016 |
| CN | 105671070 A | 6/2016 |
| CN | 105671083 A | 6/2016 |
| CN | 105671083 A | 6/2016 |
| CN | 105695485 A | 6/2016 |
| CN | 105695485 A | 6/2016 |
| CN | 105779448 A | 7/2016 |
| CN | 105779448 A | 7/2016 |
| CN | 105779449 A | 7/2016 |
| CN | 105779449 A | 7/2016 |
| CN | 105802980 A | 7/2016 |
| CN | 105802980 A | 7/2016 |
| CN | 105821039 A | 8/2016 |
| CN | 105821040 A | 8/2016 |
| CN | 105821049 A | 8/2016 |
| CN | 105821072 A | 8/2016 |
| CN | 105821075 A | 8/2016 |
| CN | 105821116 A | 8/2016 |
| CN | 105838733 A | 8/2016 |
| CN | 105861547 A | 8/2016 |
| CN | 105861552 A | 8/2016 |
| CN | 105861554 A | 8/2016 |
| CN | 105886498 A | 8/2016 |
| CN | 105886534 A | 8/2016 |

(56) References Cited

FOREIGN PATENT DOCUMENTS

| | | |
|---|---|---|
| CN | 105886616 A | 8/2016 |
| CN | 105907758 A | 8/2016 |
| CN | 105907785 A | 8/2016 |
| CN | 105925608 A | 9/2016 |
| CN | 105950560 A | 9/2016 |
| CN | 105950626 A | 9/2016 |
| CN | 105950633 A | 9/2016 |
| CN | 105950639 A | 9/2016 |
| CN | 105985985 A | 10/2016 |
| CN | 106011104 A | 10/2016 |
| CN | 106011150 A | 10/2016 |
| CN | 106011167 A | 10/2016 |
| CN | 106011171 A | 10/2016 |
| CN | 106032540 A | 10/2016 |
| CN | 106047803 A | 10/2016 |
| CN | 106047877 A | 10/2016 |
| CN | 106047930 A | 10/2016 |
| CN | 106086008 A | 11/2016 |
| CN | 106086028 A | 11/2016 |
| CN | 106086061 A | 11/2016 |
| CN | 106086062 A | 11/2016 |
| CN | 106109417 A | 11/2016 |
| CN | 106119275 A | 11/2016 |
| CN | 106119283 A | 11/2016 |
| CN | 106148286 A | 11/2016 |
| CN | 106148370 A | 11/2016 |
| CN | 106148416 A | 11/2016 |
| CN | 106167525 A | 11/2016 |
| CN | 106167808 A | 11/2016 |
| CN | 106167810 A | 11/2016 |
| CN | 106167821 A | 11/2016 |
| CN | 106172238 A | 12/2016 |
| CN | 106190903 A | 12/2016 |
| CN | 106191057 A | 12/2016 |
| CN | 106191061 A | 12/2016 |
| CN | 106191062 A | 12/2016 |
| CN | 106191064 A | 12/2016 |
| CN | 106191071 A | 12/2016 |
| CN | 106191099 A | 12/2016 |
| CN | 106191107 A | 12/2016 |
| CN | 106191113 A | 12/2016 |
| CN | 106191114 A | 12/2016 |
| CN | 106191116 A | 12/2016 |
| CN | 106191124 A | 12/2016 |
| CN | 106222177 A | 12/2016 |
| CN | 106222193 A | 12/2016 |
| CN | 106222203 A | 12/2016 |
| CN | 106244555 A | 12/2016 |
| CN | 106244591 A | 12/2016 |
| CN | 106244609 A | 12/2016 |
| CN | 106282241 A | 1/2017 |
| CN | 106318934 A | 1/2017 |
| CN | 106318973 A | 1/2017 |
| CN | 106350540 A | 1/2017 |
| CN | 106367435 A | 2/2017 |
| CN | 106399306 A | 2/2017 |
| CN | 106399311 A | 2/2017 |
| CN | 106399360 A | 2/2017 |
| CN | 106399367 A | 2/2017 |
| CN | 106399375 A | 2/2017 |
| CN | 106399377 A | 2/2017 |
| CN | 106434651 A | 2/2017 |
| CN | 106434663 A | 2/2017 |
| CN | 106434688 A | 2/2017 |
| CN | 106434737 A | 2/2017 |
| CN | 106434748 A | 2/2017 |
| CN | 106434752 A | 2/2017 |
| CN | 106434782 A | 2/2017 |
| CN | 106446600 A | 2/2017 |
| CN | 106479985 A | 3/2017 |
| CN | 106480027 A | 3/2017 |
| CN | 106480036 A | 3/2017 |
| CN | 106480067 A | 3/2017 |
| CN | 106480080 A | 3/2017 |
| CN | 106480083 A | 3/2017 |
| CN | 106480097 A | 3/2017 |
| CN | 106544351 A | 3/2017 |
| CN | 106544353 A | 3/2017 |
| CN | 106544357 A | 3/2017 |
| CN | 106554969 A | 4/2017 |
| CN | 106566838 A | 4/2017 |
| CN | 106701763 A | 5/2017 |
| CN | 106701808 A | 5/2017 |
| CN | 106701818 A | 5/2017 |
| CN | 106701823 A | 5/2017 |
| CN | 106701830 A | 5/2017 |
| CN | 106754912 A | 5/2017 |
| CN | 106755026 A | 5/2017 |
| CN | 106755077 A | 5/2017 |
| CN | 106755088 A | 5/2017 |
| CN | 106755091 A | 5/2017 |
| CN | 106755097 A | 5/2017 |
| CN | 106755424 A | 5/2017 |
| CN | 106801056 A | 6/2017 |
| CN | 106834323 A | 6/2017 |
| CN | 106834341 A | 6/2017 |
| CN | 106834347 A | 6/2017 |
| CN | 106845151 A | 6/2017 |
| CN | 106868008 A | 6/2017 |
| CN | 106868031 A | 6/2017 |
| CN | 106906240 A | 6/2017 |
| CN | 106906242 A | 6/2017 |
| CN | 106916820 A | 7/2017 |
| CN | 106916852 A | 7/2017 |
| CN | 106939303 A | 7/2017 |
| CN | 106947750 A | 7/2017 |
| CN | 106947780 A | 7/2017 |
| CN | 106957830 A | 7/2017 |
| CN | 106957831 A | 7/2017 |
| CN | 106957844 A | 7/2017 |
| CN | 106957855 A | 7/2017 |
| CN | 106957858 A | 7/2017 |
| CN | 106967697 A | 7/2017 |
| CN | 106967726 A | 7/2017 |
| CN | 106978428 A | 7/2017 |
| CN | 106987570 A | 7/2017 |
| CN | 106987757 A | 7/2017 |
| CN | 107012164 A | 8/2017 |
| CN | 107012174 A | 8/2017 |
| CN | 107012213 A | 8/2017 |
| CN | 107012250 A | 8/2017 |
| CN | 107022562 A | 8/2017 |
| CN | 107034188 A | 8/2017 |
| CN | 107034218 A | 8/2017 |
| CN | 107034229 A | 8/2017 |
| CN | 107043775 A | 8/2017 |
| CN | 107043779 A | 8/2017 |
| CN | 107043787 A | 8/2017 |
| CN | 107058320 A | 8/2017 |
| CN | 107058328 A | 8/2017 |
| CN | 107058358 A | 8/2017 |
| CN | 107058372 A | 8/2017 |
| CN | 107083392 A | 8/2017 |
| CN | 107099533 A | 8/2017 |
| CN | 107099850 A | 8/2017 |
| CN | 107119053 A | 9/2017 |
| CN | 107119071 A | 9/2017 |
| CN | 107129999 A | 9/2017 |
| CN | 107130000 A | 9/2017 |
| CN | 107142272 A | 9/2017 |
| CN | 107142282 A | 9/2017 |
| CN | 107177591 A | 9/2017 |
| CN | 107177595 A | 9/2017 |
| CN | 107177631 A | 9/2017 |
| CN | 107190006 A | 9/2017 |
| CN | 107190008 A | 9/2017 |
| CN | 107217042 A | 9/2017 |
| CN | 107217075 A | 9/2017 |
| CN | 107227307 A | 10/2017 |
| CN | 107227352 A | 10/2017 |
| CN | 107236737 A | 10/2017 |
| CN | 107236739 A | 10/2017 |
| CN | 107236741 A | 10/2017 |
| CN | 107245502 A | 10/2017 |

(56) References Cited

FOREIGN PATENT DOCUMENTS

| | | |
|---|---|---|
| CN | 107254485 A | 10/2017 |
| CN | 107266541 A | 10/2017 |
| CN | 107267515 A | 10/2017 |
| CN | 107287245 A | 10/2017 |
| CN | 107298701 A | 10/2017 |
| CN | 107299114 A | 10/2017 |
| CN | 107304435 A | 10/2017 |
| CN | 107312785 A | 11/2017 |
| CN | 107312793 A | 11/2017 |
| CN | 107312795 A | 11/2017 |
| CN | 107312798 A | 11/2017 |
| CN | 107326042 A | 11/2017 |
| CN | 107326046 A | 11/2017 |
| CN | 107354156 A | 11/2017 |
| CN | 107354173 A | 11/2017 |
| CN | 107356793 A | 11/2017 |
| CN | 107362372 A | 11/2017 |
| CN | 107365786 A | 11/2017 |
| CN | 107365804 A | 11/2017 |
| CN | 107384894 A | 11/2017 |
| CN | 107384922 A | 11/2017 |
| CN | 107384926 A | 11/2017 |
| CN | 107400677 A | 11/2017 |
| CN | 107418974 A | 12/2017 |
| CN | 107435051 A | 12/2017 |
| CN | 107435069 A | 12/2017 |
| CN | 107446922 A | 12/2017 |
| CN | 107446923 A | 12/2017 |
| CN | 107446924 A | 12/2017 |
| CN | 107446932 A | 12/2017 |
| CN | 107446951 A | 12/2017 |
| CN | 107446954 A | 12/2017 |
| CN | 107460196 A | 12/2017 |
| CN | 107474129 A | 12/2017 |
| CN | 107475300 A | 12/2017 |
| CN | 107488649 A | 12/2017 |
| CN | 107502608 A | 12/2017 |
| CN | 107502618 A | 12/2017 |
| CN | 107513531 A | 12/2017 |
| CN | 107519492 A | 12/2017 |
| CN | 107523567 A | 12/2017 |
| CN | 107523583 A | 12/2017 |
| CN | 107541525 A | 1/2018 |
| CN | 107557373 A | 1/2018 |
| CN | 107557378 A | 1/2018 |
| CN | 107557381 A | 1/2018 |
| CN | 107557390 A | 1/2018 |
| CN | 107557393 A | 1/2018 |
| CN | 107557394 A | 1/2018 |
| CN | 107557455 A | 1/2018 |
| CN | 107574179 | 1/2018 |
| CN | 107586777 | 1/2018 |
| CN | 107586779 | 1/2018 |
| CN | 107604003 | 1/2018 |
| CN | 107619829 A | 1/2018 |
| CN | 107619837 A | 1/2018 |
| CN | 107630006 A | 1/2018 |
| CN | 107630041 A | 1/2018 |
| CN | 107630042 A | 1/2018 |
| CN | 107630043 A | 1/2018 |
| CN | 107641631 A | 1/2018 |
| CN | 107653256 A | 2/2018 |
| CN | 107686848 A | 2/2018 |
| CN | 206970581 | 2/2018 |
| CN | 107760652 A | 3/2018 |
| CN | 107760663 A | 3/2018 |
| CN | 107760684 A | 3/2018 |
| CN | 107760715 A | 3/2018 |
| CN | 107784200 A | 3/2018 |
| CN | 107794272 A | 3/2018 |
| CN | 107794276 A | 3/2018 |
| CN | 107815463 A | 3/2018 |
| CN | 107828738 A | 3/2018 |
| CN | 107828794 A | 3/2018 |
| CN | 107828826 A | 3/2018 |
| CN | 107828874 A | 3/2018 |
| CN | 107858346 A | 3/2018 |
| CN | 107858373 A | 3/2018 |
| CN | 107880132 A | 4/2018 |
| CN | 107881184 A | 4/2018 |
| CN | 107893074 A | 4/2018 |
| CN | 107893075 A | 4/2018 |
| CN | 107893076 A | 4/2018 |
| CN | 107893080 A | 4/2018 |
| CN | 107893086 A | 4/2018 |
| CN | 107904261 A | 4/2018 |
| CN | 107937427 A | 4/2018 |
| CN | 107937432 A | 4/2018 |
| CN | 107937501 A | 4/2018 |
| CN | 107974466 A | 5/2018 |
| CN | 107988229 A | 5/2018 |
| CN | 107988246 A | 5/2018 |
| CN | 107988256 A | 5/2018 |
| CN | 107988268 A | 5/2018 |
| CN | 108018316 A | 5/2018 |
| CN | 108034656 A | 5/2018 |
| CN | 108048466 A | 5/2018 |
| CN | 108102940 A | 6/2018 |
| CN | 108103092 A | 6/2018 |
| CN | 108103098 A | 6/2018 |
| CN | 108103586 A | 6/2018 |
| CN | 108148835 A | 6/2018 |
| CN | 108148837 A | 6/2018 |
| CN | 108148873 A | 6/2018 |
| CN | 108192956 A | 6/2018 |
| CN | 108251423 A | 7/2018 |
| CN | 108251451 A | 7/2018 |
| CN | 108251452 A | 7/2018 |
| CN | 108342480 A | 7/2018 |
| CN | 108359691 A | 8/2018 |
| CN | 108359712 A | 8/2018 |
| CN | 108384784 A | 8/2018 |
| CN | 108396027 A | 8/2018 |
| CN | 108410877 A | 8/2018 |
| CN | 108410906 A | 8/2018 |
| CN | 108410907 A | 8/2018 |
| CN | 108410911 A | 8/2018 |
| CN | 108424931 A | 8/2018 |
| CN | 108441520 A | 8/2018 |
| CN | 108486108 A | 9/2018 |
| CN | 108486111 A | 9/2018 |
| CN | 108486145 A | 9/2018 |
| CN | 108486146 A | 9/2018 |
| CN | 108486154 A | 9/2018 |
| CN | 108486159 A | 9/2018 |
| CN | 108486234 A | 9/2018 |
| CN | 108504657 A | 9/2018 |
| CN | 108504685 A | 9/2018 |
| CN | 108504693 A | 9/2018 |
| CN | 108546712 A | 9/2018 |
| CN | 108546717 A | 9/2018 |
| CN | 108546718 A | 9/2018 |
| CN | 108559730 A | 9/2018 |
| CN | 108559732 A | 9/2018 |
| CN | 108559745 A | 9/2018 |
| CN | 108559760 A | 9/2018 |
| CN | 108570479 A | 9/2018 |
| CN | 108588071 A | 9/2018 |
| CN | 108588123 A | 9/2018 |
| CN | 108588128 A | 9/2018 |
| CN | 108588182 A | 9/2018 |
| CN | 108610399 A | 10/2018 |
| CN | 108611364 A | 10/2018 |
| CN | 108624622 A | 10/2018 |
| CN | 108642053 A | 10/2018 |
| CN | 108642055 A | 10/2018 |
| CN | 108642077 A | 10/2018 |
| CN | 108642078 A | 10/2018 |
| CN | 108642090 A | 10/2018 |
| CN | 108690844 A | 10/2018 |
| CN | 108707604 A | 10/2018 |
| CN | 108707620 A | 10/2018 |
| CN | 108707621 A | 10/2018 |
| CN | 108707628 A | 10/2018 |

(56) References Cited

FOREIGN PATENT DOCUMENTS

| | | |
|---|---|---|
| CN | 108707629 A | 10/2018 |
| CN | 108715850 A | 10/2018 |
| CN | 108728476 A | 11/2018 |
| CN | 108728486 A | 11/2018 |
| CN | 108753772 A | 11/2018 |
| CN | 108753783 A | 11/2018 |
| CN | 108753813 A | 11/2018 |
| CN | 108753817 A | 11/2018 |
| CN | 108753832 A | 11/2018 |
| CN | 108753835 A | 11/2018 |
| CN | 108753836 A | 11/2018 |
| CN | 108795902 A | 11/2018 |
| CN | 108822217 A | 11/2018 |
| CN | 108823248 A | 11/2018 |
| CN | 108823249 A | 11/2018 |
| CN | 108823291 A | 11/2018 |
| CN | 108841845 A | 11/2018 |
| CN | 108853133 A | 11/2018 |
| CN | 108866093 A | 11/2018 |
| CN | 108893529 A | 11/2018 |
| CN | 108913664 A | 11/2018 |
| CN | 108913691 A | 11/2018 |
| CN | 108913714 A | 11/2018 |
| CN | 108913717 A | 11/2018 |
| EP | 2 604 255 A1 | 6/2013 |
| EP | 2840140 A1 | 2/2015 |
| EP | 2 966 170 A1 | 1/2016 |
| EP | 3 009 511 A1 | 4/2016 |
| EP | 3 009 511 A2 | 4/2016 |
| EP | 3009511 A2 | 4/2016 |
| EP | 3031921 A1 | 6/2016 |
| EP | 3045537 A1 | 7/2016 |
| EP | 3144390 A1 | 3/2017 |
| EP | 3199632 A1 | 8/2017 |
| EP | 3216867 A1 | 9/2017 |
| EP | 3252160 A1 | 12/2017 |
| GB | 2528177 A | 1/2016 |
| GB | 2 531 454 A | 4/2016 |
| GB | 2 531 454 A1 | 4/2016 |
| GB | 2531454 A | 4/2016 |
| GB | 2542653 A | 3/2017 |
| HK | 1208045 A1 | 2/2016 |
| JP | 2007-501626 A | 2/2007 |
| JP | 2008-515405 A | 5/2008 |
| JP | 2010-539929 A | 12/2010 |
| JP | 2010-539929 A | 12/2010 |
| JP | 2011-081011 A | 4/2011 |
| JP | 2011-523353 A | 8/2011 |
| JP | 2012-525146 A | 10/2012 |
| JP | 2012-531909 A | 12/2012 |
| KR | 101584933 B1 | 1/2016 |
| KR | 20160133380 A | 11/2016 |
| KR | 20170037025 A | 4/2017 |
| KR | 20170037028 A | 4/2017 |
| KR | 101748575 B1 | 6/2017 |
| KR | 2018-0022465 A | 3/2018 |
| RU | 2016104674 A | 8/2017 |
| RU | 2634395 C1 | 10/2017 |
| RU | 2652899 C1 | 5/2018 |
| RU | 2015128057 A | 3/2019 |
| RU | 2015128098 A | 3/2019 |
| RU | 2687451 C1 | 5/2019 |
| RU | 2019112514 A | 6/2019 |
| RU | 2019127300 A | 9/2019 |
| RU | 2701850 C2 | 10/2019 |
| TW | I608100 B | 12/2017 |
| TW | 2018-29773 A | 8/2018 |
| WO | WO 2001/036452 A2 | 5/2001 |
| WO | WO-2001/38547 A2 | 5/2001 |
| WO | WO 2002/059296 A2 | 8/2002 |
| WO | WO-2002/068676 A2 | 9/2002 |
| WO | WO-2002/103028 A2 | 12/2002 |
| WO | WO-2004/007684 A2 | 1/2004 |
| WO | WO-2005/014791 A2 | 2/2005 |
| WO | WO 2005/019415 A2 | 3/2005 |
| WO | WO 2006/002547 A1 | 1/2006 |
| WO | WO 2006/042112 A2 | 4/2006 |
| WO | WO 2007/025097 A2 | 3/2007 |
| WO | WO 2007/136815 A2 | 11/2007 |
| WO | WO 2007/143574 A1 | 12/2007 |
| WO | WO-2008/108989 A2 | 9/2008 |
| WO | WO 2008/108989 A2 | 9/2008 |
| WO | WO 2009/134808 A2 | 11/2009 |
| WO | WO-2010/011961 A2 | 1/2010 |
| WO | WO 2010/054108 A2 | 5/2010 |
| WO | WO 2010/054154 A2 | 5/2010 |
| WO | WO 2010/068289 A2 | 6/2010 |
| WO | WO 2010/075424 A2 | 7/2010 |
| WO | WO 2010/102257 A2 | 9/2010 |
| WO | WO 2010/129019 A2 | 11/2010 |
| WO | WO 2010/129023 A2 * | 11/2010 |
| WO | WO 2010/144150 A2 | 12/2010 |
| WO | WO-2011/002503 A1 | 1/2011 |
| WO | WO 2011/017293 A2 | 2/2011 |
| WO | WO 2011/053868 A1 | 5/2011 |
| WO | WO 2011/053982 A2 | 5/2011 |
| WO | WO 2011/075627 A1 | 6/2011 |
| WO | WO-2011/091311 A2 | 7/2011 |
| WO | WO 2011/109031 A1 | 9/2011 |
| WO | WO-2011/143124 A2 | 11/2011 |
| WO | WO 2012/054726 A1 | 4/2012 |
| WO | WO 2012/065043 A2 | 5/2012 |
| WO | WO-2012/125445 A2 | 9/2012 |
| WO | WO 2012/138927 A2 | 10/2012 |
| WO | WO 2012/149470 A1 | 11/2012 |
| WO | WO 2012/158985 A2 | 11/2012 |
| WO | WO 2012/158986 A2 | 11/2012 |
| WO | WO 2012/164565 A1 | 12/2012 |
| WO | WO 2013/012674 A1 | 1/2013 |
| WO | WO-2013/013105 A1 | 1/2013 |
| WO | WO 2013/013105 A2 | 1/2013 |
| WO | WO 2013/047844 A1 | 4/2013 |
| WO | WO 2013/066438 A2 | 5/2013 |
| WO | WO 2013/098244 A2 | 7/2013 |
| WO | WO-2013/119602 A1 | 8/2013 |
| WO | WO 2013/126794 A1 | 8/2013 |
| WO | WO 2013/130824 A1 | 9/2013 |
| WO | WO 2013/141680 A1 | 9/2013 |
| WO | WO 2013/142378 A9 | 9/2013 |
| WO | WO 2013/142578 A1 | 9/2013 |
| WO | WO-2013/142578 A1 | 9/2013 |
| WO | WO 2013/142578 A2 | 9/2013 |
| WO | WO 2013/152359 A1 | 10/2013 |
| WO | WO 2013/160230 A1 | 10/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176772 A1 | 11/2013 |
| WO | WO-2013/176772 A1 | 11/2013 |
| WO | WO 2013/176772 A2 | 11/2013 |
| WO | WO 2013/176915 A1 | 11/2013 |
| WO | WO 2013/176916 A1 | 11/2013 |
| WO | WO 2013/181440 A1 | 12/2013 |
| WO | WO 2013/186754 A2 | 12/2013 |
| WO | WO 2013/188037 A2 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2014/005042 A2 | 1/2014 |
| WO | WO 2014/011237 A1 | 1/2014 |
| WO | WO 2014/011901 A2 | 1/2014 |
| WO | WO 2014/018423 A2 | 1/2014 |
| WO | WO 2014/020608 A1 | 2/2014 |
| WO | WO 2014/022120 A1 | 2/2014 |
| WO | WO 2014/022702 A2 | 2/2014 |
| WO | WO 2014/036219 A2 | 3/2014 |
| WO | WO 2014/039513 A2 | 3/2014 |
| WO | WO 2014/039523 A1 | 3/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/039970 A1 | 3/2014 |
| WO | WO 2014/041327 A1 | 3/2014 |

(56) References Cited

FOREIGN PATENT DOCUMENTS

| | | |
|---|---|---|
| WO | WO 2014/043143 A1 | 3/2014 |
| WO | WO 2014/047103 A2 | 3/2014 |
| WO | WO 2014/059173 A2 | 4/2014 |
| WO | WO 2014/059255 A1 | 4/2014 |
| WO | WO 2014/065596 A1 | 5/2014 |
| WO | WO 2014/066505 A1 | 5/2014 |
| WO | WO 2014/068346 A2 | 5/2014 |
| WO | WO 2014/070887 A1 | 5/2014 |
| WO | WO 2014/071006 A1 | 5/2014 |
| WO | WO 2014/071219 A1 | 5/2014 |
| WO | WO 2014/071235 A1 | 5/2014 |
| WO | WO 2014/072941 A1 | 5/2014 |
| WO | WO 2014/081729 A1 | 5/2014 |
| WO | WO 2014/081730 A1 | 5/2014 |
| WO | WO 2014/081855 A1 | 5/2014 |
| WO | WO 2014/082644 A1 | 6/2014 |
| WO | WO 2014/085261 A1 | 6/2014 |
| WO | WO 2014/085593 A1 | 6/2014 |
| WO | WO 2014/085830 A2 | 6/2014 |
| WO | WO 2014/089212 A1 | 6/2014 |
| WO | WO 2014/089290 A1 | 6/2014 |
| WO | WO 2014/089348 A1 | 6/2014 |
| WO | WO 2014/089513 A1 | 6/2014 |
| WO | WO 2014/089533 A2 | 6/2014 |
| WO | WO 2014/089541 A2 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/093736 A1 | 6/2014 |
| WO | WO 2014/093768 A1 | 6/2014 |
| WO | WO 2014/093852 A1 | 6/2014 |
| WO | WO 2014/096972 A2 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO-2014/110006 A1 | 7/2014 |
| WO | WO 2014/110552 A1 | 7/2014 |
| WO | WO 2014/113493 A1 | 7/2014 |
| WO | WO 2014/123967 A2 | 8/2014 |
| WO | WO 2014/124226 A1 | 8/2014 |
| WO | WO 2014/125668 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO-2014/130706 A1 | 8/2014 |
| WO | WO 2014/130955 A1 | 8/2014 |
| WO | WO 2014/131833 A1 | 9/2014 |
| WO | WO 2014/138379 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/144951 A1 | 9/2014 |
| WO | WO 2014/145599 A2 | 9/2014 |
| WO | WO 2014/145736 A2 | 9/2014 |
| WO | WO 2014/150624 A1 | 9/2014 |
| WO | WO 2014/152432 A2 | 9/2014 |
| WO | WO 2014/153118 A1 | 9/2014 |
| WO | WO 2014/153470 A2 | 9/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A | 10/2014 |
| WO | WO-2014/172489 A2 | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO-2015/007194 A1 | 1/2015 |
| WO | WO 2015/010114 A1 | 1/2015 |
| WO | WO 2015/011483 A1 | 1/2015 |
| WO | WO-2015/011483 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A | 2/2015 |
| WO | WO 2015/021990 A1 | 2/2015 |
| WO | WO 2015/024017 A2 | 2/2015 |
| WO | WO-2015/024986 A1 | 2/2015 |
| WO | WO 2015/024986 A1 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/032494 A2 | 3/2015 |
| WO | WO-2015/032494 A2 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A1 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO-2015/042585 A1 | 3/2015 |
| WO | WO 2015/042585 A1 | 3/2015 |
| WO | WO 2015/048577 A2 | 4/2015 |
| WO | WO 2015/048690 A1 | 4/2015 |

(56) References Cited

FOREIGN PATENT DOCUMENTS

| | | |
|---|---|---|
| WO | WO-2015/048707 A2 | 4/2015 |
| WO | WO-2015/048801 A2 | 4/2015 |
| WO | WO 2015/048801 A2 | 4/2015 |
| WO | WO-2015/049897 A1 | 4/2015 |
| WO | WO 2015/049897 A1 | 4/2015 |
| WO | WO-2015/051191 A1 | 4/2015 |
| WO | WO 2015/052133 A1 | 4/2015 |
| WO | WO 2015/052231 A2 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO-2015/054315 A1 | 4/2015 |
| WO | WO-2015/057671 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO-2015/066634 A2 | 5/2015 |
| WO | WO 2015/066634 A2 | 5/2015 |
| WO | WO-2015/066636 A2 | 5/2015 |
| WO | WO 2015/066636 A2 | 5/2015 |
| WO | WO 2015/066637 A1 | 5/2015 |
| WO | WO-2015/066638 A2 | 5/2015 |
| WO | WO 2015/066638 A2 | 5/2015 |
| WO | WO-2015/066643 A1 | 5/2015 |
| WO | WO 2015/066643 A1 | 5/2015 |
| WO | WO-2015/069682 A2 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO-2015/075175 A1 | 5/2015 |
| WO | WO 2015/075195 A1 | 5/2015 |
| WO | WO 2015/075557 A2 | 5/2015 |
| WO | WO 2015/077058 A2 | 5/2015 |
| WO | WO 2015/077290 A2 | 5/2015 |
| WO | WO 2015/077318 | 5/2015 |
| WO | WO 2015/079056 A1 | 6/2015 |
| WO | WO 2015/079057 A2 | 6/2015 |
| WO | WO-2015/086795 A1 | 6/2015 |
| WO | WO 2015/086795 A2 | 6/2015 |
| WO | WO 2015/086798 A1 | 6/2015 |
| WO | WO-2015/086798 A2 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A1 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO-2015/103057 A1 | 7/2015 |
| WO | WO 2015/103057 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO-2015/109752 A1 | 7/2015 |
| WO | WO-2015/110474 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO-2015/114365 A1 | 8/2015 |
| WO | WO 2015/115903 A1 | 8/2015 |
| WO | WO 2015/116686 A1 | 8/2015 |
| WO | WO 2015/116969 A2 | 8/2015 |
| WO | WO-2015/117021 A1 | 8/2015 |
| WO | WO 2015/117041 A1 | 8/2015 |
| WO | WO-2015/117081 A2 | 8/2015 |
| WO | WO-2015/118156 A1 | 8/2015 |
| WO | WO-2015/119941 A2 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO-2015/124715 A1 | 8/2015 |
| WO | WO 2015/124715 A1 | 8/2015 |
| WO | WO-2015/124718 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO-2015/129686 A1 | 9/2015 |
| WO | WO 2015/131101 A1 | 9/2015 |
| WO | WO-2015/133554 A1 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | WO-2015/143177 A1 | 9/2015 |
| WO | WO-2015/145417 A1 | 10/2015 |
| WO | WO-2015/148431 A1 | 10/2015 |
| WO | WO 2015/148670 A1 | 10/2015 |
| WO | WO 2015/148680 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153889 A2 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO-2015/164740 A1 | 10/2015 |
| WO | WO 2015/164748 A1 | 10/2015 |
| WO | WO-2015/165274 A1 | 11/2015 |
| WO | WO-2015/165275 A1 | 11/2015 |
| WO | WO-2015/165276 A1 | 11/2015 |
| WO | WO 2015/166272 A2 | 11/2015 |
| WO | WO-2015/167766 A1 | 11/2015 |
| WO | WO-2015/167956 A1 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |
| WO | WO 2015/168800 A1 | 11/2015 |
| WO | WO 2015/171603 A1 | 11/2015 |
| WO | WO 2015/171894 A1 | 11/2015 |
| WO | WO-2015/171932 A1 | 11/2015 |
| WO | WO-2015/172128 A1 | 11/2015 |
| WO | WO-2015/173436 A1 | 11/2015 |
| WO | WO 2015/175642 A2 | 11/2015 |
| WO | WO 2015/179540 A1 | 11/2015 |
| WO | WO-2015/183025 A1 | 12/2015 |
| WO | WO-2015/183026 A1 | 12/2015 |

(56) References Cited

FOREIGN PATENT DOCUMENTS

| | | |
|---|---|---|
| WO | WO 2015/183885 A1 | 12/2015 |
| WO | WO 2015/184259 A1 | 12/2015 |
| WO | WO-2015/184262 A1 | 12/2015 |
| WO | WO-2015/184268 A1 | 12/2015 |
| WO | WO 2015/188056 A1 | 12/2015 |
| WO | WO-2015/188065 A1 | 12/2015 |
| WO | WO 2015/188094 A1 | 12/2015 |
| WO | WO 2015/188109 A1 | 12/2015 |
| WO | WO 2015/188132 A1 | 12/2015 |
| WO | WO 2015/188135 A1 | 12/2015 |
| WO | WO 2015/188191 A | 12/2015 |
| WO | WO 2015/189693 A1 | 12/2015 |
| WO | WO 2015/191693 A2 | 12/2015 |
| WO | WO 2015/191899 A1 | 12/2015 |
| WO | WO 2015/191911 | 12/2015 |
| WO | WO 2015/193858 A1 | 12/2015 |
| WO | WO 2015/195547 A1 | 12/2015 |
| WO | WO 2015/195621 A1 | 12/2015 |
| WO | WO 2015/195798 A1 | 12/2015 |
| WO | WO 2015/198020 A1 | 12/2015 |
| WO | WO 2015/200334 A1 | 12/2015 |
| WO | WO 2015/200378 A1 | 12/2015 |
| WO | WO 2015/200555 A2 | 12/2015 |
| WO | WO 2015/200805 A2 | 12/2015 |
| WO | WO-2016/001978 A1 | 1/2016 |
| WO | WO 2016/004010 A1 | 1/2016 |
| WO | WO 2016/007347 A1 | 1/2016 |
| WO | WO 2016/007604 A1 | 1/2016 |
| WO | WO 2016/007948 A1 | 1/2016 |
| WO | WO 2016/011080 A2 | 1/2016 |
| WO | WO-2016/011210 A2 | 1/2016 |
| WO | WO-2016/011428 A1 | 1/2016 |
| WO | WO 2016/011428 A1 | 1/2016 |
| WO | WO 2016/012544 A2 | 1/2016 |
| WO | WO-2016/012552 A1 | 1/2016 |
| WO | WO 2016/014409 A1 | 1/2016 |
| WO | WO-2016/014565 A2 | 1/2016 |
| WO | WO 2016/014794 A1 | 1/2016 |
| WO | WO 2016/014837 A1 | 1/2016 |
| WO | WO 2016/016119 A1 | 2/2016 |
| WO | WO 2016/016358 A1 | 2/2016 |
| WO | WO 2016/019144 A2 | 2/2016 |
| WO | WO 2016/020399 A1 | 2/2016 |
| WO | WO 2016/021972 A1 | 2/2016 |
| WO | WO 2016/021973 A1 | 2/2016 |
| WO | WO 2016/022363 A2 | 2/2016 |
| WO | WO 2016/022866 A1 | 2/2016 |
| WO | WO 2016/022931 A1 | 2/2016 |
| WO | WO 2016/025131 A1 | 2/2016 |
| WO | WO 2016/025469 A1 | 2/2016 |
| WO | WO 2016/025759 A1 | 2/2016 |
| WO | WO 2016/026444 A1 | 2/2016 |
| WO | WO 2016/028682 A1 | 2/2016 |
| WO | WO 2016/028843 A1 | 2/2016 |
| WO | WO-2016/028843 A2 | 2/2016 |
| WO | WO 2016/028887 A1 | 2/2016 |
| WO | WO 2016/033088 A1 | 3/2016 |
| WO | WO-2016/033230 A1 | 3/2016 |
| WO | WO 2016/033246 A1 | 3/2016 |
| WO | WO 2016/033298 A1 | 3/2016 |
| WO | WO 2016/035044 A1 | 3/2016 |
| WO | WO 2016/036754 A1 | 3/2016 |
| WO | WO 2016/037157 A2 | 3/2016 |
| WO | WO 2016/040030 A1 | 3/2016 |
| WO | WO 2016/040594 A1 | 3/2016 |
| WO | WO-2016/044182 A1 | 3/2016 |
| WO | WO 2016/044416 A1 | 3/2016 |
| WO | WO-2016/046635 A1 | 3/2016 |
| WO | WO 2016/049024 A2 | 3/2016 |
| WO | WO 2016/049163 A2 | 3/2016 |
| WO | WO 2016/049230 A1 | 3/2016 |
| WO | WO 2016/049251 A1 | 3/2016 |
| WO | WO 2016/049258 A2 | 3/2016 |
| WO | WO-2016/053397 A2 | 4/2016 |
| WO | WO 2016/054326 A1 | 4/2016 |
| WO | WO 2016/057061 A2 | 4/2016 |
| WO | WO 2016/057821 A2 | 4/2016 |
| WO | WO 2016/057835 A2 | 4/2016 |
| WO | WO-2016/057850 A1 | 4/2016 |
| WO | WO 2016/057850 A2 | 4/2016 |
| WO | WO 2016/057951 A2 | 4/2016 |
| WO | WO-2016/057961 A1 | 4/2016 |
| WO | WO 2016/057961 A2 | 4/2016 |
| WO | WO 2016/061073 A1 | 4/2016 |
| WO | WO 2016/061374 A1 | 4/2016 |
| WO | WO-2016/061481 A1 | 4/2016 |
| WO | WO 2016/061523 A1 | 4/2016 |
| WO | WO 2016/064894 A2 | 4/2016 |
| WO | WO-2016/069282 A1 | 5/2016 |
| WO | WO-2016/069283 A1 | 5/2016 |
| WO | WO 2016/069591 A2 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO-2016/072399 A1 | 5/2016 |
| WO | WO-2016/072936 A1 | 5/2016 |
| WO | WO 2016/072936 A1 | 5/2016 |
| WO | WO 2016/073433 A1 | 5/2016 |
| WO | WO 2016/073559 A1 | 5/2016 |
| WO | WO 2016/073990 A2 | 5/2016 |
| WO | WO 2016/075662 A2 | 5/2016 |
| WO | WO 2016/076672 A1 | 5/2016 |
| WO | WO 2016/077273 A1 | 5/2016 |
| WO | WO 2016/077350 A1 | 5/2016 |
| WO | WO 2016/080097 A1 | 5/2016 |
| WO | WO-2016/080795 A1 | 5/2016 |
| WO | WO 2016/081923 A2 | 5/2016 |
| WO | WO 2016/081924 A1 | 5/2016 |
| WO | WO-2016/082135 A1 | 6/2016 |
| WO | WO 2016/082135 A1 | 6/2016 |
| WO | WO 2016/083811 A1 | 6/2016 |
| WO | WO-2016/083811 A1 | 6/2016 |
| WO | WO-2016/084084 A1 | 6/2016 |
| WO | WO 2016/084084 A1 | 6/2016 |
| WO | WO 2016/084088 A1 | 6/2016 |
| WO | WO-2016/084088 A1 | 6/2016 |
| WO | WO 2016/086177 A2 | 6/2016 |
| WO | WO-2016/086177 A2 | 6/2016 |
| WO | WO-2016/089433 A1 | 6/2016 |
| WO | WO 2016/089433 A1 | 6/2016 |
| WO | WO 2016/089866 A1 | 6/2016 |
| WO | WO-2016/089866 A1 | 6/2016 |
| WO | WO 2016/089883 A1 | 6/2016 |
| WO | WO-2016/089883 A1 | 6/2016 |
| WO | WO 2016/090385 A1 | 6/2016 |
| WO | WO-2016/090385 A1 | 6/2016 |
| WO | WO 2016/094679 A1 | 6/2016 |
| WO | WO-2016/094845 A2 | 6/2016 |
| WO | WO 2016/094845 A2 | 6/2016 |
| WO | WO-2016/094867 A1 | 6/2016 |
| WO | WO 2016/094867 A1 | 6/2016 |
| WO | WO-2016/094872 A1 | 6/2016 |
| WO | WO 2016/094872 A1 | 6/2016 |
| WO | WO-2016/094874 A1 | 6/2016 |
| WO | WO 2016/094874 A1 | 6/2016 |
| WO | WO 2016/094880 A1 | 6/2016 |
| WO | WO-2016/094880 A1 | 6/2016 |
| WO | WO 2016/094888 A1 | 6/2016 |
| WO | WO-2016/094888 A1 | 6/2016 |
| WO | WO-2016/097212 A1 | 6/2016 |
| WO | WO 2016/097212 A1 | 6/2016 |
| WO | WO-2016/097231 A2 | 6/2016 |
| WO | WO 2016/097231 A2 | 6/2016 |
| WO | WO 2016/097751 A1 | 6/2016 |
| WO | WO-2016/097751 A1 | 6/2016 |
| WO | WO 2016/099887 A1 | 6/2016 |
| WO | WO-2016/099887 A1 | 6/2016 |
| WO | WO 2016/100272 A1 | 6/2016 |
| WO | WO-2016/100272 A1 | 6/2016 |
| WO | WO 2016/100389 A1 | 6/2016 |
| WO | WO-2016/100389 A1 | 6/2016 |
| WO | WO 2016/100568 A1 | 6/2016 |

(56) References Cited

FOREIGN PATENT DOCUMENTS

| | | |
|---|---|---|
| WO | WO-2016/100568 A1 | 6/2016 |
| WO | WO-2016/100571 A1 | 6/2016 |
| WO | WO 2016/100571 A1 | 6/2016 |
| WO | WO 2016/100951 A2 | 6/2016 |
| WO | WO-2016/100951 A2 | 6/2016 |
| WO | WO 2016/100955 A2 | 6/2016 |
| WO | WO-2016/100955 A2 | 6/2016 |
| WO | WO 2016/100974 A1 | 6/2016 |
| WO | WO-2016/100974 A1 | 6/2016 |
| WO | WO-2016/103233 A2 | 6/2016 |
| WO | WO 2016/103233 A2 | 6/2016 |
| WO | WO 2016/104716 A1 | 6/2016 |
| WO | WO-2016/104716 A1 | 6/2016 |
| WO | WO-2016/106236 A1 | 6/2016 |
| WO | WO 2016/106236 A1 | 6/2016 |
| WO | WO 2016/106239 A1 | 6/2016 |
| WO | WO 2016/106244 A1 | 6/2016 |
| WO | WO-2016/106244 A1 | 6/2016 |
| WO | WO-2016/106338 A2 | 6/2016 |
| WO | WO-2016/108926 A1 | 7/2016 |
| WO | WO-2016/109255 A1 | 7/2016 |
| WO | WO 2016/109255 A1 | 7/2016 |
| WO | WO 2016/109840 A2 | 7/2016 |
| WO | WO-2016/109840 A2 | 7/2016 |
| WO | WO 2016/110214 A1 | 7/2016 |
| WO | WO-2016/110214 A1 | 7/2016 |
| WO | WO 2016/110453 A1 | 7/2016 |
| WO | WO-2016/110453 A1 | 7/2016 |
| WO | WO-2016/110511 A1 | 7/2016 |
| WO | WO 2016/110512 A1 | 7/2016 |
| WO | WO-2016/110512 A1 | 7/2016 |
| WO | WO 2016/111546 A2 | 7/2016 |
| WO | WO 2016/112242 A1 | 7/2016 |
| WO | WO-2016/112351 A1 | 7/2016 |
| WO | WO-2016/112963 A1 | 7/2016 |
| WO | WO-2016/114972 A1 | 7/2016 |
| WO | WO 2016/114972 A1 | 7/2016 |
| WO | WO-2016/115179 A1 | 7/2016 |
| WO | WO 2016/115326 A1 | 7/2016 |
| WO | WO-2016/115326 A1 | 7/2016 |
| WO | WO-2016/115355 A1 | 7/2016 |
| WO | WO-2016/116032 A1 | 7/2016 |
| WO | WO 2016/116032 A1 | 7/2016 |
| WO | WO-2016/120480 A1 | 8/2016 |
| WO | WO-2016/123071 A1 | 8/2016 |
| WO | WO-2016/123230 A1 | 8/2016 |
| WO | WO-2016/123243 A1 | 8/2016 |
| WO | WO-2016/123578 A1 | 8/2016 |
| WO | WO 2016/126747 A1 | 8/2016 |
| WO | WO-2016/130600 A2 | 8/2016 |
| WO | WO-2016/130697 A1 | 8/2016 |
| WO | WO 2016/131009 A1 | 8/2016 |
| WO | WO-2016/132122 A1 | 8/2016 |
| WO | WO 2016/133165 A1 | 8/2016 |
| WO | WO-2016/135507 A1 | 9/2016 |
| WO | WO-2016/135557 A2 | 9/2016 |
| WO | WO-2016/135558 A2 | 9/2016 |
| WO | WO-2016/135559 A2 | 9/2016 |
| WO | WO-2016/137774 A1 | 9/2016 |
| WO | WO-2016/137949 A1 | 9/2016 |
| WO | WO-2016/141224 A1 | 9/2016 |
| WO | WO-2016/141893 A1 | 9/2016 |
| WO | WO-2016/142719 A1 | 9/2016 |
| WO | WO-2016/145150 A2 | 9/2016 |
| WO | WO-2016/148994 A1 | 9/2016 |
| WO | WO-2016/149484 A2 | 9/2016 |
| WO | WO-2016/149547 A1 | 9/2016 |
| WO | WO-2016/150336 A1 | 9/2016 |
| WO | WO-2016/150855 A1 | 9/2016 |
| WO | WO-2016/154016 A2 | 9/2016 |
| WO | WO-2016/154579 A2 | 9/2016 |
| WO | WO-2016/154596 A1 | 9/2016 |
| WO | WO-2016/155482 A1 | 10/2016 |
| WO | WO-2016/161004 A1 | 10/2016 |
| WO | WO-2016/161207 A1 | 10/2016 |
| WO | WO-2016/161260 A1 | 10/2016 |
| WO | WO-2016/161380 A1 | 10/2016 |
| WO | WO-2016/161446 A1 | 10/2016 |
| WO | WO-2016/164356 A1 | 10/2016 |
| WO | WO-2016/164797 A1 | 10/2016 |
| WO | WO-2016/166340 A1 | 10/2016 |
| WO | WO-2016/167300 A1 | 10/2016 |
| WO | WO-2016/170484 A1 | 10/2016 |
| WO | WO-2016/172359 A2 | 10/2016 |
| WO | WO-2016/172727 A1 | 10/2016 |
| WO | WO-2016/174056 A1 | 11/2016 |
| WO | WO-2016/174151 A1 | 11/2016 |
| WO | WO-2016/174250 A1 | 11/2016 |
| WO | WO-2016/176191 A1 | 11/2016 |
| WO | WO-2016/176404 A1 | 11/2016 |
| WO | WO-2016/176690 A2 | 11/2016 |
| WO | WO-2016/177682 A1 | 11/2016 |
| WO | WO-2016/178207 A1 | 11/2016 |
| WO | WO-2016/179038 A1 | 11/2016 |
| WO | WO-2016/179112 A1 | 11/2016 |
| WO | WO-2016/181357 A1 | 11/2016 |
| WO | WO-2016/182893 A1 | 11/2016 |
| WO | WO-2016/182917 A1 | 11/2016 |
| WO | WO-2016/182959 A1 | 11/2016 |
| WO | WO-2016/183236 A1 | 11/2016 |
| WO | WO-2016/183298 A2 | 11/2016 |
| WO | WO-2016/183345 A1 | 11/2016 |
| WO | WO-2016/183402 A2 | 11/2016 |
| WO | WO-2016/183438 A1 | 11/2016 |
| WO | WO-2016/183448 A1 | 11/2016 |
| WO | WO-2016/184955 A2 | 11/2016 |
| WO | WO-2016/184989 A1 | 11/2016 |
| WO | WO-2016/185411 A1 | 11/2016 |
| WO | WO-2016/186745 A1 | 11/2016 |
| WO | WO-2016/186772 A2 | 11/2016 |
| WO | WO-2016/186946 A1 | 11/2016 |
| WO | WO-2016/186953 A1 | 11/2016 |
| WO | WO-2016/187717 A1 | 12/2016 |
| WO | WO-2016/187904 A1 | 12/2016 |
| WO | WO-2016/191684 A1 | 12/2016 |
| WO | WO-2016/191869 A1 | 12/2016 |
| WO | WO-2016/196273 A1 | 12/2016 |
| WO | WO-2016/196282 A1 | 12/2016 |
| WO | WO-2016/196308 A1 | 12/2016 |
| WO | WO-2016/196361 A1 | 12/2016 |
| WO | WO-2016/196499 A1 | 12/2016 |
| WO | WO-2016/196539 A2 | 12/2016 |
| WO | WO-2016/196655 A1 | 12/2016 |
| WO | WO-2016/196805 A1 | 12/2016 |
| WO | WO-2016/196887 A1 | 12/2016 |
| WO | WO-2016/197132 A1 | 12/2016 |
| WO | WO-2016/197133 A1 | 12/2016 |
| WO | WO-2016/197354 A1 | 12/2016 |
| WO | WO-2016/197355 A1 | 12/2016 |
| WO | WO-2016/197356 A1 | 12/2016 |
| WO | WO-2016/197357 A1 | 12/2016 |
| WO | WO-2016/197358 A1 | 12/2016 |
| WO | WO-2016/197359 A1 | 12/2016 |
| WO | WO-2016/197360 A1 | 12/2016 |
| WO | WO-2016/197361 A1 | 12/2016 |
| WO | WO-2016/197362 A1 | 12/2016 |
| WO | WO-2016/198361 A1 | 12/2016 |
| WO | WO-2016/198500 A1 | 12/2016 |
| WO | WO-2016/200263 A1 | 12/2016 |
| WO | WO-2016/201047 A1 | 12/2016 |
| WO | WO-2016/201138 A1 | 12/2016 |
| WO | WO-2016/201152 A1 | 12/2016 |
| WO | WO-2016/201153 A1 | 12/2016 |
| WO | WO-2016/201155 A1 | 12/2016 |
| WO | WO-2016/205276 A1 | 12/2016 |
| WO | WO-2016/205613 A1 | 12/2016 |
| WO | WO-2016/205623 A1 | 12/2016 |
| WO | WO-2016/205680 A1 | 12/2016 |
| WO | WO-2016/205688 A2 | 12/2016 |
| WO | WO-2016/205703 A1 | 12/2016 |
| WO | WO-2016/205711 A1 | 12/2016 |
| WO | WO-2016/205728 A1 | 12/2016 |
| WO | WO-2016/205745 A2 | 12/2016 |
| WO | WO-2016/205749 A1 | 12/2016 |

(56) References Cited

FOREIGN PATENT DOCUMENTS

| | | |
|---|---|---|
| WO | WO-2016/205759 A1 | 12/2016 |
| WO | WO-2016/205764 A1 | 12/2016 |
| WO | WO-2017/001572 A1 | 1/2017 |
| WO | WO-2017/001988 A1 | 1/2017 |
| WO | WO-2017/004261 A1 | 1/2017 |
| WO | WO-2017/004279 A2 | 1/2017 |
| WO | WO-2017/004616 A1 | 1/2017 |
| WO | WO-2017/005807 A1 | 1/2017 |
| WO | WO-2017/009399 A1 | 1/2017 |
| WO | WO 2017/010556 A1 | 1/2017 |
| WO | WO-2017/011519 A1 | 1/2017 |
| WO | WO-2017/011721 A1 | 1/2017 |
| WO | WO-2017/011804 A1 | 1/2017 |
| WO | WO-2017/015015 A1 | 1/2017 |
| WO | WO-2017/015101 A1 | 1/2017 |
| WO | WO-2017/015567 A1 | 1/2017 |
| WO | WO-2017/015637 A1 | 1/2017 |
| WO | WO-2017/017016 A1 | 2/2017 |
| WO | WO-2017/019867 A1 | 2/2017 |
| WO | WO-2017/019895 A1 | 2/2017 |
| WO | WO-2017/023803 A1 | 2/2017 |
| WO | WO-2017/023974 A1 | 2/2017 |
| WO | WO-2017/024047 A1 | 2/2017 |
| WO | WO-2017/024319 A1 | 2/2017 |
| WO | WO-2017/024343 A1 | 2/2017 |
| WO | WO-2017/024602 A1 | 2/2017 |
| WO | WO-2017/025323 A1 | 2/2017 |
| WO | WO-2017/027423 A1 | 2/2017 |
| WO | WO-2017/028768 A1 | 2/2017 |
| WO | WO-2017/029664 A1 | 2/2017 |
| WO | WO-2017/031360 A1 | 2/2017 |
| WO | WO-2017/031483 A1 | 2/2017 |
| WO | WO-2017/035416 A2 | 3/2017 |
| WO | WO-2017/040348 A1 | 3/2017 |
| WO | WO-2017/040511 A1 | 3/2017 |
| WO | WO-2017/040709 A1 | 3/2017 |
| WO | WO-2017/040786 A1 | 3/2017 |
| WO | WO-2017/040793 A1 | 3/2017 |
| WO | WO-2017/040813 A2 | 3/2017 |
| WO | WO-2017/043573 A1 | 3/2017 |
| WO | WO-2017/043656 A1 | 3/2017 |
| WO | WO-2017/044419 A1 | 3/2017 |
| WO | WO-2017/044776 A1 | 3/2017 |
| WO | WO-2017/044857 A2 | 3/2017 |
| WO | WO-2017/049129 A2 | 3/2017 |
| WO | WO-2017/050963 A1 | 3/2017 |
| WO | WO-2017/053312 A1 | 3/2017 |
| WO | WO-2017/053431 A2 | 3/2017 |
| WO | WO-2017/053713 A1 | 3/2017 |
| WO | WO-2017/053729 A1 | 3/2017 |
| WO | WO-2017/053753 A1 | 3/2017 |
| WO | WO-2017/053762 A1 | 3/2017 |
| WO | WO-2017/053879 A1 | 3/2017 |
| WO | WO 2017/054721 A1 | 4/2017 |
| WO | WO-2017/058658 A2 | 4/2017 |
| WO | WO 2017/059241 A1 | 4/2017 |
| WO | WO-2017/062605 A1 | 4/2017 |
| WO | WO-2017/062723 A1 | 4/2017 |
| WO | WO-2017/062754 A1 | 4/2017 |
| WO | WO-2017/062855 A1 | 4/2017 |
| WO | WO-2017/062886 A1 | 4/2017 |
| WO | WO-2017/062983 A1 | 4/2017 |
| WO | WO-2017/064439 A1 | 4/2017 |
| WO | WO-2017/064546 A1 | 4/2017 |
| WO | WO-2017/064566 A2 | 4/2017 |
| WO | WO-2017/066175 A1 | 4/2017 |
| WO | WO-2017/066497 A2 | 4/2017 |
| WO | WO-2017/066588 A2 | 4/2017 |
| WO | WO 2017/066707 A1 | 4/2017 |
| WO | WO 2017/068077 A1 | 4/2017 |
| WO | WO-2017/068377 A1 | 4/2017 |
| WO | WO-2017/069829 A2 | 4/2017 |
| WO | WO-2017/070029 A1 | 4/2017 |
| WO | WO-2017/070032 A1 | 4/2017 |
| WO | WO-2017/070169 A1 | 4/2017 |
| WO | WO-2017/070284 A1 | 4/2017 |
| WO | WO-2017/070598 A1 | 4/2017 |
| WO | WO-2017/070605 A1 | 4/2017 |
| WO | WO-2017/070632 A2 | 4/2017 |
| WO | WO-2017/070633 A2 | 4/2017 |
| WO | WO-2017/072590 A1 | 5/2017 |
| WO | WO-2017/074526 A1 | 5/2017 |
| WO | WO-2017/074962 A1 | 5/2017 |
| WO | WO-2017/075261 A1 | 5/2017 |
| WO | WO 2017/075335 A1 | 5/2017 |
| WO | WO-2017/075475 A1 | 5/2017 |
| WO | WO-2017/077135 A1 | 5/2017 |
| WO | WO-2017/077329 A2 | 5/2017 |
| WO | WO-2017/078751 A1 | 5/2017 |
| WO | WO-2017/079400 A1 | 5/2017 |
| WO | WO-2017/079428 A1 | 5/2017 |
| WO | WO-2017/079673 A1 | 5/2017 |
| WO | WO-2017/079724 A1 | 5/2017 |
| WO | WO-2017/081097 A1 | 5/2017 |
| WO | WO-2017/081288 A1 | 5/2017 |
| WO | WO-2017/083368 A1 | 5/2017 |
| WO | WO-2017/083722 A1 | 5/2017 |
| WO | WO-2017/083766 A1 | 5/2017 |
| WO | WO-2017/087395 A1 | 5/2017 |
| WO | WO-2017/090724 A1 | 6/2017 |
| WO | WO-2017/091510 A1 | 6/2017 |
| WO | WO-2017/091630 A1 | 6/2017 |
| WO | WO-2017/092201 A1 | 6/2017 |
| WO | WO-2017/093370 A1 | 6/2017 |
| WO | WO-2017/095111 A1 | 6/2017 |
| WO | WO-2017/096041 A1 | 6/2017 |
| WO | WO-2017/096237 A1 | 6/2017 |
| WO | WO-2017/100158 A1 | 6/2017 |
| WO | WO-2017/100431 A2 | 6/2017 |
| WO | WO-2017/104404 A1 | 6/2017 |
| WO | WO-2017/105251 A1 | 6/2017 |
| WO | WO-2017/105350 A1 | 6/2017 |
| WO | WO-2017/105991 A1 | 6/2017 |
| WO | WO-2017/106414 A1 | 6/2017 |
| WO | WO-2017/106528 A2 | 6/2017 |
| WO | WO-2017/106537 A2 | 6/2017 |
| WO | WO-2017/106569 A1 | 6/2017 |
| WO | WO-2017/106616 A1 | 6/2017 |
| WO | WO-2017/106657 A1 | 6/2017 |
| WO | WO-2017/106767 A1 | 6/2017 |
| WO | WO 2017/109134 A1 | 6/2017 |
| WO | WO 2017/109757 A1 | 6/2017 |
| WO | WO-2017/112620 A1 | 6/2017 |
| WO | WO-2017/115268 A1 | 7/2017 |
| WO | WO-2017/117395 A1 | 7/2017 |
| WO | WO 2017/118598 A1 | 7/2017 |
| WO | WO-2017/118720 A1 | 7/2017 |
| WO | WO-2017/123609 A1 | 7/2017 |
| WO | WO-2017/123910 A1 | 7/2017 |
| WO | WO-2017/124086 A1 | 7/2017 |
| WO | WO-2017/124100 A1 | 7/2017 |
| WO | WO-2017/124652 A1 | 7/2017 |
| WO | WO-2017/126987 A1 | 7/2017 |
| WO | WO-2017/127807 A1 | 7/2017 |
| WO | WO-2017/131237 A1 | 8/2017 |
| WO | WO-2017/132112 A1 | 8/2017 |
| WO | WO 2017/132580 A2 | 8/2017 |
| WO | WO-2017/136520 A1 | 8/2017 |
| WO | WO-2017/136629 A1 | 8/2017 |
| WO | WO-2017/136794 A1 | 8/2017 |
| WO | WO-2017/139264 A1 | 8/2017 |
| WO | WO-2017/139505 A2 | 8/2017 |
| WO | WO 2017/141173 A2 | 8/2017 |
| WO | WO-2017/142835 A1 | 8/2017 |
| WO | WO-2017/142999 A2 | 8/2017 |
| WO | WO-2017/143042 A2 | 8/2017 |
| WO | WO-2017/147278 A1 | 8/2017 |
| WO | WO-2017/147432 A1 | 8/2017 |
| WO | WO-2017/147446 A1 | 8/2017 |
| WO | WO-2017/147555 A1 | 8/2017 |
| WO | WO-2017/151444 A1 | 9/2017 |
| WO | WO-2017/152015 A1 | 9/2017 |
| WO | WO 2017/155717 A1 | 9/2017 |
| WO | WO-2017/157422 A1 | 9/2017 |

(56) References Cited

FOREIGN PATENT DOCUMENTS

| | | |
|---|---|---|
| WO | WO-2017/158153 A1 | 9/2017 |
| WO | WO-2017/160689 A1 | 9/2017 |
| WO | WO-2017/160752 A1 | 9/2017 |
| WO | WO-2017/160890 A1 | 9/2017 |
| WO | WO-2017/161068 A1 | 9/2017 |
| WO | WO-2017/165826 A1 | 9/2017 |
| WO | WO-2017/165862 A1 | 9/2017 |
| WO | WO-2017/172644 A2 | 10/2017 |
| WO | WO-2017/172645 A2 | 10/2017 |
| WO | WO-2017/172860 A1 | 10/2017 |
| WO | WO-2017/173004 A1 | 10/2017 |
| WO | WO 2017/173054 A1 | 10/2017 |
| WO | WO-2017/173092 A1 | 10/2017 |
| WO | WO-2017/174329 A1 | 10/2017 |
| WO | WO-2017/176529 A1 | 10/2017 |
| WO | WO 2017/176806 A1 | 10/2017 |
| WO | WO-2017/178590 A1 | 10/2017 |
| WO | WO-2017/180694 A1 | 10/2017 |
| WO | WO-2017/180711 A1 | 10/2017 |
| WO | WO-2017/180915 A2 | 10/2017 |
| WO | WO-2017/180926 A1 | 10/2017 |
| WO | WO-2017/181107 A2 | 10/2017 |
| WO | WO-2017/181735 A2 | 10/2017 |
| WO | WO-2017/182468 A1 | 10/2017 |
| WO | WO-2017/184334 A1 | 10/2017 |
| WO | WO-2017/184768 A1 | 10/2017 |
| WO | WO-2017/184786 A1 | 10/2017 |
| WO | WO-2017/186550 A1 | 11/2017 |
| WO | WO-2017/189308 A1 | 11/2017 |
| WO | WO-2017/189336 A1 | 11/2017 |
| WO | WO-2017/190257 A1 | 11/2017 |
| WO | WO-2017/190664 A1 | 11/2017 |
| WO | WO-2017/191210 A1 | 11/2017 |
| WO | WO-2017/192172 A1 | 11/2017 |
| WO | WO-2017/192512 A2 | 11/2017 |
| WO | WO-2017/192544 A1 | 11/2017 |
| WO | WO-2017/192573 A1 | 11/2017 |
| WO | WO-2017/193029 A2 | 11/2017 |
| WO | WO-2017/193053 A1 | 11/2017 |
| WO | WO-2017/196768 A1 | 11/2017 |
| WO | WO-2017/197038 A1 | 11/2017 |
| WO | WO-2017/197238 A1 | 11/2017 |
| WO | WO-2017/197301 A1 | 11/2017 |
| WO | WO 2017/201476 A1 | 11/2017 |
| WO | WO 2017/205290 A1 | 11/2017 |
| WO | WO 2017/205423 A1 | 11/2017 |
| WO | WO 2017/207589 A1 | 12/2017 |
| WO | WO 2017/208247 A1 | 12/2017 |
| WO | WO 2017/209809 A1 | 12/2017 |
| WO | WO 2017/213896 A1 | 12/2017 |
| WO | WO 2017/213898 A2 | 12/2017 |
| WO | WO 2017/214460 A1 | 12/2017 |
| WO | WO 2017/216392 A1 | 12/2017 |
| WO | WO 2017/216771 A2 | 12/2017 |
| WO | WO 2017/218185 A1 | 12/2017 |
| WO | WO 2017/219027 A1 | 12/2017 |
| WO | WO 2017/219033 A1 | 12/2017 |
| WO | WO 2017/220751 A1 | 12/2017 |
| WO | WO 2017/222370 A1 | 12/2017 |
| WO | WO 2017/222773 A1 | 12/2017 |
| WO | WO 2017/222834 A1 | 12/2017 |
| WO | WO 2017/223107 A1 | 12/2017 |
| WO | WO 2017/223330 A1 | 12/2017 |
| WO | WO 2018/000657 A1 | 1/2018 |
| WO | WO 2018/002719 A1 | 1/2018 |
| WO | WO 2018/005117 A1 | 1/2018 |
| WO | WO 2018/005289 A2 | 1/2018 |
| WO | WO 2018/005691 A1 | 1/2018 |
| WO | WO 2018/005782 A1 | 1/2018 |
| WO | WO 2018/005873 A1 | 1/2018 |
| WO | WO 2018/06693 A1 | 1/2018 |
| WO | WO 2018/009520 A1 | 1/2018 |
| WO | WO 2018/009562 A1 | 1/2018 |
| WO | WO 2018/009822 A1 | 1/2018 |
| WO | WO 2018/013821 A1 | 1/2018 |
| WO | WO 2018/013990 A1 | 1/2018 |
| WO | WO 2018/014384 A1 | 1/2018 |
| WO | WO 2018/015444 A1 | 1/2018 |
| WO | WO 2018/015936 A2 | 1/2018 |
| WO | WO 2018/017754 A1 | 1/2018 |
| WO | WO 2018/018979 A1 | 2/2018 |
| WO | WO 2018/020248 A1 | 2/2018 |
| WO | WO 2018/022480 A1 | 2/2018 |
| WO | WO 2018/022634 A1 | 2/2018 |
| WO | WO 2018/025206 A1 | 2/2018 |
| WO | WO 2018/026723 A1 | 2/2018 |
| WO | WO 2018/026976 A1 | 2/2018 |
| WO | WO 2018/027078 A1 | 2/2018 |
| WO | WO 2018/030608 A1 | 2/2018 |
| WO | WO 2018/031683 A1 | 2/2018 |
| WO | WO 2018/035250 A1 | 2/2018 |
| WO | WO 2018/035300 A1 | 2/2018 |
| WO | WO 2018/035423 A1 | 2/2018 |
| WO | WO 2018/035503 A1 | 2/2018 |
| WO | WO 2018/039145 A1 | 3/2018 |
| WO | WO 2018/039438 A1 | 3/2018 |
| WO | WO 2018/039440 A1 | 3/2018 |
| WO | WO 2018/039448 A1 | 3/2018 |
| WO | WO 2018/045630 A1 | 3/2018 |
| WO | WO 2018/048827 A1 | 3/2018 |
| WO | WO 2018/049168 A1 | 3/2018 |
| WO | WO 2018/051347 A1 | 3/2018 |
| WO | WO 2018/058064 A1 | 3/2018 |
| WO | WO 2018/062866 A2 | 4/2018 |
| WO | WO 2018/064352 A1 | 4/2018 |
| WO | WO 2018/064371 A1 | 4/2018 |
| WO | WO 2018/064516 A1 | 4/2018 |
| WO | WO 2018/067546 A1 | 4/2018 |
| WO | WO 2018/067846 A1 | 4/2018 |
| WO | WO 2018/068053 A2 | 4/2018 |
| WO | WO 2018/069474 A1 | 4/2018 |
| WO | WO 2018/071623 A2 | 4/2018 |
| WO | WO 2018/071663 A1 | 4/2018 |
| WO | WO 2018/071868 A1 | 4/2018 |
| WO | WO 2018/071892 A1 | 4/2018 |
| WO | WO 2018/074979 | 4/2018 |
| WO | WO 2018/079134 A1 | 5/2018 |
| WO | WO 2018/080573 A1 | 5/2018 |
| WO | WO 2018/081504 A1 | 5/2018 |
| WO | WO 2018/081535 A2 | 5/2018 |
| WO | WO 2018/081728 A1 | 5/2018 |
| WO | WO 2018/083128 A2 | 5/2018 |
| WO | WO 2018/083606 A1 | 5/2018 |
| WO | WO 2018/085288 A1 | 5/2018 |
| WO | WO 2018/086623 A1 | 5/2018 |
| WO | WO 2018/093990 A1 | 5/2018 |
| WO | WO 2018/098383 A1 | 5/2018 |
| WO | WO 2018/098480 A1 | 5/2018 |
| WO | WO 2018/098587 A1 | 6/2018 |
| WO | WO 2018/099256 A1 | 6/2018 |
| WO | WO 2018/103686 A1 | 6/2018 |
| WO | WO 2018/106268 A1 | 6/2018 |
| WO | WO 2018/107028 A1 | 6/2018 |
| WO | WO 2018/107103 A1 | 6/2018 |
| WO | WO 2018/107129 A1 | 6/2018 |
| WO | WO 2018/108272 A1 | 6/2018 |
| WO | WO 2018/109101 A1 | 6/2018 |
| WO | WO 2018/111946 A1 | 6/2018 |
| WO | WO 2018/111947 A1 | 6/2018 |
| WO | WO 2018/112336 A1 | 6/2018 |
| WO | WO 2018/112446 A2 | 6/2018 |
| WO | WO 2018/119354 A1 | 6/2018 |
| WO | WO 2018/119359 A1 | 6/2018 |
| WO | WO 2018/130830 A1 | 7/2018 |
| WO | WO 2018/135838 A2 | 7/2018 |
| WO | WO 2018/136396 A2 | 7/2018 |
| WO | WO 2018/138385 A1 | 8/2018 |
| WO | WO 2018/148246 A1 | 8/2018 |
| WO | WO 2018/148256 A1 | 8/2018 |
| WO | WO 2018/148647 A2 | 8/2018 |
| WO | WO 2018/149418 A1 | 8/2018 |
| WO | WO 2018/149888 A1 | 8/2018 |
| WO | WO 2018/152418 A1 | 8/2018 |
| WO | WO 2018/154380 A1 | 8/2018 |

(56) References Cited

FOREIGN PATENT DOCUMENTS

| WO | WO 2018/154387 A1 | 8/2018 |
|----|-------------------|--------|
| WO | WO 2018/154412 A1 | 8/2018 |
| WO | WO 2018/154413 A1 | 8/2018 |
| WO | WO 2018/154418 A1 | 8/2018 |
| WO | WO 2018/154439 A1 | 8/2018 |
| WO | WO 2018/154459 A1 | 8/2018 |
| WO | WO 2018/154462 A2 | 8/2018 |
| WO | WO 2018/156372 A1 | 8/2018 |
| WO | WO 2018/161009 A1 | 9/2018 |
| WO | WO 2018/165504 A1 | 9/2018 |
| WO | WO 2018/165629 A1 | 9/2018 |
| WO | WO 2018/170015 A1 | 9/2018 |
| WO | WO 2018/170340 A1 | 9/2018 |
| WO | WO 2018/175502 A2 | 9/2018 |
| WO | WO 2018/177351 A1 | 10/2018 |
| WO | WO 2018/179578 A1 | 10/2018 |
| WO | WO 2018/183403 A1 | 10/2018 |
| WO | WO 2018/195545 A2 | 10/2018 |
| WO | WO 2018-195555 A1 | 10/2018 |
| WO | WO 2018/195555 A1 | 10/2018 |
| WO | WO 2018/197020 A1 | 11/2018 |
| WO | WO 2018/197495 A1 | 11/2018 |
| WO | WO 2018/202800 A1 | 11/2018 |
| WO | WO 2018/204493 A1 | 11/2018 |
| WO | WO 2018/208755 A1 | 11/2018 |
| WO | WO 2018/208998 A1 | 11/2018 |
| WO | WO 2018/209158 A2 | 11/2018 |
| WO | WO 2018/209320 A1 | 11/2018 |
| WO | WO 2018/213708 A1 | 11/2018 |
| WO | WO 2018/213726 A1 | 11/2018 |
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |

OTHER PUBLICATIONS

Bitinaite et al., FokI dimerization is required for DNA cleavage. Proc Natl Acad Sci U S A. Sep. 1, 1998;95(18):10570-5.
Borman, Improved route to single-base genome editing. Chemical & Engineering News, Apr. 25, 2006;94(17)p5. http://cen.acs.org/articles/94/i17/Improved-route-single-base-genome.html.
Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.
Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.
Freshney, Culture of Animal Cells. A Manual of Basic Technique. Alan R. Liss, Inc. New York. 1983;4.
Hondares et al., Peroxisome Proliferator-activated Receptor α (PPARα) Induces PPARγ Coactivator 1α (PGC-1α) Gene Expression and Contributes to Thermogenic Activation of Brown Fat. J Biol. Chem Oct. 2011; 286(50):43112-22. doi: 10.1074/jbc.M111.252775.
Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2015.
Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.

Ran et al., In vivo genome editing using *Staphylococcus aureus* Cas9. Nature. Apr. 9, 2015;520(7546):186-91. doi: 10.1038/nature14299. Epub Apr. 1, 2015.
Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.
Zuris et al., Cationic lipid-mediated delivery of proteins enables efficient protein-based genome in editing in vitro and in vivo. Nat Biotechnol. 2015;33:73-80.
U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
No Author Listed, Invitrogen Lipofectamine™ 2000 product sheets, 2002. 2 pages.
No Author Listed, Invitrogen Lipofectamine™ 2000 product sheets, 2005. 3 pages.
No Author Listed, Invitrogen Lipofectamine™ LTX product sheets, 2011. 4 pages.
Adrian et al., Targeted Saint-O-Somes for improved intracellular delivery of siRNA and cytotoxic drugs into endothelial cells. J Control Release. Jun. 15, 2010;144(3):341-9. doi: 10.1016/j.jconrel. 2010.03.003. Epub Mar. 11, 2010.
Branden and Tooze, Introduction to Protein Structure. 1999; 2nd edition. Garland Science Publisher: 3-12.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Chesnoy et al., Structure and function of lipid-DNA complexes for gene delivery. Annu Rev Biophys Biomol Struct. 2000;29:27-47.
Chichili et al., Linkers in the structural biology of protein-protein interactions. Protein Science. 2013;22:153-67.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.
Genbank Submission; NIH/NCBI, Accession No. J04623. Kita et al., Apr. 26, 1993. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.

(56) References Cited

OTHER PUBLICATIONS

Genbank Submission; NIH/NCBI, Accession No. NP_472073.1. Glaser et al., Jun. 27, 2013. 2 pages.
Genbank Submission; NIH/NCBI, Accession No. P42212. Prasher et al., Mar. 19, 2014. 7 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_820832.1. Makarova et al., Aug. 27, 2013. 2 pages.
Gilbert et al., CRISPR-mediated modular RNA-guided regulation of transcription in eukaryotes. Cell. 2013 154(2):442-51.
Guo et al., Protein tolerance to random amino acid change. Proc Natl Acad Sci U S A. Jun. 22, 2004;101(25):9205-10. Epub Jun. 14, 2004.
Hale et al., RNA-guided RNA cleavage by a CRISPR RNA-Cas protein complex. Cell. Nov. 25, 2009;139(5):945-56. doi: 10.1016/j.cell.2009.07.040.
Klug et al., Zinc fingers: a novel protein fold for nucleic acid recognition. Cold Spring Harb Symp Quant Biol. 1987;52:473-82.
Lazar et al., Transforming growth factor alpha: mutation of aspartic acid 47 and leucine 48 results in different biological activities. Mol Cell Biol. Mar. 1998;8(3):1247-52.
Li et al., Current approaches for engineering proteins with diverse biological properties. Adv Exp Med Biol. 2007;620:18-33.
Liu et al., Fast Colorimetric Sensing of Adenosine and Cocaine Based on a General Sensor Design Involving Aptamers and Nanoparticles. Angew Chem. 2006;118(1):96-100.
Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.
NCBI Reference Sequence: NM_002427.3. Wu et al., May 3, 2014. 5 pages.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
Pattanayak et al., Determining the specificities of TALENs, Cas9, and other genome-editing enzymes. Methods Enzymol. 2014;546:47-78. doi: 10.1016/B978-0-12-801185-0.00003-9.
Porteus, Design and testing of zinc finger nucleases for use in mammalian cells. Methods Mol Biol. 2008;435:47-61. doi: 10.1007/978-1-59745-232-8_4.
Sheridan, First CRISPR-Cas patent opens race to stake out intellectual property. Nat Biotechnol. 2014;32(7):599-601.
Thompson et al., Cellular uptake mechanisms and endosomal trafficking of supercharged proteins. Chem Biol. Jul. 27, 2012;19(7):831-43. doi: 10.1016/j.chembiol.2012.06.014.
Thompson et al., Engineering and identifying supercharged proteins for macromolecule delivery into mammalian cells. Methods Enzymol. 2012;503:293-319. doi: 10.1016/B978-0-12-396962-0.00012-4.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
PCT/US2012/047778, May 30, 2013, International Search Report and Written Opinion.
PCT/US2012/047778, Feb. 6, 2014, International Preliminary Report on Patentability.
EP 123845790.0, Mar. 18, 2015, Partial Supplementary European Search Report.
EP 123845790.0, Oct. 12, 2015, Supplementary European Search Report.
PCT/US2014/0452231, Dec. 4, 2014, International Search Report and Written Opinion.
PCT/US2014/052231, Jan. 30, 2015, International Search Report and Written Opinion (Corrected Version).
PCT/US2014/052231, Mar. 3, 2016, International Preliminary Report on Patentability.
PCT/US2014/050283, Nov. 6, 2014, International Search Report and Written Opinion.
PCT/US2014/050283, Feb. 18, 2016, International Preliminary Report on Patentability.
PCT/US2014/054247, Mar. 27, 2015, International Search Report and Written Opinion.
PCT/US2014/054247, Mar. 17, 2016, International Preliminary Report on Patentability.
PCT/US2014/054291, Dec. 18, 2014, Invitation to Pay Additional Fees.
PCT/US2014/054291, Mar. 27, 2015, International Search Report and Written Opinion.
PCT/US2014/054291, Mar. 17, 2016, International Preliminary Report on Patentability.
PCT/US2014/054252, Mar. 5, 2015, International Search Report and Written Opinion.
PCT/US2014/054252, Mar. 17, 2016, International Search Report and Written Opinion.
PCT/US2014/070038, Apr. 14, 2015, International Search Report and Written Opinion.
PCT/US2015/042770, Feb. 23, 2016, International Search Report and Written Opinion.
PCT/US2015/058479, Feb. 11, 2016, International Search Report and Written Opinion.
PCT/US2014/070038, Jun. 23, 2016, International Preliminary Report on Patentability.
PCT/US2015/042770, Dec. 19, 2016, International Preliminary Report on Patentability.
PCT/US2015/058479, May 11, 2017, International Preliminary Report on Patentability.
PCT/US2016/058344, Mar. 1, 2017, Invitation to Pay Additional Fees.
PCT/US2016/058344, Apr. 20, 2017, International Search Report and Written Opinion.
PCT/US2017/48390, Nov. 7, 2017, Invitation to Pay Additional Fees.
PCT/US2017/046144, Oct. 10, 2017, International Search Report and Written Opinion.
PCT/US2017/045381, Oct. 26, 2017, International Search Report and Written Opinion.
Abudayyeh et al., C2c2 is a single-component programmable RNA-guided RNA-targeting CRISPR effector. Science Aug. 2016;353(6299):aaf5573. DOI: 10.1126/science.aaf5573.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Bolotin et al., Clustered regularly interspaced short palindrome repeats (CRISPRs) have spacers of extrachromosomal origin. Microbiology. Aug. 2005;151(Pt 8):2551-61.
Briner et al., Guide RNA functional modules direct Cas9 activity and orthogonality. Mol Cell. Oct. 23, 2014;56(2):333-339. doi: 10.1016/j.molcel.2014.09.019.
Brouns et al., Small CRISPR RNAs guide antiviral defense in prokaryotes. Science. Aug. 15, 2008;321(5891):960-4. doi: 10.1126/science.1159689.
Buchwald et al., Long-term, continuous intravenous heparin administration by an implantable infusion pump in ambulatory patients with recurrent venous thrombosis. Surgery. Oct. 1980;88(4):507-16.
Burstein et al., New CRISPR-Cas systems from uncultivated microbes. Nature Feb. 2017;542(7640):237-240.
Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.
Chew et al., A multifunctional AAV-CRISPR-Cas9 and its host response. Nat Methods. Oct. 2016;13(10):868-74. doi: 10.1038/nmeth.3993. Epub Sep. 5, 2016.
Covino et al., The CCL2/CCR2 Axis in the Pathogenesis of HIV-1 Infection: A New Cellular Target for Therapy? Current Drug Targets Dec. 2016;17(1):76-110. DOI: 10.2174/1389450117011151217110917.
Davis et al., DNA double strand break repair via non-homologous end-joining. Transl Cancer Res. Jun. 2013;2(3):130-143.

(56) References Cited

OTHER PUBLICATIONS

Dicarlo et al., Genome engineering in *Saccharomyces cerevisiae* using CRISPR-Cas systems. Nucleic Acids Research Apr. 2013;41(7):4336-43.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Doench et al., Optimized sgRNA design to maximize activity and minimize off-target effects of CRISPR-Cas9. Nat Biotechnol. Feb. 2016;34(2):184-191. doi: 10.1038/nbt.3437.
During et al., Controlled release of dopamine from a polymeric brain implant: in vivo characterization. Ann Neurol. Apr. 1989;25(4):351-6.
East-Seletsky et al., Two distinct RNase activities of CRISPR-C2c2 enable guide-RNA processing and RNA detection. Nature Oct. 2016;538(7624):270-3.
Endo et al., Toward establishing an efficient and versatile gene targeting system in higher plants. Biocatalysis and Agricultural Biotechnology 2014;3,(1):2-6.
Extended European Search Report for EP 15830407.1, dated Mar. 2, 2018.
Fang et al., Synthetic Studies Towards Halichondrins: Synthesis of the Left Halves of Norhalichondrins and Homohalichondrins. Tetrahedron Letters 1992;33(12):1557-1560.
Ferry et al., Rational design of inducible CRISPR guide RNAs for de novo assembly of transcriptional programs. Nat Commun. Mar. 3, 2017;8:14633. doi: 10.1038/ncomms14633.
Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fischer et al., Cryptic epitopes induce high-titer humoral immune response in patients with cancer. J Immunol. Sep. 1, 2010;185(5):3095-102. doi: 10.4049/jimmunol.0902166. Epub 2010.
Fukui et al., DNA Mismatch Repair in Eukaryotes and Bacteria. J Nucleic Acids. Jul. 27, 2010;2010. pii: 260512. doi: 10.4061/2010/260512.
Garneau et al., The CRISPR/Cas bacterial immune system cleaves bacteriophage and plasmid DNA. Nature. Nov. 4, 2010;468(7320):67-71. doi: 10.1038/nature09523.
Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.
Heller et al., Replisome assembly and the direct restart of stalled replication forks. Nat Rev Mol Cell Biol. Dec. 2006;7(12):932-43. Epub Nov. 8, 2006.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.
Howard et al., Intracerebral drug delivery in rats with lesion-induced memory deficits. J Neurosurg. Jul. 1989;71(1):105-12.
Hower et al., Shape-based peak identification for ChIP-Seq. BMC Bioinformatics. Jan. 12, 2011;12:15. doi: 10.1186/1471-2105-12-15.
Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.
Hwang et al., Efficient In Vivo Genome Editing Using RNA-Guided Nucleases. Nat Biotechnol. Mar. 2013; 31(3): 227-229. doi: 10.1038/nbt.2501. Epub Jan. 29, 2013.
International Preliminary Report on Patentability for PCT/US2016/058344, dated May 3, 2018.
International Search Report and Written Opinion for PCT/US2017/045381, dated Oct. 26, 2017.
International Search Report and Written Opinion for PCT/US2017/056671, dated Feb. 20, 2018.
International Search Report and Written Opinion for PCT/US2017/068105, dated Apr. 4, 2018.
International Search Report and Written Opinion for PCT/US2017/068114, dated Mar. 20, 2018.
International Search Report and Written Opinion for PCT/US2017/48390, dated Jan. 9, 2018.
International Search Report for PCT/US2018/021664, dated Jun. 21, 2018.
International Search Report for PCT/US2018/021878, dated Aug. 20, 2018.
International Search Report for PCT/US2018/021880, dated Jun. 20, 2018.
International Search Report for PCT/US2018/024208, dated Aug. 23, 2018.
International Search Report for PCT/US2018/025887, dated Jun. 21, 2018.
International Search Report for PCT/US2018/032460, dated Jul. 11, 2018.
Invitation to Pay Additional Fees for PCT/US2017/056671, dated Dec. 21, 2017.
Invitation to Pay Additional Fees for PCT/US2017/48390, dated Nov. 7, 2017.
Invitation to Pay Additional Fees for PCT/US2018/021878, dated Jun. 8, 2018.
Ishino et al., Nucleotide sequence of the iap gene, responsible for alkaline phosphatase isozyme conversion in *Escherichia coli*, and identification of the gene product. J Bacteriol. Dec. 1987;169(12):5429-33.
Jansen et al., Identification of genes that are associated with DNA repeats in prokaryotes. Mol Microbiol. Mar. 2002;43(6):1565-75.
Kaya et al., A bacterial Argonaute with noncanonical guide RNA specificity. Proc. Natl. Acad. Sci. USA Apr. 2016;113(15):4057-62.
Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.
Kohli et al., Local sequence targeting in the AID/APOBEC family differentially impacts retroviral restriction and antibody diversification. J Biol Chem. Dec. 24, 2010;285(52):40956-64. doi: 10.1074/jbc.M110.177402. Epub Oct. 6, 2010.
Komor et al., CRISPR-Based Technologies for the Manipulation of Eukaryotic Genomes. Cell. Jan. 12, 2017;168(1-2):20-36. doi: 10.1016/j.cell.2016.10.044.
Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.
Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.
Kunz et al., DNA Repair in mammalian cells: Mismatched repair: variations on a theme. Cell Mol Life Sci. Mar. 2009;66(6):1021-38. doi: 10.1007/s00018-009-8739-9.
Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.
Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.
Langer et al., New methods of drug delivery. Science. Sep. 28, 1990;249(4976):1527-33.
Lau et al., Molecular basis for discriminating between normal and damaged bases by the human alkyladenine glycosylase, AAG. Proc Natl Acad Sci U S A. Dec. 5, 2000;97(25):13573-8.
Lee et al., Failure to detect DNA-guided genome editing using Natronobacterium gregoryi Argonaute. Nat Biotechnol. Nov. 28, 2016;35(1):17-18. doi: 10.1038/nbt.3753.

(56) References Cited

OTHER PUBLICATIONS

Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.
Levy et al., Inhibition of calcification of bioprosthetic heart valves by local controlled-release diphosphonate. Science. Apr. 12, 1985;228(4696):190-2.
Lewis et al., Building the Class 2 CRISPR-Cas Arsenal. Mol Cell 2017;65(3);377-379.
Li et al., Base editing with a Cpf1-cytidine deaminase fusion. Nat Biotechnol. Apr. 2018;36(4):324-327. doi: 10.1038/nbt.4102. Epub Mar. 19, 2018.
Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.
Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.
Lieber et al., Mechanism and regulation of human non-homologous DNA end-joining. Nat Rev Mol Cell Biol. Sep. 2003;4(9):712-20.
Liu et al., C2c1-sgRNA Complex Structure Reveals RNA-Guided DNA Cleavage Mechanism. Molecular Cell Jan. 2017;65(2):310-22.
Liu et al., Balancing AID and DNA repair during somatic hypermutation. Trends Immunol. Apr. 2009;30(4):173-81. doi: 10.1016/j.it.2009.01.007.
Liu et al., Distance determination by GIY-YIG intron endonucleases: discrimination between repression and cleavage functions. Nucleic Acids Res. Mar. 31, 2006;34(6):1755-64. Print 2006.
Losey et al., Crystal structure of *Staphylococcus sureus* tRNA adenosine deaminase tadA in complex with RNA. Nature Struct. Mol. Biol. Feb. 2006;13(2):153-9.
Lyons et al., Efficient Recognition of an Unpaired Lesion by a DNA Repair Glycosylase. J. Am. Chem. Soc., 2009;131(49):17742-3. DOI: 10.1021/ja908378y.
Makarova et al., Prokaryotic homologs of Argonaute proteins are predicted to function as key components of a novel system of defense against mobile genetic elements. Biology Direct 2009;4:29.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015.
Makarova et al., Evolution and classification of the CRISPR-Cas systems. Nat Rev Microbiol. Jun. 2011;9(6):467-77. doi: 10.1038/nrmicro2577. Epub May 9, 2011.
Marraffini et al., CRISPR interference limits horizontal gene transfer in staphylococci by targeting DNA. Science. Dec. 19, 2008;322(5909):1843-5. doi: 10.1126/science.1165771.
Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.
Mojica et al., Intervening sequences of regularly spaced prokaryotic repeats derive from foreign genetic elements. J Mol Evol. Feb. 2005;60(2):174-82.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Pearl, Structure and function in the uracil-DNA glycosylase superfamily. Mutat Res. Aug. 30, 2000;460(3-4):165-81.
Plosky et al., CRISPR-Mediated Base Editing without DNA Double-Strand Breaks. Mol Cell. May 19, 2016;62(4):477-8. doi: 10.1016/j.molcel.2016.05.006.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.

Prashant et al., CAS9 transcriptional activators for target specificity screening and paired nickases for cooperative genome engineering. Nature Biotechnology 2013;31(9):833-8.
Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).
Ray et al., Homologous recombination: ends as the means. Trends Plant Sci. Oct. 2002;7(10):435-40.
Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.
Saudek et al., A preliminary trial of the programmable implantable medication system for insulin delivery. N Engl J Med. Aug. 31, 1989;321(9):574-9.
Sefton et al., Implantable pumps. Crit Rev Biomed Eng. 1987;14(3):201-40.
Shah et al., Inteins: nature's gift to protein chemists. Chem Sci. 2014;5(1):446-461.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shee et al., Engineered proteins detect spontaneous DNA breakage in human and bacterial cells. Elife. Oct. 29, 2013;2:e01222. doi: 10.7554/eLife.01222.
Shmakov et al., Discovery and Functional Characterization of Diverse Class 2 CRISPR Cas Systems. Molecular Cell Nov. 2015;60(3):385-97.
Stephens et al., The landscape of cancer genes and mutational processes in breast cancer. Nature Jun. 2012;486:400-404. doi:10.1038/nature11017.
Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.
Tang et al., Aptazyme-embedded guide RNAs enable ligand-responsive genome editing and transcriptional activation. Nat Commun. Jun. 28, 2017;8:15939. doi: 10.1038/ncomms15939.
Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.
Vagner et al., Efficiency of homologous DNA recombination varies along the Bacillus subtilis chromosome. J Bacteriol. Sep. 1988;170(9):3978-82.
Wang et al., CRISPR-Cas9 Targeting of PCSK9 in Human Hepatocytes In Vivo-Brief Report. Arterioscler Thromb Vasc Biol. May 2016;36(5):783-6. doi: 10.1161/ATVBAHA.116.307227. Epub Mar. 3, 2016.
Wolf et al., tadA, an essential tRNA-specific adenosine deaminase from *Escherichia coli*. EMBO J. Jul. 15, 2002;21(14):3841-51.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamamoto et al., Virological and immunological bases for HIV-1 vaccine design. Uirusu 2007;57(2):133-139. https://doi.org/10.2222/jsv.57.133.
Yamano et al., Crystal Structure of Cpf1 in Complex with Guide RNA and Target DNA. Cell May 2016;165(4)949-62.
Yang et al., Engineering and optimising deaminase fusions for genome editing. Nat Commun. Nov. 2, 2016;7:13330. doi: 10.1038/ncomms13330.
Yang et al., New CRISPR-Cas systems discovered. Cell Res. Mar. 2017;27(3):313-314. doi: 10.1038/cr.2017.21. Epub Feb. 21, 2017.
Yang et al., PAM-dependent Target DNA Recognition and Cleavage by C2C1 CRISPR-Cas endonuclease. Cell Dec. 2016;167(7):1814-28.

(56) References Cited

OTHER PUBLICATIONS

Zhang et al., Stabilized plasmid-lipid particles for regional gene therapy: formulation and transfection properties. Gene Ther. Aug. 1999;6(8):1438-47.
Zheng et al., DNA editing in DNA/RNA hybrids by adenosine deaminases that act on RNA. Nucleic Acids Res. Apr. 7, 2017;45(6):3369-3377. doi: 10.1093/nar/gkx050.
EP 15830407.1, Mar. 2, 2018, Extended European Search Report.
PCT/US2016/058344, May 3, 2018, International Preliminary Report on Patentability.
PCT/US2018/025887, Jun. 21, 2018, International Search Report and Written Opinion.
PCT/US2017/48390, Jan. 9, 2018, International Search Report and Written Opinion.
PCT/US2017/068114, Mar. 20, 2018, International Search Report and Written Opinion.
PCT/US2017/068105, Apr. 4, 2018, International Search Report and Written Opinion.
PCT/US2018/021880, Jun. 20, 2018, International Search Report and Written Opinion.
PCT/US2018/021664, Jun. 21, 2018, International Search Report and Written Opinion.
PCT/US2017/056671, Dec. 21, 2017, Invitation to Pay Additional Fees.
PCT/US2017/056671, Feb. 20, 2018, International Search Report and Written Opinion.
PCT/US2018/021878, Jun. 8, 2018, Invitation to Pay Additional Fees.
PCT/US2018/021878, Aug. 20, 2018, International Search Report and Written Opinion.
PCT/US2018/024208, Aug. 23, 2018, International Search Report and Written Opinion.
PCT/US2018/032460, Jul. 11, 2018, International Search Report and Written Opinion.
[No Author Listed], Invitrogen Lipofectamine.TM. 2000 product sheets, 2002. 2 pages.
[No Author Listed], Invitrogen Lipofectamine.TM. 2000 product sheets, 2005. 3 pages.
[No Author Listed], Invitrogen Lipofectamine.TM. LTX product sheets, 2011. 4 pages.
[No Author Listed], Thermo Fisher Scientific—How Cationic Lipid Mediated Transfection Works, retrieved from the internet Aug. 27, 2015. 2 pages.
Adrian et al., Targeted SAINT-O-Somes for improved intracellular delivery of siRNA and cytotoxic drugs into endothelial cells. J Control Release. Jun. 15, 2010;144(3):341-9. doi: 10.1016/j.jconrel.2010.03.003. Epub Mar. 11, 2010.
Aguilera et al., Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Al-Taei et al., Intracellular traffic and fate of protein transduction domains HIV-1 TAT peptide and octaarginine. Implications for their utilization as drug delivery vectors. Bioconjug Chem. Jan.-Feb. 2006;17(1):90-100.
Alexandrov et al., Signatures of mutational processes in human cancer. Nature. Aug. 22, 2013;500(7463):415-21. doi: 10.1038/nature12477. Epub Aug. 14, 2013.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Application Serial No. PCT/US2015/058479, dated May 11, 2017, International Preliminary Report on Patentability.

Application Serial No. PCT/US2016/058344, dated Apr. 20, 2017, International Search Report and Written Opinion.
Application Serial No. PCT/US2017/046144, dated Oct. 10, 2017, International Search Report and Written Opinion.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Beale et al., Comparison of the differential context-dependence of DNA deamination by APOBEC enzymes: correlation with mutation spectra in vivo. J Mol Biol. Mar. 26, 2004;337(3):585-96.
Bedell et al., In vivo genome editing using a high-efficiency TALEN system. Nature. Nov. 1, 2012;491(7422):114-8. Doi: 10.1038/nature11537. Epub Sep. 23, 2012.
Begley, Scientists unveil the 'most clever CRISPR gadget' so far. STAT, Apr. 20, 2016. https://www.statnews.com/2016/04/20/clever-crispr-advance-unveiled/.
Beumer et al., Efficient gene targeting in *Drosophila* with zinc-finger nucleases. Genetics. Apr. 2006;172(4):2391-403. Epub Feb. 1, 2006.
Bibikova et al., Targeted chromosomal cleavage and mutagenesis in *Drosophila* using zinc-finger nucleases. Genetics. Jul. 2002;161(3):1169-75.
Bitinaite et al., FokI dimerization is required for DNA cleavage. Proc Natl Acad Sci U S A. Sep. 1, 1998;95(18):10570-5.
Boch, TALEs of genome targeting. Nat Biotechnol. Feb. 2011;29(2):135-6. Doi: 10.1038/nbt.1767.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Bogdanone et al., TAL effectors: customizable proteins for DNA targeting. Science. Sep. 30, 2011;333(6051):1843-6. doi: 10.1126/science.1204094.
Borman, Improved route to single-base genome editing. Chemical & Engineering News, Apr. 25, 2016;94(17)p5. http://cen.acs.org/articles/94/i17/Improved-route-single-base-genome.html-.
Britt et al., Re-engineering plant gene targeting. Trends Plant Sci. Feb. 2003;8(2):90-5.
Brusse et al., Spinocerebellar ataxia associated with a mutation in the fibroblast growth factor 14 gene (SCA27): A new phenotype. Mov Disord. Mar. 2006;21(3):396-401.
Buchholz et al., Alteration of Cre recombinase site specificity by substrate-linked protein evolution. Nat Biotechnol. Nov. 2001;19(11):1047-52.
Bulow et al., Multienzyme systems obtained by gene fusion. Trends Biotechnol. Jul. 1991;9(7):226-31.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Caldecott et al., Single-strand break repair and genetic disease. Nat Rev Genet. Aug. 2008;9(8):619-31. doi: 10.1038/nrg2380.
Cameron, Recent advances in transgenic technology. Mol Biotechnol. Jun. 1997;7(3):253-65.
Caron et al., Intracellular delivery of a Tat-eGFP fusion protein into muscle cells. Mol Ther. Mar. 2001;3(3):310-8.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.

(56) References Cited

OTHER PUBLICATIONS

Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Chavez et al., Highly efficient Cas9-mediated transcriptional programming. Nat Methods. Apr. 2015;12(4):326-8. doi: 10.1038/nmeth.3312. Epub Mar. 2, 2015.
Chavez et al., Precise Cas9 targeting enables genomic mutation prevention. Jun. 14, 2016. doi:https://doi.org/10.1101/058974. [Preprint].
Chavez et al., Precise Cas9 targeting enables genomic mutation prevention. Proc Natl Acad Sci U S A. Apr. 3, 2018;115(14):3669-3673. doi: 10.1073/pnas.1718148115. Epub Mar. 19, 2018.
Chavez et al., Therapeutic applications of the PC31 integrase system. Curr Gene Ther. Oct. 2011;11(5):375-81. Review.
Chen et al., Fusion protein linkers: property, design and functionality. Adv Drug Deliv Rev. Oct. 2013;65(10):1357-69. doi:10.1016/j.addr.2012.09.039. Epub Sep. 29, 2012.
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Christian et al., Targeting DNA double-strand breaks with TAL effector nucleases. Genetics. Oct. 2010;186(2):757-61. Doi: 10.1534/genetics.110.120717. Epub Jul. 26, 2010.
Chu et al., Increasing the efficiency of homology-directed repair for CRISPR-Cas9-induced precise gene editing in mammalian cells. Nat Biotech. Feb. 13, 2015;33:543-8.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Colletier et al., Protein encapsulation in liposomes: efficiency depends on interactions between protein and phospholipid bilayer. BMC Biotechnol. May 10, 2002;2:9.
Cong et al., Multiplex genome engineering using CRISPR/Cas systems. Science. Feb. 15, 2013;339(6121):819-23. doi: 10.1126/science.1231143. Epub Jan. 3, 2013.
Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.
Cox et al., Therapeutic genome editing: prospects and challenges. Nat Med. Feb. 2015;21(2):121-31. doi: 10.1038/nm.3793.
Cradick et al., CRISPR/Cas9 systems targeting .beta.-globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into mammalian cells in vitro and in vivo using a supercharged protein. ACS Chem Biol. Aug. 20, 2010;5(8):747-52. doi: 10.1021/cb1001153.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Cunningham et al., Ensembl 2015. Nucleic Acids Res. Jan. 2015;43(Database issue):D662-9. doi: 10.1093/nar/gku1010. Epub Oct. 28, 2014.

Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
Deltcheva et al., CRISPR RNA maturation by trans-encoded small RNA and host factor RNase III. Nature. Mar. 31, 2011;471(7340):602-7. doi: 10.1038/nature09886.
DiCarlo et al., Genome engineering in *Saccharomyces cerevisiae* using Crispr-Cas systems.Nucleic Acids Res. Apr. 2013;41(7):4336-43. doi: 10.1093/nar/gkt135. Epub Mar. 4, 2013.
Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.
Dormiani et al., Long-term and efficient expression of human .beta.-globin gene in a hematopoietic cell line using a new site-specific integrating non-viral system. Gene Ther. Aug. 2015;22(8):663-74. doi: 10.1038/gt.2015.30. Epub Apr. 1, 2015.
Doudna et al., Genome editing. The new frontier of genome engineering with CRISPR-Cas9. Science. Nov. 28, 2014;346(6213):1258096. doi: 10.1126/science.1258096.
Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.
Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fuchs et al., Polyarginine as a multifunctional fusion tag. Protein Sci. Jun. 2005;14(6):1538-44.
Fung et al., Repair at single targeted DNA double-strand breaks in pluripotent and differentiated human cells. PLoS One. 2011;6(5):e20514. doi: 10.1371/journal.pone.0020514. Epub May 25, 2011.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gardlik et al., Vectors and delivery systems in gene therapy. Med Sci Monit. Apr. 2005;11(4):RA110-21. Epub Mar. 24, 2005.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.

(56) References Cited

OTHER PUBLICATIONS

Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.
Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.
Gordley et al., Evolution of programmable zinc finger-recombinases with activity in human cells. J Mol Biol. Mar. 30, 2007;367(3):802-13. Epub Jan. 12, 2007.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Guo et al., Protein tolerance to random amino acid change. J Gene Med. Mar.-Apr. 2002;4(2):195-204.
Hale et al., RNA-guided RNA cleavage by a CRISPR RNA-Cas protein complex. Cell. Nov. 25, 2009;139(5):945-56. doi: 10.1016/j.cell.2009.07.040.
Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based- -tech-edits-single-nucleotides-without-breaking-dna.
Harris et al., RNA editing enzyme APOBEC1 and some of its homologs can act as DNA mutators. Mol Cell. Nov. 2002;10(5):1247-53.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Hill et al., Functional analysis of conserved histidines in ADP-glucose pyrophosphorylase from *Escherichia coli*.Biochem Biophys Res Commun. Mar. 17, 1998;244(2):573-7.
Hilton et al., Enabling functional genomics with genome engineering. Genome Res. Oct. 2015;25(10)1442-55. doi: 10.1101/gr.190124.115.
Hondares et al., Peroxisome Proliferator-activated Receptor .alpha. (PPAR.alpha.) Induces PPAR.gamma. Coactivator 1.alpha. (PGC-1.alpha.) Gene Expression and Contributes to Thermogenic Activation of Brown Fat. J Biol. Chem Oct. 2011;286(50):43112-22. doi: 10.1074/jbc.M111.252775.
Hope et al., Cationic lipids, phosphatidylethanolamine and the intracellular delivery of polymeric, nucleic acid-based drugs (review). Mol Membr Biol. Jan.-Mar. 1998;15(1):1-14.
Horvath et al., CRISPR/Cas, the immune system of bacteria and archaea. Science. Jan. 8, 2010;327(5962):167-70. doi: 10.1126/science.1179555.
Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.
Houdebine, The methods to generate transgenic animals and to control transgene expression. J Biotechnol. Sep. 25, 2002;98(2-3):145-60.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.
Huang et al., Heritable gene targeting in zebrafish using customized TALENs. Nat Biotechnol. Aug. 5, 2011;29(8):699-700. doi: 10.1038/nbt.1939.
Huang et al., Long-range pseudoknot interactions dictate the regulatory response in the tetrahydrofolate riboswitch. Proc Natl Acad Sci U S A. Sep. 6, 2011;108(36):14801-6. doi: 10.1073/pnas.1111701108. Epub Aug. 22, 2011.
Humbert et al., Targeted gene therapies: tools, applications, optimization. Crit Rev Biochem Mol Biol. May-Jun. 2012;47(3):264-81. doi: 10.3109/10409238.2012.658112.
Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
International Preliminary Report on Patentability for PCT/US2012/047778, dated Feb. 6, 2014.
International Preliminary Report on patentability for PCT/US2014/050283, dated Feb. 18, 2016.
International Preliminary Report on Patentability for PCT/US2014/052231, dated Mar. 3, 2016.
International Preliminary Report on Patentability for PCT/US2014/054247, dated Mar. 17, 2016.
International Preliminary Report on Patentability for PCT/US2014/054291, dated Mar. 17, 2016.
International Preliminary Report on Patentability for PCT/US2014/070038, dated Jun. 23, 2016.
International Preliminary Report on Patentability for PCT/US2015/042770, dated Dec. 19, 2016.
International Preliminary Report on Patentability for PCT/US2015/058479, dated May 11, 2017.
International Preliminary Report on Patentability or PCT/US2014/054252, dated Mar. 17, 2016.
International Search Report and Written Opinion for PCT/US2012/047778, dated May 30, 2013.
International Search Report and Written Opinion for PCT/US2014/050283, dated Nov. 6, 2014.
International Search Report and Written Opinion for PCT/US2014/052231, dated Dec. 4, 2014.
International Search Report and Written Opinion for PCT/US2014/052231, dated Jan. 30, 2015.
International Search Report and Written Opinion for PCT/US2014/054247, dated Mar. 27, 2015.
International Search Report and Written Opinion for PCT/US2014/054252, dated Mar. 5, 2015.
International Search Report and Written Opinion for PCT/US2014/054291, dated Mar. 27, 2015.
International Search Report and Written Opinion for PCT/US2014/070038, dated Apr. 14, 2015.
International Search Report and Written Opinion for PCT/US2015/042770, dated Feb. 23, 2016.
International Search Report and Written Opinion for PCT/US2015/058479, dated Feb. 11, 2016.
International Search Report and Written Opinion for PCT/US2016/058344, dated Apr. 20, 2017.
International Search Report and Written Opinion for PCT/US2017/046144, dated Oct. 10, 2017.
International Search Report for PCT/US2013/032589, dated Jul. 26, 2013.
Invitation to Pay Additional Fees for PCT/US2014/054291, dated Dec. 18, 2014.

(56) References Cited

OTHER PUBLICATIONS

Invitation to Pay Additional Fees for PCT/US2016/058344, dated Mar. 1, 2017.
Jamieson et al., Drug discovery with engineered zinc-finger proteins. Nat Rev Drug Discov. May 2003;2(5):361-8.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Jinek et al., Structures of Cas9 endonucleases reveal RNA-mediated conformational activation. Science. Mar. 14, 2014;343(6176):1247997. doi: 10.1126/science.1247997. Epub Feb. 6, 2014.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Joung et al., TALENs: a widely applicable technology for targeted genome editing. Nat Rev Mol Cell Biol. Jan. 2013;14(1):49-55. doi: 10.1038/nrm3486. Epub Nov. 21, 2012.
Kaiser et al., Gene therapy. Putting the fingers on gene repair. Science. Dec. 23, 2005;310(5756):1894-6.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Kappel et al., Regulating gene expression in transgenic animals. Curr Opin Biotechnol. Oct. 1992;3(5):548-53.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kellendonk et al., Regulation of Cre recombinase activity by the synthetic steroid RU 486. Nucleic Acids Res. Apr. 15, 1996;24(8):1404-11.
Kim et al., A library of TAL effector nucleases spanning the human genome. Nat Biotechnol. Mar. 2013;31(3):251-8. Doi: 10.1038/nbt.2517. Epub Feb. 17, 2013.
Kim et al., Genome-wide target specificities of CRISPR RNA-guided programmable deaminases. Nat Biotechnol. May 2017;35(5):475-480. doi: 10.1038/nbt.3852. Epub Apr. 10, 2017.
Kim et al., Highly efficient RNA-guided base editing in mouse embryos. Nat Biotechnol. May 2017;35(5):435-437. doi: 10.1038/nbt.3816. Epub Feb. 27, 2017.
Kim et al., Hybrid restriction enzymes: zinc finger fusions to Fok I cleavage domain. Proc Natl Acad Sci U S A. Feb. 6, 1996;93(3):1156-60.
Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.
Kim et al., TALENs and ZFNs are associated with different mutationsignatures. Nat Methods. Mar. 2013;10(3):185. doi: 10.1038/nmeth.2364. Epub Feb. 10, 2013.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Kim et al., The role of apolipoprotein E in Alzheimer's disease. Neuron. Aug. 13, 2009;63(3):287-303. doi: 10.1016/j.neuron.2009.06.026.
Kim et al., Transcriptional repression by zinc finger peptides. Exploring the potential for applications in gene therapy. J Biol Chem. Nov. 21, 1997;272(47):29795-800.

Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.
Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.
Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.
Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.
Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.
Klippel et al., Isolation and characterization of unusual gin mutants. Embo J. Dec. 1, 1988;7(12):3983-9.
Klippel et al., The DNA invertase Gin of phage Mu: formation of a covalent complex with DNA via a phosphoserine at amino acid position 9. EMBO J. Apr. 1988;7(4):1229-37.
Komor et al., Programmable editing of a target base in genomic DNA without double-stranded DNA cleavage. Nature. Apr. 20, 2016;533(7603):420-4. doi: 10.1038/nature17946.
Krishna et al., Structural classification of zinc fingers: survey and summary. Nucleic Acids Res. Jan. 15, 2003;31(2):532-50.
Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.
Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.
Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lawrence et al., Supercharging proteins can impart unusual resilience. J Am Chem Soc. Aug. 22, 2007;129(33):10110-2. Epub Aug. 1, 2007.
Lazar et al., Transforming growth factor alpha: mutation of aspartic acid 47 and leucine 48 results in different biological activities. Mol Cell Biol. Mar. 1988;8(3):1247-52.
Ledford, Gene-editing hack yields pinpoint precision. Nature, Apr. 20, 2016. http://www.nature.com/news/gene-editing-hack-yields-pinpoint-precis- ion-1.19773.
Lee et al., A chimeric thyroid hormone receptor constitutively bound to DNA requires retinoid X receptor for hormone-dependent transcriptional activation in yeast. Mol Endocrinol. Sep. 1994;8(9):1245-52.
Lee et al., Recognition of liposomes by cells: in vitro binding and endocytosis mediated by specific lipid headgroups and surface charge density. Biochim Biophys Acta. Jan. 31, 1992;1103(2):185-97.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].

(56) References Cited

OTHER PUBLICATIONS

Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.

Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.

Lin et al., Enhanced homology-directed human genome engineering by controlled timing of CRISPR/Cas9 delivery. Elife. Dec. 15, 2014;3:e04766. doi: 10.7554/eLife.04766.

Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Liu et al., Design of polydactyl zinc-finger proteins for unique addressing within complex genomes. Proc Natl Acad Sci U S A. May 27, 1997;94(11):5525-30.

Lombardo et al., Gene editing in human stem cells using zinc finger nucleases and integrase-defective lentiviral vector delivery. Nat Biotechnol. Nov. 2007;25(11):1298-306. Epub Oct. 28, 2007.

Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.

Lundberg et al., Delivery of short interfering RNA using endosomolytic cell-penetrating peptides. FASEB J. Sep. 2007;21(11):2664-71. Epub Apr. 26, 2007.

Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.

Ma et al., Targeted AID-mediated mutagenesis (TAM) enables efficient genomic diversification in mammalian cells. Nature Methods. Oct. 2016;13:1029-35. doi:10.1038/nmeth.4027.

Maeder et al., CRISPR RNA-guided activation of endogenous human genes. Nat Methods. Oct. 2013;10(10):977-9. doi: 10.1038/nmeth.2598. Epub Jul. 25, 2013.

Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.

Maeder et al., Robust, synergistic regulation of human gene expression using TALE activators. Nat Methods. Mar. 2013;10(3):243-5. doi: 10.1038/nmeth.2366. Epub Feb. 10, 2013.

Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. EpubJan. 24, 2011.

Mali et al., Cas9 as a versatile tool for engineeringbiology. Nat Methods. Oct. 2013;10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

Mali et al., RNA-guided human genome engineering via Cas9. Science. Feb. 15, 2013;339(6121):823-6. doi: 10.1126/science.1232033. Epub Jan. 3, 2013.

Mani et al., Design, engineering, and characterization of zinc finger nucleases. Biochem Biophys Res Commun. Sep. 23, 2005;335(2):447-57.

Marioni et al., DNA methylation age of blood predicts all-cause mortality in later life. Genome Biol. Jan. 30, 2015;16:25. doi: 10.1186/s13059-015-0584-6.

Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.

McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

Meng et al., Targeted gene inactivation in zebrafish using engineered zinc-finger nucleases. Nat Biotechnol. Jun. 2008;26(6):695-701. doi: 10.1038/nbt1398. Epub May 25, 2008.

Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.

Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.

Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.

Miller et al., A TALE nuclease architecture for efficient genome editing. Nat Biotechnol. Feb. 2011;29(2):143-8. doi: 10.1038/nbt.1755. Epub Dec. 22, 2010.

Miller et al., An improved zinc-finger nuclease architecture for highly specific genome editing. Nat Biotechnol. Jul. 2007;25(7):778-85. Epub Jul. 1, 2007.

Minoche et al., Evaluation of genomic high-throughput sequencing data generated on Illumina HiSeq and genome analyzer systems. Genome Biol. Nov. 8, 2011;12(11):R112. doi: 10.1186/gb-2011-12-11-r112.

Mol et al., Crystal structure of human uracil-DNA glycosylase in complex with a protein inhibitor: protein mimicry of DNA. Cell. Sep. 8, 1995;82(5):701-8.

Moore et al., Improved somatic mutagenesis in zebrafish using transcription activator-like effector nucleases (TALENs). PLoS One. 2012;7(5):e37877. Doi: 10.1371/journal.pone.0037877. Epub May 24, 2012.

Morris et al., A peptide carrier for the delivery of biologically active proteins into mammalian cells. Nat Biotechnol. Dec. 2001;19(12):1173-6.

Mullins et al., Transgenesis in nonmurine species. Hypertension. Oct. 1993;22(4):630-3.

Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.

Nelson FK, Friedman SM, Smith GP. Filamentous phage DNA cloning vectors: a noninfective mutant with a nonpolar deletion in gene III. Virology. 1981; 108(2): 338-50.

Nishida et al., Targeted nucleotide editing using hybrid prokaryotic and vertebrate adaptive immune systems. Science. Sep. 16, 2016;353(6305). pii: aaf8729. doi: 10.1126/science.aaf8729. Epub Aug. 4, 2016.

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

No Author Listed, EMBL Accession No. Q99ZW2. Nov. 2012. 2 pages.

Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.

O'Connell et al., Programmable RNa recognition and cleavage by CRISPR/Cas9. Nature. Sep. 28, 2014. doi: 10.1038/nature13769.

Office Action for U.S. Appl. No. 14/462,163, dated Feb. 1, 2016.

(56) References Cited

OTHER PUBLICATIONS

Office Action for U.S. Appl. No. 14/462,163, dated May 22, 2015.
Office Action for U.S. Appl. No. 14/462,163, dated Nov. 28, 2014.
Office Action for U.S. Appl. No. 14/529,010, dated Jan. 23, 2017.
Office Action for U.S. Appl. No. 14/529,010, dated May 22, 2017.
Offord, Advances in Genome Editing. The Scientist, Apr. 20, 2016. http://www.the-scientist.com/?articles.view/articleNo/45903/title/Advance- s-in-Genome-Editing/.
Osborn et al., TALEN-based gene correction for epidermolysis bullosa. Mol Ther. Jun. 2013;21(6):1151-9. doi: 10.1038/mt.2013.56. Epub Apr. 2, 2013.
Pan et al., Biological and biomedical applications of engineered nucleases. Mol Biotechnol. Sep. 2013;55(1):54-62. doi: 10.1007/s12033-012-9613-9.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Partial Supplementary European Search Report for Application No. EP 12845790.0, dated Mar. 18, 2015.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.
Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Petolino et al., Editing Plant Genomes: a new era of crop improvement. Plant Biotechnol J. Feb. 2016;14(2):435-6. doi: 10.1111/pbi.12542.
Phillips, The challenge of gene therapy and DNA delivery. J Pharm Pharmacol. Sep. 2001;53(9):1169-74.
Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.
Pluciennik et al., PCNA function in the activation and strand direction of MutL.alpha. endonuclease in mismatch repair. Proc Natl Acad Sci U S A. Sep. 14, 2010;107(37):16066-71. doi: 10.1073/pnas.1010662107. Epub Aug. 16, 2010.
Prorocic et al., Zinc-finger recombinase activities in vitro. Nucleic Acids Res. Nov. 2011;39(21):9316-28. doi: 10.1093/nar/gkr652. Epub Aug. 17, 2011.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Putnam et al., Protein mimicry of DNA from crystal structures of the uracil-DNA glycosylase inhibitor protein and its complex with *Escherichia coil* uracil-DNA glycosylase. J Mol Biol. Mar. 26, 1999;287(2):331-46.
Putney et al., Improving protein therapeutics with sustained-release formulations. Nat Biotechnol. Feb. 1998;16(2):153-7.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Qi et al., Repurposing CRISPR as an RNA-guided platform for sequence-specific control of gene expression. Cell. Feb. 28, 2013;152(5):1173-83. doi: 10.1016/j.cell.2013.02.022.
Rakonjac J, Model P. Roles of PIII in filamentous phage assembly. J Mol Biol. 1998; 282(1)25-41.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.
Ran et al., Genome engineering using the CRISPR-Cas9 system. Nat Protoc. Nov. 2013;8(11):2281-308. doi: 10.1038/nprot.2013.143. Epub Oct. 24, 2013.
Ran et al., In vivo genome editing using *Staphylococcus aureus* Cas9. Nature. Apr. 9, 2015;520(7546):186-91. dol: 10.1038/nature14299. Epub Apr. 1, 2015.
Rath et al., Fidelity of end joining in mammalian episomes and the impact of Metnase on joint processing. BMC Mol Biol. Mar. 22, 2014;15:6. doi: 10.1186/1471-2199-15-6.
Rebuzzini et al., New mammalian cellular systems to study mutations introduced at the break site by non-homologous end-joining. DNA Repair (Amst). May 2, 2005;4(5):546-55.
Rees et al., Improving the DNA specificity and applicability of base editing through protein engineering and protein delivery. Nat Commun. Jun. 6, 2017;8:15790. doi: 10.1038/ncomms15790.
Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.
Riechmann L, Holliger P. The C-terminal domain of TolA is the coreceptor for filamentous phage infection of *E. coli*. Cell. 1997; 90(2):351-60. PMID:9244308.
Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.
Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.
Sadelain et al., Safe harbours for the integration of new DNA in the human genome. Nat Rev Cancer. Dec. 1, 2011;12(1):51-8. doi: 10.1038/nrc3179.
Samal et al., Cationic polymers and their therapeutic potential. Chem Soc Rev. Nov. 7, 2012;41(21):7147-94. doi: 10.1039/c2cs35094g. Epub Aug. 10, 2012.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., Targeted gene disruption in somatic zebrafish cells using engineered TALENs. Nat Biotechnol. Aug. 5, 2011;29(8):697-8. doi: 10.1038/nbt.1934.
Sang, Prospects for transgenesis in the chick. Mech Dev. Sep. 2004;121(9):1179-86.
Sanjana et al., A transcription activator-like effector toolbox for genome engineering. Nat Protoc. Jan. 5, 2012;7(1):171-92. doi: 10.1038/nprot.2011.431.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

(56) References Cited

OTHER PUBLICATIONS

Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Schriefer et al., Low pressure DNA shearing: a method for random DNA sequence analysis. Nucleic Acids Res. Dec. 25, 1990;18(24):7455-6.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Schwarze et al., In vivo protein transduction: delivery of a biologically active protein into the mouse. Science. Sep. 3, 1999;285(5433):1569-72.

Sclimenti et al., Directed evolution of a recombinase for improved genomic integration at a native human sequence. Nucleic Acids Res. Dec. 15, 2001;29(24):5044-51.

Sells et al., Delivery of protein into cells using polycationic liposomes. Biotechniques. Jul. 1995;19(1):72-6, 78.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Semple et al., Rational design of cationic lipids for siRNA delivery. Nat Biotechnol. Feb. 2010;28(2):172-6. doi: 10.1038/nbt.1602. Epub Jan. 17, 2010.

Seripa et al., The missing ApoE allele. Ann Hum Genet. Jul. 2007;71(Pt 4):496-500. Epub Jan. 22, 2007.

Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.

Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.

Shalem et al., Genome-scale CRISPR-Cas9 knockout screening in human cells. Science. Jan. 3, 2014;343(6166):84-7. doi: 10.1126/science.1247005. Epub Dec. 12, 2013.

Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.

Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.

Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi:10.1016/j.braindev.2011.04.014. Epub May 19, 2011.

Siebert et al., An improved PCR method for walking in uncloned genomic DNA. Nucleic Acids Res. Mar. 25, 1995;23(6):1087-8.

Simonelli et al., Base excision repair intermediates are mutagenic in mammalian cells. Nucleic Acids Res. Aug. 2, 2005;33(14):4404-11. Print 2005.

Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.

Sjoblom et al., The consensus coding sequences of human breast and colorectal cancers. Science. Oct. 13, 2006;314(5797):268-74. Epub Sep. 7, 2006.

Slaymaker et al., Rationally engineered Cas9 nucleases with improved specificity. Science. Jan. 1, 2016;351(6268):84-8. doi: 10.1126/science.aad5227. Epub Dec. 1, 2015.

Smith et al., Expression of a dominant negative retinoic acid receptor .gamma. In Xenopus embryos leads to partial resistance to retinoic acid. Roux Arch Dev Biol. Mar. 1994;203(5):254-265. doi: 10.1007/BF00360521.

Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.

Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.

Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.

Supplementary European Search Report for Application No. EP 12845790.0, dated Oct. 12, 2015.

Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.

Swarts et al., DNA-guided DNA interference by a prokaryotic Argonaute. Nature. Mar. 13, 2014;507(7491):258-61. doi: 10.1038/nature12971. Epub Feb. 16, 2014.

Swarts et al., The evolutionary journey of Argonaute proteins. Nat Struct Mol Biol. Sep. 2014;21(9):743-53. doi: 10.1038/nsmb.2879.

Tagalakis et al., Lack of RNA-DNA oligonucleotide (chimeraplast) mutagenic activity in mouse embryos. Mol Reprod Dev. Jun. 2005;71(2):140-4.

Thompson et al., Cellular uptake mechanisms and endosomal trafficking of supercharged proteins. Chem Biol. Jul. 27, 2012;19(7):831-43. doi: 10.1016/j.chembiol.2012.06.014.

Thorpe et al., Functional correction of episomal mutations with short DNA fragments and RNA-DNA oligonucleotides. J Gene Med. Mar.-Apr. 2002;4(2):195-204.

Thyagarajan et al., Mammalian genomes contain active recombinase recognition sites. Gene. Feb. 22, 2000;244(1-2):47-54.

Thyagarajan et al., Site-specific genomic integration in mammalian cells mediated by phage phiC31 integrase. Mol Cell Biol. Jun. 2001;21(12):3926-34.

Tirumalai et al., Recognition of core-type DNA sites by lambda integrase. J Mol Biol. Jun. 12, 1998;279(3):513-27.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.

Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.

Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.

Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.

Uniprot Submission; UniProt, Accession No. P01011. Last modified Jun. 11, 2014, version 2. 15 pages.

UniProt Submission; UniProt, Accession No. P01011. Last modified Sep. 18, 2013, version 2. 15 pages.

Uniprot Submission; UniProt, Accession No. P04264. Last modified Jun. 11, 2014, version 6. 15 pages.

Uniprot Submission; UniProt, Accession No. P04275. Last modified Jul. 9, 2014, version 107. 29 pages.

Urnov et al., Genome editing with engineered zinc finger nucleases. Nat Rev Genet. Sep. 2010;11(9):636-46. doi: 10.1038/nrg2842.

Urnov et al., Highly efficient endogenous human gene correction using designed zinc-finger nucleases. Nature. Jun. 2, 2005;435(7042):646-51. Epub Apr. 3, 2005.

(56) References Cited

OTHER PUBLICATIONS

Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wang et al., Efficient delivery of genome-editing proteins using bioreducible lipid nanoparticles. Proc Natl Acad Sci U S A. Feb. 29, 2016. pii: 201520244. [Epub ahead of print].
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., Nucleation, propagation and cleavage of target RNAs in Ago silencing complexes. Nature. Oct. 8, 2009;461(7265):754-61. doi: 10.1038/nature08434.
Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2)1163-71.
Warren et al., A chimeric Cre recombinase with regulated directionality. Proc Natl Acad Sci U S A. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Wiedenheft et al., RNA-guided genetic silencing systems in bacteria and archaea. Nature. Feb. 15, 2012;482(7385):331-8. doi: 10.1038/nature10886. Review.
Wijnker et al., Managing meiotic recombination in plant breeding. Trends Plant Sci. Dec. 2008;13(12):640-6. doi: 10.1016/j.tplants.2008.09.004. Epub Oct. 22, 2008.
Wood et al., Targeted genome editing across species using ZFNs and TALENs. Science. Jul. 15, 2011;333(6040):307. doi: 10.1126/science.1207773. Epub Jun. 23, 2011.
Wu et al., Correction of a genetic disease in mouse via use of CRISPR-Cas9. Cell Stem Cell. Dec. 5, 2013;13(6):659-62. doi: 10.1016/j.stem.2013.10.016.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Xu et al., Sequence determinants of improved CRISPR sgRNA design. Genome Res. Aug. 2015;25(8):1147-57. doi: 10.1101/gr.191452.115. Epub Jun. 10, 2015.
Yang et al., Genome editing with targeted deaminases. BioRxiv. Preprint. First posted online Jul. 28, 2016.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Yuan et al., Tetrameric structure of a serine integrase catalytic domain. Structure. Aug. 6, 2008;16(8):1275-86. doi: 10.1016/j.str.2008.04.018.
Yuan L, Kurek I, English J. Keenan R. Laboratory-directed protein evolution. Microbiol Mol Biol Rev. 2005; 69(3):373-92. PMID: 16148303.
Yuen et al., Control of transcription factor activity and osteoblast differentiation in mammalian cells using an evolved small-molecule-dependent intein. J Am Chem Soc. Jul. 12, 2006;128(27):8939-46.
Zelphati et al (Intracellular Delivery of Proteins with a New Lipid-mediated Delivery System. The Journal of Biological Chemistry vol. 276, No. 37, Issueof Sep. 14, pp. 35103-35110, 2001.
Zelphati et al., Intracellular delivery of proteins with a new lipid-mediated delivery system. J Biol Chem. Sep. 14, 2001;276(37):35103-10. Epub Jul. 10, 2001.
Zetsche et al., A split-Cas9 architecture for inducible genome editing and transcription modulation. Nat Biotechnol. Feb. 2015;33(2):139-42. doi: 10.1038/nbt.3149.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zhang et al., Comparison of non-canonical PAMs for CRISPR/Cas9-mediated DNA cleavage in human cells. Sci Rep. Jun. 2014;4:5405.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zhang et al., Programmable base editing of zebrafish genome using a modified CRISPR-Cas9 system. Nat Commun. Jul. 25, 2017;8(1):118. doi: 10.1038/s41467-017-00175-6.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zorko et al., Cell-penetrating peptides: mechanism and kinetics of cargo delivery. Adv Drug Deliv Rev. Feb. 28, 2005;57(4):529-45. Epub Jan. 22, 2005.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
U.S. Appl. No. 14/234,031, filed Mar. 24, 2014, Liu et al.
U.S. Appl. No. 14/320,271, filed Jun. 30, 2014, Liu et al.
U.S. Appl. No. 16/441,751, filed Jun. 14, 2019, Liu et al.
U.S. Appl. No. 14/320,519, filed Jun. 30, 2014, Liu et al.
U.S. Appl. No. 14/913,458, filed Feb. 22, 2016, Liu et al.
U.S. Appl. No. 16/266,937, filed Feb. 4, 2019, Liu et al.
U.S. Appl. No. 14/320,370, filed Jun. 30, 2014, Liu et al.
U.S. Appl. No. 14/320,413, filed Jun. 30, 2014, Liu et al.
U.S. Appl. No. 14/874,123, filed Oct. 2, 2015, Liu et al.
U.S. Appl. No. 14/911,117, filed Feb. 9, 2016, Liu et al.
U.S. Appl. No. 14/462,163, filed Aug. 18, 2014, Liu et al.
U.S. Appl. No. 14/462,189, filed Aug. 18, 2014, Liu et al.
U.S. Appl. No. 14/320,498, filed Jun. 30, 2014, Liu et al.
U.S. Appl. No. 14/320,467, filed Jun. 30, 2014, Liu et al.
U.S. Appl. No. 14/916,681, filed Mar. 4, 2016, Liu et al.
U.S. Appl. No. 14/326,329, filed Jul. 8, 2014, Liu et al.
U.S. Appl. No. 14/326,340, filed Jul. 8, 2014, Liu et al.
U.S. Appl. No. 14/326,361, filed Jul. 8, 2014, Liu et al.
U.S. Appl. No. 14/916,683, filed Mar. 4, 2016, Liu et al.
U.S. Appl. No. 14/325,815, filed Jul. 8, 2014, Liu et al.
U.S. Appl. No. 14/326,109, filed Jul. 8, 2014, Liu et al.
U.S. Appl. No. 14/326,140, filed Jul. 8, 2014, Liu et al.
U.S. Appl. No. 14/326,269, filed Jul. 8, 2014, Liu et al.
U.S. Appl. No. 14/326,290, filed Jul. 8, 2014, Liu et al.
U.S. Appl. No. 14/326,318, filed Jul. 8, 2014, Liu et al.
U.S. Appl. No. 14/326,303, filed Jul. 8, 2014, Liu et al.
U.S. Appl. No. 15/103,608, filed Jun. 10, 2016, Liu et al.
U.S. Appl. No. 16/374,634, filed Apr. 30, 2019, Liu et al.
U.S. Appl. No. 15/329,925, filed Jan. 27, 2017, Liu et al.
U.S. Appl. No. 16/132,276, filed Sep. 14, 2018, Liu et al.
U.S. Appl. No. 14/529,010, filed Oct. 30, 2014, Liu et al.
U.S. Appl. No. 15/958,721, filed Apr. 20, 2018, Liu et al.
U.S. Appl. No. 15/331,852, filed Oct. 22, 2016, Liu et al.

(56) References Cited

OTHER PUBLICATIONS

U.S. Appl. No. 15/960,171, filed Apr. 23, 2018, Liu et al.
U.S. Appl. No. 15/770,076, filed Apr. 20, 2018, Liu et al.
U.S. Appl. No. 16/327,744, filed Feb. 22, 2019, Maianti et al.
U.S. Appl. No. 15/852,891, filed Dec. 22, 2017, Maianti et al.
U.S. Appl. No. 15/852,526, filed Dec. 22, 2017, Maianti et al.
U.S. Appl. No. 16/324,476, filed Feb. 8, 2019, Liu et al.
U.S. Appl. No. 15/791,085, filed Oct. 23, 2017, Liu et al.
U.S. Appl. No. 16/143,370, filed Sep. 26, 2018, Liu et al.
U.S. Appl. No. 15/784,033, filed Oct. 13, 2017, Liu et al.
U.S. Appl. No. 15/934,945, filed Mar. 23, 2018, Liu et al.
EP 18199195.1, Feb. 12, 2019, Extended European Search Report.
EP 19181479.7, Oct. 31, 2019, Extended European Search Report.
PCT/US2017/48390, Mar. 7, 2019, International Preliminary Report on Patentability.
PCT/US2017/068114, Jul. 4, 2019, International Preliminary Report on Patentability.
PCT/US2017/068105, Jul. 4, 2019, International Preliminary Report on Patentability.
PCT/US2017/046144, Feb. 21, 2019, International Preliminary Report on Patentability.
PCT/US2017/045381, Feb. 14, 2019, International Preliminary Report on Patentability.
PCT/US2017/056671, Apr. 25, 2019, International Preliminary Report on Patentability.
PCT/US2018/021880, Sep. 19, 2019, International Preliminary Report on Patentability.
PCT/US2018/021664, Sep. 19, 2019, International Preliminary Report on Patentability.
PCT/US2018/021878, Sep. 19, 2019, International Preliminary Report on Patentability.
PCT/US2018/024208, Oct. 3, 2019, International Preliminary Report on Patentability.
U.S. Appl. No. 14/529,010, Aug. 28, 2019, Office Action.
U.S. Appl. No. 14/462,189, Nov. 28, 2014, Office Action.
U.S. Appl. No. 14/462,189, Mar. 23, 2015, Office Action.
U.S. Appl. No. 14/462,189, Sep. 24, 2015, Office Action.
U.S. Appl. No. 14/462,189, Jan. 20, 2016, Office Action.
U.S. Appl. No. 14/462,189, May 4, 2016, Office Action.
U.S. Appl. No. 14/462,189, Oct. 13, 2016, Office Action.
U.S. Appl. No. 14/462,189, Apr. 11, 2017, Notice of Allowance.
U.S. Appl. No. 61/838,178, filed Jun. 21, 2013, Joung et al.
U.S. Appl. No. 62/357,332, filed Jun. 30, 2016, Liu et al.
U.S. Appl. No. 62/288,661, filed Jan. 29, 2016, Muir et al.
[No Author Listed] Score result for SEQ 355 to W02017032580. Muir et al. 2016.
Aihara et al., A conformational switch controls the DNA cleavage activity of lambda integrase. Mol Cell. Jul. 2003;12(1):187-98.
Ames et al., A eubacterial riboswitch class that senses the coenzyme tetrahydrofolate. Chem Biol. Jul. 30, 2010;17(7):681-5. doi: 10.1016/j.chembiol.2010.05.020.
Batey et al., Structure of a natural guanine-responsive riboswitch complexed with the metabolite hypoxanthine. Nature. Nov. 18, 2004;432(7015):411-5.
Bershtein et al., Advances in laboratory evolution of enzymes. Curr Opin; Chem Biol. Apr. 2008;12(2):151-8. doi: 10.1016/j.cbpa.2008.01.027. Epub Mar. 7, 2008. Review.
Böck et al., Selenocysteine: the 21st amino acid. Mol Microbiol. Mar. 1991;5(3):515-20.
Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.
Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.

Buskirk et al., Directed evolution of ligand dependence: small-molecule-activated protein splicing. Proc Natl Acad Sci U S A. Jul. 20, 2004;101(29):10505-10. Epub Jul. 9, 2004.
Carroll, Genome engineering with zinc-finger nucleases. Genetics. Aug. 2011;188(4):773-82. doi: 10.1534/genetics.111.131433. Review.
Chavez et al., Precise Cas9 targeting enables genomic mutation prevention. bioRxiv. Jun. 14, 2016; http://dx/doi.oreg/10.1101/058974. 6 pages.
Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.
Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.
Edwards et al., An *Escherichia coli* tyrosine transfer RNA is a leucine-specific transfer RNA in the *Saccharomyces cerevisiae*. Proc Natl Acad Sci U S A. Feb. 15, 1991;88(4):1153-6.
Edwards et al., Crystal structures of the thi-box riboswitch bound to thiamine pyrophosphate analogs reveal adaptive RNA-small molecule recognition. Structure. Sep. 2006;14(9):1459-68.
Esvelt et al., A system for the continuous directed evolution of biomolecules. Nature. Apr. 28, 2011;472(7344):499-503. doi: 10.1038/nature09929. Epub Apr. 10, 2011.
Extended European Search Report for EP 19181479.7, dated Oct. 31, 2019.
Extended European Search Report for EP18199195.1, dated Feb. 12, 2019.
Fagerlund et al., The Cpf1 CRISPR-Cas protein expands genome-editing tools. Genome Biology Nov. 17, 2015;16:251. https://doi.org/10.1186/s13059-015-0824-9.
Farhood et al., Codelivery to mammalian cells of a transcriptional factor with cis-acting element using cationic liposomes. Anal Biochem. Feb. 10, 1995;225(1):89-93.
Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.
Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.
Hida et al., Directed evolution for drug and nucleic acid; delivery. Adv Drug Deliv Rev. Dec. 22, 2007;59(15):1562-78. Epub Aug. 28, 2007.; Review.
Husimi, Selection and evolution of bacteriophages in cellstat. Adv Biophys. 1989;25:1-43. Review.
International Preliminary Report on Patentability for PCT/US2014/048390, dated Mar. 7, 2019.
International Preliminary Report on Patentability for PCT/US2017/068114, dated Jul. 4, 2019.
International Preliminary Report on Patentability for PCT/US2017/068105, dated Jul. 4, 2019.
International Preliminary Report on Patentability for PCT/US2017/046144, dated Feb. 21, 2019.
International Preliminary Report on Patentability for PCT/US2017/045381, dated Feb. 14, 2019.
International Preliminary Report on Patentability for PCT/US2017/056671, dated Apr. 25, 2019.
International Preliminary Report on Patentability for PCT/US2018/021880, dated Sep. 19, 2019.
International Preliminary Report on Patentability for PCT/US2018/021664, dated Sep. 19, 2019.
International Preliminary Report on Patentability for PCT/US2018/021878, dated Sep. 19, 2019.
International Preliminary Report on Patentability for PCT/US2018/024208, dated Oct. 3, 2019.
Kakiyama et al., A peptide release system using a photo-cleavable linker in a cell array format for cell-toxicity analysis. Polymer J. Feb. 27, 2013;45:535-9.
Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.

(56) References Cited

OTHER PUBLICATIONS

Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.

Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.

Köhrer et al., A possible approach to site-specific insertion of two different unnatural amino acids into proteins in mammalian cells via nonsense suppression. Chem Biol. Nov. 2003;10(11):1095-102.

Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.

Kowal et al., Exploiting unassigned codons in Micrococcus luteus for tRNA-based amino acid mutagenesis. Nucleic Acids Res. Nov. 15, 1997;25(22):4685-9.

Kwon et al., Chemical basis of glycine riboswitch cooperativity. RNA. Jan. 2008;14(1):25-34. Epub Nov. 27, 2007.

Lee et al., An allosteric self-splicing ribozyme triggered by a bacterial second messenger. Science. Aug. 13, 2010;329(5993):845-8. doi: 10.1126/science.1190713.

Link et al., Engineering ligand-responsive gene-control elements: lessons learned from natural riboswitches. Gene Ther. Oct. 2009;16(10):1189-201. doi: 10.1038/gt.2009.81. Epub Jul. 9, 2009. Review.

Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.

Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.

Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.

Monahan et al., Site-specific incorporation of unnatural amino acids into receptors expressed in Mammalian cells. Chem Biol. Jun. 2003;10(6):573-80.

Montange et al., Structure of the S-adenosylmethionine riboswitch regulatory mRNA element. Nature. Jun. 29, 2006;441(7097):1172-5.

Mootz et al., Conditional protein splicing: a new tool to control protein structure and function in vitro and in vivo. J Am Chem Soc. Sep. 3, 2003;125(35):10561-9.

Mootz et al., Protein splicing triggered by a small molecule. J Am Chem Soc. Aug. 7, 2002;124(31):9044-5.

Nahvi et al., Coenzyme B12 riboswitches are widespread genetic control elements in prokaryotes. Nucleic Acids Res. Jan. 2, 2004;32(1):143-50.

Neel et al., Riboswitches: Classification, function and in silico approach, International Journal of Pharma Sciences and Research. 2010;1(9):409-420.

Ni et al., Nucleic acid aptamers: clinical applications and promising new horizons. Curr Med Chem. 2011;18(27):4206-14. Review.

Pavletich et al., Zinc finger-DNA recognition: crystal structure of a Zif268-DNA complex at 2.1 A. Science. May 10, 1991;252(5007):809-17.

Peck et al., Directed evolution of a small-molecule-triggered intein with improved splicing properties in mammalian cells. Chem Biol. May 27, 2011;18(5):619-30. doi: 10.1016/j.chembiol.2011.02.014.

Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.

Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.

Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.

Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.

Serganov et al., Structural basis for discriminative regulation of gene expression by adenine-and guanine-sensing mRNAs. Chem Biol. Dec. 2004;11(12):1729-41.

Serganov et al., Structural basis for gene regulation by a thiamine pyrophosphate-sensing riboswitch. Nature. Jun. 29, 2006;441(7097):1167-71. Epub May 21, 2006.

Sharma et al., Efficient introduction of aryl bromide functionality into proteins in vivo. FEBS Lett. Feb. 4, 2000;467(1):37-40.

Skretas et al., Regulation of protein activity with small-molecule-controlled inteins. Protein Sci. Feb. 2005;14(2):523-32. Epub Jan. 4, 2005.

Smith, Filamentous fusion phage: novel expression vectors that display cloned antigens on the virion surface. Science. Jun. 14, 1985;228(4705):1315-7.

Sudarsan et al., An mRNA structure in bacteria that controls gene expression by binding lysine. Genes Dev. Nov. 1, 2003;17(21):2688-97.

Sudarsan et al., Riboswitches in eubacteria sense the second messenger cyclic di-GMP. Science. Jul. 18, 2008;321(5887):411-3. doi: 10.1126/science.1159519.

Suess et al., A theophylline responsive riboswitch based on helix slipping controls gene expression in vivo. Nucleic Acids Res. Mar. 5, 2004;32(4):1610-4.

Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.

Wals et al., Unnatural amino acid incorporation in *E. coli*: current and future applications in the design of therapeutic proteins. Front Chem. Apr. 1, 2014;2:15. doi: 10.3389/fchem.2014.00015. eCollection 2014.

Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.

Winkler et al., An mRNA structure that controls gene expression by binding FMN. Proc Natl Acad Sci U S A. Dec. 10, 2002;99(25):15908-13. Epub Nov. 27, 2002.

Winkler et al., Control of gene expression by a natural metabolite-responsive ribozyme. Nature. Mar. 18, 2004;428(6980):281-6.

Winkler et al., Thiamine derivatives bind messenger RNAs directly to regulate bacterial gene expression. Nature. Oct. 31, 2002;419(6910):952-6. Epub Oct. 16, 2002.

Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.

Zimmermann et al., Molecular interactions and metal binding in the theophylline-binding core of an RNA aptamer. RNA. May 2000;6(5):659-67.

Office Action, dated Aug. 28, 2019 in connection with U.S. Appl. No. 14/529,010.

Notice of Allowance, dated Apr. 11, 2017 in connection with U.S. Appl. No. 14/462,189.

Office Action, dated Oct. 13, 2016 in connection with U.S. Appl. No. 14/462,189.

Office Action, dated May 4, 2016 in connection with U.S. Appl. No. 14/462,189.

Office Action, dated Jan. 20, 2016 in connection with U.S. Appl. No. 14/462,189.

Office Action, dated Sep. 24, 2015 in connection with U.S. Appl. No. 14/462,189.

Office Action, dated Mar. 23, 2015 in connection with U.S. Appl. No. 14/462,189.

(56) References Cited

OTHER PUBLICATIONS

Office Action, dated Nov. 28, 2014 in connection with U.S. Appl. No. 14/462,189.

* cited by examiner a b

Figure 43

SEQUENCE LISTING

```
<160> NUMBER OF SEQ ID NOS: 259

<210> SEQ ID NO 1
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 1

Gly Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Lys His Met
65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
            100                 105                 110

Glu Val Lys Phe Glu Gly Arg Thr Leu Val Asn Arg Ile Lys Leu Lys
        115                 120                 125

Gly Arg Asp Phe Lys Glu Lys Gly Asn Ile Leu Gly His Lys Leu Arg
    130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
```

```
                165                 170                 175
Ser Val Gln Leu Ala Asp His Tyr Gln Gln Asn Thr Pro Ile Gly Arg
        180                 185                 190

Gly Pro Val Leu Leu Pro Arg Asn His Tyr Leu Ser Thr Arg Ser Lys
        195                 200                 205

Leu Ser Lys Asp Pro Lys Glu Lys Arg Asp His Met Val Leu Leu Glu
    210                 215                 220

Phe Val Thr Ala Ala Gly Ile Lys His Gly Arg Asp Glu Arg Tyr Lys
225                 230                 235                 240

<210> SEQ ID NO 2
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 2

Gly Gly Ser Gly Gly Ser Gly Gly Ser Gly Gly Ser Gly Gly Ser Gly
1               5                   10                  15

Gly Ser

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 3

Ser Gly Ser Glu Thr Pro Gly Thr Ser Glu Ser Ala Thr Pro Glu Ser
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 4

Ser Gly Ser Glu Thr Pro Gly Thr Ser Glu Ser Ala
1               5                   10

<210> SEQ ID NO 5
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 5

Ser Gly Ser Glu Thr Pro Gly Thr Ser Glu Ser Ala Thr Pro Glu Gly
1               5                   10                  15

Gly Ser Gly Gly Ser
            20

<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide
```

```
<400> SEQUENCE: 6

Val Pro Phe Leu Leu Glu Pro Asp Asn Ile Asn Gly Lys Thr Cys
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 7

Gly Ser Ala Gly Ser Ala Ala Gly Ser Gly Glu Phe
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 8

Ser Ile Val Ala Gln Leu Ser Arg Pro Asp Pro Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 9

Met Lys Ile Ile Glu Gln Leu Pro Ser Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 10

Val Arg His Lys Leu Lys Arg Val Gly Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 11

Gly His Gly Thr Gly Ser Thr Gly Ser Gly Ser Ser
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 12
```

```
Met Ser Arg Pro Asp Pro Ala
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 13

Gly Gly Ser Met
1

<210> SEQ ID NO 14
<211> LENGTH: 238
<212> TYPE: PRT
<213> ORGANISM: Aequorea victoria

<400> SEQUENCE: 14

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 15
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 15
```

Met Gly His His His His His Gly Gly Ala Ser Lys Gly Glu Arg
1               5                   10                  15

Leu Phe Thr Gly Val Val Pro Ile Leu Val Glu Leu Asp Gly Asp Val
            20                  25                  30

Asn Gly His Lys Phe Ser Val Arg Gly Glu Gly Glu Gly Asp Ala Thr
            35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Glu Gly Tyr Val Gln Glu Arg Thr Ile Ser Phe Lys Lys
            100                 105                 110

Asp Gly Thr Tyr Lys Thr Arg Ala Glu Val Lys Phe Glu Gly Arg Thr
            115                 120                 125

Leu Val Asn Arg Ile Glu Leu Lys Gly Arg Asp Phe Lys Glu Lys Gly
            130                 135                 140

Asn Ile Leu Gly His Lys Leu Glu Tyr Asn Phe Asn Ser His Asn Val
145                 150                 155                 160

Tyr Ile Thr Ala Asp Lys Arg Lys Asn Gly Ile Lys Ala Asn Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
            195                 200                 205

His Tyr Leu Ser Thr Arg Ser Ala Leu Ser Lys Asp Pro Lys Glu Lys
            210                 215                 220

Arg Asp His Met Val Leu Leu Glu Phe Val Thr Ala Ala Gly Ile Thr
225                 230                 235                 240

His Gly Met Asp Glu Leu Tyr Lys
                245

<210> SEQ ID NO 16
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 16

Met Gly His His His His His Gly Gly Ala Ser Lys Gly Glu Arg
1               5                   10                  15

Leu Phe Thr Gly Val Val Pro Ile Leu Val Glu Leu Asp Gly Asp Val
            20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

```
Asp Gly Thr Tyr Lys Thr Arg Ala Glu Val Lys Phe Glu Gly Arg Thr
            115                 120                 125

Leu Val Asn Arg Ile Lys Leu Lys Gly Arg Asp Phe Lys Glu Lys Gly
        130                 135                 140

Asn Ile Leu Gly His Lys Leu Arg Tyr Asn Phe Asn Ser His Asn Val
145                 150                 155                 160

Tyr Ile Thr Ala Asp Lys Arg Lys Asn Gly Ile Lys Ala Asn Phe Lys
                165                 170                 175

Ile Arg His Asn Val Lys Asp Gly Ser Val Gln Leu Ala Asp His Tyr
                    180                 185                 190

Gln Gln Asn Thr Pro Ile Gly Arg Gly Pro Val Leu Leu Pro Arg Asn
                195                 200                 205

His Tyr Leu Ser Thr Arg Ser Ala Leu Ser Lys Asp Pro Lys Glu Lys
            210                 215                 220

Arg Asp His Met Val Leu Leu Glu Phe Val Thr Ala Ala Gly Ile Thr
225                 230                 235                 240

His Gly Met Asp Glu Leu Tyr Lys
                245

<210> SEQ ID NO 17
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 17

Met Gly His His His His His Gly Gly Ala Ser Lys Gly Glu Arg
1               5                   10                  15

Leu Phe Arg Gly Lys Val Pro Ile Leu Val Glu Leu Lys Gly Asp Val
                20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
        50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
                100                 105                 110

Asp Gly Lys Tyr Lys Thr Arg Ala Glu Val Lys Phe Glu Gly Arg Thr
            115                 120                 125

Leu Val Asn Arg Ile Lys Leu Lys Gly Arg Asp Phe Lys Glu Lys Gly
        130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
                    180                 185                 190

Gln Gln Asn Thr Pro Ile Gly Arg Gly Pro Val Leu Leu Pro Arg Asn
                195                 200                 205

His Tyr Leu Ser Thr Arg Ser Lys Leu Ser Lys Asp Pro Lys Glu Lys
            210                 215                 220
```

```
Arg Asp His Met Val Leu Leu Glu Phe Val Thr Ala Ala Gly Ile Lys
225                 230                 235                 240

His Gly Arg Asp Glu Arg Tyr Lys
                245

<210> SEQ ID NO 18
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 18

Met Gly His His His His His Gly Gly Arg Ser Lys Gly Lys Arg
1               5                   10                  15

Leu Phe Arg Gly Lys Val Pro Ile Leu Val Glu Leu Lys Gly Asp Val
                20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Lys Glu Arg Tyr Lys
                245

<210> SEQ ID NO 19
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 19

Met Gly His His His His His Gly Gly Arg Ser Lys Gly Lys Arg
1               5                   10                  15

Leu Phe Arg Gly Lys Val Pro Ile Leu Val Lys Leu Lys Gly Asp Val
```

```
            20                  25                  30
Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
            50                  55                  60

Val Pro Trp Pro Thr Leu Val Thr Thr Leu Thr Tyr Gly Val Gln Cys
 65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
                100                 105                 110

Asp Gly Lys Tyr Lys Thr Arg Ala Glu Val Lys Phe Lys Gly Arg Thr
                115                 120                 125

Leu Val Asn Arg Ile Lys Leu Lys Gly Arg Asp Phe Lys Glu Lys Gly
                130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Lys His Tyr
                180                 185                 190

Gln Gln Asn Thr Pro Ile Gly Arg Gly Pro Val Leu Leu Pro Arg Lys
                195                 200                 205

His Tyr Leu Ser Thr Arg Ser Lys Leu Ser Lys Asp Pro Lys Glu Lys
                210                 215                 220

Arg Asp His Met Val Leu Leu Glu Phe Val Thr Ala Ala Gly Ile Lys
225                 230                 235                 240

His Gly Arg Lys Glu Arg Tyr Lys
                245

<210> SEQ ID NO 20
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 20

Met Gly His His His His His His Gly Gly Arg Ser Lys Gly Lys Arg
 1               5                  10                  15

Leu Phe Arg Gly Lys Val Pro Ile Leu Val Lys Leu Lys Gly Asp Val
                20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
            50                  55                  60

Val Pro Trp Pro Thr Leu Val Thr Thr Leu Thr Tyr Gly Val Gln Cys
 65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
                100                 105                 110

Asp Gly Lys Tyr Lys Thr Arg Ala Glu Val Lys Phe Lys Gly Arg Thr
                115                 120                 125

Leu Val Asn Arg Ile Lys Leu Lys Gly Arg Asp Phe Lys Glu Lys Gly
```

```
                    130                 135                 140
Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Lys His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
    210                 215                 220

Arg Asp His Met Val Leu Lys Glu Phe Val Thr Ala Ala Gly Ile Lys
225                 230                 235                 240

His Gly Arg Lys Glu Arg Tyr Lys
                245

<210> SEQ ID NO 21
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 21

Met Gly His His His His His His Gly Gly Ala Ser Lys Gly Glu Glu
1               5                   10                  15

Leu Phe Asp Gly Val Val Pro Ile Leu Val Glu Leu Asp Gly Asp Val
                20                  25                  30

Asn Gly His Glu Phe Ser Val Arg Gly Glu Gly Glu Gly Asp Ala Thr
            35                  40                  45

Glu Gly Glu Leu Thr Leu Lys Phe Ile Cys Thr Thr Gly Glu Leu Pro
        50                  55                  60

Val Pro Trp Pro Thr Leu Val Thr Thr Leu Thr Tyr Gly Val Gln Cys
65                  70                  75                  80

Phe Ser Asp Tyr Pro Asp His Met Asp Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
    210                 215                 220

Arg Asp His Met Val Leu Leu Glu Phe Val Thr Ala Ala Gly Ile Asp
225                 230                 235                 240

His Gly Met Asp Glu Leu Tyr Lys
```

<210> SEQ ID NO 22
<211> LENGTH: 280
<212> TYPE: PRT
<213> ORGANISM: Artificial Sequence
<220> FEATURE:
<223> OTHER INFORMATION: Synthetic Polypeptide

<400> SEQUENCE: 22

```
Met Gly His His His His His Gly Gly Ala Ser Lys Gly Glu Arg
1               5                   10                  15

Leu Phe Arg Gly Lys Val Pro Ile Leu Val Glu Leu Lys Gly Asp Val
                20                  25                  30

Asn Gly His Lys Phe Ser Val Arg Gly Lys Gly Lys Gly Asp Ala Thr
            35                  40                  45

Arg Gly Lys Leu Thr Leu Lys Phe Ile Cys Thr Thr Gly Lys Leu Pro
        50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Asp Glu Arg Tyr Lys Gly Ser Ala Gly Ser Ala Ala Gly
                245                 250                 255

Ser Gly Glu Phe Gly Leu Phe Gly Ala Ile Ala Gly Phe Ile Glu Asn
            260                 265                 270

Gly Trp Glu Gly Met Ile Asp Gly
        275                 280
```

<210> SEQ ID NO 23
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 23

```
Gly Ile Gly Ala Val Leu Lys Val Leu Thr Thr Gly Leu Pro Ala Leu
1               5                   10                  15
```

```
Ile Ser Trp Ile Lys Arg Lys Arg Gln Gln
            20                  25
```

<210> SEQ ID NO 24
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 24

```
Cys Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 25
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 25

```
Arg Gln Ile Lys Ile Trp Phe Gln Asn Arg Arg Met Lys Trp Lys Lys
1               5                   10                  15
```

<210> SEQ ID NO 26
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 26

```
Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30
```

<210> SEQ ID NO 27
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 27

```
Gly Ala Leu Phe Leu Gly Trp Leu Gly Ala Ala Gly Ser Thr Met Gly
1               5                   10                  15

Ala Pro Lys Ser Lys Arg Lys Val
            20
```

<210> SEQ ID NO 28
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 28

```
Ala Gly Tyr Leu Leu Gly Lys Ile Asn Leu Lys Ala Leu Ala Ala Leu
1               5                   10                  15

Ala Lys Lys Ile Leu
            20
```

<210> SEQ ID NO 29
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 29

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 30
<211> LENGTH: 1653
<212> TYPE: PRT
<213> ORGANISM: Artificial Sequence
<220> FEATURE:
<223> OTHER INFORMATION: Synthetic Polypeptide

<400> SEQUENCE: 30

Met Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45

Ile Cys Thr Thr Gly Lys Leu Pro Val Pro Trp Pro Thr Leu Val Thr
50                  55                  60

Thr Leu Thr Ser Gly Val Gln Cys Phe Ser Arg Tyr Pro Lys His Met
65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
            100                 105                 110

Glu Val Lys Phe Glu Gly Arg Thr Leu Val Asn Arg Ile Lys Leu Lys
        115                 120                 125

Gly Arg Asp Phe Lys Glu Lys Gly Asn Ile Leu Gly His Lys Leu Arg
130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
            180                 185                 190

Gly Pro Val Leu Leu Pro Arg Asn His Tyr Leu Ser Thr Arg Ser Lys
        195                 200                 205

Leu Ser Lys Asp Pro Lys Glu Lys Arg Asp His Met Val Leu Leu Glu
210                 215                 220

Phe Val Thr Ala Ala Gly Ile Lys His Gly Arg Asp Glu Arg Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Leu Ala Leu
            260                 265                 270

Pro Lys Lys Lys Arg Lys Val Met Asp Lys Lys Tyr Ser Ile Gly Leu

```
                275                 280                 285
Asp Ile Gly Thr Asn Ser Val Gly Trp Ala Val Ile Thr Asp Glu Tyr
    290                 295                 300
Lys Val Pro Ser Lys Lys Phe Lys Val Leu Gly Asn Thr Asp Arg His
305                 310                 315                 320
Ser Ile Lys Lys Asn Leu Ile Gly Ala Leu Leu Phe Asp Ser Gly Glu
                325                 330                 335
Thr Ala Glu Ala Thr Arg Leu Lys Arg Thr Ala Arg Arg Arg Tyr Thr
                340                 345                 350
Arg Arg Lys Asn Arg Ile Cys Tyr Leu Gln Glu Ile Phe Ser Asn Glu
                355                 360                 365
Met Ala Lys Val Asp Asp Ser Phe Phe His Arg Leu Glu Glu Ser Phe
    370                 375                 380
Leu Val Glu Glu Asp Lys Lys His Glu Arg His Pro Ile Phe Gly Asn
385                 390                 395                 400
Ile Val Asp Glu Val Ala Tyr His Glu Lys Tyr Pro Thr Ile Tyr His
                405                 410                 415
Leu Arg Lys Lys Leu Val Asp Ser Thr Asp Lys Ala Asp Leu Arg Leu
                420                 425                 430
Ile Tyr Leu Ala Leu Ala His Met Ile Lys Phe Arg Gly His Phe Leu
                435                 440                 445
Ile Glu Gly Asp Leu Asn Pro Asp Asn Ser Asp Val Asp Lys Leu Phe
    450                 455                 460
Ile Gln Leu Val Gln Thr Tyr Asn Gln Leu Phe Glu Glu Asn Pro Ile
465                 470                 475                 480
Asn Ala Ser Gly Val Asp Ala Lys Ala Ile Leu Ser Ala Arg Leu Ser
                485                 490                 495
Lys Ser Arg Arg Leu Glu Asn Leu Ile Ala Gln Leu Pro Gly Glu Lys
                500                 505                 510
Lys Asn Gly Leu Phe Gly Asn Leu Ile Ala Leu Ser Leu Gly Leu Thr
                515                 520                 525
Pro Asn Phe Lys Ser Asn Phe Asp Leu Ala Glu Asp Ala Lys Leu Gln
    530                 535                 540
Leu Ser Lys Asp Thr Tyr Asp Asp Asp Leu Asp Asn Leu Leu Ala Gln
545                 550                 555                 560
Ile Gly Asp Gln Tyr Ala Asp Leu Phe Leu Ala Ala Lys Asn Leu Ser
                565                 570                 575
Asp Ala Ile Leu Leu Ser Asp Ile Leu Arg Val Asn Thr Glu Ile Thr
                580                 585                 590
Lys Ala Pro Leu Ser Ala Ser Met Ile Lys Arg Tyr Asp Glu His His
    595                 600                 605
Gln Asp Leu Thr Leu Leu Lys Ala Leu Val Arg Gln Gln Leu Pro Glu
    610                 615                 620
Lys Tyr Lys Glu Ile Phe Phe Asp Gln Ser Lys Asn Gly Tyr Ala Gly
625                 630                 635                 640
Tyr Ile Asp Gly Gly Ala Ser Gln Glu Glu Phe Tyr Lys Phe Ile Lys
                645                 650                 655
Pro Ile Leu Glu Lys Met Asp Gly Thr Glu Glu Leu Leu Val Lys Leu
                660                 665                 670
Asn Arg Glu Asp Leu Leu Arg Lys Gln Arg Thr Phe Asp Asn Gly Ser
                675                 680                 685
Ile Pro His Gln Ile His Leu Gly Glu Leu His Ala Ile Leu Arg Arg
    690                 695                 700
```

```
Gln Glu Asp Phe Tyr Pro Phe Leu Lys Asp Asn Arg Glu Lys Ile Glu
705                 710                 715                 720

Lys Ile Leu Thr Phe Arg Ile Pro Tyr Tyr Val Gly Pro Leu Ala Arg
            725                 730                 735

Gly Asn Ser Arg Phe Ala Trp Met Thr Arg Lys Ser Glu Glu Thr Ile
            740                 745                 750

Thr Pro Trp Asn Phe Glu Glu Val Val Asp Lys Gly Ala Ser Ala Gln
            755                 760                 765

Ser Phe Ile Glu Arg Met Thr Asn Phe Asp Lys Asn Leu Pro Asn Glu
770                 775                 780

Lys Val Leu Pro Lys His Ser Leu Leu Tyr Glu Tyr Phe Thr Val Tyr
785                 790                 795                 800

Asn Glu Leu Thr Lys Val Lys Tyr Val Thr Glu Gly Met Arg Lys Pro
                805                 810                 815

Ala Phe Leu Ser Gly Glu Gln Lys Lys Ala Ile Val Asp Leu Leu Phe
            820                 825                 830

Lys Thr Asn Arg Lys Val Thr Val Lys Gln Leu Lys Glu Asp Tyr Phe
            835                 840                 845

Lys Lys Ile Glu Cys Phe Asp Ser Val Glu Ile Ser Gly Val Glu Asp
850                 855                 860

Arg Phe Asn Ala Ser Leu Gly Thr Tyr His Asp Leu Leu Lys Ile Ile
865                 870                 875                 880

Lys Asp Lys Asp Phe Leu Asp Asn Glu Glu Asn Glu Asp Ile Leu Glu
            885                 890                 895

Asp Ile Val Leu Thr Leu Thr Leu Phe Glu Asp Arg Glu Met Ile Glu
            900                 905                 910

Glu Arg Leu Lys Thr Tyr Ala His Leu Phe Asp Asp Lys Val Met Lys
            915                 920                 925

Gln Leu Lys Arg Arg Arg Tyr Thr Gly Trp Gly Arg Leu Ser Arg Lys
930                 935                 940

Leu Ile Asn Gly Ile Arg Asp Lys Gln Ser Gly Lys Thr Ile Leu Asp
945                 950                 955                 960

Phe Leu Lys Ser Asp Gly Phe Ala Asn Arg Asn Phe Met Gln Leu Ile
            965                 970                 975

His Asp Asp Ser Leu Thr Phe Lys Glu Asp Ile Gln Lys Ala Gln Val
            980                 985                 990

Ser Gly Gln Gly Asp Ser Leu His Glu His Ile Ala Asn Leu Ala Gly
            995                 1000                1005

Ser Pro Ala Ile Lys Lys Gly Ile Leu Gln Thr Val Lys Val Val
    1010                1015                1020

Asp Glu Leu Val Lys Val Met Gly Arg His Lys Pro Glu Asn Ile
    1025                1030                1035

Val Ile Glu Met Ala Arg Glu Asn Gln Thr Thr Gln Lys Gly Gln
    1040                1045                1050

Lys Asn Ser Arg Glu Arg Met Lys Arg Ile Glu Glu Gly Ile Lys
    1055                1060                1065

Glu Leu Gly Ser Gln Ile Leu Lys Glu His Pro Val Glu Asn Thr
    1070                1075                1080

Gln Leu Gln Asn Glu Lys Leu Tyr Leu Tyr Tyr Leu Gln Asn Gly
    1085                1090                1095

Arg Asp Met Tyr Val Asp Gln Glu Leu Asp Ile Asn Arg Leu Ser
    1100                1105                1110
```

-continued

```
Asp Tyr Asp Val Asp His Ile Val Pro Gln Ser Phe Leu Lys Asp
    1115                1120                1125

Asp Ser Ile Asp Asn Lys Val Leu Thr Arg Ser Asp Lys Asn Arg
    1130                1135                1140

Gly Lys Ser Asp Asn Val Pro Ser Glu Glu Val Val Lys Lys Met
    1145                1150                1155

Lys Asn Tyr Trp Arg Gln Leu Leu Asn Ala Lys Leu Ile Thr Gln
    1160                1165                1170

Arg Lys Phe Asp Asn Leu Thr Lys Ala Glu Arg Gly Gly Leu Ser
    1175                1180                1185

Glu Leu Asp Lys Ala Gly Phe Ile Lys Arg Gln Leu Val Glu Thr
    1190                1195                1200

Arg Gln Ile Thr Lys His Val Ala Gln Ile Leu Asp Ser Arg Met
    1205                1210                1215

Asn Thr Lys Tyr Asp Glu Asn Asp Lys Leu Ile Arg Glu Val Lys
    1220                1225                1230

Val Ile Thr Leu Lys Ser Lys Leu Val Ser Asp Phe Arg Lys Asp
    1235                1240                1245

Phe Gln Phe Tyr Lys Val Arg Glu Ile Asn Asn Tyr His His Ala
    1250                1255                1260

His Asp Ala Tyr Leu Asn Ala Val Val Gly Thr Ala Leu Ile Lys
    1265                1270                1275

Lys Tyr Pro Lys Leu Glu Ser Glu Phe Val Tyr Gly Asp Tyr Lys
    1280                1285                1290

Val Tyr Asp Val Arg Lys Met Ile Ala Lys Ser Glu Gln Glu Ile
    1295                1300                1305

Gly Lys Ala Thr Ala Lys Tyr Phe Phe Tyr Ser Asn Ile Met Asn
    1310                1315                1320

Phe Phe Lys Thr Glu Ile Thr Leu Ala Asn Gly Glu Ile Arg Lys
    1325                1330                1335

Arg Pro Leu Ile Glu Thr Asn Gly Glu Thr Gly Glu Ile Val Trp
    1340                1345                1350

Asp Lys Gly Arg Asp Phe Ala Thr Val Arg Lys Val Leu Ser Met
    1355                1360                1365

Pro Gln Val Asn Ile Val Lys Lys Thr Glu Val Gln Thr Gly Gly
    1370                1375                1380

Phe Ser Lys Glu Ser Ile Leu Pro Lys Arg Asn Ser Asp Lys Leu
    1385                1390                1395

Ile Ala Arg Lys Lys Asp Trp Asp Pro Lys Lys Tyr Gly Gly Phe
    1400                1405                1410

Asp Ser Pro Thr Val Ala Tyr Ser Val Leu Val Val Ala Lys Val
    1415                1420                1425

Glu Lys Gly Lys Ser Lys Lys Leu Lys Ser Val Lys Glu Leu Leu
    1430                1435                1440

Gly Ile Thr Ile Met Glu Arg Ser Ser Phe Glu Lys Asn Pro Ile
    1445                1450                1455

Asp Phe Leu Glu Ala Lys Gly Tyr Lys Glu Val Lys Lys Asp Leu
    1460                1465                1470

Ile Ile Lys Leu Pro Lys Tyr Ser Leu Phe Glu Leu Glu Asn Gly
    1475                1480                1485

Arg Lys Arg Met Leu Ala Ser Ala Gly Glu Leu Gln Lys Gly Asn
    1490                1495                1500

Glu Leu Ala Leu Pro Ser Lys Tyr Val Asn Phe Leu Tyr Leu Ala
```

```
                1505                1510                1515

Ser His Tyr Glu Lys Leu Lys Gly Ser Pro Glu Asp Asn Glu Gln
        1520                1525                1530

Lys Gln Leu Phe Val Glu Gln His Lys His Tyr Leu Asp Glu Ile
    1535                1540                1545

Ile Glu Gln Ile Ser Glu Phe Ser Lys Arg Val Ile Leu Ala Asp
        1550                1555                1560

Ala Asn Leu Asp Lys Val Leu Ser Ala Tyr Asn Lys His Arg Asp
    1565                1570                1575

Lys Pro Ile Arg Glu Gln Ala Glu Asn Ile Ile His Leu Phe Thr
    1580                1585                1590

Leu Thr Asn Leu Gly Ala Pro Ala Ala Phe Lys Tyr Phe Asp Thr
    1595                1600                1605

Thr Ile Asp Arg Lys Arg Tyr Thr Ser Thr Lys Glu Val Leu Asp
    1610                1615                1620

Ala Thr Leu Ile His Gln Ser Ile Thr Gly Leu Tyr Glu Thr Arg
    1625                1630                1635

Ile Asp Leu Ser Gln Leu Gly Gly Asp His His His His His His
    1640                1645                1650

<210> SEQ ID NO 31
<211> LENGTH: 1653
<212> TYPE: PRT
<213> ORGANISM: Artificial Sequence
<220> FEATURE:
<223> OTHER INFORMATION: Synthetic Polypeptide

<400> SEQUENCE: 31

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Ser Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
```

```
            210                 215                 220
Phe Val Thr Ala Ala Gly Ile Asp His Gly Met Asp Glu Leu Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Leu Ala Leu
                260                 265                 270

Pro Lys Lys Arg Lys Val Met Asp Lys Lys Tyr Ser Ile Gly Leu
            275                 280                 285

Asp Ile Gly Thr Asn Ser Val Gly Trp Ala Val Ile Thr Asp Glu Tyr
            290                 295                 300

Lys Val Pro Ser Lys Lys Phe Lys Val Leu Gly Asn Thr Asp Arg His
305                 310                 315                 320

Ser Ile Lys Lys Asn Leu Ile Gly Ala Leu Leu Phe Asp Ser Gly Glu
                325                 330                 335

Thr Ala Glu Ala Thr Arg Leu Lys Arg Thr Ala Arg Arg Arg Tyr Thr
                340                 345                 350

Arg Arg Lys Asn Arg Ile Cys Tyr Leu Gln Glu Ile Phe Ser Asn Glu
            355                 360                 365

Met Ala Lys Val Asp Asp Ser Phe Phe His Arg Leu Glu Glu Ser Phe
370                 375                 380

Leu Val Glu Glu Asp Lys Lys His Glu Arg His Pro Ile Phe Gly Asn
385                 390                 395                 400

Ile Val Asp Glu Val Ala Tyr His Glu Lys Tyr Pro Thr Ile Tyr His
                405                 410                 415

Leu Arg Lys Lys Leu Val Asp Ser Thr Asp Lys Ala Asp Leu Arg Leu
                420                 425                 430

Ile Tyr Leu Ala Leu Ala His Met Ile Lys Phe Arg Gly His Phe Leu
            435                 440                 445

Ile Glu Gly Asp Leu Asn Pro Asp Asn Ser Asp Val Asp Lys Leu Phe
            450                 455                 460

Ile Gln Leu Val Gln Thr Tyr Asn Gln Leu Phe Glu Glu Asn Pro Ile
465                 470                 475                 480

Asn Ala Ser Gly Val Asp Ala Lys Ala Ile Leu Ser Ala Arg Leu Ser
                485                 490                 495

Lys Ser Arg Arg Leu Glu Asn Leu Ile Ala Gln Leu Pro Gly Glu Lys
            500                 505                 510

Lys Asn Gly Leu Phe Gly Asn Leu Ile Ala Leu Ser Leu Gly Leu Thr
            515                 520                 525

Pro Asn Phe Lys Ser Asn Phe Asp Leu Ala Glu Asp Ala Lys Leu Gln
            530                 535                 540

Leu Ser Lys Asp Thr Tyr Asp Asp Asp Leu Asp Asn Leu Leu Ala Gln
545                 550                 555                 560

Ile Gly Asp Gln Tyr Ala Asp Leu Phe Leu Ala Ala Lys Asn Leu Ser
                565                 570                 575

Asp Ala Ile Leu Leu Ser Asp Ile Leu Arg Val Asn Thr Glu Ile Thr
                580                 585                 590

Lys Ala Pro Leu Ser Ala Ser Met Ile Lys Arg Tyr Asp Glu His His
            595                 600                 605

Gln Asp Leu Thr Leu Leu Lys Ala Leu Val Arg Gln Gln Leu Pro Glu
            610                 615                 620

Lys Tyr Lys Glu Ile Phe Phe Asp Gln Ser Lys Asn Gly Tyr Ala Gly
625                 630                 635                 640
```

-continued

Tyr Ile Asp Gly Gly Ala Ser Gln Glu Glu Phe Tyr Lys Phe Ile Lys
            645                 650                 655

Pro Ile Leu Glu Lys Met Asp Gly Thr Glu Glu Leu Leu Val Lys Leu
            660                 665                 670

Asn Arg Glu Asp Leu Leu Arg Lys Gln Arg Thr Phe Asp Asn Gly Ser
            675                 680                 685

Ile Pro His Gln Ile His Leu Gly Glu Leu His Ala Ile Leu Arg Arg
690                 695                 700

Gln Glu Asp Phe Tyr Pro Phe Leu Lys Asp Asn Arg Glu Lys Ile Glu
705                 710                 715                 720

Lys Ile Leu Thr Phe Arg Ile Pro Tyr Tyr Val Gly Pro Leu Ala Arg
            725                 730                 735

Gly Asn Ser Arg Phe Ala Trp Met Thr Arg Lys Ser Glu Glu Thr Ile
            740                 745                 750

Thr Pro Trp Asn Phe Glu Glu Val Val Asp Lys Gly Ala Ser Ala Gln
            755                 760                 765

Ser Phe Ile Glu Arg Met Thr Asn Phe Asp Lys Asn Leu Pro Asn Glu
            770                 775                 780

Lys Val Leu Pro Lys His Ser Leu Leu Tyr Glu Tyr Phe Thr Val Tyr
785                 790                 795                 800

Asn Glu Leu Thr Lys Val Lys Tyr Val Thr Glu Gly Met Arg Lys Pro
            805                 810                 815

Ala Phe Leu Ser Gly Glu Gln Lys Lys Ala Ile Val Asp Leu Leu Phe
            820                 825                 830

Lys Thr Asn Arg Lys Val Thr Val Lys Gln Leu Lys Glu Asp Tyr Phe
            835                 840                 845

Lys Lys Ile Glu Cys Phe Asp Ser Val Glu Ile Ser Gly Val Glu Asp
850                 855                 860

Arg Phe Asn Ala Ser Leu Gly Thr Tyr His Asp Leu Leu Lys Ile Ile
865                 870                 875                 880

Lys Asp Lys Asp Phe Leu Asp Asn Glu Glu Asn Glu Asp Ile Leu Glu
            885                 890                 895

Asp Ile Val Leu Thr Leu Thr Leu Phe Glu Asp Arg Glu Met Ile Glu
            900                 905                 910

Glu Arg Leu Lys Thr Tyr Ala His Leu Phe Asp Asp Lys Val Met Lys
            915                 920                 925

Gln Leu Lys Arg Arg Arg Tyr Thr Gly Trp Gly Arg Leu Ser Arg Lys
930                 935                 940

Leu Ile Asn Gly Ile Arg Asp Lys Gln Ser Gly Lys Thr Ile Leu Asp
945                 950                 955                 960

Phe Leu Lys Ser Asp Gly Phe Ala Asn Arg Asn Phe Met Gln Leu Ile
            965                 970                 975

His Asp Asp Ser Leu Thr Phe Lys Glu Asp Ile Gln Lys Ala Gln Val
            980                 985                 990

Ser Gly Gln Gly Asp Ser Leu His Glu His Ile Ala Asn Leu Ala Gly
            995                 1000                1005

Ser Pro Ala Ile Lys Lys Gly Ile Leu Gln Thr Val Lys Val Val
            1010                1015                1020

Asp Glu Leu Val Lys Val Met Gly Arg His Lys Pro Glu Asn Ile
            1025                1030                1035

Val Ile Glu Met Ala Arg Glu Asn Gln Thr Thr Gln Lys Gly Gln
            1040                1045                1050

-continued

Lys Asn Ser Arg Glu Arg Met Lys Arg Ile Glu Glu Gly Ile Lys
1055              1060              1065

Glu Leu Gly Ser Gln Ile Leu Lys Glu His Pro Val Glu Asn Thr
1070              1075              1080

Gln Leu Gln Asn Glu Lys Leu Tyr Leu Tyr Tyr Leu Gln Asn Gly
1085              1090              1095

Arg Asp Met Tyr Val Asp Gln Glu Leu Asp Ile Asn Arg Leu Ser
1100              1105              1110

Asp Tyr Asp Val Asp His Ile Val Pro Gln Ser Phe Leu Lys Asp
1115              1120              1125

Asp Ser Ile Asp Asn Lys Val Leu Thr Arg Ser Asp Lys Asn Arg
1130              1135              1140

Gly Lys Ser Asp Asn Val Pro Ser Glu Glu Val Val Lys Lys Met
1145              1150              1155

Lys Asn Tyr Trp Arg Gln Leu Leu Asn Ala Lys Leu Ile Thr Gln
1160              1165              1170

Arg Lys Phe Asp Asn Leu Thr Lys Ala Glu Arg Gly Gly Leu Ser
1175              1180              1185

Glu Leu Asp Lys Ala Gly Phe Ile Lys Arg Gln Leu Val Glu Thr
1190              1195              1200

Arg Gln Ile Thr Lys His Val Ala Gln Ile Leu Asp Ser Arg Met
1205              1210              1215

Asn Thr Lys Tyr Asp Glu Asn Asp Lys Leu Ile Arg Glu Val Lys
1220              1225              1230

Val Ile Thr Leu Lys Ser Lys Leu Val Ser Asp Phe Arg Lys Asp
1235              1240              1245

Phe Gln Phe Tyr Lys Val Arg Glu Ile Asn Asn Tyr His His Ala
1250              1255              1260

His Asp Ala Tyr Leu Asn Ala Val Val Gly Thr Ala Leu Ile Lys
1265              1270              1275

Lys Tyr Pro Lys Leu Glu Ser Glu Phe Val Tyr Gly Asp Tyr Lys
1280              1285              1290

Val Tyr Asp Val Arg Lys Met Ile Ala Lys Ser Glu Gln Glu Ile
1295              1300              1305

Gly Lys Ala Thr Ala Lys Tyr Phe Phe Tyr Ser Asn Ile Met Asn
1310              1315              1320

Phe Phe Lys Thr Glu Ile Thr Leu Ala Asn Gly Glu Ile Arg Lys
1325              1330              1335

Arg Pro Leu Ile Glu Thr Asn Gly Glu Thr Gly Glu Ile Val Trp
1340              1345              1350

Asp Lys Gly Arg Asp Phe Ala Thr Val Arg Lys Val Leu Ser Met
1355              1360              1365

Pro Gln Val Asn Ile Val Lys Lys Thr Glu Val Gln Thr Gly Gly
1370              1375              1380

Phe Ser Lys Glu Ser Ile Leu Pro Lys Arg Asn Ser Asp Lys Leu
1385              1390              1395

Ile Ala Arg Lys Lys Asp Trp Asp Pro Lys Lys Tyr Gly Gly Phe
1400              1405              1410

Asp Ser Pro Thr Val Ala Tyr Ser Val Leu Val Val Ala Lys Val
1415              1420              1425

Glu Lys Gly Lys Ser Lys Lys Leu Lys Ser Val Lys Glu Leu Leu
1430              1435              1440

Gly Ile Thr Ile Met Glu Arg Ser Ser Phe Glu Lys Asn Pro Ile

-continued

```
            1445                1450                1455

Asp Phe Leu Glu Ala Lys Gly Tyr Lys Glu Val Lys Lys Asp Leu
        1460                1465                1470

Ile Ile Lys Leu Pro Lys Tyr Ser Leu Phe Glu Leu Glu Asn Gly
    1475                1480                1485

Arg Lys Arg Met Leu Ala Ser Ala Gly Glu Leu Gln Lys Gly Asn
1490                1495                1500

Glu Leu Ala Leu Pro Ser Lys Tyr Val Asn Phe Leu Tyr Leu Ala
    1505                1510                1515

Ser His Tyr Glu Lys Leu Lys Gly Ser Pro Glu Asp Asn Glu Gln
        1520                1525                1530

Lys Gln Leu Phe Val Glu Gln His Lys His Tyr Leu Asp Glu Ile
    1535                1540                1545

Ile Glu Gln Ile Ser Glu Phe Ser Lys Arg Val Ile Leu Ala Asp
    1550                1555                1560

Ala Asn Leu Asp Lys Val Leu Ser Ala Tyr Asn Lys His Arg Asp
    1565                1570                1575

Lys Pro Ile Arg Glu Gln Ala Glu Asn Ile Ile His Leu Phe Thr
1580                1585                1590

Leu Thr Asn Leu Gly Ala Pro Ala Ala Phe Lys Tyr Phe Asp Thr
    1595                1600                1605

Thr Ile Asp Arg Lys Arg Tyr Thr Ser Thr Lys Glu Val Leu Asp
    1610                1615                1620

Ala Thr Leu Ile His Gln Ser Ile Thr Gly Leu Tyr Glu Thr Arg
    1625                1630                1635

Ile Asp Leu Ser Gln Leu Gly Gly Asp His His His His His His
    1640                1645                1650
```

<210> SEQ ID NO 32
<211> LENGTH: 353
<212> TYPE: PRT
<213> ORGANISM: Artificial Sequence
<220> FEATURE:
<223> OTHER INFORMATION: Synthetic Polypeptide

<400> SEQUENCE: 32

```
Met Ala Ser Asn Leu Leu Thr Val His Gln Asn Leu Pro Ala Leu Pro
1               5                   10                  15

Val Asp Ala Thr Ser Asp Glu Val Arg Lys Asn Leu Met Asp Met Phe
            20                  25                  30

Arg Asp Arg Gln Ala Phe Ser Glu His Thr Trp Lys Met Leu Leu Ser
        35                  40                  45

Val Cys Arg Ser Trp Ala Ala Trp Cys Lys Leu Asn Asn Arg Lys Trp
    50                  55                  60

Phe Pro Ala Glu Pro Glu Asp Val Arg Asp Tyr Leu Leu Tyr Leu Gln
65                  70                  75                  80

Ala Arg Gly Leu Ala Val Lys Thr Ile Gln Gln His Leu Gly Gln Leu
                85                  90                  95

Asn Met Leu His Arg Arg Ser Gly Leu Pro Arg Pro Ser Asp Ser Asn
            100                 105                 110

Ala Val Ser Leu Val Met Arg Arg Ile Arg Lys Glu Asn Val Asp Ala
        115                 120                 125

Gly Glu Arg Ala Lys Gln Ala Leu Ala Phe Glu Arg Thr Asp Phe Asp
    130                 135                 140

Gln Val Arg Ser Leu Met Glu Asn Ser Asp Arg Cys Gln Asp Ile Arg
```

```
            145                 150                 155                 160
    Asn Leu Ala Phe Leu Gly Ile Ala Tyr Asn Thr Leu Arg Ile Ala
                    165                 170                 175
    Glu Ile Ala Arg Ile Arg Val Lys Asp Ile Ser Arg Thr Asp Gly Gly
                        180                 185                 190
    Arg Met Leu Ile His Ile Gly Arg Thr Lys Thr Leu Val Ser Thr Ala
                    195                 200                 205
    Gly Val Glu Lys Ala Leu Ser Leu Gly Val Thr Lys Leu Val Glu Arg
                    210                 215                 220
    Trp Ile Ser Val Ser Gly Val Ala Asp Asp Pro Asn Asn Tyr Leu Phe
    225                 230                 235                 240
    Cys Arg Val Arg Lys Asn Gly Val Ala Ala Pro Ser Ala Thr Ser Gln
                        245                 250                 255
    Leu Ser Thr Arg Ala Leu Glu Gly Ile Phe Glu Ala Thr His Arg Leu
                    260                 265                 270
    Ile Tyr Gly Ala Lys Asp Asp Ser Gly Gln Arg Tyr Leu Ala Trp Ser
                    275                 280                 285
    Gly His Ser Ala Arg Val Gly Ala Ala Arg Asp Met Ala Arg Ala Gly
                    290                 295                 300
    Val Ser Ile Pro Glu Ile Met Gln Ala Gly Gly Trp Thr Asn Val Asn
    305                 310                 315                 320
    Ile Val Met Asn Tyr Ile Arg Asn Leu Asp Ser Glu Thr Gly Ala Met
                        325                 330                 335
    Val Arg Leu Leu Glu Asp Gly Asp Gly Ser His His His His
                        340                 345                 350
    His

<210> SEQ ID NO 33
<211> LENGTH: 620
<212> TYPE: PRT
<213> ORGANISM: Artificial Sequence
<220> FEATURE:
<223> OTHER INFORMATION: Synthetic Polypeptide

<400> SEQUENCE: 33

Met Gly Ala Ser Lys Gly Glu Arg Leu Phe Arg Gly Lys Val Pro Ile
    1               5                   10                  15
    Leu Val Glu Leu Lys Gly Asp Val Asn Gly His Lys Phe Ser Val Arg
                        20                  25                  30
    Gly Lys Gly Lys Gly Asp Ala Thr Arg Gly Lys Leu Thr Leu Lys Phe
                    35                  40                  45
    Ile Cys Thr Thr Gly Lys Leu Pro Val Pro Trp Pro Thr Leu Val Thr
    50                  55                  60
    Thr Leu Thr Tyr Gly Val Gln Cys Phe Ser Arg Tyr Pro Lys His Met
    65                  70                  75                  80
    Lys Arg His Asp Phe Phe Lys Ser Ala Met Pro Lys Gly Tyr Val Gln
                        85                  90                  95
    Glu Arg Thr Ile Ser Phe Lys Lys Asp Gly Lys Tyr Lys Thr Arg Ala
                    100                 105                 110
    Glu Val Lys Phe Glu Gly Arg Thr Leu Val Asn Arg Ile Lys Leu Lys
                    115                 120                 125
    Gly Arg Asp Phe Lys Glu Lys Gly Asn Ile Leu Gly His Lys Leu Arg
                130                 135                 140
    Tyr Asn Phe Asn Ser His Lys Val Tyr Ile Thr Ala Asp Lys Arg Lys
    145                 150                 155                 160
```

```
Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
            180                 185                 190

Gly Pro Val Leu Leu Pro Arg Asn His Tyr Leu Ser Thr Arg Ser Lys
        195                 200                 205

Leu Ser Lys Asp Pro Lys Glu Lys Arg Asp His Met Val Leu Leu Glu
    210                 215                 220

Phe Val Thr Ala Ala Gly Ile Lys His Gly Arg Asp Glu Arg Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Ser Asn Leu
            260                 265                 270

Leu Thr Val His Gln Asn Leu Pro Ala Leu Pro Val Asp Ala Thr Ser
        275                 280                 285

Asp Glu Val Arg Lys Asn Leu Met Asp Met Phe Arg Asp Arg Gln Ala
    290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
        355                 360                 365

Arg Ser Gly Leu Pro Arg Pro Ser Asp Ser Asn Ala Val Ser Leu Val
    370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
        435                 440                 445

Arg Val Lys Asp Ile Ser Arg Thr Asp Gly Gly Arg Met Leu Ile His
    450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
        515                 520                 525

Leu Glu Gly Ile Phe Glu Ala Thr His Arg Leu Ile Tyr Gly Ala Lys
    530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575
```

```
Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
        595                 600                 605

Asp Gly Asp Gly Gly Ser His His His His His His
    610                 615                 620

<210> SEQ ID NO 34
<211> LENGTH: 620
<212> TYPE: PRT
<213> ORGANISM: Artificial Sequence
<220> FEATURE:
<223> OTHER INFORMATION: Synthetic Polypeptide

<400> SEQUENCE: 34

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Tyr Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Ser Asn Leu
            260                 265                 270

Leu Thr Val His Gln Asn Leu Pro Ala Leu Pro Val Asp Ala Thr Ser
        275                 280                 285

Asp Glu Val Arg Lys Asn Leu Met Asp Met Phe Arg Asp Arg Gln Ala
    290                 295                 300

Phe Ser Glu His Thr Trp Lys Met Leu Leu Ser Val Cys Arg Ser Trp
305                 310                 315                 320
```

```
Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
        355                 360                 365

Arg Ser Gly Leu Pro Arg Pro Ser Asp Ser Asn Ala Val Ser Leu Val
    370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
        435                 440                 445

Arg Val Lys Asp Ile Ser Arg Thr Asp Gly Gly Arg Met Leu Ile His
    450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
        515                 520                 525

Leu Glu Gly Ile Phe Glu Ala Thr His Arg Leu Ile Tyr Gly Ala Lys
    530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575

Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
        595                 600                 605

Asp Gly Asp Gly Gly Ser His His His His His
    610                 615                 620

<210> SEQ ID NO 35
<211> LENGTH: 53
<212> TYPE: PRT
<213> ORGANISM: Artificial Sequence
<220> FEATURE:
<223> OTHER INFORMATION: Synthetic Polypeptide

<400> SEQUENCE: 35

Gly Arg Ala Asp Ala Leu Asp Asp Phe Asp Leu Asp Met Leu Gly Ser
1               5                   10                  15

Asp Ala Leu Asp Asp Phe Asp Leu Asp Met Leu Gly Ser Asp Ala Leu
            20                  25                  30

Asp Asp Phe Asp Leu Asp Met Leu Gly Ser Asp Ala Leu Asp Asp Phe
        35                  40                  45

Asp Leu Asp Met Leu
    50
```

<210> SEQ ID NO 36
<211> LENGTH: 1210
<212> TYPE: PRT
<213> ORGANISM: Artificial Sequence
<220> FEATURE:
<223> OTHER INFORMATION: Synthetic Polypeptide

<400> SEQUENCE: 36

```
Met Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Lys His Met
65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
            100                 105                 110

Glu Val Lys Phe Glu Gly Arg Thr Leu Val Asn Arg Ile Lys Leu Lys
        115                 120                 125

Gly Arg Asp Phe Lys Glu Lys Gly Asn Ile Leu Gly His Lys Leu Arg
    130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
            180                 185                 190

Gly Pro Val Leu Leu Pro Arg Asn His Tyr Leu Ser Thr Arg Ser Lys
        195                 200                 205

Leu Ser Lys Asp Pro Lys Glu Lys Arg Asp His Met Val Leu Leu Glu
    210                 215                 220

Phe Val Thr Ala Ala Gly Ile Lys His Gly Arg Asp Glu Arg Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Thr Ala Pro Lys Lys
            260                 265                 270

Lys Arg Lys Val Gly Ile His Arg Gly Val Pro Met Val Asp Leu Arg
    275                 280                 285

Thr Leu Gly Tyr Ser Gln Gln Gln Gln Glu Lys Ile Lys Pro Lys Val
    290                 295                 300

Arg Ser Thr Val Ala Gln His His Glu Ala Leu Val Gly His Gly Phe
305                 310                 315                 320

Thr His Ala His Ile Val Ala Leu Ser Gln His Pro Ala Ala Leu Gly
                325                 330                 335

Thr Val Ala Val Lys Tyr Gln Asp Met Ile Ala Ala Leu Pro Glu Ala
            340                 345                 350

Thr His Glu Ala Ile Val Gly Val Gly Lys Gln Trp Ser Gly Ala Arg
        355                 360                 365
```

```
Ala Leu Glu Ala Leu Leu Thr Val Ala Gly Glu Leu Arg Gly Pro Pro
370                 375                 380

Leu Gln Leu Asp Thr Gly Gln Leu Leu Lys Ile Ala Lys Arg Gly Gly
385                 390                 395                 400

Val Thr Ala Val Glu Ala Val His Ala Trp Arg Asn Ala Leu Thr Gly
                405                 410                 415

Ala Pro Leu Asn Leu Thr Pro Asp Gln Val Ala Ile Ala Ser Asn
        420                 425                 430

Ile Gly Gly Lys Gln Ala Leu Glu Thr Val Gln Arg Leu Leu Pro Val
        435                 440                 445

Leu Cys Gln Asp His Gly Leu Thr Pro Glu Gln Val Val Ala Ile Ala
450                 455                 460

Ser Asn Ile Gly Gly Lys Gln Ala Leu Glu Thr Val Gln Arg Leu Leu
465                 470                 475                 480

Pro Val Leu Cys Gln Ala His Gly Leu Thr Pro Asp Gln Val Val Ala
                485                 490                 495

Ile Ala Ser Asn Gly Gly Lys Gln Ala Leu Glu Thr Val Gln Arg
                500                 505                 510

Leu Leu Pro Val Leu Cys Gln Ala His Gly Leu Thr Pro Ala Gln Val
                515                 520                 525

Val Ala Ile Ala Asn Asn Gly Gly Lys Gln Ala Leu Glu Thr Val
530                 535                 540

Gln Arg Leu Leu Pro Val Leu Cys Gln Asp His Gly Leu Thr Pro Asp
545                 550                 555                 560

Gln Val Val Ala Ile Ala Ser Asn Gly Gly Lys Gln Ala Leu Glu
                565                 570                 575

Thr Val Gln Arg Leu Leu Pro Val Leu Cys Gln Asp His Gly Leu Thr
                580                 585                 590

Pro Glu Gln Val Val Ala Ile Ala Ser Asn Ile Gly Gly Lys Gln Ala
        595                 600                 605

Leu Glu Thr Val Gln Arg Leu Leu Pro Val Leu Cys Gln Ala His Gly
        610                 615                 620

Leu Thr Pro Asp Gln Val Val Ala Ile Ala Ser His Asp Gly Gly Lys
625                 630                 635                 640

Gln Ala Leu Glu Thr Val Gln Arg Leu Leu Pro Val Leu Cys Gln Ala
                645                 650                 655

His Gly Leu Thr Pro Ala Gln Val Val Ala Ile Ala Ser His Asp Gly
                660                 665                 670

Gly Lys Gln Ala Leu Glu Thr Val Gln Arg Leu Leu Pro Val Leu Cys
        675                 680                 685

Gln Asp His Gly Leu Thr Pro Asp Gln Val Val Ala Ile Ala Ser Asn
690                 695                 700

Ile Gly Gly Lys Gln Ala Leu Glu Thr Val Gln Arg Leu Leu Pro Val
705                 710                 715                 720

Leu Cys Gln Asp His Gly Leu Thr Pro Glu Gln Val Val Ala Ile Ala
                725                 730                 735

Ser Asn Ile Gly Gly Lys Gln Ala Leu Glu Thr Val Gln Arg Leu Leu
                740                 745                 750

Pro Val Leu Cys Gln Ala His Gly Leu Thr Pro Asp Gln Val Val Ala
                755                 760                 765

Ile Ala Asn Asn Asn Gly Gly Lys Gln Ala Leu Glu Thr Val Gln Arg
        770                 775                 780

Leu Leu Pro Val Leu Cys Gln Ala His Gly Leu Thr Pro Ala Gln Val
```

```
                785                 790                 795                 800
Val Ala Ile Ala Ser Asn Gly Gly Lys Gln Ala Leu Glu Thr Val
                    805                 810                 815
Gln Arg Leu Leu Pro Val Leu Cys Gln Asp His Gly Leu Thr Pro Asp
                    820                 825                 830
Gln Val Val Ala Ile Ala Ser His Asp Gly Gly Lys Gln Ala Leu Glu
                    835                 840                 845
Thr Val Gln Arg Leu Leu Pro Val Leu Cys Gln Asp His Gly Leu Thr
    850                 855                 860
Pro Glu Gln Val Val Ala Ile Ala Ser Asn Gly Gly Gly Lys Gln Ala
865                 870                 875                 880
Leu Glu Thr Val Gln Arg Leu Leu Pro Val Leu Cys Gln Ala His Gly
                    885                 890                 895
Leu Thr Pro Asp Gln Val Val Ala Ile Ala Ser Asn Gly Gly Gly Lys
                    900                 905                 910
Gln Ala Leu Glu Thr Val Gln Arg Leu Leu Pro Val Leu Cys Gln Ala
                    915                 920                 925
His Gly Leu Thr Pro Ala Gln Val Val Ala Ile Ala Asn Asn Asn Gly
            930                 935                 940
Gly Lys Gln Ala Leu Glu Thr Val Gln Arg Leu Leu Pro Val Leu Cys
945                 950                 955                 960
Gln Asp His Gly Leu Thr Pro Asp Gln Val Val Ala Ile Ala Ser His
                    965                 970                 975
Asp Gly Gly Lys Gln Ala Leu Glu Thr Val Gln Arg Leu Leu Pro Val
                980                 985                 990
Leu Cys Gln Asp His Gly Leu Thr  Pro Glu Gln Val Val  Ala Ile Ala
            995                 1000                1005
Ser His  Asp Gly Gly Lys Gln  Ala Leu Glu Thr Val  Gln Arg Leu
    1010                1015                1020
Leu Pro  Val Leu Cys Gln Ala  His Gly Leu Thr Pro  Glu Gln Val
    1025                1030                1035
Val Ala  Ile Ala Ser Asn Ile  Gly Gly Arg Pro Ala  Leu Glu Ser
    1040                1045                1050
Ile Val  Ala Gln Leu Ser Arg  Pro Asp Pro Ala Leu  Ala Ala Leu
    1055                1060                1065
Thr Asn  Asp His Leu Val Ala  Leu Ala Cys Leu Gly  Gly Arg Pro
    1070                1075                1080
Ala Leu  Asp Ala Val Lys Lys  Gly Leu Pro His Ala  Pro Ala Leu
    1085                1090                1095
Ile Lys  Arg Thr Asn Arg Arg  Ile Pro Glu Arg Thr  Ser His Arg
    1100                1105                1110
Val Ala  Asp His Ala Gln Val  Val Arg Val Leu Gly  Phe Phe Gln
    1115                1120                1125
Cys His  Ser His Pro Ala Gln  Ala Phe Asp Asp Ala  Met Thr Gln
    1130                1135                1140
Phe Gly  Met Ser Gly Gly Gly  Ser Gly Arg Ala Asp  Ala Leu Asp
    1145                1150                1155
Asp Phe  Asp Leu Asp Met Leu  Gly Ser Asp Ala Leu  Asp Asp Phe
    1160                1165                1170
Asp Leu  Asp Met Leu Gly Ser  Asp Ala Leu Asp Asp  Phe Asp Leu
    1175                1180                1185
Asp Met  Leu Gly Ser Asp Ala  Leu Asp Asp Phe Asp  Leu Asp Met
    1190                1195                1200
```

Leu His His His His His His
    1205            1210

<210> SEQ ID NO 37
<211> LENGTH: 1210
<212> TYPE: PRT
<213> ORGANISM: Artificial Sequence
<220> FEATURE:
<223> OTHER INFORMATION: Synthetic Polypeptide

<400> SEQUENCE: 37

Met Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45

Ile Cys Thr Thr Gly Lys Leu Pro Val Pro Trp Pro Thr Leu Val Thr
50                  55                  60

Thr Leu Thr Tyr Gly Val Gln Cys Phe Ser Arg Tyr Pro Lys His Met
65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
            100                 105                 110

Glu Val Lys Phe Glu Gly Arg Thr Leu Val Asn Arg Ile Lys Leu Lys
        115                 120                 125

Gly Arg Asp Phe Lys Glu Lys Gly Asn Ile Leu Gly His Lys Leu Arg
130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
            180                 185                 190

Gly Pro Val Leu Leu Pro Arg Asn His Tyr Leu Ser Thr Arg Ser Lys
        195                 200                 205

Leu Ser Lys Asp Pro Lys Glu Lys Arg Asp His Met Val Leu Leu Glu
210                 215                 220

Phe Val Thr Ala Ala Gly Ile Lys His Gly Arg Asp Glu Arg Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Pro Lys Lys
            260                 265                 270

Lys Arg Lys Val Gly Ile His Arg Gly Val Pro Met Val Asp Leu Arg
        275                 280                 285

Thr Leu Gly Tyr Ser Gln Gln Gln Gln Glu Lys Ile Lys Pro Lys Val
290                 295                 300

Arg Ser Thr Val Ala Gln His His Glu Ala Leu Val Gly His Gly Phe
305                 310                 315                 320

Thr His Ala His Ile Val Ala Leu Ser Gln His Pro Ala Ala Leu Gly
                325                 330                 335

Thr Val Ala Val Lys Tyr Gln Asp Met Ile Ala Ala Leu Pro Glu Ala
            340                 345                 350

```
Thr His Glu Ala Ile Val Gly Val Gly Lys Gln Trp Ser Gly Ala Arg
        355                 360                 365

Ala Leu Glu Ala Leu Leu Thr Val Ala Gly Glu Leu Arg Gly Pro Pro
        370                 375                 380

Leu Gln Leu Asp Thr Gly Gln Leu Leu Lys Ile Ala Lys Arg Gly Gly
385                 390                 395                 400

Val Thr Ala Val Glu Ala Val His Ala Trp Arg Asn Ala Leu Thr Gly
                405                 410                 415

Ala Pro Leu Asn Leu Thr Pro Asp Gln Val Val Ala Ile Ala Ser Asn
                420                 425                 430

Gly Gly Gly Lys Gln Ala Leu Glu Thr Val Gln Arg Leu Leu Pro Val
                435                 440                 445

Leu Cys Gln Asp His Gly Leu Thr Pro Glu Gln Val Val Ala Ile Ala
                450                 455                 460

Asn Asn Asn Gly Gly Lys Gln Ala Leu Glu Thr Val Gln Arg Leu Leu
465                 470                 475                 480

Pro Val Leu Cys Gln Ala His Gly Leu Thr Pro Asp Gln Val Val Ala
                485                 490                 495

Ile Ala Asn Asn Asn Gly Gly Lys Gln Ala Leu Glu Thr Val Gln Arg
                500                 505                 510

Leu Leu Pro Val Leu Cys Gln Ala His Gly Leu Thr Pro Ala Gln Val
                515                 520                 525

Val Ala Ile Ala Ser His Asp Gly Gly Lys Gln Ala Leu Glu Thr Val
                530                 535                 540

Gln Arg Leu Leu Pro Val Leu Cys Gln Asp His Gly Leu Thr Pro Asp
545                 550                 555                 560

Gln Val Val Ala Ile Ala Ser His Asp Gly Gly Lys Gln Ala Leu Glu
                565                 570                 575

Thr Val Gln Arg Leu Leu Pro Val Leu Cys Gln Asp His Gly Leu Thr
                580                 585                 590

Pro Glu Gln Val Val Ala Ile Ala Ser His Asp Gly Gly Lys Gln Ala
                595                 600                 605

Leu Glu Thr Val Gln Arg Leu Leu Pro Val Leu Cys Gln Ala His Gly
                610                 615                 620

Leu Thr Pro Asp Gln Val Val Ala Ile Ala Ser His Asp Gly Gly Lys
625                 630                 635                 640

Gln Ala Leu Glu Thr Val Gln Arg Leu Leu Pro Val Leu Cys Gln Ala
                645                 650                 655

His Gly Leu Thr Pro Ala Gln Val Val Ala Ile Ala Asn Asn Asn Gly
                660                 665                 670

Gly Lys Gln Ala Leu Glu Thr Val Gln Arg Leu Leu Pro Val Leu Cys
                675                 680                 685

Gln Asp His Gly Leu Thr Pro Asp Gln Val Val Ala Ile Ala Asn Asn
                690                 695                 700

Asn Gly Gly Lys Gln Ala Leu Glu Thr Val Gln Arg Leu Leu Pro Val
705                 710                 715                 720

Leu Cys Gln Asp His Gly Leu Thr Pro Glu Gln Val Val Ala Ile Ala
                725                 730                 735

Ser His Asp Gly Gly Lys Gln Ala Leu Glu Thr Val Gln Arg Leu Leu
                740                 745                 750

Pro Val Leu Cys Gln Ala His Gly Leu Thr Pro Asp Gln Val Val Ala
                755                 760                 765
```

```
Ile Ala Asn Asn Asn Gly Gly Lys Gln Ala Leu Glu Thr Val Gln Arg
770                 775                 780

Leu Leu Pro Val Leu Cys Gln Ala His Gly Leu Thr Pro Ala Gln Val
785                 790                 795                 800

Val Ala Ile Ala Ser Asn Ile Gly Gly Lys Gln Ala Leu Glu Thr Val
            805                 810                 815

Gln Arg Leu Leu Pro Val Leu Cys Gln Asp His Gly Leu Thr Pro Asp
        820                 825                 830

Gln Val Val Ala Ile Ala Asn Asn Gly Gly Lys Gln Ala Leu Glu
                835                 840                 845

Thr Val Gln Arg Leu Leu Pro Val Leu Cys Gln Asp His Gly Leu Thr
850                 855                 860

Pro Glu Gln Val Val Ala Ile Ala Asn Asn Asn Gly Gly Lys Gln Ala
865                 870                 875                 880

Leu Glu Thr Val Gln Arg Leu Leu Pro Val Leu Cys Gln Ala His Gly
                885                 890                 895

Leu Thr Pro Asp Gln Val Val Ala Ile Ala Asn Asn Asn Gly Gly Lys
            900                 905                 910

Gln Ala Leu Glu Thr Val Gln Arg Leu Leu Pro Val Leu Cys Gln Ala
            915                 920                 925

His Gly Leu Thr Pro Ala Gln Val Val Ala Ile Ala Asn Asn Asn Gly
930                 935                 940

Gly Lys Gln Ala Leu Glu Thr Val Gln Arg Leu Leu Pro Val Leu Cys
945                 950                 955                 960

Gln Asp His Gly Leu Thr Pro Asp Gln Val Val Ala Ile Ala Ser Asn
            965                 970                 975

Gly Gly Gly Lys Gln Ala Leu Glu Thr Val Gln Arg Leu Leu Pro Val
            980                 985                 990

Leu Cys Gln Asp His Gly Leu Thr Pro Glu Gln Val Val Ala Ile Ala
        995                 1000                1005

Asn Asn Asn Gly Gly Lys Gln Ala Leu Glu Thr Val Gln Arg Leu
    1010                1015                1020

Leu Pro Val Leu Cys Gln Ala His Gly Leu Thr Pro Glu Gln Val
    1025                1030                1035

Val Ala Ile Ala Ser Asn Gly Gly Gly Arg Pro Ala Leu Glu Ser
    1040                1045                1050

Ile Val Ala Gln Leu Ser Arg Pro Asp Pro Ala Leu Ala Ala Leu
    1055                1060                1065

Thr Asn Asp His Leu Val Ala Leu Ala Cys Leu Gly Gly Arg Pro
    1070                1075                1080

Ala Leu Asp Ala Val Lys Lys Gly Leu Pro His Ala Pro Ala Leu
    1085                1090                1095

Ile Lys Arg Thr Asn Arg Arg Ile Pro Glu Arg Thr Ser His Arg
    1100                1105                1110

Val Ala Asp His Ala Gln Val Val Arg Val Leu Gly Phe Phe Gln
    1115                1120                1125

Cys His Ser His Pro Ala Gln Ala Phe Asp Asp Ala Met Thr Gln
    1130                1135                1140

Phe Gly Met Ser Gly Gly Ser Gly Arg Ala Asp Ala Leu Asp
    1145                1150                1155

Asp Phe Asp Leu Asp Met Leu Gly Ser Asp Ala Leu Asp Asp Phe
    1160                1165                1170

Asp Leu Asp Met Leu Gly Ser Asp Ala Leu Asp Asp Phe Asp Leu
```

```
            1175                1180                1185

Asp Met Leu Gly Ser Asp Ala Leu Asp Asp Phe Asp Leu Asp Met
        1190                1195                1200

Leu His His His His His
    1205                1210

<210> SEQ ID NO 38
<211> LENGTH: 1182
<212> TYPE: PRT
<213> ORGANISM: Artificial Sequence
<220> FEATURE:
<223> OTHER INFORMATION: Synthetic Polypeptide

<400> SEQUENCE: 38

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
50                  55                  60

Thr Leu Thr Tyr Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
210                 215                 220

Phe Val Thr Ala Ala Gly Ile Asp His Gly Met Asp Glu Leu Tyr Lys
225                 230                 235                 240

Ala Pro Lys Lys Lys Arg Lys Val Gly Ile His Arg Gly Val Pro Met
                245                 250                 255

Val Asp Leu Arg Thr Leu Gly Tyr Ser Gln Gln Gln Gln Glu Lys Ile
            260                 265                 270

Lys Pro Lys Val Arg Ser Thr Val Ala Gln His His Glu Ala Leu Val
        275                 280                 285

Gly His Gly Phe Thr His Ala His Ile Val Ala Leu Ser Gln His Pro
290                 295                 300

Ala Ala Leu Gly Thr Val Ala Val Lys Tyr Gln Asp Met Ile Ala Ala
305                 310                 315                 320

Leu Pro Glu Ala Thr His Glu Ala Ile Val Gly Val Gly Lys Gln Trp
```

```
            325                 330                 335
Ser Gly Ala Arg Ala Leu Glu Ala Leu Leu Thr Val Ala Gly Glu Leu
            340                 345                 350
Arg Gly Pro Pro Leu Gln Leu Asp Thr Gly Gln Leu Leu Lys Ile Ala
            355                 360                 365
Lys Arg Gly Gly Val Thr Ala Val Glu Ala Val His Ala Trp Arg Asn
            370                 375                 380
Ala Leu Thr Gly Ala Pro Leu Asn Leu Thr Pro Asp Gln Val Val Ala
385                 390                 395                 400
Ile Ala Ser Asn Ile Gly Gly Lys Gln Ala Leu Glu Thr Val Gln Arg
                405                 410                 415
Leu Leu Pro Val Leu Cys Gln Asp His Gly Leu Thr Pro Glu Gln Val
            420                 425                 430
Val Ala Ile Ala Ser Asn Ile Gly Gly Lys Gln Ala Leu Glu Thr Val
            435                 440                 445
Gln Arg Leu Leu Pro Val Leu Cys Gln Ala His Gly Leu Thr Pro Asp
450                 455                 460
Gln Val Val Ala Ile Ala Ser Asn Gly Gly Lys Gln Ala Leu Glu
465                 470                 475                 480
Thr Val Gln Arg Leu Leu Pro Val Leu Cys Gln Ala His Gly Leu Thr
                485                 490                 495
Pro Ala Gln Val Val Ala Ile Ala Asn Asn Asn Gly Gly Lys Gln Ala
            500                 505                 510
Leu Glu Thr Val Gln Arg Leu Leu Pro Val Leu Cys Gln Asp His Gly
            515                 520                 525
Leu Thr Pro Asp Gln Val Val Ala Ile Ala Ser Asn Gly Gly Gly Lys
            530                 535                 540
Gln Ala Leu Glu Thr Val Gln Arg Leu Leu Pro Val Leu Cys Gln Asp
545                 550                 555                 560
His Gly Leu Thr Pro Glu Gln Val Val Ala Ile Ala Ser Asn Ile Gly
                565                 570                 575
Gly Lys Gln Ala Leu Glu Thr Val Gln Arg Leu Leu Pro Val Leu Cys
            580                 585                 590
Gln Ala His Gly Leu Thr Pro Asp Gln Val Val Ala Ile Ala Ser His
            595                 600                 605
Asp Gly Gly Lys Gln Ala Leu Glu Thr Val Gln Arg Leu Leu Pro Val
            610                 615                 620
Leu Cys Gln Ala His Gly Leu Thr Pro Ala Gln Val Val Ala Ile Ala
625                 630                 635                 640
Ser His Asp Gly Gly Lys Gln Ala Leu Glu Thr Val Gln Arg Leu Leu
                645                 650                 655
Pro Val Leu Cys Gln Asp His Gly Leu Thr Pro Asp Gln Val Val Ala
            660                 665                 670
Ile Ala Ser Asn Ile Gly Gly Lys Gln Ala Leu Glu Thr Val Gln Arg
            675                 680                 685
Leu Leu Pro Val Leu Cys Gln Asp His Gly Leu Thr Pro Glu Gln Val
            690                 695                 700
Val Ala Ile Ala Ser Asn Ile Gly Gly Lys Gln Ala Leu Glu Thr Val
705                 710                 715                 720
Gln Arg Leu Leu Pro Val Leu Cys Gln Ala His Gly Leu Thr Pro Asp
                725                 730                 735
Gln Val Val Ala Ile Ala Asn Asn Asn Gly Gly Lys Gln Ala Leu Glu
            740                 745                 750
```

-continued

```
Thr Val Gln Arg Leu Leu Pro Val Leu Cys Gln Ala His Gly Leu Thr
            755                 760                 765

Pro Ala Gln Val Val Ala Ile Ala Ser Asn Gly Gly Gly Lys Gln Ala
    770                 775                 780

Leu Glu Thr Val Gln Arg Leu Leu Pro Val Leu Cys Gln Asp His Gly
785                 790                 795                 800

Leu Thr Pro Asp Gln Val Val Ala Ile Ala Ser His Asp Gly Gly Lys
                805                 810                 815

Gln Ala Leu Glu Thr Val Gln Arg Leu Leu Pro Val Leu Cys Gln Asp
            820                 825                 830

His Gly Leu Thr Pro Glu Gln Val Val Ala Ile Ala Ser Asn Gly Gly
                835                 840                 845

Gly Lys Gln Ala Leu Glu Thr Val Gln Arg Leu Leu Pro Val Leu Cys
850                 855                 860

Gln Ala His Gly Leu Thr Pro Asp Gln Val Val Ala Ile Ala Ser Asn
865                 870                 875                 880

Gly Gly Gly Lys Gln Ala Leu Glu Thr Val Gln Arg Leu Leu Pro Val
                885                 890                 895

Leu Cys Gln Ala His Gly Leu Thr Pro Ala Gln Val Val Ala Ile Ala
            900                 905                 910

Asn Asn Asn Gly Gly Lys Gln Ala Leu Glu Thr Val Gln Arg Leu Leu
            915                 920                 925

Pro Val Leu Cys Gln Asp His Gly Leu Thr Pro Asp Gln Val Val Ala
            930                 935                 940

Ile Ala Ser His Asp Gly Gly Lys Gln Ala Leu Glu Thr Val Gln Arg
945                 950                 955                 960

Leu Leu Pro Val Leu Cys Gln Asp His Gly Leu Thr Pro Glu Gln Val
                965                 970                 975

Val Ala Ile Ala Ser His Asp Gly Gly Lys Gln Ala Leu Glu Thr Val
            980                 985                 990

Gln Arg Leu Leu Pro Val Leu Cys Gln Ala His Gly Leu Thr Pro Glu
            995                 1000                1005

Gln Val Val Ala Ile Ala Ser Asn Ile Gly Gly Arg Pro Ala Leu
    1010                1015                1020

Glu Ser Ile Val Ala Gln Leu Ser Arg Pro Asp Pro Ala Leu Ala
    1025                1030                1035

Ala Leu Thr Asn Asp His Leu Val Ala Leu Ala Cys Leu Gly Gly
    1040                1045                1050

Arg Pro Ala Leu Asp Ala Val Lys Lys Gly Leu Pro His Ala Pro
    1055                1060                1065

Ala Leu Ile Lys Arg Thr Asn Arg Arg Ile Pro Glu Arg Thr Ser
    1070                1075                1080

His Arg Val Ala Asp His Ala Gln Val Val Arg Val Leu Gly Phe
    1085                1090                1095

Phe Gln Cys His Ser His Pro Ala Gln Ala Phe Asp Asp Ala Met
    1100                1105                1110

Thr Gln Phe Gly Met Ser Gly Gly Gly Ser Gly Arg Ala Asp Ala
    1115                1120                1125

Leu Asp Asp Phe Asp Leu Asp Met Leu Gly Ser Asp Ala Leu Asp
    1130                1135                1140

Asp Phe Asp Leu Asp Met Leu Gly Ser Asp Ala Leu Asp Asp Phe
    1145                1150                1155
```

```
Asp Leu Asp Met Leu Gly Ser Asp Ala Leu Asp Asp Phe Asp Leu
    1160                1165                1170
Asp Met Leu His His His His His His
    1175                1180

<210> SEQ ID NO 39
<211> LENGTH: 1182
<212> TYPE: PRT
<213> ORGANISM: Artificial Sequence
<220> FEATURE:
<223> OTHER INFORMATION: Synthetic Polypeptide

<400> SEQUENCE: 39

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Tyr Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240

Ala Pro Lys Lys Lys Arg Lys Val Gly Ile His Arg Gly Val Pro Met
                245                 250                 255

Val Asp Leu Arg Thr Leu Gly Tyr Ser Gln Gln Gln Gln Glu Lys Ile
            260                 265                 270

Lys Pro Lys Val Arg Ser Thr Val Ala Gln His His Glu Ala Leu Val
        275                 280                 285

Gly His Gly Phe Thr His Ala His Ile Val Ala Leu Ser Gln His Pro
    290                 295                 300

Ala Ala Leu Gly Thr Val Ala Val Lys Tyr Gln Asp Met Ile Ala Ala
305                 310                 315                 320

Leu Pro Glu Ala Thr His Glu Ala Ile Val Gly Val Gly Lys Gln Trp
                325                 330                 335
```

-continued

```
Ser Gly Ala Arg Ala Leu Glu Ala Leu Leu Thr Val Ala Gly Glu Leu
            340                 345                 350

Arg Gly Pro Pro Leu Gln Leu Asp Thr Gly Gln Leu Leu Lys Ile Ala
        355                 360                 365

Lys Arg Gly Gly Val Thr Ala Val Glu Ala Val His Ala Trp Arg Asn
    370                 375                 380

Ala Leu Thr Gly Ala Pro Leu Asn Leu Thr Pro Asp Gln Val Val Ala
385                 390                 395                 400

Ile Ala Ser Asn Gly Gly Lys Gln Ala Leu Glu Thr Val Gln Arg
                405                 410                 415

Leu Leu Pro Val Leu Cys Gln Asp His Gly Leu Thr Pro Glu Gln Val
            420                 425                 430

Val Ala Ile Ala Asn Asn Asn Gly Gly Lys Gln Ala Leu Glu Thr Val
            435                 440                 445

Gln Arg Leu Leu Pro Val Leu Cys Gln Ala His Gly Leu Thr Pro Asp
    450                 455                 460

Gln Val Val Ala Ile Ala Asn Asn Asn Gly Gly Lys Gln Ala Leu Glu
465                 470                 475                 480

Thr Val Gln Arg Leu Leu Pro Val Leu Cys Gln Ala His Gly Leu Thr
            485                 490                 495

Pro Ala Gln Val Val Ala Ile Ala Ser His Asp Gly Gly Lys Gln Ala
            500                 505                 510

Leu Glu Thr Val Gln Arg Leu Leu Pro Val Leu Cys Gln Asp His Gly
        515                 520                 525

Leu Thr Pro Asp Gln Val Val Ala Ile Ala Ser His Asp Gly Gly Lys
    530                 535                 540

Gln Ala Leu Glu Thr Val Gln Arg Leu Leu Pro Val Leu Cys Gln Asp
545                 550                 555                 560

His Gly Leu Thr Pro Glu Gln Val Val Ala Ile Ala Ser His Asp Gly
            565                 570                 575

Gly Lys Gln Ala Leu Glu Thr Val Gln Arg Leu Leu Pro Val Leu Cys
            580                 585                 590

Gln Ala His Gly Leu Thr Pro Asp Gln Val Val Ala Ile Ala Ser His
        595                 600                 605

Asp Gly Gly Lys Gln Ala Leu Glu Thr Val Gln Arg Leu Leu Pro Val
    610                 615                 620

Leu Cys Gln Ala His Gly Leu Thr Pro Ala Gln Val Val Ala Ile Ala
625                 630                 635                 640

Asn Asn Asn Gly Gly Lys Gln Ala Leu Glu Thr Val Gln Arg Leu Leu
            645                 650                 655

Pro Val Leu Cys Gln Asp His Gly Leu Thr Pro Asp Gln Val Val Ala
            660                 665                 670

Ile Ala Asn Asn Asn Gly Gly Lys Gln Ala Leu Glu Thr Val Gln Arg
        675                 680                 685

Leu Leu Pro Val Leu Cys Gln Asp His Gly Leu Thr Pro Glu Gln Val
    690                 695                 700

Val Ala Ile Ala Ser His Asp Gly Gly Lys Gln Ala Leu Glu Thr Val
705                 710                 715                 720

Gln Arg Leu Leu Pro Val Leu Cys Gln Ala His Gly Leu Thr Pro Asp
            725                 730                 735

Gln Val Val Ala Ile Ala Asn Asn Asn Gly Gly Lys Gln Ala Leu Glu
            740                 745                 750

Thr Val Gln Arg Leu Leu Pro Val Leu Cys Gln Ala His Gly Leu Thr
```

```
            755                 760                 765
Pro Ala Gln Val Val Ala Ile Ala Ser Asn Ile Gly Gly Lys Gln Ala
            770                 775                 780
Leu Glu Thr Val Gln Arg Leu Leu Pro Val Leu Cys Gln Asp His Gly
785                 790                 795                 800
Leu Thr Pro Asp Gln Val Ala Ile Ala Asn Asn Asn Gly Gly Lys
                805                 810                 815
Gln Ala Leu Glu Thr Val Gln Arg Leu Leu Pro Val Leu Cys Gln Asp
            820                 825                 830
His Gly Leu Thr Pro Glu Gln Val Ala Ile Ala Asn Asn Asn Gly
            835                 840                 845
Gly Lys Gln Ala Leu Glu Thr Val Gln Arg Leu Leu Pro Val Leu Cys
850                 855                 860
Gln Ala His Gly Leu Thr Pro Asp Gln Val Val Ala Ile Ala Asn Asn
865                 870                 875                 880
Asn Gly Gly Lys Gln Ala Leu Glu Thr Val Gln Arg Leu Leu Pro Val
            885                 890                 895
Leu Cys Gln Ala His Gly Leu Thr Pro Ala Gln Val Val Ala Ile Ala
            900                 905                 910
Asn Asn Asn Gly Gly Lys Gln Ala Leu Glu Thr Val Gln Arg Leu Leu
            915                 920                 925
Pro Val Leu Cys Gln Asp His Gly Leu Thr Pro Asp Gln Val Val Ala
930                 935                 940
Ile Ala Ser Asn Gly Gly Gly Lys Gln Ala Leu Glu Thr Val Gln Arg
945                 950                 955                 960
Leu Leu Pro Val Leu Cys Gln Asp His Gly Leu Thr Pro Glu Gln Val
                965                 970                 975
Val Ala Ile Ala Asn Asn Asn Gly Gly Lys Gln Ala Leu Glu Thr Val
            980                 985                 990
Gln Arg Leu Leu Pro Val Leu Cys Gln Ala His Gly Leu Thr Pro Glu
            995                 1000                1005
Gln Val Val Ala Ile Ala Ser Asn Gly Gly Gly Arg Pro Ala Leu
            1010                1015                1020
Glu Ser Ile Val Ala Gln Leu Ser Arg Pro Asp Pro Ala Leu Ala
            1025                1030                1035
Ala Leu Thr Asn Asp His Leu Val Ala Leu Ala Cys Leu Gly Gly
            1040                1045                1050
Arg Pro Ala Leu Asp Ala Val Lys Lys Gly Leu Pro His Ala Pro
            1055                1060                1065
Ala Leu Ile Lys Arg Thr Asn Arg Arg Ile Pro Glu Arg Thr Ser
            1070                1075                1080
His Arg Val Ala Asp His Ala Gln Val Val Arg Val Leu Gly Phe
            1085                1090                1095
Phe Gln Cys His Ser His Pro Ala Gln Ala Phe Asp Asp Ala Met
            1100                1105                1110
Thr Gln Phe Gly Met Ser Gly Gly Gly Ser Gly Arg Ala Asp Ala
            1115                1120                1125
Leu Asp Asp Phe Asp Leu Asp Met Leu Gly Ser Asp Ala Leu Asp
            1130                1135                1140
Asp Phe Asp Leu Asp Met Leu Gly Ser Asp Ala Leu Asp Asp Phe
            1145                1150                1155
Asp Leu Asp Met Leu Gly Ser Asp Ala Leu Asp Asp Phe Asp Leu
            1160                1165                1170
```

```
              Asp Met  Leu His His His  His His
                 1175             1180

<210> SEQ ID NO 40
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 40

Met Gly Ala Ser Lys Gly Glu Leu Phe Asp Gly Val Val Pro Ile
1               5                   10                  15

Leu Val Glu Leu Asp Gly Asp Val Asn Gly His Glu Phe Ser Val Arg
                20                  25                  30

Gly Glu Gly Glu Gly Asp Ala Thr Glu Gly Glu Leu Thr Leu Lys Phe
                35                  40                  45

Ile Cys Thr Thr Gly Glu Leu Pro Val Pro Trp Pro Thr Leu Val Thr
50                  55                  60

Thr Leu Thr Tyr Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
                100                 105                 110

Glu Val Lys Phe Glu Gly Asp Thr Leu Val Asn Arg Ile Glu Leu Lys
                115                 120                 125

Gly Ile Asp Phe Lys Glu Asp Gly Asn Ile Leu Gly His Lys Leu Glu
            130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
                180                 185                 190

Gly Pro Val Leu Leu Pro Asp Asp His Tyr Leu Ser Thr Glu Ser Ala
                195                 200                 205

Leu Ser Lys Asp Pro Asn Glu Asp Arg Asp His Met Val Leu Leu Glu
            210                 215                 220

Phe Val Thr Ala Ala Gly Ile Asp His Gly Met Asp Glu Leu Tyr Lys
225                 230                 235                 240

<210> SEQ ID NO 41
<211> LENGTH: 153
<212> TYPE: PRT
<213> ORGANISM: Artificial Sequence
<220> FEATURE:
<223> OTHER INFORMATION: Synthetic Polypeptide

<400> SEQUENCE: 41

Ala Pro Lys Lys Lys Arg Lys Val Gly Ile His Arg Gly Val Pro Met
1               5                   10                  15

Val Asp Leu Arg Thr Leu Gly Tyr Ser Gln Gln Gln Gln Glu Lys Ile
                20                  25                  30

Lys Pro Lys Val Arg Ser Thr Val Ala Gln His His Glu Ala Leu Val
                35                  40                  45

Gly His Gly Phe Thr His Ala His Ile Val Ala Leu Ser Gln His Pro
```

```
            50                  55                  60
Ala Ala Leu Gly Thr Val Ala Val Lys Tyr Gln Asp Met Ile Ala Ala
 65                  70                  75                  80

Leu Pro Glu Ala Thr His Glu Ala Ile Val Gly Val Gly Lys Gln Trp
                 85                  90                  95

Ser Gly Ala Arg Ala Leu Glu Ala Leu Leu Thr Val Ala Gly Glu Leu
            100                 105                 110

Arg Gly Pro Pro Leu Gln Leu Asp Thr Gly Gln Leu Leu Lys Ile Ala
        115                 120                 125

Lys Arg Gly Gly Val Thr Ala Val Glu Ala Val His Ala Trp Arg Asn
    130                 135                 140

Ala Leu Thr Gly Ala Pro Leu Asn Leu
145                 150
```

<210> SEQ ID NO 42
<211> LENGTH: 99
<212> TYPE: PRT
<213> ORGANISM: Artificial Sequence
<220> FEATURE:
<223> OTHER INFORMATION: Synthetic Polypeptide

<400> SEQUENCE: 42

```
Leu Glu Ser Ile Val Ala Gln Leu Ser Arg Pro Asp Pro Ala Leu Ala
 1               5                  10                  15

Ala Leu Thr Asn Asp His Leu Val Ala Leu Ala Cys Leu Gly Gly Arg
                20                  25                  30

Pro Ala Leu Asp Ala Val Lys Lys Gly Leu Pro His Ala Pro Ala Leu
            35                  40                  45

Ile Lys Arg Thr Asn Arg Arg Ile Pro Glu Arg Thr Ser His Arg Val
        50                  55                  60

Ala Asp His Ala Gln Val Val Arg Val Leu Gly Phe Phe Gln Cys His
 65                  70                  75                  80

Ser His Pro Ala Gln Ala Phe Asp Asp Ala Met Thr Gln Phe Gly Met
                85                  90                  95

Ser Gly Gly
```

<210> SEQ ID NO 43
<211> LENGTH: 4104
<212> TYPE: DNA
<213> ORGANISM: Streptococcus pyogenes

<400> SEQUENCE: 43

```
atggataaga aatactcaat aggcttagat atcggcacaa atagcgtcgg atgggcggtg     60
atcactgatg attataaggt tccgtctaaa aagttcaagg ttctgggaaa tacagaccgc    120
cacagtatca aaaaaaatct tatagggct cttttatttg gcagtggaga gacagcggaa    180
gcgactcgtc tcaaacggac agctcgtaga aggtatacac gtcggaagaa tcgtatttgt    240
tatctacagg agatttttc aaatgagatg gcgaaagtag atgatagttt ctttcatcga    300
cttgaagagt ctttttttgg ggaagaagac aagaagcatg aacgtcatcc tatttttgga    360
aatatagtag atgaagttgc ttatcatgag aaatatccaa ctatctatca tctgcgaaaa    420
aaattggcag attctactga taaagcggat ttgcgcttaa tctatttggc cttagcgcat    480
atgattaagt tcgtggtca tttttttgatt gagggagatt taaatcctga taatagtgat    540
gtggacaaac tatttatcca gttggtacaa atctacaatc aattatttga agaaaaccct    600
attaacgcaa gtagagtaga tgctaaagcg attctttctg cacgattgag taaatcaaga    660
```

```
cgattagaaa atctcattgc tcagctcccc ggtgagaaga gaaatggctt gtttgggaat    720
ctcattgctt tgtcattggg attgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatagt gaaataacta aggctcccct atcagcttca    960
atgattaagc gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agactttat ccattttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgagggaa tgcgaaaacc agcatttctt   1620
tcaggtgaac agaagaaagc cattgttgat ttactcttca aaacaaatcg aaaagtaacc   1680
gttaagcaat aaaagaaga ttatttcaaa aaaatagaat gttttgatag tgttgaaatt   1740
tcaggagttg aagatagatt taatgcttca ttaggcgcct accatgattt gctaaaaatt   1800
attaaagata aagattttt ggataatgaa gaaaatgaag atatcttaga ggatattgtt   1860
ttaacattga ccttatttga agatagggg atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gattttttga aatcagatgg ttttgccaat cgcaattta tgcagctgat ccatgatgat   2100
agtttgacat ttaagaaga tattcaaaaa gcacaggtgt ctggacaagg ccatagttta   2160
catgaacaga ttgctaactt agctggcagt cctgctatta aaaaaggtat tttacagact   2220
gtaaaaattg ttgatgaact ggtcaaagta atggggcata agccagaaaa tatcgttatt   2280
gaaatggcac gtgaaaatca gacaactcaa aagggccaga aaattcgcg agagcgtatg   2340 aaacgaatcg aagaaggtat caagaattta ggaagtcaga ttcttaaaga gcatcctgtt   2400
gaaaatactc aattgcaaaa tgaaaagctc tatctctatt atctacaaaa tggaagagac   2460
atgtatgtgg accaagaatt agatattaat cgtttaagtg attatgatgt cgatcacatt   2520
gttccacaaa gtttcattaa agacgattca atagacaata aggtactaac gcgttctgat   2580
aaaaatcgtg gtaaatcgga taacgttcca agtgaagaag tagtcaaaaa gatgaaaaac   2640
tattggagac aacttctaaa cgccaagtta atcactcaac gtaagtttga taatttaacg   2700
aaagctgaac gtggaggttt gagtgaactt gataaagctg gttttatcaa acgccaattg   2760
gttgaaactc gccaaatcac taagcatgtg gcacaaattt tggatagtcg catgaatact   2820
aaatacgatg aaaatgataa acttattcga gaggttaaag tgattacctt aaaatctaaa   2880
ttagtttctg acttccgaaa agatttccaa ttctataaag tacgtgagat taacaattac   2940
catcatgccc atgatgcgta tctaaatgcc gtcgttggaa ctgctttgat taagaaatat   3000
```

-continued

```
ccaaaacttg aatcggagtt tgtctatggt gattataaag tttatgatgt tcgtaaaatg      3060
attgctaagt ctgagcaaga aataggcaaa gcaaccgcaa atatttctt  ttactctaat      3120 atcatgaact tcttcaaaac agaaattaca cttgcaaatg agagagattcg caaacgccct     3180 ctaatcgaaa ctaatgggga aactggagaa attgtctggg ataaagggcg agattttgcc     3240
acagtgcgca aagtattgtc catgccccaa gtcaatattg tcaagaaaac agaagtacag     3300
acaggcggat tctccaagga gtcaattta  ccaaaaagaa attcggacaa gcttattgct      3360
cgtaaaaaag actgggatcc aaaaaaatat ggtggttttg atagtccaac ggtagcttat     3420
tcagtcctag tggttgctaa ggtggaaaaa gggaaatcga agaagttaaa atccgttaaa     3480
gagttactag ggatcacaat tatggaaaga agttcctttg aaaaaaatcc gattgacttt     3540
ttagaagcta aaggatataa ggaagttaaa aaagacttaa tcattaaact acctaaatat     3600 agtcttttg  agttagaaaa cggtcgtaaa cggatgctgg ctagtgccgg agaattacaa     3660
aaaggaaatg agctggctct gccaagcaaa tatgtgaatt ttttatattt agctagtcat     3720
tatgaaaagt tgaagggtag tccagaagat aacgaacaaa aacaattgtt tgtggagcag     3780
cataagcatt atttagatga gattattgag caaatcagtg aattttctaa gcgtgttatt     3840
ttagcagatg ccaatttaga taaagttctt agtgcatata acaaacatag agacaaacca     3900
atacgtgaac aagcagaaaa tattattcat ttatttacgt tgacgaatct tggagctccc     3960 gctgcttta  aatattttga tacaacaatt gatcgtaaac gatatacgtc tacaaaagaa     4020
gttttagatg ccactcttat ccatcaatcc atcactggtc tttatgaaac acgcattgat     4080
ttgagtcagc taggaggtga ctga                                             4104
```

<210> SEQ ID NO 44
<211> LENGTH: 1368
<212> TYPE: PRT
<213> ORGANISM: Streptococcus pyogenes

<400> SEQUENCE: 44

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

-continued

Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
        290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp

```
                595                 600                 605
Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                1000                1005

Val Tyr Gly Asp Tyr Lys Val Tyr Asp Val Arg Lys Met Ile Ala
                1010                1015                1020
```

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 45
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 45

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415
```

-continued

Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys

```
                835                 840                 845
Asp Asp Ser Ile Asp Asn Lys Val Leu Thr Arg Ser Asp Lys Asn Arg
            850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
```

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 46
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 46

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

-continued

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
              660                 665                 670

Lys Gln Ser Gly Lys Thr Ile Leu Asp Phe Leu Lys Ser Asp Gly Phe
          675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
              725                 730                 735

Ile Leu Gln Thr Val Lys Val Val Asp Glu Leu Val Lys Val Met Gly
              740                 745                 750

Arg His Lys Pro Glu Asn Ile Val Ile Glu Met Ala Arg Glu Asn Gln
              755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
              805                 810                 815

Gln Asn Gly Arg Asp Met Tyr Val Asp Gln Glu Leu Asp Ile Asn Arg
              820                 825                 830

Leu Ser Asp Tyr Asp Val Asp His Ile Val Pro Gln Ser Phe Leu Lys
          835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
              885                 890                 895

Phe Asp Asn Leu Thr Lys Ala Glu Arg Gly Gly Leu Ser Glu Leu Asp
          900                 905                 910

Lys Ala Gly Phe Ile Lys Arg Gln Leu Val Glu Thr Arg Gln Ile Thr
          915                 920                 925

Lys His Val Ala Gln Ile Leu Asp Ser Arg Met Asn Thr Lys Tyr Asp
          930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
              965                 970                 975

Glu Ile Asn Asn Tyr His His Ala His Asp Ala Tyr Leu Asn Ala Val
              980                 985                 990

Val Gly Thr Ala Leu Ile Lys Lys Tyr Pro Lys Leu Glu Ser Glu Phe
          995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val

```
                  1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 47
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 47

Met Ala Pro Lys Lys Lys Arg Lys Val Gly Ile His Arg Gly Val Pro
1               5                   10                  15

<210> SEQ ID NO 48
<211> LENGTH: 23
<212> TYPE: PRT
<213> ORGANISM: Artificial Sequence
<220> FEATURE:
<223> OTHER INFORMATION: Synthetic Polypeptide
```

<400> SEQUENCE: 48

Met Asp Tyr Lys Asp His Asp Gly Asp Tyr Asp His Asp Ile Asp
1               5                   10                  15
Tyr Lys Asp Asp Asp Asp Lys
            20

<210> SEQ ID NO 49
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 49

Gly Ser Gln Leu Val Lys Ser Glu Leu Glu Glu Lys Lys Ser Glu Leu
1               5                   10                  15
Arg His Lys Leu Lys Tyr Val Pro His Glu Tyr Ile Glu Leu Ile Glu
                20                  25                  30
Ile Ala Arg Asn Ser Thr Gln Asp Arg Ile Leu Glu Met Lys Val Met
                35                  40                  45
Glu Phe Phe Met Lys Val Tyr Gly Tyr Arg Gly Lys His Leu Gly Gly
    50                  55                  60
Ser Arg Lys Pro Asp Gly Ala Ile Tyr Thr Val Gly Ser Pro Ile Asp
65                  70                  75                  80
Tyr Gly Val Ile Val Asp Thr Lys Ala Tyr Ser Gly Tyr Asn Leu
                85                  90                  95
Pro Ile Gly Gln Ala Asp Glu Met Gln Arg Tyr Val Glu Glu Asn Gln
                100                 105                 110
Thr Arg Asn Lys His Ile Asn Pro Asn Glu Trp Trp Lys Val Tyr Pro
                115                 120                 125
Ser Ser Val Thr Glu Phe Lys Phe Leu Phe Val Ser Gly His Phe Lys
    130                 135                 140
Gly Asn Tyr Lys Ala Gln Leu Thr Arg Leu Asn His Ile Thr Asn Cys
145                 150                 155                 160
Asn Gly Ala Val Leu Ser Val Glu Glu Leu Leu Ile Gly Gly Glu Met
                165                 170                 175
Ile Lys Ala Gly Thr Leu Thr Leu Glu Glu Val Arg Arg Lys Phe Asn
                180                 185                 190
Asn Gly Glu Ile Asn Phe
            195

<210> SEQ ID NO 50
<211> LENGTH: 4836
<212> TYPE: DNA
<213> ORGANISM: Artificial Sequence
<220> FEATURE:
<223> OTHER INFORMATION: Synthetic Polynucleotide

<400> SEQUENCE: 50
atggataaaa agtattctat tggtttagct atcggcacta attccgttgg atgggctgtc      60
ataaccgatg aatacaaagt accttcaaag aaatttaagg tgttggggaa cacagaccgt     120
cattcgatta aaaagaatct tatcggtgcc ctcctattcg atagtggcga aacggcagag     180
gcgactcgcc tgaaacgaac cgctcggaga aggtatacac gtcgcaagaa ccgaatatgt     240
tacttacaag aaatttttag caatgagatg gccaaagttg acgattcttt ctttcaccgt     300
ttggaagagt ccttccttgt cgaagaggac aagaaacatg aacggcaccc catctttgga     360

```
aacatagtag atgaggtggc atatcatgaa aagtacccaa cgatttatca cctcagaaaa     420
aagctagttg actcaactga taaagcggac ctgaggttaa tctacttggc tcttgcccat     480
atgataaagt tccgtgggca ctttctcatt gagggtgatc taaatccgga caactcggat     540
gtcgacaaac tgttcatcca gttagtacaa acctataatc agttgtttga agagaaccct     600
ataaatgcaa gtggcgtgga tgcgaaggct attcttagcg cccgcctctc taaatcccga     660
cggctagaaa acctgatcgc acaattaccc ggagagaaga aaaatgggtt gttcggtaac     720
cttatagcgc tctcactagg cctgacacca aattttaagt cgaacttcga cttagctgaa     780
gatgccaaat tgcagcttag taaggacacg tacgatgacg atctcgacaa tctactggca     840
caaattggag atcagtatgc ggacttattt ttggctgcca aaaaccttag cgatgcaatc     900
ctcctatctg acatactgag agttaatact gagattacca aggcgccgtt atccgcttca     960
atgatcaaaa ggtacgatga acatcaccaa gacttgacac ttctcaaggc cctagtccgt    1020
cagcaactgc ctgagaaata taaggaaata ttctttgatc agtcgaaaaa cgggtacgca    1080
ggttatattg acggcggagc gagtcaagag gaattctaca agtttatcaa acccatatta    1140
gagaagatgg atgggacgga agagttgctt gtaaaactca atcgcgaaga tctactgcga    1200
aagcagcgga ctttcgacaa cggtagcatt ccacatcaaa tccacttagg cgaattgcat    1260
gctatactta gaaggcagga ggattttttat ccgttcctca aagacaatcg tgaaaagatt    1320
gagaaaatcc taacctttcg catacctttac tatgtgggac ccctggcccg agggaactct    1380
cggttcgcat ggatgacaag aaagtccgaa gaaacgatta ctccatggaa ttttgaggaa    1440
gttgtcgata aggtgcgtc agctcaatcg ttcatcgaga ggatgaccaa cttttgacaag    1500 aatttaccga acgaaaaagt attgcctaag cacagtttac tttacgagta tttcacagtg    1560
tacaatgaac tcacgaaagt taagtatgtc actgagggca tgcgtaaacc cgccttttcta    1620 agcggagaac agaagaaagc aatagtagat ctgttattca agaccaaccg caaagtgaca    1680
gttaagcaat tgaaagagga ctactttaag aaaattgaat gcttcgattc tgtcgagatc    1740
tccggggtag aagatcgatt taatgcgtca cttggtacgt atcatgacct cctaaagata    1800
attaaagata aggacttcct ggataacgaa gagaatgaag atatcttaga agatatagtg    1860
ttgactctta ccctctttga agatcgggaa atgattgagg aaagactaaa acatacgct    1920 cacctgttcg acgataaggt tatgaaacag ttaaagaggc gtcgctatac gggctgggga    1980
cgattgtcgc ggaaacttat caacgggata agagacaagc aaagtggtaa aactattctc    2040
gattttctaa agagcgacgg cttcgccaat aggaacttta tgcagctgat ccatgatgac    2100 tcttttaacct tcaaagagga tatacaaaag gcacaggttt ccggacaagg ggactcattg    2160
cacgaacata ttgcgaatct tgctggttcg ccagccatca aaaagggcat actccagaca    2220
gtcaaagtag tggatgagct agttaaggtc atgggacgtc acaaaccgga aacattgta    2280 atcgagatgg cacgcgaaaa tcaaacgact cagaaggggc aaaaaaacag tcgagagcgg    2340
atgaagagaa tagaagaggg tattaaagaa ctgggcagcc agatcttaaa ggagcatcct    2400
gtggaaaata cccaattgca gaacgagaaa ctttacctct attacctaca aaatggaagg    2460
gacatgtatg ttgatcagga actggacata aaccgtttat ctgattacga cgtcgatgcc    2520
attgtacccc aatcctttt gaaggacgat tcaatcgaca ataaagtgct tacacgctcg    2580
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
```

```
actaaagctg agaggggtgg cttgtctgaa cttgacaagg ccggatttat taaacgtcag    2760
ctcgtggaaa cccgccaaat cacaaagcat gttgcacaga tactagattc ccgaatgaat    2820
acgaaatacg acgagaacga taagctgatt cgggaagtca aagtaatcac tttaaagtca    2880
aaattggtgt cggacttcag aaaggatttt caattctata agttaggga gataaataac     2940
taccaccatg cgcacgacgc ttatcttaat gccgtcgtag ggaccgcact cattaagaaa    3000
tacccgaagc tagaaagtga gtttgtgtat ggtgattaca aagtttatga cgtccgtaag    3060
atgatcgcga aaagcgaaca ggagataggc aaggctacag ccaaatactt cttttattct    3120
aacattatga atttctttaa gacggaaatc actctggcaa acggagagat acgcaaacga    3180
cctttaattg aaaccaatgg ggagacaggt gaaatcgtat gggataaggg ccgggacttc    3240
gcgacggtga gaaagttttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct tcgatagccc tacagttgcc    3420
tattctgtcc tagtagtggc aaaagttgag aagggaaaat ccaagaaact gaagtcagtc    3480
aaagaattat tgggataaac gattatggag cgctcgtctt ttgaaaagaa ccccatcgac    3540
ttccttgagg cgaaaggtta caaggaagta aaaaaggatc tcataattaa actaccaaag    3600
tatagtctgt ttgagttaga aaatggccga aaacggatgt tggctagcgc cggagagctt    3660
caaaagggga acgaactcgc actaccgtct aaatacgtga atttcctgta tttagcgtcc    3720
cattacgaga agttgaaagg ttcacctgaa gataacgaac agaagcaact ttttgttgag    3780
cagcacaaac attatctcga cgaaatcata gagcaaattt cggaattcag taagagagtc    3840
atcctagctg atgccaatct ggacaaagta ttaagcgcat acaacaagca cagggataaa    3900
cccatacgtg agcaggcgga aaatattatc catttgttta ctcttaccaa cctcggcgct    3960
ccagccgcat tcaagtattt tgacacaacg atagatcgca aacgatacac ttctaccaag    4020
gaggtgctag acgcgacact gattcaccaa tccatcacgg gattatatga aactcggata    4080
gatttgtcac agcttggggg tgacggatcc cccaagaaga gaggaaagt ctcgagcgac      4140
tacaaagacc atgacggtga ttataaagat catgacatcg attacaagga tgacgatgac    4200
aaggctgcag gatcaggtgg aagtggcggc agcggaggtt ctggatccca actagtcaaa    4260
agtgaactgg aggagaagaa atctgaactt cgtcataaat tgaaatatgt gcctcatgaa    4320
tatattgaat taattgaaat tgccagaaat tccactcagg atagaattct tgaaatgaag    4380
gtaatggaat tttttatgaa agtttatgga tatagaggta acatttggg tggatcaagg    4440
aaaccggacg gagcaattta tactgtcgga tctcctattg attacggtgt gatcgtggat    4500
actaaagctt atagcggagg ttataatctg ccaattggcc aagcagatga aatgcaacga    4560
tatgtcgaag aaaatcaaac acgaaacaaa catatcaacc ctaatgaatg gtggaaagtc    4620
tatccatctt ctgtaacgga atttaagttt tatttgtga gtggtcactt taaaggaaac    4680
tacaaagctc agcttacacg attaaatcat atcactaatt gtaatggagc tgttcttagt    4740
gtagaagagc ttttaattgg tggagaaatg attaaagccg gcacattaac cttagaggaa    4800
gtcagacgga aatttaataa cggcgagata aacttt                              4836
```

<210> SEQ ID NO 51
<211> LENGTH: 4845
<212> TYPE: DNA
<213> ORGANISM: Artificial Sequence
<220> FEATURE:
<223> OTHER INFORMATION: Synthetic Polynucleotide

<400> SEQUENCE: 51

```
atggactaca aagaccatga cggtgattat aaagatcatg acatcgatta caaggatgac      60
gatgacaaga tggcccccaa gaagaagagg aaggtgggca ttcaccgcgg ggtacctatg     120
gataaaaagt attctattgg tttagctatc ggcactaatt ccgttggatg ggctgtcata     180
accgatgaat acaaagtacc ttcaaagaaa tttaaggtgt tggggaacac agaccgtcat     240
tcgattaaaa agaatcttat cggtgccctc ctattcgata tggcgaaac ggcagaggcg      300
actcgcctga aacgaaccgc tcggagaagg tatacacgtc gcaagaaccg aatatgttac     360
ttacaagaaa tttttagcaa tgagatggcc aaagttgacg attctttctt tcaccgtttg     420
gaagagtcct tccttgtcga agaggacaag aaacatgaac ggcaccccat ctttggaaac     480
atagtagatg aggtggcata tcatgaaaag tacccaacga tttatcacct cagaaaaaag     540
ctagttgact caactgataa agcggacctg aggttaatct acttggctct tgcccatatg     600
ataaagttcc gtgggcactt tctcattgag ggtgatctaa atccgacaa ctcggatgtc      660
gacaaactgt tcatccagtt agtacaaacc tataatcagt tgtttgaaga gaaccctata     720
aatgcaagtg gcgtggatgc gaaggctatt cttagcgccc gcctctctaa atcccgacgg     780
ctagaaaacc tgatcgcaca attcccggga gagaagaaaa atgggttgtt cggtaacctt     840
atagcgctct cactaggcct gacaccaaat tttaagtcga acttcgactt agctgaagat     900
gccaaattgc agcttagtaa ggacacgtac gatgacgatc tcgacaatct actggcacaa     960
attggagatc agtatgcgga cttattttg gctgccaaaa accttagcga tgcaatcctc     1020
ctatctgaca tactgagagt taatactgag attaccaagg cgccgttatc cgcttcaatg    1080
atcaaaaggt acgatgaaca tcaccaagac ttgacacttc tcaaggccct agtccgtcag    1140
caactgcctg agaaatataa ggaaatattc tttgatcagt cgaaaaacgg gtacgcaggt    1200
tatattgacg gcggagcgag tcaagaggaa ttctacaagt ttatcaaacc catattagag    1260
aagatggatg gacggaaga gttgcttgta aaactcaatc gcgaagatct actgcgaaag    1320
cagcggactt tcgacaacgg tagcattcca catcaaatcc acttaggcga attgcatgct    1380
atacttagaa ggcaggagga tttttatccg ttcctcaaag acaatcgtga aaagattgag    1440
aaaatcctaa cctttcgcat accttactat gtgggacccc tggcccgagg gaactctcgg    1500
ttcgcatgga tgacaagaaa gtccgaagaa acgattactc catggaattt tgaggaagtt    1560
gtcgataaag gtgcgtcagc tcaatcgttc atcgagagga tgaccaactt gacaagaat    1620
ttaccgaacg aaaaagtatt gcctaagcac agtttacttt acgagtattt cacagtgtac    1680
aatgaactca cgaaagttaa gtatgtcact gagggcatgc gtaaacccgc ctttctaagc    1740
ggagaacaga agaaagcaat agtagatctg ttattcaaga ccaaccgcaa agtgacagtt    1800
aagcaattga agaggactac ctttaagaaa attgaatgct tcgattctgt cgagatctcc    1860
ggggtagaag atcgatttaa tgcgtcactt ggtacgtatc atgaccttct aaagataatt    1920
aaagataagg acttcctgga taacgaagag aatgaagata tcttagaaga tatagtgttg    1980
actcttaccc tctttgaaga tcgggaaatg attgaggaaa gactaaaaac atacgctcac    2040
ctgttcgacg ataaggttat gaaacagtta aagaggcgtc gctatacggg ctggggacga    2100
ttgtcgcgga aacttatcaa cgggataaga gacaagcaaa gtggtaaaac tattctcgat    2160
tttctaaaga gcgacggctt cgccaatagg aactttatgc agctgatcca tgatgactct    2220
ttaaccttca agaggatat acaaaaggca caggtttccg gacaagggga ctcattgcac    2280
```

```
gaacatattg cgaatcttgc tggttcgcca gccatcaaaa agggcatact ccagacagtc    2340
aaagtagtgg atgagctagt taaggtcatg ggacgtcaca aaccggaaaa cattgtaatc    2400
gagatggcac gcgaaaatca aacgactcag aagggcaaa aaaacagtcg agagcggatg    2460
aagagaatag aagagggtat taaagaactg ggcagccaga tcttaaagga gcatcctgtg    2520
gaaaataccc aattgcagaa cgagaaactt tacctctatt acctacaaaa tggaagggac    2580
atgtatgttg atcaggaact ggacataaac cgtttatctg attacgacgt cgatgccatt    2640
gtaccccaat cctttttgaa ggacgattca atcgacaata aagtgcttac acgtcggat    2700 aagaaccgag ggaaaagtga caatgttcca agcgaggaag tcgtaaagaa aatgaagaac    2760
tattggcggc agctcctaaa tgcgaaactg ataacgcaaa gaaagttcga taacttaact    2820
aaagctgaga ggggtggctt gtctgaactt gacaaggccg gatttattaa acgtcagctc    2880
gtggaaaccc gccaaatcac aaagcatgtt gcacagatac tagattcccg aatgaatacg    2940
aaatacgacg agaacgataa gctgattcgg gaagtcaaag taatcacttt aaagtcaaaa    3000
ttggtgtcgg acttcagaaa ggattttcaa ttctataaag ttagggagat aaataactac    3060
caccatgcgc acgacgctta tcttaatgcc gtcgtaggga ccgcactcat taagaaatac    3120
ccgaagctag aaagtgagtt tgtgtatggt gattacaaag tttatgacgt ccgtaagatg    3180
atcgcgaaaa gcgaacagga gataggcaag gctacagcca aatacttctt ttattctaac    3240
attatgaatt tctttaagac ggaaatcact ctggcaaacg gagagatacg caaacgacct    3300
ttaattgaaa ccaatgggga gacaggtgaa atcgtatggg ataagggccg ggacttcgcg    3360
acggtgagaa aagttttgtc catgccccaa gtcaacatag taaagaaaac tgaggtgcag    3420
accggagggt tttcaaagga atcgattctt ccaaaaagga atagtgataa gctcatcgct    3480
cgtaaaaagg actgggaccc gaaaaagtac ggtggcttcg atagccctac agttgcctat    3540
tctgtcctag tagtggcaaa agttgagaag ggaaaatcca agaaactgaa gtcagtcaaa    3600
gaattattgg ggataacgat tatggagcgc tcgtcttttg aaaagaaccc catcgacttc    3660
cttgaggcga aaggttacaa ggaagtaaaa aaggatctca taattaaact accaaagtat    3720
agtctgtttg agttagaaaa tggccgaaaa cggatgttgg ctagcgccgg agagcttcaa    3780
aaggggaacg aactcgcact accgtctaaa tacgtgaatt tcctgtattt agcgtcccat    3840
tacgagaagt tgaaaggttc acctgaagat aacgaacaga agcaacttt tgttgagcag    3900 cacaaacatt atctcgacga aatcatagag caaatttcgg aattcagtaa gagagtcatc    3960
ctagctgatg ccaatctgga caaagtatta agcgcataca acaagcacag ggataaaccc    4020
atacgtgagc aggcggaaaa tattatccat tgtttactc ttaccaacct cggcgctcca    4080
gccgcattca gtattttga cacaacgata atcgcaaac gatacacttc taccaaggag    4140
gtgctagacg cgacactgat tcaccaatcc atcacgggat tatatgaaac tcggatagat    4200
ttgtcacagc ttgggggtga ctcaggtgga agtggcggca gcggaggttc tggatcccaa    4260
ctagtcaaaa gtgaactgga ggagaagaaa tctgaacttc gtcataaatt gaaatatgtg    4320
cctcatgaat atattgaatt aattgaaatt gccagaaatt ccactcagga tagaattctt    4380
gaaatgaagg taatgaattt ttatgaaa gtttatggat atagaggtaa acatttgggt    4440
ggatcaagga aaccggacgg agcaatttat actgtcggat ctcctattga ttacggtgtg    4500
atcgtggata ctaaagctta tagcggaggt tataatctgc caattggcca agcagatgaa    4560
atgcaacgat atgtcgaaga aaatcaaaca cgaaacaaac atatcaaccc taatgaatgg    4620
tggaaagtct atccatcttc tgtaacggaa tttaagtttt tatttgtgag tggtcacttt    4680
```

```
aaaggaaact acaaagctca gcttacacga ttaaatcata tcactaattg taatggagct   4740
gttcttagtg tagaagagct tttaattggt ggagaaatga ttaaagccgg cacattaacc   4800
ttagaggaag tcagacggaa atttaataac ggcgagataa acttt                   4845
```

<210> SEQ ID NO 52
<211> LENGTH: 4836
<212> TYPE: DNA
<213> ORGANISM: Artificial Sequence
<220> FEATURE:
<223> OTHER INFORMATION: Synthetic Polynucleotide

<400> SEQUENCE: 52

```
atgggatccc aactagtcaa aagtgaactg gaggagaaga atctgaact tcgtcataaa     60 ttgaaatatg tgcctcatga atatattgaa ttaattgaaa ttgccagaaa ttccactcag   120
gatagaattc ttgaaatgaa ggtaatggaa ttttttatga agtttatgg atatagaggt    180 aaacatttgg gtggatcaag gaaaccggac ggagcaattt atactgtcgg atctcctatt   240
gattacggtg tgatcgtgga tactaaagct tatagcggag gttataatct gccaattggc   300
caagcagatg aaatgcaacg atatgtcgaa gaaaatcaaa cacgaaacaa acatatcaac   360
cctaatgaat ggtggaaagt ctatccatct tctgtaacgg aatttaagtt tttatttgtg   420
agtggtcact ttaaaggaaa ctacaaagct cagcttacac gattaaatca tatcactaat   480
tgtaatggag ctgttcttag tgtagaagag cttttaattg gtggagaaat gattaaagcc   540
ggcacattaa ccttagagga agtcagacga aaatttaata cggcgagata aactttggc    600 ggtagtgggg gatctggggg aagtatggat aaaaagtatt ctattggttt agctatcggc   660
actaattccg ttggatgggc tgtcataacc gatgaataca agtaccttc aaagaaattt    720 aaggtgttgg ggaacacaga ccgtcattcg attaaaaaga atcttatcgg tgccctccta   780
ttcgatagtg gcgaaacggc agaggcgact cgcctgaaac gaaccgctcg agaaggtat    840 acacgtcgca agaaccgaat atgttactta caagaaattt ttagcaatga gatggccaaa   900
gttgacgatt ctttctttca ccgtttggaa gagtccttcc ttgtcgaaga ggacaagaaa   960
catgaacggc accccatctt tggaaacata gtagatgagg tggcatatca tgaaaagtac  1020
ccaacgattt atcacctcag aaaaaagcta gttgactcaa ctgataaagc ggacctgagg  1080
ttaatctact ggctcttgc ccatatgata aagttccgtg gcactttct cattgagggt    1140 gatctaaatc cggacaactc ggatgtcgac aaactgttca tccagttagt acaaacctat  1200
aatcagttgt ttgaagagaa ccctataaat gcaagtggcg tggatgcgaa ggctattctt  1260
agcgcccgcc tctctaaatc ccgacggcta gaaaacctga tcgcacaatt acccggagag  1320
aagaaaaatg ggttgttcgg taaccttata gcgctctcac taggcctgac accaaatttt  1380
aagtcgaact tcgacttagc tgaagatgcc aaattgcagc ttagtaagga cacgtacgat  1440
gacgatctcg acaatctact ggcacaaatt ggagatcagt atgcggactt attttttggct 1500 gccaaaaacc ttagcgatgc aatcctccta tctgacatac tgagagttaa tactgagatt  1560
accaaggcgc cgttatccgc ttcaatgatc aaaaggtacg atgaacatca ccaagacttg  1620
acacttctca aggccctagt ccgtcagcaa ctgcctgaga aatataagga aatattcttt  1680
gatcagtcga aaacgggta cgcaggttat attgacggcg gagcgagtca gaggaattc    1740 tacaagttta tcaaacccat attagagaag atggatggga cggaagagtt gcttgtaaaa  1800
ctcaatcgcg aagatctact gcgaaagcag cggacttcg acaacggtag cattccacat   1860
```

```
caaatccact taggcgaatt gcatgctata cttagaaggc aggaggattt ttatccgttc    1920
ctcaaagaca atcgtgaaaa gattgagaaa atcctaacct ttcgcatacc ttactatgtg    1980
ggacccctgg cccgagggaa ctctcggttc gcatggatga caagaaagtc cgaagaaacg    2040
attactccat ggaattttga ggaagttgtc gataaaggtg cgtcagctca atcgttcatc    2100
gagaggatga ccaactttga caagaattta ccgaacgaaa aagtattgcc taagcacagt    2160
ttactttacg agtatttcac agtgtacaat gaactcacga aagttaagta tgtcactgag    2220
ggcatgcgta aacccgcctt tctaagcgga gaacagaaga aagcaatagt agatctgtta    2280
ttcaagacca accgcaaagt gacagttaag caattgaaag aggactactt taagaaaatt    2340
gaatgcttcg attctgtcga gatctccggg gtagaagatc gatttaatgc gtcacttggt    2400
acgtatcatg acctcctaaa gataattaaa gataaggact tcctggataa cgaagagaat    2460
gaagatatct tagaagatat agtgttgact cttaccctct ttgaagatcg ggaaatgatt    2520
gaggaaagac taaaaacata cgctcacctg ttcgacgata aggttatgaa acagttaaag    2580
aggcgtcgct atacgggctg gggacgattg tcgcggaaac ttatcaacgg gataagagac    2640
aagcaaagtg gtaaaactat tctcgatttt ctaaagagcg acggcttcgc caataggaac    2700
tttatgcagc tgatccatga tgactcttta accttcaaag aggatataca aaaggcacag    2760
gtttccggac aaggggactc attgcacgaa catattgcga atcttgctgg ttcgccagcc    2820
atcaaaaagg gcatactcca gacagtcaaa gtagtggatg agctagttaa ggtcatggga    2880
cgtcacaaac cggaaaacat tgtaatcgag atggcacgcg aaaatcaaac gactcagaag    2940
gggcaaaaaa acagtcgaga gcggatgaag agaatagaag agggtattaa agaactgggc    3000
agccagatct taaaggagca tcctgtggaa aatacccaat gcagaacgaa gaaactttac    3060
ctctattacc tacaaaatgg aagggacatg tatgttgatc aggaactgga cataaaccgt    3120
ttatctgatt acgacgtcga tgccattgta ccccaatcct ttttgaagga cgattcaatc    3180
gacaataaag tgcttacacg ctcggataag aaccgaggga aaagtgacaa tgttccaagc    3240
gaggaagtcg taaagaaaat gaagaactat tggcggcagc tcctaaatgc gaaactgata    3300
acgcaaagaa agttcgataa cttaactaaa gctgagaggg gtggcttgtc tgaacttgac    3360
aaggccggat ttattaaacg tcagctcgtg gaaacccgcc aaatcacaaa gcatgttgca    3420
cagatactag attcccgaat gaatacgaaa tacgacgaga cgataagct gattcgggaa    3480 gtcaaagtaa tcactttaaa gtcaaaattg gtgtcggact tcagaaagga ttttcaattc    3540
tataaagtta gggagataaa taactaccac catgcgcacg acgcttatct taatgccgtc    3600
gtagggaccg cactcattaa gaaatacccg aagctagaaa gtgagtttgt gtatggtgat    3660
tacaaagttt atgacgtccg taagatgatc gcgaaaagcg aacaggagat aggcaaggct    3720
acagccaaat acttctttta ttctaacatt atgaatttct ttaagacgga aatcactctg    3780
gcaaacggag agatacgcaa acgacccttta attgaaacca atggggagac aggtgaaatc    3840
gtatgggata agggccggga cttcgcgacg gtgagaaaag ttttgtccat gccccaagtc    3900
aacatagtaa agaaaactga ggtgcagacc ggagggtttt caaggaatc gattcttcca    3960 aaaaggaata gtgataagct catcgctcgt aaaaaggact gggacccgaa aaagtacggt    4020
ggcttcgata gccctacagt tgcctattct gtcctagtag tggcaaaagt tgagaaggga    4080
aaatccaaga aactgaagtc agtcaaagaa ttattgggga taacgattat ggagcgctcg    4140
tcttttgaaa agaccccat cgacttcctt gaggcgaaag gttacaagga agtaaaaaag    4200
gatctcataa ttaaactacc aaagtatagt ctgtttgagt tagaaaatgg ccgaaaacgg    4260
```

| | |
|---|---:|
| atgttggcta gcgccggaga gcttcaaaag gggaacgaac tcgcactacc gtctaaatac | 4320 |
| gtgaatttcc tgtatttagc gtcccattac gagaagttga aaggttcacc tgaagataac | 4380 |
| gaacagaagc aacttttgt tgagcagcac aaacattatc tcgacgaaat catagagcaa | 4440 |
| atttcggaat tcagtaagag agtcatccta gctgatgcca atctggacaa agtattaagc | 4500 |
| gcatacaaca agcacaggga taaacccata cgtgagcagg cggaaaatat tatccatttg | 4560 |
| tttactctta ccaacctcgg cgctccagcc gcattcaagt attttgacac aacgatagat | 4620 |
| cgcaaacgat acacttctac caaggaggtg ctagacgcga cactgattca ccaatccatc | 4680 |
| acgggattat atgaaactcg gatagatttg tcacagcttg ggggtgacgg atcccccaag | 4740 |
| aagaagagga agtctcgag cgactacaaa gaccatgacg gtgattataa agatcatgac | 4800 |
| atcgattaca aggatgacga tgacaaggct gcagga | 4836 |

<210> SEQ ID NO 53
<211> LENGTH: 4854
<212> TYPE: DNA
<213> ORGANISM: Artificial Sequence
<220> FEATURE:
<223> OTHER INFORMATION: Synthetic Polynucleotide

<400> SEQUENCE: 53

| | |
|---|---:|
| atggactaca aagaccatga cggtgattat aaagatcatg acatcgatta caaggatgac | 60 |
| gatgacaaga tggcccccaa gaagaagagg aaggtgggca ttcaccgcgg ggtacctgga | 120 |
| ggttctatgg gatcccaact agtcaaaagt gaactggagg agaagaaatc tgaacttcgt | 180 |
| cataaattga aatatgtgcc tcatgaatat attgaattaa ttgaaattgc cagaaattcc | 240 |
| actcaggata gaattcttga atgaaggta atggaatttt ttatgaaagt ttatggatat | 300 |
| agaggtaaac atttgggtgg atcaaggaaa ccggacggag caatttatac tgtcggatct | 360 |
| cctattgatt acgtgtgat cgtggatact aaagcttata gcggaggtta taatctgcca | 420 |
| attggccaag cagatgaaat gcaacgatat gtcgaagaaa atcaaacacg aaacaaacat | 480 |
| atcaacccta tgaatggtg aaagtctat ccatcttctg taacggaatt taagttttta | 540 |
| tttgtgagtg gtcactttaa aggaaactac aaagctcagc ttacacgatt aaatcatatc | 600 |
| actaattgta atggagctgt tcttagtgta gaagagcttt taattggtgg agaaatgatt | 660 |
| aaagccggca cattaacctt agaggaagtc agacggaaat ttaataacgg cgagataaac | 720 |
| tttggcggta gtgggggatc tgggggaagt atggataaaa agtattctat tggtttagct | 780 |
| atcggcacta ttccgttgg atgggctgtc ataaccgatg aatacaaagt accttcaaag | 840 |
| aaatttaagg tgttggggaa cacagaccgt cattcgatta aaagaatct tatcggtgcc | 900 |
| ctcctattcg atagtggcga aacggcagag gcgactcgcc tgaaacgaac cgctcggaga | 960 |
| aggtatacac gtcgcaagaa ccgaatatgt tacttacaag aaattttag caatgagatg | 1020 |
| gccaaagttg acgattcttt cttcaccgt ttggaagagt ccttccttgt cgaagaggac | 1080 |
| aagaaacatg aacggcaccc catctttgga aacatagtag atgaggtggc atatcatgaa | 1140 |
| aagtacccaa cgatttatca cctcagaaaa aagctagttg actcaactga taaagcggac | 1200 |
| ctgaggttaa tctacttggc tcttgcccat atgataaagt ccgtgggca ctttctcatt | 1260 |
| gagggtgatc taaatccgga caactcggat gtcgacaaac tgttcatcca gttagtacaa | 1320 |
| acctataatc agttgtttga agagaaccct ataaatgcaa gtggcgtgga tgcgaaggct | 1380 |
| attcttagcg cccgcctctc taatcccga cggctagaaa acctgatcgc acaattaccc | 1440 |

```
ggagagaaga aaaatgggtt gttcggtaac cttatagcgc tctcactagg cctgacacca    1500
aattttaagt cgaacttcga cttagctgaa gatgccaaat tgcagcttag taaggacacg    1560
tacgatgacg atctcgacaa tctactggca caaattggag atcagtatgc ggacttattt    1620
ttggctgcca aaaaccttag cgatgcaatc ctcctatctg acatactgag agttaatact    1680
gagattacca aggcgccgtt atccgcttca atgatcaaaa ggtacgatga acatcaccaa    1740
gacttgacac ttctcaaggc cctagtccgt cagcaactgc ctgagaaata taaggaaata    1800
ttctttgatc agtcgaaaaa cgggtacgca ggttatattg acggcggagc gagtcaagag    1860
gaattctaca agtttatcaa acccatatta gagaagatgg atgggacgga agagttgctt    1920
gtaaaactca atcgcgaaga tctactgcga aagcagcgga cttttcgacaa cggtagcatt    1980 ccacatcaaa tccacttagg cgaattgcat gctatactta gaaggcagga ggattttttat    2040 ccgttcctca agacaatcg tgaaaagatt gagaaaatcc taacctttcg catacctttac    2100 tatgtgggac ccctggcccg agggaactct cggttcgcat ggatgacaag aaagtccgaa    2160
gaaacgatta ctccatggaa ttttgaggaa gttgtcgata aggtgcgtc agctcaatcg    2220 ttcatcgaga ggatgaccaa cttttgacaag aatttaccga acgaaaaagt attgcctaag    2280
cacagtttac tttacgagta tttcacagtg tacaatgaac tcacgaaagt taagtatgtc    2340
actgagggca tgcgtaaacc cgcctttcta agcggagaac agaagaaagc aatagtagat    2400
ctgttattca agaccaaccg caaagtgaca gttaagcaat tgaaagagga ctactttaag    2460
aaaattgaat gcttcgattc tgtcgagatc tccggggtag aagatcgatt taatgcgtca    2520
cttggtacgt atcatgacct cctaaagata attaaagata aggacttcct ggataacgaa    2580
gagaatgaag atatcttaga agatatagtg ttgactctta ccctcttttga agatcgggaa    2640 atgattgagg aaagactaaa aacatacgct cacctgttcg acgataaggt tatgaaacag    2700
ttaaagaggc gtcgctatac gggctgggga cgattgtcgc ggaaacttat caacgggata    2760
agagacaagc aaagtggtaa aactattctc gatttctaa agagcgacgg cttcgccaat    2820
aggaacttta tgcagctgat ccatgatgac tctttaacct tcaaagagga tatacaaaag    2880
gcacaggttt ccgacaagg ggactcattg cacgaacata ttgcgaatct tgctggttcg    2940
ccagccatca aaagggcat actccagaca gtcaaagtag tggatgagct agttaaggtc    3000
atgggacgtc acaaaccgga aaacattgta atcgagatgg cacgcgaaaa tcaaacgact    3060 cagaagggc aaaaaacag tcgagagcgg atgaagagaa tagaagaggg tattaaagaa    3120
ctgggcagcc agatcttaaa ggagcatcct gtggaaaata cccaattgca gaacgagaaa    3180
ctttacctct attacctaca aaatggaagg gacatgtatg ttgatcagga actggacata    3240
aaccgtttat ctgattacga cgtcgatgcc attgtacccc aatccttttt gaaggacgat    3300
tcaatcgaca ataaagtgct tacacgctcg gataagaacc gagggaaaag tgacaatgtt    3360
ccaagcgagg aagtcgtaaa gaaaatgaag aactattggc ggcagctcct aaatgcgaaa    3420
ctgataacgc aaagaaagtt cgataactta actaaagctg agaggggtgg cttgtctgaa    3480
cttgacaagg ccggatttat taaacgtcag ctcgtggaaa cccgccaaat cacaaagcat    3540
gttgcacaga tactagattc ccgaatgaat acgaaatacg acgagaacga taagctgatt    3600
cgggaagtca agtaatcac tttaaagtca aaattggtgt cggacttcag aaaggatttt    3660
caattctata agttaggga gataaataac taccaccatg cgcacgacgc ttatcttaat    3720
gccgtcgtag ggaccgcact cattaagaaa tacccgaagc tagaaagtga gtttgtgtat    3780
ggtgattaca agtttatga cgtccgtaag atgatcgcga aaagcgaaca ggagataggc    3840
```

-continued

```
aaggctacag ccaaatactt cttttattct aacattatga atttctttaa gacggaaatc    3900
actctggcaa acgagagat acgcaaacga cctttaattg aaaccaatgg ggagacaggt    3960
gaaatcgtat gggataaggg ccgggacttc gcgacggtga aaaagtttt gtccatgccc    4020 caagtcaaca tagtaaagaa aactgaggtg cagaccggag ggttttcaaa ggaatcgatt    4080
cttccaaaaa ggaatagtga taagctcatc gctcgtaaaa aggactggga cccgaaaaag    4140
tacggtggct tcgatagccc tacagttgcc tattctgtcc tagtagtggc aaaagttgag    4200
aagggaaaat ccaagaaact gaagtcagtc aaagaattat tggggataac gattatggag    4260
cgctcgtctt tgaaaagaa ccccatcgac ttccttgagg cgaaaggtta caggaagta    4320 aaaaaggatc tcataattaa actaccaaag tatagtctgt ttgagttaga aatggccga    4380 aaacggatgt tggctagcgc cggagagctt caaaagggga acgaactcgc actaccgtct    4440
aaatacgtga atttcctgta tttagcgtcc cattacgaga agttgaaagg ttcacctgaa    4500
gataacgaac agaagcaact ttttgttgag cagcacaaac attatctcga cgaaatcata    4560
gagcaaattt cggaattcag taagagagtc atcctagctg atgccaatct ggacaaagta    4620
ttaagcgcat acaacaagca cagggataaa cccatacgtg agcaggcgga aaatattatc    4680
catttgttta ctcttaccaa cctcggcgct ccagccgcat tcaagtattt tgacacaacg    4740
atagatcgca aacgatacac ttctaccaag gaggtgctag acgcgacact gattcaccaa    4800
tccatcacgg gattatatga aactcggata gatttgtcac agcttggggg tgac    4854
```

<210> SEQ ID NO 54
<211> LENGTH: 4869
<212> TYPE: DNA
<213> ORGANISM: Artificial Sequence
<220> FEATURE:
<223> OTHER INFORMATION: Synthetic Polynucleotide

<400> SEQUENCE: 54

```
atggactaca aagaccatga cggtgattat aaagatcatg acatcgatta caaggatgac      60
gatgacaaga tggcccccaa gaagaagagg aaggtgggca ttcaccgcgg ggtacctgga     120
ggttctggat cccaactagt caaaagtgaa ctggaggaga agaaatctga acttcgtcat     180
aaattgaaat atgtgcctca tgaatatatt gaattaattg aaattgccag aaattccact     240
caggatagaa ttcttgaaat gaaggtaatg gaatttttta tgaaagttta tggatataga     300
ggtaaacatt tgggtggatc aaggaaaccg gacggagcaa tttatactgt cggatctcct     360
attgattacg gtgtgatcgt ggatactaaa gcttatagcg gaggttataa tctgccaatt     420
ggccaagcag atgaaatgca acgatatgtc gaagaaaatc aaacacgaaa caaacatatc     480
aaccctaatg aatggtggaa agtctatcca tcttctgtaa cggaatttaa gttttttattt     540 gtgagtggtc acttttaaagg aaactacaaa gctcagctta cacgattaaa tcatatcact     600
aattgtaatg gagctgttct tagtgtagaa gagcttttaa ttggtggaga atgattaaa     660 gccggcacat taaccttaga ggaagtcaga cggaaattta ataacggcga gataaacttt     720
agcggcagcg agactcccgg gacctcagag tccgccacac ccgaaagtga taaaaagtat     780
tctattggtt tagctatcgg cactaattcc gttggatggg ctgtcataac cgatgaatac     840
aaagtacctt caaagaaatt taaggtgttg gggaacacag accgtcattc gattaaaaag     900
aatcttatcg gtgccctcct attcgatagt ggcgaaacgg cagaggcgac tcgcctgaaa     960
cgaaccgctc ggagaaggta tacacgtcgc aagaaccgaa tatgttactt acaagaaatt    1020
```

```
tttagcaatg agatggccaa agttgacgat tctttctttc accgtttgga agagtccttc   1080
cttgtcgaag aggacaagaa acatgaacgg cacccatct ttggaaacat agtagatgag    1140
gtggcatatc atgaaaagta cccaacgatt tatcacctca gaaaaaagct agttgactca   1200
actgataaag cggacctgag gttaatctac ttggctcttg cccatatgat aaagttccgt   1260
gggcactttc tcattgaggg tgatctaaat ccggacaact cggatgtcga caaactgttc   1320
atccagttag tacaaaccta taatcagttg tttgaagaga accctataaa tgcaagtggc   1380
gtggatgcga aggctattct tagcgcccgc ctctctaaat cccgacggct agaaaacctg   1440
atcgcacaat tacccggaga gaagaaaaat gggttgttcg gtaaccttat agcgctctca   1500
ctaggcctga caccaaattt taagtcgaac ttcgacttag ctgaagatgc caaattgcag   1560
cttagtaagg acacgtacga tgacgatctc gacaatctac tggcacaaat tggagatcag   1620
tatgcggact tattttttggc tgccaaaaac cttagcgatg caatcctcct atctgacata   1680
ctgagagtta atactgagat taccaaggcg ccgttatccg cttcaatgat caaaaggtac   1740
gatgaacatc accaagactt gacacttctc aaggccctag tccgtcagca actgcctgag   1800
aaatataagg aaatattctt tgatcagtcg aaaaacgggt acgcaggtta tattgacggc   1860
ggagcgagtc aagaggaatt ctacaagttt atcaaaccca tattagagaa gatggatggg   1920
acggaagagt tgcttgtaaa actcaatcgc gaagatctac tgcgaaagca gcggactttc   1980
gacaacggta gcattccaca tcaaatccac ttaggcgaat gcatgctat acttagaagg    2040 caggaggatt tttatccgtt cctcaaagac aatcgtgaaa agattgagaa aatcctaacc   2100
tttcgcatac cttactatgt gggacccctg gcccgaggga actctcggtt cgcatggatg   2160
acaagaaagt ccgaagaaac gattactcca tggaattttg aggaagttgt cgataaaggt   2220
gcgtcagctc aatcgttcat cgagaggatg accaactttg acaagaattt accgaacgaa   2280
aaagtattgc ctaagcacag tttactttac gagtatttca cagtgtacaa tgaactcacg   2340
aaagttaagt atgtcactga gggcatgcgt aaacccgcct ttctaagcgg agaacagaag   2400
aaagcaatag tagatctgtt attcaagacc aaccgcaaag tgacagttaa gcaattgaaa   2460
gaggactact ttaagaaaat tgaatgcttc gattctgtcg agatctccgg ggtagaagat   2520
cgatttaatg cgtcacttgg tacgtatcat gacctcctaa agataattaa agataaggac   2580
ttcctggata cgaagagaa tgaagatatc ttagaagata tagtgttgac tcttacccctc   2640 tttgaagatc gggaaatgat tgaggaaaga ctaaaaacat acgctcacct gttcgacgat   2700
aaggttatga acagttaaa gaggcgtcgc tatacgggct ggggacgatt gtcgcggaaa   2760
cttatcaacg ggataagaga caagcaaagt ggtaaaacta ttctcgattt tctaaagagc   2820
gacggcttcg ccaataggaa ctttatgcag ctgatccatg atgactcttt aaccttcaaa   2880
gaggatatac aaaaggcaca ggtttccgga caaggggact cattgcacga acatattgcg   2940
aatcttgctg gttcgccagc catcaaaaag ggcatactcc agacagtcaa agtagtggat   3000
gagctagtta aggtcatggg acgtcacaaa ccggaaaaca ttgtaatcga gatggcacgc   3060
gaaaatcaaa cgactcagaa ggggcaaaaa acagtcgag agcggatgaa gagaatagaa   3120
gagggtatta agaactggg cagccagatc ttaaaggagc atcctgtgga aaatacccaa   3180
ttgcagaacg agaaacttta cctctattac ctacaaaatg gaaagggacat gtatgttgat   3240 caggaactgg acataaaccg tttatctgat tacgacgtcg atgccattgt accccaatcc   3300
tttttgaagg acgattcaat cgacaataaa gtgcttacac gctcggataa gaaccgaggg   3360
aaaagtgaca atgttccaag cgaggaagtc gtaaagaaaa tgaagaacta ttggcggcag   3420
```

```
ctcctaaatg cgaaactgat aacgcaaaga aagttcgata acttaactaa agctgagagg    3480
ggtggcttgt ctgaacttga caaggccgga tttattaaac gtcagctcgt ggaaacccgc    3540
caaatcacaa agcatgttgc acagatacta gattcccgaa tgaatacgaa atacgacgag    3600
aacgataagc tgattcggga agtcaaagta atcactttaa agtcaaaatt ggtgtcggac    3660
ttcagaaagg attttcaatt ctataaagtt agggagataa ataactacca ccatgcgcac    3720
gacgcttatc ttaatgccgt cgtagggacc gcactcatta agaaataccc gaagctagaa    3780
agtgagtttg tgtatggtga ttacaaagtt tatgacgtcc gtaagatgat cgcgaaaagc    3840
gaacaggaga taggcaaggc tacagccaaa tacttctttt attctaacat tatgaatttc    3900
tttaagacgg aaatcactct ggcaaacgga gagatacgca aacgaccttt aattgaaacc    3960
aatgggggaga caggtgaaat cgtatgggat aagggccggg acttcgcgac ggtgagaaaa    4020
gttttgtcca tgcccaagt caacatagta agaaaactg aggtgcagac cggagggttt    4080
tcaaaggaat cgattcttcc aaaaggaat agtgataagc tcatcgctcg taaaaaggac    4140
tgggacccga aaaagtacgg tggcttcgat agccctacag ttgcctattc tgtcctagta    4200
gtggcaaaag ttgagaaggg aaaatccaag aaactgaagt cagtcaaaga attattgggg    4260
ataacgatta tggagcgctc gtcttttgaa aagaaccca tcgacttcct tgaggcgaaa    4320
ggttacaagg aagtaaaaaa ggatctcata attaaactac caaagtatag tctgtttgag    4380
ttagaaaatg gccgaaaacg gatgttggct agcgccggag agcttcaaaa ggggaacgaa    4440
ctcgcactac cgtctaaata cgtgaattc ctgtatttag cgtcccatta cgagaagttg    4500
aaaggttcac ctgaagataa cgaacagaag caacttttg ttgagcagca caaacattat    4560
ctcgacgaaa tcatagagca aattccggaa ttcagtaaga gagtcatcct agctgatgcc    4620
aatctggaca agtattaag cgcatacaac aagcacaggg ataaacccat acgtgagcag    4680
gcggaaaata ttatccattt gtttactctt accaaacctcg cgctccagc cgcattcaag    4740
tatttgaca caacgataga tcgcaaacga tacacttcta ccaaggaggt gctagacgcg    4800
acactgattc accaatccat cacgggatta tatgaaactc ggatagattt gtcacagctt    4860
gggggtgac                                                            4869
```

<210> SEQ ID NO 55
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 55

```
atggccctgt ttggctacgc acgcgtgtct accagtcaac agtcactcga tttgcaagtg     60
agggctctta agatgccgg agtgaaggca aacagaattt ttactgataa ggccagcgga    120
agcagcacag acagagaggg gctggatctc ctgagaatga aggtaaagga gggtgatgtg    180
atcttggtca aaaaattgga tcgactgggg agagacacag ctgatatgct tcagcttatt    240
aaagagtttg acgctcaggg tgttgccgtg aggtttatcg atgacggcat ctcaaccgac    300
tcctacattg gtcttatgtt tgtgacaatt ttgtccgctg tggctcaggc tgagcggaga    360
aggattctcg aaaggacgaa tgagggacgg caagcagcta agttgaaagg tatcaaattt    420
ggcagacgaa gg                                                        432
```

<210> SEQ ID NO 56

<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 56

Met Ala Leu Phe Gly Tyr Ala Arg Val Ser Thr Ser Gln Gln Ser Leu
1               5                   10                  15

Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Lys Glu Gly Asp Val Ile Leu Val Lys
    50                  55                  60

Lys Leu Asp Arg Leu Gly Arg Asp Thr Ala Asp Met Leu Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Ser Tyr Ile Gly Leu Met Phe Val Thr Ile Leu Ser
            100                 105                 110

Ala Val Ala Gln Ala Glu Arg Arg Arg Ile Leu Glu Arg Thr Asn Glu
        115                 120                 125

Gly Arg Gln Ala Ala Lys Leu Lys Gly Ile Lys Phe Gly Arg Arg Arg
    130                 135                 140

<210> SEQ ID NO 57
<211> LENGTH: 414
<212> TYPE: DNA
<213> ORGANISM: Artificial Sequence
<220> FEATURE:
<223> OTHER INFORMATION: Synthetic Polynucleotide

<400> SEQUENCE: 57
atggcaacca ttggctacat aagggtgtct accatcgacc aaaatatcga cctgcagcgc      60
aacgctctga catccgccaa ctgcgatcgg atcttcgagg ataggatcag tggcaagatc     120
gccaaccggc ccggtctgaa gcgggctctg aagtacgtga ataagggcga tactctggtt     180
gtgtggaagt tggatcgctt gggtagatca gtgaagaatc tcgtagccct gataagcgag     240
ctgcacgaga ggggtgcaca tttccattct ctgaccgatt ccatcgatac gtctagcgcc     300
atgggccgat tcttctttta cgtcatgtcc gccctcgctg aaatggagcg cgaacttatt     360
gttgaacgga ctttggctgg actggcagcg gctagagcac agggccgact tgga            414

<210> SEQ ID NO 58
<211> LENGTH: 138
<212> TYPE: PRT
<213> ORGANISM: Artificial Sequence
<220> FEATURE:
<223> OTHER INFORMATION: Synthetic Polypeptide

<400> SEQUENCE: 58

Met Ala Thr Ile Gly Tyr Ile Arg Val Ser Thr Ile Asp Gln Asn Ile
1               5                   10                  15

Asp Leu Gln Arg Asn Ala Leu Thr Ser Ala Asn Cys Asp Arg Ile Phe
            20                  25                  30

Glu Asp Arg Ile Ser Gly Lys Ile Ala Asn Arg Pro Gly Leu Lys Arg
        35                  40                  45

Ala Leu Lys Tyr Val Asn Lys Gly Asp Thr Leu Val Val Trp Lys Leu

```
                50                  55                  60
Asp Arg Leu Gly Arg Ser Val Lys Asn Leu Val Ala Leu Ile Ser Glu
 65                  70                  75                  80

Leu His Glu Arg Gly Ala His Phe His Ser Leu Thr Asp Ser Ile Asp
                 85                  90                  95

Thr Ser Ser Ala Met Gly Arg Phe Phe Phe Tyr Val Met Ser Ala Leu
            100                 105                 110

Ala Glu Met Glu Arg Glu Leu Ile Val Glu Arg Thr Leu Ala Gly Leu
        115                 120                 125

Ala Ala Ala Arg Ala Gln Gly Arg Leu Gly
    130                 135

<210> SEQ ID NO 59
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 59
atgctcattg gctatgtaag ggtcagcacc aatgaccaaa acacagactt gcaacgcaat    60
gctttggttt gcgccggatg tgaacagata tttgaagata aactgagcgg cactcggaca   120
gacagacctg gcttaagag agcactgaaa agactgcaga aggggacac cctggtcgtc    180 tggaaactgg atcgcctcgg acgcagcatg aaacatctga ttagcctggt tggtgagctt   240
agggagagag gaatcaactt cagaagcctg accgactcca tcgacaccag tagccccatg   300
ggacgattct tcttctatgt gatgggagca cttgctgaga tggaaagaga gcttattatc   360
gaaagaacta tggctggtat cgctgctgcc cggaacaaag cagacggtt cggcagaccg    420 ccgaagagcg gc                                                       432

<210> SEQ ID NO 60
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 60

Met Leu Ile Gly Tyr Val Arg Val Ser Thr Asn Asp Gln Asn Thr Asp
 1               5                  10                  15

Leu Gln Arg Asn Ala Leu Val Cys Ala Gly Cys Glu Gln Ile Phe Glu
             20                  25                  30

Asp Lys Leu Ser Gly Thr Arg Thr Asp Arg Pro Gly Leu Lys Arg Ala
         35                  40                  45

Leu Lys Arg Leu Gln Lys Gly Asp Thr Leu Val Val Trp Lys Leu Asp
     50                  55                  60

Arg Leu Gly Arg Ser Met Lys His Leu Ile Ser Leu Val Gly Glu Leu
 65                  70                  75                  80

Arg Glu Arg Gly Ile Asn Phe Arg Ser Leu Thr Asp Ser Ile Asp Thr
                 85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Ile Ala
        115                 120                 125

Ala Ala Arg Asn Lys Gly Arg Phe Gly Arg Pro Pro Lys Ser Gly
    130                 135                 140
```

<210> SEQ ID NO 61
<211> LENGTH: 198
<212> TYPE: PRT
<213> ORGANISM: Homo sapiens

<400> SEQUENCE: 61

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 62
<211> LENGTH: 198
<212> TYPE: PRT
<213> ORGANISM: Mus musculus

<400> SEQUENCE: 62

Met Asp Ser Leu Leu Met Lys Gln Lys Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Cys Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Glu
                85                  90                  95

Phe Leu Arg Trp Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

```
Leu His Arg Ala Gly Val Gln Ile Gly Ile Met Thr Phe Lys Asp Tyr
        130                 135                 140

Phe Tyr Cys Trp Asn Thr Phe Val Glu Asn Arg Glu Arg Thr Phe Lys
145                 150                 155                 160

Ala Trp Glu Gly Leu His Glu Asn Ser Val Arg Leu Thr Arg Gln Leu
                165                 170                 175

Arg Arg Ile Leu Leu Pro Leu Tyr Glu Val Asp Asp Leu Arg Asp Ala
            180                 185                 190

Phe Arg Met Leu Gly Phe
        195

<210> SEQ ID NO 63
<211> LENGTH: 198
<212> TYPE: PRT
<213> ORGANISM: Canis lupus

<400> SEQUENCE: 63

Met Asp Ser Leu Leu Met Lys Gln Arg Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Tyr Pro Asn Leu Ser Leu Arg Ile Phe Ala Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn Arg Glu Lys Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 64
<211> LENGTH: 199
<212> TYPE: PRT
<213> ORGANISM: Bos taurus

<400> SEQUENCE: 64

Met Asp Ser Leu Leu Lys Lys Gln Arg Gln Phe Leu Tyr Gln Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Pro Thr Ser Phe Ser Leu Asp Phe Gly His
        35                  40                  45
```

```
Leu Arg Asn Lys Ala Gly Cys His Val Glu Leu Leu Phe Leu Arg Tyr
         50                  55                  60

Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Asp
                 85                  90                  95

Phe Leu Arg Gly Tyr Pro Asn Leu Ser Leu Arg Ile Phe Thr Ala Arg
            100                 105                 110

Leu Tyr Phe Cys Asp Lys Glu Arg Lys Ala Glu Pro Glu Gly Leu Arg
        115                 120                 125

Arg Leu His Arg Ala Gly Val Gln Ile Ala Ile Met Thr Phe Lys Asp
    130                 135                 140

Tyr Phe Tyr Cys Trp Asn Thr Phe Val Glu Asn His Glu Arg Thr Phe
145                 150                 155                 160

Lys Ala Trp Glu Gly Leu His Glu Asn Ser Val Arg Leu Ser Arg Gln
                165                 170                 175

Leu Arg Arg Ile Leu Leu Pro Leu Tyr Glu Val Asp Asp Leu Arg Asp
            180                 185                 190

Ala Phe Arg Thr Leu Gly Leu
        195

<210> SEQ ID NO 65
<211> LENGTH: 429
<212> TYPE: PRT
<213> ORGANISM: Mus musculus

<400> SEQUENCE: 65

Met Gly Pro Phe Cys Leu Gly Cys Ser His Arg Lys Cys Tyr Ser Pro
 1               5                  10                  15

Ile Arg Asn Leu Ile Ser Gln Glu Thr Phe Lys Phe His Phe Lys Asn
             20                  25                  30

Leu Gly Tyr Ala Lys Gly Arg Lys Asp Thr Phe Leu Cys Tyr Glu Val
         35                  40                  45

Thr Arg Lys Asp Cys Asp Ser Pro Val Ser Leu His His Gly Val Phe
 50                  55                  60

Lys Asn Lys Asp Asn Ile His Ala Glu Ile Cys Phe Leu Tyr Trp Phe
 65                  70                  75                  80

His Asp Lys Val Leu Lys Val Leu Ser Pro Arg Glu Glu Phe Lys Ile
                 85                  90                  95

Thr Trp Tyr Met Ser Trp Ser Pro Cys Phe Glu Cys Ala Glu Gln Ile
            100                 105                 110

Val Arg Phe Leu Ala Thr His His Asn Leu Ser Leu Asp Ile Phe Ser
        115                 120                 125

Ser Arg Leu Tyr Asn Val Gln Asp Pro Glu Thr Gln Gln Asn Leu Cys
    130                 135                 140

Arg Leu Val Gln Glu Gly Ala Gln Val Ala Ala Met Asp Leu Tyr Glu
145                 150                 155                 160

Phe Lys Lys Cys Trp Lys Lys Phe Val Asp Asn Gly Gly Arg Arg Phe
                165                 170                 175

Arg Pro Trp Lys Arg Leu Leu Thr Asn Phe Arg Tyr Gln Asp Ser Lys
            180                 185                 190

Leu Gln Glu Ile Leu Arg Pro Cys Tyr Ile Pro Val Pro Ser Ser Ser
        195                 200                 205

Ser Ser Thr Leu Ser Asn Ile Cys Leu Thr Lys Gly Leu Pro Glu Thr
```

```
                   210                 215                 220
Arg Phe Cys Val Glu Gly Arg Arg Met Asp Pro Leu Ser Glu Glu
225                 230                 235                 240

Phe Tyr Ser Gln Phe Tyr Asn Gln Arg Val Lys His Leu Cys Tyr
                    245                 250                 255

Tyr His Arg Met Lys Pro Tyr Leu Cys Tyr Gln Leu Glu Gln Phe
                    260                 265                 270

Asn Gly Gln Ala Pro Leu Lys Gly Cys Leu Ser Glu Lys Gly Lys
                275                 280                 285

Gln His Ala Glu Ile Leu Phe Leu Asp Lys Ile Arg Ser Met Glu
                290                 295                 300

Leu Ser Gln Val Thr Ile Thr Cys Tyr Leu Thr Trp Ser Pro Cys
305                 310                 315

Pro Asn Cys Ala Trp Gln Leu Ala Ala Phe Lys Arg Asp Arg Pro
            320                 325                 330

Asp Leu Ile Leu His Ile Tyr Thr Ser Arg Leu Tyr Phe His Trp
                335                 340                 345

Lys Arg Pro Phe Gln Lys Gly Leu Cys Ser Leu Trp Gln Ser Gly
                350                 355                 360

Ile Leu Val Asp Val Met Asp Leu Pro Gln Phe Thr Asp Cys Trp
                365                 370                 375

Thr Asn Phe Val Asn Pro Lys Arg Pro Phe Trp Pro Trp Lys Gly
                380                 385                 390

Leu Glu Ile Ile Ser Arg Arg Thr Gln Arg Arg Leu Arg Arg Ile
                395                 400

Lys Glu Ser Trp Gly Leu Gln Asp Leu Val Asn Asp Phe Gly Asn
405                 410                 415                 420

Leu Gln Leu Gly Pro Pro Met Ser
                425

<210> SEQ ID NO 66
<211> LENGTH: 429
<212> TYPE: PRT
<213> ORGANISM: Rattus norvegicus

<400> SEQUENCE: 66

Met Gly Pro Phe Cys Leu Gly Cys Ser His Arg Lys Cys Tyr Ser
1               5                   10                  15

Pro Ile Arg Asn Leu Ile Ser Gln Glu Thr Phe Lys Phe His Phe
                20                  25                  30

Lys Asn Leu Arg Tyr Ala Ile Asp Arg Lys Asp Thr Phe Leu Cys
                35                  40                  45

Tyr Glu Val Thr Arg Lys Asp Cys Asp Ser Pro Val Ser Leu His
50                  55                  60

His Gly Val Phe Lys Asn Lys Asp Asn Ile His Ala Glu Ile Cys
                65                  70                  75

Phe Leu Tyr Trp Phe His Asp Lys Val Leu Lys Val Leu Ser Pro
80                                  85                  90

Arg Glu Glu Phe Lys Ile Thr Trp Tyr Met Ser Trp Ser Pro Cys
                    95                  100                 105

Phe Glu Cys Ala Glu Gln Val Leu Arg Phe Leu Ala Thr His His
                    110                 115                 120

Asn Leu Ser Leu Asp Ile Phe Ser Ser Arg Leu Tyr Asn Ile Arg
            125                 130                 135

Asp Pro Glu Asn Gln Gln Asn Leu Cys Arg Leu Val Gln Glu Gly
                140                 145                 150

Ala Gln Val Ala Ala Met Asp Leu Tyr Glu
                    155                 160
```

Phe Lys Lys Cys Trp Lys Lys Phe Val Asp Asn Gly Gly Arg Arg Phe
            165                 170                 175

Arg Pro Trp Lys Lys Leu Leu Thr Asn Phe Arg Tyr Gln Asp Ser Lys
            180                 185                 190

Leu Gln Glu Ile Leu Arg Pro Cys Tyr Ile Pro Val Pro Ser Ser Ser
            195                 200                 205

Ser Ser Thr Leu Ser Asn Ile Cys Leu Thr Lys Gly Leu Pro Glu Thr
            210                 215                 220

Arg Phe Cys Val Glu Arg Arg Val His Leu Leu Ser Glu Glu Glu
225                 230                 235                 240

Phe Tyr Ser Gln Phe Tyr Asn Gln Arg Val Lys His Leu Cys Tyr Tyr
            245                 250                 255

His Gly Val Lys Pro Tyr Leu Cys Tyr Gln Leu Glu Gln Phe Asn Gly
            260                 265                 270

Gln Ala Pro Leu Lys Gly Cys Leu Leu Ser Glu Lys Gly Lys Gln His
            275                 280                 285

Ala Glu Ile Leu Phe Leu Asp Lys Ile Arg Ser Met Glu Leu Ser Gln
            290                 295                 300

Val Ile Ile Thr Cys Tyr Leu Thr Trp Ser Pro Cys Pro Asn Cys Ala
305                 310                 315                 320

Trp Gln Leu Ala Ala Phe Lys Arg Asp Arg Pro Asp Leu Ile Leu His
            325                 330                 335

Ile Tyr Thr Ser Arg Leu Tyr Phe His Trp Lys Arg Pro Phe Gln Lys
            340                 345                 350

Gly Leu Cys Ser Leu Trp Gln Ser Gly Ile Leu Val Asp Val Met Asp
            355                 360                 365

Leu Pro Gln Phe Thr Asp Cys Trp Thr Asn Phe Val Asn Pro Lys Arg
            370                 375                 380

Pro Phe Trp Pro Trp Lys Gly Leu Glu Ile Ile Ser Arg Arg Thr Gln
385                 390                 395                 400

Arg Arg Leu His Arg Ile Lys Glu Ser Trp Gly Leu Gln Asp Leu Val
            405                 410                 415

Asn Asp Phe Gly Asn Leu Gln Leu Gly Pro Pro Met Ser
            420                 425

<210> SEQ ID NO 67
<211> LENGTH: 370
<212> TYPE: PRT
<213> ORGANISM: Macaca mulatta

<400> SEQUENCE: 67

Met Val Glu Pro Met Asp Pro Arg Thr Phe Val Ser Asn Phe Asn Asn
1               5                   10                  15

Arg Pro Ile Leu Ser Gly Leu Asn Thr Val Trp Leu Cys Cys Glu Val
            20                  25                  30

Lys Thr Lys Asp Pro Ser Gly Pro Pro Leu Asp Ala Lys Ile Phe Gln
            35                  40                  45

Gly Lys Val Tyr Ser Lys Ala Lys Tyr His Pro Glu Met Arg Phe Leu
        50                  55                  60

Arg Trp Phe His Lys Trp Arg Gln Leu His His Asp Gln Glu Tyr Lys
65                  70                  75                  80

Val Thr Trp Tyr Val Ser Trp Ser Pro Cys Thr Arg Cys Ala Asn Ser
            85                  90                  95

Val Ala Thr Phe Leu Ala Lys Asp Pro Lys Val Thr Leu Thr Ile Phe
            100                 105                 110

```
Val Ala Arg Leu Tyr Tyr Phe Trp Lys Pro Asp Tyr Gln Gln Ala Leu
            115                 120                 125

Arg Ile Leu Cys Gln Lys Arg Gly Pro His Ala Thr Met Lys Ile
        130                 135                 140

Met Asn Tyr Asn Glu Phe Gln Asp Cys Trp Asn Lys Phe Val Asp Gly
145                 150                 155                 160

Arg Gly Lys Pro Phe Lys Pro Arg Asn Asn Leu Pro Lys His Tyr Thr
                165                 170                 175

Leu Leu Gln Ala Thr Leu Gly Glu Leu Leu Arg His Leu Met Asp Pro
            180                 185                 190

Gly Thr Phe Thr Ser Asn Phe Asn Asn Lys Pro Trp Val Ser Gly Gln
            195                 200                 205

His Glu Thr Tyr Leu Cys Tyr Lys Val Glu Arg Leu His Asn Asp Thr
        210                 215                 220

Trp Val Pro Leu Asn Gln His Arg Gly Phe Leu Arg Asn Gln Ala Pro
225                 230                 235                 240

Asn Ile His Gly Phe Pro Lys Gly Arg His Ala Glu Leu Cys Phe Leu
                245                 250                 255

Asp Leu Ile Pro Phe Trp Lys Leu Asp Gly Gln Gln Tyr Arg Val Thr
            260                 265                 270

Cys Phe Thr Ser Trp Ser Pro Cys Phe Ser Cys Ala Gln Glu Met Ala
        275                 280                 285

Lys Phe Ile Ser Asn Asn Glu His Val Ser Leu Cys Ile Phe Ala Ala
        290                 295                 300

Arg Ile Tyr Asp Asp Gln Gly Arg Tyr Gln Glu Gly Leu Arg Ala Leu
305                 310                 315                 320

His Arg Asp Gly Ala Lys Ile Ala Met Met Asn Tyr Ser Glu Phe Glu
                325                 330                 335

Tyr Cys Trp Asp Thr Phe Val Asp Arg Gln Gly Arg Pro Phe Gln Pro
            340                 345                 350

Trp Asp Gly Leu Asp Glu His Ser Gln Ala Leu Ser Gly Arg Leu Arg
            355                 360                 365

Ala Ile
    370

<210> SEQ ID NO 68
<211> LENGTH: 384
<212> TYPE: PRT
<213> ORGANISM: Pan troglodytes

<400> SEQUENCE: 68

Met Lys Pro His Phe Arg Asn Pro Val Glu Arg Met Tyr Gln Asp Thr
1               5                   10                  15

Phe Ser Asp Asn Phe Tyr Asn Arg Pro Ile Leu Ser His Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Lys Leu Lys Tyr
    50                  55                  60

His Pro Glu Met Arg Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Val Ala Thr Phe Leu Ala Glu Asp Pro
```

```
            100                 105                 110
Lys Val Thr Leu Thr Ile Phe Val Ala Arg Leu Tyr Tyr Phe Trp Asp
            115                 120                 125
Pro Asp Tyr Gln Glu Ala Leu Arg Ser Leu Cys Gln Lys Arg Asp Gly
        130                 135                 140
Pro Arg Ala Thr Met Lys Ile Met Asn Tyr Asp Glu Phe Gln His Cys
145                 150                 155                 160
Trp Ser Lys Phe Val Tyr Ser Gln Arg Glu Leu Phe Glu Pro Trp Asn
                165                 170                 175
Asn Leu Pro Lys Tyr Tyr Ile Leu Leu His Ile Met Leu Gly Glu Ile
            180                 185                 190
Leu Arg His Ser Met Asp Pro Pro Thr Phe Thr Ser Asn Phe Asn Asn
        195                 200                 205
Glu Leu Trp Val Arg Gly Arg His Glu Thr Tyr Leu Cys Tyr Glu Val
        210                 215                 220
Glu Arg Leu His Asn Asp Thr Trp Val Leu Leu Asn Gln Arg Arg Gly
225                 230                 235                 240
Phe Leu Cys Asn Gln Ala Pro His Lys His Gly Phe Leu Glu Gly Arg
                245                 250                 255
His Ala Glu Leu Cys Phe Leu Asp Val Ile Pro Phe Trp Lys Leu Asp
            260                 265                 270
Leu His Gln Asp Tyr Arg Val Thr Cys Phe Thr Ser Trp Ser Pro Cys
        275                 280                 285
Phe Ser Cys Ala Gln Glu Met Ala Lys Phe Ile Ser Asn Asn Lys His
        290                 295                 300
Val Ser Leu Cys Ile Phe Ala Ala Arg Ile Tyr Asp Asp Gln Gly Arg
305                 310                 315                 320
Cys Gln Glu Gly Leu Arg Thr Leu Ala Lys Ala Gly Ala Lys Ile Ser
                325                 330                 335
Ile Met Thr Tyr Ser Glu Phe Lys His Cys Trp Asp Thr Phe Val Asp
            340                 345                 350
His Gln Gly Cys Pro Phe Gln Pro Trp Asp Gly Leu Glu Glu His Ser
        355                 360                 365
Gln Ala Leu Ser Gly Arg Leu Arg Ala Ile Leu Gln Asn Gln Gly Asn
        370                 375                 380

<210> SEQ ID NO 69
<211> LENGTH: 377
<212> TYPE: PRT
<213> ORGANISM: Chlorocebus sabaeus

<400> SEQUENCE: 69

Met Asn Pro Gln Ile Arg Asn Met Val Glu Gln Met Glu Pro Asp Ile
1               5                   10                  15
Phe Val Tyr Tyr Phe Asn Asn Arg Pro Ile Leu Ser Gly Arg Asn Thr
                20                  25                  30
Val Trp Leu Cys Tyr Glu Val Lys Thr Lys Asp Pro Ser Gly Pro Pro
            35                  40                  45
Leu Asp Ala Asn Ile Phe Gln Gly Lys Leu Tyr Pro Glu Ala Lys Asp
        50                  55                  60
His Pro Glu Met Lys Phe Leu His Trp Phe Arg Lys Trp Arg Gln Leu
65                  70                  75                  80
His Arg Asp Gln Glu Tyr Glu Val Thr Trp Tyr Val Ser Trp Ser Pro
                85                  90                  95
```

```
Cys Thr Arg Cys Ala Asn Ser Val Ala Thr Phe Leu Ala Glu Asp Pro
                100                 105                 110

Lys Val Thr Leu Thr Ile Phe Val Ala Arg Leu Tyr Tyr Phe Trp Lys
            115                 120                 125

Pro Asp Tyr Gln Gln Ala Leu Arg Ile Leu Cys Gln Glu Arg Gly Gly
        130                 135                 140

Pro His Ala Thr Met Lys Ile Met Asn Tyr Asn Glu Phe Gln His Cys
145                 150                 155                 160

Trp Asn Glu Phe Val Asp Gly Gln Gly Lys Pro Phe Lys Pro Arg Lys
                165                 170                 175

Asn Leu Pro Lys His Tyr Thr Leu Leu His Ala Thr Leu Gly Glu Leu
            180                 185                 190

Leu Arg His Val Met Asp Pro Gly Thr Phe Thr Ser Asn Phe Asn Asn
        195                 200                 205

Lys Pro Trp Val Ser Gly Gln Arg Glu Thr Tyr Leu Cys Tyr Lys Val
    210                 215                 220

Glu Arg Ser His Asn Asp Thr Trp Val Leu Leu Asn Gln His Arg Gly
225                 230                 235                 240

Phe Leu Arg Asn Gln Ala Pro Asp Arg His Gly Phe Pro Lys Gly Arg
                245                 250                 255

His Ala Glu Leu Cys Phe Leu Asp Leu Ile Pro Phe Trp Lys Leu Asp
            260                 265                 270

Asp Gln Gln Tyr Arg Val Thr Cys Phe Thr Ser Trp Ser Pro Cys Phe
        275                 280                 285

Ser Cys Ala Gln Lys Met Ala Lys Phe Ile Ser Asn Asn Lys His Val
290                 295                 300

Ser Leu Cys Ile Phe Ala Ala Arg Ile Tyr Asp Asp Gln Gly Arg Cys
305                 310                 315                 320

Gln Glu Gly Leu Arg Thr Leu His Arg Asp Gly Ala Lys Ile Ala Val
                325                 330                 335

Met Asn Tyr Ser Glu Phe Glu Tyr Cys Trp Asp Thr Phe Val Asp Arg
            340                 345                 350

Gln Gly Arg Pro Phe Gln Pro Trp Asp Gly Leu Asp Glu His Ser Gln
        355                 360                 365

Ala Leu Ser Gly Arg Leu Arg Ala Ile
    370                 375

<210> SEQ ID NO 70
<211> LENGTH: 384
<212> TYPE: PRT
<213> ORGANISM: Homo sapiens

<400> SEQUENCE: 70

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
                20                  25                  30

Val Trp Leu Cys Tyr Glu Val Lys Thr Lys Gly Pro Ser Arg Pro Pro
            35                  40                  45

Leu Asp Ala Lys Ile Phe Arg Gly Gln Val Tyr Ser Glu Leu Lys Tyr
        50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95
```

```
Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
            115                 120                 125

Pro Asp Tyr Gln Glu Ala Leu Arg Ser Leu Cys Gln Lys Arg Asp Gly
130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
            195                 200                 205

Glu Pro Trp Val Arg Gly Arg His Glu Thr Tyr Leu Cys Tyr Glu Val
            210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
            275                 280                 285

Phe Ser Cys Ala Gln Glu Met Ala Lys Phe Ile Ser Lys Asn Lys His
            290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Asp Glu His Ser
            355                 360                 365

Gln Asp Leu Ser Gly Arg Leu Arg Ala Ile Leu Gln Asn Gln Glu Asn
370                 375                 380

<210> SEQ ID NO 71
<211> LENGTH: 373
<212> TYPE: PRT
<213> ORGANISM: Homo sapiens

<400> SEQUENCE: 71

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Arg
            35                  40                  45

Leu Asp Ala Lys Ile Phe Arg Gly Gln Val Tyr Ser Gln Pro Glu His
            50                  55                  60

His Ala Glu Met Cys Phe Leu Ser Trp Phe Cys Gly Asn Gln Leu Pro
65                  70                  75                  80

Ala Tyr Lys Cys Phe Gln Ile Thr Trp Phe Val Ser Trp Thr Pro Cys
```

```
                    85                  90                  95
Pro Asp Cys Val Ala Lys Leu Ala Glu Phe Leu Ala Glu His Pro Asn
            100                 105                 110

Val Thr Leu Thr Ile Ser Ala Ala Arg Leu Tyr Tyr Tyr Trp Glu Arg
        115                 120                 125

Asp Tyr Arg Arg Ala Leu Cys Arg Leu Ser Gln Ala Gly Ala Arg Val
    130                 135                 140

Lys Ile Met Asp Asp Glu Glu Phe Ala Tyr Cys Trp Glu Asn Phe Val
145                 150                 155                 160

Tyr Ser Glu Gly Gln Pro Phe Met Pro Trp Tyr Lys Phe Asp Asp Asn
                165                 170                 175

Tyr Ala Phe Leu His Arg Thr Leu Lys Glu Ile Leu Arg Asn Pro Met
            180                 185                 190

Glu Ala Met Tyr Pro His Ile Phe Tyr Phe His Phe Lys Asn Leu Arg
        195                 200                 205

Lys Ala Tyr Gly Arg Asn Glu Ser Trp Leu Cys Phe Thr Met Glu Val
    210                 215                 220

Val Lys His His Ser Pro Val Ser Trp Lys Arg Gly Val Phe Arg Asn
225                 230                 235                 240

Gln Val Asp Pro Glu Thr His Cys His Ala Glu Arg Cys Phe Leu Ser
                245                 250                 255

Trp Phe Cys Asp Asp Ile Leu Ser Pro Asn Thr Asn Tyr Glu Val Thr
            260                 265                 270

Trp Tyr Thr Ser Trp Ser Pro Cys Pro Glu Cys Ala Gly Glu Val Ala
        275                 280                 285

Glu Phe Leu Ala Arg His Ser Asn Val Asn Leu Thr Ile Phe Thr Ala
    290                 295                 300

Arg Leu Tyr Tyr Phe Trp Asp Thr Asp Tyr Gln Glu Gly Leu Arg Ser
305                 310                 315                 320

Leu Ser Gln Glu Gly Ala Ser Val Glu Ile Met Gly Tyr Lys Asp Phe
                325                 330                 335

Lys Tyr Cys Trp Glu Asn Phe Val Tyr Asn Asp Asp Glu Pro Phe Lys
            340                 345                 350

Pro Trp Lys Gly Leu Lys Tyr Asn Phe Leu Phe Leu Asp Ser Lys Leu
        355                 360                 365

Gln Glu Ile Leu Glu
    370

<210> SEQ ID NO 72
<211> LENGTH: 382
<212> TYPE: PRT
<213> ORGANISM: Homo sapiens

<400> SEQUENCE: 72

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Lys Pro Gln
    50                  55                  60

Tyr His Ala Glu Met Cys Phe Leu Ser Trp Phe Cys Gly Asn Gln Leu
65                  70                  75                  80
```

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140

Val Thr Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
            165                 170                 175

Asn Tyr Ala Phe Leu His Arg Thr Leu Lys Glu Ile Leu Arg Tyr Leu
        180                 185                 190

Met Asp Pro Asp Thr Phe Thr Phe Asn Phe Asn Asn Asp Pro Leu Val
    195                 200                 205

Leu Arg Arg Arg Gln Thr Tyr Leu Cys Tyr Glu Val Glu Arg Leu Asp
210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
            245                 250                 255

Arg Phe Leu Asp Leu Val Pro Ser Leu Gln Leu Asp Pro Ala Gln Ile
        260                 265                 270

Tyr Arg Val Thr Trp Phe Ile Ser Trp Ser Pro Cys Phe Ser Trp Gly
    275                 280                 285

Cys Ala Gly Glu Val Arg Ala Phe Leu Gln Glu Asn Thr His Val Arg
290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
            325                 330                 335

Thr Tyr Asp Glu Phe Glu Tyr Cys Trp Asp Thr Phe Val Tyr Arg Gln
        340                 345                 350

Gly Cys Pro Phe Gln Pro Trp Asp Gly Leu Glu Glu His Ser Gln Ala
    355                 360                 365

Leu Ser Gly Arg Leu Arg Ala Ile Leu Gln Asn Gln Gly Asn
    370                 375                 380

<210> SEQ ID NO 73
<211> LENGTH: 190
<212> TYPE: PRT
<213> ORGANISM: Homo sapiens

<400> SEQUENCE: 73

Met Asn Pro Gln Ile Arg Asn Pro Met Lys Ala Met Tyr Pro Gly Thr
1               5                   10                  15

Phe Tyr Phe Gln Phe Lys Asn Leu Trp Glu Ala Asn Asp Arg Asn Glu
            20                  25                  30

Thr Trp Leu Cys Phe Thr Val Glu Gly Ile Lys Arg Arg Ser Val Val
        35                  40                  45

Ser Trp Lys Thr Gly Val Phe Arg Asn Gln Val Asp Ser Glu Thr His
    50                  55                  60

Cys His Ala Glu Arg Cys Phe Leu Ser Trp Phe Cys Asp Asp Ile Leu
65                  70                  75                  80

-continued

```
Ser Pro Asn Thr Lys Tyr Gln Val Thr Trp Tyr Thr Ser Trp Ser Pro
                85                  90                  95

Cys Pro Asp Cys Ala Gly Glu Val Ala Glu Phe Leu Ala Arg His Ser
            100                 105                 110

Asn Val Asn Leu Thr Ile Phe Thr Ala Arg Leu Tyr Tyr Phe Gln Tyr
        115                 120                 125

Pro Cys Tyr Gln Glu Gly Leu Arg Ser Leu Ser Gln Glu Gly Val Ala
    130                 135                 140

Val Glu Ile Met Asp Tyr Glu Asp Phe Lys Tyr Cys Trp Glu Asn Phe
145                 150                 155                 160

Val Tyr Asn Asp Asn Glu Pro Phe Lys Pro Trp Lys Gly Leu Lys Thr
                165                 170                 175

Asn Phe Arg Leu Leu Lys Arg Arg Leu Arg Glu Ser Leu Gln
            180                 185                 190

<210> SEQ ID NO 74
<211> LENGTH: 199
<212> TYPE: PRT
<213> ORGANISM: Homo sapiens

<400> SEQUENCE: 74

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 75
<211> LENGTH: 200
<212> TYPE: PRT
<213> ORGANISM: Homo sapiens

<400> SEQUENCE: 75

Met Ala Leu Leu Thr Ala Glu Thr Phe Arg Leu Gln Phe Asn Asn Lys
1               5                   10                  15
```

Arg Arg Leu Arg Arg Pro Tyr Tyr Pro Arg Lys Ala Leu Leu Cys Tyr
            20                  25                  30

Gln Leu Thr Pro Gln Asn Gly Ser Thr Pro Thr Arg Gly Tyr Phe Glu
        35                  40                  45

Asn Lys Lys Cys His Ala Glu Ile Cys Phe Ile Asn Glu Ile Lys
 50                  55                  60

Ser Met Gly Leu Asp Glu Thr Gln Cys Tyr Gln Val Thr Cys Tyr Leu
 65                  70                  75                  80

Thr Trp Ser Pro Cys Ser Ser Cys Ala Trp Glu Leu Val Asp Phe Ile
                85                  90                  95

Lys Ala His Asp His Leu Asn Leu Gly Ile Phe Ala Ser Arg Leu Tyr
            100                 105                 110

Tyr His Trp Cys Lys Pro Gln Gln Lys Gly Leu Arg Leu Leu Cys Gly
            115                 120                 125

Ser Gln Val Pro Val Glu Val Met Gly Phe Pro Lys Phe Ala Asp Cys
130                 135                 140

Trp Glu Asn Phe Val Asp His Glu Lys Pro Leu Ser Phe Asn Pro Tyr
145                 150                 155                 160

Lys Met Leu Glu Glu Leu Asp Lys Asn Ser Arg Ala Ile Lys Arg Arg
                165                 170                 175

Leu Glu Arg Ile Lys Ile Pro Gly Val Arg Ala Gln Gly Arg Tyr Met
            180                 185                 190

Asp Ile Leu Cys Asp Ala Glu Val
            195                 200

<210> SEQ ID NO 76
<211> LENGTH: 386
<212> TYPE: PRT
<213> ORGANISM: Homo sapiens

<400> SEQUENCE: 76

Met Asn Pro Gln Ile Arg Asn Pro Met Glu Arg Met Tyr Arg Asp Thr
 1               5                  10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Pro Val Leu Pro Lys Arg Gln
 50                  55                  60

Ser Asn His Arg Gln Glu Val Tyr Phe Arg Phe Glu Asn His Ala Glu
 65                  70                  75                  80

Met Cys Phe Leu Ser Trp Phe Cys Gly Asn Arg Leu Pro Ala Asn Arg
                85                  90                  95

Arg Phe Gln Ile Thr Trp Phe Val Ser Trp Asn Pro Cys Leu Pro Cys
            100                 105                 110

Val Val Lys Val Thr Lys Phe Leu Ala Glu His Pro Asn Val Thr Leu
            115                 120                 125

Thr Ile Ser Ala Ala Arg Leu Tyr Tyr Tyr Arg Asp Arg Asp Trp Arg
130                 135                 140

Trp Val Leu Leu Arg Leu His Lys Ala Gly Ala Arg Val Lys Ile Met
145                 150                 155                 160

Asp Tyr Glu Asp Phe Ala Tyr Cys Trp Glu Asn Phe Val Cys Asn Glu
                165                 170                 175

Gly Gln Pro Phe Met Pro Trp Tyr Lys Phe Asp Asp Asn Tyr Ala Ser

```
            180                 185                 190
Leu His Arg Thr Leu Lys Glu Ile Leu Arg Asn Pro Met Glu Ala Met
            195                 200                 205

Tyr Pro His Ile Phe Tyr Phe His Phe Lys Asn Leu Leu Lys Ala Cys
            210                 215                 220

Gly Arg Asn Glu Ser Trp Leu Cys Phe Thr Met Glu Val Thr Lys His
225                 230                 235                 240

His Ser Ala Val Phe Arg Lys Arg Gly Val Phe Arg Asn Gln Val Asp
                245                 250                 255

Pro Glu Thr His Cys His Ala Glu Arg Cys Phe Leu Ser Trp Phe Cys
                260                 265                 270

Asp Asp Ile Leu Ser Pro Asn Thr Asn Tyr Glu Val Thr Trp Tyr Thr
                275                 280                 285

Ser Trp Ser Pro Cys Pro Glu Cys Ala Gly Glu Val Ala Glu Phe Leu
                290                 295                 300

Ala Arg His Ser Asn Val Asn Leu Thr Ile Phe Thr Ala Arg Leu Cys
305                 310                 315                 320

Tyr Phe Trp Asp Thr Asp Tyr Gln Glu Gly Leu Cys Ser Leu Ser Gln
                325                 330                 335

Glu Gly Ala Ser Val Lys Ile Met Gly Tyr Lys Asp Phe Val Ser Cys
                340                 345                 350

Trp Lys Asn Phe Val Tyr Ser Asp Asp Glu Pro Phe Lys Pro Trp Lys
                355                 360                 365

Gly Leu Gln Thr Asn Phe Arg Leu Leu Lys Arg Arg Leu Arg Glu Ile
                370                 375                 380

Leu Gln
385

<210> SEQ ID NO 77
<211> LENGTH: 236
<212> TYPE: PRT
<213> ORGANISM: Homo sapiens

<400> SEQUENCE: 77

Met Thr Ser Glu Lys Gly Pro Ser Thr Gly Asp Pro Thr Leu Arg Arg
1               5                   10                  15

Arg Ile Glu Pro Trp Glu Phe Asp Val Phe Tyr Asp Pro Arg Glu Leu
                20                  25                  30

Arg Lys Glu Ala Cys Leu Leu Tyr Glu Ile Lys Trp Gly Met Ser Arg
            35                  40                  45

Lys Ile Trp Arg Ser Ser Gly Lys Asn Thr Thr Asn His Val Glu Val
        50                  55                  60

Asn Phe Ile Lys Lys Phe Thr Ser Glu Arg Asp Phe His Pro Ser Met
65                  70                  75                  80

Ser Cys Ser Ile Thr Trp Phe Leu Ser Trp Ser Pro Cys Trp Glu Cys
                85                  90                  95

Ser Gln Ala Ile Arg Glu Phe Leu Ser Arg His Pro Gly Val Thr Leu
                100                 105                 110

Val Ile Tyr Val Ala Arg Leu Phe Trp His Met Asp Gln Gln Asn Arg
                115                 120                 125

Gln Gly Leu Arg Asp Leu Val Asn Ser Gly Val Thr Ile Gln Ile Met
            130                 135                 140

Arg Ala Ser Glu Tyr Tyr His Cys Trp Arg Asn Phe Val Asn Tyr Pro
145                 150                 155                 160
```

```
Pro Gly Asp Glu Ala His Trp Pro Gln Tyr Pro Pro Leu Trp Met Met
            165                 170                 175

Leu Tyr Ala Leu Glu Leu His Cys Ile Ile Leu Ser Leu Pro Pro Cys
        180                 185                 190

Leu Lys Ile Ser Arg Arg Trp Gln Asn His Leu Thr Phe Phe Arg Leu
        195                 200                 205

His Leu Gln Asn Cys His Tyr Gln Thr Ile Pro Pro His Ile Leu Leu
        210                 215                 220

Ala Thr Gly Leu Ile His Pro Ser Val Ala Trp Arg
225                 230                 235

<210> SEQ ID NO 78
<211> LENGTH: 229
<212> TYPE: PRT
<213> ORGANISM: Mus musculus

<400> SEQUENCE: 78

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Val Trp Arg His Thr Ser Gln Asn Thr Ser Asn His Val Glu Val
    50                  55                  60

Asn Phe Leu Glu Lys Phe Thr Thr Glu Arg Tyr Phe Arg Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg His Pro Tyr Val Thr Leu
            100                 105                 110

Phe Ile Tyr Ile Ala Arg Leu Tyr His His Thr Asp Gln Arg Asn Arg
        115                 120                 125

Gln Gly Leu Arg Asp Leu Ile Ser Ser Gly Val Thr Ile Gln Ile Met
    130                 135                 140

Thr Glu Gln Glu Tyr Cys Tyr Cys Trp Arg Asn Phe Val Asn Tyr Pro
145                 150                 155                 160

Pro Ser Asn Glu Ala Tyr Trp Pro Arg Tyr Pro His Leu Trp Val Lys
                165                 170                 175

Leu Tyr Val Leu Glu Leu Tyr Cys Ile Ile Leu Gly Leu Pro Pro Cys
            180                 185                 190

Leu Lys Ile Leu Arg Arg Lys Gln Pro Gln Leu Thr Phe Phe Thr Ile
        195                 200                 205

Thr Leu Gln Thr Cys His Tyr Gln Arg Ile Pro Pro His Leu Leu Trp
    210                 215                 220

Ala Thr Gly Leu Lys
225

<210> SEQ ID NO 79
<211> LENGTH: 229
<212> TYPE: PRT
<213> ORGANISM: Rattus norvegicus

<400> SEQUENCE: 79

Met Ser Ser Glu Thr Gly Pro Val Ala Val Asp Pro Thr Leu Arg Arg
1               5                   10                  15
```

```
Arg Ile Glu Pro His Glu Phe Glu Val Phe Asp Pro Arg Glu Leu
             20                  25                  30

Arg Lys Glu Thr Cys Leu Leu Tyr Glu Ile Asn Trp Gly Gly Arg His
         35                  40                  45

Ser Ile Trp Arg His Thr Ser Gln Asn Thr Asn Lys His Val Glu Val
 50                  55                  60

Asn Phe Ile Glu Lys Phe Thr Thr Glu Arg Tyr Phe Cys Pro Asn Thr
 65                  70                  75                  80

Arg Cys Ser Ile Thr Trp Phe Leu Ser Trp Ser Pro Cys Gly Glu Cys
                 85                  90                  95

Ser Arg Ala Ile Thr Glu Phe Leu Ser Arg Tyr Pro His Val Thr Leu
             100                 105                 110

Phe Ile Tyr Ile Ala Arg Leu Tyr His His Ala Asp Pro Arg Asn Arg
         115                 120                 125

Gln Gly Leu Arg Asp Leu Ile Ser Ser Gly Val Thr Ile Gln Ile Met
     130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                 165                 170                 175

Leu Tyr Val Leu Glu Leu Tyr Cys Ile Ile Leu Gly Leu Pro Pro Cys
             180                 185                 190

Leu Asn Ile Leu Arg Arg Lys Gln Pro Gln Leu Thr Phe Phe Thr Ile
         195                 200                 205

Ala Leu Gln Ser Cys His Tyr Gln Arg Leu Pro Pro His Ile Leu Trp
     210                 215                 220

Ala Thr Gly Leu Lys
225

<210> SEQ ID NO 80
<211> LENGTH: 191
<212> TYPE: PRT
<213> ORGANISM: Homo sapiens

<400> SEQUENCE: 80

Met Glu Ala Lys Ala Ala Pro Lys Pro Ala Ala Ser Gly Ala Cys Ser
 1               5                  10                  15

Val Ser Ala Glu Glu Thr Glu Lys Trp Met Glu Glu Ala Met His Met
             20                  25                  30

Ala Lys Glu Ala Leu Glu Asn Thr Glu Val Pro Val Gly Cys Leu Met
         35                  40                  45

Val Tyr Asn Asn Glu Val Val Gly Lys Gly Arg Asn Glu Val Asn Gln
 50                  55                  60

Thr Lys Asn Ala Thr Arg His Ala Glu Met Val Ala Ile Asp Gln Val
 65                  70                  75                  80

Leu Asp Trp Cys Arg Gln Ser Gly Lys Ser Pro Ser Glu Val Phe Glu
                 85                  90                  95

His Thr Val Leu Tyr Val Thr Val Glu Pro Cys Ile Met Cys Ala Ala
             100                 105                 110

Ala Leu Arg Leu Met Lys Ile Pro Leu Val Val Tyr Gly Cys Gln Asn
         115                 120                 125

Glu Arg Phe Gly Gly Cys Gly Ser Val Leu Asn Ile Ala Ser Ala Asp
     130                 135                 140

Leu Pro Asn Thr Gly Arg Pro Phe Gln Cys Ile Pro Gly Tyr Arg Ala
145                 150                 155                 160
```

Glu Glu Ala Val Glu Met Leu Lys Thr Phe Tyr Lys Gln Glu Asn Pro
            165                 170                 175

Asn Ala Pro Lys Ser Lys Val Arg Lys Lys Glu Cys Gln Lys Ser
        180                 185                 190

<210> SEQ ID NO 81
<211> LENGTH: 191
<212> TYPE: PRT
<213> ORGANISM: Mus musculus

<400> SEQUENCE: 81

Met Glu Glu Lys Val Glu Ser Thr Thr Thr Pro Asp Gly Pro Cys Val
1               5                   10                  15

Val Ser Val Gln Glu Thr Glu Lys Trp Met Glu Glu Ala Met Arg Met
            20                  25                  30

Ala Lys Glu Ala Leu Glu Asn Ile Glu Val Pro Val Gly Cys Leu Met
        35                  40                  45

Val Tyr Asn Asn Glu Val Val Gly Lys Gly Arg Asn Glu Val Asn Gln
    50                  55                  60

Thr Lys Asn Ala Thr Arg His Ala Glu Met Val Ala Ile Asp Gln Val
65                  70                  75                  80

Leu Asp Trp Cys His Gln His Gly Gln Ser Pro Ser Thr Val Phe Glu
                85                  90                  95

His Thr Val Leu Tyr Val Thr Val Glu Pro Cys Ile Met Cys Ala Ala
            100                 105                 110

Ala Leu Arg Leu Met Lys Ile Pro Leu Val Val Tyr Gly Cys Gln Asn
        115                 120                 125

Glu Arg Phe Gly Gly Cys Gly Ser Val Leu Asn Ile Ala Ser Ala Asp
    130                 135                 140

Leu Pro Asn Thr Gly Arg Pro Phe Gln Cys Ile Pro Gly Tyr Arg Ala
145                 150                 155                 160

Glu Glu Ala Val Glu Leu Leu Lys Thr Phe Tyr Lys Gln Glu Asn Pro
                165                 170                 175

Asn Ala Pro Lys Ser Lys Val Arg Lys Lys Asp Cys Gln Lys Ser
        180                 185                 190

<210> SEQ ID NO 82
<211> LENGTH: 499
<212> TYPE: PRT
<213> ORGANISM: Mus musculus

<400> SEQUENCE: 82

Met Trp Thr Ala Asp Glu Ile Ala Gln Leu Cys Tyr Ala His Tyr Asn
1               5                   10                  15

Val Arg Leu Pro Lys Gln Gly Lys Pro Glu Pro Asn Arg Glu Trp Thr
            20                  25                  30

Leu Leu Ala Ala Val Val Lys Ile Gln Ala Ser Ala Asn Gln Ala Cys
        35                  40                  45

Asp Ile Pro Glu Lys Glu Val Gln Val Thr Lys Glu Val Val Ser Met
    50                  55                  60

Gly Thr Gly Thr Lys Cys Ile Gly Gln Ser Lys Met Arg Glu Ser Gly
65                  70                  75                  80

Asp Ile Leu Asn Asp Ser His Ala Glu Ile Ile Ala Arg Arg Ser Phe
                85                  90                  95

Gln Arg Tyr Leu Leu His Gln Leu His Leu Ala Ala Val Leu Lys Glu
            100                 105                 110

Asp Ser Ile Phe Val Pro Gly Thr Gln Arg Gly Leu Trp Arg Leu Arg
    115                 120                 125

Pro Asp Leu Ser Phe Val Phe Phe Ser Ser His Thr Pro Cys Gly Asp
    130                 135                 140

Ala Ser Ile Ile Pro Met Leu Glu Phe Glu Gln Pro Cys Cys Pro
145                 150                 155                 160

Val Ile Arg Ser Trp Ala Asn Asn Ser Pro Val Gln Glu Thr Glu Asn
                165                 170                 175

Leu Glu Asp Ser Lys Asp Lys Arg Asn Cys Glu Asp Pro Ala Ser Pro
                180                 185                 190

Val Ala Lys Lys Met Arg Leu Gly Thr Pro Ala Arg Ser Leu Ser Asn
                195                 200                 205

Cys Val Ala His His Gly Thr Gln Glu Ser Gly Pro Val Lys Pro Asp
210                 215                 220

Val Ser Ser Ser Asp Leu Thr Lys Glu Glu Pro Asp Ala Ala Asn Gly
225                 230                 235                 240

Ile Ala Ser Gly Ser Phe Arg Val Val Asp Val Tyr Arg Thr Gly Ala
                245                 250                 255

Lys Cys Val Pro Gly Glu Thr Gly Asp Leu Arg Glu Pro Gly Ala Ala
                260                 265                 270

Tyr His Gln Val Gly Leu Leu Arg Val Lys Pro Gly Arg Gly Asp Arg
    275                 280                 285

Thr Cys Ser Met Ser Cys Ser Asp Lys Met Ala Arg Trp Asn Val Leu
    290                 295                 300

Gly Cys Gln Gly Ala Leu Leu Met His Phe Leu Glu Lys Pro Ile Tyr
305                 310                 315                 320

Leu Ser Ala Val Val Ile Gly Lys Cys Pro Tyr Ser Gln Glu Ala Met
                325                 330                 335

Arg Arg Ala Leu Thr Gly Arg Cys Glu Glu Thr Leu Val Leu Pro Arg
                340                 345                 350

Gly Phe Gly Val Gln Glu Leu Glu Ile Gln Gln Ser Gly Leu Leu Phe
    355                 360                 365

Glu Gln Ser Arg Cys Ala Val His Arg Lys Arg Gly Asp Ser Pro Gly
    370                 375                 380

Arg Leu Val Pro Cys Gly Ala Ala Ile Ser Trp Ser Ala Val Pro Gln
385                 390                 395                 400

Gln Pro Leu Asp Val Thr Ala Asn Gly Phe Pro Gln Gly Thr Thr Lys
                405                 410                 415

Lys Glu Ile Gly Ser Pro Arg Ala Arg Ser Arg Ile Ser Lys Val Glu
                420                 425                 430

Leu Phe Arg Ser Phe Gln Lys Leu Leu Ser Ser Ile Ala Asp Asp Glu
    435                 440                 445

Gln Pro Asp Ser Ile Arg Val Thr Lys Lys Leu Asp Thr Tyr Gln Glu
    450                 455                 460

Tyr Lys Asp Ala Ala Ser Ala Tyr Gln Glu Ala Trp Gly Ala Leu Arg
465                 470                 475                 480

Arg Ile Gln Pro Phe Ala Ser Trp Ile Arg Asn Pro Pro Asp Tyr His
                485                 490                 495

Gln Phe Lys

<210> SEQ ID NO 83
<211> LENGTH: 502
<212> TYPE: PRT

<213> ORGANISM: Homo sapiens

<400> SEQUENCE: 83

Met Trp Thr Ala Asp Glu Ile Ala Gln Leu Cys Tyr Glu His Tyr Gly
1               5                   10                  15

Ile Arg Leu Pro Lys Lys Gly Lys Pro Glu Pro Asn His Glu Trp Thr
            20                  25                  30

Leu Leu Ala Ala Val Val Lys Ile Gln Ser Pro Ala Asp Lys Ala Cys
        35                  40                  45

Asp Thr Pro Asp Lys Pro Val Gln Val Thr Lys Glu Val Val Ser Met
    50                  55                  60

Gly Thr Gly Thr Lys Cys Ile Gly Gln Ser Lys Met Arg Lys Asn Gly
65                  70                  75                  80

Asp Ile Leu Asn Asp Ser His Ala Glu Val Ile Ala Arg Arg Ser Phe
                85                  90                  95

Gln Arg Tyr Leu Leu His Gln Leu Gln Leu Ala Ala Thr Leu Lys Glu
            100                 105                 110

Asp Ser Ile Phe Val Pro Gly Thr Gln Lys Gly Val Trp Lys Leu Arg
        115                 120                 125

Arg Asp Leu Ile Phe Val Phe Phe Ser Ser His Thr Pro Cys Gly Asp
    130                 135                 140

Ala Ser Ile Ile Pro Met Leu Glu Phe Glu Asp Gln Pro Cys Cys Pro
145                 150                 155                 160

Val Phe Arg Asn Trp Ala His Asn Ser Ser Val Glu Ala Ser Ser Asn
                165                 170                 175

Leu Glu Ala Pro Gly Asn Glu Arg Lys Cys Glu Asp Pro Asp Ser Pro
            180                 185                 190

Val Thr Lys Lys Met Arg Leu Glu Pro Gly Thr Ala Ala Arg Glu Val
        195                 200                 205

Thr Asn Gly Ala Ala His His Gln Ser Phe Gly Lys Gln Lys Ser Gly
    210                 215                 220

Pro Ile Ser Pro Gly Ile His Ser Cys Asp Leu Thr Val Glu Gly Leu
225                 230                 235                 240

Ala Thr Val Thr Arg Ile Ala Pro Gly Ser Ala Lys Val Ile Asp Val
                245                 250                 255

Tyr Arg Thr Gly Ala Lys Cys Val Pro Gly Glu Ala Gly Asp Ser Gly
            260                 265                 270

Lys Pro Gly Ala Ala Phe His Gln Val Gly Leu Leu Arg Val Lys Pro
        275                 280                 285

Gly Arg Gly Asp Arg Thr Arg Ser Met Ser Cys Ser Asp Lys Met Ala
    290                 295                 300

Arg Trp Asn Val Leu Gly Cys Gln Gly Ala Leu Leu Met His Leu Leu
305                 310                 315                 320

Glu Glu Pro Ile Tyr Leu Ser Ala Val Ile Gly Lys Cys Pro Tyr
                325                 330                 335

Ser Gln Glu Ala Met Gln Arg Ala Leu Ile Gly Arg Cys Gln Asn Val
            340                 345                 350

Ser Ala Leu Pro Lys Gly Phe Gly Val Gln Glu Leu Lys Ile Leu Gln
        355                 360                 365

Ser Asp Leu Leu Phe Glu Gln Ser Arg Ser Ala Val Gln Ala Lys Arg
    370                 375                 380

Ala Asp Ser Pro Gly Arg Leu Val Pro Cys Gly Ala Ala Ile Ser Trp
385                 390                 395                 400

```
Ser Ala Val Pro Glu Gln Pro Leu Asp Val Thr Ala Asn Gly Phe Pro
            405                 410                 415

Gln Gly Thr Thr Lys Lys Thr Ile Gly Ser Leu Gln Ala Arg Ser Gln
            420                 425                 430

Ile Ser Lys Val Glu Leu Phe Arg Ser Phe Gln Lys Leu Leu Ser Arg
            435                 440                 445

Ile Ala Arg Asp Lys Trp Pro His Ser Leu Arg Val Gln Lys Leu Asp
            450                 455                 460

Thr Tyr Gln Glu Tyr Lys Glu Ala Ala Ser Ser Tyr Gln Glu Ala Trp
465                 470                 475                 480

Ser Thr Leu Arg Lys Gln Val Phe Gly Ser Trp Ile Arg Asn Pro Pro
            485                 490                 495

Asp Tyr His Gln Phe Lys
            500

<210> SEQ ID NO 84
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 84

Gly Ser Gly Arg Ala Asp Ala Leu Asp Asp Phe Asp Leu Asp Met Leu
1               5                   10                  15

Gly Ser Asp Ala Leu Asp Asp Phe Asp Leu Asp Met Leu Gly Ser Asp
            20                  25                  30

Ala Leu Asp Asp Phe Asp Leu Asp Met Leu Gly Ser Asp Ala Leu Asp
        35                  40                  45

Asp Phe Asp Leu Asp Met Leu Ile Asn
    50                  55

<210> SEQ ID NO 85
<211> LENGTH: 85
<212> TYPE: PRT
<213> ORGANISM: Artificial Sequence
<220> FEATURE:
<223> OTHER INFORMATION: Synthetic Polypeptide

<400> SEQUENCE: 85

Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Gly Phe Thr Pro His
            35                  40                  45

Asp Ser Ala Pro Tyr Gly Ala Leu Asp Met Ala Asp Phe Glu Phe Glu
        50                  55                  60

Gln Met Phe Thr Asp Ala Leu Gly Ile Asp Glu Tyr Gly Gly Glu Phe
65                  70                  75                  80

Pro Gly Ile Arg Arg
            85

<210> SEQ ID NO 86
<211> LENGTH: 184
<212> TYPE: PRT
<213> ORGANISM: Artificial Sequence
<220> FEATURE:
<223> OTHER INFORMATION: Synthetic Polypeptide
```

-continued

<400> SEQUENCE: 86

```
Pro Ser Gly Gln Ile Ser Asn Gln Ala Leu Ala Leu Ala Pro Ser Ser
1               5                  10                  15

Ala Pro Val Leu Ala Gln Thr Met Val Pro Ser Ser Ala Met Val Pro
            20                  25                  30

Leu Ala Gln Pro Pro Ala Pro Val Leu Thr Pro Gly Pro Pro
        35                  40                  45

Gln Ser Leu Ser Ala Pro Val Pro Lys Ser Thr Gln Ala Gly Glu Gly
    50                  55                  60

Thr Leu Ser Glu Ala Leu Leu His Leu Gln Phe Asp Ala Asp Glu Asp
65                  70                  75                  80

Leu Gly Ala Leu Leu Gly Asn Ser Thr Asp Pro Gly Val Phe Thr Asp
                85                  90                  95

Leu Ala Ser Val Asp Asn Ser Glu Phe Gln Gln Leu Leu Asn Gln Gly
            100                 105                 110

Val Ser Met Ser His Ser Thr Ala Glu Pro Met Leu Met Glu Tyr Pro
        115                 120                 125

Glu Ala Ile Thr Arg Leu Val Thr Gly Ser Gln Arg Pro Pro Asp Pro
    130                 135                 140

Ala Pro Thr Pro Leu Gly Thr Ser Gly Leu Pro Asn Gly Leu Ser Gly
145                 150                 155                 160

Asp Glu Asp Phe Ser Ser Ile Ala Asp Met Asp Phe Ser Ala Leu Leu
                165                 170                 175

Ser Gln Ile Ser Ser Ser Gly Gln
            180
```

<210> SEQ ID NO 87
<211> LENGTH: 1467
<212> TYPE: PRT
<213> ORGANISM: Artificial Sequence
<220> FEATURE:
<223> OTHER INFORMATION: Synthetic Polypeptide

<400> SEQUENCE: 87

```
Met Asp Lys Lys Tyr Ser Ile Gly Leu Ala Ile Gly Thr Asn Ser Val
1               5                  10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
```

```
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
            195                 200                 205
Lys Ala Ile Leu Ser Ala Arg Leu Ser Lys Ser Arg Arg Leu Glu Asn
            210                 215                 220
Leu Ile Ala Gln Leu Pro Gly Glu Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
        370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
        450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
        530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
```

```
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
        835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
        995                 1000                1005
```

```
Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Gly Ser Pro Lys Lys Lys Arg Lys Val Ser Ser Asp Tyr Lys Asp
1370                1375                1380

His Asp Gly Asp Tyr Lys Asp His Asp Ile Asp Tyr Lys Asp Asp
1385                1390                1395

Asp Asp Lys Ala Ala Gly Gly Gly Gly Ser Gly Arg Ala Asp Ala
```

```
                      1400                1405                1410

Leu Asp  Asp Phe Asp Leu  Asp Met Leu Gly Ser  Asp Ala Leu Asp
    1415                 1420                 1425

Asp Phe  Asp Leu Asp Met  Leu Gly Ser Asp Ala  Leu Asp Asp Phe
    1430                 1435                 1440

Asp Leu  Asp Met Leu Gly  Ser Asp Ala Leu Asp  Asp Phe Asp Leu
    1445                 1450                 1455

Asp Met  Leu His His His  His His
    1460                 1465

<210> SEQ ID NO 88
<211> LENGTH: 94
<212> TYPE: PRT
<213> ORGANISM: Homo sapiens

<400> SEQUENCE: 88

Met Asn Met Phe Lys Glu Ala Val Thr Phe Lys Asp Val Ala Val
1               5                   10                  15

Phe Thr Glu Glu Glu Leu Gly Leu Leu Gly Pro Ala Gln Arg Lys Leu
                20                  25                  30

Tyr Arg Asp Val Met Val Glu Asn Phe Arg Asn Leu Leu Ser Val Gly
            35                  40                  45

His Pro Pro Phe Lys Gln Asp Val Ser Pro Ile Glu Arg Asn Glu Gln
50                  55                  60

Leu Trp Ile Met Thr Thr Ala Thr Arg Arg Gln Gly Asn Leu Asp Thr
65                  70                  75                  80

Leu Pro Val Lys Ala Leu Leu Leu Tyr Asp Leu Ala Gln Thr
                85                  90

<210> SEQ ID NO 89
<211> LENGTH: 74
<212> TYPE: PRT
<213> ORGANISM: Homo sapiens

<400> SEQUENCE: 89

Glu Gln Val Ser Phe Lys Asp Val Cys Val Asp Phe Thr Gln Glu Glu
1               5                   10                  15

Trp Tyr Leu Leu Asp Pro Ala Gln Lys Ile Leu Tyr Arg Asp Val Ile
                20                  25                  30

Leu Glu Asn Tyr Ser Asn Leu Val Ser Val Gly Tyr Cys Ile Thr Lys
            35                  40                  45

Pro Glu Val Ile Phe Lys Ile Glu Gln Gly Glu Pro Trp Ile Leu
50                  55                  60

Glu Lys Gly Phe Pro Ser Gln Cys His Pro
65                  70

<210> SEQ ID NO 90
<211> LENGTH: 42
<212> TYPE: PRT
<213> ORGANISM: Homo sapiens

<400> SEQUENCE: 90

Glu Ala Val Thr Phe Lys Asp Val Ala Val Phe Thr Glu Glu Glu
1               5                   10                  15

Leu Gly Leu Leu Asp Pro Ala Gln Arg Lys Leu Tyr Arg Asp Val Met
                20                  25                  30

Leu Glu Asn Phe Arg Asn Leu Leu Ser Val
            35                  40
```

<210> SEQ ID NO 91
<211> LENGTH: 69
<212> TYPE: PRT
<213> ORGANISM: Mus musculus

<400> SEQUENCE: 91

Met Asp Leu Val Thr Tyr Asp Asp Val His Val Asn Phe Thr Gln Asp
1               5                   10                  15

Glu Trp Ala Leu Leu Asp Pro Ser Gln Lys Ser Leu Tyr Lys Gly Val
            20                  25                  30

Met Leu Glu Thr Tyr Lys Asn Leu Thr Ala Ile Gly Tyr Ile Trp Glu
        35                  40                  45

Glu His Thr Ile Glu Asp His Phe Gln Thr Ser Arg Ser His Gly Ser
    50                  55                  60

Asn Lys Lys Thr His
65

<210> SEQ ID NO 92
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 92

Gly Ser Gly Met Asn Ile Gln Met Leu Leu Glu Ala Ala Asp Tyr Leu
1               5                   10                  15

Glu Arg Arg Glu Arg Glu Ala Glu His Gly Tyr Ala Ser Met Leu Pro
            20                  25                  30

<210> SEQ ID NO 93
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 93

Gly Ser Gly Met Asn Ile Gln Met Leu Leu Glu Ala Ala Asp Tyr Leu
1               5                   10                  15

Glu Arg Arg Glu Arg Glu Ala Glu His Gly Tyr Ala Ser Met Leu Pro
            20                  25                  30

Gly Ser Gly Met Asn Ile Gln Met Leu Leu Glu Ala Ala Asp Tyr Leu
        35                  40                  45

Glu Arg Arg Glu Arg Glu Ala Glu His Gly Tyr Ala Ser Met Leu Pro
    50                  55                  60

Gly Ser Gly Met Asn Ile Gln Met Leu Leu Glu Ala Ala Asp Tyr Leu
65                  70                  75                  80

Glu Arg Arg Glu Arg Glu Ala Glu His Gly Tyr Ala Ser Met Leu Pro
                85                  90                  95

Gly Ser Gly Met Asn Ile Gln Met Leu Leu Glu Ala Ala Asp Tyr Leu
            100                 105                 110

Glu Arg Arg Glu Arg Glu Ala Glu His Gly Tyr Ala Ser Met Leu Pro
        115                 120                 125

Ser Arg
    130

<210> SEQ ID NO 94

<211> LENGTH: 876
<212> TYPE: PRT
<213> ORGANISM: Homo sapiens

<400> SEQUENCE: 94

```
Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Arg Asn Ala Lys
    130                 135                 140

Ala Glu Lys Glu Lys Lys Leu Pro Pro Pro Pro Gln Ala Pro Pro
145                 150                 155                 160

Glu Glu Glu Asn Glu Ser Glu Pro Glu Glu Pro Ser Gly Gln Ala Gly
                165                 170                 175

Gly Leu Gln Asp Asp Ser Ser Gly Gly Tyr Gly Asp Gly Gln Ala Ser
            180                 185                 190

Gly Val Glu Gly Ala Ala Phe Gln Ser Arg Leu Pro His Asp Arg Met
        195                 200                 205

Thr Ser Gln Glu Ala Ala Cys Phe Pro Asp Ile Ile Ser Gly Pro Gln
    210                 215                 220

Gln Thr Gln Lys Val Phe Leu Phe Ile Arg Asn Arg Thr Leu Gln Leu
225                 230                 235                 240

Trp Leu Asp Asn Pro Lys Ile Gln Leu Thr Phe Glu Ala Thr Leu Gln
                245                 250                 255

Gln Leu Glu Ala Pro Tyr Asn Ser Asp Thr Val Leu Val His Arg Val
            260                 265                 270

His Ser Tyr Leu Glu Arg His Gly Leu Ile Asn Phe Gly Ile Tyr Lys
        275                 280                 285

Arg Ile Lys Pro Leu Pro Thr Lys Lys Thr Gly Lys Val Ile Ile Ile
    290                 295                 300

Gly Ser Gly Val Ser Gly Leu Ala Ala Ala Arg Gln Leu Gln Ser Phe
305                 310                 315                 320

Gly Met Asp Val Thr Leu Leu Glu Ala Arg Asp Arg Val Gly Gly Arg
                325                 330                 335

Val Ala Thr Phe Arg Lys Gly Asn Tyr Val Ala Asp Leu Gly Ala Met
            340                 345                 350

Val Val Thr Gly Leu Gly Gly Asn Pro Met Ala Val Val Ser Lys Gln
        355                 360                 365

Val Asn Met Glu Leu Ala Lys Ile Lys Gln Lys Cys Pro Leu Tyr Glu
    370                 375                 380

Ala Asn Gly Gln Ala Asp Thr Val Lys Val Pro Lys Glu Lys Asp Glu
```

```
            385                 390                 395                 400
Met Val Glu Gln Glu Phe Asn Arg Leu Leu Glu Ala Thr Ser Tyr Leu
                    405                 410                 415

Ser His Gln Leu Asp Phe Asn Val Leu Asn Asn Lys Pro Val Ser Leu
                    420                 425                 430

Gly Gln Ala Leu Glu Val Val Ile Gln Leu Gln Glu Lys His Val Lys
                    435                 440                 445

Asp Glu Gln Ile Glu His Trp Lys Lys Ile Val Lys Thr Gln Glu Glu
                    450                 455                 460

Leu Lys Glu Leu Leu Asn Lys Met Val Asn Leu Lys Glu Lys Ile Lys
465                 470                 475                 480

Glu Leu His Gln Gln Tyr Lys Glu Ala Ser Glu Val Lys Pro Pro Arg
                    485                 490                 495

Asp Ile Thr Ala Glu Phe Leu Val Lys Ser Lys His Arg Asp Leu Thr
                    500                 505                 510

Ala Leu Cys Lys Glu Tyr Asp Glu Leu Ala Glu Thr Gln Gly Lys Leu
                    515                 520                 525

Glu Glu Lys Leu Gln Glu Leu Glu Ala Asn Pro Pro Ser Asp Val Tyr
                    530                 535                 540

Leu Ser Ser Arg Asp Arg Gln Ile Leu Asp Trp His Phe Ala Asn Leu
545                 550                 555                 560

Glu Phe Ala Asn Ala Thr Pro Leu Ser Thr Leu Ser Leu Lys His Trp
                    565                 570                 575

Asp Gln Asp Asp Asp Phe Glu Phe Thr Gly Ser His Leu Thr Val Arg
                    580                 585                 590

Asn Gly Tyr Ser Cys Val Pro Val Ala Leu Ala Glu Gly Leu Asp Ile
                    595                 600                 605

Lys Leu Asn Thr Ala Val Arg Gln Val Arg Tyr Thr Ala Ser Gly Cys
                    610                 615                 620

Glu Val Ile Ala Val Asn Thr Arg Ser Thr Ser Gln Thr Phe Ile Tyr
625                 630                 635                 640

Lys Cys Asp Ala Val Leu Cys Thr Leu Pro Leu Gly Val Leu Lys Gln
                    645                 650                 655

Gln Pro Pro Ala Val Gln Phe Val Pro Pro Leu Pro Glu Trp Lys Thr
                    660                 665                 670

Ser Ala Val Gln Arg Met Gly Phe Gly Asn Leu Asn Lys Val Val Leu
                    675                 680                 685

Cys Phe Asp Arg Val Phe Trp Asp Pro Ser Val Asn Leu Phe Gly His
                    690                 695                 700

Val Gly Ser Thr Thr Ala Ser Arg Gly Glu Leu Phe Leu Phe Trp Asn
705                 710                 715                 720

Leu Tyr Lys Ala Pro Ile Leu Leu Ala Leu Val Ala Gly Glu Ala Ala
                    725                 730                 735

Gly Ile Met Glu Asn Ile Ser Asp Asp Val Ile Val Gly Arg Cys Leu
                    740                 745                 750

Ala Ile Leu Lys Gly Ile Phe Gly Ser Ser Ala Val Pro Gln Pro Lys
                    755                 760                 765

Glu Thr Val Val Ser Arg Trp Arg Ala Asp Pro Trp Ala Arg Gly Ser
                    770                 775                 780

Tyr Ser Tyr Val Ala Ala Gly Ser Ser Gly Asn Asp Tyr Asp Leu Met
785                 790                 795                 800

Ala Gln Pro Ile Thr Pro Gly Pro Ser Ile Pro Gly Ala Pro Gln Pro
                    805                 810                 815
```

-continued

```
Ile Pro Arg Leu Phe Phe Ala Gly Glu His Thr Ile Arg Asn Tyr Pro
        820                 825                 830

Ala Thr Val His Gly Ala Leu Leu Ser Gly Leu Arg Glu Ala Gly Arg
            835                 840                 845

Ile Ala Asp Gln Phe Leu Gly Ala Met Tyr Thr Leu Pro Arg Gln Ala
850                 855                 860

Thr Pro Gly Val Pro Ala Gln Gln Ser Pro Ser Met
865                 870                 875

<210> SEQ ID NO 95
<211> LENGTH: 852
<212> TYPE: PRT
<213> ORGANISM: Homo sapiens

<400> SEQUENCE: 95

Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Glu Arg Asn Ala Lys
    130                 135                 140

Ala Glu Lys Glu Lys Lys Leu Pro Pro Pro Pro Pro Gln Ala Pro Pro
145                 150                 155                 160

Glu Glu Glu Asn Glu Ser Glu Pro Glu Glu Pro Ser Gly Val Glu Gly
                165                 170                 175

Ala Ala Phe Gln Ser Arg Leu Pro His Asp Arg Met Thr Ser Gln Glu
            180                 185                 190

Ala Ala Cys Phe Pro Asp Ile Ile Ser Gly Pro Gln Gln Thr Gln Lys
        195                 200                 205

Val Phe Leu Phe Ile Arg Asn Arg Thr Leu Gln Leu Trp Leu Asp Asn
    210                 215                 220

Pro Lys Ile Gln Leu Thr Phe Glu Ala Thr Leu Gln Gln Leu Glu Ala
225                 230                 235                 240

Pro Tyr Asn Ser Asp Thr Val Leu Val His Arg Val His Ser Tyr Leu
                245                 250                 255

Glu Arg His Gly Leu Ile Asn Phe Gly Ile Tyr Lys Arg Ile Lys Pro
            260                 265                 270

Leu Pro Thr Lys Lys Thr Gly Lys Val Ile Ile Gly Ser Gly Val
        275                 280                 285

Ser Gly Leu Ala Ala Ala Arg Gln Leu Gln Ser Phe Gly Met Asp Val
    290                 295                 300

Thr Leu Leu Glu Ala Arg Asp Arg Val Gly Gly Arg Val Ala Thr Phe
```

```
            305                 310                 315                 320
Arg Lys Gly Asn Tyr Val Ala Asp Leu Gly Ala Met Val Val Thr Gly
                    325                 330                 335

Leu Gly Gly Asn Pro Met Ala Val Ser Lys Gln Val Asn Met Glu
                340                 345                 350

Leu Ala Lys Ile Lys Gln Lys Cys Pro Leu Tyr Glu Ala Asn Gly Gln
                355                 360                 365

Ala Val Pro Lys Glu Lys Asp Glu Met Val Glu Gln Glu Phe Asn Arg
            370                 375                 380

Leu Leu Glu Ala Thr Ser Tyr Leu Ser His Gln Leu Asp Phe Asn Val
385                 390                 395                 400

Leu Asn Asn Lys Pro Val Ser Leu Gly Gln Ala Leu Glu Val Val Ile
                405                 410                 415

Gln Leu Gln Glu Lys His Val Lys Asp Glu Gln Ile Glu His Trp Lys
                420                 425                 430

Lys Ile Val Lys Thr Gln Glu Glu Leu Lys Glu Leu Leu Asn Lys Met
                435                 440                 445

Val Asn Leu Lys Glu Lys Ile Lys Glu Leu His Gln Gln Tyr Lys Glu
            450                 455                 460

Ala Ser Glu Val Lys Pro Pro Arg Asp Ile Thr Ala Glu Phe Leu Val
465                 470                 475                 480

Lys Ser Lys His Arg Asp Leu Thr Ala Leu Cys Lys Gly Tyr Asp Glu
                485                 490                 495

Leu Ala Glu Thr Gln Gly Lys Leu Glu Glu Lys Leu Gln Glu Leu Glu
                500                 505                 510

Ala Asn Pro Pro Ser Asp Val Tyr Leu Ser Ser Arg Asp Arg Gln Ile
            515                 520                 525

Leu Asp Trp His Phe Ala Asn Leu Glu Phe Ala Asn Ala Thr Pro Leu
            530                 535                 540

Ser Thr Leu Ser Leu Lys His Trp Asp Gln Asp Asp Phe Glu Phe
545                 550                 555                 560

Thr Gly Ser His Leu Thr Val Arg Asn Gly Tyr Ser Cys Val Pro Val
                565                 570                 575

Ala Leu Ala Glu Gly Leu Asp Ile Lys Leu Asn Thr Ala Val Arg Gln
                580                 585                 590

Val Arg Tyr Thr Ala Ser Gly Cys Glu Val Ile Ala Val Asn Thr Arg
            595                 600                 605

Ser Thr Ser Gln Thr Phe Ile Tyr Lys Cys Asp Ala Val Leu Cys Thr
            610                 615                 620

Leu Pro Leu Gly Val Leu Lys Gln Gln Pro Pro Ala Val Gln Phe Val
625                 630                 635                 640

Pro Pro Leu Pro Glu Trp Lys Thr Ser Ala Val Gln Arg Met Gly Phe
                645                 650                 655

Gly Asn Leu Asn Lys Val Val Leu Cys Phe Asp Arg Val Phe Trp Asp
                660                 665                 670

Pro Ser Val Asn Leu Phe Gly His Val Gly Ser Thr Thr Ala Ser Arg
            675                 680                 685

Gly Glu Leu Phe Leu Phe Trp Asn Leu Tyr Lys Ala Pro Ile Leu Leu
            690                 695                 700

Ala Leu Val Ala Gly Glu Ala Gly Ile Met Glu Asn Ile Ser Asp
705                 710                 715                 720

Asp Val Ile Val Gly Arg Cys Leu Ala Ile Leu Lys Gly Ile Phe Gly
                725                 730                 735
```

```
Ser Ser Ala Val Pro Gln Pro Lys Glu Thr Val Val Ser Arg Trp Arg
            740                 745                 750

Ala Asp Pro Trp Ala Arg Gly Ser Tyr Ser Tyr Val Ala Ala Gly Ser
            755                 760                 765

Ser Gly Asn Asp Tyr Asp Leu Met Ala Gln Pro Ile Thr Pro Gly Pro
    770                 775                 780

Ser Ile Pro Gly Ala Pro Gln Pro Ile Pro Arg Leu Phe Phe Ala Gly
785                 790                 795                 800

Glu His Thr Ile Arg Asn Tyr Pro Ala Thr Val His Gly Ala Leu Leu
                805                 810                 815

Ser Gly Leu Arg Glu Ala Gly Arg Ile Ala Asp Gln Phe Leu Gly Ala
            820                 825                 830

Met Tyr Thr Leu Pro Arg Gln Ala Thr Pro Gly Val Pro Ala Gln Gln
            835                 840                 845

Ser Pro Ser Met
    850

<210> SEQ ID NO 96
<211> LENGTH: 817
<212> TYPE: PRT
<213> ORGANISM: Artificial Sequence
<220> FEATURE:
<223> OTHER INFORMATION: Synthetic Polypeptide

<400> SEQUENCE: 96

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Arg Pro Ala
                20                  25                  30

Leu Asp Ala Val Lys Lys Gly Leu Pro His Ala Pro Ala Leu Ile Lys
            35                  40                  45

Arg Thr Asn Arg Arg Ile Pro Glu Arg Thr Ser His Arg Val Ala Asp
    50                  55                  60

His Ala Gln Val Val Arg Val Leu Gly Phe Phe Gln Cys His Ser His
65                  70                  75                  80

Pro Ala Gln Ala Phe Asp Asp Ala Met Thr Gln Phe Gly Met Ser Gly
                85                  90                  95

Gly Gly Ser Leu Pro Thr Cys Ser Cys Leu Asp Arg Val Ile Gln Lys
            100                 105                 110

Asp Lys Gly Pro Tyr Tyr Thr His Leu Gly Ala Gly Pro Ser Val Ala
        115                 120                 125

Ala Val Arg Glu Ile Met Glu Asn Arg Tyr Gly Gln Lys Gly Asn Ala
    130                 135                 140

Ile Arg Ile Glu Ile Val Tyr Thr Lys Glu Gly Lys Ser Ser
145                 150                 155                 160

His Gly Cys Pro Ile Ala Lys Trp Val Leu Arg Arg Ser Ser Asp Glu
                165                 170                 175

Glu Lys Val Leu Cys Leu Val Arg Gln Arg Thr Gly His His Cys Pro
            180                 185                 190

Thr Ala Val Met Val Val Leu Ile Met Val Trp Asp Gly Ile Pro Leu
        195                 200                 205

Pro Met Ala Asp Arg Leu Tyr Thr Glu Leu Thr Glu Asn Leu Lys Ser
    210                 215                 220

Tyr Asn Gly His Pro Thr Asp Arg Arg Cys Thr Leu Asn Glu Asn Arg
225                 230                 235                 240
```

```
Thr Cys Thr Cys Gln Gly Ile Asp Pro Glu Thr Cys Gly Ala Ser Phe
            245                 250                 255

Ser Phe Gly Cys Ser Trp Ser Met Tyr Phe Asn Gly Cys Lys Phe Gly
            260                 265                 270

Arg Ser Pro Ser Pro Arg Arg Phe Arg Ile Asp Pro Ser Ser Pro Leu
            275                 280                 285

His Glu Lys Asn Leu Glu Asp Asn Leu Gln Ser Leu Ala Thr Arg Leu
            290                 295                 300

Ala Pro Ile Tyr Lys Gln Tyr Ala Pro Val Ala Tyr Gln Asn Gln Val
305                 310                 315                 320

Glu Tyr Glu Asn Val Ala Arg Glu Cys Arg Leu Gly Ser Lys Glu Gly
                325                 330                 335

Arg Pro Phe Ser Gly Val Thr Ala Cys Leu Asp Phe Cys Ala His Pro
            340                 345                 350

His Arg Asp Ile His Asn Met Asn Asn Gly Ser Thr Val Val Cys Thr
            355                 360                 365

Leu Thr Arg Glu Asp Asn Arg Ser Leu Gly Val Ile Pro Gln Asp Glu
    370                 375                 380

Gln Leu His Val Leu Pro Leu Tyr Lys Leu Ser Asp Thr Asp Glu Phe
385                 390                 395                 400

Gly Ser Lys Glu Gly Met Glu Ala Lys Ile Lys Ser Gly Ala Ile Glu
                405                 410                 415

Val Leu Ala Pro Arg Arg Lys Arg Thr Cys Phe Thr Gln Pro Val
            420                 425                 430

Pro Arg Ser Gly Lys Lys Arg Ala Ala Met Met Thr Glu Val Leu Ala
            435                 440                 445

His Lys Ile Arg Ala Val Glu Lys Lys Pro Ile Pro Arg Ile Lys Arg
    450                 455                 460

Lys Asn Asn Ser Thr Thr Thr Asn Asn Ser Lys Pro Ser Ser Leu Pro
465                 470                 475                 480

Thr Leu Gly Ser Asn Thr Glu Thr Val Gln Pro Glu Val Lys Ser Glu
                485                 490                 495

Thr Glu Pro His Phe Ile Leu Lys Ser Ser Asp Asn Thr Lys Thr Tyr
            500                 505                 510

Ser Leu Met Pro Ser Ala Pro His Pro Val Lys Glu Ala Ser Pro Gly
    515                 520                 525

Phe Ser Trp Ser Pro Lys Thr Ala Ser Ala Thr Pro Ala Pro Leu Lys
    530                 535                 540

Asn Asp Ala Thr Ala Ser Cys Gly Phe Ser Glu Arg Ser Ser Thr Pro
545                 550                 555                 560

His Cys Thr Met Pro Ser Gly Arg Leu Ser Gly Ala Asn Ala Ala Ala
                565                 570                 575

Ala Asp Gly Pro Gly Ile Ser Gln Leu Gly Glu Val Ala Pro Leu Pro
            580                 585                 590

Thr Leu Ser Ala Pro Val Met Glu Pro Leu Ile Asn Ser Glu Pro Ser
            595                 600                 605

Thr Gly Val Thr Glu Pro Leu Thr Pro His Gln Pro Asn His Gln Pro
    610                 615                 620

Ser Phe Leu Thr Ser Pro Gln Asp Leu Ala Ser Ser Pro Met Glu Glu
625                 630                 635                 640

Asp Glu Gln His Ser Glu Ala Asp Glu Pro Pro Ser Asp Glu Pro Leu
                645                 650                 655
```

-continued

```
Ser Asp Asp Pro Leu Ser Pro Ala Glu Glu Lys Leu Pro His Ile Asp
            660                 665                 670

Glu Tyr Trp Ser Asp Ser Glu His Ile Phe Leu Asp Ala Asn Ile Gly
        675                 680                 685

Gly Val Ala Ile Ala Pro Ala His Gly Ser Val Leu Ile Glu Cys Ala
    690                 695                 700

Arg Arg Glu Leu His Ala Thr Thr Pro Val Glu His Pro Asn Arg Asn
705                 710                 715                 720

His Pro Thr Arg Leu Ser Leu Val Phe Tyr Gln His Lys Asn Leu Asn
                725                 730                 735

Lys Pro Gln His Gly Phe Glu Leu Asn Lys Ile Lys Phe Glu Ala Lys
            740                 745                 750

Glu Ala Lys Asn Lys Lys Met Lys Ala Ser Glu Gln Lys Asp Gln Ala
        755                 760                 765

Ala Asn Glu Gly Pro Glu Gln Ser Ser Glu Val Asn Glu Leu Asn Gln
    770                 775                 780

Ile Pro Ser His Lys Ala Leu Thr Leu Thr His Asp Asn Val Val Thr
785                 790                 795                 800

Val Ser Pro Tyr Ala Leu Thr His Val Ala Gly Pro Tyr Asn His Trp
                805                 810                 815

Val

<210> SEQ ID NO 97
<211> LENGTH: 340
<212> TYPE: PRT
<213> ORGANISM: X. laevis

<400> SEQUENCE: 97

Ala Ser Ser Pro Lys Lys Arg Lys Val Glu Ala Ser Met Ser Arg
1               5                   10                  15

Val Val Lys Pro Lys Val Ala Ser Met Glu Glu Met Ala Ala Phe His
                20                  25                  30

Thr Asp Ala Tyr Leu Gln His Leu His Lys Val Ser Glu Glu Gly Asp
            35                  40                  45

Asn Asp Asp Pro Glu Thr Leu Glu Tyr Gly Leu Gly Tyr Asp Cys Pro
        50                  55                  60

Ile Thr Glu Gly Ile Tyr Asp Tyr Ala Ala Ala Val Gly Gly Ala Thr
65                  70                  75                  80

Leu Thr Ala Ala Glu Gln Leu Ile Glu Gly Lys Thr Arg Ile Ala Val
                85                  90                  95

Asn Trp Pro Gly Gly Trp His His Ala Lys Lys Asp Glu Ala Ser Gly
            100                 105                 110

Phe Cys Tyr Leu Asn Asp Ala Val Leu Gly Ile Leu Lys Leu Arg Glu
        115                 120                 125

Lys Phe Asp Arg Val Leu Tyr Val Asp Met Asp Leu His His Gly Asp
    130                 135                 140

Gly Val Glu Asp Ala Phe Ser Phe Thr Ser Lys Val Met Thr Val Ser
145                 150                 155                 160

Leu His Lys Phe Ser Pro Gly Phe Phe Pro Gly Thr Gly Asp Val Ser
                165                 170                 175

Asp Ile Gly Leu Gly Lys Gly Arg Tyr Tyr Ser Ile Asn Val Pro Leu
            180                 185                 190

Gln Asp Gly Ile Gln Asp Asp Lys Tyr Tyr Gln Ile Cys Glu Gly Val
        195                 200                 205
```

-continued

```
Leu Lys Glu Val Phe Thr Thr Phe Asn Pro Glu Ala Val Val Leu Gln
210                 215                 220

Leu Gly Ala Asp Thr Ile Ala Gly Asp Pro Met Cys Ser Phe Asn Met
225                 230                 235                 240

Thr Pro Glu Gly Ile Gly Lys Cys Leu Lys Tyr Val Leu Gln Trp Gln
                245                 250                 255

Leu Pro Thr Leu Ile Leu Gly Gly Gly Tyr His Leu Pro Asn Thr
            260                 265                 270

Ala Arg Cys Trp Thr Tyr Leu Thr Ala Leu Ile Val Gly Arg Thr Leu
                275                 280                 285

Ser Ser Glu Ile Pro Asp His Glu Phe Phe Thr Glu Tyr Gly Pro Asp
290                 295                 300

Tyr Val Leu Glu Ile Thr Pro Ser Cys Arg Pro Asp Arg Asn Asp Thr
305                 310                 315                 320

Gln Lys Val Gln Glu Ile Leu Gln Ser Ile Lys Gly Asn Leu Lys Arg
                325                 330                 335

Val Val Glu Phe
            340

<210> SEQ ID NO 98
<211> LENGTH: 331
<212> TYPE: PRT
<213> ORGANISM: S. cerevisiae

<400> SEQUENCE: 98

Ala Ser Ser Pro Lys Lys Arg Lys Val Glu Ala Ser Arg Arg Val
1               5                   10                  15

Ala Tyr Phe Tyr Asp Ala Asp Val Gly Asn Tyr Ala Tyr Gly Ala Gly
                20                  25                  30

His Pro Met Lys Pro His Arg Ile Arg Met Ala His Ser Leu Ile Met
            35                  40                  45

Asn Tyr Gly Leu Tyr Lys Lys Met Glu Ile Tyr Arg Ala Lys Pro Ala
50                  55                  60

Thr Lys Gln Glu Met Cys Gln Phe His Thr Asp Glu Tyr Ile Asp Phe
65                  70                  75                  80

Leu Ser Arg Val Thr Pro Asp Asn Leu Glu Met Phe Lys Arg Glu Ser
                85                  90                  95

Val Lys Phe Asn Val Gly Asp Asp Cys Pro Val Phe Asp Gly Leu Tyr
                100                 105                 110

Glu Tyr Cys Ser Ile Ser Gly Gly Ser Met Glu Gly Ala Ala Arg
            115                 120                 125

Leu Asn Arg Gly Lys Cys Asp Val Ala Val Asn Tyr Ala Gly Gly Leu
130                 135                 140

His His Ala Lys Lys Ser Glu Ala Ser Gly Phe Cys Tyr Leu Asn Asp
145                 150                 155                 160

Ile Val Leu Gly Ile Ile Glu Leu Leu Arg Tyr His Pro Arg Val Leu
                165                 170                 175

Tyr Ile Asp Ile Asp Val His His Gly Asp Gly Val Glu Glu Ala Phe
                180                 185                 190

Tyr Thr Thr Asp Arg Val Met Thr Cys Ser Phe His Lys Tyr Gly Glu
            195                 200                 205

Phe Phe Pro Gly Thr Gly Glu Leu Arg Asp Ile Gly Val Gly Ala Gly
210                 215                 220

Lys Asn Tyr Ala Val Asn Val Pro Leu Arg Asp Gly Ile Asp Asp Ala
225                 230                 235                 240
```

```
Thr Tyr Arg Ser Val Phe Glu Pro Val Ile Lys Lys Ile Met Glu Trp
                245                 250                 255

Tyr Gln Pro Ser Ala Val Val Leu Gln Cys Gly Gly Asp Ser Leu Ser
            260                 265                 270

Gly Asp Arg Leu Gly Cys Phe Asn Leu Ser Met Glu Gly His Ala Asn
        275                 280                 285

Cys Val Asn Tyr Val Lys Ser Phe Gly Ile Pro Met Met Val Val Gly
    290                 295                 300

Gly Gly Gly Tyr Thr Met Arg Asn Val Ala Arg Thr Trp Cys Phe Glu
305                 310                 315                 320

Thr Gly Leu Leu Asn Asn Val Val Leu Asp Lys
                325                 330

<210> SEQ ID NO 99
<211> LENGTH: 315
<212> TYPE: PRT
<213> ORGANISM: M. loti

<400> SEQUENCE: 99

Ala Ser Ser Pro Lys Lys Arg Lys Val Glu Ala Ser Met Pro Leu
1               5                   10                  15

Gln Ile Val His His Pro Asp Tyr Asp Ala Gly Phe Ala Thr Asn His
                20                  25                  30

Arg Phe Pro Met Ser Lys Tyr Pro Leu Leu Met Glu Ala Leu Arg Ala
            35                  40                  45

Arg Gly Leu Ala Ser Pro Asp Ala Leu Asn Thr Thr Glu Pro Ala Pro
50                  55                  60

Ala Ser Trp Leu Lys Leu Ala His Ala Ala Asp Tyr Val Asp Gln Val
65                  70                  75                  80

Ile Ser Cys Ser Val Pro Glu Lys Ile Glu Arg Glu Ile Gly Phe Pro
                85                  90                  95

Val Gly Pro Arg Val Ser Leu Arg Ala Gln Leu Ala Thr Gly Gly Thr
            100                 105                 110

Ile Leu Ala Ala Arg Leu Ala Leu Arg His Gly Ile Ala Cys Asn Thr
        115                 120                 125

Ala Gly Gly Ser His His Ala Arg Arg Ala Gln Gly Ala Gly Phe Cys
130                 135                 140

Thr Phe Asn Asp Val Ala Val Ala Ser Leu Val Leu Leu Asp Glu Gly
145                 150                 155                 160

Ala Ala Gln Asn Ile Leu Val Val Asp Leu Asp Val His Gln Gly Asp
                165                 170                 175

Gly Thr Ala Asp Ile Leu Ser Asp Glu Pro Gly Val Phe Thr Phe Ser
            180                 185                 190

Met His Gly Glu Arg Asn Tyr Pro Val Arg Lys Ile Ala Ser Asp Leu
        195                 200                 205

Asp Ile Ala Leu Pro Asp Gly Thr Gly Asp Ala Ala Tyr Leu Arg Arg
210                 215                 220

Leu Ala Thr Ile Leu Pro Glu Leu Ser Ala Arg Ala Arg Trp Asp Ile
225                 230                 235                 240

Val Phe Tyr Asn Ala Gly Val Asp Val His Ala Glu Asp Arg Leu Gly
                245                 250                 255

Arg Leu Ala Leu Ser Asn Gly Leu Arg Ala Arg Asp Glu Met Val
            260                 265                 270

Ile Gly His Phe Arg Ala Leu Gly Ile Pro Val Cys Gly Val Ile Gly
```

275                 280                 285
Gly Gly Tyr Ser Thr Asp Val Pro Ala Leu Ala Ser Arg His Ala Ile
    290                 295                 300
Leu Phe Glu Val Ala Ser Thr Tyr Ala Glu Phe
305                 310                 315

<210> SEQ ID NO 100
<211> LENGTH: 362
<212> TYPE: PRT
<213> ORGANISM: Homo sapiens

<400> SEQUENCE: 100

Ala Ser Ser Pro Lys Lys Arg Lys Val Glu Ala Ser Met Leu His
1               5                   10                  15

Thr Thr Gln Leu Tyr Gln His Val Pro Glu Thr Arg Trp Pro Ile Val
            20                  25                  30

Tyr Ser Pro Arg Tyr Asn Ile Thr Phe Met Gly Leu Glu Lys Leu His
            35                  40                  45

Pro Phe Asp Ala Gly Lys Trp Gly Lys Val Ile Asn Phe Leu Lys Glu
        50                  55                  60

Glu Lys Leu Leu Ser Asp Ser Met Leu Val Glu Ala Arg Glu Ala Ser
65                  70                  75                  80

Glu Glu Asp Leu Leu Val Val His Thr Arg Arg Tyr Leu Asn Glu Leu
                85                  90                  95

Lys Trp Ser Phe Ala Val Ala Thr Ile Thr Glu Ile Pro Pro Val Ile
            100                 105                 110

Phe Leu Pro Asn Phe Leu Val Gln Arg Lys Val Leu Arg Pro Leu Arg
            115                 120                 125

Thr Gln Thr Gly Gly Thr Ile Met Ala Gly Lys Leu Ala Val Glu Arg
        130                 135                 140

Gly Trp Ala Ile Asn Val Gly Gly Phe His His Cys Ser Ser Asp
145                 150                 155                 160

Arg Gly Gly Gly Phe Cys Ala Tyr Ala Asp Ile Thr Leu Ala Ile Lys
                165                 170                 175

Phe Leu Phe Glu Arg Val Glu Gly Ile Ser Arg Ala Thr Ile Ile Asp
            180                 185                 190

Leu Asp Ala His Gln Gly Asn Gly His Glu Arg Asp Phe Met Asp Asp
            195                 200                 205

Lys Arg Val Tyr Ile Met Asp Val Tyr Asn Arg His Ile Tyr Pro Gly
        210                 215                 220

Asp Arg Phe Ala Lys Gln Ala Ile Arg Arg Lys Val Glu Leu Glu Trp
225                 230                 235                 240

Gly Thr Glu Asp Asp Glu Tyr Leu Asp Lys Val Glu Arg Asn Ile Lys
                245                 250                 255

Lys Ser Leu Gln Glu His Leu Pro Asp Val Val Val Tyr Asn Ala Gly
            260                 265                 270

Thr Asp Ile Leu Glu Gly Asp Arg Leu Gly Gly Leu Ser Ile Ser Pro
            275                 280                 285

Ala Gly Ile Val Lys Arg Asp Glu Leu Val Phe Arg Met Val Arg Gly
        290                 295                 300

Arg Arg Val Pro Ile Leu Met Val Thr Ser Gly Gly Tyr Gln Lys Arg
305                 310                 315                 320

Thr Ala Arg Ile Ile Ala Asp Ser Ile Leu Asn Leu Phe Gly Leu Gly
                325                 330                 335

```
Leu Ile Gly Pro Glu Ser Pro Ser Val Ser Ala Gln Asn Ser Asp Thr
                340                 345                 350

Pro Leu Leu Pro Pro Ala Val Pro Glu Phe
        355                 360

<210> SEQ ID NO 101
<211> LENGTH: 226
<212> TYPE: PRT
<213> ORGANISM: A. thaliana

<400> SEQUENCE: 101

Ala Ser Ser Pro Lys Lys Arg Lys Val Glu Ala Ser Met Glu Phe
1               5                   10                  15

Trp Gly Ile Glu Val Lys Ser Gly Lys Pro Val Thr Val Thr Pro Glu
                20                  25                  30

Glu Gly Ile Leu Ile His Val Ser Gln Ala Ser Leu Gly Glu Cys Lys
            35                  40                  45

Asn Lys Lys Gly Glu Phe Val Pro Leu His Val Lys Val Gly Asn Gln
50                  55                  60

Asn Leu Val Leu Gly Thr Leu Ser Thr Glu Asn Ile Pro Gln Leu Phe
65                  70                  75                  80

Cys Asp Leu Val Phe Asp Lys Glu Phe Glu Leu Ser His Thr Trp Gly
                85                  90                  95

Lys Gly Ser Val Tyr Phe Val Gly Tyr Lys Thr Pro Asn Ile Glu Pro
            100                 105                 110

Gln Gly Tyr Ser Glu Glu Glu Glu Glu Glu Glu Val Pro Ala
        115                 120                 125

Gly Asn Ala Ala Lys Ala Val Ala Lys Pro Lys Ala Lys Pro Ala Glu
        130                 135                 140

Val Lys Pro Ala Val Asp Asp Glu Glu Asp Ser Asp Ser Asp Gly
145                 150                 155                 160

Met Asp Glu Asp Ser Asp Gly Glu Asp Ser Glu Glu Glu Pro
                165                 170                 175

Thr Pro Lys Lys Pro Ala Ser Ser Lys Lys Arg Ala Asn Glu Thr Thr
                180                 185                 190

Pro Lys Ala Pro Val Ser Ala Lys Lys Ala Lys Val Ala Val Thr Pro
            195                 200                 205

Gln Lys Thr Asp Glu Lys Lys Lys Gly Gly Lys Ala Ala Asn Gln Ser
        210                 215                 220

Glu Phe
225

<210> SEQ ID NO 102
<211> LENGTH: 272
<212> TYPE: PRT
<213> ORGANISM: Homo sapiens

<400> SEQUENCE: 102

Ala Ser Ser Pro Lys Lys Lys Arg Lys Val Glu Ala Ser Met Val Gly
1               5                   10                  15

Ala Gly Ile Ser Thr Pro Ser Gly Ile Pro Asp Phe Arg Ser Pro Gly
                20                  25                  30

Ser Gly Leu Tyr Ser Asn Leu Gln Gln Tyr Asp Leu Pro Tyr Pro Glu
            35                  40                  45

Ala Ile Phe Glu Leu Pro Phe Phe His Asn Pro Lys Pro Phe Phe
50                  55                  60
```

```
Thr Leu Ala Lys Glu Leu Tyr Pro Gly Asn Tyr Lys Pro Asn Val Thr
 65                  70                  75                  80

His Tyr Phe Leu Arg Leu Leu His Asp Lys Gly Leu Leu Arg Leu
                 85                  90                  95

Tyr Thr Gln Asn Ile Asp Gly Leu Glu Arg Val Ser Gly Ile Pro Ala
                100                 105                 110

Ser Lys Leu Val Glu Ala His Gly Thr Phe Ala Ser Ala Thr Cys Thr
                115                 120                 125

Val Cys Gln Arg Pro Phe Pro Gly Glu Asp Ile Arg Ala Asp Val Met
                130                 135                 140

Ala Asp Arg Val Pro Arg Cys Pro Val Cys Thr Gly Val Val Lys Pro
145                 150                 155                 160

Asp Ile Val Phe Phe Gly Glu Pro Leu Pro Gln Arg Phe Leu Leu His
                165                 170                 175

Val Val Asp Phe Pro Met Ala Asp Leu Leu Ile Leu Gly Thr Ser
                180                 185                 190

Leu Glu Val Glu Pro Phe Ala Ser Leu Thr Glu Ala Val Arg Ser Ser
                195                 200                 205

Val Pro Arg Leu Leu Ile Asn Arg Asp Leu Val Gly Pro Leu Ala Trp
210                 215                 220

His Pro Arg Ser Arg Asp Val Ala Gln Leu Gly Asp Val Val His Gly
225                 230                 235                 240

Val Glu Ser Leu Val Glu Leu Leu Gly Trp Thr Glu Glu Met Arg Asp
                245                 250                 255

Leu Val Gln Arg Glu Thr Gly Lys Leu Asp Gly Pro Asp Lys Glu Phe
                260                 265                 270

<210> SEQ ID NO 103
<211> LENGTH: 306
<212> TYPE: PRT
<213> ORGANISM: S. cerevisiae

<400> SEQUENCE: 103

Ala Ser Ser Pro Lys Lys Lys Arg Lys Val Glu Ala Ser Thr Glu Met
1                5                  10                  15

Ser Val Arg Lys Ile Ala Ala His Met Lys Ser Asn Pro Asn Ala Lys
                20                  25                  30

Val Ile Phe Met Val Gly Ala Gly Ile Ser Thr Ser Cys Gly Ile Pro
                35                  40                  45

Asp Phe Arg Ser Pro Gly Thr Gly Leu Tyr His Asn Leu Ala Arg Leu
            50                  55                  60

Lys Leu Pro Tyr Pro Glu Ala Val Phe Asp Val Asp Phe Phe Gln Ser
65                  70                  75                  80

Asp Pro Leu Pro Phe Tyr Thr Leu Ala Lys Glu Leu Tyr Pro Gly Asn
                85                  90                  95

Phe Arg Pro Ser Lys Phe His Tyr Leu Leu Lys Leu Phe Gln Asp Lys
                100                 105                 110

Asp Val Leu Lys Arg Val Tyr Thr Gln Asn Ile Asp Thr Leu Glu Arg
                115                 120                 125

Gln Ala Gly Val Lys Asp Asp Leu Ile Ile Glu Ala His Gly Ser Phe
                130                 135                 140

Ala His Cys His Cys Ile Gly Cys Gly Lys Val Tyr Pro Pro Gln Val
145                 150                 155                 160

Phe Lys Ser Lys Leu Ala Glu His Pro Ile Lys Asp Phe Val Lys Cys
                165                 170                 175
```

```
Asp Val Cys Gly Glu Leu Val Lys Pro Ala Ile Val Phe Gly Glu
            180                 185                 190

Asp Leu Pro Asp Ser Phe Ser Glu Thr Trp Leu Asn Asp Ser Glu Trp
            195                 200                 205

Leu Arg Glu Lys Ile Thr Thr Ser Gly Lys His Pro Gln Gln Pro Leu
210                 215                 220

Val Ile Val Val Gly Thr Ser Leu Ala Val Tyr Pro Phe Ala Ser Leu
225                 230                 235                 240

Pro Glu Glu Ile Pro Arg Lys Val Lys Arg Val Leu Cys Asn Leu Glu
                245                 250                 255

Thr Val Gly Asp Phe Lys Ala Asn Lys Arg Pro Thr Asp Leu Ile Val
            260                 265                 270

His Gln Tyr Ser Asp Glu Phe Ala Glu Gln Leu Val Glu Glu Leu Gly
            275                 280                 285

Trp Gln Glu Asp Phe Glu Lys Ile Leu Thr Ala Gln Gly Gly Met Gly
            290                 295                 300

Glu Phe
305

<210> SEQ ID NO 104
<211> LENGTH: 257
<212> TYPE: PRT
<213> ORGANISM: E. coli

<400> SEQUENCE: 104

Ala Ser Ser Pro Lys Lys Arg Lys Val Glu Ala Ser Met Glu Lys
1               5                   10                  15

Pro Arg Val Leu Val Leu Thr Gly Ala Gly Ile Ser Ala Glu Ser Gly
            20                  25                  30

Ile Arg Thr Phe Arg Ala Ala Asp Gly Leu Trp Glu Glu His Arg Val
        35                  40                  45

Glu Asp Val Ala Thr Pro Glu Gly Phe Asp Arg Asp Pro Glu Leu Val
    50                  55                  60

Gln Ala Phe Tyr Asn Ala Arg Arg Arg Gln Leu Gln Gln Pro Glu Ile
65                  70                  75                  80

Gln Pro Asn Ala Ala His Leu Ala Leu Ala Lys Leu Gln Asp Ala Leu
                85                  90                  95

Gly Asp Arg Phe Leu Leu Val Thr Gln Asn Ile Asp Asn Leu His Glu
            100                 105                 110

Arg Ala Gly Asn Thr Asn Val Ile His Met His Gly Glu Leu Leu Lys
        115                 120                 125

Val Arg Cys Ser Gln Ser Gly Gln Val Leu Asp Trp Thr Gly Asp Val
    130                 135                 140

Thr Pro Glu Asp Lys Cys His Cys Cys Gln Phe Pro Ala Pro Leu Arg
145                 150                 155                 160

Pro His Val Val Trp Phe Gly Glu Met Pro Leu Gly Met Asp Glu Ile
                165                 170                 175

Tyr Met Ala Leu Ser Met Ala Asp Ile Phe Ile Ala Ile Gly Thr Ser
            180                 185                 190

Gly His Val Tyr Pro Ala Ala Gly Phe Val His Glu Ala Lys Leu His
        195                 200                 205

Gly Ala His Thr Val Glu Leu Asn Leu Glu Pro Ser Gln Val Gly Asn
    210                 215                 220

Glu Phe Ala Glu Lys Tyr Tyr Gly Pro Ala Ser Gln Val Val Pro Glu
```

```
            225                 230                 235                 240

Phe Val Glu Lys Leu Leu Lys Gly Leu Lys Ala Gly Ser Ile Ala Glu
                245                 250                 255

Phe

<210> SEQ ID NO 105
<211> LENGTH: 346
<212> TYPE: PRT
<213> ORGANISM: C. albicans

<400> SEQUENCE: 105

Ala Ser Ser Pro Lys Lys Arg Lys Val Glu Ala Ser Met Pro Ser
1               5                   10                  15

Leu Asp Asp Ile Leu Lys Pro Val Ala Glu Ala Val Lys Asn Gly Lys
                20                  25                  30

Lys Val Thr Phe Phe Asn Gly Ala Gly Ile Ser Thr Gly Ala Gly Ile
            35                  40                  45

Pro Asp Phe Arg Ser Pro Asp Thr Gly Leu Tyr Ala Asn Leu Ala Lys
        50                  55                  60

Leu Asn Leu Pro Phe Ala Glu Ala Val Phe Asp Ile Asp Phe Phe Lys
65                  70                  75                  80

Glu Asp Pro Lys Pro Phe Tyr Thr Leu Ala Glu Glu Leu Tyr Pro Gly
                85                  90                  95

Asn Phe Ala Pro Thr Lys Phe His His Phe Ile Lys Leu Leu Gln Asp
                100                 105                 110

Gln Gly Ser Leu Lys Arg Val Tyr Thr Gln Asn Ile Asp Thr Leu Glu
            115                 120                 125

Arg Leu Ala Gly Val Glu Asp Lys Tyr Ile Val Glu Ala His Gly Ser
        130                 135                 140

Phe Ala Ser Asn His Cys Val Asp Cys His Lys Glu Met Thr Thr Glu
145                 150                 155                 160

Thr Leu Lys Thr Tyr Met Lys Asp Lys Lys Ile Pro Ser Cys Gln His
                165                 170                 175

Cys Glu Gly Tyr Val Lys Pro Asp Ile Val Phe Phe Gly Glu Gly Leu
                180                 185                 190

Pro Val Lys Phe Phe Asp Leu Trp Glu Asp Asp Cys Glu Asp Val Glu
            195                 200                 205

Val Ala Ile Val Ala Gly Thr Ser Leu Thr Val Phe Pro Phe Ala Ser
        210                 215                 220

Leu Pro Gly Glu Val Asn Lys Lys Cys Leu Arg Val Leu Val Asn Lys
225                 230                 235                 240

Glu Lys Val Gly Thr Phe Lys His Glu Pro Arg Lys Ser Asp Ile Ile
                245                 250                 255

Ala Leu His Asp Cys Asp Ile Val Ala Glu Arg Leu Cys Thr Leu Leu
                260                 265                 270

Gly Leu Asp Asp Lys Leu Asn Glu Val Tyr Lys Glu Lys Ile Lys
            275                 280                 285

Tyr Ser Lys Ala Glu Thr Lys Glu Ile Lys Met His Glu Ile Glu Asp
        290                 295                 300

Lys Leu Lys Glu Glu Ala His Leu Lys Glu Asp Lys His Thr Thr Lys
305                 310                 315                 320

Val Asp Lys Lys Glu Lys Gln Asn Asp Ala Asn Asp Lys Glu Leu Glu
                325                 330                 335

Gln Leu Ile Asp Lys Ala Lys Ala Glu Phe
```

<210> SEQ ID NO 106
<211> LENGTH: 289
<212> TYPE: PRT
<213> ORGANISM: Homo sapiens

<400> SEQUENCE: 106

```
Ala Ser Ser Pro Lys Lys Arg Lys Val Glu Ala Ser Ser Ser Ser
1               5                   10                  15

Met Ala Asp Phe Arg Lys Phe Ala Lys Ala Lys His Ile Val Ile
                20                  25                  30

Ile Ser Gly Ala Gly Val Ser Ala Glu Ser Gly Val Pro Thr Phe Arg
                35                  40                  45

Gly Ala Gly Gly Tyr Trp Arg Lys Trp Gln Ala Gln Asp Leu Ala Thr
            50                  55                  60

Pro Leu Ala Phe Ala His Asn Pro Ser Arg Val Trp Glu Phe Tyr His
65                  70                  75                  80

Tyr Arg Arg Glu Val Met Gly Ser Lys Glu Pro Asn Ala Gly His Arg
                85                  90                  95

Ala Ile Ala Glu Cys Glu Thr Arg Leu Gly Lys Gln Gly Arg Arg Val
                100                 105                 110

Val Val Ile Thr Gln Asn Ile Asp Glu Leu His Arg Lys Ala Gly Thr
                115                 120                 125

Lys Asn Leu Leu Glu Ile His Gly Ser Leu Phe Lys Thr Arg Cys Thr
130                 135                 140

Ser Cys Gly Val Val Ala Glu Asn Tyr Lys Ser Pro Ile Cys Pro Ala
145                 150                 155                 160

Leu Ser Gly Lys Gly Ala Pro Glu Pro Gly Thr Gln Asp Ala Ser Ile
                165                 170                 175

Pro Val Glu Lys Leu Pro Arg Cys Glu Glu Ala Gly Cys Gly Gly Leu
                180                 185                 190

Leu Arg Pro His Val Val Trp Phe Gly Glu Asn Leu Asp Pro Ala Ile
                195                 200                 205

Leu Glu Glu Val Asp Arg Glu Leu Ala His Cys Asp Leu Cys Leu Val
                210                 215                 220

Val Gly Thr Ser Ser Val Val Tyr Pro Ala Ala Met Phe Ala Pro Gln
225                 230                 235                 240

Val Ala Ala Arg Gly Val Pro Val Ala Glu Phe Asn Thr Glu Thr Thr
                245                 250                 255

Pro Ala Thr Asn Arg Phe Arg Phe His Phe Gln Gly Pro Cys Gly Thr
                260                 265                 270

Thr Leu Pro Glu Ala Leu Ala Cys His Glu Asn Glu Thr Val Ser Glu
                275                 280                 285

Phe
```

<210> SEQ ID NO 107
<211> LENGTH: 288
<212> TYPE: PRT
<213> ORGANISM: P. falciparum

<400> SEQUENCE: 107

```
Ala Ser Ser Pro Lys Lys Arg Lys Val Glu Ala Ser Met Gly Asn
1               5                   10                  15

Leu Met Ile Ser Phe Leu Lys Lys Asp Thr Gln Ser Ile Thr Leu Glu
                20                  25                  30
```

Glu Leu Ala Lys Ile Ile Lys Lys Cys Lys His Val Val Ala Leu Thr
            35                  40                  45

Gly Ser Gly Thr Ser Ala Glu Ser Asn Ile Pro Ser Phe Arg Gly Ser
    50                  55                  60

Ser Asn Ser Ile Trp Ser Lys Tyr Asp Pro Arg Ile Tyr Gly Thr Ile
65                  70                  75                  80

Trp Gly Phe Trp Lys Tyr Pro Glu Lys Ile Trp Glu Val Ile Arg Asp
                85                  90                  95

Ile Ser Ser Asp Tyr Glu Ile Glu Ile Asn Asn Gly His Val Ala Leu
            100                 105                 110

Ser Thr Leu Glu Ser Leu Gly Tyr Leu Lys Ser Val Val Thr Gln Asn
        115                 120                 125

Val Asp Gly Leu His Glu Ala Ser Gly Asn Thr Lys Val Ile Ser Leu
    130                 135                 140

His Gly Asn Val Phe Glu Ala Val Cys Cys Thr Cys Asn Lys Ile Val
145                 150                 155                 160

Lys Leu Asn Lys Ile Met Leu Gln Lys Thr Ser His Phe Met His Gln
                165                 170                 175

Leu Pro Pro Glu Cys Pro Cys Gly Gly Ile Phe Lys Pro Asn Ile Ile
            180                 185                 190

Leu Phe Gly Glu Val Val Ser Ser Asp Leu Leu Lys Glu Ala Glu Glu
        195                 200                 205

Glu Ile Ala Lys Cys Asp Leu Leu Leu Val Ile Gly Thr Ser Ser Thr
    210                 215                 220

Val Ser Thr Ala Thr Asn Leu Cys His Phe Ala Cys Lys Lys Lys Lys
225                 230                 235                 240

Lys Ile Val Glu Ile Asn Ile Ser Lys Thr Tyr Ile Thr Asn Lys Met
                245                 250                 255

Ser Asp Tyr His Val Cys Ala Lys Phe Ser Glu Leu Thr Lys Val Ala
            260                 265                 270

Asn Ile Leu Lys Gly Ser Ser Glu Lys Asn Lys Lys Ile Met Glu Phe
        275                 280                 285

<210> SEQ ID NO 108
<211> LENGTH: 304
<212> TYPE: PRT
<213> ORGANISM: Homo sapiens

<400> SEQUENCE: 108

Ala Ser Ser Pro Lys Lys Arg Lys Val Glu Ala Ser Met Ser Val
1               5                   10                  15

Asn Tyr Ala Ala Gly Leu Ser Pro Tyr Ala Asp Lys Gly Lys Cys Gly
            20                  25                  30

Leu Pro Glu Ile Phe Asp Pro Pro Glu Glu Leu Glu Arg Lys Val Trp
        35                  40                  45

Glu Leu Ala Arg Leu Val Trp Gln Ser Ser Val Val Phe His Thr
    50                  55                  60

Gly Ala Gly Ile Ser Thr Ala Ser Gly Ile Pro Asp Phe Arg Gly Pro
65                  70                  75                  80

His Gly Val Trp Thr Met Glu Glu Arg Gly Leu Ala Pro Lys Phe Asp
                85                  90                  95

Thr Thr Phe Glu Ser Ala Arg Pro Thr Gln Thr His Met Ala Leu Val
            100                 105                 110

Gln Leu Glu Arg Val Gly Leu Leu Arg Phe Leu Val Ser Gln Asn Val

```
               115                 120                 125
Asp Gly Leu His Val Arg Ser Gly Phe Pro Arg Asp Lys Leu Ala Glu
    130                 135                 140

Leu His Gly Asn Met Phe Val Glu Glu Cys Ala Lys Cys Lys Thr Gln
145                 150                 155                 160

Tyr Val Arg Asp Thr Val Val Gly Thr Met Gly Leu Lys Ala Thr Gly
                165                 170                 175

Arg Leu Cys Thr Val Ala Lys Ala Arg Gly Leu Arg Ala Cys Arg Gly
                180                 185                 190

Glu Leu Arg Asp Thr Ile Leu Asp Trp Glu Asp Ser Leu Pro Asp Arg
                195                 200                 205

Asp Leu Ala Leu Ala Asp Glu Ala Ser Arg Asn Ala Asp Leu Ser Ile
    210                 215                 220

Thr Leu Gly Thr Ser Leu Gln Ile Arg Pro Ser Gly Asn Leu Pro Leu
225                 230                 235                 240

Ala Thr Lys Arg Arg Gly Gly Arg Leu Val Ile Val Asn Leu Gln Pro
                245                 250                 255

Thr Lys His Asp Arg His Ala Asp Leu Arg Ile His Gly Tyr Val Asp
                260                 265                 270

Glu Val Met Thr Arg Leu Met Lys His Leu Gly Leu Glu Ile Pro Ala
                275                 280                 285

Trp Asp Gly Pro Arg Val Leu Glu Arg Ala Leu Pro Pro Leu Glu Phe
    290                 295                 300

<210> SEQ ID NO 109
<211> LENGTH: 234
<212> TYPE: PRT
<213> ORGANISM: C. trachomatis

<400> SEQUENCE: 109

Ala Ser Ser Pro Lys Lys Arg Lys Val Glu Ala Ser Met Thr Thr
1               5                   10                  15

Asn Ser Thr Gln Asp Thr Leu Tyr Leu Ser Leu His Gly Gly Ile Asp
                20                  25                  30

Ser Ala Ile Pro Tyr Pro Val Arg Arg Val Glu Gln Leu Leu Gln Phe
            35                  40                  45

Ser Phe Leu Pro Glu Leu Gln Phe Gln Asn Ala Ala Val Lys Gln Arg
    50                  55                  60

Ile Gln Arg Leu Cys Tyr Arg Glu Lys Arg Leu Ala Val Ser Ser
65                  70                  75                  80

Leu Ala Lys Trp Leu Gly Gln Leu His Lys Gln Arg Leu Arg Ala Pro
                85                  90                  95

Lys Asn Pro Pro Val Ala Ile Cys Trp Ile Asn Ser Tyr Val Gly Tyr
                100                 105                 110

Gly Val Phe Ala Arg Glu Ser Ile Pro Ala Trp Ser Tyr Ile Gly Glu
            115                 120                 125

Tyr Thr Gly Ile Leu Arg Arg Arg Gln Ala Leu Trp Leu Asp Glu Asn
    130                 135                 140

Asp Tyr Cys Phe Arg Tyr Pro Val Pro Arg Tyr Ser Phe Arg Tyr Phe
145                 150                 155                 160

Thr Ile Asp Ser Gly Met Gln Gly Asn Val Thr Arg Phe Ile Asn His
                165                 170                 175

Ser Asp Asn Pro Asn Leu Glu Ala Ile Gly Ala Phe Glu Asn Gly Ile
                180                 185                 190
```

Phe His Ile Ile Ile Arg Ala Ile Lys Asp Ile Leu Pro Gly Glu Glu
            195                 200                 205

Leu Cys Tyr His Tyr Gly Pro Leu Tyr Trp Lys His Arg Lys Lys Arg
210                 215                 220

Glu Glu Phe Val Pro Gln Glu Glu Phe
225                 230

<210> SEQ ID NO 110
<211> LENGTH: 134
<212> TYPE: PRT
<213> ORGANISM: P. bursaria chlorella virus

<400> SEQUENCE: 110

Ala Ser Ser Pro Lys Lys Arg Lys Val Glu Ala Ser Met Phe Asn
1               5                   10                  15

Asp Arg Val Ile Val Lys Lys Ser Pro Leu Gly Gly Tyr Gly Val Phe
            20                  25                  30

Ala Arg Lys Ser Phe Glu Lys Gly Glu Leu Val Glu Glu Cys Leu Cys
        35                  40                  45

Ile Val Arg His Asn Asp Asp Trp Gly Thr Ala Leu Glu Asp Tyr Leu
50                  55                  60

Phe Ser Arg Lys Asn Met Ser Ala Met Ala Leu Gly Phe Gly Ala Ile
65                  70                  75                  80

Phe Asn His Ser Lys Asp Pro Asn Ala Arg His Glu Leu Thr Ala Gly
                85                  90                  95

Leu Lys Arg Met Arg Ile Phe Thr Ile Lys Pro Ile Ala Ile Gly Glu
            100                 105                 110

Glu Ile Thr Ile Ser Tyr Gly Asp Asp Tyr Trp Leu Ser Arg Pro Arg
        115                 120                 125

Leu Thr Gln Asn Glu Phe
    130

<210> SEQ ID NO 111
<211> LENGTH: 349
<212> TYPE: PRT
<213> ORGANISM: Homo sapiens

<400> SEQUENCE: 111

Ala Ser Ser Pro Lys Lys Arg Lys Val Glu Ala Ser Asn Leu Lys
1               5                   10                  15

Cys Val Arg Ile Leu Lys Gln Phe His Lys Asp Leu Glu Arg Glu Leu
            20                  25                  30

Leu Arg Arg His His Arg Ser Lys Thr Pro Arg His Leu Asp Pro Ser
        35                  40                  45

Leu Ala Asn Tyr Leu Val Gln Lys Ala Lys Gln Arg Arg Ala Leu Arg
50                  55                  60

Arg Trp Glu Gln Glu Leu Asn Ala Lys Arg Ser His Leu Gly Arg Ile
65                  70                  75                  80

Thr Val Glu Asn Glu Val Asp Leu Asp Gly Pro Pro Arg Ala Phe Val
                85                  90                  95

Tyr Ile Asn Glu Tyr Arg Val Gly Glu Gly Ile Thr Leu Asn Gln Val
            100                 105                 110

Ala Val Gly Cys Glu Cys Gln Asp Cys Leu Trp Ala Pro Thr Gly Gly
        115                 120                 125

Cys Cys Pro Gly Ala Ser Leu His Lys Phe Ala Tyr Asn Asp Gln Gly
    130                 135                 140

Gln Val Arg Leu Arg Ala Gly Leu Pro Ile Tyr Glu Cys Asn Ser Arg
145                 150                 155                 160

Cys Arg Cys Gly Tyr Asp Cys Pro Asn Arg Val Val Gln Lys Gly Ile
            165                 170                 175

Arg Tyr Asp Leu Cys Ile Phe Arg Thr Asp Asp Gly Arg Gly Trp Gly
            180                 185                 190

Val Arg Thr Leu Glu Lys Ile Arg Lys Asn Ser Phe Val Met Glu Tyr
            195                 200                 205

Val Gly Glu Ile Ile Thr Ser Glu Glu Ala Glu Arg Gly Gln Ile
210                 215                 220

Tyr Asp Arg Gln Gly Ala Thr Tyr Leu Phe Asp Leu Asp Tyr Val Glu
225                 230                 235                 240

Asp Val Tyr Thr Val Asp Ala Ala Tyr Tyr Gly Asn Ile Ser His Phe
            245                 250                 255

Val Asn His Ser Cys Asp Pro Asn Leu Gln Val Tyr Asn Val Phe Ile
            260                 265                 270

Asp Asn Leu Asp Glu Arg Leu Pro Arg Ile Ala Phe Phe Ala Thr Arg
            275                 280                 285

Thr Ile Arg Ala Gly Glu Glu Leu Thr Phe Asp Tyr Asn Met Gln Val
290                 295                 300

Asp Pro Val Asp Met Glu Ser Thr Arg Met Asp Ser Asn Phe Gly Leu
305                 310                 315                 320

Ala Gly Leu Pro Gly Ser Pro Lys Lys Arg Val Arg Ile Glu Cys Lys
            325                 330                 335

Cys Gly Thr Glu Ser Cys Arg Lys Tyr Leu Phe Glu Phe
            340                 345

<210> SEQ ID NO 112
<211> LENGTH: 346
<212> TYPE: PRT
<213> ORGANISM: N. crassa

<400> SEQUENCE: 112

Ala Ser Ser Pro Lys Lys Arg Lys Val Glu Ala Ser Met Glu Lys
1               5                   10                  15

Ala Phe Arg Pro His Phe Phe Asn His Gly Lys Pro Asp Ala Asn Pro
                20                  25                  30

Lys Glu Lys Lys Asn Cys His Trp Cys Gln Ile Arg Ser Phe Ala Thr
            35                  40                  45

His Ala Gln Leu Pro Ile Ser Ile Val Asn Arg Glu Asp Asp Ala Phe
50                  55                  60

Leu Asn Pro Asn Phe Arg Phe Ile Asp His Ser Ile Ile Gly Lys Asn
65                  70                  75                  80

Val Pro Val Ala Asp Gln Ser Phe Arg Val Gly Cys Ser Cys Ala Ser
                85                  90                  95

Asp Glu Glu Cys Met Tyr Ser Thr Cys Gln Cys Leu Asp Glu Met Ala
            100                 105                 110

Pro Asp Ser Asp Glu Glu Ala Asp Pro Tyr Thr Arg Lys Lys Arg Phe
            115                 120                 125

Ala Tyr Tyr Ser Gln Gly Ala Lys Lys Gly Leu Leu Arg Asp Arg Val
130                 135                 140

Leu Gln Ser Gln Glu Pro Ile Tyr Glu Cys His Gln Gly Cys Ala Cys
145                 150                 155                 160

Ser Lys Asp Cys Pro Asn Arg Val Val Glu Arg Gly Arg Thr Val Pro
            165                 170                 175

```
Leu Gln Ile Phe Arg Thr Lys Asp Arg Gly Trp Gly Val Lys Cys Pro
                180                 185                 190

Val Asn Ile Lys Arg Gly Gln Phe Val Asp Arg Tyr Leu Gly Glu Ile
            195                 200                 205

Ile Thr Ser Glu Glu Ala Asp Arg Arg Ala Glu Ser Thr Ile Ala
        210                 215                 220

Arg Arg Lys Asp Val Tyr Leu Phe Ala Leu Asp Lys Phe Ser Asp Pro
225                 230                 235                 240

Asp Ser Leu Asp Pro Leu Leu Ala Gly Gln Pro Leu Glu Val Asp Gly
                245                 250                 255

Glu Tyr Met Ser Gly Pro Thr Arg Phe Ile Asn His Ser Cys Asp Pro
            260                 265                 270

Asn Met Ala Ile Phe Ala Arg Val Gly Asp His Ala Asp Lys His Ile
            275                 280                 285

His Asp Leu Ala Leu Phe Ala Ile Lys Asp Ile Pro Lys Gly Thr Glu
        290                 295                 300

Leu Thr Phe Asp Tyr Val Asn Gly Leu Thr Gly Leu Glu Ser Asp Ala
305                 310                 315                 320

His Asp Pro Ser Lys Ile Ser Glu Met Thr Lys Cys Leu Cys Gly Thr
                325                 330                 335

Ala Lys Cys Arg Gly Tyr Leu Trp Glu Phe
            340                 345

<210> SEQ ID NO 113
<211> LENGTH: 282
<212> TYPE: PRT
<213> ORGANISM: A. thaliana

<400> SEQUENCE: 113

Ala Ser Ser Pro Lys Lys Arg Lys Val Glu Ala Ser Asp Ile Ser
1               5                   10                  15

Gly Gly Leu Glu Phe Lys Gly Ile Pro Ala Thr Asn Arg Val Asp Asp
            20                  25                  30

Ser Pro Val Ser Pro Thr Ser Gly Phe Thr Tyr Ile Lys Ser Leu Ile
            35                  40                  45

Ile Glu Pro Asn Val Ile Ile Pro Lys Ser Ser Thr Gly Cys Asn Cys
        50                  55                  60

Arg Gly Ser Cys Thr Asp Ser Lys Lys Cys Ala Cys Ala Lys Leu Asn
65                  70                  75                  80

Gly Gly Asn Phe Pro Tyr Val Asp Leu Asn Asp Gly Arg Leu Ile Glu
                85                  90                  95

Ser Arg Asp Val Val Phe Glu Cys Gly Pro His Cys Gly Cys Gly Pro
            100                 105                 110

Lys Cys Val Asn Arg Thr Ser Gln Lys Arg Leu Arg Phe Asn Leu Glu
        115                 120                 125

Val Phe Arg Ser Ala Lys Lys Gly Trp Ala Val Arg Ser Trp Glu Tyr
    130                 135                 140

Ile Pro Ala Gly Ser Pro Val Cys Glu Tyr Ile Gly Val Val Arg Arg
145                 150                 155                 160

Thr Ala Asp Val Asp Thr Ile Ser Asp Asn Glu Tyr Ile Phe Glu Ile
                165                 170                 175

Asp Cys Gln Gln Thr Met Gln Gly Leu Gly Gly Arg Gln Arg Arg Leu
            180                 185                 190

Arg Asp Val Ala Val Pro Met Asn Asn Gly Val Ser Gln Ser Ser Glu
```

```
                      195                 200                 205
Asp Glu Asn Ala Pro Glu Phe Cys Ile Asp Ala Gly Ser Thr Gly Asn
        210                 215                 220

Phe Ala Arg Phe Ile Asn His Ser Cys Glu Pro Asn Leu Phe Val Gln
225                 230                 235                 240

Cys Val Leu Ser Ser His Gln Asp Ile Arg Leu Ala Arg Val Val Leu
            245                 250                 255

Phe Ala Ala Asp Asn Ile Ser Pro Met Gln Glu Leu Thr Tyr Asp Tyr
        260                 265                 270

Gly Tyr Ala Leu Asp Ser Val His Glu Phe
            275                 280

<210> SEQ ID NO 114
<211> LENGTH: 328
<212> TYPE: PRT
<213> ORGANISM: A. thaliana

<400> SEQUENCE: 114

Ala Ser Ser Pro Lys Lys Arg Lys Val Glu Ala Ser Gln Ser Ala
1               5                   10                  15

Tyr Leu His Val Ser Leu Ala Arg Ile Ser Asp Glu Asp Cys Cys Ala
            20                  25                  30

Asn Cys Lys Gly Asn Cys Leu Ser Ala Asp Phe Pro Cys Thr Cys Ala
        35                  40                  45

Arg Glu Thr Ser Gly Glu Tyr Ala Tyr Thr Lys Glu Gly Leu Leu Lys
    50                  55                  60

Glu Lys Phe Leu Asp Thr Cys Leu Lys Met Lys Lys Glu Pro Asp Ser
65                  70                  75                  80

Phe Pro Lys Val Tyr Cys Lys Asp Cys Pro Leu Glu Arg Asp His Asp
                85                  90                  95

Lys Gly Thr Tyr Gly Lys Cys Asp Gly His Leu Ile Arg Lys Phe Ile
            100                 105                 110

Lys Glu Cys Trp Arg Lys Cys Gly Cys Asp Met Gln Cys Gly Asn Arg
        115                 120                 125

Val Val Gln Arg Gly Ile Arg Cys Gln Leu Gln Val Tyr Phe Thr Gln
    130                 135                 140

Glu Gly Lys Gly Trp Gly Leu Arg Thr Leu Gln Asp Leu Pro Lys Gly
145                 150                 155                 160

Thr Phe Ile Cys Glu Tyr Ile Gly Glu Ile Leu Thr Asn Thr Glu Leu
                165                 170                 175

Tyr Asp Arg Asn Val Arg Ser Ser Glu Arg His Thr Tyr Pro Val
            180                 185                 190

Thr Leu Asp Ala Asp Trp Gly Ser Glu Lys Asp Leu Lys Asp Glu Glu
        195                 200                 205

Ala Leu Cys Leu Asp Ala Thr Ile Cys Gly Asn Val Ala Arg Phe Ile
    210                 215                 220

Asn His Arg Cys Glu Asp Ala Asn Met Ile Asp Ile Pro Ile Glu Ile
225                 230                 235                 240

Glu Thr Pro Asp Arg His Tyr Tyr His Ile Ala Phe Phe Thr Leu Arg
                245                 250                 255

Asp Val Lys Ala Met Asp Glu Leu Thr Trp Asp Tyr Met Ile Asp Phe
            260                 265                 270

Asn Asp Lys Ser His Pro Val Lys Ala Phe Arg Cys Cys Cys Gly Ser
        275                 280                 285
```

```
Glu Ser Cys Arg Asp Arg Lys Ile Lys Gly Ser Gln Gly Lys Ser Ile
        290                 295                 300

Glu Arg Arg Lys Ile Val Ser Ala Lys Gln Gln Gly Ser Lys Glu
305                 310                 315                 320

Val Ser Lys Lys Arg Lys Glu Phe
                325

<210> SEQ ID NO 115
<211> LENGTH: 303
<212> TYPE: PRT
<213> ORGANISM: C. elegans

<400> SEQUENCE: 115

Ala Ser Ser Pro Lys Lys Arg Lys Val Glu Ala Ser Met Gln Leu
1               5                   10                  15

His Glu Gln Ile Ala Asn Ile Ser Val Thr Phe Asn Asp Ile Pro Arg
                20                  25                  30

Ser Asp His Ser Met Thr Pro Thr Glu Leu Cys Tyr Phe Asp Asp Phe
            35                  40                  45

Ala Thr Thr Leu Val Val Asp Ser Val Leu Asn Phe Thr Thr His Lys
50                  55                  60

Met Ser Lys Lys Arg Arg Tyr Leu Tyr Gln Asp Glu Tyr Arg Thr Ala
65                  70                  75                  80

Arg Thr Val Met Lys Thr Phe Arg Glu Gln Arg Asp Trp Thr Asn Ala
                85                  90                  95

Ile Tyr Gly Leu Leu Thr Leu Arg Ser Val Ser His Phe Leu Ser Lys
                100                 105                 110

Leu Pro Pro Asn Lys Leu Phe Glu Phe Arg Asp His Ile Val Arg Phe
            115                 120                 125

Leu Asn Met Phe Ile Leu Asp Ser Gly Tyr Thr Ile Gln Glu Cys Lys
130                 135                 140

Arg Tyr Ser Gln Glu Gly His Gln Gly Ala Lys Leu Val Ser Thr Gly
145                 150                 155                 160

Val Trp Ser Arg Gly Asp Lys Ile Glu Arg Leu Ser Gly Val Val Cys
                165                 170                 175

Leu Leu Ser Ser Glu Asp Glu Asp Ser Ile Leu Ala Gln Glu Gly Ser
            180                 185                 190

Asp Phe Ser Val Met Tyr Ser Thr Arg Lys Arg Cys Ser Thr Leu Trp
            195                 200                 205

Leu Gly Pro Gly Ala Tyr Ile Asn His Asp Cys Arg Pro Thr Cys Glu
210                 215                 220

Phe Val Ser His Gly Ser Thr Ala His Ile Arg Val Leu Arg Asp Met
225                 230                 235                 240

Val Pro Gly Asp Glu Ile Thr Cys Phe Tyr Gly Ser Glu Phe Phe Gly
                245                 250                 255

Pro Asn Asn Ile Asp Cys Glu Cys Cys Thr Cys Glu Lys Asn Met Asn
            260                 265                 270

Gly Ala Phe Ser Tyr Leu Arg Gly Asn Glu Asn Ala Glu Pro Ile Ile
        275                 280                 285

Ser Glu Lys Lys Thr Lys Tyr Glu Leu Arg Ser Arg Ser Glu Phe
290                 295                 300

<210> SEQ ID NO 116
<211> LENGTH: 257
<212> TYPE: PRT
<213> ORGANISM: C. elegans
```

<400> SEQUENCE: 116

```
Ala Ser Ser Pro Lys Lys Arg Lys Val Glu Ala Ser Met Lys Val
1               5                   10                  15

Ala Ala Lys Lys Leu Ala Thr Ser Arg Met Arg Lys Asp Arg Ala Ala
            20                  25                  30

Ala Ala Ser Pro Ser Ser Asp Ile Glu Asn Ser Glu Asn Pro Ser Ser
            35                  40                  45

Leu Ala Ser His Ser Ser Ser Gly Arg Met Thr Pro Ser Lys Asn
    50                  55                  60

Thr Arg Ser Arg Lys Gly Val Ser Val Lys Asp Val Ser Asn His Lys
65                  70                  75                  80

Ile Thr Glu Phe Phe Gln Val Arg Arg Ser Asn Arg Lys Thr Ser Lys
                85                  90                  95

Gln Ile Ser Asp Glu Ala Lys His Ala Leu Arg Asp Thr Val Leu Lys
            100                 105                 110

Gly Thr Asn Glu Arg Leu Leu Glu Val Tyr Lys Asp Val Lys Gly
        115                 120                 125

Arg Gly Ile Arg Thr Lys Val Asn Phe Glu Lys Gly Asp Phe Val Val
    130                 135                 140

Glu Tyr Arg Gly Val Met Met Glu Tyr Ser Glu Ala Lys Val Ile Glu
145                 150                 155                 160

Glu Gln Tyr Ser Asn Asp Glu Gly Ile Gly Ser Tyr Met Tyr Phe Phe
                165                 170                 175

Glu His Asn Asn Lys Lys Trp Cys Ile Asp Ala Thr Lys Glu Ser Pro
            180                 185                 190

Trp Lys Gly Arg Leu Ile Asn His Ser Val Leu Arg Pro Asn Leu Lys
        195                 200                 205

Thr Lys Val Val Glu Ile Asp Gly Ser His His Leu Ile Leu Val Ala
    210                 215                 220

Arg Arg Gln Ile Ala Gln Gly Glu Glu Leu Leu Tyr Asp Tyr Gly Asp
225                 230                 235                 240

Arg Ser Ala Glu Thr Ile Ala Lys Asn Pro Trp Leu Val Asn Thr Glu
                245                 250                 255

Phe
```

<210> SEQ ID NO 117
<211> LENGTH: 224
<212> TYPE: PRT
<213> ORGANISM: Homo sapiens

<400> SEQUENCE: 117

```
Ala Ser Ser Pro Lys Lys Arg Lys Val Glu Ala Ser Ser Cys Asp
1               5                   10                  15

Ser Thr Asn Ala Ala Ile Ala Lys Gln Ala Leu Lys Lys Pro Ile Lys
            20                  25                  30

Gly Lys Gln Ala Pro Arg Lys Lys Ala Gln Gly Lys Thr Gln Gln Asn
        35                  40                  45

Arg Lys Leu Thr Asp Phe Tyr Pro Val Arg Arg Ser Ser Arg Lys Ser
    50                  55                  60

Lys Ala Glu Leu Gln Ser Glu Glu Arg Lys Arg Ile Asp Glu Leu Ile
65                  70                  75                  80

Glu Ser Gly Lys Glu Glu Gly Met Lys Ile Asp Leu Ile Asp Gly Lys
                85                  90                  95
```

```
Gly Arg Gly Val Ile Ala Thr Lys Gln Phe Ser Arg Gly Asp Phe Val
            100                 105                 110

Val Glu Tyr His Gly Asp Leu Ile Glu Ile Thr Asp Ala Lys Lys Arg
        115                 120                 125

Glu Ala Leu Tyr Ala Gln Asp Pro Ser Thr Gly Cys Tyr Met Tyr Tyr
    130                 135                 140

Phe Gln Tyr Leu Ser Lys Thr Tyr Cys Val Asp Ala Thr Arg Glu Thr
145                 150                 155                 160

Asn Arg Leu Gly Arg Leu Ile Asn His Ser Lys Cys Gly Asn Cys Gln
                165                 170                 175

Thr Lys Leu His Asp Ile Asp Gly Val Pro His Leu Ile Leu Ile Ala
            180                 185                 190

Ser Arg Asp Ile Ala Ala Gly Glu Glu Leu Leu Tyr Asp Tyr Gly Asp
        195                 200                 205

Arg Ser Lys Ala Ser Ile Glu Ala Phe Pro Trp Leu Lys His Glu Phe
    210                 215                 220
```

<210> SEQ ID NO 118
<211> LENGTH: 319
<212> TYPE: PRT
<213> ORGANISM: T. gondii

<400> SEQUENCE: 118

```
Ala Ser Ser Pro Lys Lys Arg Lys Val Glu Ala Ser Ala Ser Arg
1               5                   10                  15

Arg Thr Gly Glu Phe Leu Arg Asp Ala Gln Ala Pro Ser Arg Trp Leu
            20                  25                  30

Lys Arg Ser Lys Thr Gly Gln Asp Asp Gly Ala Phe Cys Leu Glu Thr
        35                  40                  45

Trp Leu Ala Gly Ala Gly Asp Ala Ala Gly Gly Glu Arg Gly Arg
    50                  55                  60

Asp Arg Glu Gly Ala Ala Asp Lys Ala Lys Gln Arg Glu Glu Arg Arg
65                  70                  75                  80

Gln Lys Glu Leu Glu Glu Arg Phe Glu Glu Met Lys Val Glu Phe Glu
                85                  90                  95

Glu Lys Ala Gln Arg Met Ile Ala Arg Arg Ala Ala Leu Thr Gly Glu
            100                 105                 110

Ile Tyr Ser Asp Gly Lys Gly Ser Lys Lys Pro Arg Val Pro Ser Leu
        115                 120                 125

Pro Glu Asn Asp Asp Asp Ala Leu Ile Glu Ile Ile Asp Pro Glu
    130                 135                 140

Gln Gly Ile Leu Lys Trp Pro Leu Ser Val Met Ser Ile Arg Gln Arg
145                 150                 155                 160

Thr Val Ile Tyr Gln Glu Cys Leu Arg Arg Asp Leu Thr Ala Cys Ile
                165                 170                 175

His Leu Thr Lys Val Pro Gly Lys Gly Arg Ala Val Phe Ala Ala Asp
            180                 185                 190

Thr Ile Leu Lys Asp Asp Phe Val Val Glu Tyr Lys Gly Glu Leu Cys
        195                 200                 205

Ser Glu Arg Glu Ala Arg Glu Arg Glu Gln Arg Tyr Asn Arg Ser Lys
    210                 215                 220

Val Pro Met Gly Ser Phe Met Phe Tyr Phe Lys Asn Gly Ser Arg Met
225                 230                 235                 240

Met Ala Ile Asp Ala Thr Asp Glu Lys Gln Asp Phe Gly Pro Ala Arg
                245                 250                 255
```

Leu Ile Asn His Ser Arg Arg Asn Pro Asn Met Thr Pro Arg Ala Ile
            260                 265                 270

Thr Leu Gly Asp Phe Asn Ser Glu Pro Arg Leu Ile Phe Val Ala Arg
        275                 280                 285

Arg Asn Ile Glu Lys Gly Glu Glu Leu Leu Val Asp Tyr Gly Glu Arg
    290                 295                 300

Asp Pro Asp Val Ile Lys Glu His Pro Trp Leu Asn Ser Glu Phe
305                 310                 315

<210> SEQ ID NO 119
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 119
ggcctgcttc gtggcaatgc                                                    20

<210> SEQ ID NO 120
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 120
acctgggcca gggagggagg                                                    20

<210> SEQ ID NO 121
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 121
ctcacttaga ctttctctcc                                                    20

<210> SEQ ID NO 122
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 122
ctcggagtct agctcctgca                                                    20

<210> SEQ ID NO 123
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 123
tggccccagt ctctcttcta                                                    20

<210> SEQ ID NO 124
<211> LENGTH: 20
<212> TYPE: DNA
<213> ORGANISM: Artificial Sequence
<220> FEATURE:

<223> OTHER INFORMATION: Synthetic Polynucleotide

<400> SEQUENCE: 124
cagcctctga acagctcccg                                           20

<210> SEQ ID NO 125
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 125
tgacttggcc tttgtaggaa                                           20

<210> SEQ ID NO 126
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 126
gaggctactg aaacataagt                                           20

<210> SEQ ID NO 127
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 127
tgctacctgt acatctgcac                                           20

<210> SEQ ID NO 128
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 128
catcaatgat tgggcatttc                                           20

<210> SEQ ID NO 129
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 129
actccagtcc caaatatgta                                           20

<210> SEQ ID NO 130
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 130 actaggggc gctcggccac                                            20

<210> SEQ ID NO 131
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 131
ctgagtcaac tgtaagcatt        20

<210> SEQ ID NO 132
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 132
ggccaggtgc agtgattcat        20

<210> SEQ ID NO 133
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 133
tcgtgtcatc ttgtttgtgc        20

<210> SEQ ID NO 134
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 134
ggcagagccc agcggacact        20

<210> SEQ ID NO 135
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 135
caaggtgagc ctgggtctgt        20

<210> SEQ ID NO 136
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 136
atcactgccc aagaagtgca        20

<210> SEQ ID NO 137
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 137
ttgtaggatg tttagcagca                                                         20

<210> SEQ ID NO 138
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 138
acttgctctc tttagagaac                                                         20

<210> SEQ ID NO 139
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 139
ctcaagcagg ccccgctggt                                                         20

<210> SEQ ID NO 140
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 140
ttttggacca aacctttttg                                                         20

<210> SEQ ID NO 141
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 141
tgaggttatt tgtccattgt                                                         20

<210> SEQ ID NO 142
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 142
taaggggagt atttacacca                                                         20

<210> SEQ ID NO 143
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 143
tcaagagcag aaaatgtgac                                                         20

<210> SEQ ID NO 144
<211> LENGTH: 20

```
<212> TYPE: DNA
<213> ORGANISM: Artificial Sequence
<220> FEATURE:
<223> OTHER INFORMATION: Synthetic Polynucleotide

<400> SEQUENCE: 144
cttgcaggga ccttctgatt                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 145
tgtgtgtagg actaaactct                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 146
gatagcagta tgaccttggg                                              20

<210> SEQ ID NO 147
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 147
agcgtgtccg gcgagggcga                                              20

<210> SEQ ID NO 148
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 148
agcgtgtccg gcgagggcga                                              20

<210> SEQ ID NO 149
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 149
cagaatcgga ggacaaaata caaac                                        25

<210> SEQ ID NO 150
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 150
```
acgaagcagg ccaacgggga ggaca                                           25

<210> SEQ ID NO 151
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 151
taatacgact cactataggg cacgggcagc ttgccgg                              37

<210> SEQ ID NO 152
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 152
taatacgact cactataggc ctcgaacttc acctcggcgg aaaggacgaa acacc          55

<210> SEQ ID NO 153
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 153
taatacgact cactataggc tgaagggcat cgacttcaga aaggacgaaa cacc           54

<210> SEQ ID NO 154
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 154
taatacgact cactataggc agctcgatgc ggttcaccag aaaggacgaa acacc          55

<210> SEQ ID NO 155
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 155
taatacgact cactataggc aaggaggacg gcaacatccg aaaggacgaa acacc          55

<210> SEQ ID NO 156
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 156
taatacgact cactatagga gtccgagcag aagaagaaga aaggacgaaa cacc           54

<210> SEQ ID NO 157
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 157
taatacgact cactataggg gtgggggag tttgctccga aaggacgaaa cacc      54

<210> SEQ ID NO 158
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 158
taatacgact cactataggc agatgtagtg tttccacaga aaggacgaaa cacc      54

<210> SEQ ID NO 159
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 159
aaaaaaagca ccgactcggt g      21

<210> SEQ ID NO 160
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 160
ctgtacaaaa aagcaggctt ta      22

<210> SEQ ID NO 161
<211> LENGTH: 83
<212> TYPE: DNA
<213> ORGANISM: Artificial Sequence
<220> FEATURE:
<223> OTHER INFORMATION: Synthetic Polynucleotide

<400> SEQUENCE: 161
aaaaaaagca ccgactcggt gccactttt caagttgata acggactagc cttatttaa      60 cttgctattt ctagctctaa aac      83

<210> SEQ ID NO 162
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 162
gaaaggacga acaccggcc tcgaacttca cctcggcggt tttagagcta gaaatagcaa      60

<210> SEQ ID NO 163
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 163
gaaaggacga aacaccggca gctcgatgcg gttcaccagt tttagagcta gaaatagcaa    60

<210> SEQ ID NO 164
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 164
gaaaggacga aacaccggct gaagggcatc gacttcagtt ttagagctag aaatagcaa    59

<210> SEQ ID NO 165
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 165
gaaaggacga aacaccggca aggaggacgg caacatccgt tttagagcta gaaatagcaa    60

<210> SEQ ID NO 166
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 166
gaaaggacga aacaccggca gatgtagtgt ttccacagtt ttagagctag aaatagcaa    59

<210> SEQ ID NO 167
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 167
gaaaggacga aacaccggag tccgagcaga agaagaagtt ttagagctag aaatagcaa    59

<210> SEQ ID NO 168
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 168
gaaaggacga aacaccgggg tgggggagt ttgctccgtt ttagagctag aaatagcaa    59

<210> SEQ ID NO 169
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 169
tacggcaagc tgaccctgaa    20

<210> SEQ ID NO 170
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 170
gtccatgccg agagtgatcc                                              20

<210> SEQ ID NO 171
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 171
gccaggggct gttatcttgg                                              20

<210> SEQ ID NO 172
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 172
atgcacagaa gcacaggttg a                                            21

<210> SEQ ID NO 173
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 173
ctgtgtcctc ttcctgccct                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 174
ctctccgagg agaaggccaa                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 175
ccacacagct tcccgttctc                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 176
gagagccgtt ccctctttgc                                              20

<210> SEQ ID NO 177
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 177
cactctttcc ctacacgacg ctcttccgat ctcctcccca ttggcctgct tc          52

<210> SEQ ID NO 178
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 178
cactctttcc ctacacgacg ctcttccgat cttcgtcctg ctctcactta gac         53

<210> SEQ ID NO 179
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 179
cactctttcc ctacacgacg ctcttccgat cttttgtgg cttggcccca gt           52

<210> SEQ ID NO 180
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 180
cactctttcc ctacacgacg ctcttccgat cttgcagtct catgacttgg cct         53

<210> SEQ ID NO 181
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 181
cactctttcc ctacacgacg ctcttccgat ctttctgagg gctgctacct gt          52

<210> SEQ ID NO 182
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 182
cactctttcc ctacacgacg ctcttccgat ctacatgaag caactccagt ccca        54

<210> SEQ ID NO 183
<211> LENGTH: 54
<212> TYPE: DNA
<213> ORGANISM: Artificial Sequence
<220> FEATURE:
<223> OTHER INFORMATION: Synthetic Polynucleotide

```
<400> SEQUENCE: 183
cactctttcc ctacacgacg ctcttccgat ctagcagacc cactgagtca actg         54

<210> SEQ ID NO 184
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 184
cactctttcc ctacacgacg ctcttccgat ctcccgccac agtcgtgtca t              51

<210> SEQ ID NO 185
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 185
cactctttcc ctacacgacg ctcttccgat ctcgccccgg tacaaggtga               50

<210> SEQ ID NO 186
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 186
cactctttcc ctacacgacg ctcttccgat ctgtaccgta cattgtagga tgttt         55

<210> SEQ ID NO 187
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 187
cactctttcc ctacacgacg ctcttccgat ctcctcatct ccctcaagca ggc           53

<210> SEQ ID NO 188
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 188
cactctttcc ctacacgacg ctcttccgat ctattctgct cttgaggtta tttgt         55

<210> SEQ ID NO 189
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 189
cactctttcc ctacacgacg ctcttccgat ctcacctctg cctcaagagc agaaaa        56

<210> SEQ ID NO 190
```

```
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 190
cactctttcc ctacacgacg ctcttccgat cttgtgtgtg tgtgtgtgta ggact         55

<210> SEQ ID NO 191
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 191
ggagttcaga cgtgtgctct tccgatcttc atctgtgccc ctccctcc               48

<210> SEQ ID NO 192
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 192
ggagttcaga cgtgtgctct tccgatctcg agaaggaggt gcaggag                47

<210> SEQ ID NO 193
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 193
ggagttcaga cgtgtgctct tccgatctcg ggagctgttc agaggctg               48

<210> SEQ ID NO 194
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 194
ggagttcaga cgtgtgctct tccgatctct cacctgggcg agaaaggt               48

<210> SEQ ID NO 195
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 195
ggagttcaga cgtgtgctct tccgatctaa aactcaaaga aatgcccaat ca          52

<210> SEQ ID NO 196
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 196
```

-continued

```
ggagttcaga cgtgtgctct tccgatctag acgctgctcg ctccattc          48
```

<210> SEQ ID NO 197
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 197

```
ggagttcaga cgtgtgctct tccgatctac aggcatgaat cactgcacct        50
```

<210> SEQ ID NO 198
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 198

```
ggagttcaga cgtgtgctct tccgatctgc ggcaacttca gacaaccga         49
```

<210> SEQ ID NO 199
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 199

```
ggagttcaga cgtgtgctct tccgatctga cccaggggca ccagtt            46
```

<210> SEQ ID NO 200
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 200

```
ggagttcaga cgtgtgctct tccgatctct gccttcattg cttaaaagtg gat    53
```

<210> SEQ ID NO 201
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 201

```
ggagttcaga cgtgtgctct tccgatctac agttgaagga aggaaacatg c      51
```

<210> SEQ ID NO 202
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 202

```
ggagttcaga cgtgtgctct tccgatctgc tgcatttgcc catttcca          48
```

<210> SEQ ID NO 203
<211> LENGTH: 49
<212> TYPE: DNA

<213> ORGANISM: Artificial Sequence
<220> FEATURE:
<223> OTHER INFORMATION: Synthetic Polynucleotide

<400> SEQUENCE: 203
ggagttcaga cgtgtgctct tccgatctgt tgggggagga ggagcttat           49

<210> SEQ ID NO 204
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 204
ggagttcaga cgtgtgctct tccgatctct aagagctata agggcaaatg act       53

<210> SEQ ID NO 205
<211> LENGTH: 56
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t

<400> SEQUENCE: 205
cactctttcc ctacacgacg ctcttccgat ctnnnnacgt aaacggccac aagttc    56

<210> SEQ ID NO 206
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 206
ggagttcaga cgtgtgctct tccgatctgt cgtccttgaa gaagatggtg           50

<210> SEQ ID NO 207
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 207
cactctttcc ctacacgacg ctcttccgat ctccaggtga aggtgtggtt ccag       54

<210> SEQ ID NO 208
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 208
ggagttcaga cgtgtgctct tccgatctcc cctagtcatt ggaggtgac            49

<210> SEQ ID NO 209
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 209
gagtccgagc agaagaagaa ggg                                          23

<210> SEQ ID NO 210
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 210
gaggccgagc agaagaaaga cgg                                          23

<210> SEQ ID NO 211
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 211
gagtcctagc aggagaagaa gag                                          23

<210> SEQ ID NO 212
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 212
gagtctaagc agaagaagaa gag                                          23

<210> SEQ ID NO 213
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 213
gagttagagc agaagaagaa agg                                          23

<210> SEQ ID NO 214
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 214
gggtgggggg agtttgctcc tgg                                          23

<210> SEQ ID NO 215
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 215
ggatggaggg agtttgctcc tgg                                          23

<210> SEQ ID NO 216

```
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 216
gggagggtgg agtttgctcc tgg                                              23

<210> SEQ ID NO 217
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 217
cgggggaggg agtttgctcc tgg                                              23

<210> SEQ ID NO 218
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 218
ggggagggga agtttgctcc tgg                                              23

<210> SEQ ID NO 219
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 219
gcagatgtag tgtttccaca ggg                                              23

<210> SEQ ID NO 220
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 220
acaaatgtag tatttccaca ggg                                              23

<210> SEQ ID NO 221
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 221
ccagatgtag tattcccaca ggg                                              23

<210> SEQ ID NO 222
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 222
```
ctagatgaag tgcttccaca tgg                                                23

<210> SEQ ID NO 223
<211> LENGTH: 133
<212> TYPE: DNA
<213> ORGANISM: Artificial Sequence
<220> FEATURE:
<223> OTHER INFORMATION: Synthetic Polynucleotide

<400> SEQUENCE: 223
gggcgatgcc acctacggca agctgaccct gaagttcatc tgcaccaccg gcaagctgcc      60
cgtgccctgg cccacccctcg tgaccaccct gacctacggc gtgcagtgct tcagccgcta    120
ccccgaccac atg                                                       133

<210> SEQ ID NO 224
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 224
gggcgatcgg cgtgcagtgc ttcagccgct accccgacca catg                       44

<210> SEQ ID NO 225
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 225
gggcgatgcc acctacggca agctgaccct gaagttcatc tgcaccaccg cgaccacatg      60

<210> SEQ ID NO 226
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 226
gggcgatgcc acctacggca agctgaccct gaagttcatc tgcacccggc aagctgcccg      60
tgccctggcc cacccctcgtg accaccctga cctacggcgt gcagtgcttc agccgctacc    120
ccgaccacat g                                                         131

<210> SEQ ID NO 227
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 227
gggcgatgcc acctacggca agctgcccgt gccctggccc acctcgtga ccaccctgac       60 ctacggcgtg cagtgcttca gccgctaccc cgaccacatg                           100

<210> SEQ ID NO 228
<211> LENGTH: 131
<212> TYPE: DNA
<213> ORGANISM: Artificial Sequence
<220> FEATURE:

<223> OTHER INFORMATION: Synthetic Polynucleotide

<400> SEQUENCE: 228
gggcgatgcc acctacggca agctgaccct gaagttcatc tgcaccacgc aagctgcccg      60
tgccctggcc caccctcgtg accaccctga cctacggcgt gcagtgcttc agccgctacc     120
ccgaccacat g                                                          131

<210> SEQ ID NO 229
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 229
gggcgatgcc acctacggca agctgaccct gaagttcatc tgcaccaccg gcaagctgcg      60
tgccctggcc caccctcgtg accaccctga cctacggcgt gcagtgcttc agccgctacc     120
ccgaccacat g                                                          131

<210> SEQ ID NO 230
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 230
gggcgatgcc acctacggca agctgaccct gaagttcatc tgcaccaccg gcaagctgcc      60
cgccctggcc caccctcgtg accaccctga cctacggcgt gcagtgcttc agccgctacc     120
ccgaccacat g                                                          131

<210> SEQ ID NO 231
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 231
gggcgatgcc acctacggca agctgaccct gaagttcatc tggcaagctg cccgtgccct      60
ggcccaccct cgtgaccacc ctgacctacg gcgtgcagtg cttcagccgc tacccgacc     120
acatg                                                                 125

<210> SEQ ID NO 232
<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 232
gggcgatgcc acctacggca agctgaccct gaagttcatc tgcaccaccg cgcagtgctt      60
cagccgctac cccgaccaca tg                                               82

<210> SEQ ID NO 233
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 233
gggcgatgcc acctacggca agctgaccct gaagttcatc tgcaccaccc aagctgcccg    60
tgccctggcc caccctcgtg accaccctga cctacggcgt gcagtgcttc agccgctacc   120
ccgaccacat g                                                        131

<210> SEQ ID NO 234
<211> LENGTH: 135
<212> TYPE: DNA
<213> ORGANISM: Artificial Sequence
<220> FEATURE:
<223> OTHER INFORMATION: Synthetic Polynucleotide

<400> SEQUENCE: 234
gggcgatgcc acctacggca agctgaccct gaagttcatc tgcaccaccg atgcaagctg    60
cccgtgccct ggcccaccct cgtgaccacc ctgacctacg gcgtgcagtg cttcagccgc   120
taccccgacc acatg                                                    135

<210> SEQ ID NO 235
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 235
gggcgatgcc acctacggca agctgaccct gaagttcatc tgcaccaccg gcaagctgac    60
cctgaagttc atctgcacca ccggcaagct gcccgtgccc tggcccaccc tcgtgaccac   120
cctgacctac ggcgtgcagt gcttcagccg ctaccccgac cacatg                  166

<210> SEQ ID NO 236
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 236
gggcgatgcc acctacggca agctgaccct gaagaaatga agaaatgaag aaatgcccgt    60
gccctggccc accctcgtga ccaccctgac ctacggcgtg cagtgcttca gccgctaccc   120
cgaccacatg                                                          130

<210> SEQ ID NO 237
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 237
ggcagaagct ggaagaggaa gggccggagt ctgagcagaa gaagaagggt tcccaccata    60
tcaaccggtg gcgcatcgcc                                                80

<210> SEQ ID NO 238
<211> LENGTH: 77
<212> TYPE: DNA
<213> ORGANISM: Artificial Sequence
<220> FEATURE:
<223> OTHER INFORMATION: Synthetic Polynucleotide

```
<400> SEQUENCE: 238
ggcagaagct ggaagaggaa gggccggagt ctgagcagaa gaagggttcc caccatatca        60
accggtggcg catcgcc                                                       77

<210> SEQ ID NO 239
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 239
ggcagaagct ggaagaggaa gggccggagt ctgagcagaa agaagggttc ccaccatatc        60
aaccggtggc gcatcgcc                                                      78

<210> SEQ ID NO 240
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 240
ggcagaagct ggaagaggaa gggccggagt ctgagagaag ggttcccacc atatcaaccg        60
gtggcgcatc gcc                                                           73

<210> SEQ ID NO 241
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 241
ggcagaagct ggaagaggaa gggccggagt ctgagcagag aagggttccc accatatcaa        60
ccggtggcgc atcgcc                                                        76

<210> SEQ ID NO 242
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 242
ggcagaagct ggaagaggaa gggccggagt ctgagaaggg ttcccaccat atcaaccggt        60
ggcgcatcgc c                                                             71

<210> SEQ ID NO 243
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 243
ggcagaagct ggaagaggaa gggccggagt ctgagcagaa gaaccaccat atcaaccggt        60
ggcgcatcgc c                                                             71

<210> SEQ ID NO 244
<211> LENGTH: 70
```

```
<212> TYPE: DNA
<213> ORGANISM: Artificial Sequence
<220> FEATURE:
<223> OTHER INFORMATION: Synthetic Polynucleotide

<400> SEQUENCE: 244
ggcagaagct ggaagaggaa gggccggagt ctagaagggt tcccaccata tcaaccggtg    60
gcgcatcgcc                                                           70

<210> SEQ ID NO 245
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 245
ggcagaagct ggaagaggaa gggccggagt ctgagcagaa gaagaagggt tcaccatatc    60
aaccggtggc gcatcgcc                                                  78

<210> SEQ ID NO 246
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 246
ggcagaagct ggaagaggaa gggccggagt ctgagcagaa gggttcccac catatcaacc    60
ggtggcgcat cgcc                                                      74

<210> SEQ ID NO 247
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 247
ggcagaagct ggaagaggaa gggccggagt ctgagcaggg ttcccaccat atcaaccggt    60
ggcgcatcgc c                                                         71

<210> SEQ ID NO 248
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 248
ggcagaagct ggaagaggaa gggccggagt ctgagcagaa gaccatatcc caccatatca    60
accggtggcg catcgcc                                                   77

<210> SEQ ID NO 249
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 249
ggcagaagct ggaagaggaa gggccggagt ctgagcagaa gaccatatcc aaccatatcc    60
```
caccatatca accggtggcg catcgcc 87

<210> SEQ ID NO 250
<211> LENGTH: 93
<212> TYPE: DNA
<213> ORGANISM: Artificial Sequence
<220> FEATURE:
<223> OTHER INFORMATION: Synthetic Polynucleotide

<400> SEQUENCE: 250
ggcagaagct ggaagaggaa gggccggagt ctgagcagaa gaagaagaag ggttcccacc 60
atatcccacc atatcaaccg gtggcgcatc gcc 93

<210> SEQ ID NO 251
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 251

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Thr Ala Leu Ala Leu
            20                  25                  30

Pro Lys Lys Lys Arg Lys Val
        35

<210> SEQ ID NO 252
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 252

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser
            20                  25

<210> SEQ ID NO 253
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 253

His His His His His His
1               5

<210> SEQ ID NO 254
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 254

Ala Leu Ala Leu
1

<210> SEQ ID NO 255

```
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 255

Gly Gly Ser Gly Gly Ser Gly Gly Ser Gly Gly Ser Ala Leu Ala Leu
1               5                   10                  15

Gly Gly Ser Gly Gly Ser Gly Gly Ser Gly Gly Ser
            20                  25

<210> SEQ ID NO 256
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 256

Xaa Ala Gly Val Phe Xaa
1               5

<210> SEQ ID NO 257
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 257

Xaa Gly Phe Leu Gly Xaa
1               5

<210> SEQ ID NO 258
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 258

Xaa Ala Leu Ala Leu Xaa
1               5

<210> SEQ ID NO 259
```

```
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 259

Xaa Ala Leu Ala Leu Ala Xaa
1               5
```

DELIVERY SYSTEM FOR FUNCTIONAL NUCLEASES

RELATED APPLICATIONS

This application is a national stage filing under 35 U.S.C. § 371 of international PCT application, PCT/US2014/054247, filed Sep. 5, 2014, which claims priority under 35 U.S.C. § 365(c) to U.S. application Ser. No. 14/462,189, filed Aug. 18, 2014, and to U.S. application Ser. No. 14/462,163, filed Aug. 18, 2014, and each of which also claims priority under 35 U.S.C. § 119(e) to U.S. provisional patent application Ser. No. 61/874,746, filed Sep. 6, 2013, each of which is incorporated herein by reference.

GOVERNMENT SUPPORT

This invention was made with government support under grant number GM095501 awarded by the National Institutes of Health. The government has certain rights in the invention.

BACKGROUND OF THE INVENTION

Macromolecular delivery into mammalian cells is an attractive approach for cell manipulation, as it would allow modulation of gene expression and modification of the genome, which, in turn, would open new avenues for research and enable the therapeutic targeting of molecules currently viewed as "undruggable" by small molecules. In particular, recombinant nucleases targeting genes or alleles associated with disease have great potential as therapeutic agents. The current methods of macromolecular delivery include viral delivery of nucleic acid molecules, receptor-mediated delivery of nucleic acids or proteins, and the use of protein fusions with cell-penetrating peptides such as TAT, Arg9, or Penetratin for the delivery of proteins. Each of these delivery systems offers benefits for particular applications; in most cases, however, questions regarding efficacy, cytotoxicity, and ease of preparation remain. Easily prepared reagents capable of effectively delivering macromolecules (e.g., functional effector proteins) to a variety of cell lines without significant cytotoxicity or other adverse side effect remain of considerable concern.

Most proteins do not spontaneously enter mammalian cells and are thus naturally limited in their use as research tools and their potential as therapeutic agents. Techniques for the delivery of proteins into mammalian cells have been developed recently to address intracellular targets. These techniques include the use of npia-Dasea reagents (Zelphati et al., *J. Biol. Chem.* 276, 35103-35110, 2001), nanoparticles (Hasadsri et al., *J. Biol. Chem.*, 2009), vault ribonucleoprotein particles (Lai et al., *ACS Nano* 3, 691-699, 2009); genetic or chemical fusion to receptor ligands (Gabel et al., *J. Cell Biol.* 103, 1817-1827, 1986; Rizk et al., *Proc. Natl. Acad. Sci. U.S.A.* 106, 11011-11015, 2009); and fusion to cell-penetrating peptides (Wadia et al., Curr. Protein Pept. Sci. 4, 97-104, 2003; Zhou et al., Cell Stem Cell 4, 381-384, 2009). Perhaps the most common method for protein delivery is genetic fusion to protein transduction domains (PTDs) including the HIV-1 transactivator of transcription (Tat) peptide and polyarginine peptides. These cationic PTDs promote association with negatively charged cell-surface structures and subsequent endocytosis of exogenous proteins. Both Tat and polyarginine have been used to deliver a variety of macromolecules into cells both in vitro and in vivo (Wadia et al., *Curr. Protein Pept. Sci.* 4, 97-104, 2003; Zhou et al., *Cell Stem Cell* 4, 381-384, 2009; Myou et al., *J. Immunol.* 169, 2670-2676, 2002; Bae et al., *Clin. Exp. Immunol.* 157, 128-138, 2009; Schwarze et al., *Science* 285, 1569-1572, 1999). Despite these advances, intracellular targets remain difficult to affect using exogenous proteins, and even modest success can require toxic concentrations of the respective transduction agent due to the low efficiency with which proteins are functionally delivered into cells (Zhou et al., *Cell Stem Cell* 4, 381-384, 2009; Wang et al., *Nat. Biotechnol.* 26, 901-908, 2008). Therefore, there remains a need for better delivery systems for getting functional effector proteins into cells to target intracellular biomolecules.

SUMMARY OF THE INVENTION

The present disclosure provides novel systems, compositions, preparations, kits, and related methods for delivering functional effector proteins, such as, for example, site-specific proteins that bind nucleic acids, into cells using a supercharged protein (e.g., a positively charged supercharged protein), a cationic polymer, or a cationic lipid. In some embodiments, the nucleases are TALE nucleases, RNA-programmable nucleases or engineered RNA-programmable genome-editing enzymes (such as Cas9 and variants or fusions thereof), or zinc finger nucleases. In some embodiments, the transcription factors are TALE transcriptional activators or repressors. In some embodiments, the effector proteins are recombinases. As described in greater detail herein, fusing or associating functional effector proteins (e.g., nucleases, transcriptional activators/repressors, Cas9 proteins including variants and fusions thereof, etc.) with positively charged supercharged proteins allows for delivery of the proteins to the interior of cells, for example to affect gene expression or genomic modifications. It was also found that fusing or associating functional effector proteins with negatively charged supercharged proteins allows for the proteins to associate with cationic lipids or cationic polymers, which provides potent delivery of the proteins to the interior of a cell. Further, functional effector proteins that are naturally negatively charged (e.g., VP64 transcriptional activators, the anionic 3×FLAG peptide tag, and fusions thereof) or functional effector proteins (e.g., Cas9 proteins, and variants and fusions thereof) that associate with nucleic acids (e.g., guide RNAs; "gRNAs") which are inherently negatively charged, can associate with cationic lipids or cationic polymers for delivery to cells (e.g., in the absence of a supercharged protein).

While delivery of effector proteins has proven effective for extracellular targets, their use to address intracellular targets is comparatively undeveloped due to the inability of most proteins to spontaneously enter mammalian cells. Enabling exogenous proteins to access intracellular targets is most commonly achieved by delivery of their encoding DNA sequences through chemical transfection, electroporation, or viral delivery. The introduction of exogenous DNA into cells, however, raises the possibility of permanent recombination into the genome, potential disruption of endogenous genes, and long-term exposure to the encoded agent. For some research or therapeutic applications, including genome editing applications that seek to effect a one-time, permanent modification of genomic DNA, the functional delivery of non-replicable protein agents may offer improved safety or broader applicability. Further, while the delivery of proteins using cationic compounds such as lipids and polymers has remained technically challenging and in many cases induces cellular toxicity, it was surprisingly found, using the compositions and methods provided herein, that certain functional effector proteins (e.g., Cas9 proteins and variants and fusions thereof, recombinases, transcriptional activators/repressors, etc.) can be delivered to cells with no or minimal toxicity, in some cases mediating genomic modifications with significant improvements in efficiency and reduced off-target effects. For example, as described in Example 7, delivery of Cas9:gRNA complexes with cationic lipids is highly efficient (up to 80% modification of cultured human cells from a single treatment) and also induces higher genome modification specificity compared with plasmid transfection, typically resulting in >10-fold higher on-target:off-target DNA modification ratios in human cells.

Accordingly, in one aspect, supercharged proteins are used to deliver functional effector proteins into cells, for example nucleases, transcriptional activators/repressors, Cas9 proteins (including fusions and variants thereof), etc. In some embodiments, the supercharged protein has been engineered to exhibit an increase in its overall surface charge as compared to the corresponding unmodified protein. In other embodiments, the supercharged protein has been engineered to exhibit a decrease in its overall surface charge as compared to the corresponding unmodified protein. In other embodiments, the supercharged protein used in the context of this disclosure is a naturally occurring supercharged protein. The supercharged protein may be associated with the protein to be delivered through covalent or non-covalent interactions. Without wishing to be bound by any particular theory, the Cas9 protein, variant, or fusion protein associated with a gRNA has net negative charged facilitating association with a positively charged supercharged protein. In certain embodiments, the functional effector protein associated with the supercharged protein is further associated with a cationic polymer or cationic lipid to form a composition suitable for delivery into a cell. Examples of suitable engineered or naturally occurring supercharged proteins are described in international PCT patent application PCT/US07/70254, filed Jun. 1, 2007, published as WO 2007/143574 on Dec. 13, 2007; in international PCT application PCT/US09/041984, filed on Apr. 28, 2009, published as WO 2009/134808 on Nov. 5, 2009; and in international PCT application PCT/US10/001250, filed on Apr. 28, 2010, published as WO 2010/129023 on Nov. 11, 2010; the entire contents of each of which are incorporated herein by reference. Further examples of supercharged proteins for use in delivering nucleases to cells are described herein. Additional examples of suitable functional effector proteins, for example, nucleases and RNA-programmable effector proteins such as Cas9 proteins, are described in U.S. Provisional Patent Application Ser. No. 61/868,846, filed Aug. 22, 2013, entitled "Engineered Transcription Activator-Like Effector (TALE) Domains and Uses Thereof," U.S. Provisional Patent Application Ser. No. 61/874,609, filed Sep. 6, 2013, entitled "Cas9 Variants and Uses Thereof," U.S. Provisional Patent Application Ser. No. 61/874,682, filed Sep. 6, 2013, entitled "Switchable Cas9 Nucleases and Uses Thereof," U.S. Non-provisional application Ser. No. 14/320,519, filed Jun. 20, 2014, entitled "Engineered Transcription Activator-Like Effector (TALE) Domains and Uses Thereof," U.S. Non-provisional application Ser. No. 14/320,498, filed Jun. 30, 2014, entitled "Cas9-FokI Fusion Proteins And Uses Thereof," U.S. Non-provisional Application, U.S. Ser. No. 14/320,467, filed Jun. 30, 2014, entitled "Cas9-Recombinase Fusion Proteins And Uses Thereof," U.S. Non-provisional application Ser. No. 14/326,329, filed Jul. 8, 2014, entitled "Switchable gRNAs Comprising Aptamers," U.S. Non-provisional Application, U.S. Ser. No. 14/326,340, filed Jul. 8, 2014, entitled "mRNA-Sensing Switchable gRNAs," U.S. Non-provisional application Ser. No. 14/326,361, filed Jul. 8, 2014, entitled "Extended DNA-Sensing gRNAs," U.S. Non-provisional application Ser. No. 14/325,815, filed Jul. 8, 2014, entitled "Fusions Of Cas9 Domains And Nucleic Acid-Editing Domains," U.S. Non-provisional application Ser. No. 14/326,109, filed Jul. 8, 2014, entitled "Methods For Nucleic Acid Editing," U.S. Non-provisional application Ser. No. 14/326,140, filed Jul. 8, 2014, entitled "Methods For Correcting PI3K Point Mutations," U.S. Non-provisional application Ser. No. 14/326,269, filed Jul. 9, 2014, entitled "Methods For Correcting Presenilin Point Mutations," U.S. Non-provisional application Ser. No. 14/326,290, filed Jul. 8, 2014, entitled "Methods For Correcting α-Antitrypsin Point Mutations," U.S. Non-provisional application Ser. No. 14/326,318, filed Jul. 8, 2014, entitled "Methods For Correcting Von Willebrand Factor Point Mutations," U.S. Non-provisional Application, U.S. Ser. No. 14/326,303, filed Jul. 8, 2014, entitled "Methods For Correcting Caspase-9 Point Mutations," and U.S. Provisional Application Ser. No. 62/030,943, entitled "Cas9 Proteins Including Ligand-Dependent Inteins," the entire contents of each of which are incorporated herein by reference.

In some embodiments, the supercharged protein, engineered or naturally occurring, is positively charged. In other embodiments, for example those involving delivery of certain effector proteins using cationic lipids and/or cationic polymers, the supercharged protein is negatively charged. In certain embodiments, superpositively or supernegatively charged proteins is non-covalently associated with an effector protein. Alternatively, superpositively or supernegatively charged proteins may be covalently bound to the effector protein. In some embodiments, the effector protein is fused to a supercharged protein. In certain embodiments, the resulting fusion protein comprises a linker, e.g., a cleavable linker, between the supercharged protein and the effector protein.

Some aspects of this disclosure provide compositions comprising a supercharged protein associated with a functional effector protein (e.g., nucleases, transcriptional activators/repressors, recombinases, Cas9 proteins including variants and fusions thereof, etc.). In some embodiments, the composition further comprises a cationic lipid. In some embodiments, the composition further comprises a cationic polymer. In some embodiments, the composition further comprises a buffer or excipient. In some embodiments, the supercharged protein has an overall positive charge that is greater than its corresponding unmodified protein and is in a quantity sufficient for and is formulated for delivery to and penetration into a cell. In other embodiments, for example those involving delivery of certain effector proteins using cationic lipids and/or cationic polymers, the supercharged protein has an overall negative charge that is greater than its corresponding unmodified protein. In some embodiments, the functional effector protein is a site-specific enzyme, e.g., a nuclease, Cas9 protein, recombinase, etc. In some embodiments, the Cas9 protein is a wild type Cas9 protein, a Cas9 nickase, or comprises a nuclease inactivated (dCas9) protein. In some embodiments, the Cas9 protein is a fusion protein comprising dCas9. In some embodiments, the fusion protein comprises a transcriptional activator (e.g., VP64), a transcriptional repressor (e.g., KRAB, SID) a nuclease domain (e.g., FokI), a recombinase domain (e.g., Hin, Gin, or Tn3), a deaminase (e.g., a cytidine deaminase or an adenosine deaminase) or an epigenetic modifier domain (e.g., TET1). In some embodiments involving nucleases, the nuclease is a TALE nuclease, a Cas9 nuclease, a Cas9 nickase, or a zinc finger nuclease. In some embodiments, the nuclease specifically binds and cleaves a nucleic acid sequence. In some embodiments, the targeted nucleic acid sequence is a sequence of a gene that is a therapeutic target, for example a gene that is desirable to inactivate in the treatment of a disease. In some embodiments, the targeted nucleic acid sequence is a PRDM16, PPARγ, VEGF-A, Oct-4, PI3K, presenilin, α-antitrypsin, von willebrand factor, or caspase-9 gene sequence.

In some embodiments, the functional effector protein is a transcription factor. In some embodiments, the functional effector protein is a TALE transcriptional activator or repressor. In some embodiments, the transcription factor, transcriptional activator, or transcriptional repressor specifically binds and activates or represses a gene. In some embodiments, the gene is a therapeutic target. In some embodiments, the functional effector protein is a TALE effector. In some embodiments, the supercharged protein is covalently bound to the functional effector protein, thus forming a fusion protein. In some embodiments, the supercharged protein is associated with the functional effector protein via a linker. In some embodiments, the linker is a cleavable linker. In some embodiments, the linker is a UV-cleavable linker or a linker that is cleaved by a lysosomal enzyme. In some embodiments, the supercharged protein is non-covalently associated with the functional effector protein, thus forming a complex. In some embodiments, the supercharged protein has an overall net positive charge. In other embodiments the supercharged protein has an overall net negative charge, and the protein(s) are associated with a cationic lipid. In other embodiments the supercharged protein has an overall net negative charge, and the protein(s) are associated with a cationic polymer. In some embodiments, the overall net positive charge is between about +5 and about +40, or the overall net negative charge is between about −5 and about −50. In some embodiments, the supercharged protein is more positively charged or is more negatively charged at physiological pH than its corresponding unmodified protein. In some embodiments, the corresponding unmodified protein is a naturally occurring protein. In some embodiments, the supercharged protein is at least +5 more positively or is at least −5 more negatively charged at physiological pH than its corresponding unmodified protein. In some embodiments, the supercharged protein is a fluorescent protein. In some embodiments, the supercharged protein is green fluorescent protein (GFP). In some embodiments, the supercharged protein is a superpositively charged GFP. In some embodiments, the supercharged protein is a superpositively charged GFP (+36 GFP) comprising at least 20 contiguous amino acid residues of the sequence:

(SEQ ID NO: 1)
GGASKGERLFRGKVPILVELKGDVNGHKFSVRGKGKGDATRGKLTLKFI

CTTGKLPVPWPTLVTTLTYGVQCFSRYPKHMKRHDFFKSAMPKGYVQER

TISFKKDGKYKTRAEVKFEGRTLVNRIKLKGRDFKEKGNILGHKLRYNF

NSHKVYITADKRKNGIKAKFKIRHNVKDGSVQLADHYQQNTPIGRGPVL

LPRNHYLSTRSKLSKDPKEKRDHMVLLEFVTAAGIKHGRDERYK.

In some embodiments, the supercharged protein comprises the amino acid sequence set forth in SEQ ID NO: 1. In some embodiments, the supercharged protein consists of the amino acid sequence set forth in SEQ ID NO: 1. In some embodiments, the composition is a pharmaceutical composition. In some embodiments, the composition comprises a pharmaceutically acceptable excipient. In some embodiments, the composition is formulated for administration to a subject and comprises the supercharged protein and the functional effector protein in an amount effective for delivery to at least one cell of the subject. In some embodiments, the composition comprises the supercharged protein and the functional effector protein in an amount effective for inducing a measurable therapeutic effect after administration to a subject.

Some aspects of the disclosure provide compositions comprising a Cas9 protein associated with a gRNA and a cationic lipid. It was surprisingly found that when a Cas9 protein is associated with a gRNA, the complex can be encapsulated by cationic lipids and effectively delivered to cells. This may be accomplished with or without a supercharged protein. In some embodiments, the composition comprises a Cas9 protein associated with a negatively supercharged protein (e.g., supernegatively charged GFP) and a cationic lipid, which also provides for successful delivery to a cell. In some embodiments, the composition exhibits low toxicity when delivered to a population of cells, for example, wherein at least 60%, at least 65%, at least 70%, at least 75%, at least 80%, at least 85%, at least 90%, at least 95%, or at least 99% of the cells are viable following administration of the composition. In some embodiments, the Cas9 protein is a wild type Cas9 protein, a Cas9 nickase, or comprises a nuclease inactivated (dCas9) protein. In some embodiments, the Cas9 protein is a fusion protein comprising dCas9. In some embodiments, the fusion protein comprises a transcriptional activator (e.g., VP64), a transcriptional repressor (e.g., KRAB, SID) a nuclease domain (e.g., FokI), a recombinase domain (e.g., Hin, Gin, or Tn3), a deaminase (e.g., a cytidine deaminase or an adenosine deaminase) or an epigenetic modifier domain (e.g., TET1).

Other aspects of the disclosure provide compositions comprising a Cas9 protein associated with a gRNA and a cationic polymer. As with cationic lipids, when a Cas9 protein is associated with a gRNA, the complex can associate with cationic polymers and be effectively delivered to cells. This may be accomplished with or without a supercharged protein. In some embodiments, the composition comprises a Cas9 protein associated with a negatively supercharged protein (e.g., supernegatively charged GFP) and a cationic polymer, which also provides for successful delivery to a cell. In some embodiments, the composition exhibits low toxicity when delivered to a population of cells, for example, wherein at least 60%, at least 65%, at least 70%, at least 75%, at least 80%, at least 85%, at least 90%, at least 95%, or at least 99% of the cells are viable following administration of the composition. In some embodiments, the Cas9 protein is a wild type Cas9 protein, a Cas9 nickase, or comprises a nuclease inactivated (dCas9) protein. In some embodiments, the Cas9 protein is a fusion protein comprising dCas9. In some embodiments, the fusion protein comprises a transcriptional activator (e.g., VP64), a transcriptional repressor (e.g., KRAB, SID) a nuclease domain (e.g., FokI), a recombinase domain (e.g., Hin, Gin, or Tn3), a deaminase (e.g., a cytidine deaminase or an adenosine deaminase) or an epigenetic modifier domain (e.g., LSD1, TET1).

Some aspects of this disclosure provide methods for administering a composition provided herein to a subject. In some embodiments, the method comprises administering a composition described herein to a subject. In some embodiments, the subject is susceptible to, is suffering from, or is displaying one or more symptoms of a disease, disorder, or condition. In some embodiments, the composition is administered to the subject in an amount sufficient and under suitable conditions for at least one sign or symptom to be ameliorated as a result of the administration. In some embodiments, the step of administering is performed under conditions sufficient for the functional effector protein to penetrate a cell of the subject. In some embodiments, the disease, disorder, or condition is associated with abnormally elevated levels of an mRNA, a protein, or combination thereof. In some embodiments, the composition comprises a nuclease that specifically binds and cleaves a genomic sequence, for example, a normal or a pathogenic allele; a gene associated with susceptibility to, or onset or progression of, a disease; a gene encoding a pathogenic RNA or protein; or a gene encoding an RNA or protein that is expressed at abnormally high levels in diseased cells or tissue. In some embodiments, the step of administering comprises a route of administration selected from the group consisting of oral, intravenous, intramuscular, intra-arterial, subcutaneous, intraventricular, topical, inhalational, and mucosal delivery.

Some aspects of this disclosure provide methods for introducing a functional effector protein into a cell. In some embodiments, the method comprises contacting the cell with a composition comprising a supercharged protein and a functional effector protein as described herein under conditions suitable for the functional effector protein to enter the cell, thereby introducing the functional effector protein into the cell. In some embodiments, the method comprises contacting the cell with a composition comprising a Cas9 protein and a cationic lipid and/or cationic polymer under conditions suitable for the Cas9 protein to enter the cell, thereby introducing the Cas9 protein into the cell. In some embodiments, the Cas9 protein enters the nucleus of the cell, for example the Cas9 protein is directed to the nucleus by including a nuclear localization signal (NLS) in the protein. In some embodiments, the method further comprises confirming that the functional effector protein (e.g., including Cas9) has penetrated the cell. In some embodiments, the cell is in a subject, and the contacting is done in vivo. In some embodiments, the subject is diagnosed with having or being at risk of developing a disease associated with an abnormal expression level of a gene, and wherein the functional effector protein (e.g., including Cas9) modulates the expression level of the gene. In some embodiments, the method further comprises detecting a change in the level of expression of the gene or detecting a therapeutic response in the subject. In some embodiments, the cell is a somatic cell. In some embodiments, the cell is contacted with the composition or the pharmaceutical composition in an amount, for a time, and under conditions sufficient to induce programming of the cell to a desired cell fate. In some embodiments, the method further comprises using the programmed cell in a cell replacement therapeutic approach. In some embodiments, the cell is a cell carrying a genomic allele associated with a disease and the functional effector protein specifically targets the allele. In some embodiments, the cell is contacted ex vivo and re-administered to the subject after successful targeting of the undesired allele by the functional effector protein.

Some aspects of this disclosure provide kits comprising a composition as described herein, for example, a composition comprising a supercharged protein associated with a functional effector protein. In some embodiments, the kits comprises a Cas9 protein and a supercharged protein. In some embodiments, the kits comprises a Cas9 protein and a cationic lipid. In some embodiments, the kits comprises a Cas9 protein and a cationic polymer. In some embodiments, the kit further comprises instructions for using the components included in the kit.

These and other aspects and embodiments of the invention, as well as various advantages and utilities will be more apparent with respect to the drawings and detailed description of the invention.

Definitions

As used herein and in the claims, the singular forms "a," "an," and "the" include the singular and the plural reference unless the context clearly indicates otherwise. Thus, for example, a reference to "an agent" includes a single agent and a plurality of agents.

The term "associated with" as used herein in the context of two or more moieties (e.g., proteins or protein domains) refers to the fact that the moieties are physically associated with or connected to one another, either directly or via one or more additional moieties that serve as a linking agent, to form a structure that is sufficiently stable so that the moieties remain physically associated under the conditions in which the structure is used, e.g., under physiological conditions. A supercharged protein may be associated with a functional effector protein (e.g., nucleases, transcriptional activators/repressors, recombinases, Cas9 proteins including variants and fusions thereof, etc.) through non-covalent interactions (e.g., electrostatic interactions). In certain embodiments, a supercharged protein may be associated with a functional effector protein through electrostatic interactions to form a complex. In some embodiments, a sufficient number of weaker interactions can provide sufficient stability for moieties to remain physically associated under a variety of different conditions. In certain embodiments, a supercharged protein is associated with a functional effector protein via a covalent bond (e.g., an amide bond). In some embodiments, a functional effector protein is associated with a supercharged protein directly by a peptide bond, or indirectly via a linker.

The term "Cas9" or "Cas9 nuclease" refers to an RNA-guided nuclease comprising a Cas9 protein, or a fragment thereof (e.g., a protein comprising an active or inactive DNA cleavage domain of Cas9 or a partially inactive DNA cleavage domain (e.g., a Cas9 "nickase"), and/or the gRNA binding domain of Cas9). In some embodiments, the term "Cas9" refers to a fusion protein comprising Cas9 or a fragment thereof.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisl* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

The term "cationic lipid" refers to a lipid which has a cationic, or positive, charge at physiologic pH. Cationic lipids can take a variety of forms including, but not limited to, liposomes or micelles. Cationic lipids useful for certain aspects of the present disclosure are known in the art, and, generally comprise both polar and non-polar domains, bind to polyanions, such as nucleic acid molecules or negatively supercharged proteins, and are typically known to facilitate the delivery of nucleic acids into cells. Examples of useful cationic lipids include polyethylenimine, polyamidoamine (PAMAM) starburst dendrimers, Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3,-dioleyloxy-N-[2(sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). Cationic lipids have been used in the art to deliver nucleic acid molecules to cells (see, e.g., U.S. Pat. Nos. 5,855,910; 5,851,548; 5,830,430; 5,780,053; 5,767,099; 8,569,256; 8,691,750; 8,748,667; 8,758,810; 8,759,104; 8,771,728; Lewis et al. 1996. Proc. Natl. Acad. Sci. USA 93:3176; Hope et al. 1998. Molecular Membrane Biology 15:1). In addition, other lipid compositions are also known in the art and include, e.g., those taught in U.S. Pat. Nos. 4,235,871; 4,501,728; 4,837,028; 4,737,323.

The term "cationic polymer," as used herein, refers to a polymer having a net positive charge. Cationic polymers are well known in the art, and include those described in Samal et al., Cationic polymers and their therapeutic potential. Chem Soc Rev. 2012 Nov. 7; 41(21):7147-94; in published U.S. patent applications U.S. 2014/0141487 A1, U.S. 2014/0141094 A1, U.S. 2014/0044793 A1, U.S. 2014/0018404 A1, U.S. 2014/0005269 A1, and U.S. 2013/0344117 A1; and in U.S. Pat. Nos. 8,709,466; 8,728,526; 8,759,103; and 8,790,664; the entire contents of each are incorporated herein by reference. Exemplary cationic polymers include, but are not limited to, polyallylamine (PAH); polyethyleneimine (PEI); poly(L-lysine) (PLL); poly(L-arginine) (PLA); polyvinylamine homo- or copolymer; a poly(vinylbenzyl-tri-$C_1$-$C_4$-alkylammonium salt); a polymer of an aliphatic or araliphatic dihalide and an aliphatic N,N,N',N'-tetra-$C_1$-$C_4$-alkyl-alkylenediamine; a poly(vinylpyridin) or poly(vinylpyridinium salt); a poly(N,N-diallyl-N,N-di-$C_1$-$C_4$-alkyl-ammoniumhalide); a homo- or copolymer of a quaternized di-$C_1$-$C_4$-alkyl-aminoethyl acrylate or methacrylate; POLYQUAD™; a polyaminoamide; and the like.

The term "deaminase" refers to an enzyme that catalyzes a deamination reaction. In some embodiments, the deaminase is a cytidine deaminase, catalyzing the hydrolytic deamination of cytidine or deoxycytidine to uracil or deoxyuracil, respectively.

The term "effective amount," as used herein, refers to an amount of a biologically active agent that is sufficient to elicit a desired biological response. For example, in some embodiments, an effective amount of a functional effector protein (e.g., nucleases, transcriptional activators/repressors, recombinases, Cas9 proteins including variants and fusions thereof, etc.) may refer to the amount of the protein that is sufficient to induce a detectable effect (e.g., cleavage of a target site, modification of a target site, modulation of gene expression, etc.). Such an effect may be detected in a suitable assay, e.g., in a cell-free assay, or in a target cell, tissue, or subject organism. As will be appreciated by the skilled artisan, the effective amount of an agent, e.g., a functional effector protein, may vary depending on various factors as, for example, on the desired biological response, the specific allele to be targeted, the genome, target site, cell, or tissue being targeted, and the supercharged protein being used.

The term "effector protein" refers to a protein that modulates a biological function of a cell when introduced into the cell, e.g., a modification of a nucleic acid molecule in the cell (such as a cleavage, deamination, recombination, etc.), or a modulation (e.g., increases or decreases) the expression or the expression level of a gene in the cell.

The term "engineered," as used herein refers to a protein molecule, complex, substance, or entity that has been designed, produced, prepared, synthesized, and/or manufactured by a human. Accordingly, an engineered product is a product that does not occur in nature. In some embodiments, an engineered protein or composition, e.g., an engineered supercharged protein associated with a functional effector protein, such as a nuclease, Cas9 protein (including variants and fusions thereof) is a supercharged protein that has been designed to meet particular requirements or to have particular desired features, e.g., to have a specified net charge, to specifically bind and/or cleave or modify a target sequence of interest, to have a specific minimal or maximal cleavage or enzymatic activity, and/or to have a specific stability.

The term "epigenetic modifier," as used herein, refers to a protein or catalytic domain thereof having enzymatic activity that results in the epigenetic modification of DNA, for example chromosomal DNA. Epigenetic modifications include, but are not limited to DNA methylation and demethylation; histone modifications including methylation and demethylation (e.g., mono-, di- and tri-methylation), histone acetylation and deacetylation, as well we histone ubiquitylation, phosphorylation, and sumoylation.

The term "functional protein" refers to a protein that is in a form in which it exhibits a property and/or activity by which it is characterized.

The term "fusion protein" refers to a protein comprising a plurality of heterologous proteins, protein domains, or peptides, e.g., a supercharged protein and a functional effector protein, associated with each other via a peptide linkage, thus forming a single amino acid sequence. In certain embodiments, a fusion protein is encoded by a gene.

The term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as RNAi agents, ribozymes, tRNAs, etc. For the purpose of clarity it should be noted that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

The term "isolated" refers to a molecule, complex, substance, or entity that has been (1) separated from at least some of the components with which it was associated when initially produced (whether in nature or in an experimental setting), and/or (2) produced, prepared, synthesized, and/or manufactured by a human. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The term "linker," as used herein, refers to a chemical group or a molecule linking two molecules or moieties, e.g., a supercharged protein and a nuclease. Typically, the linker is positioned between, or flanked by, two groups, molecules, or other moieties and connected to each one via a covalent bond, thus connecting the two. In some embodiments, the linker comprises an amino acid or a plurality of amino acids (e.g., a peptide or protein). In some embodiments, the linker is an organic molecule, group, polymer, or chemical moiety. In some embodiments, the linker is a cleavable linker, e.g., the linker comprises a bond that can be cleaved upon exposure to a cleaving activity, such as UV light or a hydrolytic enzyme, such as a lysosomal protease. In some embodiments, the linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids. In some embodiments, the peptide linker comprises repeats of the tri-peptide Gly-Gly-Ser, e.g., comprising the sequence $(GGS)_n$, wherein n represents at least 1, 2, 3, 4, 5, 6, 7, 8, 9, 10, or more repeats. In some embodiments, the linker comprises the sequence $(GGS)_6$ (SEQ ID NO:2). In some embodiments, the peptide linker is the 16 residue "XTEN" linker, or a variant thereof (See, e.g., Schellenberger et al. A recombinant polypeptide extends the in vivo half-life of peptides and proteins in a tunable manner. *Nat. Biotechnol.* 27, 1186-1190 (2009)). In some embodiments, the XTEN linker comprises the sequence SGSETPGTSESATPES (SEQ ID NO:3), SGSETPGTSESA (SEQ ID NO:4), or SGSETPGTSESATPEGGSGGS (SEQ ID NO:5). In some embodiments, the peptide linker is one or more selected from VPFLLEPDNINGKTC (SEQ ID NO:6), GSAGSAAGSGEF (SEQ ID NO:7), SIVAQLSRPDPA (SEQ ID NO:8), MKIIEQLPSA (SEQ ID NO:9), VRHKLKRVGS (SEQ ID NO:10), GHGTGSTGSGSS (SEQ ID NO:11), MSRPDPA (SEQ ID NO:12); or GGSM (SEQ ID NO:13).

The term "nuclease," as used herein, refers to an agent, for example, a protein or a small molecule, capable of cleaving a phosphodiester bond connecting nucleotide residues in a nucleic acid molecule. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bond within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease recognizes a single stranded target site, while in other embodiments, a nuclease recognizes a double-stranded target site, for example, a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target site asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 3' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and a "cleavage domain" that catalyzes the cleavage of the phosphodiester bond within the nucleic acid backbone. In some embodiments, a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be combined to create nucleases that bind specific target sites, are well known to those of skill in the art. For example, transcriptional activator like elements can be used as binding domains to specifically bind a desired target site, and fused or conjugated to a cleavage domain, for example, the cleavage domain of FokI, to create an engineered nuclease cleaving the desired target site.

The term "nucleic acid" and the term "nucleic acid molecule," as used interchangeably herein, refer to a compound comprising a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject, for example, in the context of treatment of a disease or disorder. In some embodiments, a pharmaceutical composition comprises an active ingredient, e.g., a supercharged protein associated with a functional effector protein, such as a nuclease, or a nucleic acid encoding a supercharged protein and a functional effector protein, e.g., in the form of a fusion protein, and a pharmaceutically acceptable excipient.

The term "physiological pH" as used herein refers to a pH value that is found in a normal, non-pathologic cell or subject. In some embodiments, physiological pH is between pH 5-8. In some embodiments, physiological pH is pH 7-7.5, for example, pH 7.0, pH 7.1, pH 7.2, pH 7.3, pH 7.4, or pH 7.5. In some embodiments, physiological pH is pH 6.5-7.5. In some embodiments, physiological pH is pH 5, pH 5.5, pH 6, pH 6.5, pH 7, pH 7.5, or pH 8.

The term "prevention" or "prevent" refer to the prophylactic treatment of a subject who is at risk of developing a disease, disorder, or condition (e.g., at an elevated risk as compared to a control subject, or a control group of subject, or at an elevated risk as compared to the average risk of an age-matched and/or gender-matched subject), resulting in a decrease in the probability that the subject will develop the disease, disorder, or condition (as compared to the probability without prevention), and/or to the inhibition of further advancement of an already established disorder.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasms are also referred to as cancers.

The term "protein" is interchangeably used herein with the terms "peptide" and "polypeptide" and refers to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a TALE effector protein may comprise a nucleic acid binding domain and an effector domain, e.g., a nucleic acid cleavage domain or a transcriptional activator or repressor domain. In some embodiments, a protein comprises a proteinaceous part, e.g., an amino acid sequence constituting a nucleic acid binding domain, and an organic compound, e.g., a compound that can act as a nucleic acid cleavage agent.

The term "RNA-programmable nuclease," and "RNA-guided nuclease" are used interchangeably herein and refer to a nuclease that forms a complex with (e.g., binds or associates with) one or more RNA molecule that is not a target for cleavage. In some embodiments, an RNA-programmable nuclease, when in a complex with an RNA, may be referred to as a nuclease:RNA complex. RNA-programmable nucleases include Cas9. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. The gRNA comprises a nucleotide sequence that complements a target site, which mediates binding of the nuclease/RNA complex to said target site and providing the sequence specificity of the nuclease:RNA complex.

The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." *Methods.* 2011; 53(4):372-9; Hirano et al., "Site-specific recombinases as tools for heterologous gene integration." *Appl. Microbiol. Biotechnol.* 2011; 92(2):227-39; Chavez and Calos, "Therapeutic applications of the ΦC31 integrase system." *Curr.*

Gene Ther. 2011; 11(5):375-81; Turan and Bode, "Site-specific recombinases: from tag-and-target- to tag-and-exchange-based genomic modifications." *FASEB J.* 2011; 25(12):4088-107; Venken and Bellen, "Genome-wide manipulations of *Drosophila melanogaster* with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Cre-ating a new biological era." *J. Zhejiang Univ. Sci. B.* 2012; 13(7):511-24; Karpenshif and Bernstein, "From yeast to mammals: recent advances in genetic control of homologous recombination." *DNA Repair (Amst).* 2012; 1; 11(10):781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety). Other examples of recombinases that are useful in the methods and compositions described herein are known to those of skill in the art, and any new recombinase that is discovered or generated is expected to be able to be used in the different embodiments of the invention. In some embodiments, a recombinase (or catalytic domain thereof) is fused to a Cas9 protein (e.g., dCas9).

The term "recombine," or "recombination," in the context of a nucleic acid modification (e.g., a genomic modification), is used to refer to the process by which two or more nucleic acid molecules, or two or more regions of a single nucleic acid molecule, are modified by the action of a recombinase protein. Recombination can result in, inter alia, the insertion, inversion, excision, or translocation of a nucleic acid sequence, e.g., in or between one or more nucleic acid molecules.

The term "subject," as used herein, refers to an individual organism. In some embodiments, the subject is a human of either sex at any stage of development. In some embodiments, the subject is a non-human mammal. In some embodiments, the subject is a non-human primate. In some embodiments, the subject is a rodent. In some embodiments, the subject is a laboratory animal, for example, a mouse, a rat, a gerbil, a guinea pig, a fish, a frog, or a fly. In some embodiments, the subject is a farm animal, for example, a sheep, a goat, a pig, or a cattle. In some embodiments, the subject is a companion animal, for example, a cat or a dog. In some embodiments, the subject is a vertebrate, an amphibian, a reptile, a fish, an insect, a fly, or a nematode. In some embodiments, the subject is genetically engineered, e.g., a genetically engineered non-human subject.

The term "supercharge" refers to any modification of a protein that results in the increase or decrease of the overall net charge of the protein. Modifications include, but are not limited to, alterations in amino acid sequence or addition of charged moieties (e.g., carboxylic acid groups, phosphate groups, sulfate groups, amino groups). Supercharging also refers to the association of an agent with a charged protein, naturally occurring or modified, to form a complex with increased or decreased charge relative to the agent alone.

The term "target site," as used herein in the context of functional effector proteins that bind a nucleic acid molecule, such as nucleases and transcriptional activators or repressors, refers to a sequence within a nucleic acid molecule that is bound and acted upon by the effector protein, e.g., cleaved by the nuclease or transcriptionally activated or repressed by the transcriptional activator or repressor, respectively. A target site may be single-stranded or double-stranded. In the context of RNA-guided (e.g., RNA-programmable) nucleases (e.g., Cas9), a target site typically comprises a nucleotide sequence that is complementary to the gRNA of the RNA-programmable nuclease, and a protospacer adjacent motif (PAM) at the 3' end adjacent to the gRNA-complementary sequence. For the RNA-guided nuclease Cas9 (or variants or fusions comprising having gRNA binding activity), the target site may be, in some embodiments, 20 base pairs plus a 3 base pair PAM (e.g., NNN, wherein N represents any nucleotide). Typically, the first nucleotide of a PAM can be any nucleotide, while the two downstream nucleotides are specified depending on the specific RNA-guided nuclease. Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to, NNAGAAW and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure [NZ]-[PAM], where each N is, independently, any nucleotide, and Z is an integer between 1 and 50, inclusive. In some embodiments, Z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, Z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20. In some embodiments, "target site" may also refer to a sequence within a nucleic acid molecule that is bound but not cleaved by a nuclease. For example, certain embodiments described herein provide proteins comprising an inactive (or inactivated) Cas9 DNA cleavage domain. Such proteins (e.g., when also including a Cas9 RNA binding domain) are able to bind the target site specified by the gRNA, however because the DNA cleavage site is inactivated, the target site is not cleaved by the particular protein. However, such proteins as described herein are typically conjugated, fused, or bound by another protein (e.g., a nuclease, transcriptional activator, recombinase, deaminase, etc.) or molecule that mediates modification of the nucleic acid molecule. In some embodiments, the sequence actually cleaved will depend on the protein (e.g., nuclease) or molecule that mediates cleavage of the nucleic acid molecule, and in some cases, for example, will relate to the proximity or distance from which the inactivated Cas9 protein(s) is/are bound. In the context of nucleases that dimerize, for example, dimers of a protein comprising an inactive Cas9 (or a Cas9 RNA binding domain) and a DNA cleavage domain (e.g., FokI cleavage domain or an active Cas9 cleavage domain), a target sites typically comprises a left-half site (bound by one protein), a right-half site (bound by the second protein), and a spacer sequence between the half sites in which the cut is made. In some embodiments, either the left-half site or the right half-site (and not the spacer sequence) is cut. This structure ([left-half site]-[spacer sequence]-[right-half site]) is referred to herein as an LSR structure. In some embodiments, the left-half site and/or the right-half site correspond to an RNA-guided target site (e.g., a Cas9 target site). In some embodiments, either or both half-sites are shorter or longer than, e.g., a typical region targeted by Cas9, for example shorter or longer than 20 nucleotides. In some embodiments, the left and right half sites comprise different nucleic acid sequences. In some embodiments, the target site is a sequence comprising three (3) RNA-guided nuclease target site sequences, for example, three sequences corresponding to Cas9 target site sequences, in which the first and second, and second and third Cas9 target site sequences are separated by a spacer sequence. In some embodiments, the spacer sequence is at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 125, at least 150, at least 175, at least 200, or at least 250 bp long.

The terms "transcriptional activator" and "transcriptional repressor" refer to an agent such as a protein (e.g., a transcription factor or fragment thereof), that binds a target nucleic acid sequence and causes an increase or decrease of the level of expression of a gene product associated with the target nucleic acid sequence, respectively. For example, if the target nucleic acid sequence is located within a regulatory region of a gene, a transcriptional activator causes an increase of the level of expression of a gene product encoded by the gene (conversely, a transcriptional repressor causes a decrease of the level of expression of a gene product encoded by the gene). The gene product can be an RNA transcribed from the gene (e.g., an mRNA) or a polypeptide translated from an mRNA transcribed from the gene. Typically an increase or decrease in the level of an mRNA results in an or decrease increase in the level of a polypeptide translated therefrom. The level of expression may be determined using standard techniques for measuring mRNA or protein.

The term "Transcriptional Activator-Like Effector," (TALE) as used herein, refers to effector proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence, and can be engineered according to methods well known to those of skill in the art to specifically bind a desired DNA sequence (see, e.g., Miller, Jeffrey; et. al. (February 2011). "A TALE nuclease architecture for efficient genome editing". *Nature Biotechnology* 29 (2): 143-8; Zhang, Feng; et.al. (February 2011). "Efficient construction of sequence-specific TAL effectors for modulating mammalian transcription". *Nature Biotechnology* 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Boch, Jens (February 2011). "TALEs of genome targeting". *Nature Biotechnology* 29 (2): 135-6; Boch, Jens; et.al. (December 2009). "Breaking the Code of DNA Binding Specificity of TAL-Type III Effectors". *Science* 326 (5959): 1509-12; and Moscou, Matthew J.; Adam J. Bogdanove (December 2009). "A Simple Cipher Governs DNA Recognition by TAL Effectors". *Science* 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs. TALE effector proteins include, without limitation, TALE nucleases (TALENs) and TALE transcriptional activators and repressors.

The term "Transcriptional Activator-Like Element Nuclease," (TALEN) as used herein, refers to an artificial nuclease comprising a transcriptional activator like effector DNA binding domain to a DNA cleavage domain, for example, a FokI domain. A number of modular assembly schemes for generating engineered TALE constructs have been reported (Zhang, Feng; et.al. (February 2011). "Efficient construction of sequence-specific TAL effectors for modulating mammalian transcription". *Nature Biotechnology* 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*.; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; each of which is incorporated herein by reference).

The term "transcriptional repressor" refers to a transcription factor, e.g., a protein, that binds a target nucleic acid sequence and causes a reduction of the level of expression of a gene product associated with the target nucleic acid sequence. For example, if the target nucleic acid sequence is located within a regulatory region of a gene, a transcriptional repressor causes a reduction of the level of expression of a gene product encoded by the gene. The gene product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

The term "zinc finger nuclease," as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway. Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo C O (May 1991). "Zinc finger-DNA recognition: crystal structure of a Zif268-DNA complex at 2.1 A". *Science* 252 (5007): 809-17, the entire contents of which are incorporated herein). In some embodiments, separate zinc fingers that each recognizes a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length. Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this non-limiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". Cold Spring Harb. Symp. Quant. Biol. 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different types of zinc finger motifs are known to those of skill in the art, including, but not limited to, $Cys_2His_2$, Gag knuckle, Treble clef, Zinc ribbon, $Zn_2/Cys_6$, and TAZ2 domain-like motifs (see, e.g., Krishna S S, Majumdar I, Grishin N V (January 2003). "Structural classification of zinc fingers: survey and summary". *Nucleic Acids Res.* 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant R A (2001). "Design and selection of novel cys2His2 Zinc finger proteins". *Annual Review of Biochemistry* 70: 313-340; Jamieson A C, Miller J C, Pabo C O (2003). "Drug discovery with engineered zinc-finger proteins". *Nature Reviews Drug Discovery* 2 (5): 361-368; and Liu Q, Segal D J, Ghiara J B, Barbas C F (May 1997). "Design of polydactyl zinc-finger proteins for unique addressing within complex genomes". *Proc. Natl. Acad. Sci. U.S.A.* 94 (11); the entire contents of each of which are incorporated herein by reference). Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

BRIEF DESCRIPTION OF THE DRAWINGS

FIG. 27(A) shows that recombinases, transcriptional-activator-like effector (TALE) proteins, and Cas9 endonucleases bind nucleic acids and are natively cationic (net theoretical charges are shown in black) and are not efficiently encapsulated by cationic lipids. These proteins can be rendered highly anionic, however, by fusion to either a supernegatively charged protein such as (−30)GFP, or by complexation with polyanionic nucleic acids. FIG. 27(B) shows a schematic representing that cationic lipids commonly used to transfect DNA and RNA encapsulate the resulting highly anionic proteins or protein:nucleic acid complexes, mediating their delivery into mammalian cells.

In FIG. 28(A), the fusion of either highly cationic (+36)GFP or highly anionic (−30)GFP to Cre recombinase is shown. A HeLa reporter cell line that expresses DsRed upon Cre-mediated recombination was used to evaluate Cre delivery efficiency; (GGS)9 corresponds to SEQ ID NO: 252 and His6 corresponds to SEQ ID NO: 253. In FIG. 28(B) HeLa dsRed cells treated with 10 nM (−30)GFP-Cre and the cationic lipid RNAiMAX. Cells were visualized after incubation for 48 hours in media containing 10% fetal bovine serum (FBS). FIG. 28(C) shows the delivery of (+36)GFP-Cre in 10% FBS media or in serum-free media, and (−30)GFP-Cre with or without the cationic lipid RNAiMAX in full-serum media. FIG. 28(D) presents the effect of cationic lipid dose on functional (−30)GFP-Cre delivery efficacy after 48 hours in 275 μL media containing 10% FBS. FIG. 28(E) is a comparison of several commercially available cationic lipids and polymers for functional delivery efficacy of (−30)dGFP-Cre. FIG. 28(F) shows the RNAiMAX-mediated delivery of multiple anionic peptide or protein sequences fused to Cre. Error bars reflect the standard deviation from three biological replicates performed on different days.

FIG. 29(A) shows the design of an 18.5-repeat TALE activator fused C-terminally to a VP64 activation domain and N-terminally to (−30)GFP and an NLS; (GGS)9 corresponds to SEQ ID NO: 251 and His6 corresponds to SEQ ID NO: 252. The overall net theoretical charge of the fusion is −43. FIG. 29(B) demonstrates the activation of NTF3 transcription by traditional transfection of plasmids encoding TALE-VP64 activators that target sites in the NTF3 gene, or by RNAiMAX cationic lipid-mediated delivery of the corresponding NTF3-targeting (−30)GFP-TALE-VP64 proteins. Gene expression levels were measured by qRT-PCR and are normalized to GAPDH expression levels. Error bars reflect the standard deviation from three biological replicates performed on different days.

FIG. 30(A) demonstrates the cationic lipid-mediated delivery of Cas9 protein variants complexed with an EGFP-targeting sgRNA or a VEGF-targeting sgRNA to U2OS EGFP reporter cells. Results are compared to that of standard transfection of Cas9 and sgRNA expression plasmids. FIG. 30(B) shows the results of a T7 endonuclease I (T7EI) assay to measure the modification of EGFP from no treatment (lane 1), treatment with EGFP-targeting sgRNA alone (lane 2), Cas9 protein alone (lane 3), Cas9 protein+VEGF-targeting sgRNA+RNAiMAX (lane 4), transfection of plasmids expressing Cas9 and EGFP-targeting sgRNA (lane 5), or Cas9 protein+EGFP-targeting sgRNA+RNAiMAX (lane 6). Indel efficiencies calculated by densitometry are shown below the gel image. FIG. 30(C) presents the results of a T7EI assay of genome modification at EGFP and three endogenous genes with a single delivery of Cas9 complexed with four sgRNAs and RNAiMAX. Indel efficiencies calculated by densitometry are shown below the gel image. FIG. 30(D) shows the delivery of Cas9 D10A nickase and pairs of sgRNAs either by plasmid transfection or by RNAiMAX-mediated protein:RNA complex delivery. EGFP-disrupting sgRNAs GFP g1+GFP g5, or GFP g3+GFP g7, are expected to result in gene disruption, while GFP g5+GFP g7 target the same strand and are therefore expected to be non-functional. FIG. 30(E) shows the delivery of catalytically dead (dCas9)-VP64 transcriptional activators that target NTF3 either by plasmid transfection or RNAiMAX-mediated protein delivery. Delivery of both VEGF g3 and VEGF g5 sgRNAs served as a negative control for NTF3 gene activation. Error bars reflect the standard deviation from six biological replicates performed on different days.

FIG. 31A-B. The DNA sequence specificity of Cas9-mediated endogenous gene cleavage in cultured human cells by plasmid transfection or by cationic lipid-mediated protein:sgRNA delivery is shown. In FIG. 31(A), a T7EI assay was performed for on-target modification of endogenous CLTA, EMX, and VEGF genes.

In FIG. 32(A), the scala media (cochlear duct) of P0 floxP-tdTomato mice (n=4) were injected with 0.3 μL of 23 μM (−30)GFP-Cre in 50% RNAiMAX or with RNAiMAX alone (control). After 5 days, tdTomato expression indicative of Cre-mediated recombination was visualized using immunohistology. Red=tdTomato; green=Myo7a; white=Sox2; blue=DAPI. Yellow brackets indicate the outer hair cell (OHC) layer. FIG. 32(B) shows that, ten days after (−30)GFP-Cre delivery, intact espin (Esp)-expressing stereocilia of tdTomato-positive outer hair cells were present (arrow), similar to stereocilia in control cochlea. Red=tdTomato; green=Esp; white=Sox2; blue=DAPI. FIG. 32(C) is identical to FIG. 32(A) except using Lipofectamine 2000 instead of RNAiMAX. (n=4). The upper and lower panels are images of mice cochlea at low and high magnification, respectively, detailing the efficiency of delivery as well as the effect on cochlear architecture and hair cell loss. FIG. 32(D) shows the results when the scala media (cochlear duct) of P2 Atoh1-GFP mice (n=3) were injected with 0.3 μL of 33 μM Cas9, 33 μM sgRNA in 50% RNAiMAX or Lipofectamine 2000. Cas9-mediated gene disruption results in the loss of GFP expression when visualized 10 days later. The upper panels show GFP signal only, while lower panels include additional immunohistological markers. Yellow boxes in the lower panels highlight hair cells that have lost GFP expression. Red=tdTomato; green=Myo7a; white/light blue=Sox2; blue=DAPI. All scale bars, shown in white, are 10 μm.

FIG. 33(A) shows the optimization of (−30)GFP-Cre delivery in BSR-TdTomato cells, a second reporter cell line used for measuring Cre recombination efficiency. FIG. 33B demonstrates the effect of RNAiMAX dosage on (−30)GFP-Cre recombination efficiency in HeLa dsRed reporter cells and toxicity as measured by FACS. HeLa cells were sorted by forward-scatter and side-scatter gating to identify live cells that retained normal morphology. FIG. 33(C) illustrates the relationship between net charge of the protein fused to Cre recombinase and cationic lipid-mediated functional Cre delivery efficiency. Cre recombinase fused to the domains listed at 25 nM were combined with 1.5 μL RNAiMAX and incubated with HeLa dsRed reporter cells. After 2 days, recombination efficiency was measured by FACS. Error bars reflect the standard deviation from three biological replicates performed on different days.

FIG. 34(A) quantifies GFP fluorescence from cells treated with either (−30)GFP-Cre and RNAiMAX or (+36) GFP-Cre after washing cells with PBS+heparin (20 U/mL) to remove unbound protein. FIG. 34(B) shows the functional Cre recombinase delivery efficiency of (−30)GFP-Cre+1.5 μL RNAiMAX relative to Cre recombinase delivery efficiency arising from fusion with (+36)GFP. FIG. 34(C) provides a comparison of mCherry uptake by (−30)GFP-fusion+1.5 μM RNAiMAX treatment versus (+36)GFP fusion by measuring mean mCherry fluorescence of total cell population 48 hours after treatment and washing cells with PBS+heparin. FIG. 34(D) shows the total cellular GFP fluorescence of (−30)GFP-Cre or (+36)GFP-Cre in the presence or absence of RNAiMAX.

FIG. 36(A) provides a schematic of EGFP disruption in U2OS cells by NHEJ induced by Cas9 double-stranded breaks. FIG. 36(B) shows the delivery of EGFP-targeting sgRNA or an off-target sgRNA complexed with (−30)dGFP-Cas9 using RNAiMAX along with a plasmid transfection positive control (orange). FIG. 36(C) provides confirmation that disruption of EGFP fluorescence is not a result of cellular toxicity by treating samples with the TO-PRO-3 live/dead stain (Life Technologies, Carlsbad Calif.) and analyzing the resulting cells by flow cytometry. FIG. 36(D) shows testing of the TO-PRO-3 stain by addition of a cell permeabilizing, but not completely membrane lysing, detergent (0.5% Tween).

In FIG. 37(A), cationic lipid-mediated delivery efficiency of two tested constructs shows that the more anionic (−30)dGFP-NLS-Cas9 facilitates more efficient delivery at low protein and sgRNA concentrations compared with native Cas9. FIG. 37(B) shows the delivery optimization of (−30)dGFP-NLS-Cas9 as a function of protein and sgRNA concentration. FIG. 37(C) shows the delivery of Cas9 protein without any fusions or tags as a function of protein and sgRNA concentration. FIG. 37(D) provides the optimal sgRNA to protein ratio for RNAiMAX-mediated delivery of (−30)dGFP-NLS-Cas9 and native Cas9. Error bars reflect standard deviation from three biological replicates performed on different days.

In FIG. 39(A), EGFP gene disruption at different Cas9 protein concentrations and a constant dose of 100 nM EGFP sgRNA in U2OS EGFP reporter cells treated for 16 hours with either RNAiMAX or Lipofectamine 2000 is shown. After 16 hours, media was removed and fresh media was added to cells until end point of assay 48-72 hours post protein delivery treatment. The live cell population was determined by FACS using TO-PRO-3 Live/Dead stain. FIG. 39(B) shows the toxicity profile for Cas9:sgRNA delivery to U2OS cells as a function of Lipofectamine 2000 dose. FIG. 39(C) provides the toxicity profile for cells as a function of RNAiMAX dose. Error bars reflect standard deviation from three biological replicates performed on different days.

FIG. 41(A) shows the on-target and off-target indel frequencies for the CLTA gene. FIG. 41(B) provides the on-target and off-target indel frequencies for the EMX gene. FIG. 41(C) demonstrates the on-target and off-target indel frequencies for the VEGF gene. Each on- and off-target sample was sequenced once with >10,000 sequences analyzed per on-target sample and an average of >111,000 sequences analyzed per off-target sample (Table 2).

FIG. 42(A) shows floating spheres treated with Cas9 protein and RNAiMAX but no sgRNA (control) retained strong GFP fluorescence (right), while those treated with Cas9:sgRNA and RNAiMAX exhibited decreased GFP fluorescence (left). Scale bars are 100 µm. FIG. 42(B) shows the control progenitor cells after cell attachment, and virtually all the control progenitor cells were GFP positive (right panels). Cas9:sgRNA treatment led to significant reduction in GFP expression (left panels) and many progenitor cells showed complete GFP knockdown (arrows) after cell attachment. Scale bars are 20 µm. FIG. 42(C) shows a T7EI assay on stem cells harvested after imaging confirm cleavage of GFP reporter. Similar gene target modification efficiencies were observed from cationic lipid-mediated Cas9:sgRNA delivery and transfection of Cas9 and EGFP sgRNA plasmids.

FIGS. 43A-B. Genome modification induced by cationic lipid-mediated protein delivery of Cas9 nuclease and sgRNA at endogenous loci in vivo. FIG. 43(A) shows representative examples of genomic DNA sequences at the EGFP on-target locus that are modified following cationic lipid-mediated delivery of Cas9 and EGFP sgRNA in mouse hair cells. For each example shown, the unmodified genomic site is the first sequence, followed by the most abundant eight sequences containing deletions and three sequences containing insertions. The numbers before each sequence indicate sequencing counts. The sgRNA target sites are bold and underlined in green. Insertions and deletions are shown in red. PAM site is shown in blue. FIG. 43(B) shows an identical analysis as in FIG. 42(A) for EMX on-target site in mouse hair cells. The sequences shown in FIG. 43(A), from top to bottom, correspond to SEQ ID NOs:223-236; and the sequences shown in FIG. 43(B), from top to bottom, correspond to SEQ ID NOs:237-250.

DETAILED DESCRIPTION OF CERTAIN EMBODIMENTS OF THE INVENTION

Figure 1:
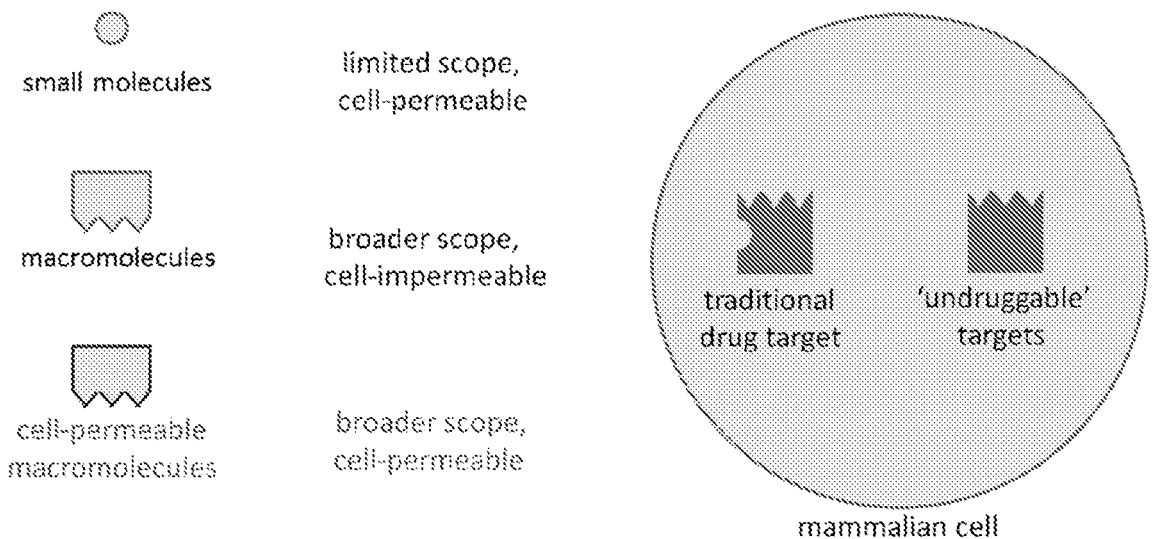
FIG. 1. Schematic of macromolecular delivery into mammalian cells.

The present invention provides complexes, compositions, preparations, kits, systems, and related methods for the delivery of functional effector proteins, e.g., nucleases, recombinases, and Cas9 proteins (including variants and fusions thereof, e.g., Cas9 nickases and Cas9 fusions to deaminases, gene editing enzymes, transcriptional repressors and activators, epigenetic modifiers, etc.), to a cell by associating the functional effector protein with one or more of a supercharged protein, cationic polymer, and/or cationic lipid. Typically, the functional effector protein is delivered to the interior of a cell, e.g., to cause a biological effect in the cell, such as cleavage of a genomic target sequence or modulation of the expression of a target gene. In some embodiments, the biological effect exerts a therapeutic benefit to a subject in which the cell is found. The complexes, compositions, preparations, systems, kits, and related methods for delivery of functional effector proteins are useful for introducing an effector protein into a cell, e.g., in the context of manipulating the cell for a research or therapeutic purpose. The compositions, preparations, systems, kits, and related methods for delivery of functional effector proteins provided herein exhibit improved efficacy and reduced cytotoxicity, and ease of preparation as compared to current technologies. The delivery of site-specific proteins, such as TALENs or Cas9 proteins (or variants or fusions thereof) using the compositions, preparations, systems, kits, and related methods provided herein allows for the targeted manipulation/modification of the genome of a host cell in vitro or in vivo while avoiding the use of more invasive delivery methods, such as viral delivery of vectors encoding site-specific proteins.

In some embodiments, the inventive technology uses a supercharged protein to deliver a functional effector protein into a cell. In certain embodiments, the supercharged protein is an engineered protein. In some embodiments, the supercharged protein is a naturally occurring supercharged protein. Some aspects of this invention are based on the recognition that supercharged proteins are endocytosed by cells; that functional effector proteins that can be associated with supercharged proteins are effectively taken up by cells together with the supercharged proteins; and that such functional effector proteins retain their biological function after cellular uptake, e.g., in that they are able to cleave or modify genomic target sites or modulate transcription of a target gene.

In some embodiments, the compositions provided herein comprising a supercharged protein associated with a functional effector protein (e.g., nucleases, transcriptional activators/repressors, recombinases, Cas9 proteins including variants and fusions thereof, etc.) are useful as therapeutic agents, diagnostic agents, or research tools. In some embodiments, a functional effector protein, such as a nuclease or a transcription factor, may be therapeutically active, e.g., in that it targets a gene associated with a disease or disorder. In some embodiments, a composition as provided herein, comprising a supercharged protein and a functional effector protein, such as a nuclease or a transcription factor, is used to modulate the expression of a gene in a cell or to modulate a biological pathway (e.g., a signaling pathway, a metabolic pathway) in a cell. In some embodiments, a cell is contacted with an inventive composition described herein to introduce a functional effector protein into the cell. In some embodiments, an inventive composition is administered to a subject in need thereof to introduce a functional effector protein into a cell within the subject, e.g., into a cell associated with a disease or disorder. Suitable cells and cell types for delivery of functional effector proteins according to some aspects of this disclosure include, but are not limited to, human cells, mammalian cells, T-cells, neurons, stem cells, progenitor cells, blood cells, fibroblasts, epithelial cells, neoplastic cells, and tumor cells.

Supercharged Proteins

Supercharged proteins for use in the present invention can be produced by changing non-conserved amino acids on the surface of a protein to more polar or charged amino acid residues. In certain embodiments, non-conserved amino acids on the surface of the protein are mutated into amino acids that are positively charged at physiological pH (pH ~7.4). The amino acid residues to be modified may be hydrophobic, hydrophilic, charged, or a combination thereof. Supercharged proteins can also be produced by the attachment of charged moieties to the protein in order to supercharge the protein. Supercharged proteins frequently are resistant to aggregation, have an increased ability to refold, resist improper folding, have improved solubility, and are generally more stable under a wide range of conditions, including denaturing conditions such as heat or the presence of a detergent.

Supercharged proteins suitable for use according to aspects of this disclosure are known in the art and include, without limitation, those supercharged proteins disclosed in international PCT patent application, PCT/US07/70254, filed Jun. 1, 2007, published as WO 2007/143574 on Dec. 13, 2007; in international PCT application, PCT/US09/041984, filed on Apr. 28, 2009, published as WO 2009/134808 on Nov. 5, 2009; and in international PCT application, PCT/US10/001250, filed on Apr. 28, 2010, published as WO 2010/129023 on Nov. 11, 2010; the entire contents of each of which are incorporated herein by reference. In some embodiments, the supercharged protein is an engineered supercharged protein. In some embodiments, the supercharged protein is a naturally occurring supercharged protein, e.g., a naturally supercharged protein disclosed in international PCT application, PCT/US10/001250, filed on Apr. 28, 2010, published as WO 2010/129023 on Nov. 11, 2010; each of which is incorporated herein by reference. In some embodiments, the supercharged protein, engineered or naturally occurring, exhibits a charge:molecular weight ratio of greater than 0.8, e.g., $\geq 0.85$, $\geq 0.9$, $\geq 0.95$, $\geq 1$, $\geq 1.1$, $\geq 1.2$, $\geq 1.3$, $\geq 1.4$, $\geq 1.5$, $\geq 1.6$, $\geq 1.7$, $\geq 1.8$, $\geq 1.9$, $\geq 2$, $\geq 2.5$, $\geq 3$, $\geq 4$, $\geq 5$, $\geq 6$, $\geq 7$, $\geq 8$, or $\geq 10$.

The supercharged protein employed may be derived from any species of plant, animal, and/or microorganism. In certain embodiments, the supercharged protein is a mammalian protein. In certain embodiments, the supercharged protein is a human protein. In certain embodiments, the protein is derived from an organism typically used in research. For example, the protein to be modified may be from a primate (e.g., ape, monkey), rodent (e.g., rabbit, hamster, gerbil), pig, dog, cat, fish (e.g., *Danio rerio*), nematode (e.g., *C. elegans*), yeast (e.g., *Saccharomyces cerevisiae*), or bacteria (e.g., *E. coli*). In certain embodiments, the protein is non-immunogenic. In certain embodiments, the protein is non-antigenic. In certain embodiments, the protein does not have inherent biological activity or has been modified to have no biological activity. In certain embodiments, the protein is chosen based on its targeting ability. In certain embodiments, the protein is a green fluorescent protein. In some embodiments, the supercharged protein is supercharged glutathione S-transferace (GST). In some embodiments, the supercharged protein is supercharged streptavidin.

In some embodiments, a supercharged protein is used that has been modified to increase the overall net charge, or to increase the total number of charged residues on the protein surface. In certain embodiments, the theoretical net charge of the supercharged protein is increased by at least +1, at least +2, at least +3, at least +4, at least +5, at least +10, at least +15, at least +20, at least +25, at least +30, at least +35, or at least +40 as compared to the unmodified protein. In certain embodiments, the theoretical net charge of the supercharged protein is at least +1, at least +2, at least +3, at least +4, at least +5, at least +10, at least +15, at least +20, at least +25, at least +30, at least +35, or at least +40 at physiological pH (i.e., ~7.4).

In other embodiments, for example those involving use of cationic lipids and/or cationic polymers, a supercharged protein is used that has been modified to decrease the overall net charge, or to decrease the total number of charged residues on the protein surface. In certain embodiments, the theoretical net charge of the supercharged protein is decreased ("minus" or "negative" represented by '-') by at least −1, at least −2, at least −3, at least −4, at least −5, at least −10, at least −15, at least −20, at least −25, at least −30, at least −35, at least −40, at least −45, or at least −50 as compared to the unmodified protein. In certain embodiments, the theoretical net charge of the supercharged protein is at least −1, at least −2, at least −3, at least −4, at least −5, at least −10, at least −15, at least −20, at least −25, at least −30, at least −35, at least −40, at least −45, or at least −50.

While some exemplary supercharged proteins are described herein in order to exemplify the inventive technology, the disclosure is not limited in this respect. Those of skill in the art will be able to ascertain additional suitable supercharged proteins for delivering functional effector proteins to cells based on the instant disclosure. A number of naturally occurring proteins may be modified to generate suitable supercharged proteins. The desired modifications in such proteins may be accomplished using any techniques known in the art. Recombinant DNA techniques for introducing such changes in a protein sequence are well known in the art. In certain embodiments, the modifications are made by site-directed mutagenesis of the polynucleotide encoding the protein. Other techniques for introducing mutations are discussed in *Molecular Cloning: A Labora-* tory Manual, 2nd Ed., ed. by Sambrook, Fritsch, and Maniatis (Cold Spring Harbor Laboratory Press: 1989); the treatise, Methods in Enzymology (Academic Press, Inc., N.Y.); Ausubel et al., Current Protocols in Molecular Biology (John Wiley & Sons, Inc., New York, 1999); each of which is incorporated herein by reference.

Supercharged proteins may be further modified. Proteins including supercharged proteins can be modified using techniques known to those of skill in the art. For example, supercharged proteins may be modified chemically or biologically. One or more amino acids may be added, deleted, or changed from the primary sequence. For example, a poly-histidine tag or other tag may be added to the supercharged protein to aid in the purification of the protein. Other peptides or proteins may be added onto the supercharged protein to alter the biological, biochemical, and/or biophysical properties of the protein. For example, an endosomolytic peptide may be added to the primary sequence of the supercharged protein, or a targeting peptide, may be added to the primary sequence of the supercharged protein. Other modifications of the supercharged protein include, but are not limited to, post-translational modifications (e.g., glycosylation, phosphorylation, acylation, lipidation, farnesylation, acetylation, proteolysis, etc.). In certain embodiments, the supercharged protein is modified to reduce its immunogenicity. In certain embodiments, the supercharged protein is modified to enhance its ability to deliver a functional effector protein (e.g., nucleases, transcriptional activators/repressors, recombinases, Cas9 proteins including variants and fusions thereof, etc.) to a cell. In certain embodiments, the supercharged protein is conjugated to a polymer. For example, the protein may be PEGylated by conjugating the protein to a polyethylene glycol (PEG) polymer. Other methods can be used to produce supercharged proteins without modification of the protein sequence. For example, moieties that alter the net charge can be attached to proteins (e.g., by chemical or enzymatic reactions) to provide surface charge to achieve supercharging. In certain embodiments, the method of modifying proteins described in Shaw et al., Protein Science 17:1446, 2008 is used to supercharge a protein that is used in the instantly disclosed inventive technology.

The design and creation of variants of several different supercharged proteins suitable for use with the instantly disclosed technology is described in international PCT patent application, PCT/US07/70254, filed Jun. 1, 2007, published as WO 2007/143574 on Dec. 13, 2007; in international PCT application, PCT/US09/041984, filed on Apr. 28, 2009, published as WO 2009/134808 on Nov. 5, 2009; and in international PCT application PCT/US10/001250, filed on Apr. 28, 2010, published as WO 2010/129023 on Nov. 11, 2010; the entire contents of each of which are incorporated herein by reference. Some of the disclosed supercharged proteins described therein have been shown to be more stable and to retain their biological function, e.g., their fluorescence in the case of fluorescent proteins. For example, a green fluorescent protein (GFP) from *Aequorea victoria* is described in GenBank Accession Number P42212, incorporated herein by reference. The amino acid sequence of this wild type GFP is as follows:

(SEQ ID NO: 14)
MSKGEELFTGVVPILVELDGDVNGHKFSVSGEGEGDATYGKLTLKFICTT

GKLPVPWPTLVTTFSYGVQCFSRYPDHMKQHDFFKSAMPEGYVQERTIFF

-continued
KDDGNYKTRAEVKFEGDTLVNRIELKGIDFKEDGNILGHKLEYNYNSHNV

YIMADKQKNGIKVNFKIRHNIEDGSVQLADHYQQNTPIGDGPVLLPDNHY

LSTQSALSKDPNEKRDHMVLLEFVTAAGITHGMDELYK

Wild type GFP has a theoretical net charge of −7. Variants with a theoretical net charge of −29, −30, −25, +15, +25, +36, +48, and +49 have been reported, e.g., in international PCT application PCT/US10/001250, filed on Apr. 28, 2010, published as WO 2010/129023 on Nov. 11, 2010, the entire contents of which are incorporated herein by reference. Even after heating the +36 GFP to 95° C., 100% of the variant protein is soluble and the protein retains ≥70% of its fluorescence.

Some aspects of this disclosure are based on the discovery that +36 GFP efficiently delivers functional effector proteins (e.g., nucleases, transcriptional activators/repressors, recombinases, Cas9 proteins including variants and fusions thereof, etc.) to target cells, and that the effector proteins so delivered retain their biological function. Therefore, GFP or other proteins with a net charge of at least +15, at least +25, at least +30, at least +35, or at least +40 are thought to be particularly useful for introducing functional effector proteins into a cell.

In some embodiments, particularly useful supercharged proteins are proteins that allow for a charge distribution or a surface charge density similar to that of +36 GFP. Further, in some embodiments, particularly useful supercharged proteins are proteins exhibiting a stable folded structure not easily perturbed by supercharging, thus allowing the supercharged protein to be well folded. In some embodiments, particularly useful supercharged proteins are proteins sharing a structural feature with a supercharged protein described herein or in international PCT patent application, PCT/US07/70254, filed Jun. 1, 2007, published as WO 2007/143574 on Dec. 13, 2007; in international PCT application, PCT/US09/041984, filed on Apr. 28, 2009, published as WO 2009/134808 on Nov. 5, 2009; and in international PCT application, PCT/US10/001250, filed on Apr. 28, 2010, published as WO 2010/129023 on Nov. 11, 2010; the entire contents of each of which are incorporated herein by reference; for example, a globular structure, or a β-barrel structure. Protein folding, protein fold structure stability and perturbation of protein folding by substitution of specific amino acids with differently charged amino acids, charge distribution, and surface charge density can be modeled in silico by methods and algorithms provided herein and others known to those of skill in the art. Accordingly, it will be apparent to those of skill in the art from no more than routine experimentation, whether a supercharged protein in question will be well folded. Thus, those of skill in the art will be able to identify from a given amino acid sequence whether a given supercharged protein will be useful for cellular delivery of a functional effector protein according to the technology described herein.

Some exemplary, suitable variants of GFP include, without limitation:

+15 GFP:
(SEQ ID NO: 15)
MGHHHHHHGGASKGERLFTGVVPILVELDGDVNGHKFSVRGEGEGDATRG

KLTLKFICTTGKLPVPWPTLVTTLTYGVQCFSRYPKHMKRHDFFKSAMPE

GYVQERTISFKKDGTYKTRAEVKFEGRTLVNRIELKGRDFKEKGNILGHK

LEYNFNSHNVYITADKRKNGIKANFKIRHNVKDGSVQLADHYQQNTPIGR

GPVLLPRNHYLSTRSALSKDPKEKRDHMVLLEFVTAAGITHGMDELYK

+25 GFP:

(SEQ ID NO: 16)
MGHHHHHHGGASKGERLFTGVVPILVELDGDVNGHKFSVRGKGKGDATRG

KLTLKFICTTGKLPVPWPTLVTTLTYGVQCFSRYPKHMKRHDFFKSAMPK

GYVQERTISFKKDGTYKTRAEVKFEGRTLVNRIKLKGRDFKEKGNILGHK

LRYNFNSHNVYITADKRKNGIKANFKIRHNVKDGSVQLADHYQQNTPIGR

GPVLLPRNHYLSTRSALSKDPKEKRDHMVLLEFVTAAGITHGMDELYK

+36 GFP:

(SEQ ID NO: 17)
MGHHHHHHGGASKGERLFRGKVPILVELKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFEGRTLVNRIKLKGRDFKEKGNILGHK

LRYNFNSHKVYITADKRKNGIKAKFKIRHNVKDGSVQLADHYQQNTPIGR

GPVLLPRNHYLSTRSKLSKDPKEKRDHMVLLEFVTAAGIKHGRDERYK

+42 GFP:

(SEQ ID NO: 18)
MGHHHHHHGGRSKGKRLFRGKVPILVELKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFEGRTLVNRIKLKGRDFKEKGNILGHK

LRYNFNSHKVYITADKRKNGIKAKFKIRHNVKDGSVQLADHYQQNTPIGR

GPVLLPRKHYLSTRSKLSKDPKEKRDHMVLLEFVTAAGIKHGRKERYK

+48 GFP:

(SEQ ID NO: 19)
MGHHHHHHGGRSKGKRLFRGKVPILVKLKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFKGRTLVNRIKLKGRDFKEKGNILGHK

LRYNFNSHKVYITADKRKNGIKAKFKIRHNVKDGSVQLAKHYQQNTPIGR

GPVLLPRKHYLSTRSKLSKDPKEKRDHMVLLEFVTAAGIKHGRKERYK

+49 GFP:

(SEQ ID NO: 20)
MGHHHHHHGGRSKGKRLFRGKVPILVKLKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFKGRTLVNRIKLKGRDFKEKGNILGHK

LRYNFNSHKVYITADKRKNGIKAKFKIRHNVKDGSVQLAKHYQQNTPIGR

GPVLLPRKHYLSTRSKLSKDPKEKRDHMVLKEFVTAAGIKHGRKERYK (-)30 GFP:

(SEQ ID NO: 21)
MGHHHHHHGGASKGEELFDGVVPILVELDGDVNGHEFSVRGEGEGDATEG

ELTLKFICTTGELPVPWPTLVTTLTYGVQCFSDYPDHMDQHDFFKSAMPE

GYVQERTISFKDDGTYKTRAEVKFEGDTLVNRIELKGIDFKEDGNILGHK

LEYNFNSHDVYITADKQENGIKAEFEIRHNVEDGSVQLADHYQQNTPIGD

GPVLLPDDHYLSTESALSKDPNEDRDHMVLLEFVTAAGIDHGMDELYK

It will be apparent to the skilled artisan that the sequences above include an N-terminal His6 tag, and that sequences without such a tag or with a different tag are also suitable.

In order to promote the biological function of the functional effector protein (e.g., nucleases, transcriptional activators/repressors, recombinases, Cas9 proteins including variants and fusions thereof, etc.) after delivery to a cell, it may be desirable to enhance endosomal escape of the functional effector protein after cellular uptake. A supercharged protein or a functional effector protein may be fused to or associated with a protein, peptide, or other entity known to enhance endosome degradation or lysis of the endosome. In certain embodiments, the peptide is hemagglutinin 2 (HA2) peptide which is known to enhance endosome degradation. In certain particular embodiments, HA2 peptide is fused to supercharged GFP (e.g., +36 GFP). In certain particular embodiments, the fused protein is of the sequence:

+36 GFP-HA2

(SEQ ID NO: 22)
MGHHHHHHGGASKGERLFRGKVPILVELKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFEGRTLVNRIKLKGRDFKEKGNILGHK

LRYNFNSHKVYITADKRKNGIKAKFKIRHNVKDGSVQLADHYQQNTPIGR

GPVLLPRNHYLSTRSKLSKDPKEKRDHMVLLEFVTAAGIKHGRDERYKGS

AGSAAGSGEFGLFGAIAGFIENGWEGMIDG

In certain embodiments, the endosomolytic peptide is melittin peptide (GIGAVLKVLTTGLPALISWIKRKRQQ, SEQ ID NO: 23) (Meyer et al., JACS 130(11): 3272-3273, 2008; which is incorporated herein by reference). In certain embodiments, the melittin peptide is modified by one, two, three, four, or five amino acid substitutions, deletions, and/or additions. In certain embodiments, the melittin peptide is of the sequence: CIGAVLKVLTTGLPALISWIKRKRQQ (SEQ ID NO:24). In certain particular embodiments, the melittin peptide is fused to supercharged GFP (e.g., +36 GFP).

In certain embodiments, the endosomolytic peptide is penetratin peptide (RQIKIWFQNRRMKWKK-amide, SEQ ID NO:25), bovine PrP (1-30) peptide (MVKSKIGSWILV-LFVAMWSDVGLCKKRPKP-amide, SEQ ID NO: 26), MPGΔ$^{NLS}$ peptide (which lacks a functional nuclear localization sequence because of a K→S substitution) (GALFL-GWLGAAGSTMGAPKSKRKV, SEQ ID NO:27), TP-10 peptide (AGYLLGKINLKALAALAKKIL-amide, SEQ ID NO:28), and/or EB1 peptide (LIRLWSHLIHIWFQN-RRLKWKKK-amide, SEQ ID NO:29) (Lundberg et al., 2007, FASEB J. 21:2664; incorporated herein by reference). In certain embodiments, the penetratin, PrP (1-30), MPG, TP-10, and/or EB1 peptide is modified by one, two, three, four, or five amino acid substitutions, deletions, and/or additions. In certain particular embodiments, the PrP (1-30), MPG, TP-10, and/or EB1 peptide is fused to supercharged GFP (e.g., +36 GFP). In some embodiments, an Aurein peptide is fused to the supercharged protein.

Other peptides or proteins may also be fused to the supercharged protein or to a fusion protein comprising a supercharged protein and a functional effector protein (e.g., nucleases, transcriptional activators/repressors, recombinases, Cas9 proteins including variants and fusions thereof, etc.). For example, a targeting peptide may be fused to the supercharged protein in order to selectively deliver a functional effector protein to a particular cell type. Peptides or proteins that enhance cellular uptake of the functional effector protein may also be used. In certain embodiments, the peptide fused to the supercharged protein is a peptide hormone. In certain embodiments, the peptide fused to the supercharged protein is a peptide ligand.

The exemplary supercharged proteins described in detail herein are not meant to limit the disclosure, and one of skill in the art will appreciate that other supercharged proteins may be used for the cellular delivery of functional effector proteins (e.g., nucleases, transcriptional activators/repressors, recombinases, Cas9 proteins including variants and fusions thereof, etc.), including, but not limited to, other GFP-style fluorescent proteins. In certain embodiments, the supercharged protein is a supercharged version of blue fluorescent protein. In certain embodiments, the supercharged protein is a supercharged version of cyan fluorescent protein. In certain embodiments, the supercharged protein is a supercharged version of yellow fluorescent protein. Exemplary suitable fluorescent proteins include, but are not limited to, enhanced green fluorescent protein (EGFP), AcGFP, TurboGFP, Emerald, Azami Green, ZsGreen, EBFP, Sapphire, T-Sapphire, ECFP, mCFP, Cerulean, CyPet, AmCyan1, Midori-Ishi Cyan, mTFP1 (Teal), enhanced yellow fluorescent protein (EYFP), Topaz, Venus, mCitrine, YPet, PhiYFP, ZsYellow1, mBanana, Kusabira Orange, mOrange, dTomato, dTomato-Tandem, DsRed, DsRed2, DsRed-Express (T1), DsRed-Monomer, mTangerine, mStrawberry, AsRed2, mRFP1, JRed, mCherry, HcRed1, mRaspberry, HcRed1, HcRed-Tandem, mPlum, and AQ143.

Yet other proteins that may be supercharged and used, e.g., in the delivery of functional effector proteins as disclosed herein (e.g., nucleases, transcriptional activators/repressors, recombinases, Cas9 proteins including variants and fusions thereof, etc.), include histone components or histone-like proteins, high-mobility-group proteins (HMGs), enzymes (e.g., amylases, pectinases, hydrolases, proteases, glucose isomerase, lipases, phytases, alglucerase, imiglucerase, agalsidase beta, α-1-iduronidase, acid α-glucosidase, and iduronate-2-sulfatase, N-acetylgalactosamine-4-sulfatase.

Charged polymers other than proteins may also be used to deliver functional effector proteins. Additionally, as described in greater detail herein, cationic lipids and lipid-like materials as well as cationic polymers can also be used to deliver functional effector proteins. Suitable cationic lipids, lipid-like materials and cationic polymers are disclosed herein and additional suitable lipids and lipid-like materials are known to those of skill in the art (see, e.g., those described in Akinc et al., *Nature Biotechnology* 26, 561-569 (2008), the entire contents of which are incorporated herein by reference).

Delivery of Functional Effector Proteins Using Supercharged Proteins

The present invention provides systems and methods for the delivery of functional effector proteins (e.g., nucleases, transcriptional activators/repressors, recombinases, Cas9 proteins including variants and fusions thereof, etc.) to cells in vivo, ex vivo, or in vitro. Such systems and methods typically involve association of the functional effector protein with a supercharged protein to form a complex or a fusion protein, and delivery of the complex or fusion protein to a cell. In some embodiments, the functional effector protein to be delivered by the supercharged protein has therapeutic activity. In some embodiments, delivery of the complex or fusion protein to a cell involves administering the complex or fusion protein comprising a supercharged protein associated with a functional effector protein to a subject in need thereof.

In some embodiments, a functional effector protein (e.g., nucleases, transcriptional activators/repressors, recombinases, Cas9 proteins including variants and fusions thereof, etc.) by itself may not be able to enter a cell, but is able to enter a cell when associated with a supercharged protein, for example, via a covalent bond or a non-covalent interaction. In some embodiments, a composition is provided that includes a functional effector protein that is covalently bound to a supercharged protein. In some embodiments, the composition includes a functional effector protein fused to a supercharged protein via a peptide bond, for example, via direct fusion or via a peptide linker. In some embodiments, the composition includes a functional effector protein that is bound to a supercharged protein by non-covalent interaction. In some embodiments, a supercharged protein is utilized to allow a functional effector protein to enter a cell. In some embodiments, the functional effector protein delivered to the cell associated with a supercharged protein is separated from the supercharged protein after delivery to the cell, for example, by cleavage of a linker peptide by a cellular protease (e.g., an endosomal protease) or by dissociation of the functional effector protein from the supercharged protein in a specific cellular microenvironment, for example, in the endosome. In some embodiments, functional effector proteins delivered to a cell by a system or method provided by this disclosure have therapeutic activity.

In some embodiments, a functional effector protein (e.g., nucleases, transcriptional activators/repressors, recombinases, Cas9 proteins including variants and fusions thereof, etc.) is delivered to a cell in vivo, ex vivo, or in vitro by a system, composition, or method provided herein. In some embodiments, a functional effector protein is a protein able to carry out a biological function within the target cell, for example, an enzyme able to bind its substrate and to catalyze an enzymatic reaction in the target cell, e.g., a nuclease able to bind and cut a nucleic acid molecule within a target cell, or a transcription factor able to interact with the genome of a target cell and to activate or inhibit transcription of a target gene in the cell.

In some embodiments, a method for generating a fusion of a functional effector protein and a supercharged protein includes the generation of an expression nucleic acid construct containing the coding sequences of the functional protein and the supercharged protein, as well as, optionally, a peptide linker, in frame; the expression of such a recombinant fusion protein in a prokaryotic or eukaryotic cell in culture, the extraction and purification of the fusion protein of the fusion protein. In some embodiments, a nucleic acid construct is generated in the form of an expression vector, for example, a vector suitable for propagation in a bacterial host and for expression in a prokaryotic or eukaryotic cell.

In some embodiments, a vector suitable for fusion protein expression is generated by cloning of a nucleotide sequence coding for a functional effector protein to be delivered into a cloning vector including a nucleotide sequence coding for a supercharged protein under the control of a eukaryotic and/or a prokaryotic promoter, by a cloning approach that results in both coding sequences being in frame with each other. In some embodiments, the cloning vector includes a nucleotide sequence coding for a peptide linker between a nucleotide sequence coding for a supercharged protein and a restriction site useful for inserting a nucleotide sequence coding for a protein in frame with the linker and the supercharged protein. In some embodiments, the cloning vector further includes an additional sequence enhancing expression of a fusion protein in a prokaryotic or eukaryotic cell or facilitating purification of expressed fusion proteins from such cells, for example, a sequence stabilizing a transcript encoding the fusion protein, such as a poly-A signal, a spliceable intron, a sequence encoding an in-frame peptide or protein domain tag (e.g., an Arg-tag, calmodulin-binding peptide tag, cellulose-binding domain tag, DsbA tag, c-myc-tag, glutathione S-transferase tag, FLAG-tag, HAT-tag, His-tag, maltose-binding protein tag, NusA tag, S-tag, SBP-tag, Strep-tag, or thioredoxin tag), or a selection marker or reporter cassette allowing for identification of cells harboring and expressing the expression construct and/or quantifying the level of expression in such cells. Methods for cloning and expressing fusion proteins are well known to those in the art, see, for example Sambrook et al., *Molecular Cloning: A Laboratory Manual*, Volume 1-3, CSHL Press (1989); Gellissen et al., Production of recombinant proteins, Wiley-VCH, 2005.

In some embodiments, the functional effector protein is associated with a supercharged GFP, for example, +36 GFP or −30 GFP, for delivery to a target cell. The benefit of endosomal disruption in the delivery of macromolecules by supercharged proteins has been previously demonstrated (Wadia et al., *Nat. Med.* 10, 310-315, 2004) and in some embodiments, additional steps to effect enhanced endosomal escape, as provided herein or known in the art, are performed. Highly efficient protein internalization, when coupled with effective endosomal release, has the potential to minimize the requisite doses of exogenous protein agents, enhancing their potential as research tools and leads for therapeutic development.

In some embodiments, a composition comprising a functional effector protein associated with a supercharged protein is administered to a target cell after isolation and/or purification. Protein isolation methods and technologies are well known to those of skill in the art and include, for example, affinity chromatography or immunoprecipitation. The methods suitable for isolating and/or purifying a specific functional effector proteins, supercharged proteins, and/or fusion proteins will depend on the nature of the respective protein. For example, a His-tagged fusion protein can readily be isolated and purified via Ni or Co ion chromatography, while fusion proteins tagged with other peptides or domains or untagged fusion proteins can be purified by other well established methods.

Functional effector proteins suitable for delivery to a target cell in vivo, ex vivo, or in vitro, by a system or method provided herein will be apparent to those of skill in the art and include, for example, DNA-binding proteins, such as transcription factors and nucleases, as well as Cas9 proteins (including variants and fusions thereof).

In some embodiments, a method, composition, or system provided herein is used to deliver a therapeutic functional effector protein to a cell. Examples of therapeutic proteins include, but are not limited to, nucleases and Cas9 proteins (including variants and fusions thereof) targeting a genomic allele associated with a disease or disorder, and transcription factors activating a beneficial gene or repressing a pathogenic gene.

In some embodiments, Cas9 is fused to a supercharged protein for delivery to a cell. In some embodiments, the supercharged protein is positively charged. In some embodiments, the supercharged protein fused to Cas9 is (+36)GFP. In some embodiments, the fusion of Cas9 and (+36)GFP comprises the amino acid sequence of SEQ ID NO:30 (e.g., with or without a nuclear localization signal (NLS) and with or without a 6xHis tag), or comprises an amino acid sequence that is at least 80%, at least 85%, at least 90%, at least 95%, at least 98%, or at least 99% identical to the amino acid sequence of SEQ ID NO:30 (e.g., with or without a nuclear localization signal (NLS) and with or without a 6xHis tag). In some embodiments, the supercharged protein fused to Cas9 is (−30)GFP. In some embodiments, the fusion of Cas9 and (−30)GFP comprises the amino acid sequence of SEQ ID NO:31 (e.g., with or without a nuclear localization signal (NLS) and with or without a 6xHis tag), or comprises an amino acid sequence that is at least 80%, at least 85%, at least 90%, at least 95%, at least 98%, or at least 99% identical to the amino acid sequence of SEQ ID NO:31 (e.g., with or without a nuclear localization signal (NLS) and with or without a 6xHis tag).

(+36)dGFP-NLS-Cas9-6xHis (Y67S):
(SEQ ID NO: 30)
MGASKGERLFRGKVPILVELKGDVNGHKFSVRGKGKGDATRGKLTLKFIC

TTGKLPVPWPTLVTTLTSGVQCFSRYPKHMKRHDFFKSAMPKGYVQERTI

SFKKDGKYKTRAEVKFEGRTLVNRIKLKGRDFKEKGNILGHKLRYNFNSH

KVYITADKRKNGIKAKFKIRHNVKDGSVQLADHYQQNTPIGRGPVLLPRN

HYLSTRSKLSKDPKEKRDHMVLLEFVTAAGIKHGRDERYKTGGSGGSGGS

GGSGGSGGSGGSGGSGGTALALPKKKRKVMDKKYSIGLDIGTNSVGWAVI

TDEYKVPSKKFKVLGNTDRHSIKKNLIGALLFDSGETAEATRLKRTARRR

YTRRKNRICYLQEIFSNEMAKVDDSFFHRLEESFLVEEDKKHERHPIFGN

IVDEVAYHEKYPTIYHLRKKLVDSTDKADLRLIYLALAHMIKFRGHFLIE

GDLNPDNSDVDKLFIQLVQTYNQLFEENPINASGVDAKAILSARLSKSRR

LENLIAQLPGEKKNGLFGNLIALSLGLTPNFKSNFDLAEDAKLQLSKDTY

DDDLDNLLAQIGDQYADLFLAAKNLSDAILLSDILRVNTEITKAPLSASM

IKRYDEHHQDLTLLKALVRQQLPEKYKEIFFDQSKNGYAGYIDGGASQEE

FYKFIKPILEKMDGTEELLVKLNREDLLRKQRTFDNGSIPHQIHLGELHA

ILRRQEDFYPFLKDNREKIEKILTFRIPYYVGPLARGNSRFAWMTRKSEE

TITPWNFEEVVDKGASAQSFIERMTNFDKNLPNEKVLPKHSLLYEYFTVY

NELTKVKYVTEGMRKPAFLSGEQKKAIVDLLFKTNRKVTVKQLKEDYFKK

IECFDSVEISGVEDRFNASLGTYHDLLKIIKDKDFLDNEENEDILEDIVL

TLTLFEDREMIEERLKTYAHLFDDKVMKQLKRRRYTGWGRLSRKLINGIR

DKQSGKTILDFLKSDGFANRNFMQLIHDDSLTFKEDIQKAQVSGQGDSLH

EHIANLAGSPAIKKGILQTVKVVDELVKVMGRHKPENIVIEMARENQTTQ

KGQKNSRERMKRIEEGIKELGSQILKEHPVENTQLQNEKLYLYYLQNGRD

MYVDQELDINRLSDYDVDHIVPQSFLKDDSIDNKVLTRSDKNRGKSDNVP

SEEVVKKMKNYWRQLLNAKLITQRKFDNLTKAERGGLSELDKAGFIKRQL

VETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIA

RKKDWDPKKYGGFDSPTVAYSVLVVAKVEKGKSKKLKSVKELLGITIMER

SSFEKNPIDFLEAKGYKEVKKDLIIKLPKYSLFELENGRKRMLASAGELQ

KGNELALPSKYVNFLYLASHYEKLKGSPEDNEQKQLFVEQHKHYLDEIIE

QISEFSKRVILADANLDKVLSAYNKHRDKPIREQAENIIHLFTLTNLGAP

AAFKYFDTTIDRKRYTSTKEVLDATLIHQSITGLYETRIDLSQLGGD<ins>HHH</ins>

-continued

HHH (-30)dGFP-NLS-Cas9-6xHis (Y67S):
(SEQ ID NO: 31)
MGASKGEELFDGVVPILVELDGDVNGHEFSVRGEGEGDATEGELTLKFIC

TTGELPVPWPTLVTTLT<u>S</u>GVQCFSDYPDHMDQHDFFKSAMPEGYVQERTI

SFKDDGTYKTRAEVKFEGDTLVNRIELKGIDFKEDGNILGHKLEYNFNSH

DVYITADKQENGIKAEFEIRHNVEDGSVQLADHYQQNTPIGDGPVLLPDD

HYLSTESALSKDPNEDRDHMVLLEFVTAAGIDHGMDELYKTGGSGGSGGS

GGSGGSGGSGGSGGSGGTALALPKKKRKVMDKKYSIGLDIGTNSVGWAVI

TDEYKVPSKKFKVLGNTDRHSIKKNLIGALLFDSGETAEATRLKRTARRR

YTRRKNRICYLQEIFSNEMAKVDDSFFHRLEESFLVEEDKKHERHPIFGN

IVDEVAYHEKYPTIYHLRKKLVDSTDKADLRLIYLALAHMIKFRGHFLIE

GDLNPDNSDVDKLFIQLVQTYNQLFEENPINASGVDAKAILSARLSKSRR

LENLIAQLPGEKKNGLFGNLIALSLGLTPNFKSNFDLAEDAKLQLSKDTY

DDDLDNLLAQIGDQYADLFLAAKNLSDAILLSDILRVNTEITKAPLSASM

IKRYDEHHQDLTLLKALVRQQLPEKYKEIFFDQSKNGYAGYIDGGASQEE

FYKFIKPILEKMDGTEELLVKLNREDLLRKQRTFDNGSIPHQIHLGELHA

ILRRQEDFYPFLKDNREKIEKILTFRIPYYVGPLARGNSRFAWMTRKSEE

TITPWNFEEVVDKGASAQSFIERMTNFDKNLPNEKVLPKHSLLYEYFTVY

NELTKVKYVTEGMRKPAFLSGEQKKAIVDLLFKTNRKVTVKQLKEDYFKK

IECFDSVEISGVEDRFNASLGTYHDLLKIIKDKDFLDNEENEDILEDIVL

TLTLFEDREMIEERLKTYAHLFDDKVMKQLKRRRYTGWGRLSRKLINGIR

DKQSGKTILDFLKSDGFANRNFMQLIHDDSLTFKEDIQKAQVSGQGDSLH

EHIANLAGSPAIKKGILQTVKVVDELVKVMGRHKPENIVIEMARENQTTQ

KGQKNSRERMKRIEEGIKELGSQILKEHPVENTQLQNEKLYLYYLQNGRD

MYVDQELDINRLSDYDVDHIVPQSFLKDDSIDNKVLTRSDKNRGKSDNVP

SEEVVKKMKNYWRQLLNAKLITQRKFDNLTKAERGGLSELDKAGFIKRQL

VETRQITKHVAQILDSRMNTKYDENDKLIREVKVITLKSKLVSDFRKDFQ

FYKVREINNYHHAHDAYLNAVVGTALIKKYPKLESEFVYGDYKVYDVRKM

IAKSEQEIGKATAKYFFYSNIMNFFKTEITLANGEIRKRPLIETNGETGE

IVWDKGRDFATVRKVLSMPQVNIVKKTEVQTGGFSKESILPKRNSDKLIA

RKKDWDPKKYGGFDSPTVAYSVLVVAKVEKGKSKKLKSVKELLGITIMER

SSFEKNPIDFLEAKGYKEVKKDLIIKLPKYSLFELENGRKRMLASAGELQ

KGNELALPSKYVNFLYLASHYEKLKGSPEDNEQKQLFVEQHKHYLDEIIE

QISEFSKRVILADANLDKVLSAYNKHRDKPIREQAENIIHLFTLTNLGAP

AAFKYFDTTIDRKRYTSTKEVLDATLIHQSITGLYETRIDLSQLGGD<u>HHH</u>

<u>HHH</u>

Compositions of Functional Effector Proteins and Cationic Lipids

Certain aspects of the disclosure relate to the use of cationic lipids for the delivery of effector proteins (e.g., nucleases, transcriptional activators/repressors, recombinases, Cas9 proteins including variants and fusions thereof, etc.), for example as opposed to delivering "naked" protein preparations. Surprisingly, existing liposomal delivery reagents that have been engineered for the delivery of nucleic acids such as DNA and RNA were found to effectively deliver certain effector proteins (e.g., Cas9 proteins including variants and fusions thereof) both in vitro and in vivo, as described herein. Nucleic acid delivery has benefited greatly from the development of liposomal reagents over the past two decades. Cationic liposomal formulations have enabled DNA and RNA transfection to become a routine technique in basic research and have even been used in clinical trials. The lipid bilayer of the liposome protects encapsulated nucleic acids from degradation and can prevent specific neutralization by antibodies that can bind naked preparations of the nucleic acids. Importantly, fusion of the liposome with the endosomal membrane during endosomal maturation can enable highly efficient endosomal escape of cationic lipid-delivered cargo. Other non-cationic, but reversibly ionizable, lipid nanoparticle formulations have enabled efficient encapsulation and delivery of nucleic acids, while avoiding non-specific electrostatic interactions and consequent sequestration. However, proteins are chemically diverse, and therefore unlike highly anionic nucleic acids, liposomal formulations have not been similarly successful for the efficient delivery of proteins. For example, while proteins can be encapsulated non-specifically and delivered by rehydrated lipids in vitro, the efficacy of encapsulation is dependent on protein concentration and is generally inefficient, and thus has not seen widespread application. Aspects of the present disclosure relate to the recognition that anionic proteins or protein complexes (including those proteins associated with nucleic acids) may be able to take advantage of the same electrostatics-driven encapsulation used by cationic liposomal reagents for nucleic acid delivery. While few proteins natively possess the density of negative charges found in the phosphate backbone of nucleic acids, translational fusion to, or non-covalent association with, an anionic carrier such as a negatively supercharged protein or a nucleic acid as described herein render the resulting effector protein or protein complex sufficiently anionic to drive efficient encapsulation of such protein cargoes by cationic liposomal reagents.

In some embodiments, association or fusion with an engineered supernegatively charged GFP is capable of driving efficient encapsulation and delivery of proteins into cultured mammalian cells by cationic lipids commonly used to transfect nucleic acids. This approach is effective even at low nanomolar protein concentrations and in the presence of serum, resulting in up to 1,000-fold more efficient functional protein delivery than protein delivery methods that use fusion to cationic peptides or proteins. As shown in the Examples, the efficacy of delivery depends, in some embodiments, on e.g., the theoretical net charge of the fusion tag, and that popular natively anionic peptide tags e.g., 3×FLAG and VP64, can likewise enable liposomal protein delivery.

The Examples further show that Cas9 nuclease protein associated with polyanionic guide RNAs (gRNA) can be efficiently delivered in functional form into mammalian cells by these common cationic liposomal formulations because, while not wishing to be bound by any particular theory, it is believed that the gRNA acts as a polyanionic mediator between the otherwise cationic Cas9 protein and the cationic lipids. Delivery of Cas9:gRNA complexes is not only highly efficient (e.g., up to 80% modification from a single treatment) but also results in markedly higher genome modification specificity compared with plasmid transfection, typically resulting in >10-fold higher on-target:off-target modification ratios, presumably due to the transient nature of the delivered Cas9:gRNA activity. In some embodiments, delivery of Cas9:gRNA complexes results in at least a 2-fold, 3-fold, 4-fold, 5-fold, 6-fold, 7-fold, 8-fold, 9-fold, 10-fold, 11-fold, 12-fold, 13-fold, 14-fold, 15-fold, 20-fold or 25-fold or higher on-target:off-target modification ratio. The Examples also demonstrate that this protein delivery approach can be effective in vivo, for example by delivering functional Cre recombinase and functional Cas9:gRNA complexes to hair cells in the inner ear of mice.

Accordingly, some aspects of the disclosure provide compositions comprising a Cas9 protein (e.g., as described herein; see e.g., Cas9 effector proteins below) and a cationic lipid capable of delivering the Cas9 protein to the interior of a cell. In some embodiments, the Cas9 protein is associated with a gRNA, which e.g., provides anionic charge to the complex thereby allowing the Cas9:gRNA complex to be encapsulated by the cationic lipids. In some embodiments, the Cas9 protein need not be associated with a gRNA for effective encapsulation by a cationic lipid, but instead is associated with a negatively supercharged protein, as described herein. In some embodiments where a Cas9 protein is associated with a negatively supercharged protein, the Cas9 protein is also associated with a gRNA. In some embodiments, the Cas9 protein is a wild type Cas9 protein, a fragment of a wild type Cas9 protein, or a variant of a wild type Cas9 protein. In some embodiments, the Cas9 protein comprises a dCas9 domain (e.g., as described herein). In some embodiments, the Cas9 protein is a fusion protein comprising a dCas9 domain (e.g., as described herein). In some embodiments, the Cas9 protein is a Cas9 nickase.

In other embodiments, compositions comprising an effector protein (e.g., other than a Cas9 protein) and a cationic lipid are provided which are capable of delivering the effector protein to the interior of a cell (e.g., to the nucleus of the cell). The effector protein is either naturally negatively charged, is modified to have a net overall negative charge, or is associated with a negatively supercharged protein, as described herein. In some embodiments, the effector protein is any effector protein described herein. In some embodiments, the effector protein is a recombinase, e.g., any recombinase described herein. In some embodiments, the recombinase is Cre recombinase. In some embodiments, the Cre recombinase comprises the amino acid sequence of SEQ ID NO:32 (e.g., with or without the 6xHis tag). In some embodiments, the Cre recombinase comprises an amino acid sequence that is at least 80%, at least 85%, at least 90%, at least 95%, at least 98%, or at least 99% identical to the amino acid sequence of SEQ ID NO:32 (e.g., with or without the 6xHis tag). In some embodiments, the Cre recombinase is fused to a supercharged protein (e.g., +36 GFP or −30GFP). In some embodiments, the Cre recombinase fused to a supercharged protein comprises the amino acid sequence of SEQ ID NO:33 (e.g., with or without the 6xHis tag) or SEQ ID NO:34 (e.g., with or without the 6xHis tag), or comprises an amino acid sequence that is at least 80%, at least 85%, at least 90%, at least 95%, at least 98%, or at least 99% identical to the amino acid sequence of SEQ ID NO:33 or SEQ ID NO:34 (e.g., with or without the 6xHis tag). In some embodiments, the effector protein is a TALE protein, (e.g., as described herein including those provided in the Examples). In some embodiments, the TALE protein comprises one or more of a VP64 transcriptional activator domain (e.g., SEQ ID NO:35). In some embodiments, the TALE protein with a VP64 transcriptional activator domain further comprises an amino acid sequence selected from the group consisting of SEQ ID NO:36-39 (e.g., with or without the 6xHis tag). In some embodiments, the TALE protein with a VP64 transcriptional activator domain comprises an amino acid sequence that is at least 80%, at least 85%, at least 90%, at least 95%, at least 98%, or at least 99% identical to an amino acid sequence selected from the group consisting of SEQ ID NO:36-39 (e.g., with or without the 6xHis tag). In some embodiments, the TALE effector protein comprises a (−30)GFP domain (e.g., SEQ ID NO:21 or SEQ ID NO:40), a N-terminal region of a TALE domain (e.g., SEQ ID NO:41), a variable repeat domain (e.g., an 18.5mer repeat domain as provided in Maeder et al., "Robust, synergistic regulation of human gene expression using TALE activators." Nat. Methods. 2013; 10, 243-245), a C-terminal TALE domain (e.g., SEQ ID NO:42), a VP64 activation domain (e.g., SEQ ID NO:35), and optionally one or more linkers (e.g., GGS(9), SEQ ID NO: 252) between any domain and optionally a sequence tag (e.g., 6xHis, SEQ ID NO:253).

While liposomal delivery of cargo such as DNA and RNA has been known to induce toxicity in targeted cells, it was found that the inventive compositions described herein deliver their cargo both in vitro and in vivo surprisingly with no or low toxicity. For example, in some embodiments, the compositions comprising a Cas9 protein or other effector proteins described herein exhibit low toxicity when administered to a population of cells (e.g., in vitro or in vivo). In some embodiments, at least 60%, at least 65%, at least 70%, at least 75%, at least 80%, at least 85%, at least 90%, at least 95%, or at least 99% of the cells in a population are viable following administration of an inventive composition comprising a Cas9 protein or other effector protein and cationic lipids. Methods for assessing the toxicity of a composition when administered to a population of cells are well known in the art and include those described in the Examples.

```
Cre-6xHis (6xHis tag underlined):
                                                    (SEQ ID NO: 32)
MASNLLTVHQNLPALPVDATSDEVRKNLMDMFRDRQAFSEHTWKMLLSVCRSWAAWCKLNNRKWFPAE

PEDVRDYLLYLQARGLAVKTIQQHLGQLNMLHRRSGLPRPSDSNAVSLVMRRIRKENVDAGERAKQAL

AFERTDFDQVRSLMENSDRCQDIRNLAFLGIAYNTLLRIAEIARIRVKDISRTDGGRMLIHIGRTKTL

VSTAGVEKALSLGVTKLVERWISVSGVADDPNNYLFCRVRKNGVAAPSATSQLSTRALEGIFEATHRL

IYGAKDDSGQRYLAWSGHSARVGAARDMARAGVSIPEIMQAGGWTNVNIVMNYIRNLDSETGAMVRLL

EDGDGGSHHHHHH (+36)GFP-Cre-6xHis (+36 GFP double-underlined; 6xHis tag underlined):
                                                    (SEQ ID NO: 33)
MGASKGERLFRGKVPILVELKGDVNGHKFSVRGKGKGDATRGKLTLKFICTTGKLPVPWPTLVTTLTY

GVQCFSRYPKHMKRHDFFKSAMPKGYVQERTISFKKDGKYKTRAEVKFEGRTLVNRIKLKGRDFKEKG
```

-continued

NILGHKLRYNFNSHKVYITADKRKNGIKAKFKIRHNVKDGSVQLADHYQQNTPIGRGPVLLPRNHYLS

TRSKLSKDPKEKRDHMVLLEFVTAAGIKHGRDERYKTGGSGGSGGSGGSGGSGGSGGSGGSGGTASNL

LTVHQNLPALPVDATSDEVRKNLMDMFRDRQAFSEHTWKMLLSVCRSWAAWCKLNNRKWFPAEPEDVR

DYLLYLQARGLAVKTIQQHLGQLNMLHRRSGLPRPSDSNAVSLVMRRIRKENVDAGERAKQALAFERT

DFDQVRSLMENSDRCQDIRNLAFLGIAYNTLLRIAEIARIRVKDISRTDGGRMLIHIGRTKTLVSTAG

VEKALSLGVTKLVERWISVSGVADDPNNYLFCRVRKNGVAAPSATSQLSTRALEGIFEATHRLIYGAK

DDSGQRYLAWSGHSARVGAARDMARAGVSIPEIMQAGGWTNVNIVMNYIRNLDSETGAMVRLLEDGDG

GSHHHHHH (-30)GFP-Cre-6xHis (-30 GFP double-underlined; 6xHis tag underlined):
(SEQ ID NO: 34)

MGASKGEELFDGVVPILVELDGDVNGHEFSVRGEGEGDATEGELTLKFICTTGELPVPWPTLVTTLTY

GVQCFSDYPDHMDQHDFFKSAMPEGYVQERTISFKDDGTYKTRAEVKFEGDTLVNRIELKGIDFKEDG

NILGHKLEYNFNSHDVYITADKQENGIKAEFEIRHNVEDGSVQLADHYQQNTPIGDGPVLLPDDHYLS

TESALSKDPNEDRDHMVLLEFVTAAGIDHGMDELYKTGGSGGSGGSGGSGGSGGSGGSGGSGGTASNL

LTVHQNLPALPVDATSDEVRKNLMDMFRDRQAFSEHTWKMLLSVCRSWAAWCKLNNRKWFPAEPEDVR

DYLLYLQARGLAVKTIQQHLGQLNMLHRRSGLPRPSDSNAVSLVMRRIRKENVDAGERAKQALAFERT

DFDQVRSLMENSDRCQDIRNLAFLGIAYNTLLRIAEIARIRVKDISRTDGGRMLIHIGRTKTLVSTAG

VEKALSLGVTKLVERWISVSGVADDPNNYLFCRVRKNGVAAPSATSQLSTRALEGIFEATHRLIYGAK

DDSGQRYLAWSGHSARVGAARDMARAGVSIPEIMQAGGWTNVNIVMNYIRNLDSETGAMVRLLEDGDG

GSHHHHHH (+36)GFP-PPARγ-TALE-2 (+36 GFP double-underlined; 6xHis tag underlined):
(SEQ ID NO: 36)

MGASKGERLFRGKVPILVELKGDVNGHKFSVRGKGKGDATRGKLTLKFICTTGKLPVPWPTLVTTLTY

GVQCFSRYPKHMKRHDFFKSAMPKGYVQERTISFKKDGKYKTRAEVKFEGRTLVNRIKLKGRDFKEKG

NILGHKLRYNFNSHKVYITADKRKNGIKAKFKIRHNVKDGSVQLADHYQQNTPIGRGPVLLPRNHYLS

TRSKLSKDPKEKRDHMVLLEFVTAAGIKHGRDERYKTGGSGGSGGSGGSGGSGGSGGSGGSGGTAPKK

KRKVGIHRGVPMVDLRTLGYSQQQQEKIKPKVRSTVAQHHEALVGHGFTHAHIVALSQHPAALGTVAV

KYQDMIAALPEATHEAIVGVGKQWSGARALEALLTVAGELRGPPLQLDTGQLLKIAKRGGVTAVEAVH

AWRNALTGAPLNLTPDQVVAIASNIGGKQALETVQRLLPVLCQDHGLTPEQVVAIASNIGGKQALETV

QRLLPVLCQAHGLTPDQVVAIASNGGGKQALETVQRLLPVLCQAHGLTPAQVVAIANNNGGKQALETV

QRLLPVLCQDHGLTPDQVVAIASNGGGKQALETVQRLLPVLCQDHGLTPEQVVAIASNIGGKQALETV

QRLLPVLCQAHGLTPDQVVAIASHDGGKQALETVQRLLPVLCQAHGLTPAQVVAIASHDGGKQALETV

QRLLPVLCQDHGLTPDQVVAIASNIGGKQALETVQRLLPVLCQDHGLTPEQVVAIASNIGGKQALETV

QRLLPVLCQAHGLTPDQVVAIANNNGGKQALETVQRLLPVLCQAHGLTPAQVVAIASNGGGKQALETV

QRLLPVLCQDHGLTPDQVVAIASHDGGKQALETVQRLLPVLCQDHGLTPEQVVAIASNGGGKQALETV

QRLLPVLCQAHGLTPDQVVAIASNGGGKQALETVQRLLPVLCQAHGLTPAQVVAIANNNGGKQALETV

QRLLPVLCQDHGLTPDQVVAIASHDGGKQALETVQRLLPVLCQDHGLTPEQVVAIASHDGGKQALETV

QRLLPVLCQAHGLTPEQVVAIASNIGGRPALESIVAQLSRPDPALAALTNDHLVALACLGGRPALDAV

KKGLPHAPALIKRTNRRIPERTSHRVADHAQVVRVLGFFQCHSHPAQAFDDAMTQFGMSGGGSGRADA

LDDFDLDMLGSDALDDFDLDMLGSDALDDFDLDMLGSDALDDFDLDMLHHHHHH

-continued (+36)GFP-PRDM16_TALE-3(+36 GFP double-underlined; 6xHis tag underlined):

(SEQ ID NO: 37)

<u>MGASKGERLFRGKVPILVELKGDVNGHKFSVRGKGKGDATRGKLTLKFICTTGKLPVPWPTLVTTLTY</u>

<u>GVQCFSRYPKHMKRHDFFKSAMPKGYVQERTISFKKDGKYKTRAEVKFEGRTLVNRIKLKGRDFKEKG</u>

<u>NILGHKLRYNFNSHKVYITADKRKNGIKAKFKIRHNVKDGSVQLADHYQQNTPIGRGPVLLPRNHYLS</u>

<u>TRSKLSKDPKEKRDHMVLLEFVTAAGIKHGRDERYKT</u>GGSGGSGGSGGSGGSGGSGGSGGSGGTAPKK

KRKVGIHRGVPMVDLRTLGYSQQQQEKIKPKVRSTVAQHHEALVGHGFTHAHIVALSQHPAALGTVAV

KYQDMIAALPEATHEAIVGVGKQWSGARALEALLTVAGELRGPPLQLDTGQLLKIAKRGGVTAVEAVH

AWRNALTGAPLNLTPDQVVAIASNGGGKQALETVQRLLPVLCQDHGLTPEQVVAIANNNGGKQALETV

QRLLPVLCQAHGLTPDQVVAIANNNGGKQALETVQRLLPVLCQAHGLTPAQVVAIASHDGGKQALETV

QRLLPVLCQDHGLTPDQVVAIASHDGGKQALETVQRLLPVLCQDHGLTPEQVVAIASHDGGKQALETV

QRLLPVLCQAHGLTPDQVVAIASHDGGKQALETVQRLLPVLCQAHGLTPAQVVAIANNNGGKQALETV

QRLLPVLCQDHGLTPDQVVAIANNNGGKQALETVQRLLPVLCQDHGLTPEQVVAIASHDGGKQALETV

QRLLPVLCQAHGLTPDQVVAIANNNGGKQALETVQRLLPVLCQAHGLTPAQVVAIASNIGGKQALETV

QRLLPVLCQDHGLTPDQVVAIANNNGGKQALETVQRLLPVLCQDHGLTPEQVVAIANNNGGKQALETV

QRLLPVLCQAHGLTPDQVVAIANNNGGKQALETVQRLLPVLCQAHGLTPAQVVAIANNNGGKQALETV

QRLLPVLCQDHGLTPDQVVAIASNGGGKQALETVQRLLPVLCQDHGLTPEQVVAIANNNGGKQALETV

QRLLPVLCQAHGLTPEQVVAIASNGGGRPALESIVAQLSRPDPALAALTNDHLVALACLGGRPALDAV

KKGLPHAPALIKRTNRRIPERTSHRVADHAQVVRVLGFFQCHSHPAQAFDDAMTQFGMSGGGSGRADA

LDDFDLDMLGSDALDDFDLDMLGSDALDDFDLDML<u>HHHHHH</u>

(-30)GFP-PPARγ-TALE-2 (-30 GFP double-underlined; 6xHis tag underlined):

(SEQ ID NO: 38)

<u>MGASKGEELFDGVVPILVELDGDVNGHEFSVRGEGEGDATEGELTLKFICTTGELPVPWPTLVTTLTY</u>

<u>GVQCFSDYPDHMDQHDFFKSAMPEGYVQERTISFKDDGTYKTRAEVKFEGDTLVNRIELKGIDFKEDG</u>

<u>NILGHKLEYNFNSHDVYITADKQENGIKAEFEIRHNVEDGSVQLADHYQQNTPIGDGPVLLPDDHYLS</u>

<u>TESALSKDPNEDRDHMVLLEFVTAAGIDHGMDELYK</u>APKKKRKVGIHRGVPMVDLRTLGYSQQQQEKI

KPKVRSTVAQHHEALVGHGFTHAHIVALSQHPAALGTVAVKYQDMIAALPEATHEAIVGVGKQWSGAR

ALEALLTVAGELRGPPLQLDTGQLLKIAKRGGVTAVEAVHAWRNALTGAPLNLTPDQVVAIASNIGGK

QALETVQRLLPVLCQDHGLTPEQVVAIASNIGGKQALETVQRLLPVLCQAHGLTPDQVVAIASNGGGK

QALETVQRLLPVLCQAHGLTPAQVVAIANNNGGKQALETVQRLLPVLCQDHGLTPDQVVAIASNGGGK

QALETVQRLLPVLCQDHGLTPEQVVAIASNIGGKQALETVQRLLPVLCQAHGLTPDQVVAIASHDGGK

QALETVQRLLPVLCQAHGLTPAQVVAIASHDGGKQALETVQRLLPVLCQDHGLTPDQVVAIASNIGGK

QALETVQRLLPVLCQDHGLTPEQVVAIASNIGGKQALETVQRLLPVLCQAHGLTPDQVVAIANNNGGK

QALETVQRLLPVLCQAHGLTPAQVVAIASNGGGKQALETVQRLLPVLCQDHGLTPDQVVAIASHDGGK

QALETVQRLLPVLCQDHGLTPEQVVAIASNGGGKQALETVQRLLPVLCQAHGLTPDQVVAIASNGGGK

QALETVQRLLPVLCQAHGLTPAQVVAIANNNGGKQALETVQRLLPVLCQDHGLTPDQVVAIASHDGGK

QALETVQRLLPVLCQDHGLTPEQVVAIASHDGGKQALETVQRLLPVLCQAHGLTPEQVVAIASNIGGR

PALESIVAQLSRPDPALAALTNDHLVALACLGGRPALDAVKKGLPHAPALIKRTNRRIPERTSHRVAD

HAQVVRVLGFFQCHSHPAQAFDDAMTQFGMSGGGSGRADALDDFDLDMLGSDALDDFDLDMLGSDALD

DFDLDMLGSDALDDFDLDML<u>HHHHHH</u>

-continued (-30)GFP-PRDM16_TALE-3(-30 GFP double-underlined; 6xHis tag underlined):
(SEQ ID NO: 39)
<u>MGASKGEELFDGVVPILVELDGDVNGHEFSVRGEGEGDATEGELTLKFICTTGELPVPWPTLVTTLTY</u>

<u>GVQCFSDYPDHMDQHDFFKSAMPEGYVQERTISFKDDGTYKTRAEVKFEGDTLVNRIELKGIDFKEDG</u>

<u>NILGHKLEYNFNSHDVYITADKQENGIKAEFEIRHNVEDGSVQLADHYQQNTPIGDGPVLLPDDHYLS</u>

<u>TESALSKDPNEDRDHMVLLEFVTAAGIDHGMDELYK</u>APKKKRKVGIHRGVPMVDLRTLGYSQQQQEKI

KPKVRSTVAQHHEALVGHGFTHAHIVALSQHPAALGTVAVKYQDMIAALPEATHEAIVGVGKQWSGAR

ALEALLTVAGELRGPPLQLDTGQLLKIAKRGGVTAVEAVHAWRNALTGAPLNLTPDQVVAIASNGGGK

QALETVQRLLPVLCQDHGLTPEQVVAIANNGGKQALETVQRLLPVLCQAHGLTPDQVVAIANNNGGK

QALETVQRLLPVLCQAHGLTPAQVVAIASHDGGKQALETVQRLLPVLCQDHGLTPDQVVAIASHDGGK

QALETVQRLLPVLCQDHGLTPEQVVAIASHDGGKQALETVQRLLPVLCQAHGLTPDQVVAIASHDGGK

QALETVQRLLPVLCQAHGLTPAQVVAIANNGGKQALETVQRLLPVLCQDHGLTPDQVVAIANNNGGK

QALETVQRLLPVLCQDHGLTPEQVVAIASHDGGKQALETVQRLLPVLCQAHGLTPDQVVAIANNGGK

QALETVQRLLPVLCQAHGLTPAQVVAIASNIGGKQALETVQRLLPVLCQDHGLTPDQVVAIANNNGGK

QALETVQRLLPVLCQDHGLTPEQVVAIANNGGKQALETVQRLLPVLCQAHGLTPDQVVAIANNNGGK

QALETVQRLLPVLCQAHGLTPAQVVAIANNGGKQALETVQRLLPVLCQDHGLTPDQVVAIASNGGGK

QALETVQRLLPVLCQDHGLTPEQVVAIANNGGKQALETVQRLLPVLCQAHGLTPEQVVAIASNGGGR

PALESIVAQLSRPDPALAALTNDHLVALACLGGRPALDAVKKGLPHAPALIKRTNRRIPERTSHRVAD

HAQVVRVLGFFQCHSHPAQAFDDAMTQFGMSGGGSGRADALDDFDLDMLGSDALDDFDLDMLGSDALD

DFDLDMLGSDALDDFDLDML<u>HHHHHH</u>

(-30)GFP:
(SEQ ID NO: 40)
MGASKGEELFDGVVPILVELDGDVNGHEFSVRGEGEGDATEGELTLKFICTTGELPVPWPTLVTTLTY

GVQCFSDYPDHMDQHDFFKSAMPEGYVQERTISFKDDGTYKTRAEVKFEGDTLVNRIELKGIDFKEDG

NILGHKLEYNFNSHDVYITADKQENGIKAEFEIRHNVEDGSVQLADHYQQNTPIGDGPVLLPDDHYLS

TESALSKDPNEDRDHMVLLEFVTAAGIDHGMDELYK

N-terminal TALE domain:
(SEQ ID NO: 41)
APKKKRKVGIHRGVPMVDLRTLGYSQQQQEKIKPKVRSTVAQHHEALVGHGFTHAHIVALSQHPAALG

TVAVKYQDMIAALPEATHEAIVGVGKQWSGARALEALLTVAGELRGPPLQLDTGQLLKIAKRGGVTAV

EAVHAWRNALTGAPLNL

C-terminal TALE domain:
(SEQ ID NO: 42)
LESIVAQLSRPDPALAALTNDHLVALACLGGRPALDAVKKGLPHAPALIKRTNRRIPERTSHRVADHA

QVVRVLGFFQCHSHPAQAFDDAMTQFGMSGGGS

VP64 activation domain:
(SEQ ID NO: 35)
GRADALDDFDLDMLGSDALDDFDLDMLGSDALDDFDLDMLGSDALDDFDLDML Compositions of Functional Effector Proteins and Cationic Polymers Certain aspects of the disclosure relate to the use of cationic polymers for the delivery of effector proteins (e.g., nucleases, transcriptional activators/repressors, recombinases, Cas9 proteins including variants and fusions thereof, etc.), for example as opposed to delivering "naked" protein preparations. As with cationic lipids, aspects of the present disclosure relate to the recognition that anionic proteins or protein complexes (including those proteins associated with nucleic acids) can take advantage of electrostatics-driven encapsulation by and/or association with cationic polymers for delivery of functional effector proteins. While few proteins natively possess the density of negative charges found in the phosphate backbone of nucleic acids, translational fusion to, or non-covalent association with, an anionic carrier such as a negatively supercharged protein or a nucleic acid as described herein render the resulting effector protein or protein complex sufficiently anionic to drive efficient encapsulation/association of such protein cargoes by cationic polymers.

In some embodiments, association or fusion with an engineered supernegatively charged GFP is capable of driving efficient encapsulation/association and delivery of proteins into cultured mammalian cells by cationic polymers. In some embodiments, Cas9 protein associated with polyanionic guide RNAs (gRNA) can be efficiently delivered in functional form into mammalian cells using cationic polymers. Accordingly, in some embodiments, a composition comprising a Cas9 protein and a cationic polymer is provided, wherein the Cas9 protein is associated with a gRNA, and the composition is capable of delivering the Cas9 protein to the interior of a cell. In some embodiments, delivery of Cas9:gRNA complexes using cationic polymers results in at least a 2-fold, 3-fold, 4-fold, 5-fold, 6-fold, 7-fold, 8-fold, 9-fold, 10-fold, 11-fold, 12-fold, 13-fold, 14-fold, 15-fold, 20-fold or 25-fold or higher on-target:off-target modification ratio as compared with plasmid transfection of the Cas9 protein.

Accordingly, some aspects of the disclosure provide compositions comprising a Cas9 protein (e.g., as described herein; see e.g., Cas9 effector proteins below) and a cationic polymer capable of delivering the Cas9 protein to the interior of a cell. In some embodiments, the Cas9 protein is associated with a gRNA, which e.g., provides anionic charge to the complex thereby allowing the Cas9:gRNA complex to be encapsulated and/or associated with the cationic polymers. In some embodiments, the Cas9 protein need not be associated with a gRNA for effective encapsulation by and/or association with a cationic lipid, but instead is associated with a negatively supercharged protein, as described herein. In some embodiments where a Cas9 protein is associated with a negatively supercharged protein, the Cas9 protein is also associated with a gRNA. In some embodiments, the Cas9 protein is a wild type Cas9 protein, a fragment of a wild type Cas9 protein, or a variant of a wild type Cas9 protein. In some embodiments, the Cas9 protein comprises a dCas9 domain (e.g., as described herein). In some embodiments, the Cas9 protein is a fusion protein comprising a dCas9 domain (e.g., as described herein). In some embodiments, the Cas9 protein is a Cas9 nickase.

In other embodiments, compositions comprising an effector protein (e.g., other than a Cas9 protein) and a cationic polymer are provided which are capable of delivering the effector protein to the interior of a cell (e.g., to the nucleus of the cell). The effector protein is either naturally negatively charged, is modified to have a net overall negative charge, or is associated with a negatively supercharged protein, as described herein. In some embodiments, the effector protein is any effector protein described herein. In some embodiments, the effector protein is a recombinase, e.g., any recombinase described herein. In some embodiments, the recombinase is Cre recombinase. In some embodiments, the Cre recombinase comprises the amino acid sequence of SEQ ID NO:32 (e.g., with or without the 6×His tag). In some embodiments, the Cre recombinase comprises an amino acid sequence that is at least 80%, at least 85%, at least 90%, at least 95%, at least 98%, or at least 99% identical to the amino acid sequence of SEQ ID NO:32 (e.g., with or without the 6×His tag). In some embodiments, the Cre recombinase is fused to a supercharged protein (e.g., +36 GFP or −30GFP). In some embodiments, the Cre recombinase fused to a supercharged protein comprises the amino acid sequence of SEQ ID NO:33 (e.g., with or without the 6×His tag) or SEQ ID NO:34 (e.g., with or without the 6×His tag), or comprises an amino acid sequence that is at least 80%, at least 85%, at least 90%, at least 95%, at least 98%, or at least 99% identical to the amino acid sequence of SEQ ID NO:33 or SEQ ID NO:34 (e.g., with or without the 6×His tag). In some embodiments, the effector protein is a TALE protein, (e.g., as described herein including those provided in the Examples). In some embodiments, the TALE protein comprises one or more of a VP64 transcriptional activator domain (e.g., SEQ ID NO:35). In some embodiments, the TALE protein with a VP64 transcriptional activator domain further comprises an amino acid sequence selected from the group consisting of SEQ ID NO:36-39 (e.g., with or without the 6×His tag). In some embodiments, the TALE protein with a VP64 transcriptional activator domain comprises an amino acid sequence that is at least 80%, at least 85%, at least 90%, at least 95%, at least 98%, or at least 99% identical to an amino acid sequence selected from the group consisting of SEQ ID NO:36-39 (e.g., with or without the 6×His tag). In some embodiments, the TALE effector protein comprises a (−30)GFP domain (e.g., SEQ ID NO:21 or SEQ ID NO:40), a N-terminal region of a TALE domain (e.g., SEQ ID NO:41), a variable repeat domain (e.g., an 18.5mer repeat domain as provided in Maeder et al., "Robust, synergistic regulation of human gene expression using TALE activators." Nat. Methods. 2013; 10, 243-245), a C-terminal TALE domain (e.g., SEQ ID NO:42), a VP64 activation domain (e.g., SEQ ID NO:35), and optionally one or more linkers (e.g., GGS(9), SEQ ID NO: 252) between any domain and optionally a sequence tag (e.g., 6×His. SEQ ID NO: 253).

In some embodiments, the compositions comprising a Cas9 protein or other effector proteins described herein and a cationic polymer exhibit low toxicity when administered to a population of cells (e.g., in vitro or in vivo). In some embodiments, at least 60%, at least 65%, at least 70%, at least 75%, at least 80%, at least 85%, at least 90%, at least 95%, or at least 99% of the cells in a population are viable following administration of an inventive composition comprising a Cas9 protein or other effector protein and cationic polymers. Methods for assessing the toxicity of a composition when administered to a population of cells are well known in the art and include those described in the Examples.

Cas9 Effector Proteins

In some embodiments, effector proteins comprising a RNA-programmable protein (or fragment or variant thereof) is delivered to a target cell by a system or method provided herein. In some embodiments, an RNA-guided or RNA-programmable nuclease is delivered to a target cell by a system or method provided herein. In some embodiments, the RNA-programmable protein is a Cas9 nuclease, a Cas9 variant, or a fusion of a Cas9 protein, which is delivered to a target cell by a system or method provided herein.

In some embodiments, the RNA-programmable nuclease is a (CRISPR-associated system) Cas9 endonuclease, for example, Cas9 (Csn 1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., *Proc. Natl. Acad. Sci. U.S.A.* 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., *Nature* 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference. Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. Science 339, 819-823 (2013); Mali, P. et al. RNA-guided human genome engineering via Cas9. Science 339, 823-826 (2013); Hwang, W. Y. et al. Efficient genome editing in zebrafish using a CRISPR-Cas system. Nature biotechnology 31, 227-229 (2013); Jinek, M. et al. RNA-programmed genome editing in human cells. eLife 2, e00471 (2013); Dicarlo, J. E. et al. Genome engineering in *Saccharomyces cerevisiae* using CRISPR-Cas systems. Nucleic acids research (2013); Jiang, W. et al. RNA-guided editing of bacterial genomes using CRISPR-Cas systems. Nature biotechnology 31, 233-239 (2013); the entire contents of each of which are incorporated herein by reference).

A Cas9 nuclease may also be referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand that is not complementary to the crRNA is first cut endonucleolytically, then trimmed 3'-5' exonucleolytically. In nature, DNA-binding and cleavage typically requires protein and both RNA. However, single guide RNAs ("sgRNA", or simply "gNRA") can be engineered so as to incorporate aspects of both the crRNA and tracrRNA into a single RNA species. See e.g., Jinek M., Chylinski K., Fonfara I., Hauer M., Doudna J. A., Charpentier E. Science 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference).

Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, proteins comprising Cas9 proteins or fragments thereof are referred to as "Cas9 variants." A Cas9 variant shares homology to Cas9, or a fragment thereof. For example, a Cas9 variant is at least about 70% identical, at least about 80% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain, an N-terminal domain or a C-terminal domain, etc.), such that the fragment is at least about 70% identical, at least about 80% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO:43 (nucleotide); SEQ ID NO:44 (amino acid)). In some embodiments, a Cas9 protein has an inactive (e.g., an inactivated) DNA cleavage domain. A nuclease-inactivated Cas9 protein may interchangeably be referred to as a "dCas9" protein (for nuclease "dead" Cas9). In some embodiments, dCas9 corresponds to, or comprises in part or in whole, the amino acid set forth as SEQ ID NO:45, below. In some embodiments, variants of dCas9 (e.g., variants of SEQ ID NO:45) are provided. For example, in some embodiments, variants having mutations other than D10A and H840A are provided, which result in nuclease inactivated Cas9 (dCas9). Such mutations, by way of example, include other amino acid substitutions at D10 and H840, or other substitutions within the nuclease domain of Cas9 (e.g., substitutions in the HNH nuclease subdomain and/or the RuvC1 subdomain). In some embodiments, variants or homologues of dCas9 (e.g., variants of SEQ ID NO:45) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:45. In some embodiments, variants of dCas9 (e.g., variants of SEQ ID NO:45) are provided having amino acid sequences which are shorter, or longer than SEQ ID NO:45, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more. In some embodiments, Cas9 "nickases" are provided which comprise a mutation which inactivates a single nuclease domain in Cas9. Such nickases induce a single strand break in a target nucleic acid as opposed to a double strand break.

Cas9

(SEQ ID NO: 43)
ATGGATAAGAAATACTCAATAGGCTTAGATATCGGCACAAATAGCGTCGGATGGGCGGTGATCACTGATGATTAT
AAGGTTCCGTCTAAAAAGTTCAAGGTTCTGGGAAATACAGACCGCCACAGTATCAAAAAAAATCTTATAGGGCT
CTTTTATTTGGCAGTGGAGAGACAGCGGAAGCGACTCGTCTCAAACGGACAGCTCGTAGAAGGTATACACGTCGG
AAGAATCGTATTTGTTATCTACAGGAGATTTTTTCAAATGAGATGGCGAAAGTAGATGATAGTTTCTTTCATCGA
CTTGAAGAGTCTTTTTTGGTGGAAGAAGACAAGAAGCATGAACGTCATCCTATTTTTGGAAATATAGTAGATGAA
GTTGCTTATCATGAGAAATATCCAACTATCTATCATCTGCGAAAAAAATTGGCAGATTCTACTGATAAAGCGGAT
TTGCGCTTAATCTATTTGGCCTTAGCGCATATGATTAAGTTTCGTGGTCATTTTTTGATTGAGGGAGATTTAAAT
CCTGATAATAGTGATGTGGACAAACTATTTATCCAGTTGGTACAAATCTACAATCAATTATTTGAAGAAACCCT
ATTAACGCAAGTAGAGTAGATGCTAAAGCGATTCTTTCTGCACGATTGAGTAAATCAAGACGATTAGAAAATCTC
ATTGCTCAGCTCCCCGGTGAGAAGAGAAATGGCTTGTTTGGGAATCTCATTGCTTTGTCATTGGGATTGACCCCT
AATTTTAAATCAAATTTTGATTTGGCAGAAGATGCTAAATTACAGCTTTCAAAAGATACTTACGATGATGATTTA
GATAATTTATTGGCGCAAATTGGAGATCAATATGCTGATTTGTTTTGGCAGCTAAGAATTTATCAGATGCTATT
TTACTTTCAGATATCCTAAGAGTAAATAGTGAAATAACTAAGGCTCCCCTATCAGCTTCAATGATTAAGCGCTAC
GATGAACATCATCAAGACTTGACTCTTTTAAAAGCTTTAGTTCGACAACAACTTCCAGAAAAGTATAAAGAAATC
TTTTTTGATCAATCAAAAAACGGATATGCAGGTTATATTGATGGGGGAGCTAGCCAAGAAGAATTTTATAAATTT
ATCAAACCAATTTTAGAAAAAATGGATGGTACTGAGGAATTATTGGTGAAACTAAATCGTGAAGATTTGCTGCGC
AAGCAACGGACCTTTGACAACGGCTCTATTCCCCATCAAATTCACTTGGGTGAGCTGCATGCTATTTTGAGAAGA
CAAGAAGACTTTTATCCATTTTTAAAAGACAATCGTGAGAAGATTGAAAAAATCTTGACTTTTCGAATTCCTTAT
TATGTTGGTCCATTGGCGCGTGGCAATAGTCGTTTTGCATGGATGACTCGGAAGTCTGAAGAAACAATTACCCCA
TGGAATTTTGAAGAAGTTGTCGATAAAGGTGCTTCAGCTCAATCATTTATTGAACGCATGACAAACTTTGATAAA
AATCTTCCAAATGAAAAGTACTACCAAAACATAGTTTGCTTTATGAGTATTTTACGGTTTATAACGAATTGACA
AAGGTCAAATATGTTACTGAGGGAATGCGAAAACCAGCATTTCTTTCAGGTGAACAGAAGAAAGCCATTGTTGAT
TTACTCTTCAAAACAAATCGAAAAGTAACCGTTAAGCAATTAAAAGAAGATTATTTCAAAAAAATAGAATGTTTT
GATAGTGTTGAAATTTCAGGAGTTGAAGATAGATTTAATGCTTCATTAGGCGCCTACCATGATTTGCTAAAAATT
ATTAAAGATAAAGATTTTTTGGATAATGAAGAAAATGAAGATATCTTAGAGGATATTGTTTTAACATTGACCTTA
TTTGAAGATAGGGGGATGATTGAGGAAAGACTTAAAACATATGCTCACCTCTTTGATGATAAGGTGATGAAACAG
CTTAAACGTCGCCGTTATACTGGTTGGGGACGTTTGTCTCGAAAATTGATTAATGGTATTAGGGATAAGCAATCT
GGCAAAACAATATTAGATTTTTTGAAATCAGATGGTTTTGCCAATCGCAATTTTATGCAGCTGATCCATGATGAT
AGTTTGACATTTAAAGAAGATATTCAAAAAGCACAGGTGTCTGGACAAGGCCATAGTTTACATGAACAGATTGCT
AACTTAGCTGGCAGTCCTGCTATTAAAAAAGGTATTTTACAGACTGTAAAAATTGTTGATGAACTGGTCAAAGTA
ATGGGGCATAAGCCAGAAAATATCGTTATTGAAATGGCACGTGAAAATCAGACAACTCAAAAGGGCCAGAAAAAT
TCGCGAGAGCGTATGAAACGAATCGAAGAAGGTATCAAAGAATTAGGAAGTCAGATTCTTAAAGAGCATCCTGTT
GAAAATACTCAATTGCAAAATGAAAAGCTCTATCTCTATTATCTACAAAATGGAAGAGACATGTATGTGGACCAA
GAATTAGATATTAATCGTTTAAGTGATTATGATGTCGATCACATTGTTCCACAAAGTTTCATTAAAGACGATTCA
ATAGACAATAAGGTACTAACGCGTTCTGATAAAAATCGTGGTAAATCGGATAACGTTCCAAGTGAAGAAGTAGTC
AAAAAGATGAAAAACTATTGGAGACAACTTCTAAACGCCAAGTTAATCACTCAACGTAAGTTTGATAATTTAACG
AAAGCTGAACGTGGAGGTTTGAGTGAACTTGATAAAGCTGGTTTTATCAAACGCCAATTGGTTGAAACTCGCCAA
ATCACTAAGCATGTGGCACAAATTTTGGATAGTCGCATGAATACTAAATACGATGAAAATGATAAACTTATTCGA
GAGGTTAAAGTGATTACCTTAAAATCTAAATTAGTTTCTGACTTCCGAAAAGATTTCCAATTCTATAAAGTACGT
GAGATTAACAATTACCATCATGCCCATGATGCGTATCTAAATGCCGTCGTTGGAACTGCTTTGATTAAGAAATAT

-continued

```
CCAAAACTTGAATCGGAGTTTGTCTATGGTGATTATAAAGTTTATGATGTTCGTAAAATGATTGCTAAGTCTGAG

CAAGAAATAGGCAAAGCAACCGCAAAATATTTCTTTTACTCTAATATCATGAACTTCTTCAAAACAGAAATTACA

CTTGCAAATGGAGAGATTCGCAAACGCCCTCTAATCGAAACTAATGGGGAAACTGGAGAAATTGTCTGGGATAAA

GGGCGAGATTTTGCCACAGTGCGCAAAGTATTGTCCATGCCCCAAGTCAATATTGTCAAGAAAACAGAAGTACAG

ACAGGCGGATTCTCCAAGGAGTCAATTTTACCAAAAAGAAATTCGGACAAGCTTATTGCTCGTAAAAAGACTGG

GATCCAAAAAAATATGGTGGTTTTGATAGTCCAACGGTAGCTTATTCAGTCCTAGTGGTTGCTAAGGTGGAAAAA

GGGAAATCGAAGAAGTTAAAATCCGTTAAAGAGTTACTAGGGATCACAATTATGGAAAGAAGTTCCTTTGAAAAA

AATCCGATTGACTTTTTAGAAGCTAAAGGATATAAGGAAGTTAAAAAAGACTTAATCATTAAACTACCTAAATAT

AGTCTTTTTGAGTTAGAAAACGGTCGTAAACGGATGCTGGCTAGTGCCGGAGAATTACAAAAAGGAAATGAGCTG

GCTCTGCCAAGCAAATATGTGAATTTTTTATATTTAGCTAGTCATTATGAAAAGTTGAAGGGTAGTCCAGAAGAT

AACGAACAAAAACAATTGTTTGTGGAGCAGCATAAGCATTATTTAGATGAGATTATTGAGCAAATCAGTGAATTT

TCTAAGCGTGTTATTTTAGCAGATGCCAATTTAGATAAAGTTCTTAGTGCATATAACAAACATAGAGACAAACCA

ATACGTGAACAAGCAGAAAATATTATTCATTTATTTACGTTGACGAATCTTGGAGCTCCCGCTGCTTTTAAATAT

TTTGATACAACAATTGATCGTAAACGATATACGTCTACAAAAGAAGTTTTAGATGCCACTCTTATCCATCAATCC

ATCACTGGTCTTTATGAAACACGCATTGATTTGAGTCAGCTAGGAGGTGACTGA
```

(SEQ ID NO: 44)

MDKK<u>YSIGLAIGTNSVGWAVITDEYKVPSKKFKVLGNTDRHSIKKNLIGALLFDSGETA</u>EATRLKRTARRRYTRR
KNRICYLQEIFSNEMAKVDDSFFHRLEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENPINASGVDAKAILSARLSKSRRLENL
IAQLPGEKKNGLFGNLIALSLGLTPNFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEIFFDQSKNGYAGYIDGGASQEEFYKF
IKPILEKMDGTEELLVKLNREDLLRKQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDKNLPNEKVLPKHSLLYEYFTVYNELT
KVKYVTEGMRKPAFLSGEQKKAIVDLLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQLKRRRYTGWGRLSRKLINGIRDKQS
GKTILDFLKSDGFANRNFMQLIHDDSLTFKEDIQKAQVSGQG<u>DSLHEHIANLAGSPAIKKGILQTVKVVDELVKV</u>
<u>MGRHKPENIVIEMARE</u>NQTTQK<u>GQKNSRERMKRIEEGIKELGSQILKEHPVENTQLQNEKLYLYYLQNGRDMYVD</u>
<u>QELDINRLSDYDVDHIVPQSFLKDDSIDNKVLTRSDKNRGKSDNVPSEEVVKKMKNYWRQLLNAKLITQRKFDNL</u>
<u>TKAERG</u><u>GLSELDKAGFIKRQLVETRQITKHVAQILDSRMNTKYDENDKLIREVKVITLKSKLVSDFRKDFQFYKV</u>
<u>REINNYHHAHDAYLNAVVGTALIKKYPKLESEFVYGDYKVYDVRKMIAKSEQEIGKATAKYFFYSNIMNFFKTEI</u>
<u>TLANGEIRKRPLIETNGETGEIVWDKGRDFATVRKVLSMPQVNIVKKTEVQT</u>GGFSKESILPKRNSDKLIARKKD
WDPKKYGGFDSPTVAYSVLVVAKVEKGKSKKLKSVKELLGITIMERSSFEKNPIDFLEAKGYKEVKKDLIIKLPK
YSLFELENGRKRMLASAGELQKGNELALPSKYVNFLYLASHYEKLKGSPEDNEQKQLFVEQHKHYLDEIIEQISE
FSKRVILADANLDKVLSAYNKHRDKPIREQAENIIHLFTLTNLGAPAAFKYFDTTIDRKRYTSTKEVLDATLIHQ
SITGLYETRIDLSQLGGD (single underline: HNH domain; double underline: RuvC domain)

dCas9 (D10A and H840A):

(SEQ ID NO: 45)

MDKK<u>YSIGLAIGTNSVGWAVITDEYKVPSKKFKVLGNTDRHSIKKNLIGALLFDSGETA</u>EATRLKRTARRRYTRR
KNRICYLQEIFSNEMAKVDDSFFHRLEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENPINASGVDAKAILSARLSKSRRLENL
IAQLPGEKKNGLFGNLIALSLGLTPNFKSNFDLAEDAKLQLSKDTYDDDLDNLLAQIGDQYADLFLAAKNLSDAI

```
LLSDILRVNTEITKAPLSASMIKRYDEHHQDLTLLKALVRQQLPEKYKEIFFDQSKNGYAGYIDGGASQEEFYKF

IKPILEKMDGTEELLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNEKLYLYYLQNGRDMYVD

QELDINRLSDYDVDAIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQ

SITGLYETRIDLSQLGGD
(single underline: HNH domain; double underline: RuvC domain)

Cas9 nickase (D10A):
                                                        (SEQ ID NO: 46)
MDKKYSIGLAIGTNSVGWAVITDEYKVPSKKFKVLGNTDRHSIKKNLIGALLFDSGETAEATRLKRTARRRYTRR

KNRICYLQEIFSNEMAKVDDSFFHRLEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENPINASGVDAKAILSARLSKSRRLENL

IAQLPGEKKNGLFGNLIALSLGLTPNFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEIFFDQSKNGYAGYIDGGASQEEFYKF

IKPILEKMDGTEELLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNEKLYLYYLQNGRDMYVD

QELDINRLSDYDVDHIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQ

SITGLYETRIDLSQLGGD
```

In some embodiments, fusion proteins comprising a Cas9 protein are provided for use in any of the compositions and methods described herein. In some embodiments, the fusion protein comprises a dCas9 protein (e.g., as described herein). In some embodiments, the fusion protein comprises a linker (e.g., as described herein) between dCas9 and one or more domains (e.g., enzymatic domains). In some embodiments, the fusion protein comprises dCas9 and a transcriptional activator domain, a transcriptional repressor domain, a recombinase domain, a gene editing domain (e.g., a deaminase doman), or an epigenetic modifier domain.

In some embodiments, the general architecture of exemplary fusion proteins provided herein comprises the structure:

[NH$_2$]-[enzymatic domain]-[dCas9]-[COOH] or

[NH$_2$]-[dCas9]-[enzymatic domain]-[COOH];

wherein NH₂ is the N-terminus of the fusion protein, COOH is the C-terminus of the fusion protein, and the enzymatic domain comprises a nuclease domain (e.g., FokI), a recombinase catalytic domain (e.g., Hin, Gin, or Tn3 recombinase domains), a nucleic acid-editing domain (e.g., a deaminase domain), a transcriptional activator domain (e.g., VP64, p65), a transcriptional repressor domain (e.g., KRAB, SID), or an epigenetic modifier (e.g., LSD1 histone demethylase, TET1 hydroxylase).

Additional features may be present, for example, one or more linker sequences between certain domains. Other exemplary features that may be present are localization sequences, such as nuclear localization sequences (NLS; e.g., MAPKKKRKVGIHRGVP (SEQ ID NO:47)); cytoplasmic localization sequences; export sequences, such as nuclear export sequences; or other localization sequences, as well as sequence tags that are useful for solubilization, purification, or detection of the fusion proteins. Suitable localization signal sequences and sequences of protein tags are provided herein and are known in the art, and include, but are not limited to, biotin carboxylase carrier protein (BCCP) tags, myc-tags, calmodulin-tags, FLAG-tags (e.g., 3×FLAG TAG: MDYKDHDGDYKDHDIDYKDDDDK (SEQ ID NO:48)), hemagglutinin (HA) tags, polyhistidine tags, also referred to as histidine tags or His-tags, maltose binding protein (MBP)-tags, nus-tags, glutathione-S-transferase (GST) tags, green fluorescent protein (GFP) tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art.

In some embodiments, the enzymatic domain comprises a nuclease or a catalytic domain thereof. For example, in some embodiments, the general architecture of exemplary ligand-dependent dCas9 fusion proteins with a nuclease domain comprises the structure:

[NH₂]-[NLS]-[dCas9]-[nuclease]-[COOH],

[NH₂]-[NLS]-[nuclease]-[dCas9]-[COOH],

[NH₂]-[dCas9]-[nuclease]-[COOH], or

[NH₂]-[nuclease]-[dCas9]-[COOH];

wherein NLS is a nuclear localization signal, NH₂ is the N-terminus of the fusion protein, and COOH is the C-terminus of the fusion protein. In some embodiments, a linker is inserted between the dCas9 and the nuclease domain. In some embodiments, a linker is inserted between the NLS and the nuclease and/or dCas9 domain. In some embodiments, the NLS is located C-terminal of the nuclease and/or the dCas9 domain. In some embodiments, the NLS is located between the nuclease and the dCas9 domain. Additional features, such as sequence tags, may also be present. In some aspects, the nuclease domain is a nuclease requiring dimerization (e.g., the coming together of two monomers of the nuclease) in order to cleave a target nucleic acid (e.g., DNA). In some embodiments, the nuclease domain is a monomer of the FokI DNA cleavage domain. The FokI DNA cleavage domain is known, and in some aspects corresponds to amino acids 388-583 of FokI (NCBI accession number J04623). In some embodiments, the FokI DNA cleavage domain corresponds to amino acids 300-583, 320-583, 340-583, or 360-583 of FokI. See also Wah et al., "Structure of FokI has implications for DNA cleavage" Proc. Natl. Acad. Sci. USA. 1998; 1; 95(18):10564-9; Li et al., "TAL nucleases (TALNs): hybrid proteins composed of TAL effectors and FokI DNA-cleavage domain" Nucleic Acids Res. 2011; 39(1):359-72; Kim et al., "Hybrid restriction enzymes: zinc finger fusions to Fok I cleavage domain" Proc. Natl Acad. Sci. USA. 1996; 93:1156-1160; the entire contents of each are herein incorporated by reference). In some embodiments, the FokI DNA cleavage domain corresponds to, or comprises in part or whole, the amino acid sequence set forth as SEQ ID NO:49. In some embodiments, the FokI DNA cleavage domain is a variant of FokI (e.g., a variant of SEQ ID NO:49), as described herein. Other exemplary compositions and methods of using dCas9-nuclease fusion proteins can be found in U.S. patent application U.S. Ser. No. 14/320,498; titled "Cas9-FokI fusion Proteins and Uses Thereof," filed Jun. 30, 2014; the entire contents of which are incorporated herein by reference.

FokI nuclease domain:
(SEQ ID NO: 49)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINF fCas9 (e.g., dCas9-NLS-GGS3linker-FokI):
(SEQ ID NO: 50)
ATGGATAAAAAGTATTCTATTGGTTTAGCTATCGGCACTAATTCCGTTGG

ATGGGCTGTCATAACCGATGAATACAAAGTACCTTCAAAGAAATTTAAGG

TGTTGGGGAACACAGACCGTCATTCGATTAAAAAGAATCTTATCGGTGCC

CTCCTATTCGATAGTGGCGAAACGGCAGAGGCGACTCGCCTGAAACGAAC

CGCTCGGAGAAGGTATACACGTCGCAAGAACCGAATATGTTACTTACAAG

AAATTTTTAGCAATGAGATGGCCAAAGTTGACGATTCTTTCTTTCACCGT

TTGGAAGAGTCCTTCCTTGTCGAAGAGGACAAGAAACATGAACGGCACCC

CATCTTTGGAAACATAGTAGATGAGGTGGCATATCATGAAAAGTACCCAA

CGATTTATCACCTCAGAAAAAAGCTAGTTGACTCAACTGATAAAGCGGAC

CTGAGGTTAATCTACTTGGCTCTTGCCCATATGATAAAGTTCCGTGGGCA

CTTTCTCATTGAGGGTGATCTAAATCCGGACAACTCGGATGTCGACAAAC

TGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTC

TAAATCCCGACGGCTAGAAAACCTGATCGCACAATTACCCGGAGAGAAGA

AAAATGGGTTGTTCGGTAACCTTATAGCGCTCTCACTAGGCCTGACACCA

AATTTTAAGTCGAACTTCGACTTAGCTGAAGATGCCAAATTGCAGCTTAG

TAAGGACACGTACGATGACGATCTCGACAATCTACTGGCACAAATTGGAG

ATCAGTATGCGGACTTATTTTTGGCTGCCAAAAACCTTAGCGATGCAATC

CTCCTATCTGACATACTGAGAGTTAATACTGAGATTACCAAGGCGCCGTT

ATCCGCTTCAATGATCAAAAGGTACGATGAACATCACCAAGACTTGACAC

TTCTCAAGGCCCTAGTCCGTCAGCAACTGCCTGAGAAATATAAGGAAATA

TTCTTTGATCAGTCGAAAAACGGGTACGCAGGTTATATTGACGGCGGAGC

GAGTCAAGAGGAATTCTACAAGTTTATCAAACCCATATTAGAGAAGATGG

ATGGGACGGAAGAGTTGCTTGTAAAACTCAATCGCGAAGATCTACTGCGA

AAGCAGCGGACTTTCGACAACGGTAGCATTCCACATCAAATCCACTTAGG

-continued

CGAATTGCATGCTATACTTAGAAGGCAGGAGGATTTTTATCCGTTCCTCA

AAGACAATCGTGAAAAGATTGAGAAAATCCTAACCTTTCGCATACCTTAC

TATGTGGGACCCCTGGCCCGAGGGAACTCTCGGTTCGCATGGATGACAAG

AAAGTCCGAAGAAACGATTACTCCATGGAATTTTGAGGAAGTTGTCGATA

AAGGTGCGTCAGCTCAATCGTTCATCGAGAGGATGACCAACTTTGACAAG

AATTTACCGAACGAAAAGTATTGCCTAAGCACAGTTTACTTTACGAGTA

TTTCACAGTGTACAATGAACTCACGAAAGTTAAGTATGTCACTGAGGGCA

TGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGA

CTACTTTAAGAAAATTGAATGCTTCGATTCTGTCGAGATCTCCGGGGTAG

AAGATCGATTTAATGCGTCACTTGGTACGTATCATGACCTCCTAAAGATA

ATTAAAGATAAGGACTTCCTGGATAACGAAGAGAATGAAGATATCTTAGA

AGATATAGTGTTGACTCTTACCCTCTTTGAAGATCGGGAAATGATTGAGG

AAAGACTAAAAACATACGCTCACCTGTTCGACGATAAGGTTATGAAACAG

TTAAAGAGGCGTCGCTATACGGGCTGGGGACGATTGTCGCGGAAACTTAT

CAACGGGATAAGAGACAAGCAAAGTGGTAAAACTATTCTCGATTTTCTAA

AGAGCGACGGCTTCGCCAATAGGAACTTTATGCAGCTGATCCATGATGAC

TCTTTAACCTTCAAAGAGGATATACAAAAGGCACAGGTTTCCGGACAAGG

GGACTCATTGCACGAACATATTGCGAATCTTGCTGGTTCGCCAGCCATCA

AAAAGGGCATACTCCAGACAGTCAAAGTAGTGGATGAGCTAGTTAAGGTC

ATGGGACGTCACAAACCGGAAAACATTGTAATCGAGATGGCACGCGAAAA

TCAAACGACTCAGAAGGGGCAAAAAAACAGTCGAGAGCGGATGAAGAGAA

TAGAAGAGGGTATTAAAGAACTGGGCAGCCAGATCTTAAAGGAGCATCCT

GTGGAAAATACCCAATTGCAGAACGAGAAACTTTACCTCTATTACCTACA

AAATGGAAGGGACATGTATGTTGATCAGGAACTGGACATAAACCGTTTAT

CTGATTACGACGTCGATGCCATTGTACCCCAATCCTTTTTGAAGGACGAT

TCAATCGACAATAAAGTGCTTACACGCTCGGATAAGAACCGAGGGAAAAG

TGACAATGTTCCAAGCGAGGAAGTCGTAAAGAAAATGAAGAACTATTGGC

GGCAGCTCCTAAATGCGAAACTGATAACGCAAAGAAAGTTCGATAACTTA

ACTAAAGCTGAGAGGGGTGGCTTGTCTGAACTTGACAAGGCCGGATTTAT

TAAACGTCAGCTCGTGGAAACCCGCCAAATCACAAAGCATGTTGCACAGA

TACTAGATTCCCGAATGAATACGAAATACGACGAGAACGATAAGCTGATT

CGGGAAGTCAAAGTAATCACTTTAAAGTCAAAATTGGTGTCGGACTTCAG

AAAGGATTTTCAATTCTATAAAGTTAGGGAGATAAATAACTACCACCATG

CGCACGACGCTTATCTTAATGCCGTCGTAGGGACCGCACTCATTAAGAAA

TACCCGAAGCTAGAAAGTGAGTTTGTGTATGGTGATTACAAAGTTTATGA

CGTCCGTAAGATGATCGCGAAAAGCGAACAGGAGATAGGCAAGGCTACAG

CCAAATACTTCTTTTATTCTAACATTATGAATTTCTTTAAGACGGAAATC

ACTCTGGCAAACGGAGAGATACGCAAACGACCTTTAATTGAAACCAATGG

GGAGACAGGTGAAATCGTATGGGATAAGGGCCGGGACTTCGCGACGGTGA

GAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGA

TAAGCTCATCGCTCGTAAAAAGGACTGGGACCCGAAAAAGTACGGTGGCT

TCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAAC

GATTATGGAGCGCTCGTCTTTTGAAAAGAACCCCATCGACTTCCTTGAGG

CGAAAGGTTACAAGGAAGTAAAAAAGGATCTCATAATTAAACTACCAAAG

TATAGTCTGTTTGAGTTAGAAAATGGCCGAAAACGGATGTTGGCTAGCGC

CGGAGAGCTTCAAAAGGGGAACGAACTCGCACTACCGTCTAAATACGTGA

ATTTCCTGTATTTAGCGTCCCATTACGAGAAGTTGAAAGGTTCACCTGAA

GATAACGAACAGAAGCAACTTTTTGTTGAGCAGCACAAACATTATCTCGA

CGAAATCATAGAGCAAATTTCGGAATTCAGTAAGAGAGTCATCCTAGCTG

ATGCCAATCTGGACAAAGTATTAAGCGCATACAACAAGCACAGGGATAAA

CCCATACGTGAGCAGGCGGAAAATATTATCCATTTGTTTACTCTTACCAA

CCTCGGCGCTCCAGCCGCATTCAAGTATTTTGACACAACGATAGATCGCA

AACGATACACTTCTACCAAGGAGGTGCTAGACGCGACACTGATTCACCAA

TCCATCACGGGATTATATGAAACTCGGATAGATTTGTCACAGCTTGGGGG

TGACGGATCCCCCAAGAAGAAGAGGAAAGTCTCGAGCGACTACAAAGACC

ATGACGGTGATTATAAAGATCATGACATCGATTACAAGGATGACGATGAC

AAGGCTGCAGGATCAGGTGGAAGTGGCGGCAGCGGAGGTTCTGGATCCCA

ACTAGTCAAAAGTGAACTGGAGGAGAAGAAATCTGAACTTCGTCATAAAT

TGAAATATGTGCCTCATGAATATATTGAATTAATTGAAATTGCCAGAAAT

TCCACTCAGGATAGAATTCTTGAAATGAAGGTAATGGAATTTTTTATGAA

AGTTTATGGATATAGAGGTAAACATTTGGGTGGATCAAGGAAACCGGACG

GAGCAATTTATACTGTCGGATCTCCTATTGATTACGGTGTGATCGTGGAT

ACTAAAGCTTATAGCGGAGGTTATAATCTGCCAATTGGCCAAGCAGATGA

AATGCAACGATATGTCGAAGAAAATCAAACACGAAACAAACATATCAACC

CTAATGAATGGTGGAAAGTCTATCCATCTTCTGTAACGGAATTTAAGTTT

TTATTTGTGAGTGGTCACTTTAAAGGAAACTACAAAGCTCAGCTTACACG

ATTAAATCATATCACTAATTGTAATGGAGCTGTTCTTAGTGTAGAAGAGC

TTTTAATTGGTGGAGAAATGATTAAAGCCGGCACATTAACCTTAGAGGAA

GTCAGACGGAAATTTAATAACGGCGAGATAAACTTT fCas9 (e.g., NLS-dCas9-GGS3linker-FokI):
(SEQ ID NO: 51)
ATGGACTACAAAGACCATGACGGTGATTATAAAGATCATGACATCGATTA

CAAGGATGACGATGACAAGATGGCCCCCAAGAAGAAGAGGAAGGTGGGCA

TTCACCGCGGGTACCTATGGATAAAAAGTATTCTATTGGTTTAGCTATC

GGCACTAATTCCGTTGGATGGGCTGTCATAACCGATGAATACAAAGTACC

TTCAAAGAAATTTAAGGTGTTGGGGAACACAGACCGTCATTCGATTAAAA

AGAATCTTATCGGTGCCCTCCTATTCGATAGTGGCGAAACGGCAGAGGCG

ACTCGCCTGAAACGAACCGCTCGGAGAAGGTATACACGTCGCAAGAACCG

AATATGTTACTTACAAGAAATTTTTAGCAATGAGATGGCCAAAGTTGACG

```
ATTCTTTCTTTCACCGTTTGGAAGAGTCCTTCCTTGTCGAAGAGGACAAG
AAACATGAACGGCACCCCATCTTTGGAAACATAGTAGATGAGGTGGCATA
TCATGAAAAGTACCCAACGATTTATCACCTCAGAAAAAGCTAGTTGACT
CAACTGATAAAGCGGACCTGAGGTTAATCTACTTGGCTCTTGCCCATATG
ATAAAGTTCCGTGGGCACTTTCTCATTGAGGGTGATCTAAATCCGGACAA
CTCGGATGTCGACAAACTGTTCATCCAGTTAGTACAAACCTATAATCAGT
TGTTTGAAGAGAACCCTATAAATGCAAGTGGCGTGGATGCGAAGGCTATT
CTTAGCGCCCGCCTCTCTAAATCCCGACGGCTAGAAAACCTGATCGCACA
ATTACCCGGAGAGAAGAAAATGGGTTGTTCGGTAACCTTATAGCGCTCT
CACTAGGCCTGACACCAAATTTTAAGTCGAACTTCGACTTAGCTGAAGAT
GCCAAATTGCAGCTTAGTAAGGACACGTACGATGACGATCTCGACAATCT
ACTGGCACAAATTGGAGATCAGTATGCGGACTTATTTTTGGCTGCCAAAA
ACCTTAGCGATGCAATCCTCCTATCTGACATACTGAGAGTTAATACTGAG
ATTACCAAGGCGCCGTTATCCGCTTCAATGATCAAAAGGTACGATGAACA
TCACCAAGACTTGACACTTCTCAAGGCCCTAGTCCGTCAGCAACTGCCTG
AGAAATATAAGGAAATATTCTTTGATCAGTCGAAAAACGGGTACGCAGGT
TATATTGACGGCGGAGCGAGTCAAGAGGAATTCTACAAGTTTATCAAACC
CATATTAGAGAAGATGGATGGGACGGAAGAGTTGCTTGTAAAACTCAATC
GCGAAGATCTACTGCGAAAGCAGCGGACTTTCGACAACGGTAGCATTCCA
CATCAAATCCACTTAGGCGAATTGCATGCTATACTTAGAAGGCAGGAGGA
TTTTTATCCGTTCCTCAAAGACAATCGTGAAAAGATTGAGAAAATCCTAA
CCTTTCGCATACCTTACTATGTGGGACCCCTGGCCCGAGGGAACTCTCGG
TTCGCATGGATGACAAGAAAGTCCGAAGAACGATTACTCCATGGAATTT
TGAGGAAGTTGTCGATAAAGGTGCGTCAGCTCAATCGTTCATCGAGAGGA
TGACCAACTTTGACAAGAATTTACCGAACGAAAAAGTATTGCCTAAGCAC
AGTTTACTTTACGAGTATTTCACAGTGTACAATGAACTCACGAAAGTTAA
GTATGTCACTGAGGGCATGCGTAAACCCGCCTTTCTAAGCGGAGAACAGA
AGAAAGCAATAGTAGATCTGTTATTCAAGACCAACCGCAAAGTGACAGTT
AAGCAATTGAAAGAGGACTACTTTAAGAAAATTGAATGCTTCGATTCTGT
CGAGATCTCCGGGGTAGAAGATCGATTTAATGCGTCACTTGGTACGTATC
ATGACCTCCTAAAGATAATTAAAGATAAGGACTTCCTGGATAACGAAGAG
AATGAAGATATCTTAGAAGATATAGTGTTGACTCTTACCCTCTTTGAAGA
TCGGGAAATGATTGAGGAAAGACTAAAAACATACGCTCACCTGTTCGACG
ATAAGGTTATGAAACAGTTAAAGAGGCGTCGCTATACGGGCTGGGGACGA
TTGTCGCGGAAACTTATCAACGGGATAAGAGACAAGCAAAGTGGTAAAAC
TATTCTCGATTTTCTAAAGAGCGACGGCTTCGCCAATAGGAACTTTATGC
AGCTGATCCATGATGACTCTTTAACCTTCAAAGAGGATATACAAAAGGCA
CAGGTTTCCGGACAAGGGGACTCATTGCACGAACATATTGCGAATCTTGC
TGGTTCGCCAGCCATCAAAAAGGGCATACTCCAGACAGTCAAGTAGTGG
ATGAGCTAGTTAAGGTCATGGGACGTCACAAACCGGAAACATTGTAATC

GAGATGGCACGCGAAAATCAAACGACTCAGAAGGGGCAAAAAAACAGTCG
AGAGCGGATGAAGAGAATAGAAGAGGGTATTAAAGAACTGGGCAGCCAGA
TCTTAAAGGAGCATCCTGTGGAAAATACCCAATTGCAGAACGAGAAACTT
TACCTCTATTACCTACAAAATGGAAGGGACATGTATGTTGATCAGGAACT
GGACATAAACCGTTTATCTGATTACGACGTCGATGCCATTGTACCCCAAT
CCTTTTTGAAGGACGATTCAATCGACAATAAAGTGCTTACACGCTCGGAT
AAGAACCGAGGGAAAAGTGACAATGTTCCAAGCGAGGAAGTCGTAAAGAA
AATGAAGAACTATTGGCGGCAGCTCCTAAATGCGAAACTGATAACGCAAA
GAAAGTTCGATAACTTAACTAAAGCTGAGAGGGGTGGCTTGTCTGAACTT
GACAAGGCCGGATTTATTAAACGTCAGCTCGTGGAAACCCGCCAAATCAC
AAAGCATGTTGCACAGATACTAGATTCCCGAATGAATACGAAATACGACG
AGAACGATAAGCTGATTCGGGAAGTCAAAGTAATCACTTTAAAGTCAAAA
TTGGTGTCGGACTTCAGAAAGGATTTTCAATTCTATAAAGTTAGGGAGAT
AAATAACTACCACCATGCGCACGACGCTTATCTTAATGCCGTCGTAGGGA
CCGCACTCATTAAGAAATACCCGAAGCTAGAAAGTGAGTTTGTGTATGGT
GATTACAAAGTTTATGACGTCCGTAAGATGATCGCGAAAAGCGAACAGGA
GATAGGCAAGGCTACAGCCAAATACTTCTTTTATTCTAACATTATGAATT
TCTTTAAGACGGAAATCACTCTGGCAAACGGAGAGATACGCAAACGACCT
TTAATTGAAACCAATGGGGAGACAGGTGAAATCGTATGGGATAAGGGCCG
GGACTTCGCGACGGTGAGAAAAGTTTTGTCCATGCCCCAAGTCAACATAG
TAAAGAAAACTGAGGTGCAGACCGGAGGGTTTTCAAAGGAATCGATTCTT
CCAAAAAGGAATAGTGATAAGCTCATCGCTCGTAAAAAGGACTGGGACCC
GAAAAAGTACGGTGGCTTCGATAGCCCTACAGTTGCCTATTCTGTCCTAG
TAGTGGCAAAAGTTGAGAAGGGAAAATCCAAGAAACTGAAGTCAGTCAAA
GAATTATTGGGGATAACGATTATGGAGCGCTCGTCTTTTGAAAAGAACCC
CATCGACTTCCTTGAGGCGAAAGGTTACAAGGAAGTAAAAAAGGATCTCA
TAATTAAACTACCAAAGTATAGTCTGTTTGAGTTAGAAAATGGCCGAAAA
CGGATGTTGGCTAGCGCCGGAGAGCTTCAAAAGGGGAACGAACTCGCACT
ACCGTCTAAATACGTGAATTTCCTGTATTTAGCGTCCCATTACGAGAAGT
TGAAAGGTTCACCTGAAGATAACGAACAGAAGCAACTTTTTGTTGAGCAG
CACAAACATTATCTCGACGAAATCATAGAGCAAATTTCGGAATTCAGTAA
GAGAGTCATCCTAGCTGATGCCAATCTGGACAAAGTATTAAGCGCATACA
ACAAGCACAGGGATAAACCCATACGTGAGCAGGCGGAAAATATTATCCAT
TTGTTTACTCTTACCAACCTCGGCGCTCCAGCCGCATTCAAGTATTTTGA
CACAACGATAGATCGCAAACGATACACTTCTACCAAGGAGGTGCTAGACG
CGACACTGATTCACCAATCCATCACGGGATTATATGAAACTCGGATAGAT
TTGTCACAGCTTGGGGGTGACTCAGGTGGAAGTGGCGGCAGCGGAGGTTC
TGGATCCCAACTAGTCAAAGTGAACTGGAGGAGAAGAAATCTGAACTTC
GTCATAAATTGAAATATGTGCCTCATGAATATATTGAATTAATTGAAATT
GCCAGAAATTCCACTCAGGATAGAATTCTTGAAATGAAGGTAATGGAATT
TTTTATGAAAGTTTATGGATATAGAGGTAAACATTTGGGTGGATCAAGGA
```

```
AACCGGACGGAGCAATTTATACTGTCGGATCTCCTATTGATTACGGTGTG
ATCGTGGATACTAAAGCTTATAGCGGAGGTTATAATCTGCCAATTGGCCA
AGCAGATGAAATGCAACGATATGTCGAAGAAAATCAAACACGAAACAAAC
ATATCAACCCTAATGAATGGTGGAAAGTCTATCCATCTTCTGTAACGGAA
TTTAAGTTTTTATTTGTGAGTGGTCACTTTAAAGGAAACTACAAAGCTCA
GCTTACACGATTAAATCATATCACTAATTGTAATGGAGCTGTTCTTAGTG
TAGAAGAGCTTTTAATTGGTGGAGAAATGATTAAAGCCGGCACATTAACC
TTAGAGGAAGTCAGACGGAAATTTAATAACGGCGAGATAAACTTT
``` fCas9 (e.g., FokI-GGS3linker-dCas9-NLS):
(SEQ ID NO: 52)
```
ATGGGATCCCAACTAGTCAAAAGTGAACTGGAGGAGAAGAAATCTGAACT
TCGTCATAAATTGAAATATGTGCCTCATGAATATATTGAATTAATTGAAA
TTGCCAGAAATTCCACTCAGGATAGAATTCTTGAAATGAAGGTAATGGAA
TTTTTTATGAAAGTTTATGGATATAGAGGTAAACATTTGGGTGGATCAAG
GAAACCGGACGGAGCAATTTATACTGTCGGATCTCCTATTGATTACGGTG
TGATCGTGGATACTAAAGCTTATAGCGGAGGTTATAATCTGCCAATTGGC
CAAGCAGATGAAATGCAACGATATGTCGAAGAAAATCAAACACGAAACAA
ACATATCAACCCTAATGAATGGTGGAAAGTCTATCCATCTTCTGTAACGG
AATTTAAGTTTTTATTTGTGAGTGGTCACTTTAAAGGAAACTACAAAGCT
CAGCTTACACGATTAAATCATATCACTAATTGTAATGGAGCTGTTCTTAG
TGTAGAAGAGCTTTTAATTGGTGGAGAAATGATTAAAGCCGGCACATTAA
CCTTAGAGGAAGTCAGACGGAAATTTAATAACGGCGAGATAAACTTTGGC
GGTAGTGGGGGATCTGGGGGAAGTATGGATAAAAAGTATTCTATTGGTTT
AGCTATCGGCACTAATTCCGTTGGATGGGCTGTCATAACCGATGAATACA
AAGTACCTTCAAAGAAATTTAAGGTGTTGGGGAACACAGACCGTCATTCG
ATTAAAAAGAATCTTATCGGTGCCCTCCTATTCGATAGTGGCGAAACGGC
AGAGGCGACTCGCCTGAAACGAACCGCTCGGAGAAGGTATACACGTCGCA
AGAACCGAATATGTTACTTACAAGAAATTTTTAGCAATGAGATGGCCAAA
GTTGACGATTCTTTCTTTCACCGTTTGGAAGAGTCCTTCCTTGTCGAAGA
GGACAAGAAACATGAACGGCACCCCATCTTTGGAAACATAGTAGATGAGG
TGGCATATCATGAAAGTACCCAACGATTTATCACCTCAGAAAAAAGCTA
GTTGACTCAACTGATAAAGCGGACCTGAGGTTAATCTACTTGGCTCTTGC
CCATATGATAAAGTTCCGTGGGCACTTTCTCATTGAGGGTGATCTAAATC
CGGACAACTCGGATGTCGACAAACTGTTCATCCAGTTAGTACAAACCTAT
AATCAGTTGTTTGAAGAGAACCCTATAAATGCAAGTGGCGTGGATGCGAA
GGCTATTCTTAGCGCCCGCCTCTCTAAATCCCGACGGCTAGAAACCTGA
TCGCACAATTACCCGGAGAGAAGAAAATGGGTTGTTCGGTAACCTTATA
GCGCTCTCACTAGGCCTGACACCAAATTTTAAGTCGAACTTCGACTTAGC
TGAAGATGCCAAATTGCAGCTTAGTAAGGACACGTACGATGACGATCTCG
ACAATCTACTGGCACAAATTGGAGATCAGTATGCGGACTTATTTTGGCT
GCCAAAAACCTTAGCGATGCAATCCTCCTATCTGACATACTGAGAGTTAA
```

```
TACTGAGATTACCAAGGCGCCGTTATCCGCTTCAATGATCAAAAGGTACG
ATGAACATCACCAAGACTTGACACTTCTCAAGGCCCTAGTCCGTCAGCAA
CTGCCTGAGAAATATAAGGAAATATTCTTTGATCAGTCGAAAAACGGGTA
CGCAGGTTATATTGACGGCGGAGCGAGTCAAGAGGAATTCTACAAGTTTA
TCAAACCCATATTAGAGAAGATGGATGGGACGGAAGAGTTGCTTGTAAAA
CTCAATCGCGAAGATCTACTGCGAAAGCAGCGGACTTTCGACAACGGTAG
CATTCCACATCAAATCCACTTAGGCGAATTGCATGCTATACTTAGAAGGC
AGGAGGATTTTATCCGTTCCTCAAAGACAATCGTGAAAAGATTGAGAAA
ATCCTAACCTTTCGCATACCTTACTATGTGGGACCCCTGGCCCGAGGGAA
CTCTCGGTTCGCATGGATGACAAGAAAGTCCGAAGAAACGATTACTCCAT
GGAATTTTGAGGAAGTTGTCGATAAAGGTGCGTCAGCTCAATCGTTCATC
GAGAGGATGACCAACTTTGACAAGAATTTACCGAACGAAAAAGTATTGCC
TAAGCACAGTTTACTTTACGAGTATTTCACAGTGTACAATGAACTCACGA
AAGTTAAGTATGTCACTGAGGGCATGCGTAAACCCGCCTTTCTAAGCGGA
GAACAGAAGAAAGCAATAGTAGATCTGTTATTCAAGACCAACCGCAAAGT
GACAGTTAAGCAATTGAAAGAGGACTACTTTAAGAAAATTGAATGCTTCG
ATTCTGTCGAGATCTCCGGGGTAGAAGATCGATTTAATGCGTCACTTGGT
ACGTATCATGACCTCCTAAAGATAATTAAAGATAAGGACTTCCTGGATAA
CGAAGAGAATGAAGATATCTTAGAAGATATAGTGTTGACTCTTACCCTCT
TTGAAGATCGGGAAATGATTGAGGAAAGACTAAAAACATACGCTCACCTG
TTCGACGATAAGGTTATGAAACAGTTAAAGAGGCGTCGCTATACGGGCTG
GGGACGATTGTCGCGGAAACTTATCAACGGGATAAGAGACAAGCAAAGTG
GTAAAACTATTCTCGATTTTCTAAAGAGCGACGGCTTCGCCAATAGGAAC
TTTATGCAGCTGATCCATGATGACTCTTTAACCTTCAAAGAGGATATACA
AAAGGCACAGGTTTCCGGACAAGGGGACTCATTGCACGAACATATTGCGA
ATCTTGCTGGTTCGCCAGCCATCAAAAAGGGCATACTCCAGACAGTCAAA
GTAGTGGATGAGCTAGTTAAGGTCATGGGACGTCACAAACCGGAAAACAT
TGTAATCGAGATGGCACGCGAAAATCAAACGACTCAGAAGGGGCAAAAAA
ACAGTCGAGAGCGGATGAAGAGAATAGAAGAGGGTATTAAAGAACTGGGC
AGCCAGATCTTAAAGGAGCATCCTGTGGAAAATACCCAATTGCAGAACGA
GAAACTTTACCTCTATTACCTACAAAATGGAAGGGACATGTATGTTGATC
AGGAACTGGACATAAACCGTTTATCTGATTACGACGTCGATGCCATTGTA
CCCCAATCCTTTTTGAAGGACGATTCAATCGACAATAAAGTGCTTACACG
CTCGGATAAGAACCGAGGGAAAAGTGACAATGTTCCAAGCGAGGAAGTCG
TAAAGAAAATGAAGAACTATTGGCGGCAGCTCCTAAATGCGAAACTGATA
ACGCAAAGAAAGTTCGATAACTTAACTAAAGCTGAGAGGGGTGGCTTGTC
TGAACTTGACAAGGCCGGATTTATTAAACGTCAGCTCGTGGAAACCCGCC
AAATCACAAAGCATGTTGCACAGATACTAGATTCCCGAATGAATACGAAA
TACGACGAGAACGATAAGCTGATTCGGGAAGTCAAAGTAATCACTTTAAA
GTCAAAATTGGTGTCGGACTTCAGAAAGGATTTTCAATTCTATAAAGTTA
GGGAGATAAATAACTACCACCATGCGCACGACGCTTATCTTAATGCCGTC
```

```
GTAGGGACCGCACTCATTAAGAAATACCCGAAGCTAGAAAGTGAGTTTGT
GTATGGTGATTACAAAGTTTATGACGTCCGTAAGATGATCGCGAAAAGCG
AACAGGAGATAGGCAAGGCTACAGCCAAATACTTCTTTTATTCTAACATT
ATGAATTTCTTTAAGACGGAAATCACTCTGGCAAACGGAGAGATACGCAA
ACGACCTTTAATTGAAACCAATGGGGAGACAGGTGAAATCGTATGGATA
AGGGCCGGGACTTCGCGACGGTGAGAAAGTTTTGTCCATGCCCCAAGTC
AACATAGTAAAGAAAACTGAGGTGCAGACCGGAGGGTTTTCAAAGGAATC
GATTCTTCCAAAAAGGAATAGTGATAAGCTCATCGCTCGTAAAAAGGACT
GGGACCCGAAAAAGTACGGTGGCTTCGATAGCCCTACAGTTGCCTATTCT
GTCCTAGTAGTGGCAAAAGTTGAGAAGGGAAAATCCAAGAAACTGAAGTC
AGTCAAAGAATTATTGGGGATAACGATTATGGAGCGCTCGTCTTTTGAAA
AGAACCCCATCGACTTCCTTGAGGCGAAAGGTTACAAGGAAGTAAAAAAG
GATCTCATAATTAAACTACCAAAGTATAGTCTGTTTGAGTTAGAAAATGG
CCGAAAACGGATGTTGGCTAGCGCCGGAGAGCTTCAAAAGGGGAACGAAC
TCGCACTACCGTCTAAATACGTGAATTTCCTGTATTTAGCGTCCCATTAC
GAGAAGTTGAAAGGTTCACCTGAAGATAACGAACAGAAGCAACTTTTTGT
TGAGCAGCACAAACATTATCTCGACGAAATCATAGAGCAAATTTCGGAAT
TCAGTAAGAGAGTCATCCTAGCTGATGCCAATCTGGACAAAGTATTAAGC
GCATACAACAAGCACAGGGATAAACCCATACGTGAGCAGGCGGAAAATAT
TATCCATTTGTTTACTCTTACCAACCTCGGCGCTCCAGCCGCATTCAAGT
ATTTTGACACAACGATAGATCGCAAACGATACACTTCTACCAAGGAGGTG
CTAGACGCGACACTGATTCACCAATCCATCACGGGATTATATGAAACTCG
GATAGATTTGTCACAGCTTGGGGGTGACGGATCCCCCAAGAAGAAGAGGA
AAGTCTCGAGCGACTACAAAGACCATGACGGTGATTATAAAGATCATGAC
ATCGATTACAAGGATGACGATGACAAGGCTGCAGGA fCas9 (e.g., NLS-FokI-GGS3linker-dCas9):
                                          (SEQ ID NO: 53)
ATGGACTACAAAGACCATGACGGTGATTATAAAGATCATGACATCGATTA
CAAGGATGACGATGACAAGATGGCCCCCAAGAAGAAGAGGAAGGTGGGCA
TTCACCGCGGGGTACCTGGAGGTTCTATGGGATCCCAACTAGTCAAAAGT
GAACTGGAGGAGAAGAAATCTGAACTTCGTCATAAATTGAAATATGTGCC
TCATGAATATATTGAATTAATTGAAATTGCCAGAAATTCCACTCAGGATA
GAATTCTTGAAATGAAGGTAATGGAATTTTTTATGAAAGTTTATGGATAT
AGAGGTAAACATTTGGGTGGATCAAGGAAACCGGACGGAGCAATTTATAC
TGTCGGATCTCCTATTGATTACGGTGTGATCGTGGATACTAAAGCTTATA
GCGGAGGTTATAATCTGCCAATTGGCCAAGCAGATGAAATGCAACGATAT
GTCGAAGAAAATCAAACACGAAACAAACATATCAACCCTAATGAATGGTG
GAAAGTCTATCCATCTTCTGTAACGGAATTTAAGTTTTTATTTGTGAGTG
GTCACTTTAAAGGAAACTACAAAGCTCAGCTTACACGATTAAATCATATC
ACTAATTGTAATGGAGCTGTTCTTAGTGTAGAAGAGCTTTTAATTGGTGG
AGAAATGATTAAAGCCGGCACATTAACCTTAGAGGAAGTCAGACGGAAAT
```
```
TTAATAACGGCGAGATAAACTTTGGCGGTAGTGGGGGATCTGGGGGAAGT
ATGGATAAAAGTATTCTATTGGTTTAGCTATCGGCACTAATTCCGTTGG
ATGGGCTGTCATAACCGATGAATACAAAGTACCTTCAAAGAAATTTAAGG
TGTTGGGGAACACAGACCGTCATTCGATTAAAAAGAATCTTATCGGTGCC
CTCCTATTCGATAGTGGCGAAACGGCAGAGGCGACTCGCCTGAAACGAAC
CGCTCGGAGAAGGTATACACGTCGCAAGAACCGAATATGTTACTTACAAG
AAATTTTTAGCAATGAGATGGCCAAAGTTGACGATTCTTTCTTTCACCGT
TTGGAAGAGTCCTTCCTTGTCGAAGAGGACAAGAAACATGAACGGCACCC
CATCTTTGGAAACATAGTAGATGAGGTGGCATATCATGAAAAGTACCCAA
CGATTTATCACCTCAGAAAAAAGCTAGTTGACTCAACTGATAAAGCGGAC
CTGAGGTTAATCTACTTGGCTCTTGCCCATATGATAAAGTTCCGTGGGCA
CTTTCTCATTGAGGGTGATCTAAATCCGGACAACTCGGATGTCGACAAAC
TGTTCATCCAGTTAGTACAAACCTATAATCAGTTGTTTGAAGAGAACCCT
ATAAATGCAAGTGGCGTGGATGCGAAGGCTATTCTTAGCGCCCGCCTCTC
TAAATCCCGACGGCTAGAAAAACCTGATCGCACAATTACCCGGAGAGAAGA
AAAATGGGTTGTTCGGTAACCTTATAGCGCTCTCACTAGGCCTGACACCA
AATTTTAAGTCGAACTTCGACTTAGCTGAAGATGCCAAATTGCAGCTTAG
TAAGGACACGTACGATGACGATCTCGACAATCTACTGGCACAAATTGGAG
ATCAGTATGCGGACTTATTTTGGCTGCCAAAAACCTTAGCGATGCAATC
CTCCTATCTGACATACTGAGAGTTAATACTGAGATTACCAAGGCGCCGTT
ATCCGCTTCAATGATCAAAAGGTACGATGAACATCACCAAGACTTGACAC
TTCTCAAGGCCCTAGTCCGTCAGCAACTGCCTGAGAAATATAAGGAAATA
TTCTTTGATCAGTCGAAAAACGGGTACGCAGGTTATATTGACGGCGGAGC
GAGTCAAGAGGAATTCTACAAGTTTATCAAACCCATATTAGAGAAGATGG
ATGGGACGGAAGAGTTGCTTGTAAAACTCAATCGCGAAGATCTACTGCGA
AAGCAGCGGACTTTCGACAACGGTAGCATTCCACATCAAATCCACTTAGG
CGAATTGCATGCTATACTTAGAAGGCAGGAGGATTTTTATCCGTTCCTCA
AAGACAATCGTGAAAAGATTGAGAAAATCCTAACCTTTCGCATACCTTAC
TATGTGGGACCCCTGGCCCGAGGGAACTCTCGGTTCGCATGGATGACAAG
AAAGTCCGAAGAAACGATTACTCCATGGAATTTTGAGGAAGTTGTCGATA
AGGGTGCGTCAGCTCAATCGTTCATCGAGAGGATGACCAACTTTGACAAG
AATTTACCGAACGAAAAGTATTGCCTAAGCACAGTTTACTTTACGAGTA
TTTCACAGTGTACAATGAACTCACGAAAGTTAAGTATGTCACTGAGGGCA
TGCGTAAACCCGCCTTTCTAAGCGGAGAACAGAAGAAAGCAATAGTAGAT
CTGTTATTCAAGACCAACCGCAAAGTGACAGTTAAGCAATTGAAAGAGGA
CTACTTTAAGAAAATTGAATGCTTCGATTCTGTCGAGATCTCCGGGGTAG
AAGATCGATTTAATGCGTCACTTGGTACGTATCATGACCTCCTAAAGATA
ATTAAAGATAAGGACTTCCTGGATAACGAAGAGAATGAAGATATCTTAGA
AGATATAGTGTTGACTCTTACCCTCTTTGAAGATCGGGAAATGATTGAGG
AAAGACTAAAAACATACGCTCACCTGTTCGACGATAAGGTTATGAAACAG
TTAAAGAGGCGTCGCTATACGGGCTGGGGACGATTGTCGCGGAAACTTAT
```

-continued

```
CAACGGGATAAGAGACAAGCAAAGTGGTAAAACTATTCTCGATTTTCTAA
AGAGCGACGGCTTCGCCAATAGGAACTTTATGCAGCTGATCCATGATGAC
TCTTTAACCTTCAAAGAGGATATACAAAAGGCACAGGTTTCCGGACAAGG
GGACTCATTGCACGAACATATTGCGAATCTTGCTGGTTCGCCAGCCATCA
AAAAGGGCATACTCCAGACAGTCAAAGTAGTGGATGAGCTAGTTAAGGTC
ATGGGACGTCACAAACCGGAAAACATTGTAATCGAGATGGCACGCGAAAA
TCAAACGACTCAGAAGGGGCAAAAAAACAGTCGAGAGCGGATGAAGAGAA
TAGAAGAGGGTATTAAAGAACTGGGCAGCCAGATCTTAAAGGAGCATCCT
GTGGAAAATACCCAATTGCAGAACGAGAAACTTTACCTCTATTACCTACA
AAATGGAAGGGACATGTATGTTGATCAGGAACTGGACATAAACCGTTTAT
CTGATTACGACGTCGATGCCATTGTACCCCAATCCTTTTTGAAGGACGAT
TCAATCGACAATAAAGTGCTTACACGCTCGGATAAGAACCGAGGGAAAAG
TGACAATGTTCCAAGCGAGGAAGTCGTAAAGAAAATGAAGAACTATTGGC
GGCAGCTCCTAAATGCGAAACTGATAACGCAAAGAAAGTTCGATAACTTA
ACTAAAGCTGAGAGGGGTGGCTTGTCTGAACTTGACAAGGCCGGATTTAT
TAAACGTCAGCTCGTGGAAACCCGCCAAATCACAAAGCATGTTGCACAGA
TACTAGATTCCCGAATGAATACGAAATACGACGAGAACGATAAGCTGATT
CGGGAAGTCAAAGTAATCACTTTAAAGTCAAAATTGGTGTCGGACTTCAG
AAAGGATTTTCAATTCTATAAAGTTAGGGAGATAAATAACTACCACCATG
CGCACGACGCTTATCTTAATGCCGTCGTAGGGACCGCACTCATTAAGAAA
TACCCGAAGCTAGAAAGTGAGTTTGTGTATGGTGATTACAAAGTTTATGA
CGTCCGTAAGATGATCGCGAAAAGCGAACAGGAGATAGGCAAGGCTACAG
CCAAATACTTCTTTTATTCTAACATTATGAATTTCTTTAAGACGGAAATC
ACTCTGGCAAACGGAGAGATACGCAAACGACCTTTAATTGAAACCAATGG
GGAGACAGGTGAAATCGTATGGGATAAGGGCCGGGACTTCGCGACGGTGA
GAAAAGTTTTGTCCATGCCCCAAGTCAACATAGTAAAGAAAACTGAGGTG
CAGACCGGAGGGTTTTCAAAGGAATCGATTCTTCCAAAAAGGAATAGTGA
TAAGCTCATCGCTCGTAAAAAGGACTGGGACCCGAAAAAGTACGGTGGCT
TCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAAC
GATTATGGAGCGCTCGTCTTTTGAAAAGAACCCCATCGACTTCCTTGAGG
CGAAAGGTTACAAGGAAGTAAAAAAGGATCTCATAATTAAACTACCAAAG
TATAGTCTGTTTGAGTTAGAAAATGGCCGAAAACGGATGTTGGCTAGCGC
CGGAGAGCTTCAAAAGGGGAACGAACTCGCACTACCGTCTAAATACGTGA
ATTTCCTGTATTTAGCGTCCCATTACGAGAAGTTGAAAGGTTCACCTGAA
GATAACGAACAGAAGCAACTTTTTGTTGAGCAGCACAAACATTATCTCGA
CGAAATCATAGAGCAAATTTCGGAATTCAGTAAGAGAGTCATCCTAGCTG
ATGCCAATCTGGACAAAGTATTAAGCGCATACAACAAGCACAGGGATAAA
CCCATACGTGAGCAGGCGGAAAATATTATCCATTTGTTTACTCTTACCAA
CCTCGGCGCTCCAGCCGCATTCAAGTATTTTGACACAACGATAGATCGCA
AACGATACACTTCTACCAAGGAGGTGCTAGACGCGACACTGATTCACCAA
TCCATCACGGGATTATATGAAACTCGGATAGATTTGTCACAGCTTGGGGG
TGAC
``` fCas9:
(SEQ ID NO: 54)
```
ATGGACTACAAAGACCATGACGGTGATTATAAAGATCATGACATCGATTA
CAAGGATGACGATGACAAGATGGCCCCCAAGAAGAAGAGGAAGGTGGGCA
TTCACCGCGGGGTACCTGGAGGTTCTGGATCCCAACTAGTCAAAAGTGAA
CTGGAGGAGAAGAAATCTGAACTTCGTCATAAATTGAAATATGTGCCTCA
TGAATATATTGAATTAATTGAAATTGCCAGAAATTCCACTCAGGATAGAA
TTCTTGAAATGAAGGTAATGGAATTTTTTATGAAAGTTTATGGATATAGA
GGTAAACATTTGGGTGGATCAAGGAAACCGGACGGAGCAATTTATACTGT
CGGATCTCCTATTGATTACGGTGTGATCGTGGATACTAAAGCTTATAGCG
GAGGTTATAATCTGCCAATTGGCCAAGCAGATGAAATGCAACGATATGTC
GAAGAAATCAAACACGAAACAAACATATCAACCCTAATGAATGGTGGAA
AGTCTATCCATCTTCTGTAACGGAATTTAAGTTTTTATTTGTGAGTGGTC
ACTTTAAAGGAAACTACAAAGCTCAGCTTACACGATTAAATCATATCACT
AATTGTAATGGAGCTGTTCTTAGTGTAGAAGAGCTTTTAATTGGTGGAGA
AATGATTAAAGCCGGCACATTAACCTTAGAGGAAGTCAGACGGAAATTTA
ATAACGGCGAGATAAACTTTAGCGGCAGCGAGACTCCCGGGACCTCAGAG
TCCGCCACACCCGAAAGTGATAAAAGTATTCTATTGGTTTAGCTATCGG
CACTAATTCCGTTGGATGGGCTGTCATAACCGATGAATACAAAGTACCTT
CAAAGAAATTTAAGGTGTTGGGAACACAGACCGTCATTCGATTAAAAAG
AATCTTATCGGTGCCCTCCTATTCGATAGTGGCGAAACGGCAGAGGCGAC
TCGCCTGAAACGAACCGCTCGGAGAAGGTATACACGTCGCAAGAACCGAA
TATGTTACTTACAAGAAATTTTTAGCAATGAGATGGCCAAAGTTGACGAT
TCTTTCTTTCACCGTTTGGAAGAGTCCTTCCTTGTCGAAGAGGACAAGAA
ACATGAACGGCACCCCATCTTTGGAAACATAGTAGATGAGGTGGCATATC
ATGAAAAGTACCCAACGATTTATCACCTCAGAAAAAAGCTAGTTGACTCA
ACTGATAAAGCGGACCTGAGGTTAATCTACTTGGCTCTTGCCCATATGAT
AAAGTTCCGTGGGCACTTTCTCATTGAGGGTGATCTAAATCCGGACAACT
CGGATGTCGACAAACTGTTCATCCAGTTAGTACAAACCTATAATCAGTTG
TTTGAAGAGAACCCTATAAATGCAAGTGGCGTGGATGCGAAGGCTATTCT
TAGCGCCCGCCTCTCTAAATCCCGACGGCTAGAAAACCTGATCGCACAAT
TACCCGGAGAGAAGAAAAATGGGTTGTTCGGTAACCTTATAGCGCTCTCA
CTAGGCCTGACACCAAATTTTAAGTCGAACTTCGACTTAGCTGAAGATGC
CAAATTGCAGCTTAGTAAGGACACGTACGATGACGATCTCGACAATCTAC
TGGCACAAATTGGAGATCAGTATGCGGACTTATTTTTGGCTGCCAAAAAC
CTTAGCGATGCAATCCTCCTATCTGACATACTGAGAGTTAATACTGAGAT
TACCAAGGCGCCGTTATCCGCTTCAATGATCAAAAGGTACGATGAACATC
ACCAAGACTTGACACTTCTCAAGGCCCTAGTCCGTCAGCAACTGCCTGAG
AAATATAAGGAAATATTCTTTGATCAGTCGAAAAACGGGTACGCAGGTTA
```

```
TATTGACGGCGGAGCGAGTCAAGAGGAATTCTACAAGTTTATCAAACCCA
TATTAGAGAAGATGGATGGGACGGAAGAGTTGCTTGTAAAACTCAATCGC
GAAGATCTACTGCGAAAGCAGCGGACTTTCGACAACGGTAGCATTCCACA
TCAAATCCACTTAGGCGAATTGCATGCTATACTTAGAAGGCAGGAGGATT
TTTATCCGTTCCTCAAAGACAATCGTGAAAAGATTGAGAAAATCCTAACC
TTTCGCATACCTTACTATGTGGGACCCCTGGCCCGAGGGAACTCTCGGTT
CGCATGGATGACAAGAAAGTCCGAAGAAACGATTACTCCATGGAATTTTG
AGGAAGTTGTCGATAAAGGTGCGTCAGCTCAATCGTTCATCGAGAGGATG
ACCAACTTTGACAAGAATTTACCGAACGAAAAGTATTGCCTAAGCACAG
TTTACTTTACGAGTATTTCACAGTGTACAATGAACTCACGAAAGTTAAGT
ATGTCACTGAGGGCATGCGTAAACCCGCCTTTCTAAGCGGAGAACAGAAG
AAAGCAATAGTAGATCTGTTATTCAAGACCAACCGCAAAGTGACAGTTAA
GCAATTGAAAGAGGACTACTTTAAGAAAATTGAATGCTTCGATTCTGTCG
AGATCTCCGGGTAGAAGATCGATTTAATGCGTCACTTGGTACGTATCAT
GACCTCCTAAAGATAATTAAAGATAAGGACTTCCTGGATAACGAAGAGAA
TGAAGATATCTTAGAAGATATAGTGTTGACTCTTACCCTCTTTGAAGATC
GGGAAATGATTGAGGAAAGACTAAAAACATACGCTCACCTGTTCGACGAT
AAGGTTATGAAACAGTTAAAGAGGCGTCGCTATACGGGCTGGGGACGATT
GTCGCGGAAACTTATCAACGGGATAAGAGACAAGCAAAGTGGTAAAACTA
TTCTCGATTTTCTAAAGAGCGACGGCTTCGCCAATAGGAACTTTATGCAG
CTGATCCATGATGACTCTTTAACCTTCAAAGAGGATATACAAAAGGCACA
GGTTTCCGGACAAGGGGACTCATTGCACGAACATATTGCGAATCTTGCTG
GTTCGCCAGCCATCAAAAAGGGCATACTCCAGACAGTCAAAGTAGTGGAT
GAGCTAGTTAAGGTCATGGGACGTCACAAACCGGAAAACATTGTAATCGA
GATGGCACGCGAAAATCAAACGACTCAGAAGGGGCAAAAAAACAGTCGAG
AGCGGATGAAGAGAATAGAAGAGGGTATTAAAGAACTGGGCAGCCAGATC
TTAAAGGAGCATCCTGTGGAAAATACCCAATTGCAGAACGAGAAACTTTA
CCTCTATTACCTACAAAATGGAAGGGACATGTATGTTGATCAGGAACTGG
ACATAAACCGTTTATCTGATTACGACGTCGATGCCATTGTACCCCAATCC
TTTTTGAAGGACGATTCAATCGACAATAAAGTGCTTACACGCTCGGATAA
GAACCGAGGGAAAAGTGACAATGTTCCAAGCGAGGAAGTCGTAAAGAAAA
TGAAGAACTATTGGCGGCAGCTCCTAAATGCGAAACTGATAACGCAAAGA
AAGTTCGATAACTTAACTAAAGCTGAGAGGGGTGGCTTGTCTGAACTTGA
CAAGGCCGGATTTATTAAACGTCAGCTCGTGGAAACCCGCCAAATCACAA
AGCATGTTGCACAGATACTAGATTCCCGAATGAATACGAAATACGACGAG
AACGATAAGCTGATTCGGGAAGTCAAAGTAATCACTTTAAAGTCAAAATT
GGTGTCGGACTTCAGAAAGGATTTTCAATTCTATAAAGTTAGGGAGATAA
ATAACTACCACCATGCGCACGACGCTTATCTTAATGCCGTCGTAGGGACC
GCACTCATTAAGAAATACCCGAAGCTAGAAAGTGAGTTTGTGTATGGTGA
TTACAAAGTTTATGACGTCCGTAAGATGATCGCGAAAAGCGAACAGGAGA
TAGGCAAGGCTACAGCCAAATACTTCTTTTATTCTAACATTATGAATTTC
TTTAAGACGGAAATCACTCTGGCAAACGGAGAGATACGCAAACGACCTTT
AATTGAAACCAATGGGGAGACAGGTGAAATCGTATGGGATAAGGGCCGGG
ACTTCGCGACGGTGAGAAAAGTTTTGTCCATGCCCCAAGTCAACATAGTA
AAGAAAACTGAGGTGCAGACCGGAGGGTTTTCAAAGGAATCGATTCTTCC
AAAAAGGAATAGTGATAAGCTCATCGCTCGTAAAAAGGACTGGGACCCGA
AAAAGTACGGTGGCTTCGATAGCCCTACAGTTGCCTATTCTGTCCTAGTA
GTGGCAAAAGTTGAGAAGGGAAAATCCAAGAAACTGAAGTCAGTCAAAGA
ATTATTGGGGATAACGATTATGGAGCGCTCGTCTTTTGAAAAGAACCCCA
TCGACTTCCTTGAGGCGAAAGGTTACAAGGAAGTAAAAAAGGATCTCATA
ATTAAACTACCAAAGTATAGTCTGTTTGAGTTAGAAAATGGCCGAAAACG
GATGTTGGCTAGCGCCGGAGAGCTTCAAAAGGGGAACGAACTCGCACTAC
CGTCTAAATACGTGAATTTCCTGTATTTAGCGTCCCATTACGAGAAGTTG
AAAGGTTCACCTGAAGATAACGAACAGAAGCAACTTTTTGTTGAGCAGCA
CAAACATTATCTCGACGAAATCATAGAGCAAATTTCGGAATTCAGTAAGA
GAGTCATCCTAGCTGATGCCAATCTGGACAAAGTATTAAGCGCATACAAC
AAGCACAGGGATAAACCCATACGTGAGCAGGCGGAAAATATTATCCATTT
GTTTACTCTTACCAACCTCGGCGCTCCAGCCGCATTCAAGTATTTTGACA
CAACGATAGATCGCAAACGATACACTTCTACCAAGGAGGTGCTAGACGCG
ACACTGATTCACCAATCCATCACGGGATTATATGAAACTCGGATAGATTT
GTCACAGCTTGGGGGTGAC
```

In some embodiments, the enzymatic domain comprises a recombinase or catalytic domain thereof. For example, in some embodiments, the general architecture of exemplary ligand-dependent dCas9 fusion proteins with a recombinase domain comprises the structure:

[NH$_2$]-[NLS]-[dCas9]-[recombinase]-[COOH],

[NH$_2$]-[NLS]-[recombinase]-[dCas9]-[COOH],

[NH$_2$]-[dCas9]-[recombinase]-[COOH], or

[NH$_2$]-[recombinase]-[dCas9]-[COOH];

wherein NLS is a nuclear localization signal, NH$_2$ is the N-terminus of the fusion protein, and COOH is the C-terminus of the fusion protein. In some embodiments, a linker is inserted between the dCas9 and the recombinase domain. In some embodiments, a linker is inserted between the NLS and the recombinase and/or dCas9 domain. In some embodiments, the NLS is located C-terminal of the recombinase domain and/or the dCas9 domain. In some embodiments, the NLS is located between the recombinase domain and the dCas9 domain. Additional features, such as sequence tags, may also be present. By "catalytic domain of a recombinase," it is meant that a fusion protein includes a domain comprising an amino acid sequence of (e.g., derived from) a recombinase, such that the domain is sufficient to induce recombination when contacted with a target nucleic acid (either alone or with additional factors including other recombinase catalytic domains which may or may not form part of the fusion protein). In some embodiments, a catalytic domain of a recombinase does not include the DNA binding domain of the recombinase. In some embodiments, the catalytic domain of a recombinase includes part or all of a recombinase, e.g., the catalytic domain may include a recombinase domain and a DNA binding domain, or parts thereof, or the catalytic domain may include a recombinase domain and a DNA binding domain that is mutated or truncated to abolish DNA binding activity. Recombinases and catalytic domains of recombinases are known to those of skill in the art, and include, for example, those described herein. In some embodiments, the catalytic domain is derived from any recombinase. In some embodiments, the recombinase catalytic domain is a catalytic domain of aTn3 resolvase, a Hin recombinase, or a Gin recombinase. In some embodiments, the catalytic domain comprises a Tn3 resolvase (e.g., Stark Tn3 recombinase) that is encoded by a nucleotide sequence comprising, in part or in whole, SEQ ID NO:55, as provided below. In some embodiments, a Tn3 catalytic domain is encoded by a variant of SEQ ID NO:55. In some embodiments, a Tn3 catalytic domain is encoded by a polynucleotide (or a variant thereof) that encodes the polypeptide corresponding to SEQ ID NO:56. In some embodiments, the catalytic domain comprises a Hin recombinase that is encoded by a nucleotide sequence comprising, in part or in whole, SEQ ID NO:57, as provided below. In some embodiments, a Hin catalytic domain is encoded by a variant of SEQ ID NO:57. In some embodiments, a Hin catalytic domain is encoded by a polynucleotide (or a variant thereof) that encodes the polypeptide corresponding to SEQ ID NO:58. In some embodiments, the catalytic domain comprises a Gin recombinase (e.g., Gin beta recombinase) that is encoded by a nucleotide sequence comprising, in part or in whole, SEQ ID NO:59, as provided below. In some embodiments, a Gin catalytic domain is encoded by a variant of SEQ ID NO:59. In some embodiments, a Gin catalytic domain is encoded by a polynucleotide (or a variant thereof) that encodes the polypeptide corresponding to SEQ ID NO:60. Other exemplary compositions and methods of using dCas9-recombinase fusion proteins can be found in U.S. patent application U.S. Ser. No. 14/320,467; titled "Cas9 Variants and Uses Thereof," filed Jun. 30, 2014; the entire contents of which are incorporated herein by reference.

```
Stark Tn3 recombinase (nucleotide: SEQ ID NO: 55; amino acid:SEQ ID
NO: 56):
                                                        (SEQ ID NO: 55)
ATGGCCCTGTTTGGCTACGCACGCGTGTCTACCAGTCAACAGTCACTCGATTTGCAAGTGAGGGCTCTTAAAGAT

GCCGGAGTGAAGGCAAACAGAATTTTTACTGATAAGGCCAGCGGAAGCAGCACAGACAGAGAGGGGCTGGATCTC

CTGAGAATGAAGGTAAAGGAGGGTGATGTGATCTTGGTCAAAAAATTGGATCGACTGGGGAGAGACACAGCTGAT

ATGCTTCAGCTTATTAAAGAGTTTGACGCTCAGGGTGTTGCCGTGAGGTTTATCGATGACGGCATCTCAACCGAC

TCCTACATTGGTCTTATGTTTGTGACAATTTTGTCCGCTGTGGCTCAGGCTGAGCGGAGAAGGATTCTCGAAAGG

ACGAATGAGGGACGGCAAGCAGCTAAGTTGAAAGGTATCAAATTTGGCAGACGAAGG (SEQ ID NO: 56)
MALFGYARVSTSQQSLDLQVRALKDAGVKANRIFTDKASGSSTDREGLDLLRMKVKEGDVILVKKLDRLGRDTAD

MLQLIKEFDAQGVAVRFIDDGISTDSYIGLMFVTILSAVAQAERRRILERTNEGRQAAKLKGIKFGRRR

Hin Recombinase (nucleotide: SEQ ID NO: 57; amino acid: SEQ ID NO: 58):
                                                        (SEQ ID NO: 57)
ATGGCAACCATTGGCTACATAAGGGTGTCTACCATCGACCAAAATATCGACCTGCAGCGCAACGCTCTGACATCC

GCCAACTGCGATCGGATCTTCGAGGATAGGATCAGTGGCAAGATCGCCAACCGGCCCGGTCTGAAGCGGGCTCTG

AAGTACGTGAATAAGGGCGATACTCTGGTTGTGTGGAAGTTGGATCGCTTGGGTAGATCAGTGAAGAATCTCGTA

GCCCTGATAAGCGAGCTGCACGAGAGGGGTGCACATTTCCATTCTCTGACCGATTCCATCGATACGTCTAGCGCC

ATGGGCCGATTCTTCTTTTACGTCATGTCCGCCCTCGCTGAAATGGAGCGCGAACTTATTGTTGAACGGACTTTG

GCTGGACTGGCAGCGGCTAGAGCACAGGGCCGACTTGGA (SEQ ID NO: 58)
MATIGYIRVSTIDQNIDLQRNALTSANCDRIFEDRISGKIANRPGLKRALKYVNKGDTLVVWKLDRLGRSVKNLV

ALISELHERGAHFHSLTDSIDTSSAMGRFFFYVMSALAEMERELIVERTLAGLAAARAQGRLG

Gin beta recombinase (nucleotide: SEQ ID NO: 59; amino acid: SEQ ID
NO: 60):
                                                        (SEQ ID NO: 59)
ATGCTCATTGGCTATGTAAGGGTCAGCACCAATGACCAAAACACAGACTTGCAACGCAATGCTTTGGTTTGCGCC

GGATGTGAACAGATATTTGAAGATAAACTGAGCGGCACTCGGACAGACAGACCTGGGCTTAAGAGAGCACTGAAA

AGACTGCAGAAGGGGGACACCCTGGTCGTCTGGAAACTGGATCGCCTCGGACGCAGCATGAAACATCTGATTAGC

CTGGTTGGTGAGCTTAGGGAGAGAGGAATCAACTTCAGAAGCCTGACCGACTCCATCGACACCAGTAGCCCCATG

GGACGATTCTTCTTCTATGTGATGGGAGCACTTGCTGAGATGGAAAGAGAGCTTATTATCGAAAGAACTATGGCT

GGTATCGCTGCTGCCCGGAACAAAGGCAGACGGTTCGGCAGACCGCCGAAGAGCGGC
```

-continued (SEQ ID NO: 60)
MLIGYVRVSTNDQNTDLQRNALVCAGCEQIFEDKLSGTRTDRPGLKRALKRLQKGDTLVVWKLDRLGRSMKHLIS

LVGELRERGINFRSLTDSIDTSSPMGRFFFYVMGALAEMERELIIERTMAGIAAARNKGRRFGRPPKSG

In some embodiments, the enzymatic domain comprises a deaminase or a catalytic domain thereof. For example, in some embodiments, the general architecture of exemplary dCas9 fusion proteins with a deaminase enzyme or domain comprises the structure:

[NH₂]-[NLS]-[Cas9]-[deaminase]-[COOH],

[NH₂]-[NLS]-[deaminase]-[Cas9]-[COOH],

[NH₂]-[Cas9]-[deaminase]-[COOH], or

[NH₂]-[deaminase]-[Cas9]-[COOH];

wherein NLS is a nuclear localization signal, NH₂ is the N-terminus of the fusion protein, and COOH is the C-terminus of the fusion protein. In some embodiments, a linker is inserted between the dCas9 and the deaminase domain. In some embodiments, a linker is inserted between the NLS and the deaminase and/or dCas9 domain. In some embodiments, the NLS is located C-terminal of the deaminase and/or the dCas9 domain. In some embodiments, the NLS is located between the deaminase domain and the dCas9 domain. Additional features, such as sequence tags, may also be present. One exemplary suitable type of nucleic acid-editing enzymes and domains are cytosine deaminases, for example, of the apolipoprotein B mRNA-editing complex (APOBEC) family of cytosine deaminase enzymes, including activation-induced cytidine deaminase (AID) and apolipoprotein B editing complex 3 (APOBEC3) enzyme. Another exemplary suitable type of nucleic acid-editing enzyme and domain thereof suitable for use in the present invention include adenosine deaminases. For example, an ADAT family adenosine deaminase can be fused to a dCas9 domain. Some exemplary suitable nucleic-acid editing enzymes and domains, e.g., deaminases and deaminase domains, that can be fused to dCas9 domains according to aspects of this disclosure are provided below. It will be understood that, in some embodiments, the active domain of the respective sequence can be used, e.g., the domain without a localizing signal (nuclear localizing signal, without nuclear export signal, cytoplasmic localizing signal). Other exemplary compositions and methods of using dCas9-nuclease fusion proteins can be found in U.S. patent application U.S. Ser. No. 14/325,815; titled "Fusions of Cas9 Domains and Nucleic Acid-Editing Domains," filed Jul. 8, 2014; the entire contents of which are incorporated herein by reference.

Human AID:

(SEQ ID NO: 61)
MDSLLMNRRKFLYQFKNVRWAKGRRETYLCYVVKRRDSATSFSLDFGYLRNKNGCHVELLFLRYISDWDLDPGRC

YRVTWFTSWSPCYDCARHVADFLRGNPNLSLRIFTARLYFCEDRKAEPEGLRRLHRAGVQIAIMTFKDYFYCWNT

FVENHERTFKAWEGLHENSVRLSRQLRRILLPLYEVDDLRDAFRTLGL
(underline: nuclear localization signal; double underline: nuclear export signal)

Mouse AID:

(SEQ ID NO: 62)
MDSLLMKQKKFLYHFKNVRWAKGRHETYLCYVVKRRDSATSCSLDFGHLRNKSGCHVELLFLRYISDWDLDPGRC

YRVTWFTSWSPCYDCARHVAEFLRWNPNLSLRIFTARLYFCEDRKAEPEGLRRLHRAGVQIGIMTFKDYFYCWNT

FVENRERTFKAWEGLHENSVRLTRQLRRILLPLYEVDDLRDAFRMLGF
(underline: nuclear localization signal; double underline: nuclear export signal)

Dog AID:

(SEQ ID NO: 63)
MDSLLMKQRKFLYHFKNVRWAKGRHETYLCYVVKRRDSATSFSLDFGHLRNKSGCHVELLFLRYISDWDLDPGRC

YRVTWFTSWSPCYDCARHVADFLRGYPNLSLRIFAARLYFCEDRKAEPEGLRRLHRAGVQIAIMTFKDYFYCWNT

FVENREKTFKAWEGLHENSVRLSRQLRRILLPLYEVDDLRDAFRTLGL
(underline: nuclear localization signal; double underline: nuclear export signal)

Bovine AID:

(SEQ ID NO: 64)
MDSLLKKQRQFLYQFKNVRWAKGRHETYLCYVVKRRDSPTSFSLDFGHLRNKAGCHVELLFLRYISDWDLDPGRC

YRVTWFTSWSPCYDCARHVADFLRGYPNLSLRIFTARLYFCDKERKAEPEGLRRLHRAGVQIAIMTFKDYFYCWN

TFVENHERTFKAWEGLHENSVRLSRQLRRILLPLYEVDDLRDAFRTLGL
(underline: nuclear localization signal; double underline: nuclear export signal)

Mouse APOBEC-3:

(SEQ ID NO: 65)
MGPFCLGCSHRKCYSPIRNLISQETFKFHFKNLGYAKGRKDTFLCYEVTRKDCDSPVSLHHGVFKNKDNIHAEIC

FLYWFHDKVLKVLSPREEFKITWYMSWSPCFECAEQIVRFLATHHNLSLDIFSSRLYNVQDPETQQNLCRLVQEG

AQVAAMDLYEFKKCWKKFVDNGGRRFRPWKRLLTNFRYQDSKLQEILRPCYIPVPSSSSSTLSNICLTKGLPETR

FCVEGRRMDPLSEEEFYSQFYNQRVKHLCYYHRMKPYLCYQLEQFNGQAPLKGCLLSEKGKQHAEILFLDKIRSM

<u>ELSQVTITCYLTWSPCPNC</u>AWQLAAFKRDRPDLILHIYTSRLYFHWKRPFQKGLCSLWQSGILVDVMDLPQFTDC

WTNFVNPKRPFWPWKGLEIISRRTQRRLRRIKESWGLQDLVNDFGNLQLGPPMS
(underline: nucleic acid editing domain)

Rat APOBEC-3:

(SEQ ID NO: 66)

MGPFCLGCSHRKCYSPIRNLISQETFKFHFKNLRYAIDRKDTFLCYEVTRKDCDSPVSLHHGVFKNKDNI<u>HAEIC</u>

<u>FLYWFHDKVLKVLSPREEFKITWYMSWSPCFEC</u>AEQVLRFLATHHNLSLDIFSSRLYNIRDPENQQNLCRLVQEG

AQVAAMDLYEFKKCWKKFVDNGGRRFRPWKKLLTNFRYQDSKLQEILRPCYIPVPSSSSSTLSNICLTKGLPETR

FCVERRRVHLLSEEEFYSQFYNQRVKHLCYYHGVKPYLCYQLEQFNGQAPLKGCLLSEKGKQ<u>HAEILFLDKIRSM</u>

<u>ELSQVIITCYLTWSPCPNC</u>AWQLAAFKRDRPDLILHIYTSRLYFHWKRPFQKGLCSLWQSGILVDVMDLPQFTDC

WTNFVNPKRPFWPWKGLEIISRRTQRRLHRIKESWGLQDLVNDFGNLQLGPPMS
(underline: nucleic acid editing domain)

Rhesus macaque APOBEC-3G:

(SEQ ID NO: 67)

<u>MVEPMDPRTFVSNFNNRPILSGLNTVWLCCEVKTKDPSGPPLDAKIFQGKVYSKAKY</u>*HPEMRFL*<u>RWFHKWRQ LHH</u>

*DQEYKVTWYVSWSPCTRC*ANSVATFLAKDPKVTLTIFVARLYYFWKPDYQQALRILCQKRGGPHATMKIMNYNEF

QDCWNKFVDGRGKPFKPRNNLPKHYTLLQATLGELLRHLMDPGTFTSNFNNKPWVSGQHETYLCYKVERLHNDTW

VPLNQHRGFLRNQAPNIHGFPKGR*HAELCFLDLIPFWKLDGQQYRVTCFTSWSPCFSC*AQEMAKFISNNEHVSLC

IFAARIYDDQGRYQEGLRALHRDGAKIAMMNYSEFEYCWDTFVDRQGRPFQPWDGLDEHSQALSGRLRAI
(bold italic: nucleic acid editing domain; underline: cytoplasmic localization
signal)

Chimpanzee APOBEC-3G:

(SEQ ID NO: 68)

<u>MKPHFRNPVERMYQDTFSDNFYNRPILSHRNTVWLCYEVKTKGPSRPPLDAKIFRGQVYSKLKYHPEMRFFHWFS</u>

<u>KWRKLHRDQEYEVTWYISWSPCTKC</u>TRDVATFLAEDPKVTLTIFVARLYYFWDPDYQEALRSLCQKRDGPRATMK

IMNYDEFQHCWSKFVYSQRELFEPWNNLPKYYILLHIMLGEILRHSMDPPTFTSNFNNELWVRGRHETYLCYEVE

RLHNDTWVLLNQRRGFLCNQAPHKHGFLEGR<u>HAELCFLDVIPFWKLDLHQDYRVTCFTSWSPCFSC</u>AQEMAKFIS

NNKHVSLCIFAARIYDDQGRCQEGLRTLAKAGAKISIMTYSEFKHCWDTFVDHQGCPFQPWDGLEEHSQALSGRL

RAILQNQGN
(underline: nucleic acid editing domain; double underline: cytoplasmic
localization signal)

Green monkey APOBEC-3G:

(SEQ ID NO: 69)

<u>MNPQIRNMVEQMEPDIFVYYFNNRPILSGRNTVWLCYEVKTKDPSGPPLDANIFQGKLYPEAKDHPEMKFLHWFR</u>

<u>KWRQLHRDQEYEVTWYVSWSPCTRC</u>ANSVATFLAEDPKVTLTIFVARLYYFWKPDYQQALRILCQERGGPHATMK

IMNYEFQHCWNEFVDGQGKPFKPRKNLPKHYTLLHATLGELLRHVMDPGTFTSNFNNKPWVSGQRETYLCYKVE

RSHNDTWVLLNQHRGFLRNQAPDRHGFPKGR<u>HAELCFLDLIPFWKLDDQQYRVTCFTSWSPCFSC</u>AQKMAKFISN

NKHVSLCIFAARIYDDQGRCQEGLRTLHRDGAKIAVMNYSEFEYCWDTFVDRQGRPFQPWDGLDEHSQALSGRLR

AI
(underline: nucleic acid editing domain; double underline: cytoplasmic
localization signal)

Human APOBEC-3G:

(SEQ ID NO: 70)

<u>MKPHFRNTVERMYRDTFSYNFYNRPILSRRNTVWLCYEVKTKGPSRPPLDAKIFRGQVYSELKYHPEMRFFHWFS</u>

<u>KWRKLHRDQEYEVTWYISWSPCTKC</u>TRDMATFLAEDPKVTLTIFVARLYYFWDPDYQEALRSLCQKRDGPRATMK

IMNYDEFQHCWSKFVYSQRELFEPWNNLPKYYILLHIMLGEILRHSMDPPTFTFNNEPWVRGRHETYLCYEVE

RMHNDTWVLLNQRRGFLCNQAPHKHGFLEGR<u>HAELCFLDVIPFWKLDLDQDYRVTCFTSWSPCFSC</u>AQEMAKFIS

KNKHVSLCIFTARIYDDQGRCQEGLRTLAEAGAKISIMTYSEFKHCWDTFVDHQGCPFQPWDGLDEHSQDLSGRL

RAILQNQEN

-continued
(underline: nucleic acid editing domain; double underline: cytoplasmic
localization signal)

Human APOBEC-3F:
(SEQ ID NO: 71)
MKPHFRNTVERMYRDTFSYNFYNRPILSRRNTVWLCYEVKTKGPSRPRLDAKIFRGQVYSQPEH<u>HAEMCFLSWFC</u>

<u>GNQLPAYKCFQITWFVSWTPCPDC</u>VAKLAEFLAEHPNVTLTISAARLYYWERDYRRALCRLSQAGARVKIMDDE

EFAYCWENFVYSEGQPFMPWYKFDDNYAFLHRTLKEILRNPMEAMYPHIFYFHFKNLRKAYGRNESWLCFTMEVV

KHHSPVSWKRGVFRNQVDPETHC<u>HAERCFLSWFCDDILSPNTNYEVTWYTSWSPCPEC</u>AGEVAEFLARHSNVNLT

IFTARLYYFWDTDYQEGLRSLSQEGASVEIMGYKDFKYCWENFVYNDDEPFKPWKGLKYNLFLDSKLQEILE
(underline: nucleic acid editing domain)

Human APOBEC-3B:
(SEQ ID NO: 72)
MNPQIRNPMERMYRDTFYDNFENEPILYGRSYTWLCYEVKIKRGRSNLLWDTGVFRGQVYFKPQY<u>HAEMCFLSWF</u>

<u>CGNQLPAYKCFQITWFVSWTPCPDC</u>VAKLAEFLSEHPNVTLTISAARLYYWERDYRRALCRLSQAGARVTIMDY

EEFAYCWENFVYNEGQQFMPWYKFDENYAFLHRTLKEILRYLMDPDTFTFNFNNDPLVLRRRQTYLCYEVERLDN

GTWVLMDQHMGFLCNEAKNLLCGFY<u>GRHAELRFLDLVPSLQLDPAQIYRVTWFISWSPCFSWGC</u>AGEVRAFLQEN

THVRLRIFAARIYDYDPLYKEALQMLRDAGAQVSIMTYDEFEYCWDTFVYRQGCPFQPWDGLEEHSQALSGRLRA

ILQNQGN
(underline: nucleic acid editing domain)

Human APOBEC-3C:
(SEQ ID NO: 73)
MNPQIRNPMKAMYPGTFYFQFKNLWEANDRNETWLCFTVEGIKRRSVVSWKTGVFRNQVDSETH<u>CHAERCFLSWF</u>

<u>CDDILSPNTKYQVTWYTSWSPCPDC</u>AGEVAEFLARHSNVNLTIFTARLYYFQYPCYQEGLRSLSQEGVAVEIMDY

EDFKYCWENFVYNDNEPFKPWKGLKTNFRLLKRRLRESLQ
(underline: nucleic acid editing domain)

Human APOBEC-3A:
(SEQ ID NO: 74)
MEASPASGPRHLMDPHIFTSNFNNGIGRHKTYLCYEVERLDNGTSVKMDQHRGFLHNQAKNLLCGFYGR<u>HAELRF</u>

<u>LDLVPSLQLDPAQIYRVTWFISWSPCFSWGC</u>AGEVRAFLQENTHVRLRIFAARIYDYDPLYKEALQMLRDAGAQV

SIMTYDEFKHCWDTFVDHQGCPFQPWDGLDEHSQALSGRLRAILQNQGN
(underline: nucleic acid editing domain)

Human APOBEC-3H:
(SEQ ID NO: 75)
MALLTAETFRLQFNNKRRLRRPYYPRKALLCYQLTPQNGSTPTRGYFENKKKC<u>HAEICFINEIKSMGLDETQCYQ</u>

<u>VTCYLTWSPCSSC</u>AWELVDFIKAHDHLNLGIFASRLYYHWCKPQQKGLRLLCGSQVPVEVMGFPKFADCWENFVD

HEKPLSFNPYKMLEELDKNSRAIKRRLERIKIPGVRAQGRYMDILCDAEV
(underline: nucleic acid editing domain)

Human APOBEC-3D:
(SEQ ID NO: 76)
MNPQIRNPMERMYRDTFYDNFENEPILYGRSYTWLCYEVKIKRGRSNLLWDTGVFRGPVLPKRQSNHRQEVYFRF EN<u>HAEMCFLSWFCGNRLPANRRFQITWFVSWNPCLPC</u>VVKVTKFLAEHPNVTLTISAARLYYYRDRDWRWVLLRL

HKAGARVKIMDYEDFAYCWENFVCNEGQPFMPWYKFDDNYASLHRTLKEILRNPMEAMYPHIFYFHFKNLLKACG

RNESWLCFTMEVTKHHSAVFRKRGVFRNQVDPETHC<u>HAERCFLSWFCDDILSPNTNYEVTWYTSWSPCPEC</u>AGEV

AEFLARHSNVNLTIFTARLCYFWDTDYQEGLCSLSQEGASVKIMGYKDFVSCWKNFVYSDDEPFKPWKGLQTNFR

LLKRRLREILQ
(underline: nucleic acid editing domain)

Human APOBEC-1:
(SEQ ID NO: 77)
MTSEKGPSTGDPTLRRRIEPWEFDVFYDPRELRKEACLLYEIKWGMSRKIWRSSGKNTTNHVEVNFIKKFTSERD

FHPSMSCSITWFLSWSPCWECSQAIREFLSRHPGVTLVIYVARLFWHMDQQNRQGLRDLVNSGVTIQIMRASEYY

HCWRNFVNYPPGDEAHWPQYPPLWMMLYALELHCIILSLPPCLKISRRWQNHLTFFRLHLQNCHYQTIPPHILLA

TGLIHPSVAWR

Mouse APOBEC-1:
(SEQ ID NO: 78)
MSSETGPVAVDPTLRRRIEPHEFEVFFDPRELRKETCLLYEINWGGRHSVWRHTSQNTSNHVEVNFLEKFTTERY

FRPNTRCSITWFLSWSPCGECSRAITEFLSRHPYVTLFIYIARLYHHTDQRNRQGLRDLISSGVTIQIMTEQEYC

YCWRNFVNYPPSNEAYWPRYPHLWVKLYVLELYCIILGLPPCLKILRRKQPQLTFFTITLQTCHYQRIPPHLLWA

TGLK

Rat APOBEC-1:
(SEQ ID NO: 79)
MSSETGPVAVDPTLRRRIEPHEFEVFFDPRELRKETCLLYEINWGGRHSIWRHTSQNTNKHVEVNFIEKFTTERY

FCPNTRCSITWFLSWSPCGECSRAITEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQPQLTFFTIALQSCHYQRLPPHILWA

TGLK

Human ADAT-2:
(SEQ ID NO: 80)
MEAKAAPKPAASGACSVSAEETEKWMEEAMHMAKEALENTEVPVGCLMVYNNEVVGKGRNEVNQTKNATRHAEMV

AIDQVLDWCRQSGKSPSEVFEHTVLYVTVEPCIMCAAALRLMKIPLVVYGCQNERFGGCGSVLNIASADLPNTGR

PFQCIPGYRAEEAVEMLKTFYKQENPNAPKSKVRKKECQKS

Mouse ADAT-2:
(SEQ ID NO: 81)
MEEKVESTTTPDGPCVVSVQETEKWMEEAMRMAKEALENIEVPVGCLMVYNNEVVGKGRNEVNQTKNATRHAEMV

AIDQVLDWCHQHGQSPSTVFEHTVLYVTVEPCIMCAAALRLMKIPLVVYGCQNERFGGCGSVLNIASADLPNTGR

PFQCIPGYRAEEAVELLKTFYKQENPNAPKSKVRKKDCQKS

Mouse ADAT-1:
(SEQ ID NO: 82)
MWTADEIAQLCYAHYNVRLPKQGKPEPNREWTLLAAVVKIQASANQACDIPEKEVQVTKEVV<u>SMGTGTKCIGQSK</u>

<u>MRESGDILNDSHAEIIARRSFQRYLLHQLHLAAVLKEDSIFVPGTQRGLWRLRPDLSFVFFSSHTPCGDASIIPM</u>

<u>LEFEEQPCCPVIRSWANNSPVQETENLEDSKDKRNCEDPASPVAKKMRLGTPARSLSNCVAHHGTQESGPVKPDV</u>

<u>SSSDLTKEEPDAANGIASGSFRVVDVYRTGAKCVPGETGDLREPGAAYHQVGLLRVKPGRGDRTCSMSCSDKMAR</u>

<u>WNVLGCQGALLMHFLEKPIYLSAVVIGKCPYSQEAMRRALTGRCEETLVLPRGFGVQELEIQQSGLLFEQSRCAV</u>

<u>HRKRGDSPGRLVPCGAAISWSAVPQQPLDVTANGFPQGTTKKEIGSPRARSRISKVELFRSFQKLLSSIADDEQP</u>

<u>DSIRVTKKLDTYQEYKDAASAYQEAWGALRRIQPFASWIRNPPDYHQFK</u>
(underline: nucleic acid editing domain)

Human ADAT-1:
(SEQ ID NO: 83)
MWTADEIAQLCYEHYGIRLPKKGKPEPNHEWTLLAAVVKIQSPADKACDTPDKPVQVTKEVV<u>SMGTGTKCIGQSK</u>

<u>MRKNGDILNDSHAEVIARRSFQRYLLHQLQLAATLKEDSIFVPGTQKGVWKLRRDLIFVFFSSHTPCGDASIIPM</u>

<u>LEFEDQPCCPVFRNWAHNSSVEASSNLEAPGNERKCEDPDSPVTKKMRLEPGTAAREVTNGAAHHQSFGKQKSGP</u>

<u>ISPGIHSCDLTVEGLATVTRIAPGSAKVIDVYRTGAKCVPGEAGDSGKPGAAFHQVGLLRVKPGRGDRTRSMSCS</u>

<u>DKMARWNVLGCQGALLMHLLEEPIYLSAVVIGKCPYSQEAMQRALIGRCQNVSALPKGFGVQELKILQSDLLFEQ</u>

<u>SRSAVQAKRADSPGRLVPCGAAISWSAVPEQPLDVTANGFPQGTTKKTIGSLQARSQISKVELFRSFQKLLSRIA</u>

<u>RDKWPHSLRVQKLDTYQEYKEAASSYQEAWSTLRKQVFGSWIRNPPDYHQFK</u>
(underline: nucleic acid editing domain)

In some embodiments, the enzymatic domain comprises one or more of a transcriptional activator. For example, in some embodiments, the general architecture of exemplary dCas9 fusion proteins with a transcriptional activator domain comprises the structure:

[NH$_2$]-[NLS]-[Cas9]-[(transcriptional activator)$_n$]-[COOH],

[NH$_2$]-[NLS]-[(transcriptional activator)$_n$]-[Cas9]-[COOH],

[NH₂]-[Cas9]-[(transcriptional activator)ₙ]-[COOH],
or

[NH₂]-[(transcriptional activator)ₙ]-[Cas9]-[COOH];

wherein NLS is a nuclear localization signal, NH₂ is the N-terminus of the fusion protein, and COOH is the C-terminus of the fusion protein. In some embodiments, the fusion proteins comprises one or more repeats of the transcriptional activator, for example wherein n=1-10 (e.g., n is 1, 2, 3, 4, 5, 6, 7, 8, 9, or 10). In some embodiments, n=1-20. In some embodiments, a linker is inserted between the dCas9 and the transcriptional activator domain. In some embodiments, a linker is inserted between the NLS and the transcriptional activator and/or dCas9 domain. In some embodiments, the NLS is located C-terminal of the transcriptional activator and/or the dCas9 domain. In some embodiments, the NLS is located between the transcriptional activator domain and the dCas9 domain. Additional features, such as sequence tags, may also be present. In some embodiments, the transcriptional activator is selected from the group consisting of VP64, (SEQ ID NO:84 or SEQ ID NO:35), VP16 (SEQ ID NO:85), and p65 (SEQ ID NO:86). In some embodiments, a dCas9-VP64 fusion protein comprises the amino acid sequence of SEQ ID NO:87 (e.g., with or without the 6×His tag) or comprises an amino acid sequence that is at least 80%, at least 85%, at least 90%, at least 95%, at least 98%, or at least 99% identical to the amino acid sequence of SEQ ID NO:87 (e.g., with or without the 6×His tag).

```
VP64
                                                      (SEQ ID NO: 84)
GSGRADALDDFDLDMLGSDALDDFDLDMLGSDALDDFDLDMLGSDALDDFDLDMLIN

VP16
                                                      (SEQ ID NO: 85)
APPTDVSLGDELHLDGEDVAMAHADALDDFDLDMLGDGDSPGPGFTPHDSAPYGALDMADFEFEQMFT

DALGIDEYGGEFPGIRR p65:
                                                      (SEQ ID NO: 86)
PSGQISNQALALAPSSAPVLAQTMVPSSAMVPLAQPPAPAPVLTPGPPQSLSAPVPKSTQAGEGTLSE

ALLHLQFDADEDLGALLGNSTDPGVFTDLASVDNSEFQQLLNQGVSMSHSTAEPMLMEYPEAITRLVT

GSQRPPDPAPTPLGTSGLPNGLSGDEDFSSIADMDFSALLSQISSSGQ dCas9-VP64-6xHis:
                                                      (SEQ ID NO: 87)
MDKKYSIGLAIGTNSVGWAVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPIFGNIVDEVAYHEKYPTIY

HLRKKLVDSTDKADLRLIYLALAHMIKFRGHFLIEGDLNPDNSDVDKLFIQLVQTYNQLFEENPINAS

GVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVR

QQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPW

NFEEVVDKGASAQSFIERMTNFDKNLPNEKVLPKHSLLYEYFTVYNELTKVKYVTEGMRKPAFLSGEQ

KKAIVDLLFKTNRKVTVKQLKEDYFKKIECFDSVEISGVEDRFNASLGTYHDLLKIIKDKDFLDNEEN

EDILEDIVLTLTLFEDREMIEERLKTYAHLFDDKVMKQLKRRRYTGWGRLSRKLINGIRDKQSGKTIL

DFLKSDGFANRNFMQLIHDDSLTFKEDIQKAQVSGQGDSLHEHIANLAGSPAIKKGILQTVKVVDELV

KVMGRHKPENIVIEMARENQTTQKGQKNSRERMKRIEEGIKELGSQILKEHPVENTQLQNEKLYLYYL

QNGRDMYVDQELDINRLSDYDVDAIVPQSFLKDDSIDNKVLTRSDKNRGKSDNVPSEEVVKKMKNYWR

QLLNAKLITQRKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYGDYKVYDVRK

MIAKSEQEIGKATAKYFFYSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRMLASAGELQKGN

ELALPSKYVNFLYLASHYEKLKGSPEDNEQKQLFVEQHKHYLDEIIEQISEFSKRVILADANLDKVLS

AYNKHRDKPIREQAENIIHLFTLTNLGAPAAFKYFDTTIDRKRYTSTKEVLDATLIHQSITGLYETRI
```

-continued

DLSQLGGDGSPKKKRKVSSDYKDHDGDYKDHDIDYKDDDDKAAGGGGSGRADALDDFDLDMLGSDALD

DFDLDMLGSDALDDFDLDMLGSDALDDFDLDMLHHHHHH

In some embodiments, the enzymatic domain comprises one or more of a transcriptional repressor. For example, in some embodiments, the general architecture of exemplary dCas9 fusion proteins with a transcriptional repressor domain comprises the structure:

[NH$_2$]-[NLS]-[Cas9]-[(transcriptional repressor)$_n$]-[COOH],

[NH$_2$]-[NLS]-[(transcriptional repressor)$_n$]-[Cas9]-[COOH],

[NH$_2$]-[Cas9]-[(transcriptional repressor)$_n$]-[COOH], or

[NH$_2$]-[(transcriptional repressor)$_n$]-[Cas9]-[COOH];

wherein NLS is a nuclear localization signal, NH$_2$ is the N-terminus of the fusion protein, and COOH is the C-terminus of the fusion protein. In some embodiments, the fusion proteins comprises one or more repeats of the transcriptional repressor, for example wherein n=1-10 (e.g., n is 1, 2, 3, 4, 5, 6, 7, 8, 9, or 10). In some embodiments, n=1-20. In some embodiments, a linker is inserted between the dCas9 and the transcriptional repressor domain. In some embodiments, a linker is inserted between the NLS and the transcriptional repressor and/or dCas9 domain. In some embodiments, the NLS is located C-terminal of the transcriptional repressor and/or the dCas9 domain. In some embodiments, the NLS is located between the transcriptional repressor domain and the dCas9 domain. Additional features, such as sequence tags, may also be present. In some embodiments, the transcriptional repressor is selected from the group consisting of the KRAB (Krüppel associated box) domain of Kox1, SID (mSin3 interaction domain), the CS (Chromo Shadow) domain of HP1α, or the WRPW domain of Hes1. These and other repressor domains are known in the art, and in some embodiments correspond to those described in Urrutia, KRAB-containing zinc-finger repressor proteins. *Genome Biol.* 2003; 4(10):231; Gilbert et al. CRISPR-mediated modular RNA-guided regulation of transcription in eukaryotes. *Cell.* 2013; 154, 442-451; Konermann et al., Optical control of mammalian endogenous transcription and epigenetic states. *Nature.* 2013; 500, 472-476; and published U.S. patent application U.S. Ser. No. 14/105,017, published as U.S. 2014/0186958 A1, the entire contents of which are incorporated herein by reference. In some embodiments, the transcription repressor domain comprises one or more repeats (e.g., 2, 3, 4, 5, 6, 7, 8, 9, or 10 repeats) of a KRAB domain. In some embodiments, the KRAB domain comprises an amino acid sequence selected from the group consisting of SEQ ID NOs:88-91. In some embodiments, the transcriptional repressor domains comprises one or more repeats of a SID protein. In some embodiments, the SID protein comprises an amino acid sequence set forth as SEQ ID NO:80. In some embodiments, the repressor domain comprises 2, 3, 4, 5, 6, 7, 8, 9, or 10 repeats of a SID protein (e.g., SEQ ID NO:92). In some embodiments, the repressor domain comprises four repeats of SID (e.g., SID4x; SEQ ID NO:93).

KRAB (human; GenBank: AAD20972.1)
(SEQ ID NO: 88)
MNMFKEAVTFKDVAVAFTEEELGLLGPAQRKLYRDVMVENFRNLLSVGHP

PFKQDVSPIERNEQLWIMTTATRRQGNLDTLPVKALLLYDLAQT

KRAB protein domain, partial (human; GenBank: CAB52478.1):
(SEQ ID NO: 89)
EQVSFKDVCVDFTQEEWYLLDPAQKILYRDVILENYSNLVSVGYCITKPE

VIFKIEQGEEPWILEKGFPSQCHP

KRAB A domain, partial (human; GenBank: AAB03530.1):
(SEQ ID NO: 90)
EAVTFKDVAVVFTEEELGLLDPAQRKLYRDVMLENFRNLLSV KRAB (mouse; C2H2 type domain containing protein; GenBank: CAM27971.1):
(SEQ ID NO: 91)
MDLVTYDDVHVNFTQDEWALLDPSQKSLYKGVMLETYKNLTAIGYIWEEH

TIEDHFQTSRSHGSNKKTH

SID repressor domain:
(SEQ ID NO: 92)
GSGMNIQMLLEAADYLERREREAEHGYASMLP

SID4x repressor domain:
(SEQ ID NO: 93)
GSGMNIQMLLEAADYLERREREAEHGYASMLPGSGMNIQMLLEAADYLER

REREAEHGYASMLPGSGMNIQMLLEAADYLERREREAEHGYASMLPGSGM

NIQMLLEAADYLERREREAEHGYASMLPSR

In some embodiments, the enzymatic domain comprises an epigenetic modifier or a catalytic domain thereof. For example, in some embodiments, the general architecture of exemplary dCas9 fusion proteins with an epigenetic modifier or domain comprises the structure:

[NH$_2$]-[NLS]-[Cas9]-[epigenetic modifier]-[COOH],

[NH$_2$]-[NLS]-[epigenetic modifier]-[Cas9]-[COOH],

[NH$_2$]-[Cas9]-[epigenetic modifier]-[COOH], or

[NH$_2$]-[epigenetic modifier]-[Cas9]-[COOH];

wherein NLS is a nuclear localization signal, NH$_2$ is the N-terminus of the fusion protein, and COOH is the C-terminus of the fusion protein. In some embodiments, a linker is inserted between the dCas9 and the epigenetic modifier domain. In some embodiments, a linker is inserted between the NLS and the epigenetic modifier and/or dCas9 domain. In some embodiments, the NLS is located C-terminal of the epigenetic modifier and/or the dCas9 domain. In some embodiments, the NLS is located between the epigenetic modifier domain and the dCas9 domain. Additional features, such as sequence tags, may also be present. Epigenetic modifiers are well known in the art, and typically catalyze DNA methylation (and demethylation) or histone modifications (e.g., histone methylation/demethylation, acetylation/deacetylation, ubiquitylation, phosphorylation, sumoylation, etc.). The presence of one more epigenetic modifications can affect the transcriptional activity of one or more genes, for example turning genes from an "on" state to an "off" state, and vice versa. Epigenetic modifiers include, but are not limited to, histone demethylase, histone methyltransferase, hydroxylase, histone deacetylase, and histone acetyltransferase. Exemplary epigenetic modifying proteins can be found in Konermann et al., Optical control of mammalian endogenous transcription and epigenetic states. *Nature.* 2013; 500, 472-476; Mendenhall et al., Locus-specific editing of histone modifications at endogenous enhancers. *Nat. Biotechnol.* 2013; 31, 1133-1136; and Maeder et al., Targeted DNA demethylation and activation of endogenous genes using programmable TALE-TET1 fusion proteins. *Nat. Biotechnol.* 2013; 31, 1137-1142; the entire contents of each are incorporated herein by reference. In some embodiments, the epigenetic modifier domain is LSD1 (Lysine (K)-specific demethylase 1A) histone demethylase, which in some embodiments, comprises in whole or in part, an amino acid sequence set forth as SEQ ID NO:94 or SEQ ID NO:95. In some embodiments, the epigenetic modifier domain is TET1 hydroxylase catalytic domain, which in some embodiments, comprises an amino acid sequence set forth as SEQ ID NO:96. In some embodiments, the epigenetic modifier is a histone deacetylase (HDAC) effector domain. In some embodiments, the HDAC effector domain comprises in whole in part, an amino acid sequence corresponding to any of the HDAC effector proteins provided in Supplementary Table 2 of Konermann et al., Optical control of mammalian endogenous transcription and epigenetic states. *Nature.* 2013; 500, 472-476; SEQ ID NOs:97-108. In some embodiments, the epigenetic modifier is a histone methyltransferase (HMT) effector domain. In some embodiments, the HMT effector domain comprises in whole in part, an amino acid sequence corresponding to any of the HDAC effector proteins provided in Supplementary Table 3 of Konermann et al., Optical control of mammalian endogenous transcription and epigenetic states. *Nature.* 2013; 500, 472-476; SEQ ID NOs:109-118.

```
LSD1, isoform a (human):
                                                  (SEQ ID NO: 94)
MLSGKKAAAAAAAAAAAATGTEAGPGTAGGSENGSEVAAQPAGLSGPAEVGPGAVGERTPRKKEPPRA

SPPGGLAEPPGSAGPQAGPTVVPGSATPMETGIAETPEGRRTSRRKRAKVEYREMDESLANLSEDEYY

SEEERNAKAEKEKKLPPPPPQAPPEEENESEPEEPSGQAGGLQDDSSGGYGDGQASGVEGAAFQSRLP

HDRMTSQEAACFPDIISGPQQTQKVFLFIRNRTLQLWLDNPKIQLTFEATLQQLEAPYNSDTVLVHRV

HSYLERHGLINFGIYKRIKPLPTKKTGKVIIIGSGVSGLAAARQLQSFGMDVTLLEARDRVGGRVATF

RKGNYVADLGAMVVTGLGGNPMAVVSKQVNMELAKIKQKCPLYEANGQADTVKVPKEKDEMVEQEFNR

LLEATSYLSHQLDFNVLNNKPVSLGQALEVVIQLQEKHVKDEQIEHWKKIVKTQEELKELLNKMVNLK

EKIKELHQQYKEASEVKPPRDITAEFLVKSKHRDLTALCKEYDELAETQGKLEEKLQELEANPPSDVY

LSSRDRQILDWHFANLEFANATPLSTLSLKHWDQDDDFEFTGSHLTVRNGYSCVPVALAEGLDIKLNT

AVRQVRYTASGCEVIAVNTRSTSQTFIYKCDAVLCTLPLGVLKQQPPAVQFVPPLPEWKTSAVQRMGF

GNLNKVVLCFDRVFWDPSVNLFGHVGSTTASRGELFLFWNLYKAPILLALVAGEAAGIMENISDDVIV

GRCLAILKGIFGSSAVPQPKETVVSRWRADPWARGSYSYVAAGSSGNDYDLMAQPITPGPSIPGAPQP

IPRLFFAGEHTIRNYPATVHGALLSGLREAGRIADQFLGAMYTLPRQATPGVPAQQSPSM

LSD1, isoform b (human):
                                                  (SEQ ID NO: 95)
MLSGKKAAAAAAAAAAAATGTEAGPGTAGGSENGSEVAAQPAGLSGPAEVGPGAVGERTPRKKEPPRA

SPPGGLAEPPGSAGPQAGPTVVPGSATPMETGIAETPEGRRTSRRKRAKVEYREMDESLANLSEDEYY

SEEERNAKAEKEKKLPPPPPQAPPEEENESEPEEPSGVEGAAFQSRLPHDRMTSQEAACFPDIISGPQ

QTQKVFLFIRNRTLQLWLDNPKIQLTFEATLQQLEAPYNSDTVLVHRVHSYLERHGLINFGIYKRIKP

LPTKKTGKVIIIGSGVSGLAAARQLQSFGMDVTLLEARDRVGGRVATFRKGNYVADLGAMVVTGLGGN

PMAVVSKQVNMELAKIKQKCPLYEANGQAVPKEKDEMVEQEFNRLLEATSYLSHQLDFNVLNNKPVSL

GQALEVVIQLQEKHVKDEQIEHWKKIVKTQEELKELLNKMVNLKEKIKELHQQYKEASEVKPPRDITA

EFLVKSKHRDLTALCKEYDELAETQGKLEEKLQELEANPPSDVYLSSRDRQILDWHFANLEFANATPL

STLSLKHWDQDDDFEFTGSHLTVRNGYSCVPVALAEGLDIKLNTAVRQVRYTASGCEVIAVNTRSTSQ

TFIYKCDAVLCTLPLGVLKQQPPAVQFVPPLPEWKTSAVQRMGFGNLNKVVLCFDRVFWDPSVNLFGH

VGSTTASRGELFLFWNLYKAPILLALVAGEAAGIMENISDDVIVGRCLAILKGIFGSSAVPQPKETVV

SRWRADPWARGSYSYVAAGSSGNDYDLMAQPITPGPSIPGAPQPIPRLFFAGEHTIRNYPATVHGALL

SGLREAGRIADQFLGAMYTLPRQATPGVPAQQSPSM
```

TET1 catalytic domain:
(SEQ ID NO: 96)
SIVAQLSRPDPALAALTNDHLVALACLGGRPALDAVKKGLPHAPALIKRTNRRIPERTSHRVADHAQV
VRVLGFFQCHSHPAQAFDDAMTQFGMSGGGSLPTCSCLDRVIQKDKGPYYTHLGAGPSVAAVREIMEN
RYGQKGNAIRIEIVVYTGKEGKSSHGCPIAKWVLRRSSDEEKVLCLVRQRTGHHCPTAVMVLIMVWD
GIPLPMADRLYTELTENLKSYNGHPTDRRCTLNENRTCTCQGIDPETCGASFSFGCSWSMYFNGCKFG
RSPSPRRFRIDPSSPLHEKNLEDNLQSLATRLAPIYKQYAPVAYQNQVEYENVARECRLGSKEGRPFS
GVTACLDFCAHPHRDIHNMNNGSTVVCTLTREDNRSLGVIPQDEQLHVLPLYKLSDTDEFGSKEGMEA
KIKSGAIEVLAPRRKKRTCFTQPVPRSGKKRAAMMTEVLAHKIRAVEKKPIPRIKRKNNSTTTNNSKP
SSLPTLGSNTETVQPEVKSETEPHFILKSSDNTKTYSLMPSAPHPVKEASPGFSWSPKTASATPAPLK
NDATASCGFSERSSTPHCTMPSGRLSGANAAAADGPGISQLGEVAPLPTLSAPVMEPLINSEPSTGVT
EPLTPHQPNHQPSFLTSPQDLASSPMEEDEQHSEADEPPSDEPLSDDPLSPAEEKLPHIDEYWSDSEH
IFLDANIGGVAIAPAHGSVLIECARRELHATTPVEHPNRNHPTRLSLVFYQHKNLNKPQHGFELNKIK
FEAKEAKNKKMKASEQKDQAANEGPEQSSEVNELNQIPSHKALTLTHDNVVTVSPY-
ALTHVAGPYNHWV HDAC effector domains:
HDAC8 (X. laevis):
(SEQ ID NO: 97)
ASSPKKKRKVEASMSRVVKPKVASMEEMAAFHTDAYLQHLHKVSEEGDNDDPETLEYGLGYDCPITEG
IYDYAAAVGGATLTAAEQLIEGKTRIAVNWPGGWHHAKKDEASGFCYLNDAVLGILKLREKFDRVLYV
DMDLHHGDGVEDAFSFTSKVMTVSLHKFSPGFFPGTGDVSDIGLGKGRYYSINVPLQDGIQDDKYYQI
CEGVLKEVFTTFNPEAVVLQLGADTIAGDPMCSFNMTPEGIGKCLKYVLQWQLPTLILGGGGYHLPNT
ARCWTYLTALIVGRTLSSEIPDHEFFTEYGPDYVLEITPSCRPDRNDTQKVQEILQSIKGNLKRVVEF RPD3 (S. cerevisiae):
(SEQ ID NO: 98)
ASSPKKKRKVEASRRVAYFYDADVGNYAYGAGHPMKPHRIRMAHSLIMNYGLYKKMEIYRAKPATKQE
MCQFHTDEYIDFLSRVTPDNLEMFKRESVKFNVGDDCPVFDGLYEYCSISGGGSMEGAARLNRGKCDV
AVNYAGGLHHAKKSEASGFCYLNDIVLGIIELLRYHPRVLYIDIDVHHGDGVEEAFYTTDRVMTCSFH
KYGEFFPGTGELRDIGVGAGKNYAVNVPLRDGIDDATYRSVFEPVIKKIMEWYQPSAVVLQCGGDSLS
GDRLGCFNLSMEGHANCVNYVKSFGIPMMVVGGGGYTMRNVARTWCFETGLLNNVVLDKDLPYEF MesoLo4 (M. loti):
(SEQ ID NO: 99)
ASSPKKKRKVEASMPLQIVHHPDYDAGFATNHRFPMSKYPLLMEALRARGLASPDALNTTEPAPASWL
KLAHAADYVDQVISCSVPEKIEREIGFPVGPRVSLRAQLATGGTILAARLALRHGIACNTAGGSHHAR
RAQGAGFCTFNDVAVASLVLLDEGAAQNILVVDLDVHQGDGTADILSDEPGVFTFSMHGERNYPVRKI
ASDLDIALPDGTGDAAYLRRLATILPELSARARWDIVFYNAGVDVHAEDRLGRLALSNGGLRARDEMV
IGHFRALGIPVCGVIGGGYSTDVPALASRHAILFEVASTYAEF HDAC11 (human):
(SEQ ID NO: 100)
ASSPKKKRKVEASMLHTTQLYQHVPETRWPIVYSPRYNITFMGLEKLHPFDAGKWGKVINFLKEEKLL
SDSMLVEAREASEEDLLVVHTRRYLNELKWSFAVATITEIPPVIFLPNFLVQRKVLRPLRTQTGGTIM
AGKLAVERGWAINVGGGFHHCSSDRGGGFCAYADITLAIKFLFERVEGISRATIIDLDAHQGNGHERD
FMDDKRVYIMDVYNRHIYPGDRFAKQAIRRKVELEWGTEDDEYLDKVERNIKKSLQEHLPDVVVYNAG
TDILEGDRLGGLSISPAGIVKRDELVFRMVRGRRVPILMVTSGGYQKRTARIIADSILNLFGLGLIGP
ESPSVSAQNSDTPLLPPAVPEF HDT1 (*A. thaliana*):
(SEQ ID NO: 101)
ASSPKKKRKVEASMEFWGIEVKSGKPVTVTPEEGILIHVSQASLGECKNKKGEFVPLHVKVGNQNLVL

GTLSTENIPQLFCDLVFDKEFELSHTWGKGSVYFVGYKTPNIEPQGYSEEEEEEEEEVPAGNAAKAVA

KPKAKPAEVKPAVDDEEDESDSDGMDEDDSDGEDSEEEEPTPKKPASSKKRANETTPKAPVSAKKAKV

AVTPQKTDEKKKGGKAANQSEF

SIRT3 (human):
(SEQ ID NO: 102)
ASSPKKKRKVEASMVGAGISTPSGIPDFRSPGSGLYSNLQQYDLPYPEAIFELPFFFHNPKPFFTLAK

ELYPGNYKPNVTHYFLRLLHDKGLLLRLYTQNIDGLERVSGIPASKLVEAHGTFASATCTVCQRPFPG

EDIRADVMADRVPRCPVCTGVVKPDIVFFGEPLPQRFLLHVVDFPMADLLLILGTSLEVEPFASLTEA

VRSSVPRLLINRDLVGPLAWHPRSRDVAQLGDVVHGVESLVELLGWTEEMRDLVQRETGKLDGPDKEF

HST2 (*S. cerevisiae*):
(SEQ ID NO: 103)
ASSPKKKRKVEASTEMSVRKIAAHMKSNPNAKVIFMVGAGISTSCGIPDFRSPGTGLYHNLARLKLPY

PEAVFDVDFFQSDPLPFYTLAKELYPGNFRPSKFHYLLKLFQDKDVLKRVYTQNIDTLERQAGVKDDL

IIEAHGSFAHCHCIGCGKVYPPQVFKSKLAEHPIKDFVKCDVCGELVKPAIVFFGEDLPDSFSETWLN

DSEWLREKITTSGKHPQQPLVIVVGTSLAVYPFASLPEEIPRKVKRVLCNLETVGDFKANKRPTDLIV

HQYSDEFAEQLVEELGWQEDFEKILTAQGGMGEF

CobB (*E. coli* (K12)):
(SEQ ID NO: 104)
ASSPKKKRKVEASMEKPRVLVLTGAGISAESGIRTFRAADGLWEEHRVEDVATPEGFDRDPELVQAFY

NARRRQLQQPEIQPNAAHLALAKLQDALGDRFLLVTQNIDNLHERAGNTNVIHMHGELLKVRCSQSGQ

VLDWTGDVTPEDKCHCCQFPAPLRPHVVWFGEMPLGMDEIYMALSMADIFIAIGTSGHVYPAAGFVHE

AKLHGAHTVELNLEPSQVGNEFAEKYYGPASQVVPEFVEKLLKGLKAGSIAEF

HST2 (*C. albicans*):
(SEQ ID NO: 105)
ASSPKKKRKVEASMPSLDDILKPVAEAVKNGKKVTFFNGAGISTGAGIPDFRSPDTGLYANLAKLNLP

FAEAVFDIDFFKEDPKPFYTLAEELYPGNFAPTKFHHFIKLLQDQGSLKRVYTQNIDTLERLAGVEDK

YIVEAHGSFASNHCVDCHKEMTTETLKTYMKDKKIPSCQHCEGYVKPDIVFFGEGLPVKFFDLWEDDC

EDVEVAIVAGTSLTVFPFASLPGEVNKKCLRVLVNKEKVGTFKHEPRKSDIIALHDCDIVAERLCTLL

GLDDKLNEVYEKEKIKYSKAETKEIKMHEIEDKLKEEAHLKEDKHTTKVDKKEKQNDANDKELEQLID

KAKAEF

SIRT5 (human):
(SEQ ID NO: 106)
ASSPKKKRKVEASSSSMADFRKFFAKAKHIVIISGAGVSAESGVPTFRGAGGYWRKWQAQDLATPLAF

AHNPSRVWEFYHYRREVMGSKEPNAGHRAIAECETRLGKQGRRVVVITQNIDELHRKAGTKNLLEIHG

SLFKTRCTSCGVVAENYKSPICPALS GKGAPEPGTQDASIPVEKLPRCEEAGCGGLLRPHVVWF-
GENL

DPAILEEVDRELAHCDLCLVVGTSSVVYPAAMFAPQVAARGVPVAEFNTETTPATNRFRFHFQGPCGT

TLPEALACHENETVSEF

Sir2A (*P. falciparum*):
(SEQ ID NO: 107)
ASSPKKKRKVEASMGNLMISFLKKDTQSITLEELAKIIKKCKHVVALTGSGTSAESNIPSFRGSSNSI

WSKYDPRIYGTIWGFWKYPEKIWEVIRDISSDYEIEINNGHVALSTLESLGYLKSVVTQNVDGLHEAS

GNTKVISLHGNVFEAVCCTCNKIVKLNKIMLQKTSHFMHQLPPECPCGGIFKPNIILFGEVVSSDLLK

EAEEEIAKCDLLLVIGTSSTVSTATNLCHFACKKKKKIVEINISKTYITNKMSDYHVCAKFSELTKVA

NILKGSSEKNKKIMEF

SIRT6 (human):
(SEQ ID NO: 108)
ASSPKKKRKVEASMSVNYAAGLSPYADKGKCGLPEIFDPPEELERKVWELARLVWQSSSVVFHTGAGI

STASGIPDFRGPHGVWTMEERGLAPKFDTTFESARPTQTHMALVQLERVGLLRFLVSQNVDGLHVRSG

FPRDKLAELHGNMFVEECAKCKTQYVRDTVVGTMGLKATGRLCTVAKARGLRACRGELRDTILDWEDS

LPDRDLALADEASRNADLSITLGTSLQIRPSGNLPLATKRRGGRLVIVNLQPTKHDRHADLRIHGYVD

EVMTRLMKHLGLEIPAWDGPRVLERALPPLEF

HMT effector domains:
NUE (*C. trachomatis*):
(SEQ ID NO: 109)
ASSPKKKRKVEASMTTNSTQDTLYLSLHGGIDSAIPYPVRRVEQLLQFSFLPELQFQNAAVKQRIQRL

CYREEKRLAVSSLAKWLGQLHKQRLRAPKNPPVAICWINSYVGYGVFARESIPAWSYIGEYTGILRRR

QALWLDENDYCFRYPVPRYSFRYFTIDSGMQGNVTRFINHSDNPNLEAIGAFENGIFHIIIRAIKDIL

PGEELCYHYGPLYWKHRKKREEFVPQEEEF vSET (*P. bursaria chlorella* virus):
(SEQ ID NO: 110)
ASSPKKKRKVEASMFNDRVIVKKSPLGGYGVFARKSFEKGELVEECLCIVRHNDDWGTALEDYLFSRK

NMSAMALGFGAIFNHSKDPNARHELTAGLKRMRIFTIKPIAIGEEITISYGDDYWLSRPRLTQNEF

SUV39H1 (human):
(SEQ ID NO: 111)
ASSPKKKRKVEASNLKCVRILKQFHKDLERELLRRHHRSKTPRHLDPSLANYLVQKAKQRRALRRWEQ

ELNAKRSHLGRITVENEVDLDGPPRAFVYINEYRVGEGITLNQVAVGCECQDCLWAPTGGCCPGASLH

KFAYNDQGQVRLRAGLPIYECNSRCRCGYDCPNRVVQKGIRYDLCIFRTDDGRGWGVRTLEKIRKNSF

VMEYVGEIITSEEAERRGQIYDRQGATYLFDLDYVEDVYTVDAAYYGNISHFVNHSCDPNLQVYNVFI

DNLDERLPRIAFFATRTIRAGEELTFDYNMQVDPVDMESTRMDSNFGLAGLPGSPKKRVRIECKCGTE

SCRKYLFEF

DIM5 (*N. crassa*):
(SEQ ID NO: 112)
ASSPKKKRKVEASMEKAFRPHFFNHGKPDANPKEKKNCHWCQIRSFATHAQLPISIVNREDDAFLNPN

FRFIDHSIIGKNVPVADQSFRVGCSCASDEECMYSTCQCLDEMAPDSDEEADPYTRKKRFAYYSQGAK

KGLLRDRVLQSQEPIYECHQGCACSKDCPNRVVERGRTVPLQIFRTKDRGWGVKCPVNIKRGQFVDRY

LGEIITSEEADRRRAESTIARRKDVYLFALDKFSDPDSLDPLLAGQPLEVDGEYMSGPTRFINHSCDP

NMAIFARVGDHADKHIHDLALFAIKDIPKGTELTFDYVNGLTGLESDAHDPSKISEMTKCLCGTAKCR

GYLWEF

KYP (*A. thaliana*):
(SEQ ID NO: 113)
ASSPKKKRKVEASDISGGLEFKGIPATNRVDDSPVSPTSGFTYIKSLIIEPNVIIPKSSTGCNCRGSC

TDSKKCACAKLNGGNFPYVDLNDGRLIESRDVVFECGPHCGCGPKCVNRTSQKRLRFNLEVFRSAKKG

WAVRSWEYIPAGSPVCEYIGVVRRTADVDTISDNEYIFEIDCQQTMQGLGGRQRRLRDVAVPMNNGVS

QSSEDENAPEFCIDAGSTGNFARFINHSCEPNLFVQCVLSSHQDIRLARVVLFAADNISPMQELTYDY

GYALDSVHEF

SUVR4 (*A. thaliana*):
(SEQ ID NO: 114)
ASSPKKKRKVEASQSAYLHVSLARISDEDCCANCKGNCLSADFPCTCARETSGEYAYTKEGLLKEKFL

DTCLKMKKEPDSFPKVYCKDCPLERDHDKGTYGKCDGHLIRKFIKECWRKCGCDMQCGNRVVQRGIRC

QLQVYFTQEGKGWGLRTLQDLPKGTFICEYIGEILTNTELYDRNVRSSSERHTYPVTLDADWGSEKDL

KDEEALCLDATICGNVARFINHRCEDANMIDIPIEIETPDRHYYHIAFFTLRDVKAMDELTWDYMIDF

NDKSHPVKAFRCCCGSESCRDRKIKGSQGKSIERRKIVSAKKQQGSKEVSKKRKEF

```
Set4 (C. elegans):
                                                          (SEQ ID NO: 115)
ASSPKKKRKVEASMQLHEQIANISVTFNDIPRSDHSMTPTELCYFDDFATTLVVDSVLNFTTHKMSKK

RRYLYQDEYRTARTVMKTFREQRDWTNAIYGLLTLRSVSHFLSKLPPNKLFEFRDHIVRFLNMFILDS

GYTIQECKRYSQEGHQGAKLVSTGVWSRGDKIERLSGVVCLLSSEDEDSILAQEGSDFSVMYSTRKRC

STLWLGPGAYINHDCRPTCEFVSHGSTAHIRVLRDMVPGDEITCFYGSEFFGPNNIDCECCTCEKNMN

GAFSYLRGNENAEPIISEKKTKYELRSRSEF

Set1 (C. elegans):
                                                          (SEQ ID NO: 116)
ASSPKKKRKVEASMKVAAKKLATSRMRKDRAAAASPSSDIENSENPSSLASHSSSSGRMTPSKNTRSR

KGVSVKDVSNHKITEFFQVRRSNRKTSKQISDEAKHALRDTVLKGTNERLLEVYKDVVKGRGIRTKVN

FEKGDFVVEYRGVMMEYSEAKVIEEQYSNDEEIGSYMYFFEHNNKKWCIDATKESPWKGRLINHSVLR

PNLKTKVVEIDGSHHLILVARRQIAQGEELLYDYGDRSAETIAKNPWLVNTEF

SETD8 (human):
                                                          (SEQ ID NO: 117)
ASSPKKKRKVEASSCDSTNAAIAKQALKKPIKGKQAPRKKAQGKTQQNRKLTDFYPVRRSSRKSKAEL

QSEERKRIDELIESGKEEGMKIDLIDGKGRGVIATKQFSRGDFVVEYHGDLIEITDAKKREALYAQDP

STGCYMYYFQYLSKTYCVDATRETNRLGRLINHSKCGNCQTKLHDIDGVPHLILIASRDIAAGEELLY

DYGDRSKASIEAFPWLKHEF

TgSET8 (T. gondii):
                                                          (SEQ ID NO: 118)
ASSPKKKRKVEASASRRTGEFLRDAQAPSRWLKRSKTGQDDGAFCLETWLAGAGDDAAGGERGRDREG

AADKAKQREERRQKELEERFEEMKVEFEEKAQRMIARRAALTGEIYSDGKGSKKPRVPSLPENDDDAL

IEIIIDPEQGILKWPLSVMSIRQRTVIYQECLRRDLTACIHLTKVPGKGRAVFAADTILKDDFVVEYK

GELCSEREAREREQRYNRSKVPMGSFMFYFKNGSRMMAIDATDEKQDFGPARLINHSRRNPNMTPRAI

TLGDFNSEPRLIFVARRNIEKGEELLVDYGERDPDVIKEHPWLNSEF
```

Those of skill in the art will understand that any of the exemplary Cas9 proteins, including the exemplary Cas9 nucleases, variants, and fusions thereof, e.g., described herein, can be delivered to cells using the instantly disclosed technology, and that the disclosure is not limited in this respect.

Nuclease Effector Proteins

TALE nucleases, or TALENs, are artificial nucleases comprising a transcriptional activator-like effector DNA binding domain associated with a DNA cleavage domain, for example, a FokI domain. A number of modular assembly schemes for generating engineered TALE constructs have been reported (Zhang, Feng; et.al. (February 2011). "Efficient construction of sequence-specific TAL effectors for modulating mammalian transcription". *Nature Biotechnology* 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*.; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; the entire contents of each of which are incorporated herein by reference). Those of skill in the art will understand that TALE nucleases can be engineered to target virtually any genomic sequence with high specificity, and that such engineered nucleases can be used in embodiments of the present technology to manipulate the genome of a cell, e.g., by delivering the respective TALEN via a method or strategy disclosed herein under circumstances suitable for the TALEN to bind and cleave its target sequence within the genome of the cell. In some embodiments, the delivered TALEN targets a gene or allele associated with a disease or disorder. In some embodiments, delivery of the TALEN to a subject confers a therapeutic benefit to the subject.

Zinc finger nucleases are a class of artificial nucleases that comprise a DNA cleavage domain and a zinc finger DNA binding domain. In some embodiments, the DNA cleavage domain is a non-specific DNA cleavage domain of a restriction endonuclease, for example, of FokI. In some embodiments, the DNA cleavage domain is a domain that only cleaves double-stranded DNA when dimerized with a second DNA cleavage domain of the same type. In some embodiments, the DNA cleavage domain is fused to the C-terminus of the zinc finger domain via a linker, for example, a peptide linker. In some embodiments, the zinc finger domain comprises between about 3 and about 6 zinc fingers and specifically recognizes and binds a target sequence of about 9-20 nucleotides in length. In some embodiments, a plurality of zinc finger nuclease molecules is delivered to a target cell by a system or method provided by this invention, with the zinc finger domain of one zinc finger nuclease molecule binding a target sequence in close proximity of the target sequence of a second zinc finger nuclease molecule. In some embodiments, the zinc finger domains of the zinc finger nuclease molecules binding target sequences in close proximity to each other are different. In some embodiments, a zinc finger nuclease molecule delivered to a cell by a system or method provided herein binds a target nucleic acid sequence in close proximity to the target sequence of another zinc finger nuclease molecule, so that the DNA cleavage domains of the molecules dimerize and cleave a DNA molecule at a site between the two target sequences.

In some embodiments, the genome of the target cell is edited by a nuclease delivered to the cell via a strategy or method disclosed herein, e.g., by a TALEN, or a zinc-finger nuclease, or a plurality or combination of such nucleases. In some embodiments, a single- or double-strand break is introduced at a specific site within the genome of a target cell by the nuclease, resulting in a disruption of the targeted genomic sequence. In some embodiments, the targeted genomic sequence is a nucleic acid sequence within the coding region of a gene. In some embodiments, the strand break introduced by the nuclease leads to a mutation within the target gene that impairs the expression of the encoded gene product. In some embodiments, a nucleic acid is co-delivered to the cell with the nuclease. In some embodiments, the nucleic acid comprises a sequence that is identical or homologous to a sequence adjacent to the nuclease target site. In some such embodiments, the strand break effected by the nuclease is repaired by the cellular DNA repair machinery to introduce all or part of the co-delivered nucleic acid into the cellular DNA at the break site, resulting in a targeted insertion of the co-delivered nucleic acid, or part thereof. In some embodiments, the insertion results in the disruption or repair of a pathogenic allele. In some embodiments, the insertion is detected by a suitable assay, e.g., a DNA sequencing assay, a southern blot assay, or an assay for a reporter gene encoded by the co-delivered nucleic acid, e.g., a fluorescent protein or resistance to an antibiotic. In some embodiments, the nucleic acid is co-delivered by association to a supercharged protein. In some embodiments, the supercharged protein is also associated to the functional effector protein, e.g., the nuclease. In some embodiments, the delivery of a nuclease to a target cell results in a clinically or therapeutically beneficial disruption of the function of a gene.

In some embodiments, cells from a subject are obtained and a nuclease or other effector protein is delivered to the cells by a system or method provided herein ex vivo. In some embodiments, the treated cells are selected for those cells in which a desired nuclease-mediated genomic editing event has been effected. In some embodiments, treated cells carrying a desired genomic mutation or alteration are returned to the subject they were obtained from.

Methods for engineering, generation, and isolation of nucleases targeting specific sequences, e.g., TALE, or zinc finger nucleases, and editing cellular genomes at specific target sequences, are well known in the art (see, e.g., Mani et al., *Biochemical and Biophysical Research Communications* 335:447-457, 2005; Perez et al., *Nature Biotechnology* 26:808-16, 2008; Kim et al., *Genome Research*, 19:1279-88, 2009; Urnov et al., *Nature* 435:646-51, 2005; Carroll et al., *Gene Therapy* 15:1463-68, 2005; Lombardo et al., *Nature Biotechnology* 25:1298-306, 2007; Kandavelou et al., *Biochemical and Biophysical Research Communications* 388: 56-61, 2009; and Hockemeyer et al., *Nature Biotechnology* 27(9):851-59, 2009, as well as the reference recited in the respective section for each nuclease). The skilled artisan will be able to ascertain suitable methods for use in the context of the present disclosure based on the guidance provided herein.

TALE Effector Proteins

In some embodiments, effector proteins comprising a TALE domain are delivered to a target cell by a system or method provided herein. In some embodiments, a TALE effector, e.g., an engineered TALE transcription factor comprising a TALE DNA binding domain and a heterologous transcriptional activator or repressor domain, is delivered to a cell by a system or method provided by aspects of this invention. In some embodiments, the TALE effector, e.g., a transcription factor, is delivered to a cell in an amount sufficient to activate or inhibit transcription of a target gene of the transcription factor within the cell. In some embodiments, a transcription factor is delivered in an amount and over a time period sufficient to effect a change in the phenotype of a target cell, for example, a change in cellular function, or a change in developmental potential. Exemplary TALE transcription factors are described herein, and the skilled artisan will be able to identify additional suitable TALE transcription factors based on the guidance provided herein and the knowledge of such TALE transcription factors in the art.

In some embodiments, a target cell, for example, a somatic cell, is contacted with a TALE transcription factor, or a combination of such factors, associated with a supercharged protein provided herein. In some embodiments the target cell is a primary somatic cell and is contacted in vitro or ex vivo with a TALE transcription factor associated with a supercharged protein. In some embodiments, the TALE transcription factor is associated with a positively charged supercharged protein, e.g., as described herein. In some embodiments, the TALE transcription factor is associated with a negatively charged supercharged proteins, e.g., as described herein. In some embodiments, the TALE transcription factor is associated with a cationic lipid and/or cationic polymer, e.g., as described herein. In some embodiments, the TALE transcription factor is associated with a negatively charged supercharged protein and a cationic lipid and/or cationic polymer, e.g., as described herein.

In some embodiments, a target cell is contacted, or repeatedly contacted, with a TALE transcription factor associated with a supercharged protein (and optionally a cationic lipid and/or cationic polymer) as provided herein, and a desired change in cellular phenotype or gene expression is detected. In some embodiments, a target cell is contacted repeatedly with a TALE transcription factor associated with a supercharged protein (and optionally a cationic lipid and/or cationic polymer) as provided herein until the formation of a desired cellular phenotype is detected. Methods for detecting cellular phenotypes and gene expression are well known to those in the art and include, for example, morphological analysis, and detection of marker gene expression by well-established methods such as immunohistochemistry, fluorescence activated cell sorting (FACS), or fluorescent microscopy. In some embodiments, a target cell is contacted with a TALE transcription factor associated with a supercharged protein as provided herein for a period of at least 3 hours, at least 6 hours, at least 12 hours, at least 1 day, at least 2 days, at least 3 days, at least 4 days, at least 5 days, at least 6 days, at least 7 days, at least 10-12 days, at least 12-15 days, at least 15-20 days, at least 20-25 days, at least 25-30 days, at least 30-40 days, at least 40-50 days, at least 50-60 days, at least 60-70, or at least 70-100 days.

In some embodiments, a target cell is contacted with a TALE transcription factor associated with a supercharged protein (and optionally a cationic lipid and/or cationic polymer) as provided herein in an amount and for a time period effective to program the cell towards a different cell state. As will be apparent to those of skill in the art, the amount necessary to program or re-program a cell will dependent on various factors, for example, on the cell type and the treatment schedule. In general, delivery of a TALE transcription factor to a target somatic cell by a system or method provided herein will be at a concentration below a concentration at which significant toxicity can be observed. The critical concentration will depend, for example, on the specific TALE transcription factor, the supercharged protein it is associated with, the type of association, and the type of cell being treated.

A useful concentration of a functional effector protein associated with a supercharged protein (and optionally a cationic lipid and/or cationic polymer) for delivery to a specific cell type can be established by those of skill in the art by routine experimentation. In some embodiments a target cell is contacted in vitro or ex vivo with a functional effector protein associated with a supercharged protein (and optionally a cationic lipid and/or cationic polymer) at a concentration of about 1 pM to about 1 µM. In some embodiments, a target cell is contacted in vitro or ex vivo with the functional effector protein associated to a supercharged protein at a concentration of about 1 pM, about 2.5 pM, about 5 pM, about 7.5 pM, about 10 pM, about 20 pM, about 25 pM, about 30 pM, about 40 pM, about 50 pM, about 60 pM, about 70 pM, about 75 pM, about 80 pM, about 90 pM, about 100 pM, about 200 pM, about 250 pM, about 300 pM, about 400 pM, about 500 pM, about 600 pM, about 700 pM, about 750 pM, about 800 pM, about 900 pM, about 1 nM, about 2 nM, about 3 nM, about 4 nM, about 5 nM, about 6 nM, about 7 nM, about 8 nM, about 9 nM, about 10 nM, about 20 nM, about 25 nM, about 30 nM, about 40 nM, about 50 nM, about 60 nm, about 70 nM, about 75 nM, about 80 nM, about 90 nM, about 100 nM, about 200 nM, about 250 nM, about 300 nM, about 400 nM, about 500 nM, about 600 nM, about 700 nM, about 750 nM, about 800 nM, about 900 nM, or about 1 µM. A useful time of exposure of the target cell to the functional effector protein, and, if necessary, incubation after administration in the absence of the functional effector protein, as well as a number of administration/incubation cycles useful to achieve a desired biological effect (e.g., change in gene transcription, cleavage of a target site by a delivered nuclease, etc.), or a desired cellular phenotype can also be established by those of skill in the art by routine experimentation.

In some embodiments, the target cell for delivery of a functional effector protein by a system or method provided herein, is a primary cell obtained by a biopsy from a subject. In some embodiments, the subject is diagnosed as having a disease. In some embodiments the disease is a degenerative disease characterized by diminished function of a specific cell type, for example, a neural cell. In some embodiments, a cell treated with a functional effector protein according to the strategies or methods disclosed herein, or the progeny of such a cell, is used in a cell-replacement therapeutic approach. In some embodiments, the treated cells are administered to the subject from which the somatic cell was obtained in an autologous cell replacement therapeutic approach.

In some embodiments, a functional effector protein, e.g., TALE transcription factor able to convert a cell from one differentiated state into another, is delivered to a target cell in vitro or in vivo by a system or method provided herein. Transcription factors that effect transdifferentiation are known in the art (see, e.g., Zhou et al., *Nature* 455:627-33, 2008). In some embodiments, a TALE transcription factor modulating the expression of PPARγ or PRDM16 are delivered to fibroblast cells by a system or method as provided by this invention. It is known in the art that expression these transcription factors is a pivotal step in the programming of fibroblasts towards a brown fat or white fat cell state. In some embodiments, a programmed brown fat cell is generated from a fibroblast obtained from a subject in need of brown fat cells, and is administered to the subject, e.g., used in a cell-replacement therapeutic approach involving the subject.

Formation of Complexes

The present invention provides complexes comprising supercharged proteins associated with one or more functional effector proteins to be delivered. In some embodiments, supercharged proteins are associated with one or more functional effector proteins to be delivered through non-covalent interactions. In some embodiments, supercharged proteins are associated with one or more functional effector proteins through electrostatic interactions. In certain embodiments, supercharged proteins have an overall net positive charge, and the functional effector proteins to be delivered have an overall net negative charge. In some embodiments, the complex further comprises a cationic lipid and/or cationic polymer. For example, in some embodiments, the supercharged protein of the complex is supernegatively charged, allowing for association with cationic lipids and/or polymers.

In certain embodiments, supercharged proteins are associated with one or more functional effector proteins to be delivered via covalent bond. For example, a supercharged protein may be fused to a functional effector protein to be delivered. Covalent attachment may be direct or indirect (e.g., through a linker). In some embodiments, a covalent attachment is mediated through one or more linkers. In some embodiments, the linker is a cleavable linker. In certain embodiments, the cleavable linker comprises an amide, ester, or disulfide bond. For example, the linker may be an amino acid sequence that is cleavable by a cellular enzyme. In certain embodiments, the enzyme is a protease. In other embodiments, the enzyme is an esterase. In some embodiments, the enzyme is one that is more highly expressed in certain cell types than in other cell types. For example, the enzyme may be one that is more highly expressed in tumor cells than in non-tumor cells. Exemplary linkers and enzymes that cleave those linkers are presented below.

| Cleavable inkers | |
|---|---|
| Linker Sequence | Enzyme(s) Targeting Linker |
| $X^1$-AGVF-X (SEQ ID NO: 256) | lysosomal thiol proteinases (see, e.g., Duncan et al., 1982, Biosci. Rep., 2:1041-46; incorporated herein by reference) |

-continued

| Cleavable linkers | |
|---|---|
| Linker Sequence | Enzyme(s) Targeting Linker |
| X-GFLG-X (SEQ ID NO: 257) | lysosomal cysteine proteinases (see, e.g., Vasey et al., Clin. Canc. Res., 1999, 5:83-94; incorporated herein by reference) |
| X-FK-X | Cathepsin B-ubiquitous, overexpressed in many solid tumors, such as breast cancer (see, e.g., Dubowchik et al., 2002, Bioconjugate Chem., 13:855-69; incorporated herein by reference) |
| X-A*L-X | Cathepsin B-ubiquitous, overexpressed in many solid tumors, such as breast cancer (see, e.g., Trouet et al., 1982, Proc. Natl. Acad.Sci., U.S.A., 79:626-29; incorporated herein by reference) |
| X-A*LA*L-X (SEQ ID NO: 258) | Cathepsin B-ubiquitous, overexpressed in many solid tumors (see, e.g., Schmid et al., 2007, Bioconjugate Chem, 18:702-16; incorporated herein by reference) |
| X-AL*AL*A-X (SEQ ID NO: 259) | Cathepsin D-ubiquitous (see, e.g., Czerwinski et al., 1998, Proc.Natl. Acad.Sci., U.S.A., 95:11520-25; incorporated herein by reference) |

[1]X denotes a supercharged protein or a functional effector protein to be delivered
*refers to observed cleavage site To give but one particular example, a +36 GFP may be associated with a functional effector protein to be delivered by a cleavable linker, such as ALAL (SEQ ID NO: 254), to generate +36 GFP-(GGS)$_4$-ALAL-(GGS)$_4$-[functional effector protein X] (SEQ ID NO: 255).

In certain embodiments, the functional effector protein to be delivered is contacted with the supercharged protein to form a complex. In some embodiments, formation of complexes is carried out at or around pH 7. In some embodiments, formation of complexes is carried out at about pH 5, about pH 6, about pH 7, about pH 8, or about pH 9. Formation of complexes is typically carried out at a pH that does not negatively affect the function of the supercharged protein and/or the functional effector protein. In some embodiments, formation of complexes is carried out at room temperature. In some embodiments, formation of complexes is carried out at or around 37° C. In some embodiments, formation of complexes is carried out below 4° C., at about 4° C., at about 10° C., at about 15° C., at about 20° C., at about 25° C., at about 30° C., at about 35° C., at about 37° C., at about 40° C., or higher than 40° C. Formation of complexes is typically carried out at a temperature that does not negatively affect the function of the supercharged protein and/or functional effector protein. In some embodiments, formation of complexes is carried out in serum-free medium. In some embodiments, formation of complexes is carried out in the presence of $CO_2$ (e.g., about 1%, about 2%, about 3%, about 4%, about 5%, about 6%, or more).

In some embodiments, formation of complexes is carried out using concentrations of functional effector protein of about 100 nM. In some embodiments, formation of complexes is carried out using concentrations of functional effector protein of about 25 nM, about 50 nM, about 75 nM, about 90 nM, about 100 nM, about 110 nM, about 125 nM, about 150 nM, about 175 nM, or about 200 nM. In some embodiments, formation of complexes is carried out using concentrations of supercharged protein of about 40 nM. In some embodiments, formation of complexes is carried out using concentrations of supercharged protein of about 10 nM, about 20 nM, about 30 nM, about 40 nM, about 50 nM, about 60 nM, about 70 nM, about 80 nM, about 90 nM, or about 100 nM.

In some embodiments, formation of complexes is carried out under conditions of excess functional effector protein. In some embodiments, formation of complexes is carried out with ratios of functional effector protein:supercharged protein of about 20:1, about 10:1, about 9:1, about 8:1, about 7:1, about 6:1, about 5:1, about 4:1, about 3:1, about 2:1, or about 1:1. In some embodiments, formation of complexes is carried out with ratios of functional effector protein:supercharged protein of about 3:1. In some embodiments, formation of complexes is carried out with ratios of supercharged protein:functional effector protein of about 20:1, about 10:1, about 9:1, about 8:1, about 7:1, about 6:1, about 5:1, about 4:1, about 3:1, about 2:1, or about 1:1.

In some embodiments, formation of complexes is carried out by mixing supercharged protein with functional effector protein, and agitating the mixture (e.g., by inversion). In some embodiments, formation of complexes is carried out by mixing supercharged protein with functional effector protein, and allowing the mixture to sit still. In some embodiments, the formation of the complex is carried out in the presence of a pharmaceutically acceptable carrier or excipient. In some embodiments, the complex is further combined with a pharmaceutically acceptable carrier or excipient. Exemplary excipients or carriers include water, solvents, lipids, proteins, peptides, endosomolytic agents (e.g., chloroquine, pyrene butyric acid), small molecules, carbohydrates, buffers, natural polymers, synthetic polymers (e.g., PLGA, polyurethane, polyesters, polycaprolactone, polyphosphazenes), pharmaceutical agents, etc.

In some embodiments, complexes comprising supercharged protein and functional effector protein may migrate more slowly in gel electrophoresis assays than either the supercharged protein alone or the functional effector protein alone.

Applications

The present invention provides compositions comprising supercharged proteins, naturally occurring or engineered, associated with functional effector proteins (e.g., nucleases, transcriptional activators/repressors, recombinases, Cas9 proteins including variants and fusions thereof, etc.) to be delivered to a cell, as well as methods of using such compositions and uses of such compositions. In certain embodiments, compositions are provided comprising a Cas9 protein (e.g., wherein the Cas9 protein is associated with a gRNA) and a cationic lipid. In certain embodiments, compositions are provided comprising a Cas9 protein (e.g., wherein the Cas9 protein is associated with a gRNA) and a cationic polymer. The inventive compositions may be used to treat or prevent any disease that can benefit, e.g., from the delivery of an agent to a cell. The inventive compositions may also be used to transfect or treat cells for research purposes.

In some embodiments, compositions in accordance with the invention may be used for research purposes, e.g., to efficiently deliver functional effector proteins to cells in a research context. In some embodiments, compositions in accordance with the present invention may be used for therapeutic purposes. In some embodiments, compositions in accordance with the present invention may be used for treatment of any of a variety of diseases, disorders, and/or conditions, including, but not limited to, one or more of the following: autoimmune disorders (e.g., diabetes, lupus, multiple sclerosis, psoriasis, rheumatoid arthritis); inflammatory disorders (e.g., arthritis, pelvic inflammatory disease); infectious diseases (e.g., viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Compositions of the invention may be used in a clinical setting. For example, a supercharged protein may be associated with a functional effector protein that can be used for therapeutic applications. Such functional effector protein may be, for example, nucleases or transcriptional activators. Other compositions comprising a Cas9 protein and a cationic lipid may also be used for therapeutic applications.

In some embodiments, the supercharged protein or functional effector protein associated with a supercharged protein includes a detectable label. These molecules can be used in detection, imaging, disease staging, diagnosis, or patient selection. Suitable labels include fluorescent, chemiluminescent, enzymatic labels, colorimetric, phosphorescent, density-based labels, e.g., labels based on electron density, and in general contrast agents, and/or radioactive labels.

Pharmaceutical Compositions

The present invention provides compositions comprising supercharged proteins associated with at least one functional effector protein to be delivered, and in some embodiments are encapsulated by cationic lipids. Other compositions comprising a Cas9 protein and a cationic lipid are provided. Thus, the present invention provides pharmaceutical compositions comprising one or more supercharged proteins associated with a functional effector protein, and/or one or more functional effector proteins associated with a cationic lipid and/or cationic polymer, and one or more pharmaceutically acceptable excipients. Pharmaceutical compositions may optionally comprise one or more additional therapeutically active substances. In accordance with some embodiments, a method of administering pharmaceutical compositions comprising one or more supercharged proteins associated with a functional effector protein to be delivered to a subject in need thereof is provided. In some embodiments, compositions are administered to humans. For the purposes of the present disclosure, the phrase "active ingredient" generally refers to a Cas9 protein and/or supercharged protein associated with a functional effector protein, or to the functional effector protein to be delivered as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. *Remington's The Science and Practice of Pharmacy, 21$^{st}$ Edition*, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween® 20), polyoxyethylene sorbitan (Tween® 60), polyoxyethylene sorbitan monooleate [Tween® 80], sorbitan monopalmitate [Span® 40], sorbitan monostearate [Span® 60], sorbitan tristearate [Span® 65], glyceryl monooleate, sorbitan monooleate [Span® 80]), polyoxyethylene esters (e.g. polyoxyethylene monostearate [Myrj® 45], polyoxyethylene hydrogenated castor oil, polyethoxylated castor oil, polyoxymethylene stearate, and Solutol®), sucrose fatty acid esters, polyethylene glycol fatty acid esters (e.g. Cremophor®), polyoxyethylene ethers, (e.g. polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F 68, Poloxamer® 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall® 115, Germaben® II, Neolone™, Kathon™, and/or Euxyl®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices. Intradermal compositions may be administered by devices which limit the effective penetration length of a needle into the skin and functional equivalents thereof. Jet injection devices which deliver liquid compositions to the dermis via a liquid jet injector and/or via a needle which pierces the stratum corneum and produces a jet which reaches the dermis are suitable. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005 (incorporated herein by reference).

Administration

The present invention provides methods comprising administering compositions of supercharged proteins associated with functional effector proteins to a subject in need thereof. In some embodiments, methods of administering compositions comprising other functional effector proteins (e.g., a Cas9 protein) and cationic lipid and/or cationic polymers are provided. Such compositions may be administered to a subject using any amount and any route of administration effective for preventing, treating, diagnosing, or imaging a disease, disorder, and/or condition. The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective, prophylactially effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Compositions of supercharged proteins associated with functional effector proteins to be delivered as well as compositions comprising e.g., a Cas9 protein and cationic lipid may be administered by any route. In some embodiments, such compositions are administered by one or more of a variety of routes, including oral, intravenous, intramuscular, intra-arterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter. In some embodiments, supercharged proteins or complexes, and/or pharmaceutical, prophylactic, diagnostic, or imaging compositions thereof, are administered by systemic intravenous injection. In specific embodiments, supercharged proteins or complexes and/or pharmaceutical, prophylactic, diagnostic, or imaging compositions thereof may be administered intravenously and/or orally. In specific embodiments, such compositions may be administered in a way which allows the functional effector protein to cross the blood-brain barrier, vascular barrier, or other epithelial barrier.

In certain embodiments, compositions in accordance with the invention may be administered at dosage levels sufficient to deliver an amount of functional effector protein of from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Compositions comprising supercharged proteins associated with functional effector proteins may be administered in combination with one or more other therapeutic, prophylactic, diagnostic, or imaging agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In general, each agent will be administered at a dose and/or on a time schedule determined for that agent. In some embodiments, the invention encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments. In some embodiments, kits comprise one or more of (i) a supercharged protein, as described herein; (ii) a functional effector protein to be delivered; (ii) a cationic lipid and/or cationic polymer; and (iv) instructions for formulating a composition comprising the functional protein associated to the supercharged protein. In some embodiments, the kits comprise a Cas9 protein and a cationic lipid. In some embodiments, kits comprise a nucleic acid encoding for the supercharged protein and/or the functional protein to be delivered. In some embodiments, the kit comprises a cloning vector encoding a supercharged protein and a cloning site allowing the in-frame cloning of a functional effector protein to generate a fusion protein. In some embodiments, kits comprise a pharmaceutical composition provided herein comprising a supercharged protein associated with a functional effector protein; a syringe, needle, or applicator for administration of the pharmaceutical composition to a subject; and instructions for administration of the pharmaceutical composition to the subject.

These and other aspects of the present invention will be further appreciated upon consideration of the following Examples, which are intended to illustrate certain particular embodiments of the invention but are not intended to limit its scope, as defined by the claims.

EXAMPLES

Example 1: Delivery of TALE Activators Fused to Supercharged GFP

A major target for reprogramming fibroblast cell fate towards brown or white adipocyte cell fate lies in the switch from White Adipose Tissue (WAT) to Brown Adipose Tissue (BAT), which is governed by expression of PRDM16 and PPARγ. Robust TALE transcriptional activators fused to a +36 GFP were engineered that target PPARγ and PRDM16 genomic sequences in fibroblasts. Fusion proteins were purified using a heparin column and/or an SEC and gels show a single band at 130 kD The modulation of expression and effect on cellular phenotype after delivery of the TALE activators was compared to the modulation after viral delivery of a PPARγ cDNA followed by 7-day treatment with adipogenesis cocktail. It was observed that adipocytes formed upon treatment with +36 GFP TALEPRDM16 fusion. Expression of white adipose tissue marker genes was detected after delivery of supercharged PRDM16 TALE activators.

A one-time supercharged protein-mediated delivery of a TALE activator for PPARγ was found to induce expression of white-fat genes and to differentiate fibroblasts into white-fat cells. Supercharged protein-mediated delivery of both a PPARγ and PRDM16 TALE activator induced the differentiation of fat cells with increased expression of brown-fat markers such as PRDM16, cox8b, elov13, and cidea as well as a small increase in thermogenic gene expression markers PGC1a and UCP1.

An Aurein peptide was fused to the N-terminus of the +36GFP-TALE-activator fusion protein. Delivery of Aurein+36 GFP TALE purified by heparin column was observed by detecting fluorescence in nucleus of the treated cells.

Figure 2:
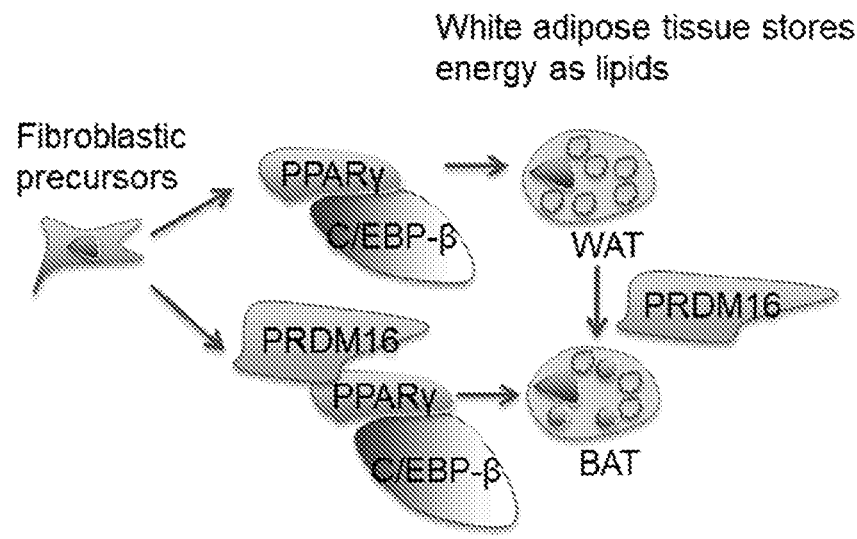
FIG. 2. Programming adipocyte cell fate: the switch from White Adipose Tissue (WAT) to Brown Adipose Tissue (BAT).
Figure 3:
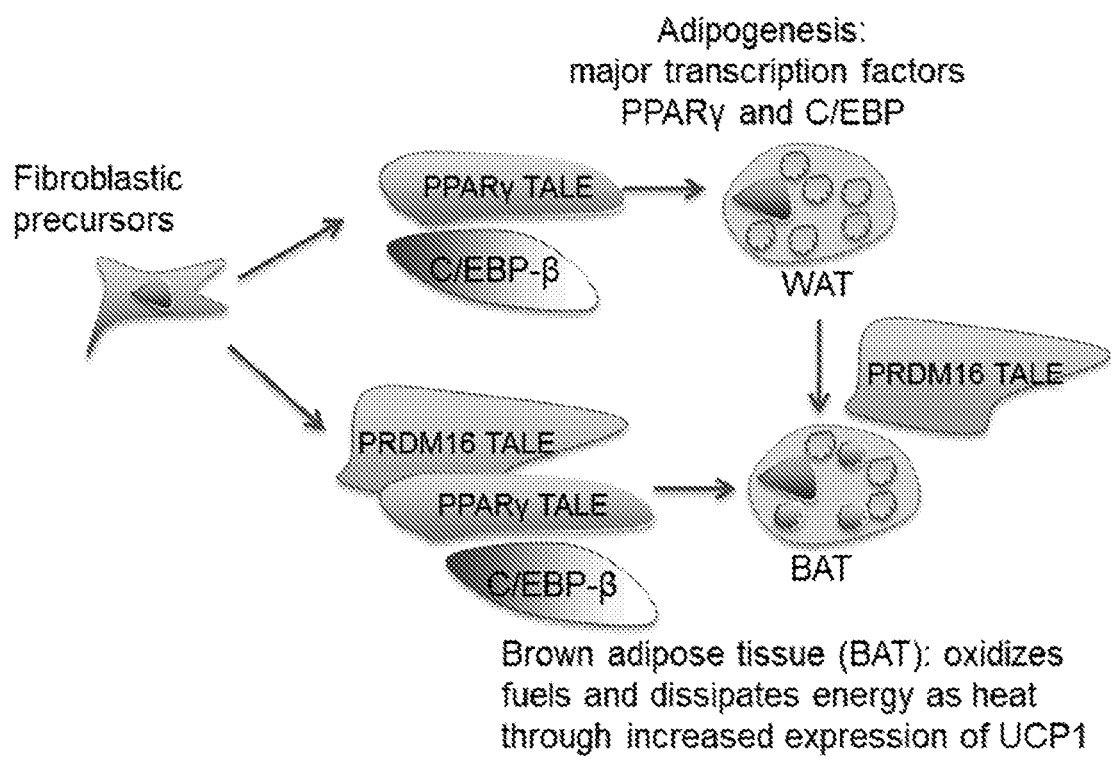
FIG. 3. Using supercharged delivery platforms to deliver TALE activators programmed to target PPARγ or PRDM16.
Figure 4:
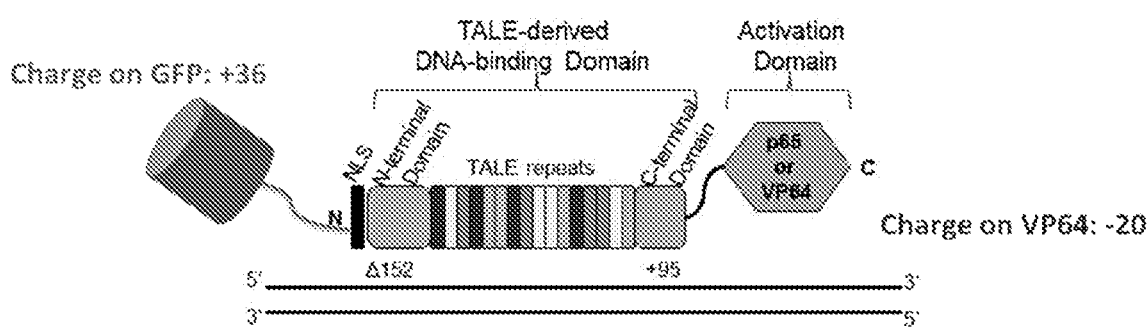
FIG. 4. Schematic of a fusion protein comprising a +36 GFP fusion, an 18.5 mer TALE domain, and a VP64 activation domain.
Figure 5:
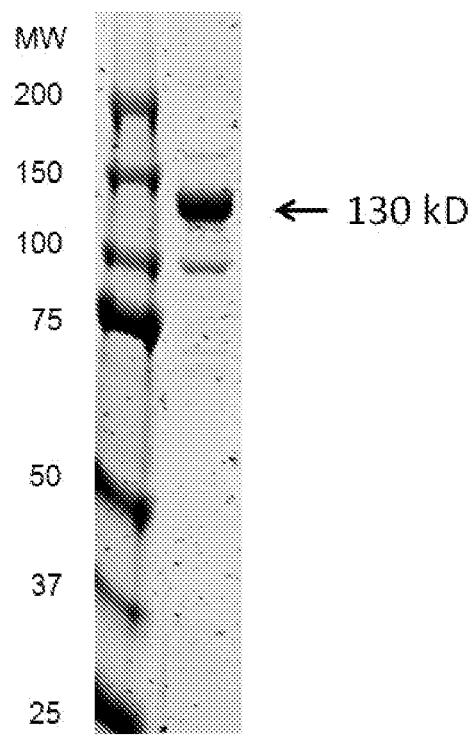
FIG. 5. Expression and purification of the +36 GFP-TALE activator-fusion protein.
Figure 6:
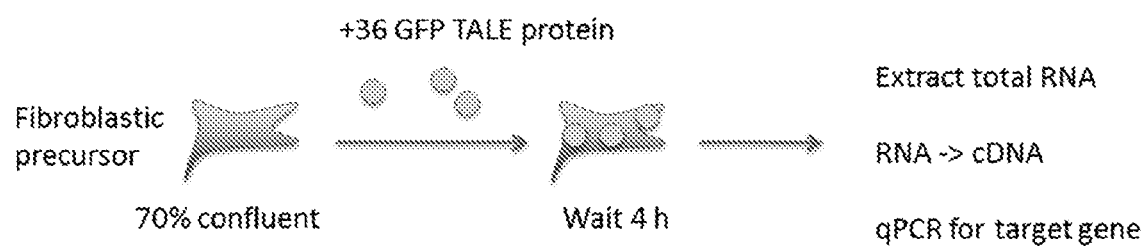
FIG. 6. Testing for activation of fat cell regulator genes upon delivery of +36 GFP PPARγ and PRDM16 TALE activator fusion proteins.

FIG. 1 shows a schematic of macromolecular delivery into mammalian cells. FIG. 2 shows an overview of the switch from White Adipose Tissue (WAT) to Brown Adipose Tissue (BAT). FIG. 3 shows a schematic of supercharged delivery platforms to deliver TALE activators programmed to target PPARγ or PRDM16. FIG. 4 shows a schematic of a fusion protein comprising a +36 GFP fusion, an 18.5 mer TALE domain, and a VP64 activation domain. FIG. 5 shows expression and purification of the +36 GFP-TALE activator-fusion protein. FIG. 6 shows testing assays for activation of fat cell regulator genes upon delivery of +36 GFP PPARγ and PRDM16 TALE activator fusion proteins.

Figure 7:
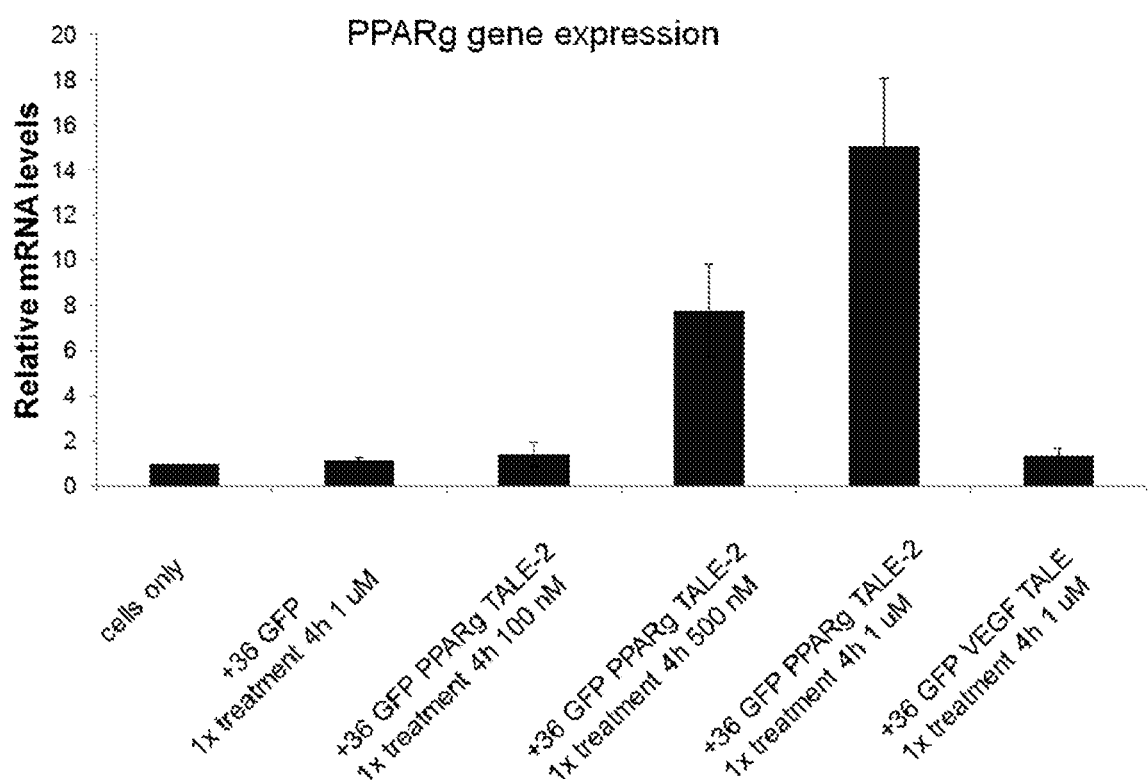
FIG. 7. Delivery efficacy of +36 GFP TALE activator fusion proteins at different concentrations.
Figure 8:
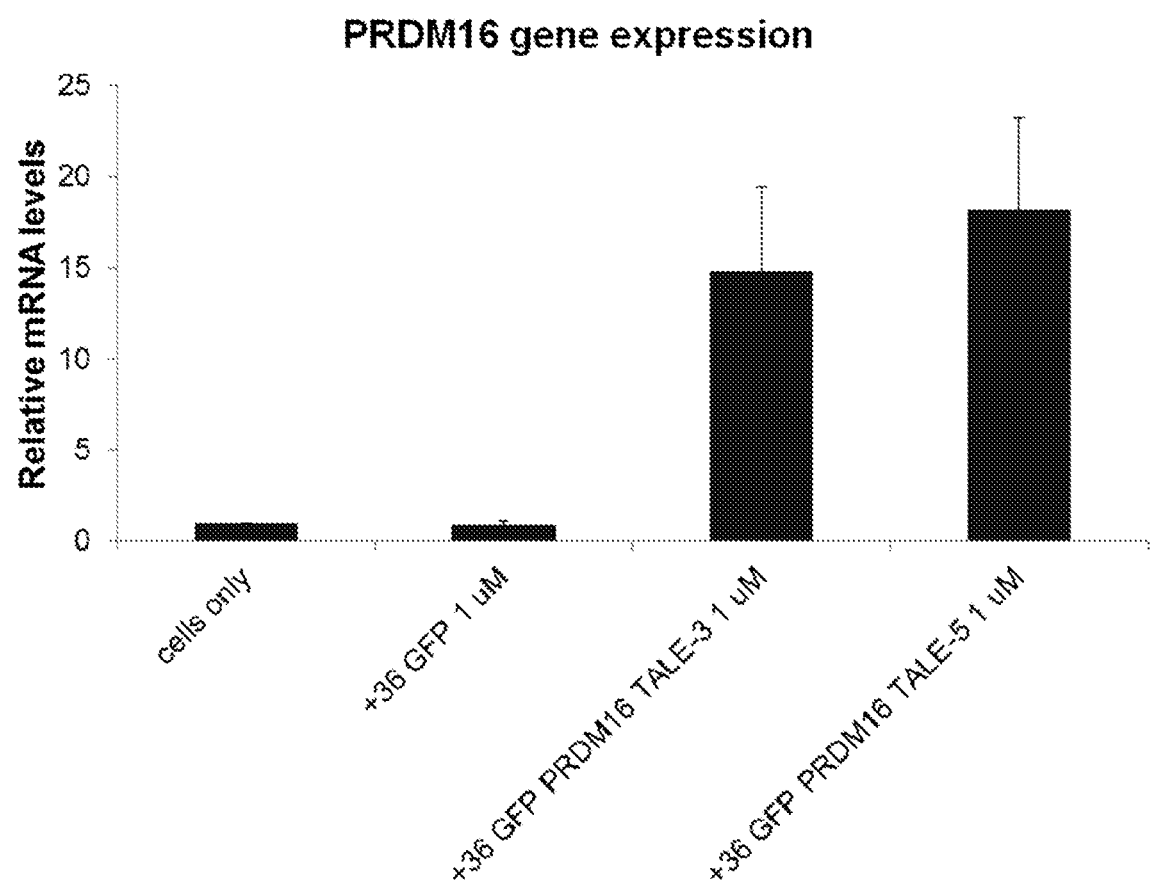
FIG. 8. Comparison of delivery efficacy of two different +36 GFP-PRDM16 TALE fusion proteins in NIH 3T3 cells.
Figure 9:
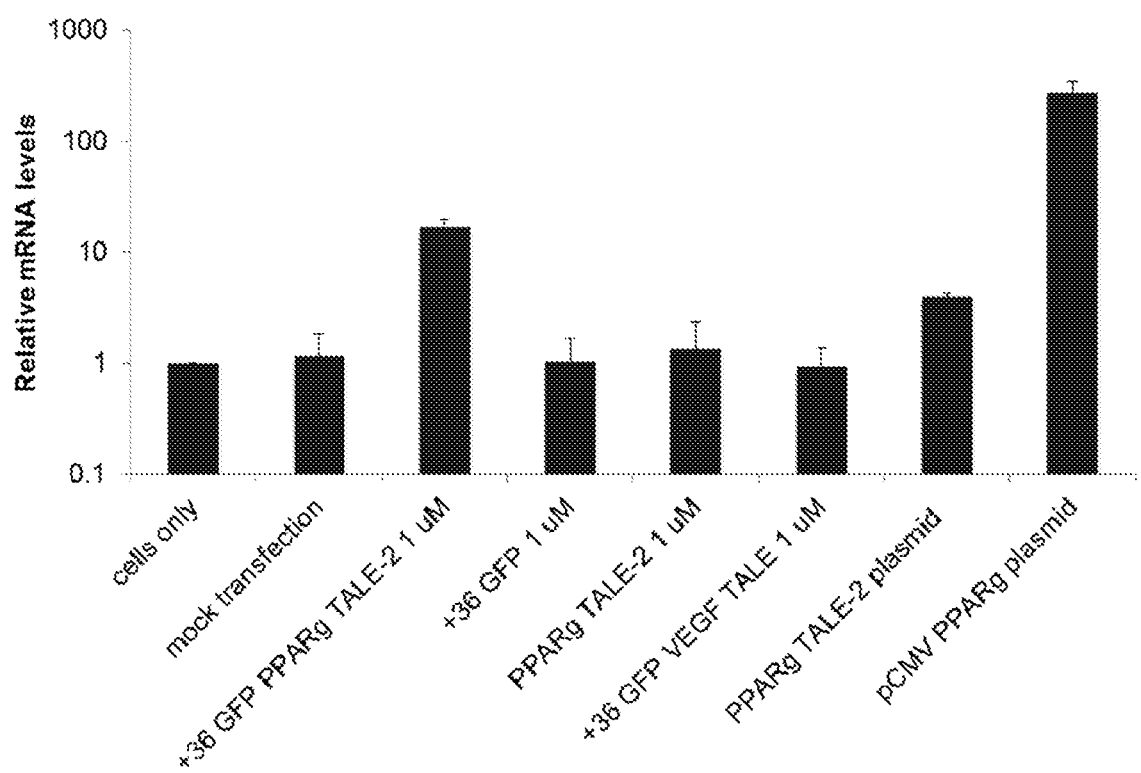
FIG. 9. PPARγ gene expression after delivery of PPARγ-TALE activator fusion and comparison to various controls.
Figure 10:
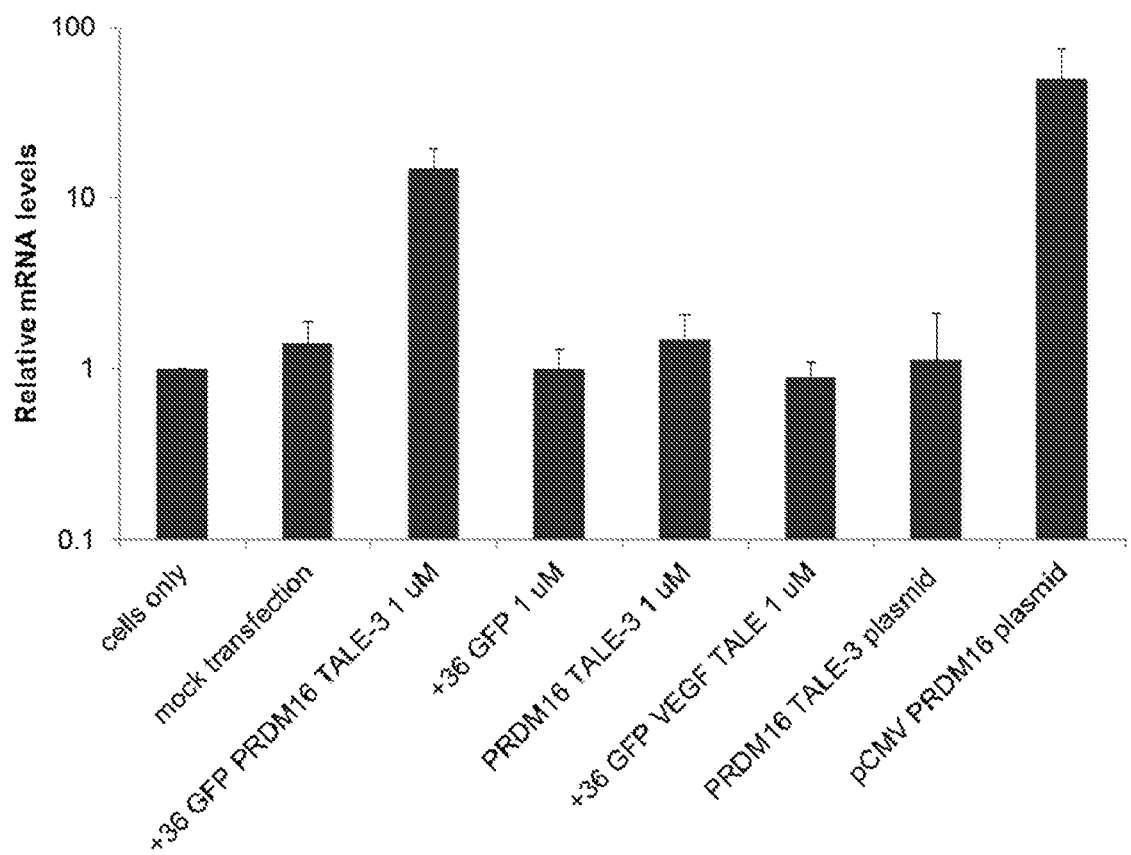
FIG. 10. PRDM16 gene expression after delivery of RDM16-TALE activator fusion and comparison to various controls.
Figure 11:
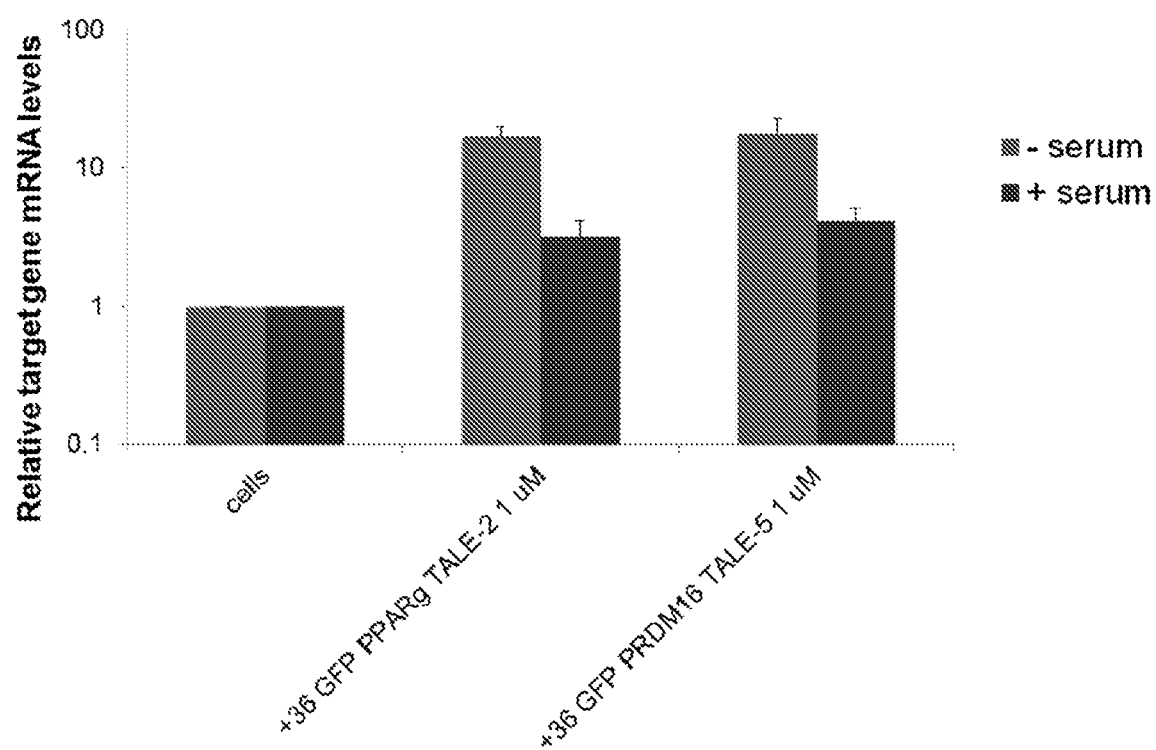
FIG. 11. Moderate TALE activity is observed in the presence of serum.

FIG. 7 shows delivery efficacy of +36 GFP TALE activator fusion proteins at different concentrations. FIG. 8 shows a comparison of delivery efficacy of two different +36 GFP-PRDM16 TALE fusion proteins in NIH 3T3 cells. FIG. 9 shows PPARγ gene expression after delivery of PPARγ-TALE activator fusion and comparison to various controls. FIG. 10 shows PRDM16 gene expression after delivery of RDM16-TALE activator fusion and comparison to various controls. FIG. 11 shows moderate TALE activity observed in the presence of serum.

Figure 12:
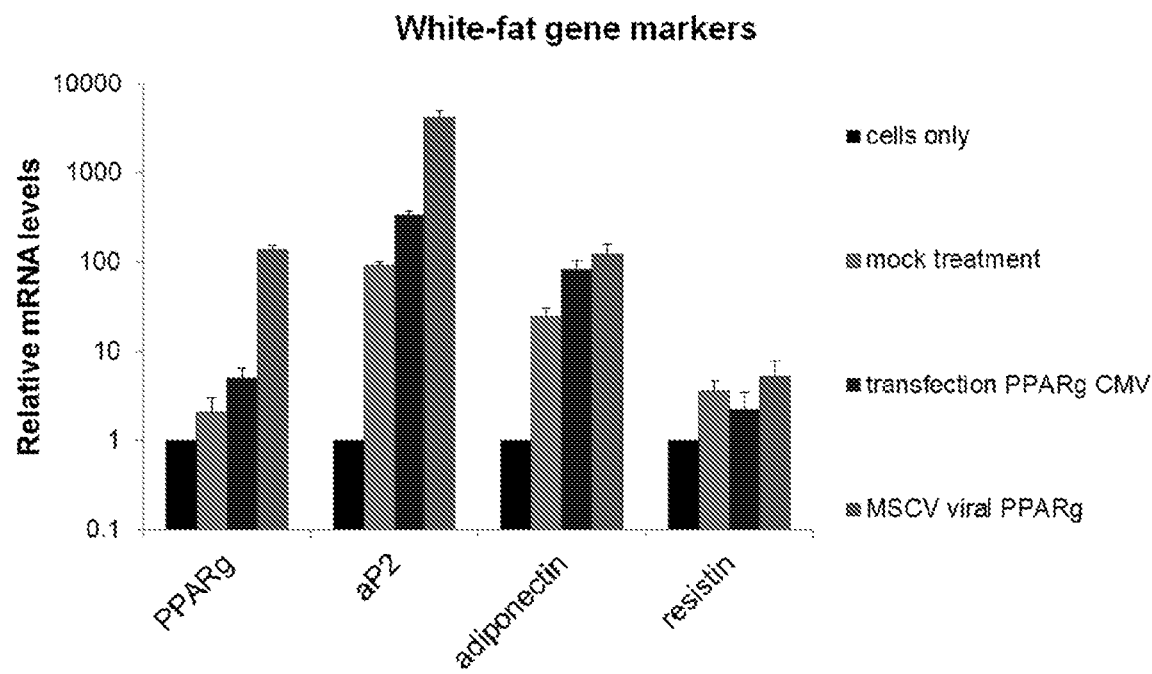
FIG. 12. Validation of viral delivery of PPARγ followed by 7-day treatment with adipogenesis cocktail.
Figure 13:
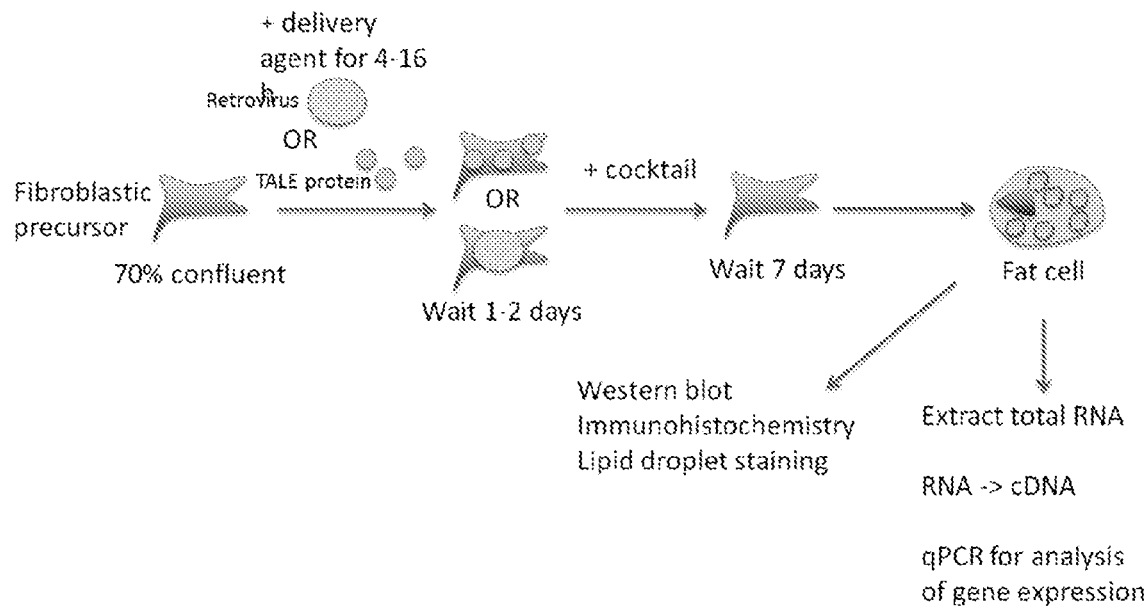
FIG. 13. Schematic of an assay for programming fibroblasts into WAT and BAT.
Figure 14:
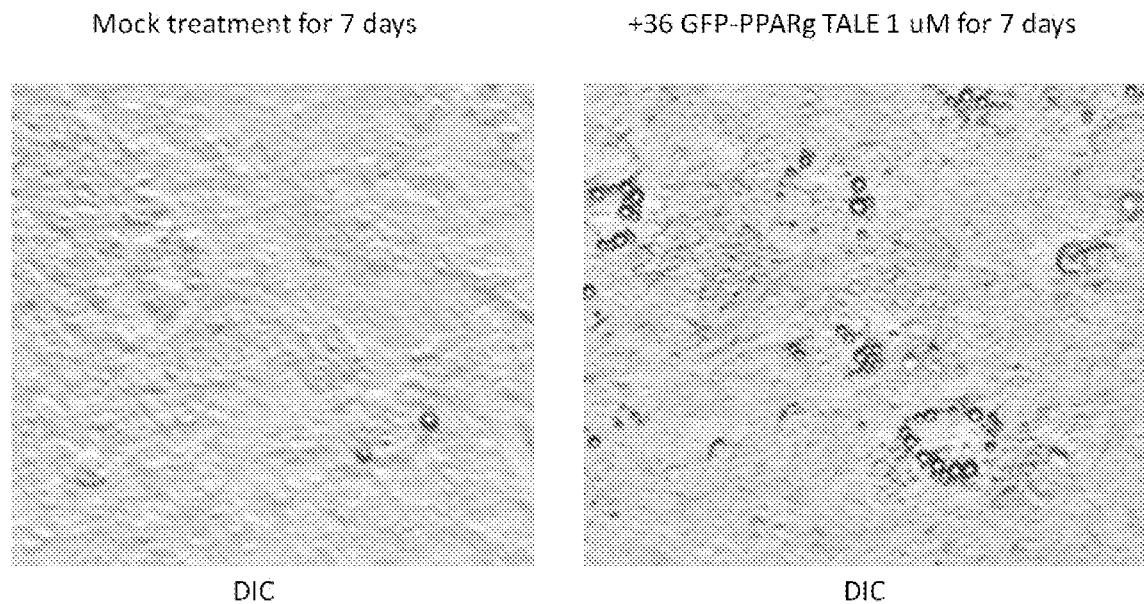
FIG. 14. Adipocyte formation observed upon treatment with +36 GFP TALE activator fusion protein.
Figure 15:
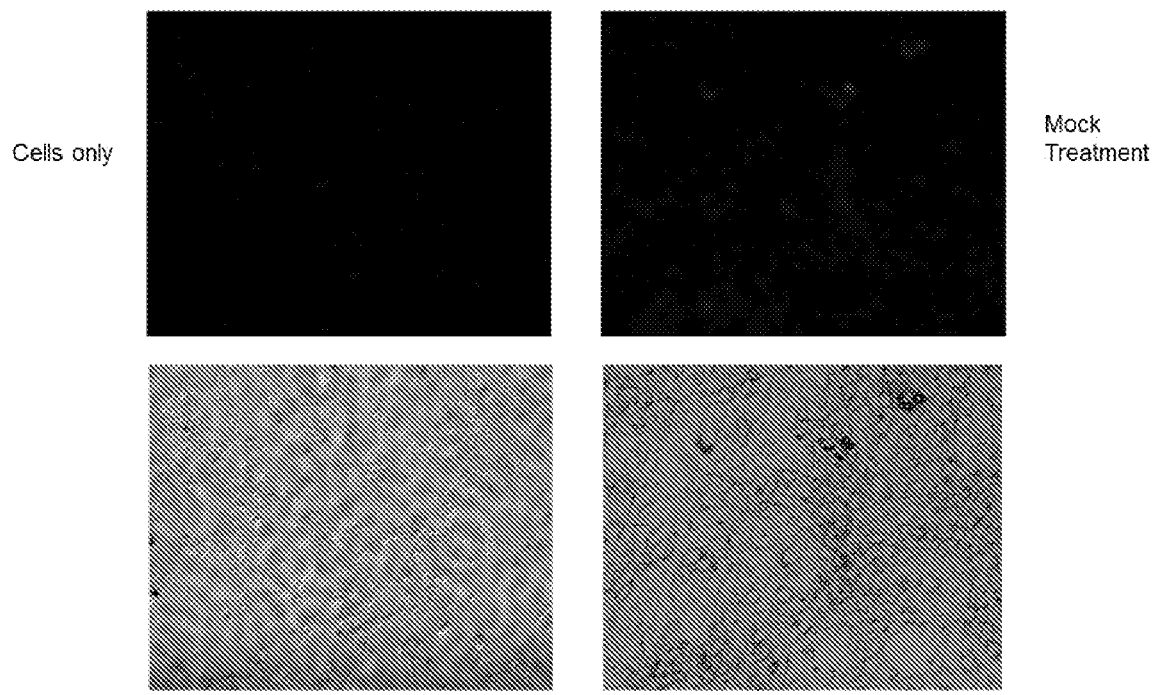
FIG. 15. Staining of various treatments after 7 days with LipidTOX red shows formation of adipocytes after viral delivery as well as after delivery of supercharged PPARγ TALE activator fusion protein.
Figure 16:
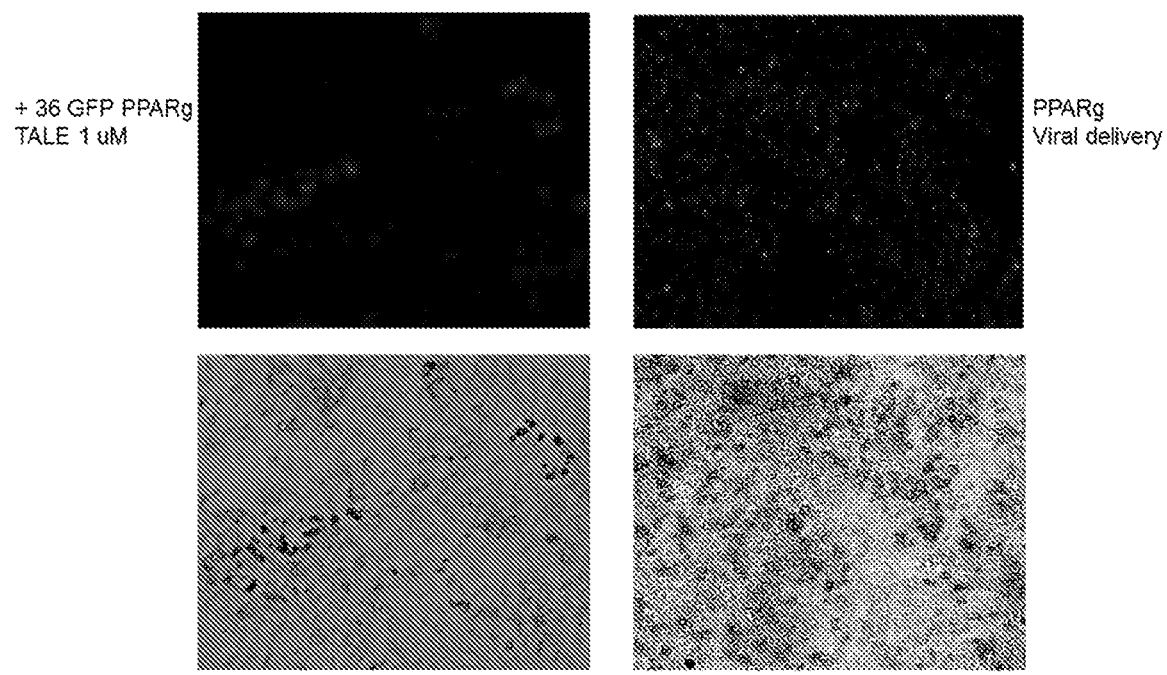
FIG. 16. Staining of various treatments after 7 days with LipidTOX red shows formation of adipocytes after viral delivery as well as after delivery of supercharged PPARγ TALE activator fusion protein.
Figure 17:
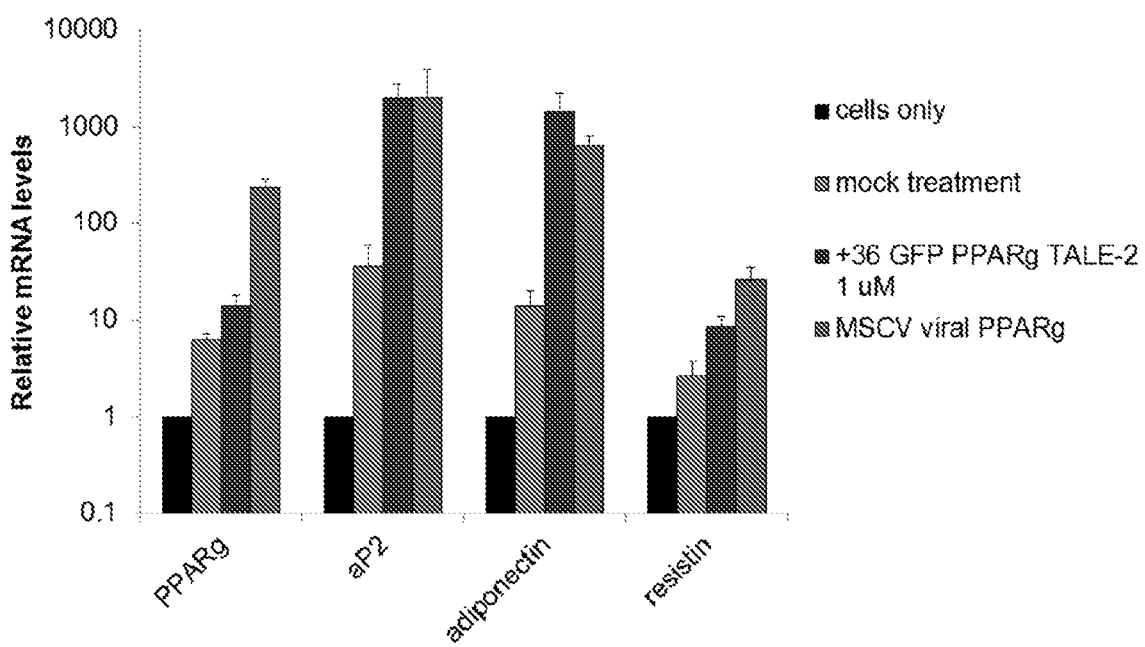
FIG. 17. Expression of WAT biomarker genes after viral delivery as well as after delivery of supercharged PPARγ TALE activator fusion protein.

FIG. 12 shows a validation of viral delivery of PPARγ followed by 7-day treatment with adipogenesis cocktail. FIG. 13 shows a schematic of an assay for programming fibroblasts into WAT and BAT. FIG. 14 shows adipocyte formation observed upon treatment with +36 GFP TALE activator fusion protein. FIG. 15 shows staining of various treatments after 7 days with LipidTOX red, demonstrating formation of adipocytes after viral delivery as well as after delivery of supercharged PPARγ TALE activator fusion protein. FIG. 16 shows staining of cells after various treatments after 7 days with LipidTOX red, demonstrating formation of adipocytes after viral delivery as well as after delivery of supercharged PPARγ TALE activator fusion protein. FIG. 17 shows expression of WAT biomarker genes after viral delivery as well as after delivery of supercharged PPARγ TALE activator fusion protein.

Example 2: In Vivo Delivery of TALE Activators Fused to Supercharged GFP

NIH 3T3 cells were grown to 70-90% confluence and treated with 1 μM or between 0.5-5 μM of +36 GFP PPARγ TALE and/or +36 GFP PRDM16 TALE fusion protein in DMEM without serum. A serum-free medium was chosen, because serum can decrease the effectiveness of protein-based delivery. Cells were incubated with the respective fusion protein solution for 4 hours before the media was removed and full DMEM containing serum was added back to cells. Control cells were infected with a viral construct encoding PPARγ or PRDM16 in order to serve as a positive control for expression of WAT and BAT genes according to known protocols (see, e.g., Seale et al. 2008 *Nature* 454, 961-967, the entire contents of which are incorporated herein by reference). Once all cells reached 100% confluence an adipogenesis cocktail containing isobutylmethylxanthine, insulin, rosiglitazone, dexamethosone, T3, and indomethacin was added to the cells and replaced 48 hours later with a form of the cocktail containing only insulin, T3, and rosiglitazone. At 48 hours after this second replacement of cocktail another dosage of T3, insulin, and rosiglitazone was added to the cells. The next day, which is now one week from the start of the experiment, cells were harvested with TRIzol, total RNA was extracted, and qRT-PCR was performed to measure gene expression levels of PPARγ, PRDM16, and other brown fat marker genes such as UCP1, PGC1a, Elov13, and Cidea.

Figure 18:
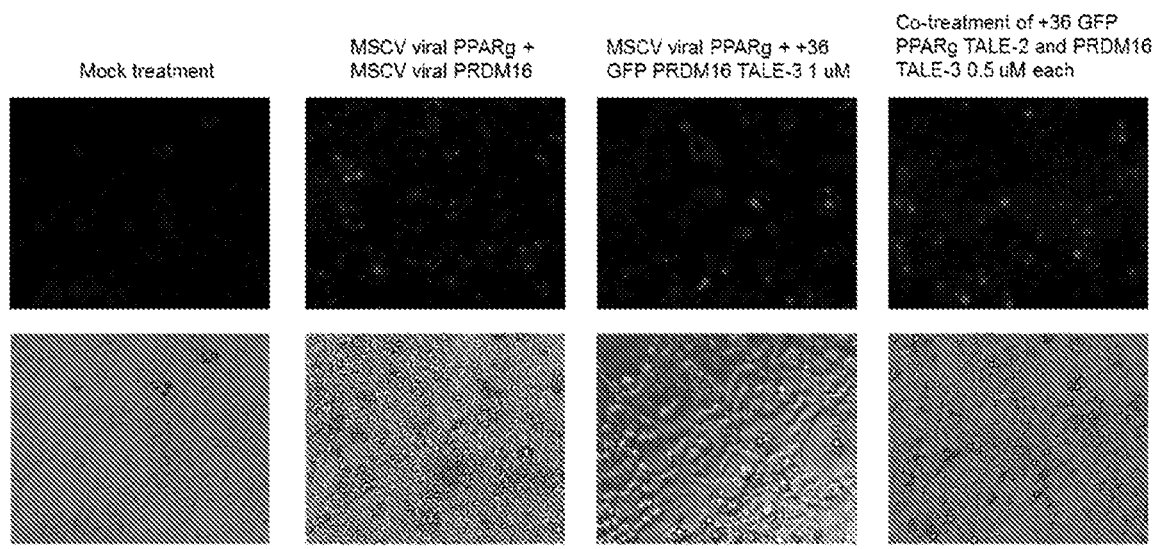
FIG. 18. Delivery of supercharged PRDM16 TALE activator fusion proteins to induce brown-fat adipocytes in vivo. Robust adipocyte formation was observed after viral delivery of PPARγ and PRDM16 and also after delivery of supercharged TALE activator protein fusions.
Figure 19:
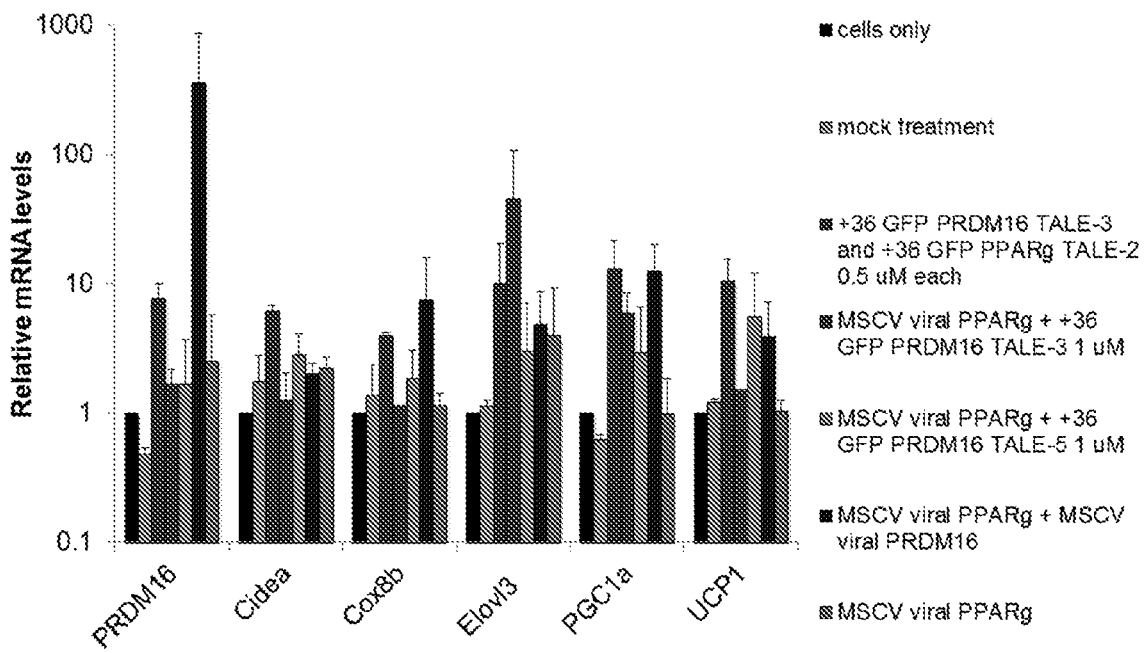
FIG. 19. Comparison of TALE/TALE, viral/TALE, and viral/viral-induced expression of brown fat markers by expression of PPARγ and PRDM16.
Figure 20:
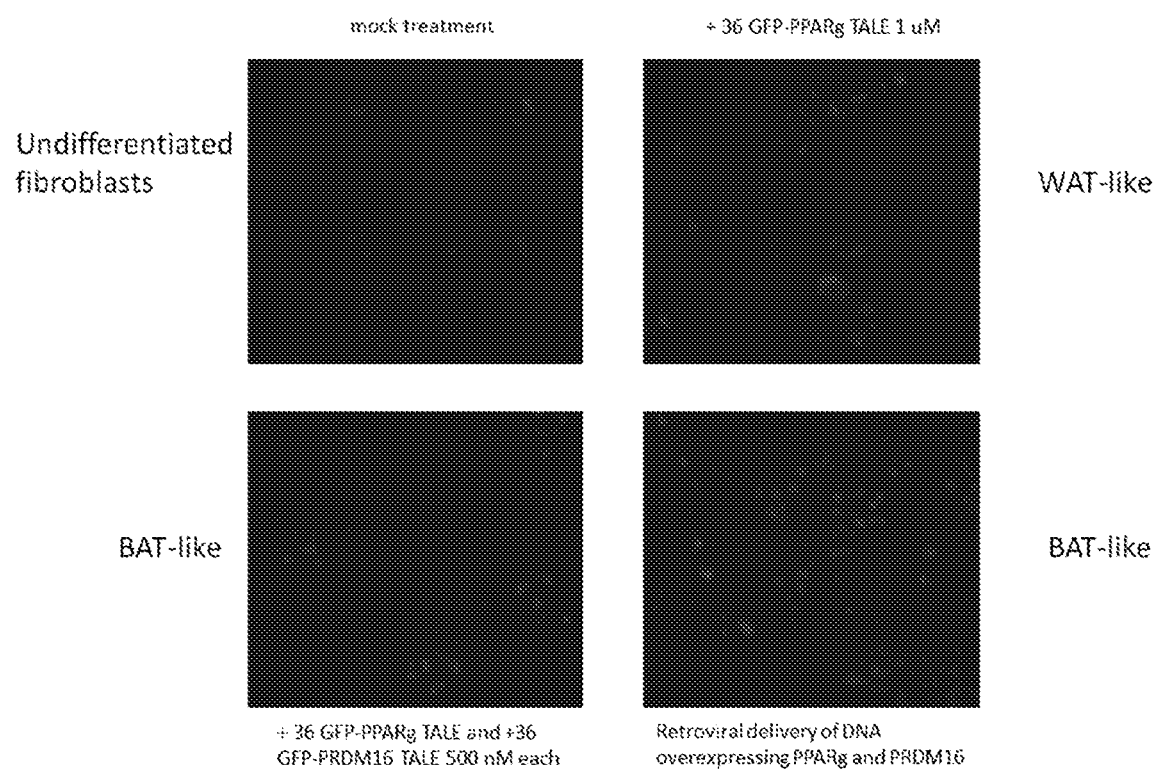
FIG. 20. RT-qPCR assessments are consistent with fat cell differentiation observed by LipidTOX staining.

FIG. 18 shows delivery of supercharged PRDM16 TALE activator fusion proteins to induce brown-fat adipocytes in vivo. Robust adipocyte formation was observed after viral delivery of PPARγ and PRDM16 and also after delivery of supercharged TALE activator protein fusions. FIG. 19 shows a comparison of supercharged (TALE) and viral delivery of PPARγ and PRDM16 to cells. The figure shows TALE/TALE, viral/TALE, and viral/viral-induced expression of brown fat markers by expression of PPARγ and PRDM16. FIG. 20 shows RT-qPCR assessments consistent with fat cell differentiation, which were also observed by LipidTOX staining.

Example 3: Delivery of TALE Activators Complexed with Supercharged GFP

Figure 21:
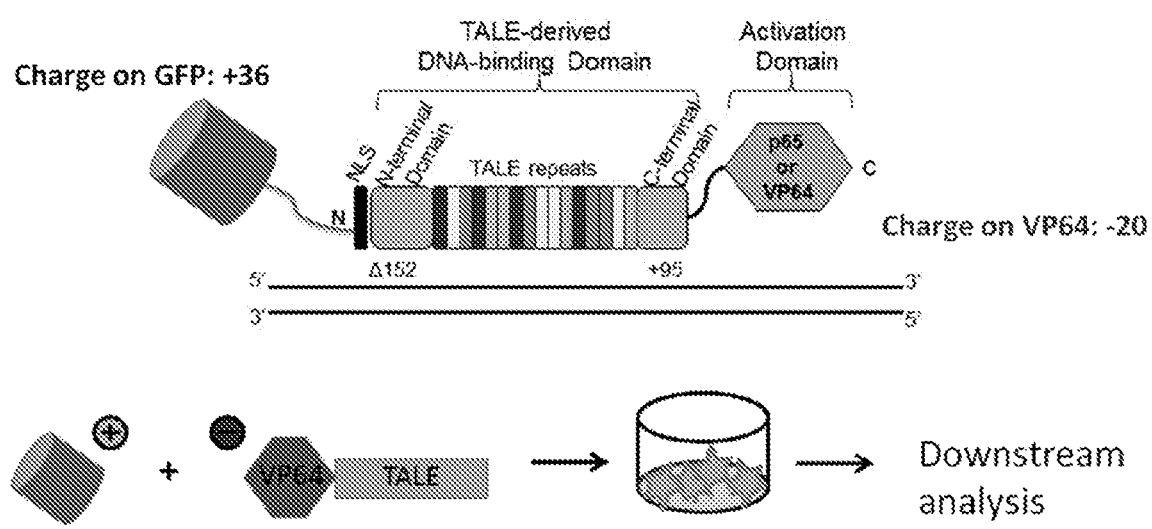
FIG. 21. Delivery of functional TALE activator fusion proteins as complexes with +36 GFP improves TALE activator activity after delivery.
Figure 22:
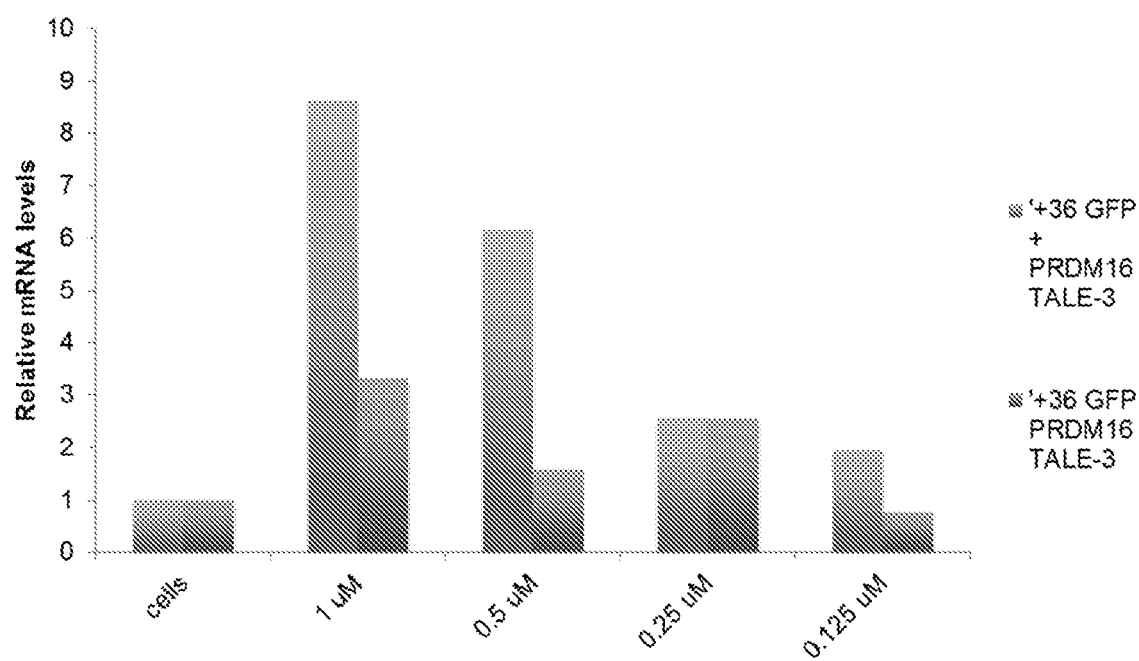
FIG. 22. PRDM16 gene expression after TALE activator fusion delivery either as a fusion (+36GFP PRDM16 TALE-3) or a complex (+36GFP+PRDM16 TALE-3) with +36GFP. Delivery of complexes tends to increase TALE activator activity.

In order to improve delivery efficacy, protein complexes in which the functional protein was non-covalently associated with the supercharged protein were generated and administered to cells. FIG. 21. shows that delivery of functional TALE activator fusion proteins as complexes with +36 GFP improves TALE activator activity after delivery. FIG. 22 shows PRDM16 gene expression after TALE activator fusion delivery either as a fusion (+36GFP PRDM16 TALE-3) or a complex (+36GFP+PRDM16 TALE-3) with +36GFP. It was observed that delivery of complexes tended to increase TALE activator activity.

Example 4: Effect of Aurein Fusions on Delivery Efficacy

Figure 23:
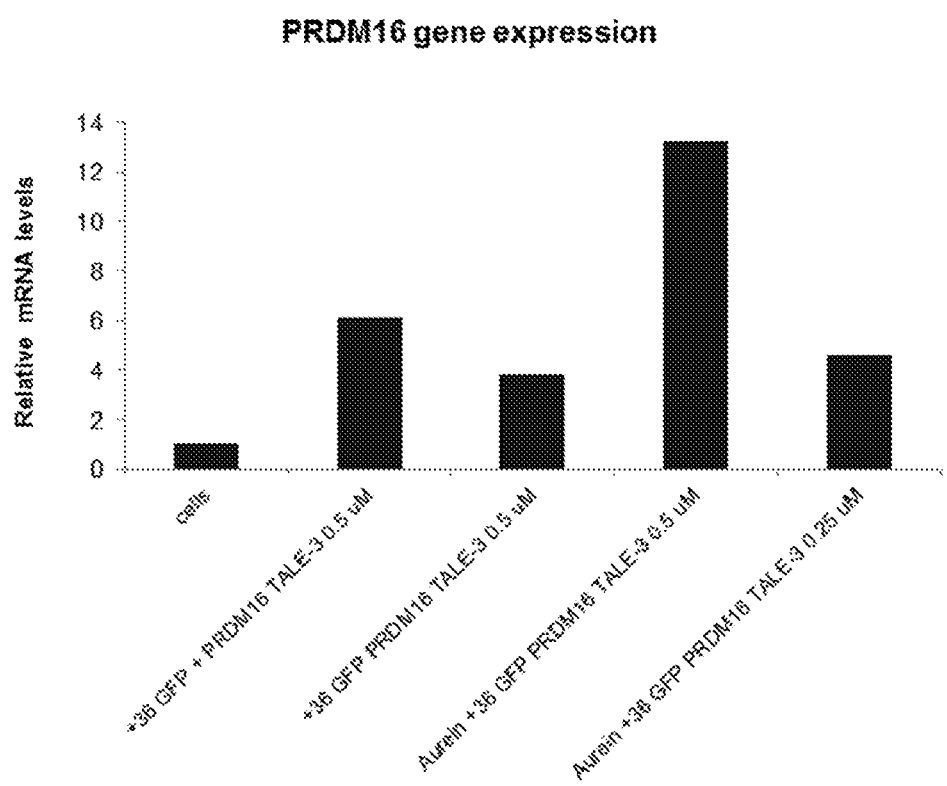
FIG. 23. Effect of Aurein peptide fusion to +36GFP on PRDM16 gene expression after TALE activator fusion delivery (either as a fusion or a complex with +36GFP).

FIG. 23 shows the effect of an N-terminal Aurein peptide fusion to +36GFP on PRDM16 gene expression after TALE activator fusion delivery (either as a fusion or a complex with +36GFP). The Aurein peptide was fused to the N-terminus of the GFP-TALE construct via a GGS(9) (SEQ ID NO: 252) linker, resulting in an Aurein peptide-GGS(9) linker-(+)36 GFP protein-GGS(9) linker -PRDM16 TALE-3 fusion protein. The protein was purified using size exclusion chromatography.

Figure 24:
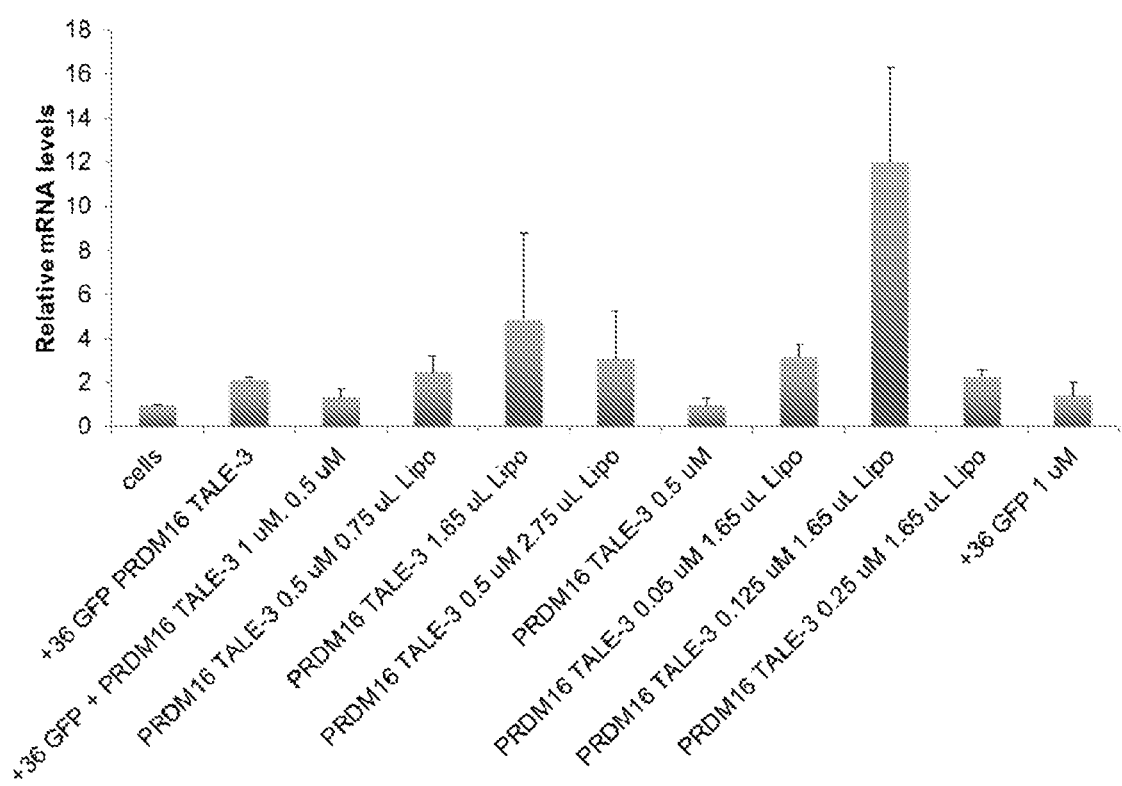
FIG. 24. PRDM16 gene expression after TALE activator fusion delivery either as a fusion (+36GFP PRDM16 TALE-3) or a complex (+36GFP+PRDM16 TALE-3) with Lipofectamine LTX.

Example 5: Delivery of TALE Activators Complexed with Supercharged GFP or Cationic Lipids FIG. 24 shows PRDM16 gene expression after TALE PRDM16 activator protein delivery either as a fusion with +36 GFP (+36GFP PRDM16 TALE-3), a complex with +36 GFP (+36GFP+PRDM16 TALE-3), or a complex with Lipofectamine LTX, for which an increase in gene expression was observed.

Example 6: Delivery of Cas9 Fused to Supercharged GFP

Figure 25:
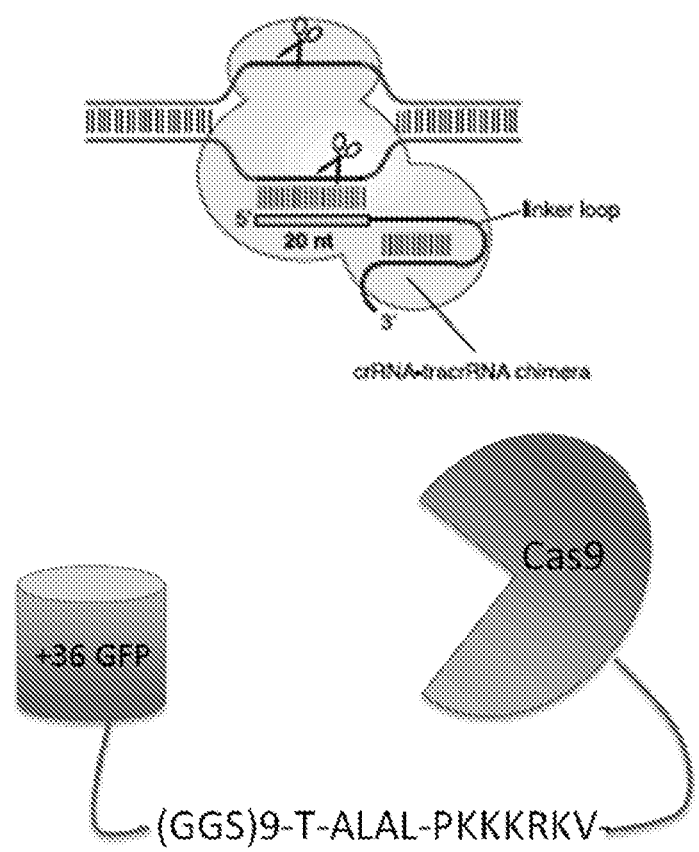
FIG. 25. Delivery of supercharged fusion proteins or complexes with Cas9 into mammalian cells. (GGS)9-T-ALAL-PKKKRKV corresponds to SEQ ID NO: 251.
Figure 26:
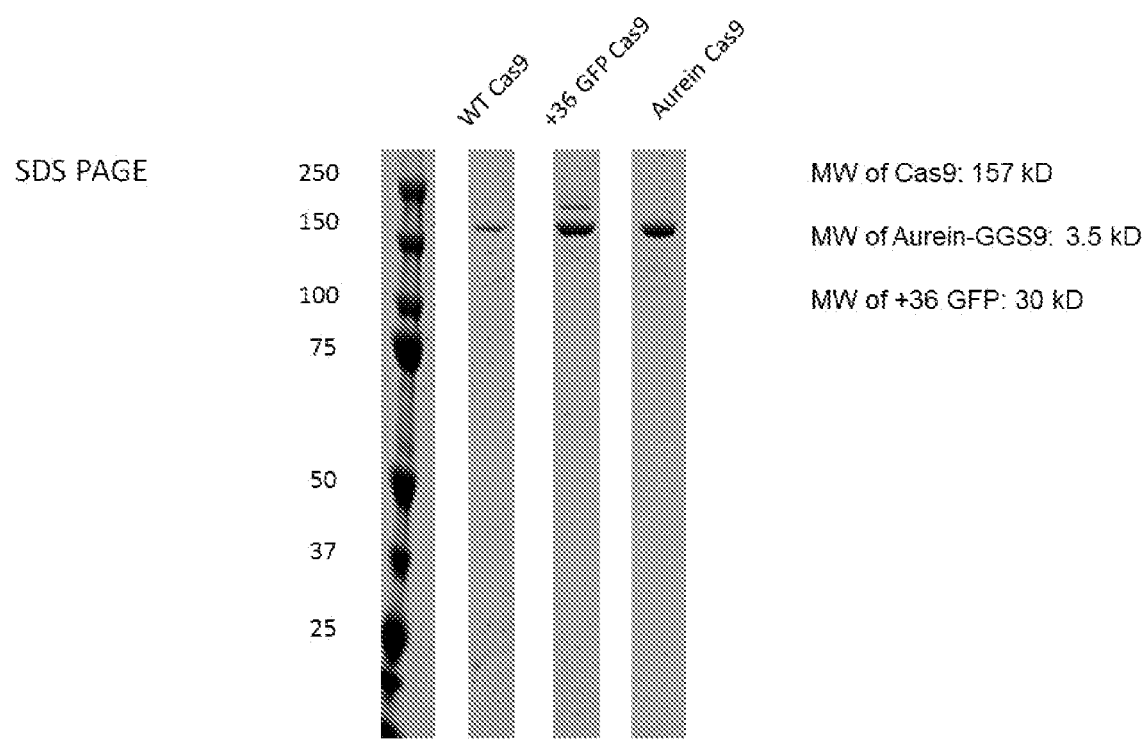
FIG. 26. Purification of wild-type Cas9 protein and Cas9 fusion proteins with +36GFP and Aurein-GGS9.

Supercharged delivery of Cas9 into mammalian cells would allow the application of powerful RNA-programmable nuclease technology in cells without the drawbacks of prior delivery methods. To this end, a Cas9 fusion with +36GFP was generated, using an ALAL linker. FIG. 25 shows a schematic of the supercharged fusion protein with Cas9. FIG. 26 shows the purification of wild-type Cas9 protein and Cas9 fusion proteins with +36GFP and Aurein-GGS9. The fusion protein is administered to cells in the same manner as the TALE activator fusion proteins above. The Cas9, once delivered to the cells, binds and cleaves its target site in the cellular genome. Nuclease activity in the target cells is detected via a suitable assay, e.g., via southern blot or sequencing assay.

Example 7: Efficient Delivery of Genome Editing Proteins In Vitro and In Vivo Efficient intracellular delivery of proteins to the nucleus or cytoplasm is needed to fully realize the potential of protein therapeutics including genome-editing agents. Current methods of protein delivery often suffer from low tolerance for serum proteins, poor endosomal escape, and limited in vivo efficacy. As demonstrated in this Example, common cationic lipid reagents originally developed for nucleic acid transfection can potently deliver proteins that are fused to negatively supercharged proteins, that contain natural anionic domains, or that natively bind to anionic nucleic acids. This approach mediates the functional delivery of Cre recombinase, TALE- and Cas9-based transcriptional activators, and Cas9:sgRNA nuclease complexes into cultured human cells at low nanomolar concentrations in media containing 10% serum. Lipid-based delivery can be >1,000-fold more potent than cationic protein delivery strategies. Delivery of Cas9:sgRNA complexes resulted in genome modification efficiencies as high as 80% with substantially higher specificity compared to standard DNA transfection, likely due to the transient nature of delivered Cas9:sgRNA complexes. This approach also mediated efficient delivery of Cre recombinase and Cas9:sgRNA complexes into the mouse inner ear in vivo, achieving up to 90% Cre-mediated recombination and 20% Cas9-mediated genome modification in the targeted hair-cell population.

Materials and Methods

Construction of Cas9, Cre, and TALE Fusion and sgRNA Expression Plasmids.

Sequences of all constructs used in this paper are listed below or provided elsewhere in the specification. All protein constructs were generated from previously reported plasmids for protein of interest cloned into a pET29a expression plasmid.

Expression and Purification of S. pyogenes Cas9 and Other Proteins.

E. coli BL21 STAR (DE3) competent cells (Life Technologies) were transformed with pMJ806[47] encoding the S. pyogenes Cas9 fused to an N-terminal 10×His-tag/maltose binding protein. The resulting expression strain was inoculated in Luria-Bertani (LB) broth containing 100 μg/mL of ampicillin at 37° C. overnight. The cells were diluted 1:100 into the same growth medium and grown at 37° C. to $OD_{600}$=~0.6. The culture was incubated at 20° C. for 30 min, and isopropyl β-D-1-thiogalactopyranoside (IPTG) was added at 0.5 mM to induce Cas9 expression. After approximately 16 hours, the cells were collected by centrifugation at 8,000 g and resuspended in lysis buffer (50 mM tris (hydroxymethyl)-aminomethane (Tris)-HCl, pH 8.0, 1 M NaCl, 20% glycerol, 10 mM tris(2-carboxyethyl)phosphine (TCEP)). The cells were lysed by sonication (1 sec pulse-on, 1 sec pulse-off for 15 minutes total at 6 W output) and the soluble lysate was obtained by centrifugation at 20,000 g for 30 minutes.

The cell lysate was incubated with His-Pur nickel-nitriloacetic acid (nickel-NTA) resin (Thermo Scientific) at 4° C. for 30 minutes to capture His-tagged Cas9. The resin was transferred to a 20-mL column and washed with 20 column volumes of lysis buffer. Cas9 was eluted in 50 mM Tris-HCl (pH 8), 0.1 M NaCl, 20% glycerol, 10 mM TCEP, and 300 mM imidazole, and concentrated by Amicon ultra centrifugal filter (Millipore, 100-kDa molecular weight cut-off) to ~50 mg/mL. The 6×His tag and maltose-binding protein were removed by TEV protease treatment at 4° C. for 20 hours and captured by a second Ni-affinity purification step. The eluent, containing Cas9, was injected into a HiTrap SP HP column (GE Healthcare) in purification buffer containing 50 mM Tris-HCl (pH 8), 0.1 M NaCl, 20% glycerol, and 10 mM TCEP. Cas9 was eluted with purification buffer containing a linear NaCl gradient from 0.1 M to 1 M over five column volumes. The eluted fractions containing Cas9 were concentrated down to a concentration of 200 μM as quantified by Bicinchoninic acid assay (BCA) (Pierce Biotechnology), snap-frozen in liquid nitrogen, and stored in aliquots at −80° C. All other proteins were purified by this method but without TEV cleavage step and proteins containing (−30)GFP were purified by anion exchange using a Hi-Trap Q HP anion exchange column (GE Healthcare) using the same purification protocol.

In Vitro Transcription of sgRNAs.

Linear DNA fragments containing the T7 promoter binding site followed by the 20-bp sgRNA target sequence were transcribed in vitro using the T7 High Yield RNA Synthesis Kit (NEB) according to the manufacturer's instructions. In vitro transcribed RNA was precipitated with ethanol and purified by gel electrophoresis on a Criterion 10% polyacrylamide TBE-Urea gel (Bio-Rad). Excised gel fragments were extracted in 420 μL of 300 mM NaCl overnight on a rocking surface at 4° C. Gel-purified sgRNA was precipitated with ethanol and redissolved in water and sgRNA concentration was finally quantified by UV absorbance and snap-frozen at −80° C.

Plasmid Transfection.

Plasmid DNA was transfected using Lipofectamine 2000 (Life Technologies) according the manufacturer's protocol. For TALE activator plasmids, 300 ng of DNA was transfected, and for the activator synergy experiments 60 ng of each of five plasmids was pooled and transfected. For Cas9 nuclease delivery experiments, linear DNA PCR products expressing sgRNAs were used in transfection experiments targeting genomic sites in CLTA, EMX, VEGF, and GFP (sgRNA GFP g1, GFP g3, GFP g5, and GFP g7 for nickase studies). Linear DNA PCR products were generated using plasmid containing the U6 promoter as template and forward primers bearing the U6 promoter upstream sequence and reverse primers containing U6 downstream sequence followed by the sgRNA sequence (20-bp sequence unique to each target plus constant sgRNA backbone architecture sequence). sgRNAs expressed from linear DNA templates contained at least two 5' guanosines to match in vitro transcribed sgRNAs that required these bases for T7 transcription. Primer sequences and PCR conditions are listed below. For dCas9 activator experiments, 700 ng of Cas9 or dCas9-VP64 plasmid DNA was co-transfected with 250 ng of the appropriate sgRNA expression plasmid. For activator synergy experiments 50 ng of DNA from each of the six sgRNA was pooled and co-transfected with 700 ng of dCas9-VP64 plasmid.

Delivery of Transcription Factor Proteins Complexed with Cationic Lipids in Cell Culture.

A more in-depth description of the delivery of genome-editing proteins both in vitro and in vivo can be found below. Briefly, cultured cells were plated in 48-well format (250 µL volume) in Dulbecco's Modified Eagle's Media plus GlutaMAX (Life Technologies, Carlsbad, Calif.) with 10% FBS ("full serum media") and antibiotics at a cell density necessary to reach ~70% confluence the next day. Full serum media was replaced with the same media but containing no antibiotics one hour before delivery. Delivery of Cre and TALE proteins was performed by combining 1 nM to 1 µM protein (in 275 µL final volume) with 0.5-1.5 µL of commercially available cationic lipids in 25 µL OPTIMEM media (Life Technologies, Carlsbad, Calif.) according to the manufacturer's protocol for normal plasmid transfection, including incubation time. For Cas9 delivery in vitro, transcribed sgRNA was incubated with Cas9 protein for 5 min before complexing with the cationic lipid reagent. 25 µL lipid complexes in OPTIMEM media were added to cells and media was replaced 12-16 hours later fresh media unless otherwise noted. Cells were assayed for recombination 48 hours after delivery, for gene activation either 4 or 16 hours after delivery, and for gene modification 72 hours after delivery.

T7 Endonuclease I Assay to Detect Genomic Modifications.

U2OS-EGFP cells or HEK293T cells were transfected with Cas9 expression and sgRNA expression plasmids or linear DNA PCR products as described above or treated with only Cas9 protein, only in vitro transcribed sgRNA, or only RNAiMAX. Genomic DNA was isolated from cells 2 days after transfection using the DNAdvance Kit (Agencourt) following the manufacturer's instructions. 200 ng of genomic DNA was used as template in PCR reactions to amplify the targeted genomic loci with flanking survey primer pairs specified below. PCR products were purified with a QIAquick PCR Purification Kit (Qiagen) and quantified with Quant-iT™ PicoGreen® dsDNA Kit (Life Technologies). 250 ng of purified PCR DNA was combined with 2 µL of NEBuffer 2 (NEB) in a total volume of 19 µL and denatured then re-annealed with thermocycling at 95° C. for 5 minutes, 95 to 85° C. at 2° C./s; 85 to 20° C. at 0.2° C./s. The re-annealed DNA was incubated with 1 µl of T7 Endonuclease I (10 U/µl, NEB) at 37° C. for 15 minutes. 10 µL of 50% glycerol was added to the T7 Endonuclease reaction and 12 µL was analyzed on a 5% TBE 18-well Criterion PAGE gel (Bio-Rad) electrophoresed for 30 minutes at 200 V, then stained with 1×SYBR Gold (Life Technologies) for 30 min. Cas9-induced cleavage bands and the uncleaved band were visualized on an AlphaImager HP (Alpha Innotech) and quantified using ImageJ software[54]. The peak intensities of the cleaved bands were divided by the total intensity of all bands (uncleaved+cleaved bands) to determine the fraction cleaved which was used to estimate gene modification levels as previously described.[46] For each sample, transfections and subsequent modification measurements were performed in triplicate on different days.

Stem Cell Culture and Delivery.

Mouse embryonic stem cell (ES) line Tau-GFP containing a permanent GFP gene insertion was cultured in DMEM with 15% FBS (Gibco), 100 mM MEM nonessential amino acids (Gibco), 0.55 mM 2-mercaptoethanol, and leukemia inhibitory factor (1,000 units/ml; Chemicon). After 5 days floating spheres were formed that exhibited GFP fluorescence. Complexes of Cas9:sgRNA and RNAiMAX were added to the culture containing the floating spheres for 16 hours. After Cas9:sgRNA treatment, the cells were cultured in the above media for 3 days. The floating spheres were treated with trypsin for 5 minutes then passed through a 70 µm filter to collect single cells. The cells were cultured on laminin-coated slides in DMEM/F12 (1:1) supplemented with 1×N2, 1×B27, penicillin-streptomycin (100 µg/mL) and 10% FBS for two days before labeling. Immunohistochemistry was performed using an anti-GFP antibody (# ab 13970, Abcam) to assess GFP expression. To quantify the number of GFP-negative cells, we counted the total number of GFP-positive and GFP-negative cells from three representative visual fields at 20× magnification, and calculated the average efficiency. Three independent experiments were performed for each condition.

Microinjection of Proteins to Mouse Inner Ear.

P0 floxP-tdTomato mice were used for (−30)GFP-Cre injection and P2 Atoh1-GFP mice were used for Cas9: sgRNA injection. Animals were used under protocols approved by the Massachusetts Eye & Ear Infirmary ALCUC committee. Mice were anesthetized by lowering their temperature on ice. Cochleostomies were performed by making an incision behind the ear to expose the otic bulla. Glass micropipettes held by a micromanipulator were used to deliver the complex into the scala media, which allows access to inner ear hair cells. For delivery of (−30)GFP-Cre, 3 µL of 45 µM protein was mixed with 3 µL of either RNAiMAX or Lipofectamine 2000 and incubated at room temperature for 30 minutes prior to injection. Four mice were injected per treatment group. For delivery of Cas9: sgRNA complexes, 1 µL of 200 µM Cas9 protein was mixed with 2 µL of 100 µM sgRNA and incubated for 5 minutes at room temperature before mixing with 3 µL of either RNAiMAX or Lipofectamine 2000 and incubating for an additional 30 minutes prior to injection. Three mice were injected per treatment group. The total delivery volume for every injection was 0.3 µL per cochlea and the release was controlled by a micromanipulator at the speed of 32 nL/sec.

Immunohistochemistry and Quantification.

5-10 days after injection, the mice were sacrificed and cochlea were harvested by standard protocols.[55] For immunohistochemistry, antibodies against hair-cell markers (Myo7a and Esp) and supporting cells (Sox2) were used following a previously described protocol.[55] To quantify the number of tdTomato positive cells after (−30)GFP-Cre or GFP negative cells after Cas9: sgRNA delivery, we counted the total number of outer hair cells in a region spanning 200 µm around the site of injection in the base turn of the cochlea. The efficiency of (−30)GFP-Cre-induced recombination or Cas9:sgRNA-induced genome modification was calculated as the percentage of outer hair cells that expressed tdTomato or that lost GFP expression.

High-Throughput DNA Sequencing of Genome Modifications.

HEK293T cells were either transfected with Cas9 and sgRNA expression plasmids or linear DNA PCR products or treated with 50 nM Cas9 protein, 250 nM purified sgRNA, and cationic lipids as described earlier for Cas9 protein delivery to U2OS-EGFP reporter cells. For plasmid-based transfection experiments, 700 ng of Cas9 expression plasmid plus 250 ng of sgRNA plasmid or 50 ng of a linear DNA PCR product expressing sgRNA for targeting either the EMX1, CLTA2, or VEGF locus were transfected with Lipofectamine 2000 (Life Technologies) and cells were isolated 2 days later. For protein delivery experiments in vivo, ~30 mg of mouse tissue was isolated as previously described[55] from anesthetized mice and genomic DNA was extracted using the Agencourt DNAAdvance Genomic DNA Isolation Kit (Beckman Coulter). For cell culture experiments genomic DNA was isolated as described above. 150 ng of genomic DNA was used as template to amplify by PCR the on-target and off-target genomic sites with flanking HTS primer pairs specified below. Relative amounts of crude PCR with primers containing sequencing adapters, purified, and sequenced on a MiSeq high-throughput DNA sequencer (Illumina) as previously described.[47]

Data Analysis

Illumina sequencing reads were filtered and parsed with scripts written in Unix Bash as outlined below. Sample sizes for sequencing experiments were maximized (within practical experimental considerations) to ensure greatest power to detect effects. Statistical analyses for Cas9-modified genomic sites (Table 2) were performed as previously described[56] with multiple comparison correction using the Bonferroni method.

The following is a list of upstream and downstream flanking sequences for each genomic target site.

| TargetSite | Downstream genomic sequence | Upstream genomic sequence |
|---|---|---|
| EMX_On | GGCCTGCTTCGTGGCAATGC (SEQ ID NO: 119) | ACCTGGGCCAGGGAGGGAGG (SEQ ID NO: 120) |
| EMX_Off1 | CTCACTTAGACTTTCTCTCC (SEQ ID NO: 121) | CTCGGAGTCTAGCTCCTGCA (SEQ ID NO: 122) |
| EMX_Off2 | TGGCCCCAGTCTCTCTTCTA (SEQ ID NO: 123) | CAGCCTCTGAACAGCTCCCG (SEQ ID NO: 124) |
| EMX_Off3 | TGACTTGGCCTTTGTAGGAA (SEQ ID NO: 125) | GAGGCTACTGAAACATAAGT (SEQ ID NO: 126) |
| EMX_Off4 | TGCTACCTGTACATCTGCAC (SEQ ID NO: 127) | CATCAATGATTGGGCATTTC (SEQ ID NO: 128) |
| VEG_On | ACTCCAGTCCCAAATATGTA (SEQ ID NO: 129) | ACTAGGGGGCGCTCGGCCAC (SEQ ID NO: 130) |
| VEG_Off1 | CTGAGTCAACTGTAAGCATT (SEQ ID NO: 131) | GGCCAGGTGCAGTGATTCAT (SEQ ID NO: 132) |
| VEG_Off2 | TCGTGTCATCTTGTTTGTGC (SEQ ID NO: 133) | GGCAGAGCCCAGCGGACACT (SEQ ID NO: 134) |
| VEG_Off3 | CAAGGTGAGCCTGGGTCTGT (SEQ ID NO: 135) | ATCACTGCCCAAGAAGTGCA (SEQ ID NO: 136) |
| VEG_Off4 | TTGTAGGATGTTTAGCAGCA (SEQ ID NO: 137) | ACTTGCTCTCTTTAGAGAAC (SEQ ID NO: 138) |
| CLT2_On | CTCAAGCAGGCCCCGCTGGT (SEQ ID NO: 139) | TTTTGGACCAAACCTTTTTG (SEQ ID NO: 140) |
| CLT2_Off1 | TGAGGTTATTTGTCCATTGT (SEQ ID NO: 141) | TAAGGGGAGTATTTACACCA (SEQ ID NO: 142) |
| CLT2_Off2 | TCAAGAGCAGAAAATGTGAC (SEQ ID NO: 143) | CTTGCAGGGACCTTCTGATT (SEQ ID NO: 144) |
| CLT2_Off3 | TGTGTGTAGGACTAAACTCT (SEQ ID NO: 145) | GATAGCAGTATGACCTTGGG (SEQ ID NO: 146) |
| EGFP | AGCGTGTCCGGCGAGGGCGA (SEQ ID NO: 147) | AGCGTGTCCGGCGAGGGCGA (SEQ ID NO: 148) |
| MusEMX | CAGAATCGGAGGACAAAATACAAAC (SEQ ID NO: 149) | ACGAAGCAGGCCAACGGGGAGGACA (SEQ ID NO: 150) |

PCR products were quantified by gel electrophoresis and samples treated with different sgRNA pairs or Cas9 nuclease types were separately pooled in equimolar concentrations before purification with the QIAquick PCR Purification Kit (Qiagen). Approximately 150 ng of pooled DNA was electrophoresed using a 5% TBE 18-well Criterion PAGE gel (BioRad) for 30 min at 200 V and DNAs ~125 bp to ~300 bp in length were isolated and purified by QIAquick PCR Purification Kit (Qiagen). Purified DNA was amplified by Primers Used for Generating PCR Products to Serve as Substrates for T7 Transcription of Sgrnas.

T7_gRNA-Rev was used in all cases. DNA template used was EGFP sgRNA plasmid as noted above. NTF3 and VEGF sgRNAs for dCas9-VP64 activator experiments were reported previously (Maeder et al., CRISPR RNA-guided activation of endogenous human genes. *Nat. Methods.* 2013; 10, 977-979).

T7_EGFP1-Fwd
(SEQ ID NO: 151)
TAA TAC GAC TCA CTA TA GGGCACGGGCAGCTTGCCGG

T7-GFP g1-Fwd
(SEQ ID NO: 152)
TAA TAC GAC TCA CTA TA GGCCTCGAACTTCACCTCGGCG
GAAAGGACGAAACACC

T7-GFP g5-Fwd
(SEQ ID NO: 153)
TAA TAC GAC TCA CTA TA GGCTGAAGGGCATCGACTTCA
GAAAGGACGAAACACC

T7-GFP g3-Fwd
(SEQ ID NO: 154)
TAA TAC GAC TCA CTA TA GGCAGCTCGATGCGGTTCACCA
GAAAGGACGAAACACC

T7-GFP g7-Fwd
(SEQ ID NO: 155)
TAA TAC GAC TCA CTA TA GGCAAGGAGGACGGCAACATCC
GAAAGGACGAAACACC

T7-EMX-Fwd
(SEQ ID NO: 156)
TAA TAC GAC TCA CTA TA GGAGTCCGAGCAGAAGAAGAA
GAAAGGACGAAACACC

T7-VEG-Fwd
(SEQ ID NO: 157)
TAA TAC GAC TCA CTA TA GGGGTGGGGGAGTTTGCTCC
GAAAGGACGAAACACC

T7-CLT2-Fwd
(SEQ ID NO: 158)
TAA TAC GAC TCA CTA TA GGCAGATGTAGTGTTTCCACA
GAAAGGACGAAACACC

T7_gRNA-Rev
(SEQ ID NO: 159)
AAAAAAAGCACCGACTCGGTG

Primers for Generating Linear DNA PCR Product for Transfection.

PCR extension at (72° C., 3 min) on plasmid containing U6 promoter as template with PCR_sgRNA-fwd1, PCR_sgRNA-rev2 and appropriate PCR_sgRNA primers listed below.

PCR_gRNA-fwd 1
(SEQ ID NO: 160)
CTGTACAAAAAAGCAGGCTTTA

PCR_gRNA-rev2
(SEQ ID NO: 161)
AAAAAAAGCACCGACTCGGTGCCACTTTTTCAAGTTGATAACGG
ACTAGCCTTATTTTAACTTGCTATTTCTAGCTCTAAAAC PCR-G-GFP 1
(SEQ ID NO: 162)
GAAAGGACGAAACACC
GGCCTCGAACTTCACCTCGGCGGTTTTAGAGCTAGAAATAGCAA PCR-G-GFP3
(SEQ ID NO: 163)
GAAAGGACGAAACACC
GGCAGCTCGATGCGGTTCACCAGTTTTAGAGCTAGAAATAGCAA PCR-G-GFP5
(SEQ ID NO: 164)
GAAAGGACGAAACACC
GGCTGAAGGGCATCGACTTCAGTTTTAGAGCTAGAAATAGCAA PCR-G-GFP7
(SEQ ID NO: 165)
GAAAGGACGAAACACC
GGCAAGGAGGACGGCAACATCCGTTTTAGAGCTAGAAATAGCAA PCR-G-CLT2
(SEQ ID NO: 166)
GAAAGGACGAAACACC
GGCAGATGTAGTGTTTCCACAGTTTTAGAGCTAGAAATAGCAA PCR-G-EMX
(SEQ ID NO: 167)
GAAAGGACGAAACACC
GGAGTCCGAGCAGAAGAAGTTTTAGAGCTAGAAATAGCAA PCR-G-VEG
(SEQ ID NO: 168)
GAAAGGACGAAACACC
GGGGTGGGGGAGTTTGCTCCGTTTTAGAGCTAGAAATAGCAA Primers for Performing T7 Endonuclease I DNA Cleavage Assay.

Survey_GFP-fwd
(SEQ ID NO: 169)
TACGGCAAGCTGACCCTGAA

Survey_GFP-rev
(SEQ ID NO: 170)
GTCCATGCCGAGAGTGATCC

Survey_CLTA-fwd
(SEQ ID NO: 171)
GCCAGGGGCTGTTATCYTGG

Survey_CLTA-rev
(SEQ ID NO: 172)
ATGCACAGAAGCACAGGTTGA

Survey_EMX-fwd
(SEQ ID NO: 173)
CTGTGTCCTCTTCCTGCCCT

Survey_EMX-rev
(SEQ ID NO: 174)
CTCTCCGAGGAGAAGGCCAA

Survey_VEGF-fwd
(SEQ ID NO: 175)
CCACACAGCTTCCCGTTCTC

Survey_VEGF-rev
(SEQ ID NO: 176)
GAGAGCCGTTCCCTCTTTGC

Primers for High-Throughput Sequencing of on-Target and Off-Target Sites in Human Genome.

HTS_EMX_ON-fwd
(SEQ ID NO: 177)
CACTCTTTCCCTACACGACGCTCTTCCGATCT
CCTCCCCATTGGCCTGCTTC HTS_EMX_Off1-fwd
                                 (SEQ ID NO: 178)
CACTCTTTCCCTACACGACGCTCTTCCGATCT

TCGTCCTGCTCTCACTTAGAC

HTS_EMX_Off2-fwd
                                 (SEQ ID NO: 179)
CACTCTTTCCCTACACGACGCTCTTCCGATCT

TTTTGTGGCTTGGCCCCAGT

HTS_EMX_Off3-fwd
                                 (SEQ ID NO: 180)
CACTCTTTCCCTACACGACGCTCTTCCGATCT

TGCAGTCTCATGACTTGGCCT

HTS_EMX_Off4-fwd
                                 (SEQ ID NO: 181)
CACTCTTTCCCTACACGACGCTCTTCCGATCT

TTCTGAGGGCTGCTACCTGT

HTS_VEFG_ON-fwd
                                 (SEQ ID NO: 182)
CACTCTTTCCCTACACGACGCTCTTCCGATCT

ACATGAAGCAACTCCAGTCCCA

HTS_VEGF_Off1-fwd
                                 (SEQ ID NO: 183)
CACTCTTTCCCTACACGACGCTCTTCCGATCT

AGCAGACCCACTGAGTCAACTG

HTS_VEGF_Off2-fwd
                                 (SEQ ID NO: 184)
CACTCTTTCCCTACACGACGCTCTTCCGATCT

CCCGCCACAGTCGTGTCAT

HTS_VEGF_Off3-fwd
                                 (SEQ ID NO: 185)
CACTCTTTCCCTACACGACGCTCTTCCGATCT

CGCCCCGGTACAAGGTGA

HTS_VEGF_Off4-fwd
                                 (SEQ ID NO: 186)
CACTCTTTCCCTACACGACGCTCTTCCGATCT

GTACCGTACATTGTAGGATGTTT

HTS_CLTA2_ON-fwd
                                 (SEQ ID NO: 187)
CACTCTTTCCCTACACGACGCTCTTCCGATCT

CCTCATCTCCCTCAAGCAGGC

HTS_CLTA2_Off1-fwd
                                 (SEQ ID NO: 188)
CACTCTTTCCCTACACGACGCTCTTCCGATCT

ATTCTGCTCTTGAGGTTATTTGT

HTS_CLTA2_Off2-fwd
                                 (SEQ ID NO: 189)
CACTCTTTCCCTACACGACGCTCTTCCGATCT

CACCTCTGCCTCAAGAGCAGAAAA

HTS_CLTA2_Off3-fwd
                                 (SEQ ID NO: 190)
CACTCTTTCCCTACACGACGCTCTTCCGATCT

TGTGTGTGTGTGTGTAGGACT

HTS_EMX_ON-rev
                                 (SEQ ID NO: 191)
GGAGTTCAGACGTGTGCTCTTCCGATCT

TCATCTGTGCCCCTCCCTCC

HTS_EMX_Off-rev
                                 (SEQ ID NO: 192)
GGAGTTCAGACGTGTGCTCTTCCGATCT

CGAGAAGGAGGTGCAGGAG

HTS_EMX_Off-rev
                                 (SEQ ID NO: 193)
GGAGTTCAGACGTGTGCTCTTCCGATCT

CGGGAGCTGTTCAGAGGCTG

HTS_EMX_Off-rev
                                 (SEQ ID NO: 194)
GGAGTTCAGACGTGTGCTCTTCCGATCT

CTCACCTGGGCGAGAAAGGT

HTS_EMX_Off-rev
                                 (SEQ ID NO: 195)
GGAGTTCAGACGTGTGCTCTTCCGATCT

AAAACTCAAAGAAATGCCCAATCA

HTS_VEFG_ON-rev
                                 (SEQ ID NO: 196)
GGAGTTCAGACGTGTGCTCTTCCGATCT

AGACGCTGCTCGCTCCATTC

HTS_VEGF_Off1-rev
                                 (SEQ ID NO: 197)
GGAGTTCAGACGTGTGCTCTTCCGATCT

ACAGGCATGAATCACTGCACCT

HTS_VEGF_Off2-rev
                                 (SEQ ID NO: 198)
GGAGTTCAGACGTGTGCTCTTCCGATCT

GCGGCAACTTCAGACAACCGA

HTS_VEGF_Off3-rev
                                 (SEQ ID NO: 199)
GGAGTTCAGACGTGTGCTCTTCCGATCT

GACCCAGGGGCACCAGTT

HTS_VEGF_Off4-rev
                                 (SEQ ID NO: 200)
GGAGTTCAGACGTGTGCTCTTCCGATCT

CTGCCTTCATTGCTTAAAAGTGGAT

HTS_CLTA2_ON-rev
                                 (SEQ ID NO: 201)
GGAGTTCAGACGTGTGCTCTTCCGATCT

ACAGTTGAAGGAAGGAAACATGC

HTS_CLTA2_Off1-rev
                                 (SEQ ID NO: 202)
GGAGTTCAGACGTGTGCTCTTCCGATCT GCTGCATTTGCCCATTTCCA
HTS_CLTA2_Off2-rev
                                 (SEQ ID NO: 203)
GGAGTTCAGACGTGTGCTCTTCCGATCT

GTTGGGGGAGGAGGAGCTTAT

-continued

HTS_CLTA2_Off3-rev
(SEQ ID NO: 204)
GGAGTTCAGACGTGTGCTCTTCCGATCT

CTAAGAGCTATAAGGGCAAATGACT

HTS_EGFP-fwd
(SEQ ID NO: 205)
CACTCTTTCCCTACACGACGCTCTTCCGATCTNNNN

ACGTAAACGGCCACAAGTTC

HTS_EGFP-rev
(SEQ ID NO: 206)
GGAGTTCAGACGTGTGCTCTTCCGATCT

GTCGTCCTTGAAGAAGATGGTG

HTS_MusEMX_ON-fwd
(SEQ ID NO: 207)
CACTCTTTCCCTACACGACGCTCTTCCGATCT

CCAGGTGAAGGTGTGGTTCCAG

HTS_MusEMX_ON-rev
(SEQ ID NO: 208)
GGAGTTCAGACGTGTGCTCTTCCGATCT

CCCCTAGTCATTGGAGGTGAC

Results

Figure 27:
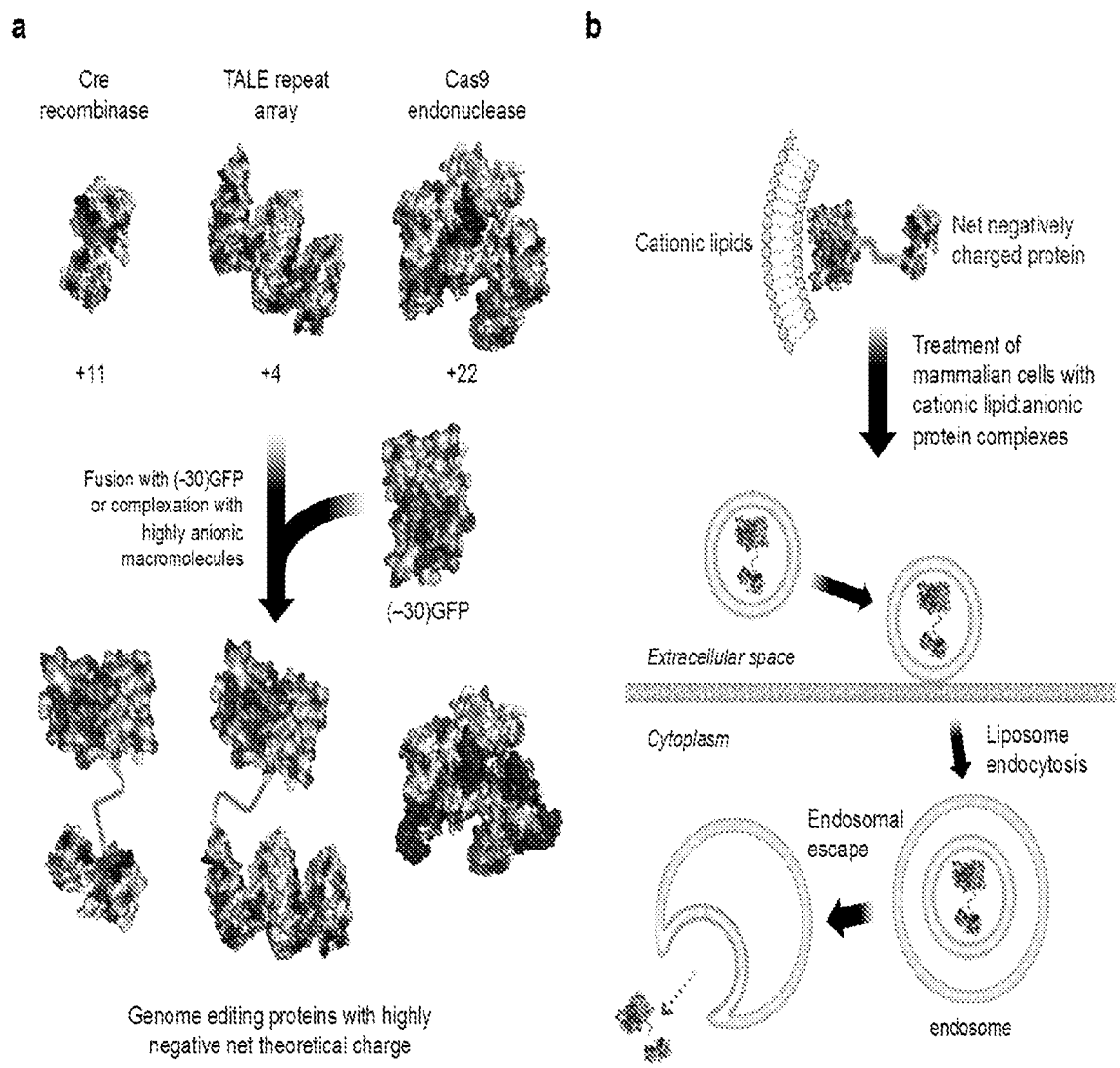
FIG. 27A-B. A strategy for delivering proteins into mammalian cells by fusion or non-covalent complexation with polyanionic macromolecules and encapsulation with cationic lipids is shown.

Highly Efficient Delivery of Cre Recombinase Fused to a Supernegatively Charged Protein It was speculated that imparting the highly anionic electrostatic properties of nucleic acids to genome-editing proteins may enable their efficient delivery into mammalian cells using cationic lipids (FIG. 27(A)). For proteins of interest that are not natively highly negatively charged, it was thought that fusion with a natural or engineered supernegatively charged protein[17] would impart a polyanionic character. For nucleic acid-binding proteins, it was speculated that simple complexation with native DNA or RNA substrates might provide sufficient anionic character to support cationic lipid-based delivery (FIG. 27(A)).

It was first tested whether the engineered supernegatively charged GFP variant,[35] (−30)GFP, could mediate encapsulation and delivery of fused protein cargo (FIG. 27(B)). (−30)GFP was fused to Cre recombinase and several commercially available cationic lipids were tested for their ability to functionally deliver the fusion into HeLa cells that only express DsRed upon Cre-mediated recombination (FIG. 28(A)). Delivery of 10 nM (−30)GFP-Cre complexed with 1.5 µL Lipofectamine RNAiMAX (hereafter referred to as "RNAiMAX", Life Technologies, Carlsbad Calif.) in media containing 10% fetal bovine serum (FBS) led to strong DsRed fluorescence signal among treated cells. Fluorescence-activated cell sorting (FACS) revealed that 48 hours after treatment 52% of cells expressed DsRed consistent with Cre recombination (FIG. 28(B)).

Figure 28:
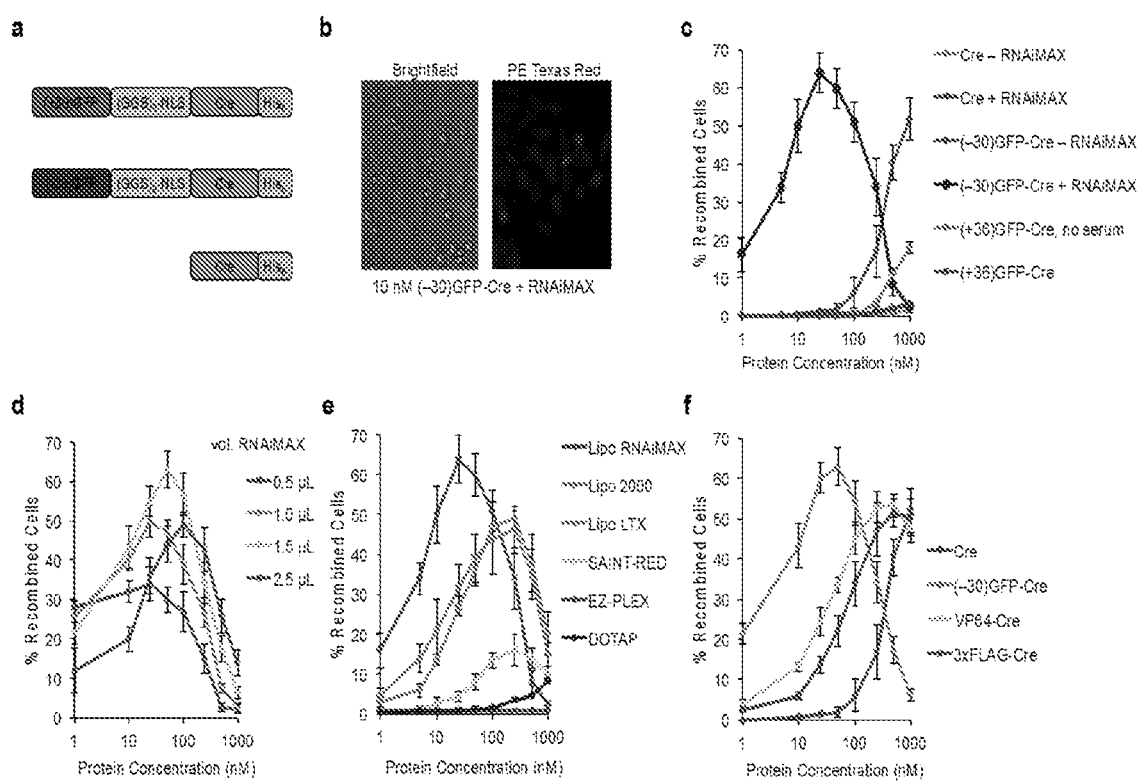
FIG. 28A-F. Delivery of Cre recombinase to cultured human cells.

Optimization resulted in recombination efficiencies of 65% using 25 nM (−30)GFP-Cre complexed with 1.5 µL RNAiMAX in 250 µL of media containing 10% FBS (FIG. 28(C)). The potency of lipid-mediated anionic Cre delivery is notable compared to that of cationic protein-mediated delivery. Only 1 nM (−30)GFP-Cre with cationic lipid was needed to result in 15-20% recombined cells, whereas 1 µM (+36)GFP-Cre was required to achieve this extent of recombination, representing a 1,000-fold difference in delivery potency (FIG. 28(C)). Nearly identical results were observed in a second Cre reporter cell line (BSR TdTomato) (FIG. 33(A)). Increasing the amount of cationic lipid increased toxicity (FIG. 33(B)) and it was found that 1.5 µL RNAiMAX per 250 µL sample maximized recombination efficiency while inducing minimal cell toxicity. Under these conditions, cationic lipids did not increase the delivery potency of neutral or cationic Cre recombinase fusions (FIG. 28(C) and FIG. 33(C)), indicating that the strongly negative charge of (−30)GFP-Cre was required to participate in cationic lipid-mediated delivery. It was also observed that increasing the amount of cationic lipid increased the concentration of protein required for maximal recombination, consistent with a model in which deliverable proteins are complexed with specific stiochiometries of cationic lipids (FIG. 28(D)). These observations collectively indicate that cationic lipids can mediate the potent delivery of polyanionic proteins into mammalian cells even in the presence of serum.

Figure 34:
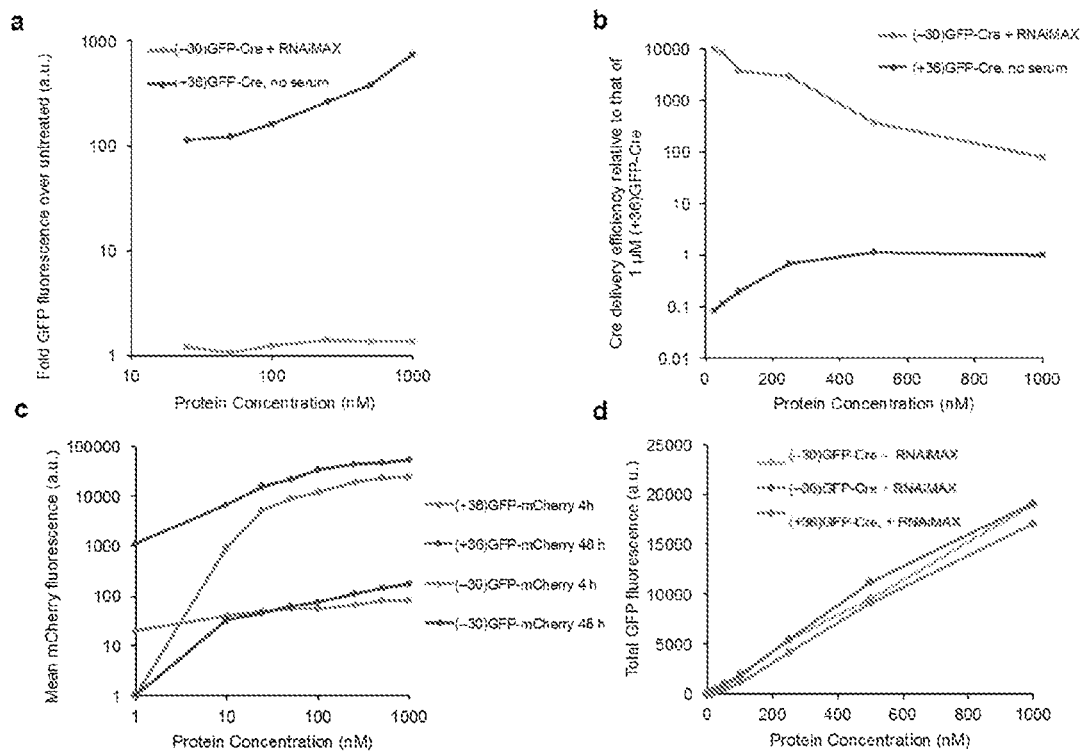
FIGS. 34A-D. Protein uptake by cationic lipid-mediated delivery versus superpositively charged cationic protein delivery.

To determine if the higher potency of cationic lipid-mediated (−30)GFP-Cre delivery relative to cationic protein-mediated delivery arises from more total protein uptake by cells, or from a higher fraction of functional, non-endosomal protein molecules that enter cells, flow cytometry was used to measure GFP fluorescence of cells treated with either (+36)GFP-Cre or liposomal (−30)GFP-Cre under their respective optimal Cre delivery conditions. Comparison of cellular fluorescence and recombination efficiency reveals that lipid-mediated functional delivery of (−30)GFP-Cre is 9,800-fold more potent per amount of endocytosed protein than delivery of (+36)GFP-Cre (FIG. 34). Taken together, these results suggest that the unusually high potency of lipid-mediated delivery of anionic proteins does not arise from unusually high protein uptake in each cell, but rather from post-endocytosis processes that likely include endosomal escape into the cytoplasm and the avoidance of lysosomal protein degradation.

To test whether the ability to deliver polyanionic proteins is dependent on proprietary components in RNAiMAX or if other cationic lipids are capable of mediating similarly potent delivery, several other transfection reagents designed to deliver nucleic acids were tested (FIG. 28(E)). While RNAiMAX remained the most effective functional delivery agent for (−30)GFP-Cre, other cationic lipid formulations also resulted in potent delivery. Lipofectamine 2000 and Lipofectamine LTX (Life Technologies, Carlsbad Calif.), two plasmid transfection reagents based on cationic lipid formulations,[21] and SAINT-Red (Synvolux Therapeutics, Groningen Netherlands), an siRNA delivery formulation containing a synthetic pyridium-containing cationic lipid, all resulted in strong functional (−30)GFP-Cre delivery over a range of concentrations (FIG. 28(E)). In contrast, strong deliveries with the cationic lipid DOTAP (Roche Diagnostics, Indianapolis Ind.) or the peptide-based nucleic acid delivery agent EZ-PLEX (Ascension Bio, Tampa Fla.) were not observed (FIG. 28(E)). These observations collectively indicate that several (but not all) cationic lipids are able to encapsulate and deliver negatively charged proteins into human cells.

It was speculated that it should be possible to use cationic lipids to deliver polyanionic proteins other than (−30)GFP. Engineered polyanionic protein domains commonly used in biomedical research include the VP64 activation domain (−22 net theoretical charge) widely used in fusions with engineered zinc finger arrays, TALE repeat arrays, or dCas9 for transcriptional activation, and 3×FLAG (−7 net theoretical charge), an epitope tag used for protein purification and visualization (FIG. 28(F)). It was observed that both VP64 and 3×FLAG enhance functional delivery of Cre recombinase with cationic lipids, though not as effectively as (−30)

Figure 33:
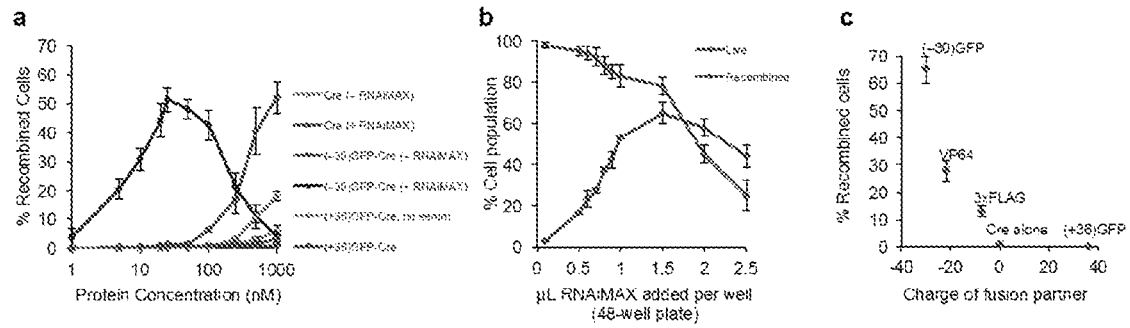
FIG. 33A-C. Optimization of cationic lipid-mediated delivery of Cre recombinase.

GFP, likely due to their lower overall negative charge (FIG. 33(C)). These observations demonstrate that unusually negatively charged proteins beyond (−30)GFP can mediate efficient cationic lipid-based delivery into mammalian cells.

Functional Delivery of TALE Activator Proteins

Figure 29:
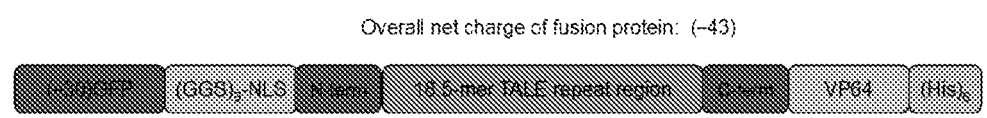
FIG. 29A-B. Delivery of TALE transcriptional activators into cultured human cells.
Figure 29:
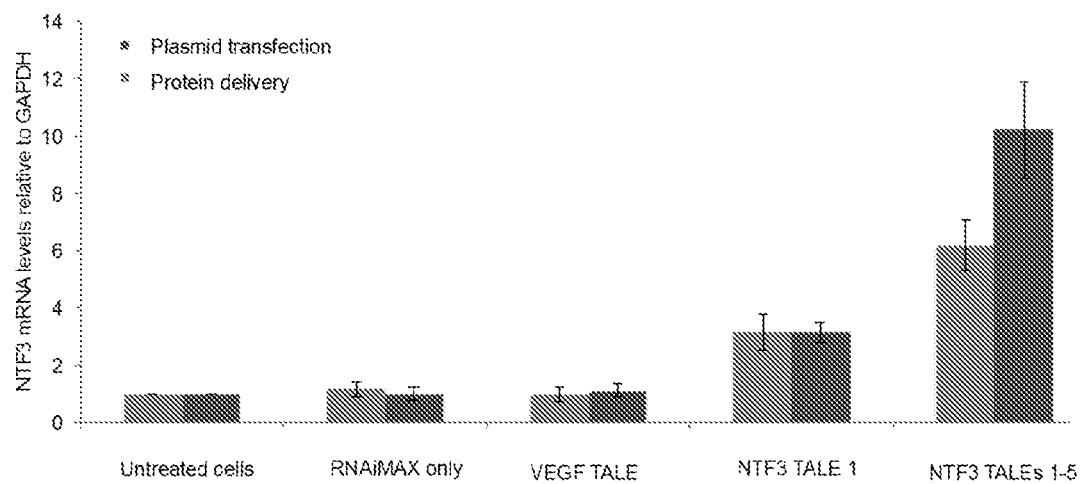

The lipid-mediated delivery of TALE-VP64 transcriptional activators (approximately +4 theoretical net charge, depending on TALE variant used) into cultured human cells was tested. While modestly effective cleavage of endogenous genes by delivered TALEN proteins has been demonstrated in mammalian cells in the absence of serum using cationic peptides such as $Arg_9$,[36] the delivery of TALE-based transcription factor proteins has not yet been reported, and no effective delivery of TALE proteins in serum has been previously described to our knowledge. The gene for neurotrophin-3 (NTF3), a neural growth factor that has been associated with neurodegenerative diseases, was targeted.[37] A previously described NTF3-targetting TALE-VP64[38] was fused to (−30)GFP (FIG. 29(A)) and treated HEK293T cells with 25 nM (−30)GFP-NTF3 TALE1-VP64 and RNAiMAX under the conditions optimized for Cre delivery. Gene expression levels of NTF3 4 hours after treatment were 3.5-fold higher in cells treated with 25 nM (−30)GFP-NTF3 TALE-VP64 and RNAiMAX than untreated cells, cells treated with RNAiMAX only, or cells treated with a VEGF-targeting TALE transcriptional activator (FIG. 29(B)). Comparable levels of NTF3 expression were observed 48 hours after transfection of plasmids encoding the same NTF3-targeting TALE-VP64 (FIG. 29(B)).

Figure 35:
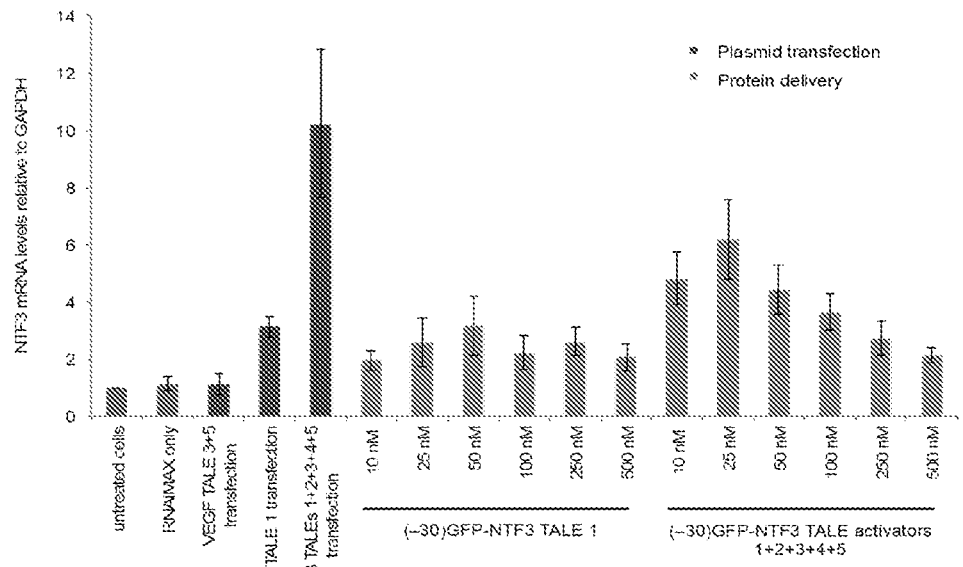
FIG. 35. Delivery optimization of TALE activators designed to target the NTF3 gene. HEK293T cells were treated with either NTF3 TALE plasmid by transfection of by liposomal delivery of NTF3 TALE proteins. Cells were harvested after empirically determined optimal incubation time for both treatments and analyzed by qRT-PCR for mRNA levels of NTF3. Optimal protein (25-50 nM) and lipid dosage (1.5 μL RNAiMAX) was chosen for comparison of two delivery techniques in FIG. 29B. Error bars reflect the standard deviation from six biological replicates performed on different days.

Since the synergistic expression of multiple TALE activators targeting different sites on the same gene has been shown to augment gene activation,[38] five distinct NTF3-targeting TALE activators fused to (−30) GFP using RNAiMAX were simultaneously delivered. Protein-lipid complexes were prepared as above by adding the five (−30)GFP-NTF3-TALE-VP64 proteins at 5 nM each, for a total of 25 nM protein. A 6.5-fold increase in NTF3 expression was observed after a 4-hour incubation (FIG. 29(B) and FIG. 35), while plasmid co-transfection of all five NTF3 TALE activators, followed by a 48-hour incubation, resulted in a 10-fold increase in NTF3 expression levels (FIG. 29(B)). These findings demonstrate that TALE activator proteins can be delivered using cationic lipids to transiently activate gene expression in human cells. The delivery of programmable transcriptional activator proteins may enable the one-time activation of a target gene while avoiding chronic gene expression, a general concern with DNA-based delivery of programmable transcription factors. This capability may prove especially valuable for proteins that effect a one-time permanent change in cell state or cell fate when transiently expressed.[39]

Highly Efficient Delivery of Cas9:sgRNA Protein:RNA Complexes into Human Cells

Figure 36:
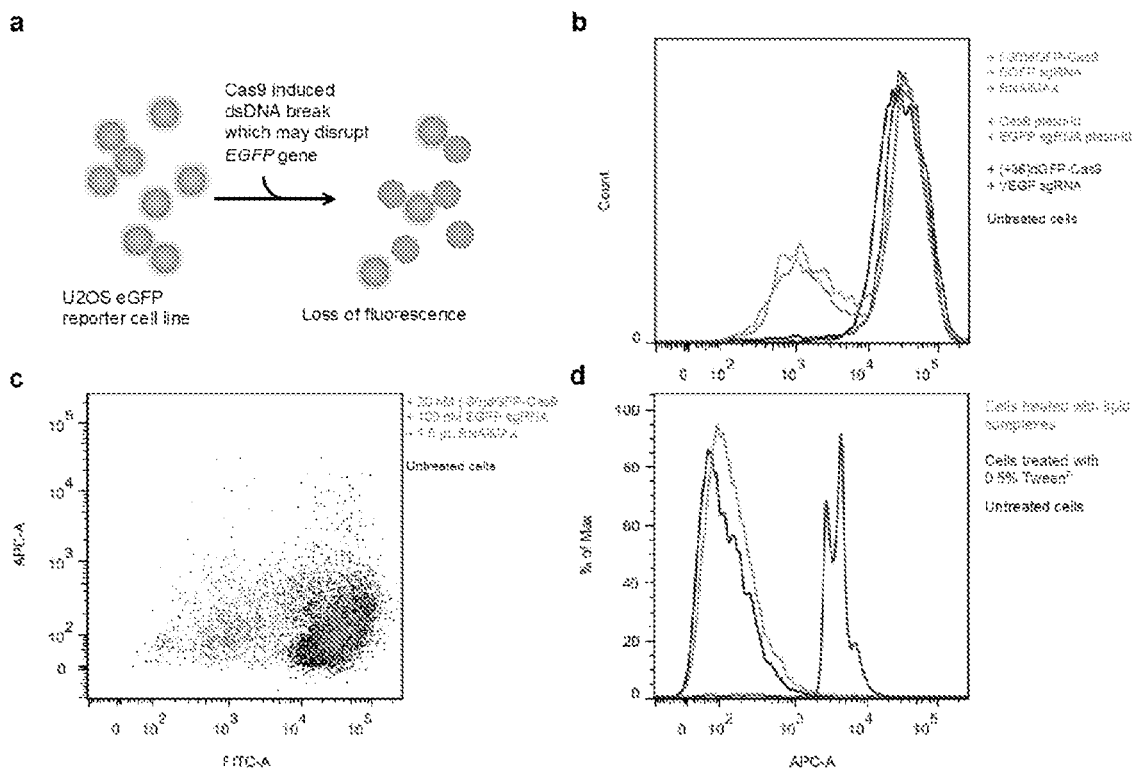
FIGS. 36A-D. Determination of gene disruption frequency of an EGFP reporter gene by delivery of Cas9: sgRNA and analyzing by flow cytometry.

Given the potent lipid-mediated delivery of polyanionic Cre and TALE activator protein variants in full-serum media, it was speculated that CRISPR-Cas9:sgRNA complexes, either as fusions with (−30)GFP or as native polyanionic Cas9:guide RNA complexes, might also be delivered into human cells using this approach. Using a well-established Cas9-induced gene disruption assay,[40] specific sites within a genomic EGFP reporter gene in human U2OS cells were targeted (FIG. 36(A)). On-target Cas9 cleavage induces non-homologous end joining (NHEJ) in EGFP and the loss of cell fluorescence. To avoid interference from the fluorescence of (−30)GFP, a Y67S mutation was introduced into (−30)GFP to eliminate its fluorescence, and designated this non-fluorescent variant as (−30)dGFP.

Figure 30:
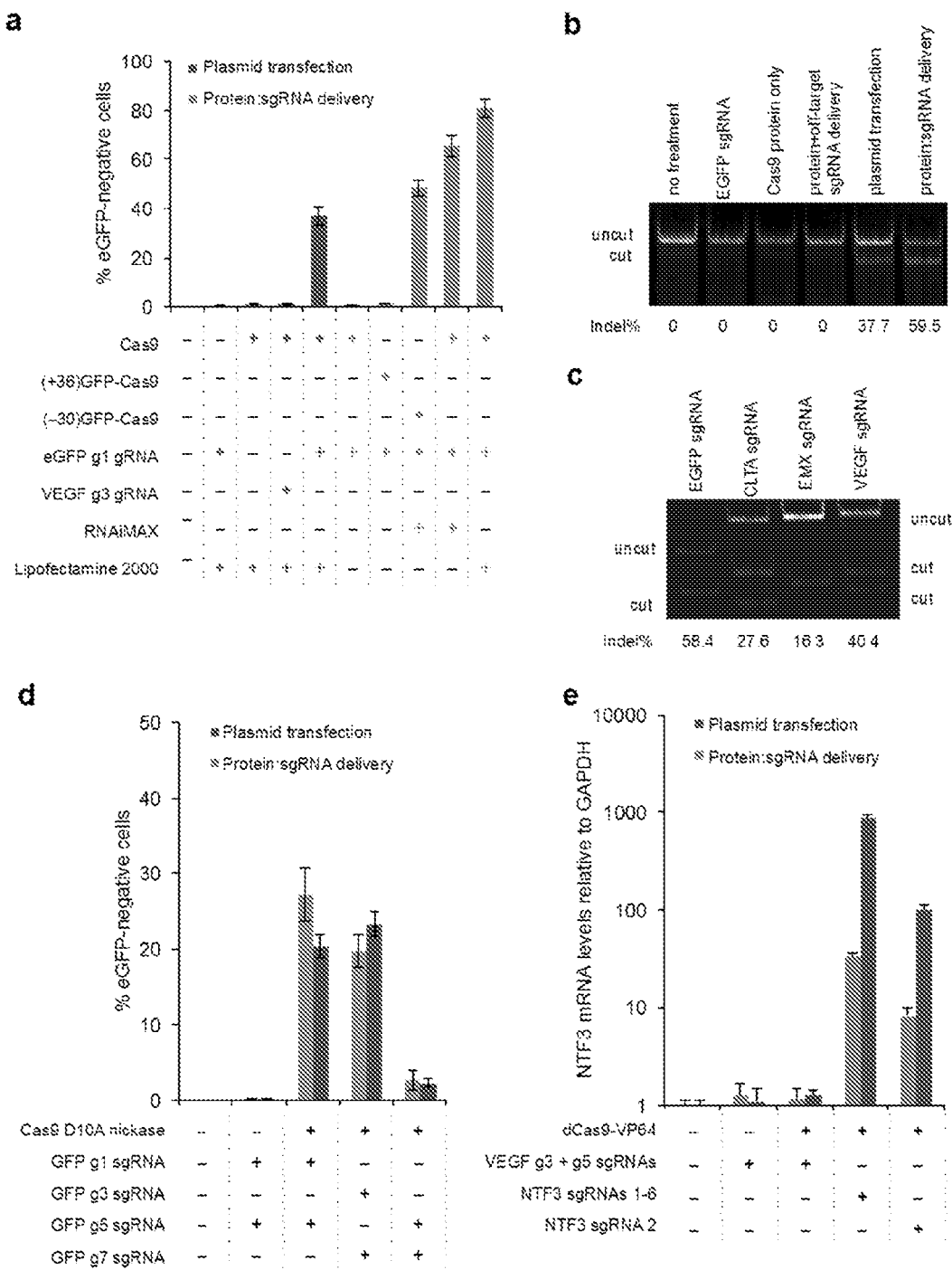
FIG. 30A-E. Delivery of Cas9:sgRNA, Cas9 D10A nickase, and dCas9-VP64 transcriptional activators to cultured human cells.

Treatment of U2OS reporter cells with 25 nM (−30) dGFP-NLS-Cas9 and 50 nM EGFP-targeting sgRNA with RNAiMAX in media containing 10% FBS showed loss of EGFP expression in 48% of cells (FIG. 30(A)). Cotransfection of plasmids expressing Cas9 or sgRNA resulted in similar EGFP loss in 37% of cells (FIG. 30(A)). No significant EGFP disruption was observed upon transfection of plasmids encoding EGFP sgRNA alone, Cas9 alone, or cotransfection of plasmids encoding Cas9 and an sgRNA designed to target a VEGF locus (FIG. 30(A), FIG. 36(B)). It was confirmed that the robust disruption of EGFP was not a result of cellular toxicity (FIGS. 36(C)-(D)). It was also observed that treatment of cells with (+36)dGFP-NLS-Cas9 and sgRNA in the presence of 10% FBS serum did not lead to efficient gene disruption (FIG. 30(A)), suggesting that cationic-peptide based methods of delivery for Cas9 and sgRNA are not effective perhaps due to interference of gRNA:Cas9 complex formation or nuclease function by superpositively charged proteins.[41] Together, these results establish that cationic lipid-mediated delivery of (−30) dGFP-NLS-Cas9:sgRNA complexes can result in efficient sgRNA-dependent target gene disruption in human cells.

Polyanionic sgRNA is Necessary and Sufficient for Efficient Lipid-Mediated Cas9 Delivery Since the complex of native Cas9 protein (+22 net theoretical charge) and an sgRNA (−103 anionic phosphate groups) should be overall highly anionic, next it was tested if native Cas9:sgRNA complexes without fusion to polyanionic proteins can be delivered into human cells using cationic lipids. Treatment of U2OS EGFP reporter cells with 100 nM Cas9, 100 nM EGFP sgRNA, and 0.8 μL RNAiMAX resulted in 65% disruption of the EGFP reporter gene (FIG. 30(A)). Treatment of cells with Cas9 protein and sgRNA, but without RNAiMAX, resulted in no loss of GFP fluorescence (FIG. 30(A)). These observations suggest that sgRNA alone, even in the absence of a supernegatively charged fusion protein, can provide the highly anionic character needed to mediate cationic lipid-based delivery of Cas9.

Figure 37:
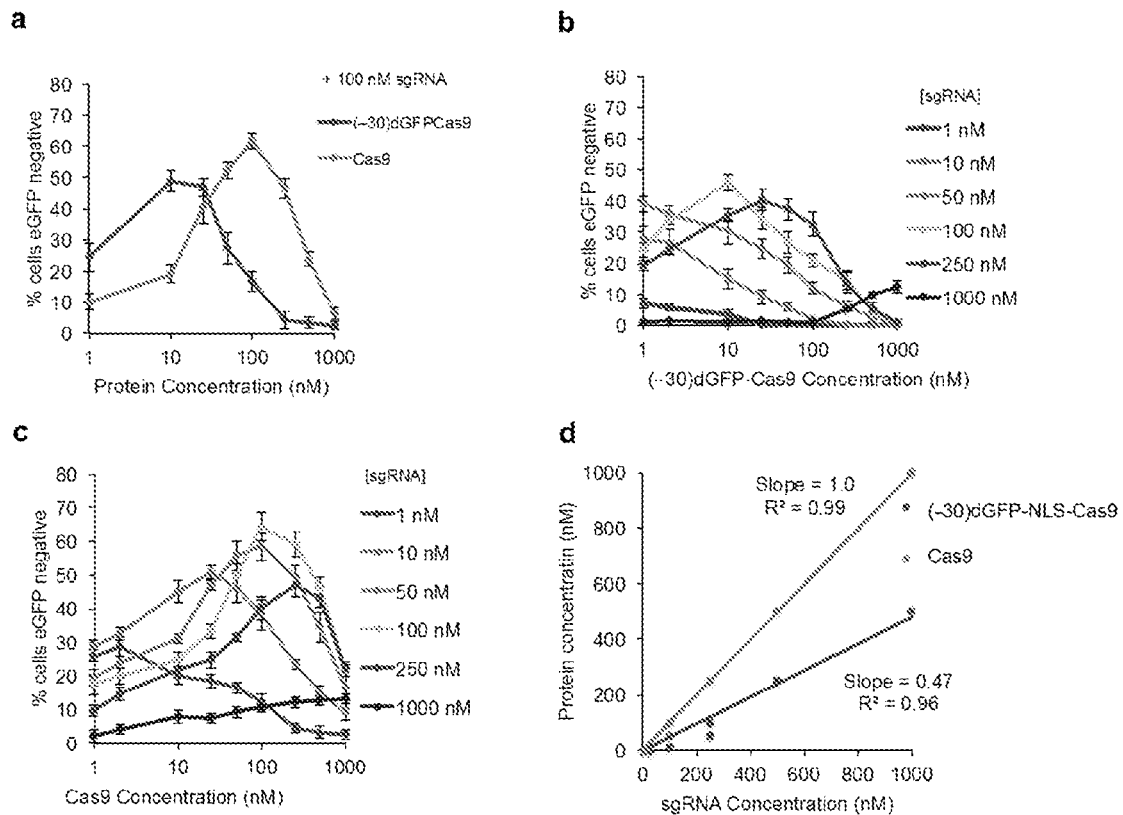
FIGS. 37A-D. Optimization of Cas9:sgRNA functional delivery.

Comparison of gene disruption efficiency arising from the cationic lipid-mediated delivery of (−30)dGFP-NLS-Cas9: sgRNA versus Cas9:sgRNA revealed that at low doses (−30)dGFP-NLS-Cas9 results in more efficient gene disruption than native Cas9 (FIG. 37(A)), it is outperformed by native Cas9 at higher concentrations, as well as at the respective optimal protein:sgRNA dose of either protein (FIGS. 37(B)-37(C)). These results further establish that sgRNA can supply sufficient negative charge to support cationic lipid-based delivery of complexed Cas9 protein.

Figure 38:
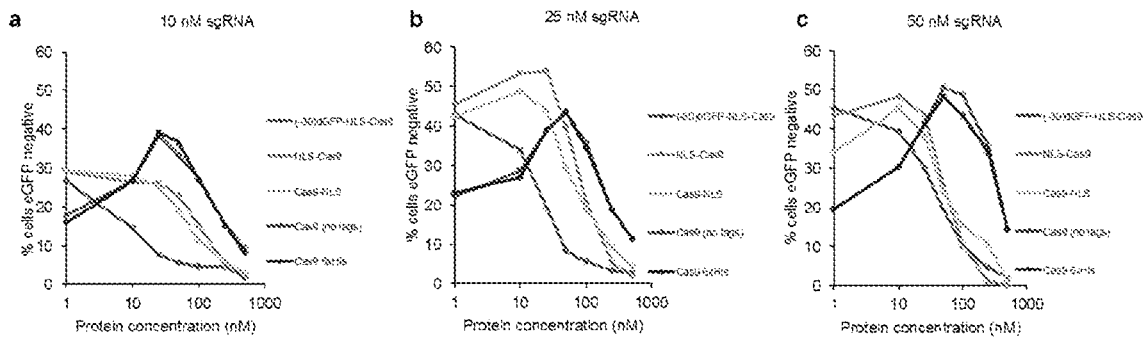
FIGS. 38A-C. The effect of the NLS and/or (−30)dGFP on functional Cas9 delivery as a function of both sgRNA and Cas9 concentration. EGFP gene disruption was measured at three fixed sgRNA concentrations: 10 nM (FIG. 38(A)), 25 nM (FIG. 38(B)), and 50 nM (FIG. 38(C)), along with varying protein concentrations show in the graphs. Delivery was performed using 0.8 µL RNAiMAX and assayed by FACS 48 hours later for loss of EGFP fluorescence signal.

It was also observed that while overall less protein was required for optimal delivery of (−30)dGFP-NLS-Cas9 than Cas9, a higher sgRNA:protein ratio was required for maximal (−30)dGFP-NLS-Cas9-mediated EGFP gene disruption than for native Cas9-mediated gene disruption (FIG. 37(D)). It was speculated that more equivalents of sgRNA are needed to complex with (−30)dGFP-NLS-Cas9 since fused (−30)dGFP may electrostatically interfere with Cas9:sgRNA complexation. As the ideal protein dose for (−30)dGFP-NLS-Cas9 mediated EGFP gene disruption is 10-fold lower than that of wild-type Cas9, the results also suggest that (−30)dGFP-Cas9 is better encapsulated by cationic liposomes than Cas9:sgRNA due to its higher overall negative charge, but this charge magnitude may interfere with Cas9: sgRNA interactions, necessitating more sgRNA per protein and potentially reducing total delivered Cas9 activity. In addition, NLS-Cas9 and Cas9-NLS proteins were generated and tested, and it was observed that while the presence of an NLS in (−30)dGFP-NLS-Cas9 could at least partially explain differences in delivery efficacy at very low concentrations, Cas9, NLS-Cas9, and Cas9-NLS all result in higher efficiency of EGFP disruption than (−30)dGFP-NLS-Cas9 at 25 nM or higher concentrations (FIGS. 38(A)-(C)).

Figure 39:
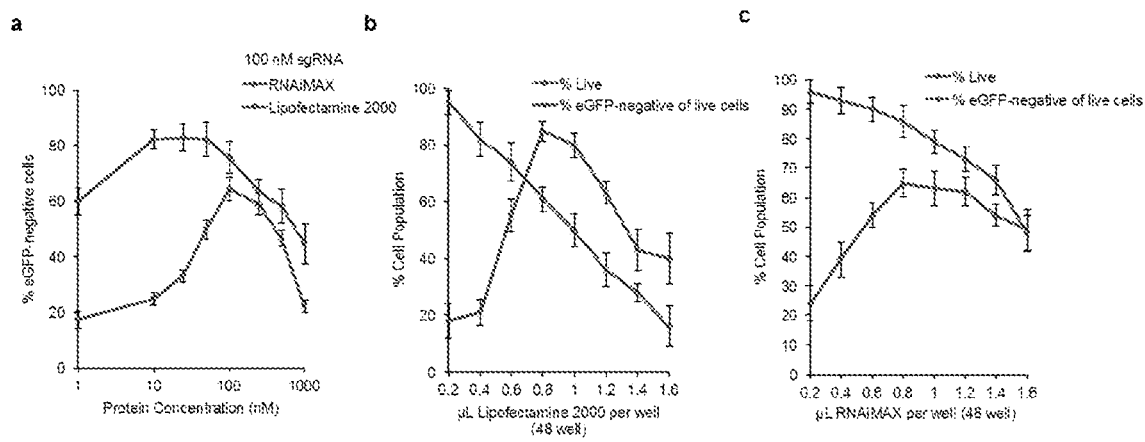
FIGS. 39A-C. Effects of RNAiMAX and Lipofectamine 2000 on Cas9:sgRNA delivery efficiency and cellular toxicity.

Cas9:sgRNA delivery with cationic lipid formulations other than RNAiMAX was also tested. Delivery with Lipofectamine 2000 was notably more efficient than with RNAiMAX, resulting in up to 80% Cas9-mediated gene disruption (FIG. 39(A)), and maintaining high efficiency (60% gene disruption) even at 1 nM protein (FIG. 39(A)). However, due to the somewhat higher toxicity of Lipofectamine 2000 compared to RNAiMAX under cell culture conditions (FIGS. 33(B)-C)), RNAiMAX was used for all subsequent cell culture studies.

To verify that EGFP disruption arose from genome modification and not only from Cas9 binding,[42] the T7 endonuclease I (T7EI) assay[43] was used to detect and quantify the frequency of Cas9-mediated genomic insertion/deletion mutations (indels) at the target EGFP locus (FIG. 30(B)). The T7EI assay results showed that only those cells treated with both Cas9 and EGFP sgRNA plasmids, or Cas9 protein and purified EGFP sgRNA, contained indels at the target site. Taken together, these findings establish that active Cas9:sgRNA complexes can be potently delivered into human cells with cationic lipids in a manner dependent on the negative charge provided by the sgRNA.

U2OS EGFP reporter cells were also treated with a single lipid-mediated delivery treatment of Cas9 complexed with a mixture of four gRNAs targeting EGFP, CLTA, EMX, and VEGF. This treatment resulted in efficient disruption of all four targets, with cleavage efficiencies of 58%, 28%, 16%, and 40%, respectively, as measured by T7E1 cleavage assay. These high gene disruption efficiencies from a single delivery of 50 nM Cas9 and 25 nM of each sgRNA (100 nM total sgRNA) demonstrate that lipid-mediated Cas9: sgRNA delivery can support efficient multiplexed genome editing (FIG. 30(C)).

Functional Delivery of Cas9 Nickases and dCas9 Activators

Next, whether cationic lipid-based protein delivery could be extended to deliver other Cas9-derived genome engineering tools such as Cas9 nickases[44] and Cas9-based transcriptional activators was tested.[45] Gene disruption efficiency in U2OS EGFP reporter cells resulting from delivery of Cas9 D10A nickase was measured, either by cotransfection of nickase and appropriate paired EGFP-targeting sgRNA plasmids, or as purified protein complexed with pairs of EGFP sgRNAs using RNAiMAX (FIG. 30(D)). Both plasmid and cationic lipid-mediated protein:RNA delivery of dual Cas9 nickases resulted in EGFP disruption with similar efficiencies (FIG. 30(D)) only in the presence of sgRNA pairs targeting opposite strands, (sgRNA pairs g1+g5, and g3+g7), but not with sgRNA pairs targeting the same strand (sgRNA pair g5+g7) (FIG. 30(D)), consistent with previous reports of Cas9 nickase cleavage requirements.[46]

Figure 40:
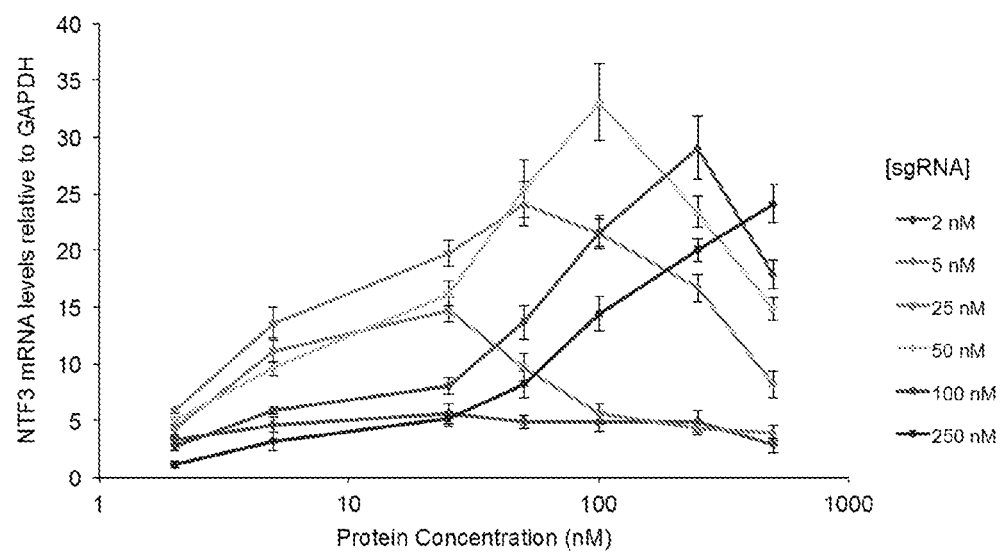
FIG. 40. Optimization of dCas9-VP64 delivery targeting the NTF3 gene at varying concentrations of protein and sgRNA. HEK293T cells were treated with dCas9-VP64 activator and either NTF3-targeting gRNA g2 or a mixture of all six NTF3-targeting sgRNAs for 16 hours and 0.8 µL RNAiMAX in 48-well plate format (275 µL final volume). NTF3 mRNA levels were determined by qRT-PCR and normalized to those of GAPDH. Error bars reflect standard deviation from six biological replicates performed on different days.

The NTF3 transcriptional activation efficiencies in HEK293T cells resulting from either plasmid transfection or direct protein: sgRNA complex delivery of dCas9 fused to a VP64 activation domain were also compared.[45] Delivery of dCas9-VP64 activators either by plasmid transfection or RNAiMAX-mediated protein delivery resulted in strong (≥~10-fold) activation of NTF3 transcription (FIG. 30(E) and FIG. 40). Transcriptional activation levels resulting from plasmid transfection were more potent than activation resulting from protein delivery at optimal assay times for each delivery method (FIG. 30(E)), potentially due to the sustained expression both Cas9 activator protein and sgRNA from the plasmids compared to the transient, single dose of purified protein and RNA. While the above results indicate that such factors do not limit the potency of irreversible genome modification by delivered Cas9 nuclease and nickase proteins (FIGS. 40(A) and 40(D)), the low dose and transient nature of the delivered protein may more strongly limit potency of dynamic processes such as transcriptional activation. Nevertheless, these results collectively indicate that both Cas9 nickases and Cas9 transcriptional activators can also be delivered effectively by cationic lipid-mediated protein:RNA complex delivery.

Figure 31:
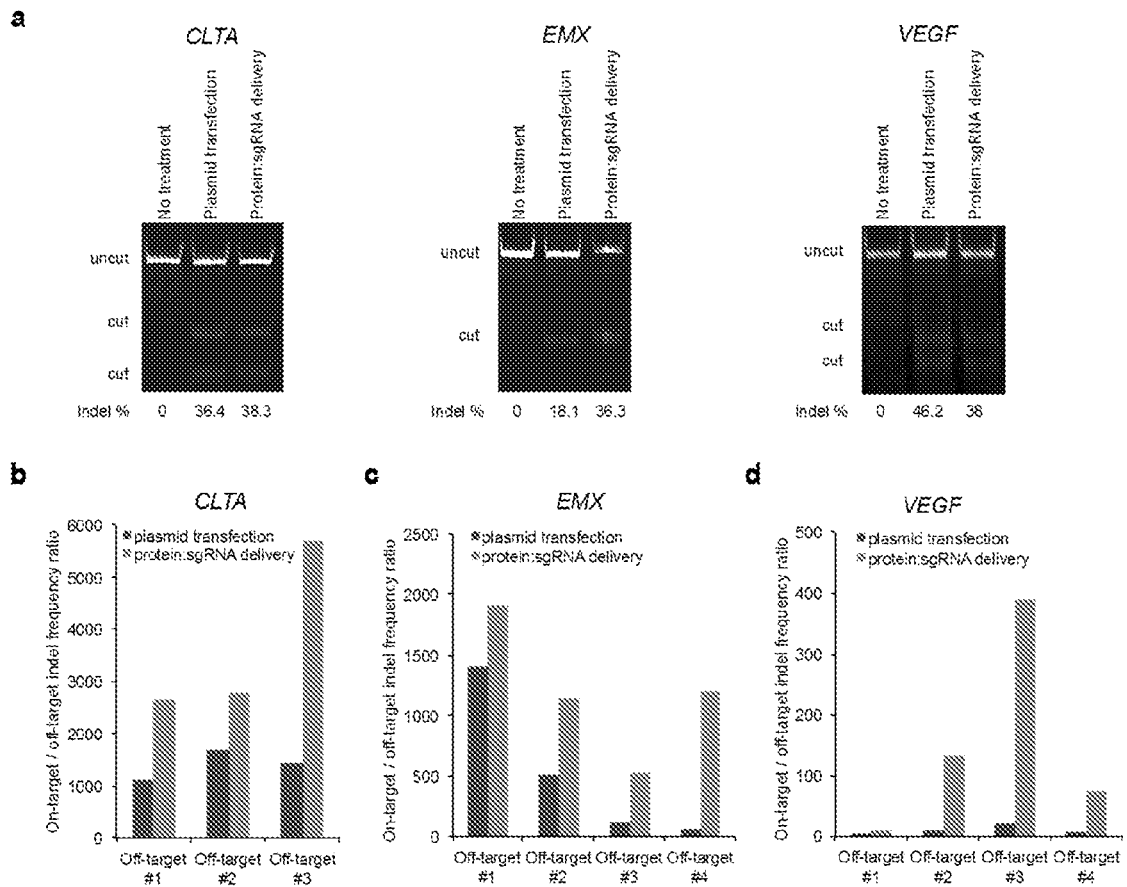
In FIG. 31(B-D) the on-target:off-target DNA modification ratio resulting from Cas9:sgRNA for plasmid transfection or cationic lipid-mediated protein:sgRNA delivery is shown. The conditions for each treatment were adjusted to result in ~10% on-target cleavage, enabling a comparison of DNA cleavage specificity between the two delivery methods under conditions in which on-target gene modification efficiencies are comparable. P values are listed in Table 2. Each on- and off-target sample was sequenced once with >10,000 sequences analyzed per on-target sample and an average of >111,000 sequences analyzed per off-target sample (Table 2).

Cas9:sgRNA Delivery Modifies Genomes with Greater Specificity than DNA Transfection DNA-free delivery of functional Cas9:sgRNA complexes circumvents risks associated with viral or other gene delivery methods and has the potential to improve the specificity of genome modification by avoiding the unnecessary expression of genome-editing agent after the target locus is modified. To test if the described approach can disrupt endogenous genes in human cells, genomic loci in the EMX1, CLTA2, and VEGF genes were targeted due to their potential biomedical relevance and their use in previous studies[40,46,47] of Cas9 off-target cleavage activity. Cationic lipid-mediated delivery of Cas9:sgRNA complexes into HEK293T cells resulted in robust cleavage of all three human genes with efficiencies comparable to or greater than those of plasmid transfection methods as revealed by the T7EI assay using the same Cas9:sgRNA delivery conditions previously optimized for U2OS cells (FIG. 31(A)).

Figure 41:
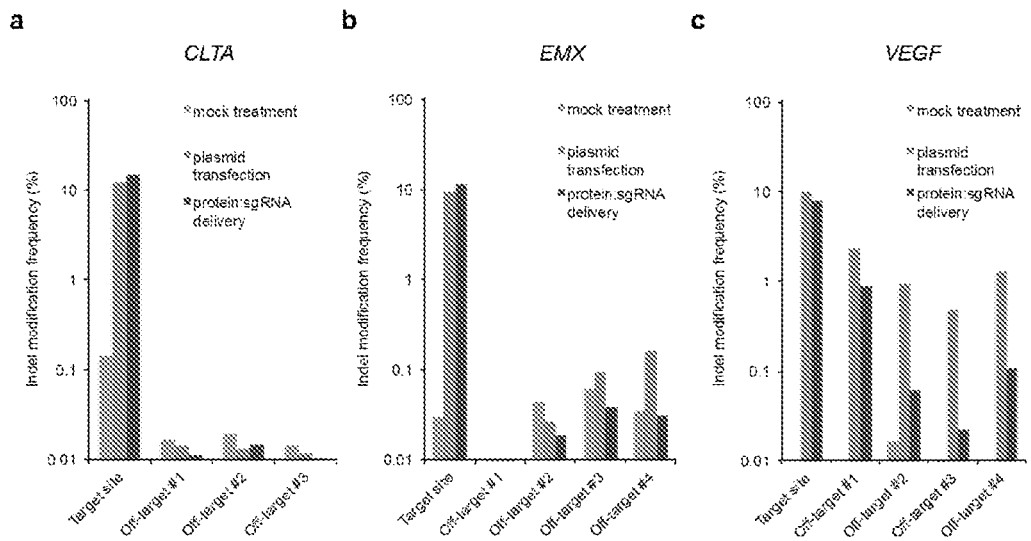
FIGS. 41A-C. Indel frequencies, measured by high-throughput sequencing, of several human genes treated either by a mock treatment, by transfection of Cas9 plasmid and sgRNA linear DNA PCR product, or by cationic lipid-mediated protein:sgRNA delivery are depicted. Mock treatment involved cationic lipid-mediated protein: sgRNA delivery of EGFP-targeting sgRNA instead of one of the three human gene-targeting sgRNAs.

To compare the endogenous gene modification specificity of plasmid versus protein:RNA delivery methods for Cas9, the on-target locus was amplified as well as several known off-target sites (FIG. 44) from genomic DNA isolated from HEK293 cells treated either by transfection of Cas9 and sgRNA expression plasmids, or by RNAiMAX-mediated Cas9:sgRNA complex delivery under conditions that resulted in comparable on-target modification efficiencies. The indel frequencies at the three on-target and 11 off-target sites were assayed by high-throughput DNA sequencing (FIG. 45). For all three target genes, the frequency of on-target DNA modification resulting from either plasmid or protein:sgRNA delivery was approximately 10% (FIGS. 41(A)-(C)), enabling a comparison of off-target modification between the two techniques under treatment conditions that result in very similar on-target genome modification efficiencies. Importantly, the frequency of off-target genome modification for all 11 off-target sites was lower from protein:sgRNA delivery compared with plasmid delivery, and as a result the ratio of on-target to off-target modification for all sites tested was up to 19-fold higher for protein: sgRNA delivery than for plasmid delivery (FIGS. 31(B)-(D)).

DNA modification specificity was higher for protein: sgRNA delivery than for plasmid delivery at loci with high levels of off-target modification (such as the four VEGF off-target sites, for which plasmid delivery yielded average on-target:off-target modification ratios between 4- and 20-fold but protein:RNA delivery yielded average on-target: off-target modification ratios between 9- and 400-fold) as well as for loci with lower levels of off-target modification (such as the three EMX off-target loci, for which plasmid delivery yielded average on-target:off-target modification ratios as low as 64-fold but protein:RNA delivery yielded average on-target:off-target modification ratios of 500- to 2,000-fold). Taken together, these results indicate that the delivery of Cas9:sgRNA complexes using cationic lipids can effect target gene modification at high efficiency and with substantially greater specificity than the delivery of DNA expressing Cas9 and sgRNA.

Delivery of Cas9:sgRNA into Mouse Embryonic Stem Cells

Figure 42:
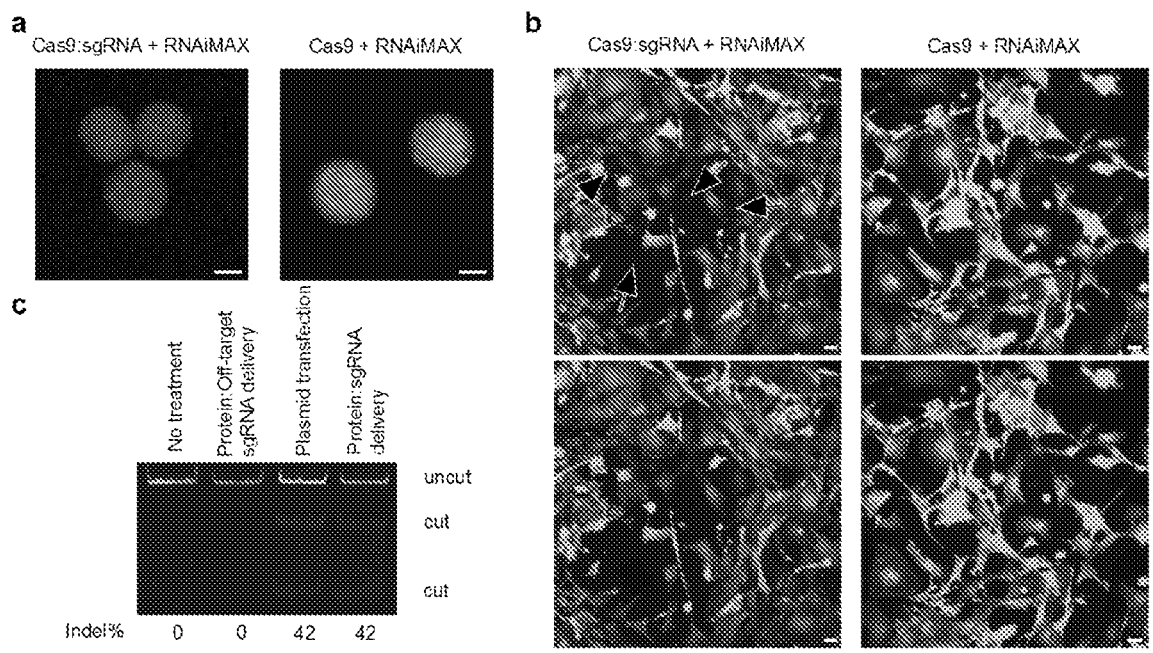
FIGS. 42A-C. Delivery of Cas9 endonuclease to mouse embryonic stem cells.

The potent and transient cationic lipid-mediated delivery of Cas9:sgRNA to effect efficient, permanent, and highly specific gene editing could be especially useful in stem cells. To test this possibility, mouse embryonic stem cells expressing Tau-EGFP[48] were treated with Cas9 and an EGFP-targeting sgRNA. Under standard stem-cell culture conditions, EGFP-positive floating spheres were formed. The floating spheres were treated with Cas9:sgRNA complexed with RNAiMAX, or with Cas9 and RNAiMAX without sgRNA as a control. Three days post-treatment, a reduction in GFP fluorescence in the Cas9:sgRNA-treated spheres compared to the control samples was observed (FIG. 42(A)). The treated spheres were dissociated, and the cells were allowed to attach to a gelatin-coated dish and differentiate into progenitor cells. Immunohistochemistry using an anti-GFP antibody confirmed knockdown of EGFP expression in the cells of Cas9:sgRNA treated samples, with many nuclei lacking any apparent EGFP. In contrast, all cells derived from control spheres were EGFP positive (FIG. 42(B)). Genomic DNA harvested from Cas9:sgRNA-treated cells was subjected to T7EI assay, resulting in clear evidence of indels at the Tau-EGFP locus (FIG. 42(C)). From this assay, an indel frequency of 42% was calculated from both cationic lipid-mediated Cas9:sgRNA delivery and transfection of Cas9 and sgRNA DNA. No target modification was detected in control samples lacking Cas9:sgRNA or containing Cas9 and an unrelated gRNA. These findings demonstrate that cationic lipid-mediated Cas9: sgRNA delivery can effect highly efficient gene disruption in mouse embryonic stem cells.

In Vivo Cationic Lipid-Mediated Delivery of Cre Recombinase and Cas9:sgRNA

The high-efficiency delivery of functional genome-editing proteins in vivo enables a wide range of applications including non-viral therapeutic genome editing to correct genetic diseases. To evaluate the protein delivery method described above in a living mammal, delivery to the mouse inner ear was chosen, due to its confined space, well-characterized inner ear cell types, and the existence of genetic deafness mouse models that may enable future hearing recovery studies. The in vivo deliveries of two types of proteins into the mouse inner year were attempted. First, the delivery of (−30)GFP-Cre protein was tested to assess the targeting of inner ear cell types and the efficiency of functional protein delivery. Second, the delivery of Cas9:sgRNA complexes to the inner ear were evaluated to determine if cationic lipid-mediated protein:gRNA complex delivery can support CRISPR-based gene editing in vivo.

It has been previously shown that (+36)GFP-Cre can be delivered to mouse retina,[16] although the protein resulted in only modest levels of recombinant conversion suggestive of inefficient in vivo delivery. For our initial inner ear delivery trials, (−30)GFP-Cre was complexed with RNAiMAX and the complex was injected into the cochlea of postnatal day 0 (P0) reporter mice with a genomically integrated floxed-STOP tdTomato reporter. As with the previously described in vitro Cre reporter cell line, functional delivery of Cre to the inner ear cells, followed by endosomal escape, nuclear localization, and Cre-mediated recombination results in expression of tdTomato. After injection, the cochleas were harvested for immunolabeling with inner ear cell markers for co-localization with tdTomato. RNAiMAX injection alone was used as control. Five days following injection of (−30)GFP-Cre and RNAiMAX, cochlear outer hair cells, the auditory sensory cells that detect sound, showed strong tdTomato signal that co-localized with the hair cell marker myosin VIIa (Myo7a), demonstrating functional Cre delivery to hair cells (FIGS. 32(A)-(B)). No tdTomato expression was detected in control cochleas (FIG. 32(A)). The tdTomato signal was concentrated in the region of the injection site at the basal turn of the cochlea. On average 33±3% of outer hair cells were tdTomato positive at the base of the cochlea ($P<0.001$; mean±SEM, n=4).

To further determine the effect of cationic lipid-mediated (−30)GFP-Cre protein delivery on targeted cells, hair cell stereocilia, a delicate structure that is essential for hearing, were examined 10 days post-injection. TdTomato positive outer hair cells had typical stereocilia structure as imaged by espin expression, similar to control stereocilia (FIG. 32(B)). No tdTomato expression was detected in control cochleas. These observations indicate that cationic lipid-mediated delivery of (−30)GFP-Cre protein effects recombination in cochlear outer hair cells without apparently affecting hair cell architecture.

Because target volume, protein dose, and sgRNA dose in vivo are different than in cell culture experiments, the above experiments were repeated under different delivery conditions. Delivery using Lipofectamine 2000 was tested due to its higher potency in vitro (FIG. 39(A)) and dramatically higher recombination efficiency was observed: over 90% outer hair cells in cochleas treated with (−30)GFP-Cre+Lipofectamine 2000 were tdTomato positive (FIG. 32(C)). In comparison to control samples, some outer hair cell loss was observed (FIG. 32(C)), consistent with the previous observation of the higher cell toxicity of Lipofectamine 2000, although the overall cochlear architecture was preserved.

Figure 43:
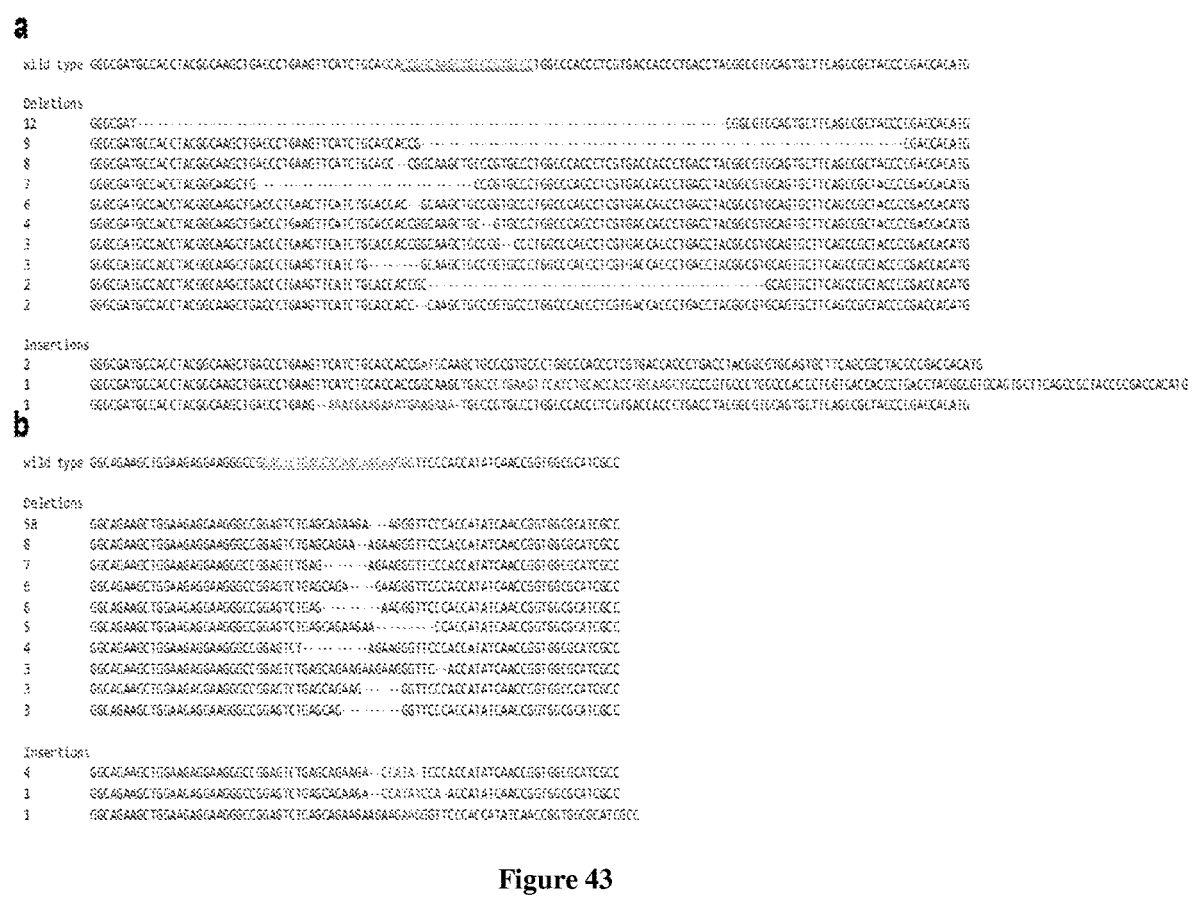

To test the effectiveness of Cas9:sgRNA delivery in vivo, Cas9 and sgRNA targeting EGFP were combined with RNAiMAX and the resulting complexes were injected into postnatal day 2 (P2) transgenic Atoh1-GFP mouse cochlea in which all hair cells express GFP under the control of a hair cell-specific enhancer for transcription factor Atoh1.[49] Using this model, Cas9:sgRNA-mediated disruption of EGFP results in loss of EGFP fluorescence in outer hair cells. Ten days after injection of Cas9:sgRNA with cationic lipid, the absence of GFP was observed in 13% of outer hair cells near the injection site. In contrast, control cochlea injected with Cas9 protein and RNAiMAX without any sgRNA showed no loss of EGFP signal (FIG. 32(D)). The outer hair cells of cochlea injected with Cas9:sgRNA RNAiMAX complexes appeared to be otherwise unaffected, with stereotypical expression of Myo7a and healthy nuclei, consistent with minimal hair cell toxicity (FIG. 32(D)). High-throughput DNA sequencing of genomic DNA isolated from cochlea tissue samples revealed indels consistent with GFP target gene disruption in the treated samples, but not in the control samples that lacked sgRNA (FIG. 43(A)). In addition, the inner ear in vivo delivery of Cas9:sgRNA using an sgRNA that targets the EMX gene was repeated and indels in the EMX gene in treated animals, but not control animals were similarly observed (FIG. 43(B))

Figure 32:
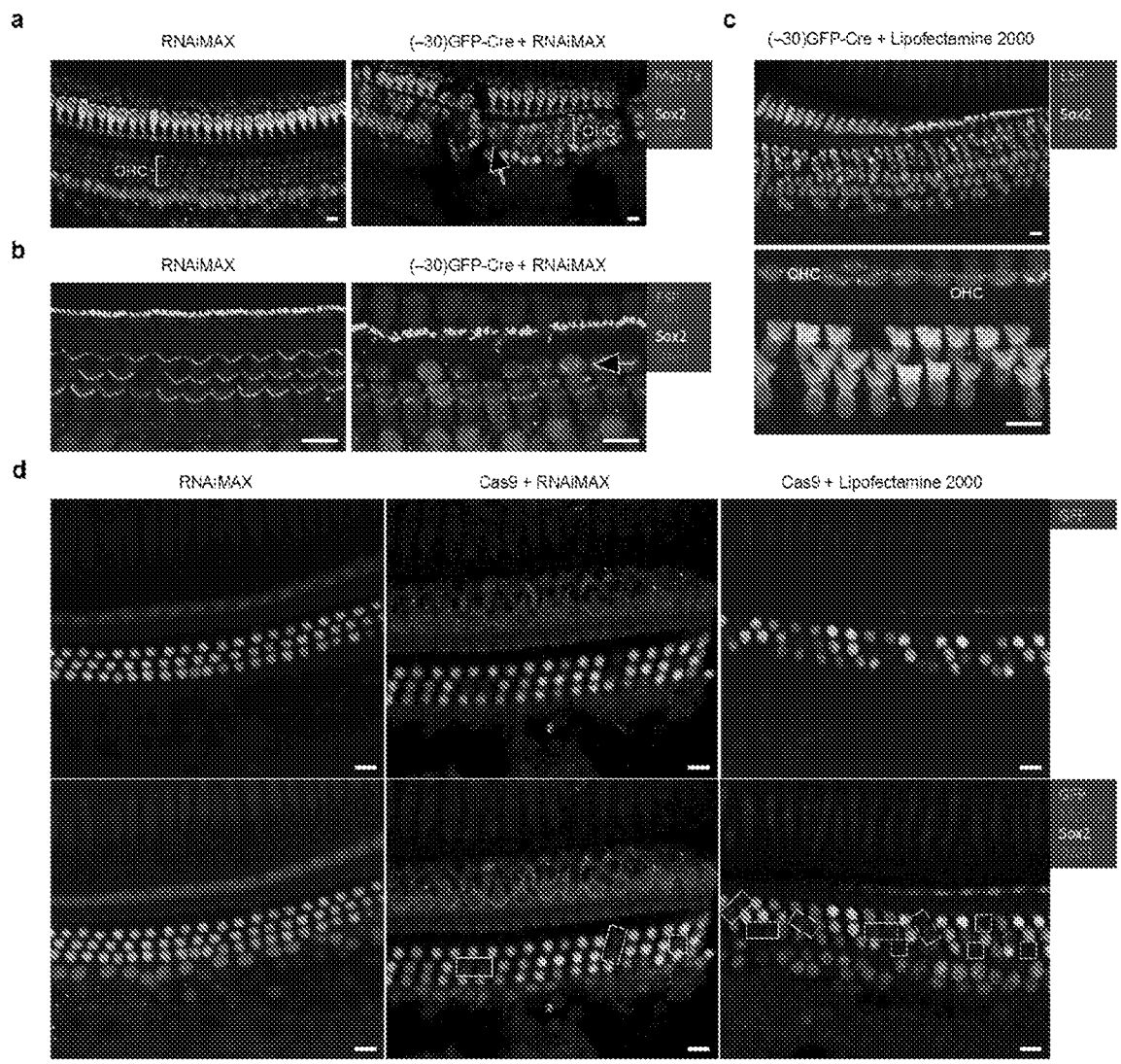
FIGS. 32A-D. The in vivo delivery of Cre recombinase and Cas9:sgRNA complexes to hair cells in the mouse inner ear is shown.

As (−30)GFP-Cre complexed with Lipofectamine 2000 resulted in more efficient modification of the target hair cell population than (−30)GFP-Cre complexed with RNAiMAX (FIGS. 32(A) and 32(C)), its use on Cas9:sgRNA delivery to Atoh1-GFP cochlea was tested as above. Loss of GFP expression was observed in 20% of outer hair cells near the injection site after 10 days, whereas all outer hair cells maintained strong GFP expression in control cochlea injected with Cas9 and Lipofectamine 2000 but no sgRNA (FIG. 32(D)). In contrast to modest hair cell loss observed following Lipofectamine 2000 delivery of (−30)GFP-Cre (FIG. 32(C)), outer hair cells targeted by Cas9:sgRNA exhibited no obvious toxicity or structural alteration (FIG. 32(D)).

As with (−30)GFP-Cre, virus-free, cationic lipid-mediated delivery of Cas9:sgRNA into the mouse inner ear successfully modified a specific genomic locus in the outer hair cell population, leading to loss of target gene expression. Nearly half of all types of genetic deafness arise from hair cell loss or dysfunction,[50] the results presented herein suggest a potential strategy based on the delivery of Cas9: sgRNA complexes to genetically modify these cells to effect hearing recovery.

Determination of Protein Delivery Efficacy for (−30)GFP-Cre

To determine if the higher potency of liposome-mediated (−30)GFP-Cre delivery compared with that of cationic protein delivery arises from more total protein uptake by cells or from a higher fraction of functional, non-endosomal protein molecules taken up by the cells, flow cytometry was used to measure GFP fluorescence of cells treated with either (+36)GFP-Cre or liposomal (−30)GFP-Cre under their respective optimal Cre delivery conditions. Cell fluorescence reports total endocytosed (−30)GFP-Cre or (+36) GFP-Cre regardless of endosomal or non-endosomal localization.[1] Lipid-mediated protein delivery resulted in surprisingly small increases in total protein uptake (FIG. 34(A)), despite the high efficiency of lipid-mediated functional Cre delivery. While (+36)GFP-Cre treatment increased cellular GFP fluorescence by up to three orders of magnitude in a dose-dependent manner (FIG. 34(A)), consistent with previous reports,[1,2] liposomal (−30)GFP-Cre treatment induced at most 5-fold increases in cellular GFP fluorescence (FIG. 34(A)). Comparison of cellular fluorescence and recombination efficiency reveals that lipid-mediated functional delivery of (−30)GFP-Cre is 9,800-fold more potent per amount of endocytosed protein than delivery of (+36)GFP-Cre (FIG. 34(B)).

To test if complexation of anionic (−30)GFP with cationic lipids interferes with GFP fluorescence and thus masks the true amount of cargo that enters the cell mCherry, which is fluorescent but not highly anionic, was fused to either (−30)GFP or (+36)GFP and delivered both protein fusions to HeLa cells. After washing away protein that may have adhered to cell surface but did not enter the cell with PBS+heparin (20 U/mL), the cells were analyzed by FACS for mCherry fluorescence 4 hours and 24 hours after treatment. It was observed that lipid-mediated delivery of (−30) GFP-fused mCherry results in only slight increases in cellular mCherry fluorescence, whereas mCherry fluorescence upon delivery of (+36)GFP-mCherry was generally ≥100-fold higher (FIG. 34(C)) suggesting that fusion to (−30)GFP does not cause substantial amounts of protein cargo to enter the cell. Moreover, addition of lipids to (−30)GFP-Cre did not measurably alter the GFP fluorescence signal (FIG. 34(D)), despite the fact that cationic lipids and anionic (−30)GFP clearly interact. Taken together, these results suggest that the unusually high potency of lipid-mediated delivery of anionic proteins does not arise from unusually high protein uptake in each cell, but rather from post-endocytosis processes that likely include avoidance of protein degradation and endosomal escape into the cytoplasm.

Sensitivity Limit of Off-Target Cleavage Assays

The sensitivity of the high-throughput sequencing method for detecting genomic off-target cleavage is limited by the amount genomic DNA (gDNA) input into the PCR amplification of each genomic target site. A 1 ng sample of human gDNA represents only approximately 330 unique genomes, and thus only approximately 330 unique copies of each genomic site are present. PCR amplification for each genomic target was performed on a total of 150 ng of input gDNA, which provides amplicons derived from at most 50,000, unique gDNA copies, respectively. Therefore, the high-throughput sequencing assay cannot detect rare genome modification events that occur at a frequency of less than 1 in 50,000 (0.002%). This limit is noted in Table 2.

Taken together, these findings suggest that cationic lipid-mediated delivery of genome-editing proteins can serve as a powerful tool and an in vivo strategy for the treatment of genetic disease.

CONCLUSIONS

Efficient intracellular protein delivery in vitro and especially in vivo has been a persistent challenge in biomedical research and protein therapeutics. While delivery using cationic peptides and proteins has been widely studied for over two decades, sensitivity to serum proteins, neutralization by antibodies, degradation by extracellular and intracellular proteases, and poor endosomal escape post-internalization have limited the scope of protein delivery applications using that approach.

In the current Example, a general strategy for protein delivery that makes use of anionic protein complexation with cationic liposomes is demonstrated. This method was used to deliver diverse protein classes, including the Cre tyrosine recombinase, TALE transcriptional activators, and Cas9 nucleases, nickases, and transcriptional activators (FIG. 27(A)) to cultured cell lines, stem cell colonies, and therapeutically relevant in vivo sites within the mouse inner ear. The described approach is highly efficient, producing modification rates on par with established nucleic acid transfection methods in cell culture, and enabling Cre recombinase and Cas9-mediated genome modification rates of up to 90% and 20%, respectively, within the inner ear hair cell population of live mice (FIGS. 32(C)-(D)). These results also suggest that it may be possible to use cationic lipids to efficiently deliver other nucleic acid-binding proteins, including transcription factors that induce therapeutically relevant changes in cell fate, by complexing them with nucleic acids.

Cationic lipid-based anionic protein delivery outperforms a potent cationic protein delivery fusion partner, (+36)GFP, by up to 9,800-fold per amount of endocytosed protein, inducing more efficient modification of treated cells with orders of magnitude lower doses of protein (FIGS. 28(C) 34). For Cas9 nuclease delivery, this approach also results in >10-fold more specific genome modification than traditional plasmid transfection (FIGS. 31(B)-(D)), likely due to the transient window of Cas9 activity to which each genome is exposed compared to DNA delivery methods, consistent with previous reports.[51]

The described approach is simple to implement, requiring only the purified deliverable protein and the use of popular commercial nucleic acid transfection reagents (FIG. 27(B)). Rendering a given protein amenable to this approach requires simple translational fusion to a highly anionic partner, such as (−30)GFP (FIG. 27(A)), and is even effective with common translational fusion tags including the VP64 activation domain, and the 3×FLAG affinity tag (FIG. 28(F) and FIG. 33(C)). In certain cases, as with the Cas9 protein, pre-complexation with a cognate nucleic acid (sgRNA in this case) is sufficient (FIG. 30(A)), as the partially exposed bound nucleic acid likely provides sufficient anionic charge to mediate complexation with cationic lipids.

Others groups have reported the in vivo delivery of Cas9 expression constructs in DNA or mRNA form.[52,53] The present Example demonstrates that protein delivery is a viable approach to in vivo genome editing.

TABLE 1

| | |
|---|---|
| EMX_On | GAGTCCGAGCAGAAGAAGAAGGG (SEQ ID NO: 209) |
| EMX_Off1 | GAGgCCGAGCAGAAGAAagACGG (SEQ ID NO: 210) |
| EMX_Off2 | GAGTCCtAGCAGgAGAAGAAGaG (SEQ ID NO: 211) |
| EMX_Off3 | GAGTCtaAGCAGAAGAAGAAGaG (SEQ ID NO: 212) |
| EMX_Off4 | GAGTtaGAGCAGAAGAAGAAAGG (SEQ ID NO: 213) |
| VEGF_On | GGGTGGGGGGAGTTTGCTCCTGG (SEQ ID NO: 214) |
| VEGF_Off1 | GGaTGGaGGGAGTTTGCTCCTGG (SEQ ID NO: 215) |
| VEGF_Off2 | GGGaGGGtGGAGTTTGCTCCTGG (SEQ ID NO: 216) |
| VEGF_Off3 | cGGgGGaGGGAGTTTGCTCCTGG (SEQ ID NO: 217) |
| VEGF_Off4 | GGGgaGGGGaAGTTTGCTCCTGG (SEQ ID NO: 218) |
| CLTA_On | GCAGATGTAGTGTTTCCACAGGG (SEQ ID NO: 219) |
| CLTA_Off1 | aCAaATGTAGTaTTTCCACAGGG (SEQ ID NO: 220) |
| CLTA_Off2 | cCAGATGTAGTaTTcCCACAGGG (SEQ ID NO: 221) |
| CLTA_Off3 | ctAGATGaAGTGcTTCCACATGG (SEQ ID NO: 222) |

Table 1. On-target and known off-target substrates of Cas9: sgRNAs that target sites in EMX, VEGF, and CLTA. A list of genomic on-target and off-targets sites of the EMX, VEGF, and CLTA are shown with mutations from the on-target sequence shown in lower case and bold. PAMs are shown in underline.

TABLE 2

| CLTA Sites delivery | Mock treatment | Plasmid transfection | Protein: sgRNA |
|---|---|---|---|
| CLTA_On | | | |
| Indels | 14 | 1228 | 1498 |
| Total | 10000 | 10000 | 10000 |
| Modified (%) | 0.140 | 12.280 | 14.980 |
| P-value | | <1.0E−300 | <1.0E−300 |
| On: off specificity | 1 | 1 | 1 |
| CLTA_Off1 | | | |
| Indels | 7 | 29 | 14 |
| Total | 41518 | 205204 | 125370 |
| Modified (%) | 0.017 | 0.014 | 0.011 |
| P-value | | 6.6E−01 | 4.5E−01 |
| On: off specificity | | 869 | 1341 |
| CLTA_Off2 | | | |
| Indels | 5 | 11 | 8 |
| Total | 25338 | 83944 | 54409 |
| Modified (%) | 0.020 | 0.013 | 0.015 |
| P-value | | 5.5E−01 | 5.7E−01 |
| On: off specificity | | 937 | 1019 |
| CLTA_Off3 | | | |
| Indels | 6 | 22 | 8 |
| Total | 41643 | 189886 | 76863 |
| Modified (%) | 0.014 | 0.012 | 0.010 |
| P-value | | 6.2E−01 | 5.8E−01 |
| On: off specificity | | 1060 | 1439 |
| EMX Sites delivery | Mock treatment | Plasmid transfection | Protein: sgRNA |
| EMX_On | | | |
| Indels | 3 | 930 | 1140 |
| Total | 10000 | 10000 | 10000 |
| Modified (%) | | 0.030 | 9.300 |
| P-value | | 1.6E−264 | <1.0E−300 |
| On: off specificity | 1 | 1 | 1 |
| EMX_Off1 | | | |
| Indels | 0 | 6 | 6 |
| Total | 24623 | 90935 | 100778 |
| Modified (%) | | <0.002 | 0.007 |
| P-value | | 3.5E−01 | 6.1E−01 |
| On: off specificity | | 1409 | 1915 |
| EMX_Off2 | | | |
| Indels | 16 | 53 | 38 |
| Total | 36061 | 204068 | 130084 |
| Modified (%) | | 0.044 | 0.026 |
| P-value | | 6.4E−02 | 1.8E−01 |
| On: off specificity | | 358 | 390 |
| EMX_Off3 | | | |
| Indels | 20 | 147 | 44 |
| Total | 32575 | 157848 | 110878 |
| Modified (%) | | 0.061 | 0.093 |
| P-value | | 8.1E−02 | 1.3E−01 |
| On: off specificity | | 100 | 287 |
| EMX_Off4 | | | |
| Indels | 16 | 141 | 23 |
| Total | 45548 | 86586 | 73451 |
| Modified (%) | | 0.035 | 0.163 |
| P-value | | 2.8E−12 | 7.4E−01 |
| On: off specificity | | 57 | 364 |
| VEGF Sites delivery | Mock treatment | Plasmid transfection | Protein: sgRNA |
| VEGF_On | | | |
| Indels | 1 | 989 | 785 |
| Total | | 10000 | 10000 |
| Modified (%) | 0.010 | 9.890 | 7.850 |
| P-value | | 1.5E−285 | 5.7E−228 |
| On: off specificity | 1 | 1 | 1 |
| VEGF_Off1 | | | |
| Indels | 4 | 4240 | 602 |
| Total | | 38625 | 184554 |
| Modified (%) | 0.010 | 2.297 | 0.394 |
| P-value | | <1.0E−300 | 3.7E−52 |
| On: off specificity | | 4 | 20 |
| VEGF_Off2 | | | |
| Indels | 5 | 727 | 18 |
| Total | | 30301 | 79164 |
| Modified (%) | 0.017 | 0.918 | <0.002 |
| P-value | | 4.7E−93 | 1.3E−04 |
| On: off specificity | | 11 | 3925 |

TABLE 2-continued

| VEGF_Off3 | | | |
|---|---|---|---|
| Indels | 2 | 536 | 21 |
| Total | | 26379 | 110902 |
| Modified (%) | 0.008 | 0.483 | 0.022 |
| P-value | | 2.0E−46 | 2.0E−01 |
| On: off specificity | | 20 | 352 |
| VEGF_Off4 | | | |
| Indels | 0 | 1531 | 45 |
| Total | | 26012 | 122403 |

Table 2. Indel frequencies, P values, and on-target:off-target cleavage specificity ratios for EMX, CLTA, and VEGF on-target sites and 11 known off-target sites. CLTA sites: Total: total number of sequence counts; only the first 10,000 sequences were analyzed for the on-target site sequences. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/49,500; see Results above), whichever value was larger. P-values: for mock treatment, Cas9 plasmid transfection, and liposomal Cas9 protein:sgRNA delivery, P-values were calculated as using a two-sided Fisher's exact test between each CLTA-targeted treatment sample (either DNA transfection or protein:sgRNA delivery) versus the control sample (mock treatment) treated with Cas9 protein and an sgRNA targeting EGFP. On:off specificity is the ratio of on-target to off-target genomic modification frequency for each site. EMX sites shows the experimental and analytic methods of CLTA analysis applied to EMX target sites. VEGF sites shows the experimental and analytic methods of CLTA analysis as applied to VEGF target sites. Indel numbers in the mock treatment control were subtracted from both plasmid transfection and protein:sgRNA delivery indel numbers for determining total number of indels and for calculating on-target:off-target ratios in FIG. 31 in the main text and also for FIG. 41.

REFERENCES

1. Putney, S. D. & Burke, P. A. Improving protein therapeutics with sustained-release formulations. *Nat. Biotechnol.* 16, 153-157 (1998).
2. Mullen, L. et al. Latent cytokines for targeted therapy of inflammatory disorders. *Expert Opin. Drug Deliv.* 11, 101-110 (2014).
3. Song, E. et al. Antibody mediated in vivo delivery of small interfering RNAs via cell-surface receptors. *Nat. Biotechnol.* 23, 709-717 (2005).
4. Leader, B., Baca, Q. J. & Golan, D. E. Protein therapeutics: a summary and pharmacological classification. *Nat. Rev. Drug Discov.* 7, 21-39 (2008).
5. Hartung, S. D. et al. Correction of Metabolic, Craniofacial, and Neurologic Abnormalities in MPS I Mice Treated at Birth with Adeno-associated Virus Vector Transducing the Human α-L-Iduronidase Gene. *Mol. Ther.* 9, 866-875 (2004).
6. Wang, J. et al. Neutralizing antibodies to therapeutic enzymes: considerations for testing, prevention and treatment. *Nat. Biotechnol.* 26, 901-908 (2008).
7. Urnov, F. D., Rebar, E. J., Holmes, M. C., Zhang, H. S. & Gregory, P. D. Genome editing with engineered zinc finger nucleases. *Nat. Rev. Genet.* 11, 636-646 (2010).
8. Sander, J. D. & Joung, J. K. CRISPR-Cas systems for editing, regulating and targeting genomes. *Nat. Biotechnol.* 32, 347-355 (2014).
9. Gaj, T., Gersbach, C. A. & Barbas, C. F. ZFN, TALEN, and CRISPR/Cas-based methods for genome engineering. *Trends Biotechnol.* 31, 397-405 (2013).
10. Midoux, P., Pichon, C., Yaouanc, J.-J. & Jaffrès, P.-A. Chemical vectors for gene delivery: a current review on polymers, peptides and lipids containing histidine or imidazole as nucleic acids carriers. *Br. J. Pharmacol.* 157, 166-178 (2009).
11. Bodles-Brakhop, A. M., Heller, R. & Draghia-Akli, R. Electroporation for the Delivery of DNA-based Vaccines and Immunotherapeutics: Current Clinical Developments. *Mol. Ther.* 17, 585-592 (2009).
12. Kay, M. A., Glorioso, J. C. & Naldini, L. Viral vectors for gene therapy: the art of turning infectious agents into vehicles of therapeutics. *Nat. Med.* 7, 33-40 (2001).
13. Zangi, L. et al. Modified mRNA directs the fate of heart progenitor cells and induces vascular regeneration after myocardial infarction. *Nat. Biotechnol.* 31, 898-907 (2013).
14. Wadia, J. S., Stan, R. V. & Dowdy, S. F. Transducible TAT-HA fusogenic peptide enhances escape of TAT-fusion proteins after lipid raft macropinocytosis. *Nat. Med.* 10, 310-315 (2004).
15. Daniels, D. S. & Schepartz, A. Intrinsically cell-permeable miniature proteins based on a minimal cationic PPII motif. *J. Am. Chem. Soc.* 129, 14578-14579 (2007).
16. Cronican, J. J. et al. Potent delivery of functional proteins into Mammalian cells in vitro and in vivo using a supercharged protein. *ACS Chem. Biol.* 5, 747-752 (2010).
17. Thompson, D. B., Cronican, J. J. & Liu, D. R. Engineering and identifying supercharged proteins for macromolecule delivery into mammalian cells. *Methods Enzymol.* 503, 293-319 (2012).
18. Thompson, D. B., Villaseflor, R., Don, B. M., Zerial, M. & Liu, D. R. Cellular uptake mechanisms and endosomal trafficking of supercharged proteins. *Chem. Biol.* 19, 831-843 (2012).
19. Heitz, F., Morris, M. C. & Divita, G. Twenty years of cell-penetrating peptides: from molecular mechanisms to therapeutics. *Br. J. Pharmacol.* 157, 195-206 (2009).
20. Caron, N. J. et al. Intracellular delivery of a Tat-eGFP fusion protein into muscle cells. *Mol. Ther. J. Am. Soc. Gene Ther.* 3, 310-318 (2001).
21. Chesnoy, S. & Huang, L. Structure and function of lipid-DNA complexes for gene delivery. *Annu. Rev. Biophys. Biomol. Struct.* 29, 27-47 (2000).
22. Al-Taei, S. et al. Intracellular traffic and fate of protein transduction domains HIV-1 TAT peptide and octaarginine. Implications for their utilization as drug delivery vectors. *Bioconjug. Chem.* 17, 90-100 (2006).
23. Shete, H. K., Prabhu, R. H. & Patravale, V. B. Endosomal escape: a bottleneck in intracellular delivery. *J. Nanosci. Nanotechnol.* 14, 460-474 (2014).
24. Aguilera, T. A., Olson, E. S., Timmers, M. M., Jiang, T. & Tsien, R. Y. Systemic in vivo distribution of activatable cell penetrating peptides is superior to that of cell penetrating peptides. *Integr. Biol. Quant. Biosci. Nano Macro* 1, 371-381 (2009).
25. Coelho, T. et al. Safety and efficacy of RNAi therapy for transthyretin amyloidosis. *N. Engl. J. Med.* 369, 819-829 (2013).

26. Judge, A. D., Bola, G., Lee, A. C. H. & MacLachlan, I. Design of noninflammatory synthetic siRNA mediating potent gene silencing in vivo. *Mol. Ther. J. Am. Soc. Gene Ther.* 13, 494-505 (2006).
27. Basha, G. et al. Influence of cationic lipid composition on gene silencing properties of lipid nanoparticle formulations of siRNA in antigen-presenting cells. *Mol. Ther. J. Am. Soc. Gene Ther.* 19, 2186-2200 (2011).
28. Semple, S. C. et al. Rational design of cationic lipids for siRNA delivery. *Nat. Biotechnol.* 28, 172-176 (2010).
29. Boeckle, S., Fahrmeir, J., Roedl, W., Ogris, M. & Wagner, E. Melittin analogs with high lytic activity at endosomal pH enhance transfection with purified targeted PEI polyplexes. *J. Control. Release Off. J. Control. Release Soc.* 112, 240-248 (2006).
30. Allen, T. M. & Cullis, P. R. Liposomal drug delivery systems: from concept to clinical applications. *Adv. Drug Deliv. Rev.* 65, 36-48 (2013).
31. Zelphati, O. et al. Intracellular delivery of proteins with a new lipid-mediated delivery system. *J. Biol. Chem.* 276, 35103-35110 (2001).
32. Adrian, J. E. et al. Targeted SAINT-O-Somes for improved intracellular delivery of siRNA and cytotoxic drugs into endothelial cells. *J. Control. Release Off. J. Control. Release Soc.* 144, 341-349 (2010).
33. Morris, M. C., Depollier, J., Mery, J., Heitz, F. & Divita, G. A peptide carrier for the delivery of biologically active proteins into mammalian cells. *Nat. Biotechnol.* 19, 1173-1176 (2001).
34. Colletier, J.-P., Chaize, B., Winterhalter, M. & Fournier, D. Protein encapsulation in liposomes: efficiency depends on interactions between protein and phospholipid bilayer. *BMC Biotechnol.* 2, 9 (2002).
35. Lawrence, M. S., Phillips, K. J. & Liu, D. R. Supercharging proteins can impart unusual resilience. *J. Am. Chem. Soc.* 129, 10110-10112 (2007).
36. Liu, J., Gaj, T., Patterson, J. T., Sirk, S. J. & Barbas III, C. F. Cell-Penetrating Peptide-Mediated Delivery of TALEN Proteins via Bioconjugation for Genome Engineering. *PLoS ONE* 9, e85755 (2014).
37. Tessarollo, L., Vogel, K. S., Palko, M. E., Reid, S. W. & Parada, L. F. Targeted mutation in the neurotrophin-3 gene results in loss of muscle sensory neurons. *Proc. Natl. Acad. Sci. U.S.A.* 91, 11844-11848 (1994).
38. Maeder, M. L. et al. Robust, synergistic regulation of human gene expression using TALE activators. *Nat. Methods* 10, 243-245 (2013).
39. Jopling, C., Boue, S. & Belmonte, J. C. I. Dedifferentiation, transdifferentiation and reprogramming: three routes to regeneration. *Nat. Rev. Mol. Cell Biol.* 12, 79-89 (2011).
40. Fu, Y., Sander, J. D., Reyon, D., Cascio, V. M. & Joung, J. K. Improving CRISPR-Cas nuclease specificity using truncated guide RNAs. *Nat. Biotechnol.* 32, 279-284 (2014).
41. McNaughton, B. R., Cronican, J. J., Thompson, D. B. & Liu, D. R. Mammalian cell penetration, siRNA transfection, and DNA transfection by supercharged proteins. *Proc. Natl. Acad. Sci. U.S.A.* 106, 6111-6116 (2009).
42. Qi, L. S. et al. Repurposing CRISPR as an RNA-Guided Platform for Sequence-Specific Control of Gene Expression. *Cell* 152, 1173-1183 (2013).
43. Guschin, D. Y. et al. A rapid and general assay for monitoring endogenous gene modification. *Methods Mol. Biol. Clifton N.J.* 649, 247-256 (2010).
44. Ran, F. A. et al. Double nicking by RNA-guided CRISPR Cas9 for enhanced genome editing specificity. *Cell* 154, 1380-1389 (2013).
45. Maeder, M. L. et al. CRISPR RNA-guided activation of endogenous human genes. *Nat. Methods* 10, 977-979 (2013).
46. Guilinger, J. P., Thompson, D. B. & Liu, D. R. Fusion of catalytically inactive Cas9 to FokI nuclease improves the specificity of genome modification. *Nat. Biotechnol.* 32, 577-582 (2014).
47. Pattanayak, V. et al. High-throughput profiling of off-target DNA cleavage reveals RNA-programmed Cas9 nuclease specificity. *Nat. Biotechnol.* 31, 839-843 (2013).
48. Li, H. et al. Differentiation of neurons from neural precursors generated in floating spheres from embryonic stem cells. *BMC Neurosci.* 10, 122 (2009).
49. Lumpkin, E. A. et al. Math1-driven GFP expression in the developing nervous system of transgenic mice. *Gene Expr. Patterns GEP* 3, 389-395 (2003).
50. Van Camp, G. & Smith, R. Hereditary Hearing Loss. at <http://hereditaryhearingloss.org>
51. Kim, S., Kim, D., Cho, S. W., Kim, J. & Kim, J.-S. Highly efficient RNA-guided genome editing in human cells via delivery of purified Cas9 ribonucleoproteins. *Genome Res.* 24, 1012-1019 (2014).
52. Yin, H. et al. Genome editing with Cas9 in adult mice corrects a disease mutation and phenotype. *Nat. Biotechnol.* 32, 551-553 (2014).
53. Wang, H. et al. One-step generation of mice carrying mutations in multiple genes by CRISPR/Cas-mediated genome engineering. *Cell* 153, 910-918 (2013).
54. Schneider, C. A., Rasband, W. S. & Eliceiri, K. W. NIH Image to ImageJ: 25 years of image analysis. *Nat. Methods* 9, 671-675 (2012).
55. Sage, C. et al. Proliferation of functional hair cells in vivo in the absence of the retinoblastoma protein. *Science* 307, 1114-1118 (2005).
56. Sander, J. D. et al. In silico abstraction of zinc finger nuclease cleavage profiles reveals an expanded landscape of off-target sites. *Nucleic Acids Res.* 41, e181 (2013).

EQUIVALENTS AND SCOPE

Those skilled in the art will recognize, or be able to ascertain using no more than routine experimentation, many equivalents to the specific embodiments, described herein. The scope of the present invention is not intended to be limited to the above Description, but rather is as set forth in the appended claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any supercharged protein; any nucleic acid; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

What is claimed is:

1. A composition comprising a Cas9 protein and a cationic lipid, wherein the Cas9 protein is associated with a gRNA, and wherein the Cas9 protein is fused to a deaminase.

2. The composition of claim 1, wherein the composition exhibits low toxicity when administered to a population of cells.

3. The composition of claim 2, wherein at least 60% of the cells are viable following administration of the composition to the cells.

4. The composition of claim 1, wherein the cationic lipid is selected from the group consisting of Lipofectamine® 2000, Lipofectamine® 3000, Lipofectamine® RNAiMAX, and Lipofectamine® LTX.

5. The composition of claim 1, wherein the Cas9 protein comprises a wild type Cas9 protein or a Cas9 variant that comprises an amino acid sequence that is at least 90% identical to the amino acid sequence of SEQ ID NO: 44, a Cas9 nickase, or a nuclease-inactivated Cas9 (dCas9) that comprises an amino acid sequence that is at least 90% identical to the amino acid sequence of SEQ ID NO: 45 and comprises a D10A and/or a H840A substitution as compared to the amino acid sequence of a wild type Cas9.

6. The composition of claim 1, wherein the deaminase comprises a cytidine deaminase.

7. A method comprising administering the pharmaceutical composition of claim 1, to a subject in need thereof.

8. A method of introducing a Cas9 protein into a cell, the method comprising contacting the cell with the composition of claim 1, under conditions suitable for the Cas9 protein to enter the cell, thereby introducing the Cas9 protein into the cell.

9. The composition of claim 6, wherein the cytidine deaminase is selected from the group consisting of APOBEC1, AID, and ACF1/ASE deaminases.

10. The composition of claim 1, wherein the deaminase comprises an adenosine deaminase.

11. The composition of claim 10, wherein the adenosine deaminase comprises an ADAT family deaminase.

12. The composition of claim 1, wherein the Cas9 protein is fused to the deaminase via a linker.

13. The composition of claim 12, wherein the linker comprises an amino acid sequence selected from the group consisting of SGSETPGTSESATPES (SEQ ID NO:3), SGSETPGTSESA (SEQ ID NO:4), SGSETPGTSESAT-PEGGSGGS (SEQ ID NO:5), VPFLLEPDNINGKTC (SEQ ID NO:6), GSAGSAAGSGEF (SEQ ID NO:7), SIVAQLSRPDPA (SEQ ID NO:8), MKIIEQLPSA (SEQ ID NO:9), VRHKLKRVGS (SEQ ID NO:10), GHGTG-STGSGSS (SEQ ID NO:11), MSRPDPA (SEQ ID NO:12), GGSM (SEQ ID NO:13), GGS, and (GGS)$_n$, wherein n is from 1 to 10.

14. The composition of claim 1, wherein the Cas9 protein fused to the deaminase comprises the structure:

[NH$_2$]-[Cas9]-[deaminase]-[COOH] or

[NH$_2$]-[deaminase]-[Cas9]-[COOH].

15. The composition of claim 1 further comprising a nuclear localization signal (NLS) fused to the Cas9 protein or the deaminase.

16. The composition of claim 15, wherein the nuclear localization signal comprises the amino acid sequence MAPKKKRKVGIHRGVP (SEQ ID NO: 47).

17. The composition of claim 15, wherein the NLS is C-terminal of the deaminase.

18. The composition of claim 15, wherein the NLS is C-terminal of the Cas9 domain.

19. The composition of claim 15, wherein the Cas9 protein fused to the deaminase comprises the structure:

[NH$_2$]-[NLS]-[Cas9]-[deaminase]-[COOH] or

[NH$_2$]-[NLS]-[deaminase]-[Cas9]-[COOH].

20. The method of claim 8 further comprising confirming that the deaminase has penetrated the cell.

21. The method of claim 8, wherein the cell is in a subject, and the contacting is done in vivo.

22. The composition of claim 2, wherein at least at least 70% of the cells are viable following administration of the composition to the cells.

23. The composition of claim 2, wherein at least at least 80% of the cells are viable following administration of the composition to the cells.

24. The composition of claim 2, wherein at least at least 90% of the cells are viable following administration of the composition to the cells.

25. The composition of claim 1, wherein the Cas9 protein comprises a wild type Cas9 protein or a Cas9 variant that comprises an amino acid sequence that is at least 90% identical to the amino acid sequence of SEQ ID NO: 44.

26. The composition of claim 1, wherein the Cas9 protein comprises a Cas9 nickase.

27. The composition of claim 1, wherein the Cas9 protein comprises a nuclease-inactivated Cas9 (dCas9) that comprises an amino acid sequence that is at least 90% identical to the amino acid sequence of SEQ ID NO: 45 and comprises a D10A and/or a H840A substitution as compared to the amino acid sequence of a wild type Cas9.

28. The composition of claim 6, wherein the cytidine deaminase is an APOBEC1 deaminase.

29. The composition of claim 6, wherein the cytidine deaminase is an AID deaminase.

30. The composition of claim 6, wherein the cytidine deaminase is an ACF1/ASE deaminase.

* * * * *